(12) United States Patent
Gomez-Galeno et al.

(10) Patent No.: US 10,239,829 B2
(45) Date of Patent: *Mar. 26, 2019

(54) ANTAGONISTS OF THE GLUCAGON RECEPTOR

(71) Applicant: Metabasis Therapeutics, Inc., San Diego, CA (US)

(72) Inventors: Jorge E. Gomez-Galeno, San Diego, CA (US); Raja K. Reddy, San Diego, CA (US); Paul D. van Poelje, La Jolla, CA (US); Robert Huerta Lemus, Escondido, CA (US); Thanh Huu Nguyen, Solana Beach, CA (US); Matthew P. Grote, Carlsbad, CA (US); Qun Dang, San Diego, CA (US); Scott J. Hecker, Del Mar, CA (US); Venkat Reddy Mali, San Diego, CA (US); Mingwei Chen, San Diego, CA (US); Zhili Sun, San Diego, CA (US); Serge Henri Boyer, San Diego, CA (US); Haiqing Li, San Diego, CA (US); William Craigo, San Diego, CA (US)

(73) Assignee: Metabasis Therapeutics, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/614,418

(22) Filed: Jun. 5, 2017

(65) Prior Publication Data

US 2017/0275246 A1 Sep. 28, 2017

Related U.S. Application Data

(63) Continuation of application No. 14/860,593, filed on Sep. 21, 2015, now Pat. No. 9,701,626, which is a
(Continued)

(51) Int. Cl.
| | |
|---|---|
| *C07C 309/15* | (2006.01) |
| *C07C 317/44* | (2006.01) |
| *C07C 323/62* | (2006.01) |
| *C07D 209/20* | (2006.01) |
| *C07D 213/53* | (2006.01) |
| *C07D 213/75* | (2006.01) |
| *C07D 235/30* | (2006.01) |
| *C07D 261/08* | (2006.01) |
| *C07D 263/56* | (2006.01) |
| *C07C 309/11* | (2006.01) |
| *C07D 307/68* | (2006.01) |
| *C07D 307/81* | (2006.01) |

(Continued)

(52) U.S. Cl.
CPC .......... *C07C 309/15* (2013.01); *C07C 307/02* (2013.01); *C07C 309/11* (2013.01); *C07C 317/44* (2013.01); *C07C 323/62* (2013.01); *C07D 209/20* (2013.01); *C07D 213/53* (2013.01); *C07D 213/75* (2013.01); *C07D 235/30* (2013.01); *C07D 261/08* (2013.01); *C07D 263/56* (2013.01); *C07D 277/66* (2013.01); *C07D 307/68* (2013.01); *C07D 307/81* (2013.01); *C07D 317/66* (2013.01); *C07D 333/38* (2013.01); *C07D 405/04* (2013.01); *C07D 409/12* (2013.01); *C07D 413/04* (2013.01); *C07D 471/04* (2013.01); *C07D 498/04* (2013.01); *C07C 2601/02* (2017.05); *C07C 2601/14* (2017.05); *C07C 2601/16* (2017.05); *C07C 2602/08* (2017.05); *C07C 2602/10* (2017.05); *C07C 2603/74* (2017.05)

(58) Field of Classification Search
None
See application file for complete search history.

(56) References Cited

U.S. PATENT DOCUMENTS

| | | |
|---|---|---|
| 3,524,846 A | 8/1970 | Moffatt et al. |
| 3,536,809 A | 10/1970 | Applezweig |

(Continued)

FOREIGN PATENT DOCUMENTS

| | | |
|---|---|---|
| CA | 2678265 | 10/2015 |
| CN | 1774433 A | 5/2006 |

(Continued)

OTHER PUBLICATIONS

Alexander, P., et al., "Preparation of 9-(2-Phosphonomethoxyethyl) Adenine Esters as Potential Prodrugs," Col/ect. Czech. Chem. Commun. (in prior U.S. Appl. No. 12/526,45859),1853-1869, Nakladatelstvi Ceskoslovenski Akademie Ved. (1994).

(Continued)

*Primary Examiner* — Po-Chih Chen

(57) ABSTRACT

The present invention provides for novel compounds of Formula (I) and pharmaceutically acceptable salts and co-crystals thereof which have glucagon receptor antagonist or inverse agonist activity. The present invention further provides for pharmaceutical compositions comprising the same as well as methods of treating, preventing, delaying the time to onset or reducing the risk for the development or progression of a disease or condition for which one or more glucagon receptor antagonist is indicated, including Type I and II diabetes, insulin resistance and hyperglycemia. The present invention also provides for processes of making the compounds of Formula I, including salts and co-crystals thereof, and pharmaceutical compositions comprising the same.

20 Claims, 1 Drawing Sheet

Related U.S. Application Data continuation of application No. 14/147,457, filed on Jan. 3, 2014, now Pat. No. 9,169,201, which is a continuation of application No. 13/083,321, filed on Apr. 8, 2011, now Pat. No. 8,710,236, which is a continuation of application No. 12/526,458, filed as application No. PCT/US2008/053581 on Feb. 11, 2008, now abandoned.

(60) Provisional application No. 60/989,287, filed on Nov. 20, 2007, provisional application No. 60/889,183, filed on Feb. 9, 2007.

(51) Int. Cl.
| | |
|---|---|
| C07D 317/66 | (2006.01) |
| C07D 333/38 | (2006.01) |
| C07D 405/04 | (2006.01) |
| C07D 409/12 | (2006.01) |
| C07D 413/04 | (2006.01) |
| C07D 471/04 | (2006.01) |
| C07D 498/04 | (2006.01) |
| C07C 307/02 | (2006.01) |
| C07D 277/66 | (2006.01) |

(56) References Cited

U.S. PATENT DOCUMENTS

| | | | |
|---|---|---|---|
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,157,027 | A | 10/1992 | Biller et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 6,132,420 | A | 10/2000 | Dionne et al. |
| 6,245,357 | B1 | 6/2001 | Edgren et al. |
| 6,270,787 | B1 | 8/2001 | Ayer |
| 6,283,953 | B1 | 9/2001 | Ayer et al. |
| 6,287,295 | B1 | 9/2001 | Chen et al. |
| 6,333,050 | B2 | 12/2001 | Wong et al. |
| 6,342,249 | B1 | 1/2002 | Wong et al. |
| 6,365,185 | B1 | 4/2002 | Ritschel et al. |
| 6,368,626 | B1 | 4/2002 | Bhatt et al. |
| 6,375,975 | B1 | 4/2002 | Modi |
| 6,375,978 | B1 | 4/2002 | Kleiner et al. |
| 6,503,949 | B1 | 1/2003 | Lau et al. |
| 6,875,760 | B2 | 4/2005 | Lau et al. |
| 6,881,746 | B2 | 4/2005 | Lau et al. |
| 7,301,036 | B2 | 11/2007 | Parmee et al. |
| 8,519,145 | B2 | 8/2013 | Kang et al. |
| 8,710,236 | B2 | 4/2014 | Gomez-Galeno et al. |
| 8,907,103 | B2 | 12/2014 | Gomez-Galeno et al. |
| 9,169,201 | B2 | 10/2015 | Gomez-Galeno et al. |
| 2003/0212119 | A1 | 11/2003 | Lau et al. |
| 2003/0236292 | A1 | 12/2003 | Kodra et al. |
| 2004/0014789 | A1 | 1/2004 | Lau et al. |
| 2004/0152750 | A1 | 8/2004 | Kodra et al. |
| 2005/0288329 | A1 | 12/2005 | Yao et al. |
| 2006/0084681 | A1 | 4/2006 | Parmee et al. |
| 2006/0116366 | A1 | 6/2006 | Parmee et al. |
| 2007/0015757 | A1 | 1/2007 | Madsen et al. |
| 2007/0054902 | A1 | 3/2007 | Fukui et al. |
| 2007/0088071 | A1 | 4/2007 | Kim et al. |
| 2007/0105930 | A1 | 5/2007 | Parmee et al. |
| 2007/0203186 | A1 | 8/2007 | Beeson et al. |
| 2007/0249688 | A1 | 10/2007 | Conner et al. |
| 2008/0085926 | A1 | 4/2008 | Stelmach et al. |
| 2008/0108620 | A1 | 5/2008 | Brockunier et al. |
| 2008/0125468 | A1 | 5/2008 | Chappell et al. |
| 2015/0087680 | A1 | 3/2015 | Gomez-Galeno et al. |

FOREIGN PATENT DOCUMENTS

| | | |
|---|---|---|
| CN | 101610995 | 12/2009 |
| CN | 102292316 | 7/2015 |
| CN | 104803891 A | 7/2015 |
| EP | 0 284 240 B2 | 6/1993 |
| EP | 0 632 048 A1 | 1/1995 |
| EP | 2 129 654 A1 | 12/2009 |
| EP | 2 326 618 A1 | 10/2014 |
| EP | 2 786 985 A1 | 10/2014 |
| EP | 2 799 428 | 11/2016 |
| HK | 1203481 A | 10/2015 |
| IN | 273645 | 6/2010 |
| JP | 63-32538 | 2/1988 |
| JP | 09-241284 A | 9/1997 |
| JP | 11-97740 A | 4/1999 |
| JP | 2004-501897 | 1/2004 |
| JP | 2005-511683 | 4/2005 |
| JP | 2010-511604 | 4/2010 |
| JP | 2010-518124 A | 5/2010 |
| JP | 5322951 | 10/2013 |
| JP | 5684126 | 1/2015 |
| JP | 2015-129133 | 7/2015 |
| KR | 10-2008-0050348 | 12/2006 |
| KR | 10-2015-0008922 | 1/2015 |
| KR | 10-1538810 | 7/2015 |
| KR | 10-1599089 | 2/2016 |
| MX | 318858 | 3/2014 |
| WO | WO 90/08155 A1 | 7/1990 |
| WO | WO 90/10636 A1 | 9/1990 |
| WO | WO 91/19721 A1 | 12/1991 |
| WO | WO 00/069810 A1 | 11/2000 |
| WO | WO 00/071510 A2 | 11/2000 |
| WO | WO 01/019830 A1 | 3/2001 |
| WO | WO 01/062717 A1 | 8/2001 |
| WO | WO 02/00612 A1 | 1/2002 |
| WO | WO 02/040444 A1 | 5/2002 |
| WO | WO 03/048109 A1 | 6/2003 |
| WO | WO 03/053938 A1 | 7/2003 |
| WO | WO 04/002480 A1 | 1/2004 |
| WO | WO 04/050039 A2 | 6/2004 |
| WO | WO 04/052869 A1 | 6/2004 |
| WO | WO 04/069158 A2 | 8/2004 |
| WO | WO 04/100875 A2 | 11/2004 |
| WO | WO 05/051298 A1 | 6/2005 |
| WO | WO 05/054213 A1 | 6/2005 |
| WO | WO 05/065680 A1 | 7/2005 |
| WO | WO 05/118542 A1 | 12/2005 |
| WO | WO 05/121097 A2 | 12/2005 |
| WO | WO 05/123668 A1 | 12/2005 |
| WO | WO 06/086488 A2 | 8/2006 |
| WO | WO 06/102067 A1 | 9/2006 |
| WO | WO 06/104826 A2 | 10/2006 |
| WO | WO 07/015999 A2 | 2/2007 |
| WO | WO 07/047177 A1 | 4/2007 |
| WO | WO 07/106181 A2 | 9/2007 |
| WO | WO 07/111864 A2 | 10/2007 |
| WO | WO 07/114855 A2 | 10/2007 |
| WO | WO 07/120270 A2 | 10/2007 |
| WO | WO 07/120284 A2 | 10/2007 |
| WO | WO 07/123581 A2 | 11/2007 |
| WO | WO 07/136577 A2 | 11/2007 |
| WO | WO 08/001883 A1 | 1/2008 |
| WO | WO 08/042223 A1 | 4/2008 |
| WO | WO 08/066356 A1 | 6/2008 |
| WO | WO 08/098244 A1 | 8/2008 |
| WO | WO 10/019830 A1 | 2/2010 |
| WO | WO 2013/012959 A1 | 1/2013 |

OTHER PUBLICATIONS

Alza Corporation, "L-Oros™ Technology—Advancing New Therapies Through Alza's Liquid Drug Formation," Delivery Times, vol. II, Issue II, 2002, 12 pages.

(56) References Cited

OTHER PUBLICATIONS

American Heart Association, "Metabolic Syndrome" <http://www.americanheart.org/presenter.jhtml?identifier=4756>, Accessed Mar. 31, 2009.
Ash and Ash, Eds., Handbook of Pharmaceutical Additives, 3rd ed, Gower Publishing Company, 2007, 3 pages.
Baddiley et al., "Structure of Coenzyme A," Nature 171:76 (1953).
Benzaria et al., "Synthesis, in Vitro Antiviral Evaluation, and Stability Studies of Bis(S-acyl-2-thioethyl) Ester Derivatives of 9-[2-(Phosphonomethoxy)ethyl] adenine (PMEA) as Potential PMEA Prodrugs with Improved Oral Bioavailability," J. Med. Chem 39(25):4958-4965 (1996).
Bhongle et al., "Expedient and High-Yield Synthesis of Alkylphosphonyl Cichlorides Under Mile, Neutral Conditions: Reaction of BIS (Trimethylsilyl) Slkyl Phosphonates with Oxalyl Chloridel Dimethylformarnide," Synth. Commu. 17:1071-1706 (1987).
Blackburn et al., "Specific Dealkylation of Phosphonate Esters using Iodotrimcthylsilanc," J. Chem. Soc. , Chem. Commun. 870-871 (1978).
Brand et al., "Evidence for a Major Role of Glucagon in the Hyperglycemia of Experimental Diabetes," A Journal of the American Diabetes Association, 1994, 43 (Suppl. 1), 172A.
Brand et al., "Immunoneutralization of endogenous glucagon with monoclonal glucagon antibody normalizes hyperglycaemia in moderately streptozotocin-diabetic rats," Diabetologia 1994, vol. 37, pp. 985-993.
Brechbühler et al., "Die Reaktion von Carbonsauren mit Acetalen des N, N-Dimethylformmids: eine Veresterungsmethode," Helv. Chim. Acta. 48(7):1746-1771 (1965).
Bundgaaard, ed., Design of Prodrugs, Elsevier Science, Amsterdam, 1985.
Busch-Peterson et al., "Lithium N-trityl-N-(R)-1-phenethylamide, a readily available and useful base for the enantioselective formation of chiral cnolates from achiral ketones," Tetrahedron Letters 41(36):6941-6944 (2000).
Campagne, J.-M. et al., "Synthesis of Mixed Phosphonate Diester Analogues of Dipeptides using BOP or PyBOP Reagents," Tetrahedron Left. 34(42), 6743-6744, Pergamon Press Ltd. (1993).
Campbell, DA, "The Synthesis of Phosphonate Esters, an Extension of the Mitsunobu Reaction," J. Org. Chem. 57,6331-6335, American Chemical Society (1992).
CAS Registry No. 852460-16-3, STN Entry Date Jun. 17, 2005.
CAS Registry No. 131055-48-6, STN Entry Date Dec. 14, 1990.
CAS Registry No. 127192-35-2, STN Entry Date May 18, 1990.
CAS Registry No. 141740-28-5, STN Entry Date Jun. 12, 1992.
CAS Registry No. 141220-32-8, STN Entry Date May 8, 1992.
CAS Registry No. 127192-36-3, STN Entry Date May 18, 1990.
CAS Registry 699001-74-6, STN Entry Date Jun. 25, 2004.
Casara, P.J. et al., Synthesis of Acid Stable 5'-O-Fluoromethyl Phosphonates of Nucleosides. Evaluation as Inhibitors of Reverse Transcriptase,• Bioorg. Med. Chem. Left. 2(2), 145-148, Pergamon Press pic. (1992).
Cereda et al., "Solid-phase synthesis of 3-hydroxymethyl isoxazoles via resin bound nitrile oxides," Tetrahedron Lett. 42(30):4951-4953(2001).
Coppi et al., "Lewis Acid Mediated Condensation of Alkenols and Aldehydes. A Selective Synthesis of Tetrahydropyrans and Oxepanes," J. Org. Chern. 53(4) 911-913 (1988).
Curran et al., "Thermolysis of bis[2-[(trimethylsilyl)oxy]prop-2-yl] furoxan (TOP-furoxan). The First Practical Method for Intermolecular Cycloaddition of an in Situ Generated Nitrile Oxide with 1, 2-Di- and Trisubstituted Olefins," J. Am. Chem. Soc. 107(21):6023-6028 (1985).
DeLambert et al., "N-Phosphonomethyl Dipeptides and Their Phosphonate Prodrugs, a New Generation of Neutral Endopeptidase (NEP, TIC3.4.24.11) Inhibitors," J. Med. Chem. 37(7):498-511 (1994).

Egron et al., "Synthesis and Anti-HIV Activity of Some S-Acyl-2-thioethyl (SATE) Phosphoramidate Derivatives of 3'-Acido-2' 3'-dideoxythymidine," Nucleosides & Nucleotides 18(4):981-982 (1999).
Elhaddadi et al., "A Convenient Synthesis of Alkyl and Dialkyl 1-benzyloxyamino alkyl phosphonates and phosphinates," Phosphorus, Sulfur and Silicon 54:143-150 (1990).
Elliott, RL. et al., "Synthesis and Biological Evaluation of Phosphonamidate Peptide Inhibitors of Enkephalinase and Angiotensin-Converting Enzyme," J. Med. Chem. 28: 1208-1216, American Chemical Society (1985).
Farquhar et al., "Biologically Reversible Phosphate-Protective Groups," J. Pharm. Sci. 72(3):324-325 (1983).
Faulon, J-L., et al.: "The Signature Molecular Descriptor. 2. Enumerating Molecules from Their Extended Valence Sequences," Journal of Chemical Information and Computer Sciences, 2003, vol. 43, No. 3, pp. 721-734.
Federal Register 2011, 76 (27), p. 7166.
Ferres, "Pro-Drugs of B-Lactam Antibiotics," Drugs of Today 19(9):499-538 (1983).
Franchetti, P. et al.: Potent and selective inhibitors of human Immunodeficiency virus protease structurally related to L-694,746, Antiviral Chemistry and Chemotherapy, 1998, vol. 9, No. 4, pp. 303-309.
Freed et al., "Evidence for Acyloxmethyl Esters of Pyrimidine 5'-Deoxyribonucleotides as Extracellular Sources of Active 5'-Deoxyribonucleotides in Cultured Cells," Biochem. Pharmac. 38:3193-3198 (1989).
Garbisch et al, "Conformations. IV. The Conformational Preference of the Phenyl Group in Cyclohexane," J. Am. Chem. Soc., 1963, vol. 85, pp. 3228-3231.
Gibson, Ed., Pharmaceutical Preformulation and Formulation, CRC Press LLC, Boca Raton, FL, 2004.
Greene et al., Protective Groups in Organic Synthesis, John Wiley, New York, 1990.
Grundy et al., "Diagnosis and Management of the Metabolic Syndrome," Circulation, 112 (2005), p. 2735-2752.
Gupta et al., "An Improved Synthesis of Vinylic Phosphonates from Ketones," Synth. Commun. 10(4):299-304 (1980).
Hoffman, "A Simple Efficient Synthesis of Dibenzyl and Di-p-nitrobenzyl 1-Hydroxyalkanephosphonates," Synthesis 1988(1):62-64 (1988).
Huang et al., "a-Hypervalent Iodine Functionalized Phosphonium and Arsonium Ylides and Their Tandem Reaction as Umpolung Reagents," J Org. Chem. 67(23):8261-8264 (2002).
Inanaga et al., "A Rapid Esterification by Means of Mixed Anydride and Its Application to Large-ring Lactonization," Bulletin of the Chemical Society of Japan 52(7):1989-1993 (1979).
Johnson et al., "The Regulation of Gluconeogenesis in Isolated Rat Liver Cells by Glucagon, Insulan, Dibutyrl Cyclic Adenosine Monophosphate, and Fatty Acids," J. Biol. Chem., 1972, vol. 247, No. 10, pp. 3229-3235.
Juliano, Ed., Drug Delivery Systems, Oxford Univ. Press, Oxford, 1980.
Kerns et al., "Selective N-Sulfation of Glucosamine Derivatives Using Phenyl Chlorosulfate in Non-Qqueous Solvent," Synthetic Communications., 26:2671-2680, 1996.
Khamnei, S. et al., "Neighboring Group Catalysis in the Design of Nucleotide Prodrugs," J. Med. Chem. 39, 4109-4115, American Chemical Society (1996).
Kim, Cherug-ju, Controlled Release Dosage Form Design, 231-238, Technomic Publishing, Lancaster PA 2000.
Kozma, CRC Handbook of Optical resolutions via Diastereomeric Salt Formation, CRC Press, 2001.
Kurti et al., Strategic Applications of Named Reactions in Organic Synthesis, Elsvier, 340-342, 2005.
Kurukulasuriya et al., "Biaryl amide glucagon receptor antagonists," Bioorg. Med. Chem. Lett. 14(9):2047-2050 (2004).
Larock, Comprehensive Organic transformations, VCH, New York, 1989.
Latour et al., "Simple Syntheses of 2-Hydroxymethy-1, 3-propanediol and Related Compounds," Synthesis 1987(8):742-745 (1987).

(56) References Cited

OTHER PUBLICATIONS

Lee et al., "Synthesis and in Vitro Activity of Novel Isoxazolyl Tetrahydropyridinyl Oxazolidinone Antibacterial Agents," Bioorg. Med. Chern. Lett. 13(22):4117-4120 (2003).
Lejczak et al., Transestcrification ofDiphenyl Phosphonates Using the Potassium Fluoride/Crown Ether/Alcohol System; Part 2. The Use of Diphenyl l-Aminoalkanephosphonates in Phosphonopeptide Synthesis 1982(5):412-414 (1982).
Li et al.: "Chiral Drug Separation," Encyclopedia of Chemical Processing (2006), pp. 449-458.
Lyapkalo et al., (Enantioselective Synthesis of Cyclohexenylalkenes by Asymmetric Depprotonation of 4-tert-Butylcyclohexanone Followed by O-Nonatlation and Heck Couplings, SynZett 1292-1295 (2001).
Martin et al., "Synthesis and Antiviral Activity of Various Esters of 9-[(1 ,3-Dihydroxy-2-propoxy)methyl]guanine," J. Pharm. Sci. 76(2):180-184 (1987).
Mathur,"Metabolic Syndrome" see section "How is metabolic syndrome defined?" <http://www.medicinenet.com/metabolic syndrome/article.htm>, pp. 2-3, Accessed Mar. 31, 2009.
McGuigan, C. et al., "Kinase Bypass: A New Strategy for Anti-HIV Drug Design," Bioorganic & Medicinal Chemistry Letters 3(6): 1207-1210, Pergamon Press Ltd. (1993).
McKenna et al., "The facile dealkylation of phosphonic acid dialkyl esters by bromotrimcthylsilanc," Tetrahedron Lett. 2:155-158 (1977).
Meier, C. et al., "Cyclic Saligenyl Phosphotriesters of 2',3'-Dideoxy-2',3'-didehydrothymidine (d4T)—A New Pro-Nucleotide Approach," Bioorganic Med. Chem. Lett. 7(2), 99-104, Elsevier Science Ltd. (1997).
Mitchell, A.G. et al., "Bioreversible Protection for the Phospho Group: Bioactivation of the Di(4-acyloxybenzyl) and Mono(4-acyloxybenzyl) Phosphoesters of Methylphosphonate and Phosphonacetate," J. Chem. Soc. Perkin Trans. 1 38:2345-2353, Chemical Society, London (1992).
Mitsunobu, 0., "The Use of Diethyl Azodicarboxylate and Triphenylphosphine in Synthesis and Transformation of Natural Products," Synthesis 1-28, Georg Thieme Verlag (1981).
Moriarty et al., "Diphenyl Methylphosphonate as a Phosphonylation Reagent with High Diastereoselectivity at Phosphorus," Tetrahedron Lett. 38(15):2597-2600 (1997).
Mukalyama et al., "Synthesis of Oligothymidylates and Nucleoside Cyclic Phosphates by Oxidation-Reduction Condensation," J. Am. Chem. Soc. 94(24):8528-8532 (1972).
Nishimura et al., "Orally Active 1-(Cyclohexyloxycarbonyloxy)alkyl Ester Prodrugs of Cefotiam," J. Antibiotics 40(1):81-90 (1987).
Ogg, M.S. et al., "A Reporter Gene Assay to Assess the Molecular Mechanisms of Xenobiotic-dependent Induction of the Human CYP3A4 Gene in Vitro," Xenobiotica 29(3), 269-279, Taylor & Francis Ltd. (Mar. 1999).
Ohashi, K. et al., "Synthesis of Phosphonosphingoglycolipid Found in Marine Snail Turbo Cornutus," Tetrahedron Lett. 29(10), 1189-1192, Pergamon Press pic. (1988).
Patois et al., "Easy preparation of alkylphosphonyl dichlorides," Bull. Soc. Chim Fr. 130:485-487 (1993).
Pelchowicz, "Organic Phosphorus Compounds. Part 1.The Reaction of Dialkyl Mthylphosphnates and Methylphosphonothionates with Inorganic Acid Chlorides," J Chern. Soc. 238-240 (1961).
Petasis et al., "The boronic acid mannich reaction: A new method for the synthesis of geometrically pure allylarnines," Tetrahedron Lett. 34(4):583-586 (1993).
Posner et al., "3-bromo-2-pyrone: an easily prepared chameleon diene and a synthetic equivalent of 2-pyrone in thermal diels-alder cycloadditions," Tetrahedron Letters 32(39):5295-5298 (1991).
PubMed Health,"Type 1 diabetes" Jun. 28, 2011.
Puech et al., "Intracellular delivery ofnucleoside monophosphates through a reductase-mediated activation process," Antiviral Res. 22(2-3):155-174 (1993).
Quast et al., "Herstellung von Methylphosphonsaure-dichlorid," Synthesis 1974(7):490 (1974).

Rabinowitz, "The Reactions of Phosphonic Acid Esters with Acid Chlorides. A Very Mild Ilydrolytic Route," J. Org. Chem. 28(11):2975-2978 (1963).
Ramachandran et al., "Efficient General Synthesis of 1,2- and 1 ,3-diols in High Enantiomeric Excess via the Intramolecular Asymmetric Reduction of the Corresponding Ketoalkyl Diisopinocampheylborinate Intermediates," Tetrahedron, 38(5):761-764 (1997).
Rao et al., "Studies directed towards the synthesis of immunosuppressive agent FK-506: synthesis of the entire top-half," Tetrahedron Letters 32(4):547-550 (1991).
Rathbone et al, Eds., Modified-Release Drug Deliver Technology, Drugs and the Pharmaceutical Science, Marcel Dekker, Inc.: New York, NY, vol. 126, 2003.
Remington: The Science and Practice of Pharmacy, 21st Ed., Lippincott Williams & Wilkins, Philadephia, PA, 2005.
Remington's Pharmaceutical Sciences, 18th ed., Mack Publishing, Easton PA, 173, 1990, and pp. 172-174.
Roche, Ed., Design of Biopharmaceutical Properties through Prodrugs and Analogs, American Pharmaceutical Association, Washington, 1977.
Roden et al., "The Roles of Insulin and Glucagon in the Regulation of Hepatic Glycogen Synthesis and Turnover in Humans," J. Clin. Invest. 1996, vol. 97, No. 3, pp. 642-648.
Rosowsky et al., "Methotrexate Analogues. 32. Chain Extension, a-Carboxyl Delection, and y-Carboxyl Replacement by Sulfonate and Phosphonate: Effect on Enzyme Binding and Cell-Growth Inhibition," J. Med. Chem. 31: 1326-1331 (1988).
Rowe et al., Eds., Handbook of Pharmaceutical Excipients, 5th Ed., The Pharmaceutical Press and the Merican Pharmaceutical Association, 2006.
Sakamoto et al., "The palladium-catalyzed arylation of 4H-1 ,3-dioxin," Tetrahedron Lett. 33(45):6845-6848 (1992).
Schoeller, et al., "Measurement of energy expenditure in humans by doubly labeled water method," J. Appl Physiol., 53(4), pp. 955-959, (1982).
Serafinowska et al., "Synthesis and in Vivo Evaluation of Prodrugs of 9-[2-(Phosphonomethoxy)ethoxy] adenine," J. Med. Chem. 38(8):1372-1379 (1995).
Shafer et al., "On the Mechanism of Reductive Cleavage of Aryl Phosphates," J. Am. Chem. Soc. 99(15):5118-5123 (1977).
Shaw-Ponter et al., "New synthesis of both D- and L-3-O-Carbamoyl-2-deoxy-4-thioribosides, Substrates for I)-selective Glycosylations," Tetrahedron Letters 37:1871-1874 (1981).
Shono et al., "Electroreductive Elimination of Phenolic Hydroxyl Groups and a New Synthesis of Olivetol," J. Org. Chem. 44(25):4508-4511.
Siddiqui et al., "The Presence of Substituents on the Aryl Moeity of the Aryl Phosphoramidate Derivative of d4T Enhances Anti-HIV Efficacy in Cell Culture: A Structure-Activity Relationship," J. Med. Chem. 42: 393-399 (1999).
Silverman, Chapter 8: "Prodrugs and Drug Delivery Systems", The Organic Chemistry of Drug Design and Drug Action, Academic Press, 1992, pp. 352-401.
Singh et al., "Design and Synthesis ofIsoxazole Containing Bioisosteres of Epihatidine as Potent Nicotinic Acetylcholine Receptor Agonists," Chem. Pharm. Bull. 47(10):1501-1505 (1999).
Slavica et al., "Systhesis and Biological Activities of a New Set of Irreversibly Acting 2-(4'-Isothiocyanatobenzyl)imidazoline Analogs in Rat Thoracic Aorta," J. Med. Chem. 1994, vol. 37, No. 12, pp. 1874-1881.
Starrett, Jr. et al., "Synthesis, Oral Bioavailability Determination, and in Vitro Evaluation of Prodrugs of the Antiviral Agent 9-[2-(Phosphonomethoxy)ethyl]adenine (PMEA)," J. Med, Chem 37:1857-1864 (1994).
Still et al., "Direct synthesis of Z-unsaturated esters. A useful modification of the hormer-emmons olefination," Tetrahedron Letters 24(41):4405-4408 (1983).
Stowell et al., "The Mild Preparation of Synthetically Useful Phosphonic Dichlorides: Applicationt to the Synthesis of Cyclic Phosphonic Diesters and Diamides," Tetrahedron Letters 31(23):3261-3262 (1990).

(56) References Cited

OTHER PUBLICATIONS

Tawfik et al., "1,8-Diazabicyclo[5.4.0]undecene Mediated Transesterification ofp-Nitrophenyl Phosphonates: A Novel Route to Phosphono Esters," Synthesis 1993(10):968-972 (1993).
Toke et al., "A Versatile Building Block for the Synthesis of Substituted Cyclopropanephosphonic Acid Esters," Tetrahedron Letters 51(33):9167-9178 (1995).
Turner, JA, "A General Approach to the Synthesis of 1,6-,1,7-, and 1,8-Naphthyridines," J. Org. Chem. 55(15),4744-4750, American Chemical Society (1990).
United States Pharmacopeia, The, 23rd ed., pp. 1843-1844, 1995.
Valette et al., "Decomposition Pathways and in Vitro HIV Inhibitory Effects of IsoddA Pronucleotides: Toward a Rational Approach for Intracellular Delivery of Nucleotide 5'-Monophosphates," J. Med. Chem. 39(10):1981-1990 (1996).
Vanderwal et al., "An Enantioscicctivc Synthesis of FR182877 Provides a Chemical Rationalization ofIts Structure and Affords Multigram Quantities ofIts Direct Precursor," J. Am. Chem. Soc. 125(18):5393-5407.
Xu et al. "A General Route to the Synthesis of N-Protected 1-Substituted and 1,2-Disubstituted Taurines," Synthesis 2004(2):276-282 (2004).
Yamamoto et. al., "Synthesis of Pyridine N-Oxide-SbCls Complexes and Their Intramolecular and Oxygen-Transfer Reaction," Tetrahedron 37:1871-1873 (1981).
Yan et al., "Preparation, Properties, Reactions, and Adenosine Receptor Affinities of Sulfophenylxanthine Nitrophenyl Esters: Toward the Development of Sulfonic Acid Prodrugs with Peroral Bioavailability," J. Med. Chem. 47(4):1031-1043 (2004).
Yao et al., "Generation of Nitroalkanes, Hydroximoyl Halides and Nitrile Oxides from the Reactions of B-Nitrostyrenes with Grignard or Organolithium Reagents," Tetrahedron Letters 54(5/6):791-822 (1998).
Younker et al., "A mechanistic Study of the Alkaline Hydrolysis of Diaryl Sulfate Diesters," J. Org. Chem. 69(26):9043-9048 (2004).
Ballatore: "Carboxylic Acid (Bio)Isosteres in Drug Design," ChemMedChem 8.3 (2013): 385-395.
R. Jason Herr: "5-Substituted-1H-tetrazoles as Carboxylic Acid Isosteres: Medicinal Chemistry and Synthetic Methods," Bioorg. Med. Chem. 10 (2002) 3379-3393.
Macchiarulo, et al.: "Exploring the other side of bilogically relevant chemical space: Insights into carboxylic, sulfonic and phosphonic acid bioisosteric relationships Roberto Pellicciari," Journal of Molecular Graphics and Modelling 26 (2007) 728-739.
Lidia Moerira Lima, et al.: "Bioisosterism: A Useful Strategy for Molecular Modificaion and Drug Design, Current Medicinal Chemistry," 2005, 12, 23-49.
Australian Office Action in AU Application No. 2008212816, dated Nov. 9, 2012.
Australian Office Action in AU Application No. 2008212816, dated Dec. 20, 2012.
Office Action in U.S. Appl. No. 13/083,321, dated Jul. 12, 2013.
Canadian Office Action in CA Application No. 2,678,265, dated Feb. 4, 2014.
Canadian Office Action in CA Application No. 2,678,265, dated Jul. 11, 2014.
First Office Action in Chinese Application No. 200880004461.9 dated Jun. 15, 2012.
Second Office Action in Chinese Application No. 200880004461.9 dated Apr. 28, 2013.
Third Office Action in Chinese Application No. 200880004461.9 dated Jan. 17, 2014.
Decision on Rejection in Chinese Application No. 200880004461.9 dated Jun. 27, 2014.
Supplementary Partial European Search Report dated Jul. 17, 2012, European Patent Application No. EP 08 72 9528, 7 pages.
Examination Report, re EP Application No. EP 08 729 528.3, dated Feb. 20, 2013.
Extended Search Report, re EP Application No. 14162609.3, dated Jan. 8, 2015.
Indian Office Action, re IN Application No. 5771/DELNP/2009, dated Sep. 13, 2009.
Japanese Office Action, re JP Application No. JP 2009-549286, dated Feb. 26, 2013.
Japanese Office Action, re JP Application No. JP 2013-110101, dated Jun. 3, 2014.
Japanese Office Action, re JP Application No. JP 2013-110101, dated Jun. 2, 2015.
Japanese Pre-appeal Exam Report, re JP Application No. JP 2013-110101, dated Oct. 29, 2015.
Korean Office Action (Reasons for Rejection), re KR Application No. 10-2012-7025865, (undated/docketing lists as Nov. 14, 2014).
Korean Office Action, re KR Application No. 10-2014-7036395, dated Mar. 23, 2015.
Korean Office Action, re KR Application No. 10-2014-7036395, dated Jan. 4, 2016. No new art cited.
Office Action in Mexico Application No. MX/a/2009/008534 dated Jun. 27, 2013.
Office Action in Mexico Application No. MX/a/2009/008534 (FA correspondence dated Nov. 5, 2013).
International Search Report dated Jul. 17, 2008, in International Application No. PCT/US2008/053581.
International Preliminary Report on Patentability dated Aug. 11, 2009, in International Application No. PCT/US2008/053581.
Canadian Office Action, re CA Application No. 2,770,298, dated Jun. 8, 2015.
Canadian Office Action, re CA Application No. 2,770,298, dated Feb. 17, 2016.
Chinese Office Action in CN Application No. 200980141324.4, dated Apr. 15, 2013.
Chinese Search Report in CN Application No. 200980141324.4, dated Apr. 3, 2013.
Chinese Office Action in CN Application No. 200980141324.4, dated Jan. 6, 2014.
Chinese Third Office Action in CN Application No. 200980141324.4, dated Aug. 5, 2014.
European Exam Report, re EP Application No. 09 791 510.2, dated Feb. 7, 2013.
European Exam Report, re EP Application No. 09 791 510.2, dated Apr. 2, 2014.
European Extended Search Report, re EP Application No. 14179199.6, dated Nov. 17, 2104.
Japanese Office Action, re JP Application No. JP 2011-523184, dated Jan. 14, 2014.
Japanese Office Action, re JP Application No. JP 2015-005005, dated Dec. 1, 2015.
Korean Office Action, re KR Application No. 10-2014-7036395 (Original KR App. No. 10-2009-7016602), dated Mar. 20, 2015.
Korean Notice of Preliminary Rejection, re KR Application No. 10-2014-7036395 (Original KR App. No. 10-2009-7016602), dated Aug. 11, 2015.
Korean Notice of Preliminary Rejection, re KR Application No. 10-2015-7027964 (Original KR App. No. 10-2011-7005737), dated Dec. 1, 2015.
Korean Notice of Allowance, re KR Application No. 10-2015-7027964 (Original KR App. No. 10-2011-7005737), dated Mar. 24, 2016.
Mexican Office Action, re MX Application No. MX/a/2011/001708, dated Jul. 23, 2013.
International Search Report in Application No. PCT/US2009/053795 (now International Publication No. WO 2010/019830 A1), dated Dec. 18, 2009 (2 pages).
Australian Office Action in AU Application No. 2014204420, dated Aug. 22, 2016.
Australian Office Action in AU Application No. 2014204420, dated Mar. 17, 2017.
Office Action in U.S. Appl. No. 14/860,593, dated Jan. 5, 2016.
Canadian Office Action in CA Application No. 2,894,112, dated Jul. 4, 2016.
Canadian Office Action in CA Application No. 2,894,112, dated Apr. 26, 2017.
Fourth Office Action in Chinese Application No. 200880004461.9 dated Jan. 13, 2017.

(56) References Cited

OTHER PUBLICATIONS

Exam Report, re EP Application No. 14162609.3, dated Feb. 2, 2017.
Japanese Office Action, re JP Application No. JP 2015-196171, dated Nov. 8, 2016.
Korean Notice on the Result of Reexamination, re KR Applicaton No. 10-2014-7036395, dated (appx.) Jun. 16, 2016. no translation.
Korean Office Action, re KR Application No. 10-2016-7011147, dated Jul. 19, 2016.
Korean Office Action re KR Application No. 10-2016-7011147, dated May 17, 2017.
Office in Mexico Application No. MX/a/2014/003565, dated May 16, 2016.
Office in Mexico Application No. MX/a/2014/003565, dated Oct. 26, 2016.
Chinese First Office Action in CN Application No. 201510257808.2, dated Feb. 16, 2016.
Chinese Second Office Action in CN Application No. 201510257808.2, dated Oct. 26, 2016.
Chinese Third Office Action in CN Application No. 201510257808.2, dated Apr. 20, 2017.
Indian Office Action, re IN Application No. 1841/DELNP/2011, dated Mar. 23, 2017.
Japanese Office Action, re JP Application No. JP 2015-005005, dated Sep. 6, 2016.
European Extended Search Report, re EP Application No. 16198552.8, dated Mar. 1, 2017.
International Search Report and Written Opinion in Application No. PCT/US15/35400, dated Sep. 3, 2015. (23 pages).
International Preliminary Report on Patentability in Application No. PCT/US15/35400, dated Dec. 15, 2016. (14 pages).
San Diego, "Ligand Initiates Phase 1 Trial with Glucagon Receptor Antagonist for Type 2 Diatests," Diabetes Week, Nov. 25, 2013.
Vajda et al., "Pharmacokinetics and pharmacodynamics of single and multiple doses of the glucagon receptor antagonist LGD-6972 in healthy subjects and subjects with type 2 diabetes mellitus," Diabetes, Obesity and Metabolism, vol. 19, No. 1, Aug. 31, 2016.
European Extended Search Report re EP Application No. 15805822.2, dated Dec. 20, 2016.
Chinese Office action dated May 2, 2017, issued in corresponding CN 201510884273.1.

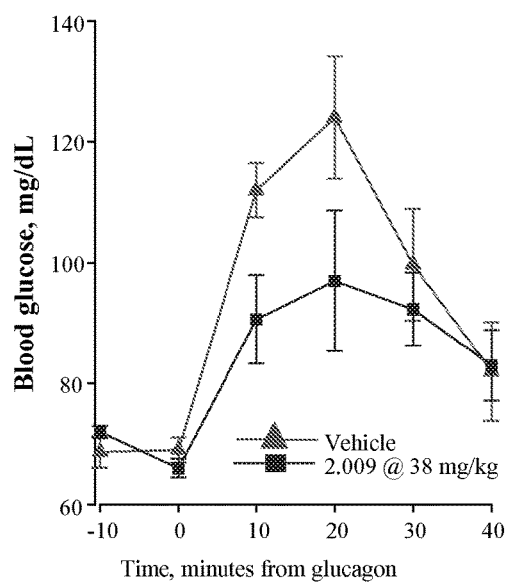 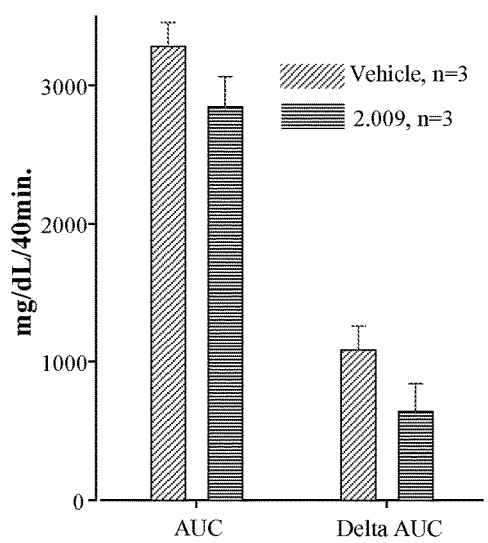
Figure 1A                    Figure 1B

ANTAGONISTS OF THE GLUCAGON RECEPTOR

CROSS-REFERENCE TO RELATED APPLICATIONS

This application is a continuation of U.S. patent application Ser. No. 14/860,593 filed Sep. 21, 2015, which is a continuation of U.S. patent application Ser. No. 14/147,457 filed Jan. 3, 2014, which is a continuation of U.S. patent application Ser. No. 13/083,321 filed Apr. 8, 2011, which is a continuation of U.S. patent application Ser. No. 12/526,458 filed Aug. 7, 2009, which is a national phase under 35 U.S.C. § 371 of International Application No. PCT/US2008/053581 filed Feb. 11, 2008, which claims the benefit of U.S. Provisional Application No. 60/889,183 filed Feb. 9, 2007, and U.S. Provisional Application No. 60/989,287 filed Nov. 20, 2007, the disclosures of which are hereby incorporated by reference in their entirety, including all figures, tables and amino acid or nucleic acid sequences.

FIELD OF THE INVENTION

The present invention is directed towards novel antagonists of the glucagon receptor.

BRIEF SUMMARY OF THE INVENTION

The present invention relates to compounds and pharmaceutical compositions of Formula I, including pharmaceutically acceptable salts or co-crystals, and prodrugs thereof which have glucagon receptor antagonist or inverse agonist activity. The present invention further provides for pharmaceutical compositions comprising the same as well as methods of treating, preventing, delaying the time to onset or reducing the risk for the development or progression of a disease or condition for which one or more glucagon receptor antagonist is indicated, including Type I and II diabetes, insulin resistance and hyperglycemia. Also provided are methods of making or manufacturing compounds of Formula I and pharmaceutically acceptable salts or co-crystals, and prodrugs thereof.

BRIEF DESCRIPTION OF THE FIGURES

FIGS. 1A and 1B illustrate results of treatment with an exemplary compound of the disclosure, showing attenuation of glucagon-induced glucose excursion.

DETAILED DESCRIPTION OF THE INVENTION

Definitions

As used herein, the following terms are defined with the following meanings:

"Acyl" refers to —C(O)R$^s$ where R$^s$ is alkyl, heterocycloalkyl, or aryl.

"Acylalkyl-" refers to an alkyl-C(O)-alk-, wherein "alk" is alkylene.

"Acylamino-" refers to and R$^w$C(O)—NR$^w$—, wherein each R$^w$ is independently —H, alkyl, aryl, aralkyl, and heterocycloalkyl.

"Acyloxy-" refers to the ester group —O—C(O)R$^t$, where R$^t$ is H, alkyl, alkenyl, alkynyl, aryl, aralkyl, or heterocycloalkyl.

"Alicyclic" refers to a cyclic group or compound comprising the properties of aliphatic and cyclic compounds and include but are not limited to cycloalkyl and bridged cycloalkyl compounds. The cyclic compound includes heterocycles. Cyclohexenylethyl, cyclohexanylethyl, and norbornyl are suitable alicyclic groups. Such groups may be optionally substituted.

"Alkanoyl" refers to the group alkyl-C(O)—.

"Alkenyl" refers to unsaturated groups which have 2 to 12 atoms and contain at least one carbon-carbon double bond and includes straight-chain, branched-chain and cyclic groups included alkenylene and alkynylene. Alkenyl groups may be optionally substituted. Suitable alkenyl groups include allyl. "1-alkenyl" refers to alkenyl groups where the double bond is between the first and second carbon atom. If the 1-alkenyl group is attached to another group, it is attached at the first carbon.

"Alkyl" refers to a straight or branched chain or cyclic chain or combination of cyclic chain and either straight and/or branched chain(s), optionally substituted, hydrocarbon radical wherein all of the carbon-carbon bonds are single carbon-carbon bonds. Included are alkyl-groups substituted, e.g., with alkenes and alkynes. Representative examples of alkyl-groups include methyl, ethyl, propyl, isopropyl, cyclopropyl, butyl, isobutyl, tert-butyl, cyclobutyl, pentyl, cyclopentyl, hexyl, and cyclohexyl, all of which may be optionally substituted. Alkyl groups are $C_1$-$C_{12}$.

"Alkylaminoalkyl-" refers to the group alkyl-NR$^u$-alk- wherein each "alk" is an independently selected alkylene, and R$^u$ is H or lower alkyl. "Lower alkylaminoalkyl-" refers to groups where the alkyl and the alkylene group is lower alkyl and alkylene, respectively.

"Alkylaminoalkylcarboxy-" refers to the group alkyl-NR$^u$-alk-C(O)—O— where "alk" is an alkylene group, and R$^u$ is a H or lower alkyl.

"Alkylaminoaryl-" refers to the group alkyl-NR$^v$-aryl- wherein "aryl" is a multivalent group and R$^v$ is —H, alkyl, aralkyl, or heterocycloalkyl. In "lower alkylaminoaryl-", the alkyl group is lower alkyl.

"Alkylaryl-" or "alkaryl-" refers to an aryl group substituted with an alkyl group. "Lower alkylaryl-" refers to such groups where alkyl is lower alkyl.

"Alkoxy-" or "alkyloxy-" refers to the group alkyl-O—.

"Alkoxyalkyl-" or "alkyloxyalkyl-" refers to the group alkyl-O-alk- wherein "alk" is an alkylene group. In "lower alkoxyalkyl-", each alkyl and alkylene is lower alkyl and alkylene, respectively.

"Alkoxyaryl-" or "alkyloxyaryl-" refers to an aryl group substituted with an alkyloxy group (alkyl-O-aryl-). In "lower alkyloxyaryl-", the alkyl group is lower alkyl.

"Alkoxycarbonyloxy-" refers to alkyl-O—C(O)—O—.

"Alkylene" refers to a divalent straight chain, branched chain or cyclic saturated aliphatic group. In one aspect the alkylene group contains up to and including 10 atoms. In another aspect the alkylene chain contains up to and including 6 atoms. In a further aspect the alkylene groups contains up to and including 4 atoms. The alkylene group can be either straight, branched chain or cyclic.

"Alkylthio-" and "alkylthio-" refer to the group alkyl-S—.

"Alkylthioalkyl-" refers to the group alkyl-S-alk- wherein "alk" is an alkylene group. In "lower alkylthioalkyl-" each alkyl and alkylene is lower alkyl and alkylene, respectively.

"Alkylthiocarbonyloxy-" refers to alkyl-S—C(O)—O—.

"Alkynyl" refers to unsaturated groups which have 2 to 12 atoms and contain at least one carbon-carbon triple bond and includes straight-chain, branched-chain and cyclic groups.

Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g., it is a W substituent attached to the cyclic phosphonate, it is attached at the first carbon.

"Amido" refers to a group wherein an $NR^w$ or $NR^w_2$ is linked through the nitrogen atom to an acyl group as in $NR^w_2$—C(O)—$R^{w'}$, or where an $NR^w$ is next to an acyl group as in —$NR^w$—C(O)$R^{w'}$, wherein each $R^w$ independently includes —H, alkyl, aryl, aralkyl, and heterocycloalkyl and each $R^{w'}$ independently includes alkyl, aryl, aralkyl, and heterocycloalkyl.

"Amino" refers to —$NR^xR^x$ wherein each $R^x$ is independently selected from hydrogen, alkyl, aryl, aralkyl and heterocycloalkyl, all except H are optionally substituted, or wherein both $R^x$ together form a cyclic ring system.

"Aminoalkyl" refers to the group $NR^t_2$-alk- wherein "alk" is an alkylene group and $R^t$ is selected from —H, alkyl, aryl, aralkyl, and heterocycloalkyl.

"Aminocarboxamidoalkyl" refers to the group $NR^y_2$—C(O)—N($R^y$)-alk- wherein each $R^y$ is independently an alkyl group or H and "alk" is an alkylene group. "Lower aminocarboxamidoalkyl-" refers to such groups wherein "alk" is lower alkylene.

"Animal" includes birds and mammals, in one embodiment a mammal, including a dog, cat, cow, horse, goat, sheep, pig or human. In one embodiment the animal is a human. In another embodiment the animal is a male. In another embodiment the animal is a female.

"Aralkyl" refers to an alkylene group substituted with an aryl group. Suitable aralkyl groups include benzyl, picolyl, and the like, and may be optionally substituted.

"Aralkyloxyalkyl-" refers to the group aryl-alk-O-alk- wherein "alk" is an alkylene group. "Lower aralkyloxyalkyl-" refers to such groups where the alkylene groups are lower alkylene.

"Aroyl" or "arylketyl" or "arketyl-" refers to the group aryl-C(O)—.

"Aryl" refers to aromatic groups which have 5-17 ring atoms and at least one ring having a conjugated pi electron system and includes carbocyclic aryl, heterocyclic aryl (heteroaryl), monocyclic aryl (e.g., phenyl), bicylic aryl (e.g., naphthyl) and biaryl groups (e.g., biphenyl), all of which may be optionally substituted. "Carbocyclic monoaryl" refers to an aryl group that is both carbocyclic and monocyclic (e.g., phenyl). "Heterocyclic monoaryl" or "monocyclic heteroaryl" refers to an aryl group that is both heterocyclic and monocyclic (e.g., pyridyl). "Carbocyclic bicyclic aryl" refers to an aryl group that is both carbocyclic and bicyclic (e.g., naphthyl). "Heterocyclic bicylic aryl" or "bicyclic heteroaryl" refers to an aryl group that is both heterocyclic and bicyclic (e.g., benzofuranyl).

"Arylamino" refers to the group aryl-NH—

"Arylalketyl" or "aralketyl" refers to aryl-alk-C(O)— wherein "alk" is alkylene.

"Aralkylamino" refers to the group —N-alk-aryl wherein "alk" is alkylene.

"Arylene" refers to multivalent aromatic ring systems which have 5-14 atoms and at least one ring having a conjugated pi electron system and includes carbocyclic arylene, heterocyclic arylene and biarylene groups, all of which may be optionally substituted.

"Arylaminoalkyl-" refers to the group aryl-N($R^w$)-alk- wherein "alk" is an alkylene group and $R^w$ is —H, alkyl, aryl, aralkyl, or heterocycloalkyl. In "lower arylaminoalkyl-", the alkylene group is lower alkylene.

"Aryloxy" refers to aryl-O—.

"Aryloxyalkyl-" refers to an alkyl group substituted with an aryloxy group.

"Aryloxycarbonyl" refers to the group aryl-O—C(O)—

"Aryloxycarbonyloxy-" refers to aryl-O—C(O)—O—.

"Atherosclerosis" refers to a condition characterized by irregularly distributed lipid deposits in the intima of large and medium-sized arteries wherein such deposits provoke fibrosis and calcification. Atherosclerosis raises the risk of angina, stroke, heart attack, or other cardiac or cardiovascular conditions.

"Benzoxy" or "benzyl-oxy" refers to the group benzyl-O—.

"Biaryl" represents an aryl group substituted with a second aryl group, e.g., biphenyl, each aryl being further optionally substituted.

"Bicyclic aryl" refers to bicyclic ring system composed of two fused rings. Bicyclic aryls contain from 8 to 17 ring atoms. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings.

"Binding" means the specific association of the compound of interest to the target of interest, e.g., a receptor.

"$C_{2-6}$-perfluoroalkyl" refers to a 2 to 6 carbon alkyl group where all of the carbon atoms are exhaustively substituted with fluorine. Non limiting examples include trifluoromethyl, pentafluoroethyl, heptafluoropropyl, pentafluorocyclopropyl, and the like.

"$C_{4-8}$-cycloalkenyl" refers to a non-aromatic, carbocyclic group having 4 to 8 carbon atoms and containing at least one double bond.

"$C_{3-8}$-cycloalkyloxy" refers to —O—$C_{3-8}$-cycloalkyl where $C_{3-8}$-cycloalkyl is an aliphatic carbocyclic group having 3 to 8 carbon atoms "$C_{3-8}$-cycloalkylthio" refers to —S—$C_{3-8}$-cycloalkyl where $C_{3-8}$-cycloalkyl is a 3 to 8 aliphatic carbocyclic group having 3 to 8 carbon atoms "-Carboxylamido" or "carboxamido" refer to $NR^w_2$—C(O)—$R^{w'}$, wherein each $R^w$ and $R^{w'}$ include —H, alkyl, aryl, aralkyl, and heterocycloalkyl.

"Carboxamidoalkylaryl" refers to $NR^w_2$—C(O)-alk-aryl-, where $R^w$ includes H, alkyl, aryl, aralkyl, and heterocycloalkyl.

"Carboxamidoaryl" refers to $NR^w$—C(O)-aryl- wherein "alk" is alkylene and $R^w$ include H, alkyl, aryl, aralkyl, and heterocycloalkyl.

"Carbocyclic aryl" groups are groups which have 6-14 ring atoms wherein the ring atoms on the aromatic ring are carbon atoms. Carbocyclic aryl groups include monocyclic carbocyclic aryl groups and polycyclic or fused compounds such as optionally substituted naphthyl groups.

"Carboxy esters" refers to —C(O)$OR^z$ where $R^z$ is alkyl, aryl, aralkyl, cyclic alkyl, or heterocycloalkyl, each optionally substituted.

"Carboxyl" refers to —C(O)OH.

"Cyano" refers to —C≡N.

"Cyclic alkyl" or "cycloalkyl" refers to alkyl groups that are cyclic of 3 to 10 carbon atoms, and, in one aspect, are 3 to 6 carbon atoms. The cycloalkyl groups include fused cyclic, bridged cyclic and spirocyclic groups. Examples of cyclic alkyl groups include but are not limited to cyclopropyl, cyclobutyl, cyclopentyl, cyclohexyl, cycloheptyl, decalin, bicycle[3.1.1]heptane, bycyclo[2.2.1]heptane, bycyclo[2.2.2]octane, bicycle[3.2.2]nonane, spiro[2.5]octane, spiro[3.5]nonane, adamantyl and the like. Such groups may be substituted.

"Cycloalkenylalkyl-" refers to the group cycloalkenylalkyl-.

"Cycloalkylalkyl-" refers to the group cycloalkyl-alkyl-.

"Cycloalkylaryl-" or "cycloalkaryl-" refers to the group cycloalkyl-aryl-.

"Cycloalkyloxy-" refers to the group cycloalkyl-O—.

"Cycloalkylalkoxy-" refers to the group cycloalkyl-alkyl-O—.

"Cycloalkylalkoxyaryl-" refers to the group cycloalkyl-alkyl-O-aryl.

"Co-crystal" as used herein means a crystalline material comprised of two or more unique solids at room temperature that are H-bonded.

"Coronary heart disease" or "coronary disease" refers to an imbalance between myocardial functional requirements and the capacity of the coronary vessels to supply sufficient blood flow. It is a form of myocardial ischemia (insufficient blood supply to the heart muscle) caused by a decreased capacity of the coronary vessels.

"Diabetes" refers to a heterogeneous group of disorders that share glucose intolerance in common. It refers to disorders in which carbohydrate utilization is reduced and that of lipid and protein enhanced; and may be characterized by hyperglycemia, glycosuria, ketoacidosis, neuropathy or nephropathy, increased hepatic glucose production, insulin resistance in various tissues, insufficient insulin secretion and enhanced or poorly controlled glucagon secretion from the pancreas.

The phrase "optionally substituted" can be interchangeably used with the phrase "substituted or unsubstituted" throughout this application.

Several pathogenic processes are involved in the development of diabetes. These range from autoimmune destruction of the beta-cells of the pancreas with consequent insulin deficiency to abnormalities that result in resistance to insulin action. The basis of the abnormalities in carbohydrate, fat, and protein metabolism in diabetes is deficient action of insulin on target tissues. Deficient insulin action results from inadequate insulin secretion and/or diminished tissue responses to insulin at one or more points in the complex pathways of hormone action. Impairment of insulin secretion and defects in insulin action frequently coexist in the same patient.

Symptoms of marked hyperglycemia include polyuria, polydipsia, weight loss, sometimes with polyphagia, and blurred vision. The vast majority of cases of diabetes fall into two broad etiopathogenetic categories. In one category, type 1 diabetes, the cause is an absolute deficiency of insulin secretion. Individuals at increased risk of developing this type of diabetes can often be identified by serological evidence of an autoimmune pathologic process occurring in the pancreatic islets and by genetic markers. In the other, much more prevalent category, type 2 diabetes, the cause is a combination of resistance to insulin action and an inadequate compensatory insulin secretory response. In the latter category, a degree of hyperglycemia sufficient to cause pathologic and functional changes in various target tissues, but without clinical symptoms, may be present for a long period of time before diabetes is detected. During this asymptomatic period, it is possible to demonstrate an abnormality in carbohydrate metabolism by measurement of plasma glucose in the fasting state or after a challenge with an oral glucose load.

Criteria for the diagnosis of diabetes include:
1. Symptoms of diabetes plus casual plasma glucose concentration 200 mg/dl (11.1 mmol/l). Casual is defined as any time of day without regard to time since last meal. The classic symptoms of diabetes include polyuria, polydipsia, and unexplained weight loss; or 2. FPG 126 mg/dl (7.0 mmol/l). Fasting is defined as no caloric intake for at least 8 h; or 3.2-h postload glucose 200 mg/dl (11.1 mmol/l) during an OGTT. The test should be performed as described by WHO, using a glucose load containing the equivalent of 75 g anhydrous glucose dissolved in water.

Etiologic classification of diabetes mellitus, as embodiments, are as follows:
I. Type 1 diabetes (ß-cell destruction, usually leading to absolute insulin deficiency)
  A. Immune mediated
  B. Idiopathic
II. Type 2 diabetes (may range from predominantly insulin resistance with relative insulin deficiency to a predominantly secretory defect with insulin resistance)
III. Other specific types
  A. Genetic defects of ß-cell function
    1. Chromosome 12, HNF-1α (MODY3)
    2. Chromosome 7, glucokinase (MODY2)
    3. Chromosome 20, HNF-4α (MODY1)
    4. Chromosome 13, insulin promoter factor-1 (IPF-1; MODY4)
    5. Chromosome 17, HNF-1ß (MODY5)
    6. Chromosome 2, NeuroD1 (MODY6)
    7. Mitochondrial DNA
    8. Others
  B. Genetic defects in insulin action
    1. Type A insulin resistance
    2. Leprechaunism
    3. Rabson-Mendenhall syndrome
    4. Lipoatrophic diabetes
    5. Others
  C. Diseases of the exocrine pancreas
    1. Pancreatitis
    2. Trauma/pancreatectomy
    3. Neoplasia
    4. Cystic fibrosis
    5. Hemochromatosis
    6. Fibrocalculous pancreatopathy
    7. Others
  D. Endocrinopathies
    1. Acromegaly
    2. Cushing's syndrome
    3. Glucagonoma
    4. Pheochromocytoma
    5. Hyperthyroidism
    6. Somatostatinoma
    7. Aldosteronoma
    8. Others
  E. Drug- or chemical-induced
    1. Vacor
    2. Pentamidine
    3. Nicotinic acid
    4. Glucocorticoids
    5. Thyroid hormone
    6. Diazoxide
    7. ß-adrenergic agonists
    8. Thiazides
    9. Dilantin
    10. α-Interferon
    11. Others
  F. Infections
    1. Congenital rubella
    2. Cytomegalovirus
    3. Others G. Uncommon forms of immune-mediated diabetes
 1. "Stiff-man" syndrome
 2. Anti-insulin receptor antibodies
 3. Others
H. Other genetic syndromes sometimes associated with diabetes
 1. Down's syndrome
 2. Klinefelter's syndrome
 3. Turner's syndrome
 4. Wolfram's syndrome
 5. Friedreich's ataxia
 6. Huntington's chorea
 7. Laurence-Moon-Biedl syndrome
 8. Myotonic dystrophy
 9. Porphyria
 10. Prader-Willi syndrome
 11. Others
IV. Gestational diabetes mellitus (GDM)

"Energy expenditure" means basal or resting metabolic rate as defined by Schoeller et al., J Appl Physiol.; 53(4): 955-9 (1982). Increases in the resting metabolic rate can also be measured using increases in $O_2$ consumption and/or $CO_2$ efflux and/or increases in organ or body temperature.

"Enhanced oral bioavailability" refers to an increase of at least 50% of the absorption of the dose of the parent drug, unless otherwise specified. In an additional aspect the increase in oral bioavailability of the prodrug (compared to the parent drug) is at least 100% (at least a doubling of the absorption). Measurement of oral bioavailability usually refers to measurements of the prodrug, drug, or drug metabolite in blood, plasma, tissues, or urine following oral administration compared to measurements following systemic administration of the compound administered orally.

"Enhancing" refers to increasing or improving a specific property.

"Haloalkyl" refers to an alkyl group substituted with one or more halo/halogens.

"Haloaryl" refers to an aryl group substituted with one or more halo/halogens.

"Halogen" or "halo" refers to —F, —Cl, —Br and —I.

"Heteroalicyclic" refers to an alicyclic group or compound having 1 to 4 heteroatoms selected from nitrogen, sulfur, phosphorus and oxygen.

"Heteroarylalkyl" refers to an alkylene group substituted with a heteroaryl group.

"Heteroarylene" refers to a divalent, aromatic, heterocyclic ring containing 5-14 ring atoms wherein 1 to 4 heteroatoms in the aromatic ring are ring atoms and the remainder of the ring atoms being carbon atoms.

Alternative: "Heteroarylene" refers to a divalent heterocyclic aryl or heteroaryl group.

"Heterocyclic" or "heterocyclyl" refer to cyclic groups of 3 to 10 atoms or cyclic groups of 3 to 6 atoms. These groups contain at least one heteroatom, and in some aspects contain 1 to 3 heteroatoms. Suitable heteroatoms include oxygen, sulfur, and nitrogen. Heterocyclic groups may be attached through a nitrogen or carbon atom in the ring. Heterocyclic and heterocyclyl cyclic groups include, e.g., heterocyclic alkyl or heterocycloalkyl groups. The heterocyclic alkyl groups include unsaturated cyclic, fused cyclic and spirocyclic groups. Suitable heterocyclic groups include pyrrolidinyl, morpholino, morpholinoethyl, and pyridyl.

"Heterocyclic aryl" or "heteroaryl groups" are groups which have 5-14 ring atoms wherein 1 to 4 heteroatoms are ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, benzimidazolyl, benzofuranyl, benzothiophenyl, and the like, all optionally substituted.

"Heteroaroyl-" or "heteroarylketyl-" or "heteroarketyl-" refers to heteroaryl-C(O)—.

"Heteroarylalketyl-" or "heteroaralketyl-" refers to heteroaryl-alkyl-C(O)—.

"Hydroxyalkyl" refers to an alkyl group substituted with one —OH.

"Hypercholesterolemia" refers to presence of an abnormally large amount of cholesterol in the cells and plasma of the circulating blood.

"Hyperinsulinemia" refers to a patient with a fasting serum insulin concentration of at least 12 µU/mL.

"Hyperlipidemia" or "lipemia" refers to the presence of an abnormally large amount of lipids in the circulating blood.

"Insulin resistance" is defined clinically as the impaired ability of a known quantity of exogenous or endogenous insulin to increase whole body glucose uptake and utilization.

"Impaired glucose tolerance (IGT)" refers to a condition known to precede the development of overt Type 2 diabetes. It is characterized by abnormal blood glucose excursions following a meal. The current criteria for the diagnosis of IGT are based on 2-h plasma glucose levels post a 75 g oral glucose test (144-199 mg/dL). Although variable from population to population studied, IGT progresses to full-blown NIDDM at a rate of 1.5 to 7.3% per year, with a mean of 3-4% per year. Individuals with IGT are believed to have a 6 to 10-fold increased risk in developing Type 2 diabetes. IGT is an independent risk factor for the development of cardiovascular disease.

"Increased or enhanced liver specificity" refers to an increase in the liver specificity ratio in animals treated with a compound of the present invention and a control compound.

"Lower" referred to herein in connection with organic radicals or compounds respectively defines such radicals or compounds as containing up to and including 10 carbon atoms. One aspect of this invention provides organic radicals or compounds as containing up to and including 6 carbon atoms. Yet another aspect of the invention provides organic radicals or compounds that contain one to four carbon atoms. Such groups may be straight chain, branched, or cyclic.

"Liver" refers to the liver organ.

"Liver specificity" refers to the ratio:

$$\frac{[\text{drug or a drug metabolite in liver tissue}]}{[\text{drug or a drug metabolite in blood or another tissue}]}$$

as measured in animals treated with the drug or a prodrug. The ratio can be determined by measuring tissue levels at a specific time or may represent an AUC based on values measured at three or more time points.

"Metabolic disease" includes diseases and conditions such as obesity, diabetes and lipid disorders such as hypercholesterolemia, hyperlipidemia, hypertriglyceridemia as well as disorders that are associated with abnormal levels of lipoproteins, lipids, carbohydrates and insulin such as metabolic syndrome X, diabetes, impaired glucose tolerance, atherosclerosis, coronary heart disease, cardiovascular disease.

"Metabolic Syndrome" or "Metabolic Syndrome X" refers to a condition identified by the presence of three or more of these components:
Central obesity as measured by waist circumference:
Men: Greater than 40 inches
Women: Greater than 35 inches
Fasting blood triglycerides greater than or equal to 150 mg/dL
Blood HDL cholesterol:
Men: Less than 40 mg/dL
Women: Less than 50 mg/dL
Blood pressure greater than or equal to 130/85 mmHg
Fasting blood glucose greater than or equal to 110 mg/dL
"Nitro" refers to —$NO_2$.

"Obesity" refers to the condition of being obese. Being obese is defined as a BMI of 30.0 or greater; and extreme obesity is defined at a BMI of 40 or greater. "Overweight" is defined as a body mass index of 25.0 to 29.9.

"Oxo" refers to =O in an alkyl or heterocycloalkyl group.

"Perhalo" refers to groups wherein every C—H bond has been replaced with a C-halo bond on an aliphatic or aryl group. Non-linking examples of perhaloalkyl groups include —$CF_3$ and —$CFCl_2$.

"Pharmaceutically acceptable salt" includes salts of compounds of the invention derived from the combination of a compound of this invention and an organic or inorganic acid or base. Suitable acids include acetic acid, adipic acid, benzenesulfonic acid, (+)-7,7-dimethyl-2-oxobicyclo[2.2.1] heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis [3-hydroxy-2-naphthalenecarboxylic acid], phosphoric acid, polygalacturonic acid, stearic acid, succinic acid, sulfuric acid, sulfosalicylic acid, tannic acid, tartaric acid, terphthalic acid, and p-toluenesulfonic acid.

"Patient" means an animal.

"Phenoxy" or "phenyl-oxy" refers to the group phenyl-O—.

"Preventing" includes a slowing of the progress or development of a disease before onset or precluding onset of a disease.

"Prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, —NHR, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of the invention, fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, and/or pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

"Significant" or "statistically significant" means a result (i.e. experimental assay result) where the p-value is ≤0.05 (i.e. the chance of a type I error is less than 5%) as determined by an art-accepted measure of statistical significance appropriate to the experimental design.

"Substituted" or "optionally substituted" includes groups substituted by one to six substituents, independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halo, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, sulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, and lower arylalkyloxyalkyl.

"Substituted aryl" and "substituted heteroaryl" refers to aryl and heteroaryl groups substituted with 1-3 substituents. These substituents are selected from the group consisting of lower alkyl, lower alkoxy, lower perhaloalkyl, halo, hydroxy, and amino.

"Sulphon(yl)amido" or "sulfon(yl)amido" refer to $NR^w{}_2$—S(=O)$_2$— and $R^w$S(=O)$_2$—$NR^w$—, wherein each $R^w$ independedly include alkyl, aryl, aralkyl, and heterocycloalkyl.

"Sulfonamidoalkylaryl" and "sulfonamidoaryl" refers to an aryl-alk-$NR^w$—S(=O)$_2$—, and ar-$NR^w$—S(=O)$_2$—, respectively where "ar" is aryl, "alk" is alkylene, $R^w$ includes —H, alkyl, aryl, aralkyl, and heterocycloalkyl.

"Sulphonate" or "sulfonate" refers to —$SO_2OR^w$, where $R^w$ is —H, alkyl, aryl, aralkyl, or heterocycloalkyl.

"Sulfonic acid containing compounds" or "sulphonic acid containing compounds" refer to compounds containing —$SO_3H$ or —$SO_3^-$.

"Sulphonyl" or "sulfonyl" refers to —$SO_2R^w$, where $R^w$ is alkyl, aryl, aralkyl, or heterocycloalkyl.

"Therapeutically effective amount" means an amount of a compound or a combination of compounds that ameliorates, attenuates or eliminates one or more of the symptoms of a particular disease or condition or prevents, modifies, or delays the onset of one or more of the symptoms of a particular disease or condition.

"Treating" or "treatment" of a disease includes a slowing of the progress or development of a disease after onset or actually reversing some or all of the disease affects. Treatment also includes palliative treatment.

"Type 1 diabetes" (formerly known as "childhood," "juvenile," "insulin-dependent" diabetes [IDDM]) is a form of diabetes characterized by an absolute deficiency of insulin secretion. Individuals at increased risk of developing this type of diabetes can often be identified by serological evidence of an autoimmune pathologic process occurring in the pancreatic islets and by genetic markers. Type 1 diabetes may be caused by immune mediated beta-cell destruction, usually leading to absolute insulin deficiency or may be idiopathic, having no known etiologies.

"Type 2 diabetes" refers to a heterogeneous disorder characterized by impaired insulin secretion by the pancreas and insulin resistance in tissues such as the liver, muscle and adipose tissue. The manifestations of the disease include one or more of the following: impaired glucose tolerance, fasting hyperglycemia, glycosuria, decreased levels of insulin, increased levels of glucagon, increased hepatic glucose output, reduced hepatic glucose uptake and glycogen storage, reduced whole body glucose uptake and utilization, dyslipidemia, fatty liver, ketoacidosis, microvascular diseases such as retinopathy, nephropathy and neuropathy, and macrovascular diseases such as coronary heart disease.

"Phosphonate, phosphonic acid monoester and phosphinate prodrug" refers to compounds that break down chemically or enzymatically to a phosphonic acid or phosphinc acid group in vivo. As employed herein the term includes, but is not limited to, the following groups and combinations of these groups:

Acyloxyalkyl esters which are well described in the literature (Farquhar et al., J. Pharm. Sci., 72: 324-325 (1983)).

Other acyloxyalkyl esters are possible in which a cyclic alkyl ring is formed. These esters have been shown to generate phosphorus-containing nucleotides inside cells through a postulated sequence of reactions beginning with deesterification and followed by a series of elimination reactions (e.g., Freed et al., Biochem. Pharm., 38: 3193-3198 (1989)).

Another class of these double esters known as alkyloxycarbonyloxymethyl esters, as shown in formula A, where $R^a$ is alkoxy, aryloxy, alkylthio, arylthio, alkylamino, or arylamino; each $R^c$ is independently —H, alkyl, aryl, alkylaryl, or heterocycloalkyl have been studied in the area of β-lactam antibiotics (Nishimura et al., J. Antibiotics, 40(1): 81-90 (1987); for a review see Ferres, H., Drugs of Today, 19: 499 (1983)). More recently Cathy, M. S., et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

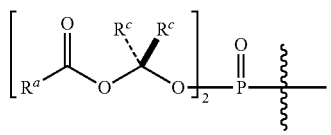

Formula A1

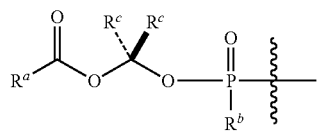

Formula A2 wherein $R^a$ and $R^c$ are independently H, alkyl, aryl, alkylaryl, and alicyclic; (see WO 90/08155; WO 90/10636) and $R^b$, for e.g., is selected from —OH, —CH$_3$, —H, —O—CH$_3$ or monoester prodrug moiety.

Other acyloxyalkyl esters are possible in which a cyclic alkyl ring is formed such as shown in formula B. These esters have been shown to generate phosphorus-containing nucleotides inside cells through a postulated sequence of reactions beginning with deesterification and followed by a series of elimination reactions (e.g., Freed et al., Biochem. Pharm., 38: 3193-3198 (1989)).

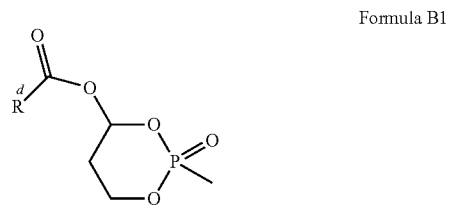

Formula B1

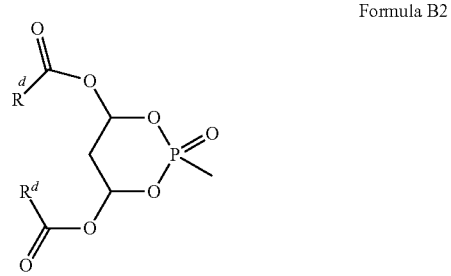

Formula B2 wherein $R^d$ is —H, alkyl, aryl, alkylaryl, alkoxy, aryloxy, alkylthio, arylthio, alkylamino, arylamino, or cycloalkyl.

Aryl esters have also been used as phosphonate prodrugs (e.g., DeLambert et al., J. Med. Chem. 37(7): 498-511 (1994); Serafinowska et al., J. Med. Chem. 38(8): 1372-9 (1995). Phenyl as well as mono and poly-substituted phenyl proesters have generated the parent phosphonic acid in studies conducted in animals and in man (Formula C). Another approach has been described where $R^e$ is a carboxylic ester ortho to the phosphate (Khamnci et al., J. Med. Chem. 39: 4109-15 (1996)).

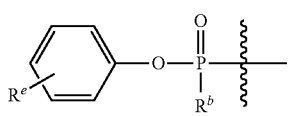

Formula C1

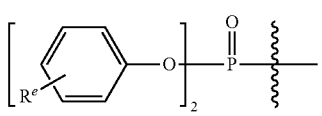

Formula C2 wherein $R^e$ is —H, alkyl, aryl, alkylaryl, alkoxy, acyloxy, halogen, amino, alkoxycarbonyl, hydroxy, cyano, or heterocycloalkyl and $R^b$ is selected, for e.g., from —OH, —CH$_3$, —H, —O—CH$_3$ or monoester prodrug moiety.

Benzyl esters have also been reported to generate the parent phosphonic acid. In some cases, using substituents at the para-position can accelerate the hydrolysis. Benzyl analogs with 4-acyloxy or 4-alkyloxy group [Formula D, X═—H, OR or O(CO)R or O(CO)OR] can generate the 4-hydroxy compound more readily through the action of enzymes, e.g., oxidases, esterases, etc. Examples of this class of prodrugs are described in Mitchell et al., J. Chem. Soc. Perkin Trans. I 2345 (1992); WO 91/19721.

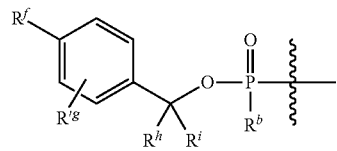

Formula D1

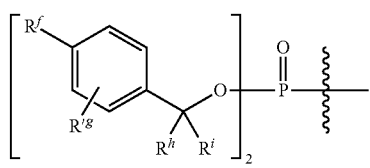

Formula D2 wherein $R^f$ and $R^g$ are independently —H, alkyl, aryl, alkylaryl, alkoxy, acyloxy, hydroxy, cyano, nitro, perhaloalkyl, halo, or alkyloxycarbonyl; $R^b$ is selected, for e.g., from —OH, —CH$_3$, —H, —O—CH$_3$ or monoester prodrug moiety, as described therein.

$R^h$ and $R^i$ are independently —H, alkyl, aryl, alkylaryl, halogen, or cyclic alkyl.

Thio-containing phosphonate proesters may also be useful in the delivery of drugs to hepatocytes. These proesters contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., Antiviral Res. 22: 155-174 (1993)). Thioesters will also generate free thiolates after esterase-mediated hydrolysis Benzaria, et al., J. Med. Chem., 39(25): 4958-65 (1996)). Cyclic analogs are also possible and were shown to liberate phosphonate in isolated rat hepatocytes. The cyclic disulfide shown below has not been previously described and is novel.

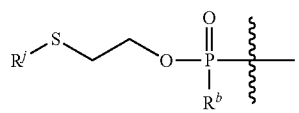

Formula E1

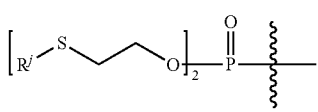

Formula E1

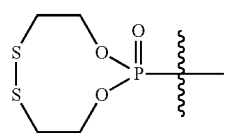

Formula E3 wherein $R^j$ is alkylcarbonyl, alkoxycarbonyl, arylcarbonyl, aryloxycarbonyl, or alkylthio and $R^b$ is selected, for e.g., from —OH, —CH$_3$, —H, —O—CH$_3$ or monoester prodrug moiety.

Other examples of suitable prodrugs include proester classes exemplified by Biller and Magnin (U.S. Pat. No. 5,157,027); Serafinowska et al., J. Med. Chem. 38(8):

1372-9 (1995); Starrett et al., J. Med. Chem, 37: 1857 (1994); Martin et al. J. Pharm. Sci. 76: 180 (1987); Alexander et al., Collect. Czech. Chem. Commun, 59: 1853 (1994); and EP 0 632 048 A1. Some of the structural classes described are optionally substituted, including fused lactones attached at the omega position (formulae E4 and E5) and optionally substituted 2-oxo-1,3-dioxolenes attached through a methylene to the phosphorus oxygen (formula E6) such as:

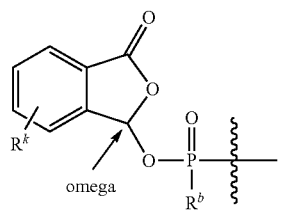

Formula E4a

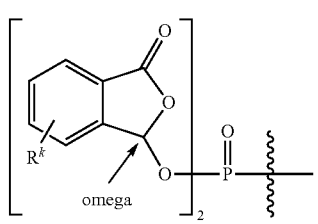

Formula E4b

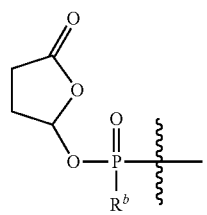

Formula E5a

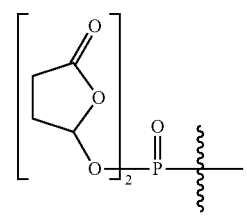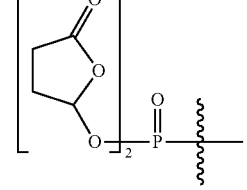

Formula E5b

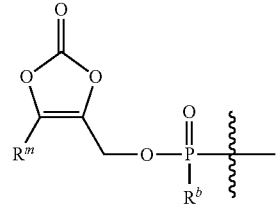

Formula E6a

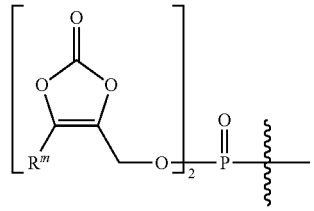

Formula E6b wherein $R^m$ is —H, alkyl, cycloalkyl, or heterocycloalkyl; $R^b$ is selected, for e.g., from —OH, —CH$_3$, —H, —O—CH$_3$ or monoester prodrug moiety and $R^k$ is —H, alkyl, aryl, alkylaryl, cyano, alkoxy, acyloxy, halogen, amino, heterocycloalkyl, or alkoxycarbonyl.

The prodrugs of Formula E6 are an example of "optionally substituted heterocycloalkyl where the cyclic moiety contains a carbonate or thiocarbonate."

Propyl phosphonate proesters (ethyl ester phosphonate proesters) can also be used to deliver drugs into hepatocytes. These proesters may contain a hydroxyl and hydroxyl group derivatives at the 3-position of the propyl group as shown in formula F1. The $R^n$ and $R^p$ groups can form a cyclic ring system as shown in formula F2. One or more of the oxygens of the phosphonate can be esterified.

Formula F1a

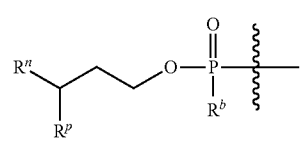

Formula F1b

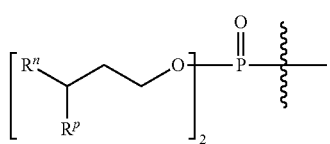

Formula F2a

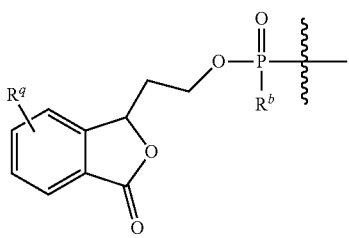

Formula F2b

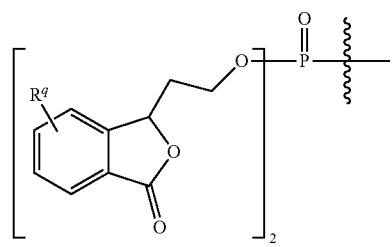

wherein $R^n$ is alkyl, aryl, or heteroaryl:

$R^p$ is alkylcarbonyloxy, or alkyloxycarbonyloxy;

$R^b$ is selected, for e.g., from —OH, —CH$_3$, —H, —O—CH$_3$ or monoester prodrug moiety; and $R^q$ is alkyl, aryl, heteroaryl, alkoxy, alkylamino, alkylthio, halogen, hydrogen, hydroxy, acyloxy, or amino.

Phosphoramidate derivatives have been explored as phosphate prodrugs (e.g., McGuigan et al., J. Med. Chem., 42: 393 (1999) and references cited therein) as shown in Formula G and H, wherein $R^r$, for example, is lower alkyl, lower aryl, lower aralkyl, and as described therein.

Formula G1

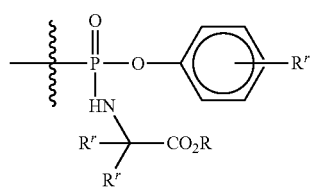

Formula G2

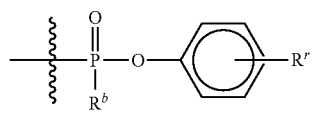

Formula H1

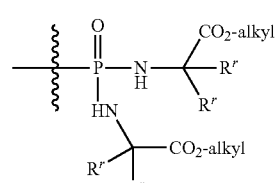

Formula H2

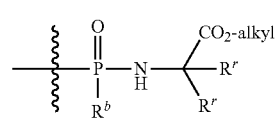

Cyclic phosphoramidates have also been studied as phosphonate prodrugs because of their speculated higher stability compared to non-cyclic phosphoramidates (e.g., Starrett et al., J. Med. Chem., 37: 1857 (1994)).

Another type of phosphoramidate prodrug was reported as the combination of S-acyl-2-thioethyl ester and phosphoramidate (Egron et al., Nucleosides & Nucleotides, 18, 981 (1999)) as shown in Formula J wherein $R^c$ is alkoxy, aryloxy, alkylthio, arylthio, alkylamino, or arylamino and $R^a$ is —H, alkyl, aryl, alkylaryl, or heterocycloalkyl:

Formula J

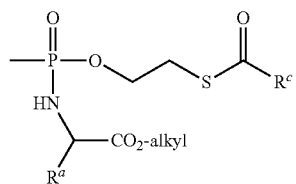

Other prodrugs are possible based on literature reports such as substituted ethyls for example, bis(trichloroethyl) esters as disclosed by McGuigan, et al., Bioorg Med. Chem. Lett., 3:1207-1210 (1993), and the phenyl and benzyl combined nucleotide esters reported by Meier, C. et al., Bioorg. Med. Chem. Lett. 7:99-104 (1997).

"Sulfonate prodrugs", are compounds that break down chemically or enzymatically to a sulfonic acid group in vivo. Examples of sulfonate prodrugs include aryl esters such as nitrophenylsulfonyl esters and have been demonstrated to generate the corresponding sulfonic acids under physiological conditions (Yan and Muller, J. Med. Chem 47, 1031 (2004)). An example of a nitrophenylsulfonyl ester prodrug is:

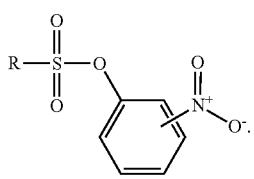

The structure of formula L has a plane of symmetry running through the phosphorus-oxygen double bond when both $R^{60}$s are the same, V=W, and V and W (defined herein) are either both pointing up or both pointing down. The same is true of structures where both —$NR^{60}$s are replaced with —O—.

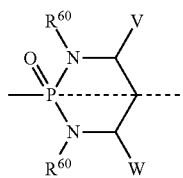

Formula L

The term "cyclic phosphonate ester of 1,3-propane diol", "cyclic phosphonate diester of 1,3-propane diol", "2-oxo-$2\lambda^5$-[1,3,2]-dioxaphosphonane", "2-oxo-[1,3,2]-dioxaphosphonane", "dioxaphosphonane" refers to the following:

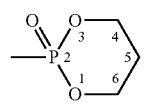

Formula M

The phrase "together V and Z are connected via an additional 3-5 atoms to form a cyclic group containing 5-7 atoms, optionally containing 1 heteroatom, substituted with hydroxy, acyloxy, alkylthiocarbonyloxy, alkoxycarbonyloxy, or aryloxycarbonyloxy attached to a carbon atom that is three atoms from both Y groups attached to the phosphorus" includes the following:

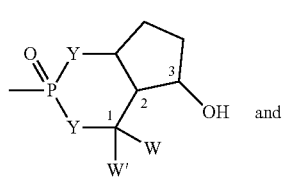

Formula N1 and

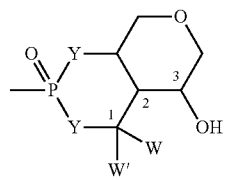

Formula N2

The structure shown above (left) has an additional 3 carbon atoms that forms a five member cyclic group. Such cyclic groups must possess the listed substitution to be oxidized.

The phrase "together V and Z are connected via an additional 3-5 atoms to form a cyclic group, optionally containing one heteroatom, that is fused to an aryl group attached at the beta and gamma position to the G attached to the phosphorus" includes the following:

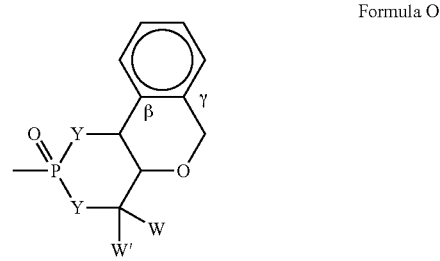

Formula O

The phrase "together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus" includes the following:

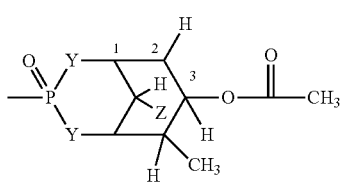

Formula P

The structure above has an acyloxy substituent that is three carbon atoms from a Y, and an optional substituent, —$CH_3$, on the new 6-membered ring. There has to be at least one hydrogen at each of the following positions: the carbon attached to Z; both carbons alpha to the carbon labeled "3"; and the carbon attached to "OC(O)$CH_3$" above.

The phrase "together W and W' are connected via an additional 2-5 atoms to form a cyclic group, optionally containing 0-2 heteroatoms, and V must be aryl, substituted aryl, heteroaryl, or substituted heteroaryl" includes the following:

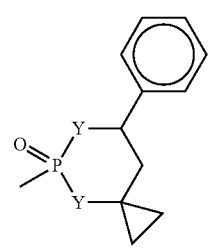

Formula Q

The structure above has V=aryl, and a spiro-fused cyclopropyl group for W and W'.

The term "cyclic phosphon(amid)ate" refers to:

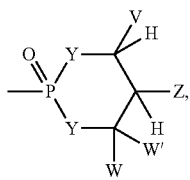

Formula R wherein Y is independently —O— or —NR$^{60}$—. The carbon attached to V must have a C—H bond. The carbon attached to Z must also have a C—H bond.

For cylic 1,3-propanyl phosphonate prodrugs of compounds of the present invention the term "cis" stereochemistry refers to the spatial relationship of the V group and the carbon attached to the phosphorus atom on the six-membered ring. The formula below shows a cis stereochemistry.

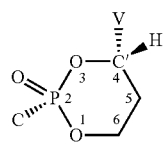

Formula S

The term "trans" stereochemistry for the same moiety refers to the spatial relationship of the V group and the carbon, attached to the phosphorus atom, on the six-membered ring. The formula below shows a trans-stereochemistry.

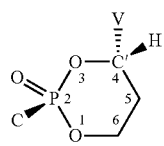

Formula T

The formula below shows another trans-stereochemistry of the same moiety.

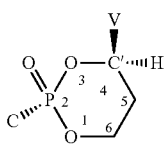

Formula U

The terms "S-configuration", "S-isomer" and "S-prodrug" of the same refers to the absolute configuration S of carbon C'. The formula below shows the S-stereochemistry.

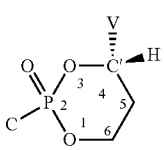

Formula W

The terms "R-configuration", "R-isomer" and "R-prodrug" of the same refers to the absolute configuration R of carbon C'. The formula below shows the R-stereochemistry.

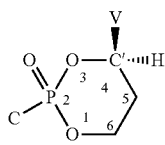

Formula Y

The term "percent enantiomeric excess (% ee)" refers to optical purity. It is obtained by using the following formula:

$$\frac{[R]-[S]}{[R]+[S]} \times 100 = \% R - \% S$$

where [R] is the amount of the R isomer and [S] is the amount of the S isomer. This formula provides the % ee when R is the dominant isomer.

The term "enantioenriched" or "enantiomerically enriched" refers to a sample of a chiral compound that consists of more of one enantiomer than the other. The extent to which a sample is enantiomerically enriched is quantitated by the enantiomeric ratio or the enantiomeric excess.

Compounds and Uses Thereof

One aspect of the present invention provides compounds of general formula (I)

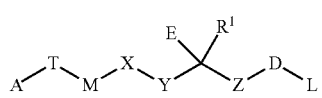

(I)

wherein:

D is a substituted group selected from carbocyclic aryl, $C_{1-8}$-alkyl carbocyclic aryl, heteroaryl, cycloalkyl or heterocyclyl, wherein said group is substituted with L and, optionally, one or more additional groups;

L is a group selected from hydrogen, carbocyclic aryl, carbocyclic aryloxy-, carbocyclic arylalkoxy-, carbocyclic arylalketyl-, carbocyclic arylketyl-, carbocyclic aryl-N ($R^{12}$)—, heteroaryl, heteroaryloxy-, heteroarylalkoxy, heteroarylketyl, heteroarylalketyl, heteroaryl —N($R^{12}$)—, cycloalkyl, cycloalkylalkyl, cycloalkylalkoxy-, cycloalkyloxy-, cycloalkylketyl-, cycloalkylalketyl-, cycloalkyl-N ($R^{12}$)—, heterocyclyl, heterocyclyloxy-, heterocyclylalkoxy-, heterocyclylketyl-, heterocyclylalketyl-, heterocyclyl-N($R^{12}$)—, alkenyl, cycloakenyl or alkynyl, wherein said group, excluding hydrogen, is optionally substituted;

$R^{12}$ is selected from hydrogen or $C_{1-3}$-alkyl;

Z is a group selected from -isoxazol-3,5-diyl- or —C(O)N($R^2$)—, provided that when Z is —C(O)NH—, M is —NHC(O)—, the connection to X is through the C(O) group and T is $(CH_2)_n$—, then A is not —$CH_2CO_2H$ or —$(CH_2)_q$ tetrazol-5-yl;

$R^2$ is a group selected from hydrogen or $C_{1-8}$-alkyl; or, together, Z and D form a group

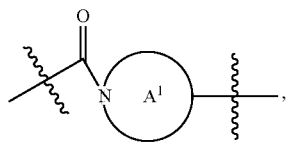

wherein the ring $A^1$ is a 4-8 membered heterocyclic ring, optionally containing an additional heteroatom selected from oxygen, nitrogen or sulfur, wherein said $A^1$ is optionally substituted with a group selected from $C_{1-4}$-alkyl- or $C_{3-5}$-cycloalkyl-;

Y is a group selected from —C(O)—, —O—, —$NR^{26}$—, —S—, —S(O)—, —S(O)$_2$—, —$CR^{26}R^{27}$— or —$CF_2$—;

$R^{26}$ is a group selected from hydrogen or $C_{1-6}$-alkyl, $C_{1-6}$-perfluoroalkyl and fluoro $R^1$ is a group selected from hydrogen, fluoro or $C_{1-8}$-alkyl optionally substituted with fluoro up to perfluoro, or $R^1$ is absent, Y is —$CR^{27}$=, wherein said —$CR^{27}$= is attached by a double bond to the C to which $R^1$ would otherwise be attached if present;

$R^{27}$ is a group selected from hydrogen, $C_{1-6}$-alkyl, hydroxyl or fluoro;

E is a group selected from $C_{1-12}$-alkyl, $C_{2-12}$-alkenyl, $C_{2-12}$-alkynyl, $C_{3-8}$-cycloalkyl, $C_{4-8}$-cycloalkenyl, carbocyclic aryl, t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, or heteroaryl, each optionally substituted;

X is a group selected from phenylene, heterocyclic monoarylene, $C_{5-8}$-cycloalkylene or $C_{5-8}$-cycloalkenylene, each optionally substituted;

M is a group selected from —C(O)$NR^{30}$—, —$NR^{30}$C(O)—, —S(O)$_2NR^{30}$—, —$NR^{30}$S(O)$_2$—, —C(S)$NR^{30}$—, —$NR^{30}$C(S)—, —O— or —S—;

$R^{30}$ is a group independently selected from hydrogen or $C_{1-6}$-alkyl optionally substituted with fluoro up to perfluoro;

T is a group selected from —(CHR$^{30}$)$_n$—, phenylene or five- or six-membered heterocyclic monoarylene, each optionally substituted; wherein when n=0, T is absent and A is connected directly to M;

A is a group selected from —(CHR$^{36}$)$_m$CO$_2$H, —(CHR$^{36}$)$_m$R$^5$, —(CHR$^{36}$)$_m$SO$_3$H, —(CHR$^{36}$)$_m$QSO$_2$R$^{39}$ or —(CHR$^{36}$)$_q$tetrazol-5-yl;

$R^5$ is —P(O)(GR$^{21}$)G'R$^{21}$;

$R^{36}$ is a group selected from hydrogen, $C_{1-6}$-alkyl, hydroxyl, fluoro or —(CH$_2$)$_p$OR$^{38}$;

p is 0 or 1;

n is 0, 1, 2 or 3;

m is 1, 2 or 3;

q is 0, 1, 2 or 3;

wherein n+m is 1, 2 or 3 and n+q is 0, 1, 2 or 3;

$R^{38}$ is a group selected from hydrogen or optionally substituted $C_{1-3}$-alkyl;

$R^{39}$ is a group selected from —OH, —NHOH or —NH$_2$;

Q is a group selected from oxygen or $NR^{43}$;

$R^{43}$ is a group independently selected from $C_{1-6}$-alkyl or hydrogen; and G and G' are each independently selected from —O— or —NR$^v$—;

wherein, when G and G' are both —O—, $R^{21}$ attached to —O— is independently selected from —H, alkyl, optionally substituted aryl, optionally substituted heterocycloalkyl, optionally substituted —CH$_2$-heterocycloakyl wherein the cyclic moiety contains a carbonate or thiocarbonate, optionally substituted -alkylaryl, —C(R$^z$)$_2$OC(O)NR$^z$$_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S—S-alkylhydroxy, and -alkyl-S—S—S-alkylhydroxy; or when G and G' are both —NR$^v$—, then $R^{21}$ attached to —NR$^v$— is independently selected from —H, —[C(R$^z$)$_2$]$_r$—COOR$^y$, —C(R$^x$)$_2$COOR$^y$, —[C(R$^z$)$_2$]$_r$—C(O)SR$^y$, and -cycloalkylene-COOR$^y$; or when G is —O— and G' is NR$^v$, then $R^{21}$ attached to —O— is independently selected from —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR$^z$$_2$, —NR$^z$—C(O)—R$^y$, —C(R$^z$)$_2$—OC(O)R$^y$, —C(R$^z$)$_2$—O—C(O) OR$^y$, —C(R$^z$)$_2$OC(O)SR$^y$, -alkyl-S—C(O)R$^y$, -alkyl-S—S-alkylhydroxy, and -alkyl-S—S—S-alkylhydroxy, and $R^{21}$ attached to —NR$^v$— is independently selected from —H, —[C(R$^z$)$_2$]$_r$—COOR$^y$, —C(R$^x$)$_2$COOR$^y$, —[C(R$^z$)$_2$]$_r$—C(O)SR$^y$, and -cycloalkylene-COOR$^y$, wherein if both $R^{21}$ are alkyl, at least one is higher alkyl; or when G and G' are independently selected from —O— and —NR$^v$—, then $R^{21}$ and $R^{21}$ together form a cyclic group comprising -alkyl-S—S-alkyl-, or $R^{21}$ and $R^{21}$ together are the group

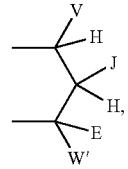

wherein,

V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl; and J is —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH=CR$^z$$_2$)OH, —CH(C≡CR$^z$)OH, —R$^z$, —NR$^z$$_2$, —OCOR$^y$, —OCO$_2$R$^y$, —SCOR$^y$, —SCO$_2$R$^y$, —NHCOR$^z$, —NHCO$_2$R$^y$, —CH$_2$NHaryl, —(CH$_2$)$_r$—OR$^z$ or —(CH$_2$)$_r$—SR$^z$; or together V and J are connected via an additional 3-5 atoms to form a cyclic group containing 5-7 atoms, wherein 0-1 atoms are heteroatoms and the remaining atoms are carbon; or together V and W are connected via an additional 3 carbon atoms to form an optionally substituted cyclic group containing 6 carbon atoms or carbon substituted by hydrogen and substituted with one substituent selected from hydroxy, acyloxy, alkoxycarbonyloxy, alkylthiocarbonyloxy or aryloxycarbonyloxy which is attached to one of said carbon atoms that is three atoms from a G attached to the phosphorus; or together J and W are connected via an additional 3-5 atoms to form a cyclic group, wherein 0-1 atoms are heteroatoms and the remaining atoms are carbon or carbon substituted by hydrogen, and V must be aryl, substituted aryl, heteroaryl, or substituted heteroaryl; or together W and W' are connected via an additional 2-5 atoms to form a cyclic group, wherein 0-2 atoms are heteroatoms and the remaining atoms are carbon, where V must be aryl, substituted aryl, heteroaryl, or substituted heteroaryl;

$R^z$ is $R^y$ or —H;

$R^y$ is alkyl, aryl, heterocycloalkyl or aralkyl;

$R^x$ is independently selected from —H or alkyl, or together $R^x$ and $R^x$ form a cycloalkylene group;

$R^v$ is —H, lower alkyl, acyloxyalkyl, alkoxycarbonyloxyalkyl, lower acyl, $C_{1-6}$-perfluoroalkyl or $NH(CR^{43}R^{43})_rCH_3$;

f is 0, 1 or 2;

r is 2 or 3;

wherein,

V, J, W, W' are not all —H, when J is —$R^z$, then at least one of V, W, and W' is not —H, alkyl, aralkyl, or heterocycloalkyl, and when Z is —C(O)NH—, M is —NHC(O)— (where the connection to X is through the C(O) group) and T is $(CH_2)_n$—, then A is not —$CH_2CO_2H$ or —$(CH_2)_q$ tetrazol-5-yl; and pharmaceutically acceptable salts, cocrystals and prodrugs thereof.

In one embodiment, compounds of the invention are able to displace radiolabeled glucagon from the human glucagon receptor by at least 15% at 1000 nM. Preferably, compounds of the invention are able to displace at least 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of radiolabeled glucagon from the human glucagon receptor as described in Example A.

Alternatively, the activities of the compounds of the invention can be described in terms of the concentrations of compounds required for displacement of 50% of the radiolabeled glucagon from the human glucagon receptor (the $IC_{50}$ values) according to the methods of Example A. Preferably, the $IC_{50}$ values for compounds of the subject invention are less than <10,000 nM, 9,000 nM, 8,000 nM, 7,000 nM, 6,000 nM, 5,000 nM, 4,000 nM, 3,000 nM, 2,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM or 5 nM.

In another alternative, the activities of the compounds of the invention can be described in terms of the concentrations of compounds required for functional antagonism of glucagon in hepatocytes from various species. The $EC_{50}$ is determined using the method of Example B. Preferably, the $EC_{50}$ values for compounds of the subject invention are less than <10,000 nM, 9,000 nM, 8,000 nM, 7,000 nM, 6,000 nM, 5,000 nM, 4,000 nM, 3,000 nM, 2,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM or 5 nM.

Compounds of the present invention also exhibit the ability to reduce blood glucose in an animal. In various aspects of the invention, circulating blood glucose in fasting or non-fasting (freely-feeding) animals can be reduced between 10% and 100%. A reduction of 100% refers to complete normalization of blood glucose levels, not 0% blood glucose levels. Normal blood glucose in rats, for example, is approximately 80 mg/dl (fasted) and approximately 120 mg/dl (fed). Thus, the subject invention contemplates reducing excessive circulating blood glucose levels in fasting or freely fed animals (e.g. rat), administered 10 mg/kg of a compound of the present invention, by at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In one embodiment, D is a substituted group selected from carbocyclic aryl, heteroaryl, cycloalkyl or heterocyclyl, wherein said group is substituted with L and, optionally, one or more additional substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{3-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$CF_3$, —$NO_2$, —CN, —$NR^{10}R^{10}$, —$OR^9$, —$SR^9$, —$S(O)R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —$OC(O)NR^{10}R^{10}$, —$CH_2NR^{10}R^{10}$, —$OC(O)R^9$, —$C(O)R^9$ or —$COOR^9$;

wherein $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, D is a substituted group selected from carbocyclic aryl, heteroaryl, cycloalkyl or heterocyclyl, wherein said group is substituted with L and, optionally, one or more additional substituents independently selected from optionally substituted $C_{1-4}$-alkyl, optionally substituted $C_{2-4}$-alkenyl or optionally substituted $C_{2-6}$-alkynyl, optionally substituted $C_{1-4}$-alkoxy-, optionally substituted $C_{3-8}$-cycloalkyl, optionally substituted $C_{4-8}$-cycloalkenyl, optionally substituted $C_{3-8}$-cycloalkyloxy, optionally substituted $C_{3-8}$-cycloalkylthio, halogen, —$CF_3$, —$NO_2$, —CN, —$NR^{10}R^{10}$, —$OR^9$, —$SR^9$, —$NR^9SOR^{10}$, —$SO_2NR^{10}R^{10}$, —$CONR^{10}R^{10}$, —$OC(O)NR^{10}R^{10}$, —$CH_2NR^{10}R^{10}$ or —$C(O)R^9$;

wherein said heterocyclyl or heteroaryl independently contain one, two, three or four heteroatoms independently selected from nitrogen, oxygen and sulfur;

wherein $R^9$ is aralkyl, $C_{1-6}$-alkyl or aryl, each optionally substituted with one, two or three substituents independently selected from halogen, —$NO_2$, —CN, —$OR^x$, —$SR^x$ or —$NR^xSOR^{10}$;

wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

wherein $R^x$ is selected from $C_{1-3}$-alkyl optionally substituted with one or more halogens, up to and including perhalo; and, wherein said $C_{1-4}$-alkyl, $C_{2-4}$-alkenyl or $C_{2-6}$-alkynyl is optionally substituted with one, two or three substituents independently selected from halogen, —CN, —CF$_3$, —OCHF$_2$, —OCF$_3$, —NO$_2$, —OR$^9$ or $C_{1-6}$-alkyl.

In another embodiment, D is a substituted first group selected from phenyl or heteroaryl, wherein said first group is substituted with L and is substituted with a second group —(CR$^{11}$R$^{11}$)$_a$—O—(CR$^{11}$R$^{11}$)$_c$—O— to form a third group; wherein said —(CR$^{11}$R$^{11}$)$_a$—O—(CR$^{11}$R$^{11}$)$_c$—O— is attached at two adjacent positions on D to form a 5- or 6-membered ring; wherein a is 0 or 1; wherein c is 1 or 2; and wherein each $R^{11}$ is independently selected from hydrogen, $C_{1-6}$-alkyl or fluoro;

wherein said third group is optionally substituted with one, two, three or four substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{1-6}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein, $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, D is a substituted group selected from phenyl or heteroaryl, wherein said group is substituted with L and, optionally, one or more additional substituents independently selected from halogen, —CF$_3$, —CN, —OR$^9$, —SR$^9$, —C(O)R$^9$, —C$_{1-4}$-alkyl, —C$_{2-4}$-alkenyl, —C$_{2-6}$-alkynyl, —O—C$_{1-4}$-alkyl, —CH$_2$CN, —CHF$_2$, —CF$_3$, —CH$_2$CF$_3$, —C$_{3-6}$-alkyl-CF$_3$, —C$_{2-3}$-perfluoroalkyl, —OCF$_3$, —OCH$_2$CF$_3$, —O—C$_{3-6}$-alkyl-CF$_3$, —OC$_{2-3}$-perfluoroalkyl, —CH$_2$OR$^9$, —CH$_2$NR$^9$R$^{10}$, —CH$_2$CONR$^9$R$^{10}$ or —OCH$_2$CONR$^9$R$^{10}$;

wherein said heteroaryl contains one or two heteroatoms independently selected from nitrogen, oxygen or sulfur;

wherein $R^9$ is selected from $C_{1-6}$-alkyl, optionally substituted with halogen, —CN, —O—C$_{1-3}$-alkyl or —S—C$_{1-3}$-alkyl; wherein said $C_{1-3}$-alkyl of —O—C$_{1-3}$-alkyl or —S—C$_{1-3}$-alkyl is optionally substituted with one or more halogens, up to and including perhalo; and, wherein $R^{10}$ is selected from hydrogen, optionally substituted $C_{1-6}$-alkyl or optionally substituted aryl.

In another embodiment, D is a substituted group selected from phenyl or heteroaryl, wherein said group is substituted with L and, optionally, one or more additional substituents independently selected from halogen, —CF$_3$, —CN, optionally substituted $C_{1-6}$-alkyl or optionally substituted $C_{1-6}$-alkoxy-.

In another embodiment, D is a substituted group selected from phenyl or heteroaryl, wherein said group is substituted with L and, optionally, one or more additional substituents independently selected from halogen, —CF$_3$, —CN, $C_{1-6}$-haloalkyl, $C_{1-6}$-alkyl, $C_{1-6}$-haloalkoxy or $C_{1-6}$-alkoxy-.

In another embodiment, D is a substituted group selected from phenyl, nine- or ten-membered carbocyclic bicyclic aryl or heteroaryl, wherein said group is substituted with L and, optionally, one or more additional substituents independently selected from F—, Cl—, Br—, —CN, $C_{1-6}$-alkyl, —CF$_3$, —CH$_2$—CF$_3$, —O—CF$_3$, —O—CH$_2$—CF$_3$ or $C_{1-6}$-alkoxy-.

In another embodiment, D is a substituted group selected from phenyl, five- or six-membered heterocyclic monoaryl, nine- or ten-membered carbocyclic bicyclic aryl, nine- or ten-membered bicyclic heteroaryl, five- or six-membered cycloalkyl or five- or six-membered heterocyclyl, wherein said group is substituted with L and, optionally, one or more additional substituents.

In another embodiment, D is a substituted group selected from phenyl, five- or six-membered heterocyclic monoaryl, nine- or ten-membered carbocyclic bicyclic aryl, nine- or ten-membered bicyclic heteroaryl, five- or six-membered cycloalkyl or five- or six-membered heterocyclyl, wherein said group is substituted with L and, optionally, one or more additional substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{3-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —CF$_3$, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein, $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, D is a substituted group selected from phenyl, five- or six-membered heterocyclic monoaryl, nine- or ten-membered carbocyclic bicyclic aryl, nine- or ten-membered bicyclic heteroaryl, five- or six-membered cycloalkyl or five- or six-membered heterocyclyl, wherein said group is substituted with L and, optionally, one or more additional substituents independently selected from optionally substituted $C_{1-6}$-alkyl, optionally substituted $C_{2-6}$-alkenyl, optionally substituted $C_{2-6}$-alkynyl, optionally substituted $C_{3-8}$-cycloalkyl, optionally substituted $C_{4-8}$-cycloalkenyl, optionally substituted $C_{3-8}$-alkoxy, optionally substituted $C_{3-8}$-cycloalkylalkoxy, optionally substituted $C_{3-8}$-cycloalkyloxy, optionally substituted $C_{3-8}$-cycloalkylthio, halogen, —NO$_2$, —CN, —NR$^{10}$R$^{10}$, —OR$^9$, —CF$_3$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein R$^9$ is aralkyl, $C_{1-6}$-alkyl or aryl, each optionally substituted with one, two or three substituents independently selected from halogen, —NO$_2$, —CN, —OR$^x$, —SR$^x$ or —NR$^x$SOR$^{10}$;

wherein each R$^{10}$ is independently selected from hydrogen, optionally substituted $C_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

wherein said $C_{1-6}$-alkyl, $C_{2-6}$-alkenyl or $C_{2-6}$-alkynyl is optionally substituted with one, two or three substituents independently selected from halogen, —CN, —CF$_3$, —OCHF$_2$, —OCF$_3$, —NO$_2$, —OR$^9$ or $C_{1-6}$-alkyl.

In another embodiment, D is a first group that is substituted with a second group —(CR$^{11}$R$^{11}$)$_a$—O—(CR$^{11}$R$^{11}$)$_c$—O—, and L, said first group being selected from phenyl, five- or six-membered heterocyclic monoaryl, nine- or ten-membered, carbocyclic bicyclic aryl, nine- or ten-membered bicyclic heteroaryl, five- or six-membered cycloalkyl or five- or six-membered heterocyclyl;

wherein said first group substituted with said second group forms a third group and said second group, —(CR$^{11}$R$^{11}$)$_a$—O—(CR$^{11}$R$^{11}$)$_c$—O—, is attached at two adjacent positions on D to form a 5- or 6-membered ring; wherein a is 0 or 1; wherein c is 1 or 2; and wherein each R$^{11}$ is independently selected from hydrogen, $C_{1-6}$-alkyl or fluoro and said third group is optionally substituted with one, two, three or four substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{1-6}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein, R$^9$ is independently selected from hydrogen, optionally substituted aralkyl, $C_{1-6}$-alkyl or optionally substituted aryl; and, wherein each R$^{10}$ is independently selected from hydrogen, optionally substituted $C_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, D is a substituted group selected from phenyl, five- or six-membered heterocyclic monoaryl, nine- or ten-membered, carbocyclic bicyclic aryl, nine- or ten-membered bicyclic heteroaryl, five- or six-membered cycloalkyl or five- or six-membered heterocyclyl, wherein said group is substituted with L and, optionally, one or more additional substituents independently selected from halogen, —CN, —CF$_3$, —OR$^9$, —SR$^9$, —C(O)R$^9$, —C$_{1-4}$-alkyl, —C$_{2-4}$-alkenyl, —C$_{2-6}$-alkynyl, —O—C$_{1-4}$-alkyl, —CH$_2$CN, —CHF$_2$, —CF$_3$, —CH$_2$CF$_3$, —C$_{3-6}$-alkyl-CF$_3$, —C$_{2-3}$-perfluoroalkyl, —OCF$_3$, —OCH$_2$CF$_3$, —O—C$_{3-6}$-alkyl-CF$_3$, —OC$_{2-3}$-perfluoroalkyl, —CH$_2$OR$^9$, —CH$_2$NR$^9$R$^{10}$, —CH$_2$CONR$^9$R$^{10}$ or —OCH$_2$CONR$^9$R$^{10}$;

wherein said heteroaryl or heterocyclyl contains one or two heteroatoms independently selected from nitrogen, oxygen or sulfur;

wherein R$^9$ is selected from aralkyl, $C_{1-6}$-alkyl or aryl, each optionally substituted with halogen, —CN, —O—$C_{1-3}$-alkyl or —S—$C_{1-3}$-alkyl; wherein said $C_{1-3}$-alkyl of —O—$C_{1-3}$-alkyl or —S—$C_{1-3}$-alkyl is optionally substituted with one or more halogens, up to and including perhalo; and, wherein each R$^{10}$ is independently selected from hydrogen, optionally substituted $C_{1-6}$-alkyl or optionally substituted aryl; and, wherein R$^x$ is selected from $C_{1-3}$-alkyl optionally substituted with one or more halogens, up to and including perhalo.

In another embodiment, D is a substituted group selected from a substituted phenyl or a substituted five- or six-membered heterocyclic monoaryl, wherein said group is substituted with L and, optionally, one or more additional substituents independently selected from halogen, —CF$_3$, —CN, optionally substituted $C_{1-6}$-alkyl or optionally substituted $C_{1-6}$-alkoxy-.

In another embodiment, D is a substituted group selected from a substituted phenyl or a substituted five- or six-membered heterocyclic monoaryl, wherein said group is substituted with L and, optionally, one or more additional substituents independently selected from halogen, —CF$_3$, —CN, $C_{1-6}$-haloalkyl, $C_{1-6}$-alkyl, $C_{1-6}$-haloalkoxy or $C_{1-6}$-alkoxy-.

In another embodiment, D is a substituted group selected from a substituted phenyl or a substituted five- or six-membered heterocyclic monoaryl, wherein said group is substituted with L and, optionally, one or more additional substituents independently selected from F—, Cl—, Br—, —CN, $C_{1-6}$-alkyl, —CF$_3$, —CH$_2$—CF$_3$, O—CF$_3$, —O—CH$_2$—CF$_3$ or $C_{1-6}$-alkoxy-.

In another embodiment, D is a substituted group selected from phenyl, pyridyl, pyrimidinyl, benzimidazolyl, benzoxazolyl, benzofuranyl, or benzothiazolyl, wherein said group is substituted with L and, optionally, one or more additional substituents.

In another embodiment, D is a substituted group selected from phenyl, pyridyl, pyrimidinyl, benzimidazolyl, benzoxazolyl, benzofuranyl, or benzothiazolyl, wherein said group is substituted with L and, optionally, one or more additional substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{3-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —CF$_3$, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, D is a phenyl group substituted with L and further substituted with a second group, —(CR$^{11}$R$^{11}$)$_a$—O—(CR$^{11}$R$^{11}$)$_c$—O—, to form a third group; wherein said second group, —(CR$^{11}$R$^{11}$)$_a$—O—(CR$^{11}$R$^{11}$)$_c$—O—, is attached at two adjacent positions on D to form a 5- or 6-membered ring; wherein a is 0 or 1; wherein c is 1 or 2; and wherein each R$^{11}$ is independently selected from hydrogen, C$_{1-6}$-alkyl or fluoro;

wherein said third group is optionally substituted with one, two, three or four substituents independently selected from optionally substituted C$_{1-6}$-alkyl, optionally substituted C$_{2-6}$-alkenyl, optionally substituted C$_{2-6}$-alkynyl, optionally substituted C$_{3-4}$-cycloalkyl, optionally substituted C$_{4-8}$-cycloalkenyl, optionally substituted C$_{1-6}$-alkoxy, optionally substituted C$_{3-8}$-alkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein, R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur and wherein said heterocyclic ring optionally contains 0, 1 or 2 double bonds.

In another embodiment, D is a substituted group selected from phenyl, pyridyl, pyrimidinyl, benzimidazolyl, benzoxazolyl, benzofuranyl, or benzothiazolyl, wherein said group is substituted with L and, optionally, one or more additional substituents independently selected from optionally substituted C$_{1-6}$-alkyl, optionally substituted C$_{2-6}$-alkenyl, optionally substituted C$_{2-6}$-alkynyl, optionally substituted C$_{3-8}$-cycloalkyl, optionally substituted C$_{4-8}$-cycloalkenyl, optionally substituted C$_{3-8}$-cycloalkyloxy, optionally substituted C$_{3-8}$-cycloalkylthio, halogen, —CF$_3$, —NO$_2$, —CN, —NR$^{10}$R$^{10}$, —OR$^9$, —SR$^9$, —NR$^9$SOR$^{10}$, —SO$_2$NR$^{10}$R$^{10}$, —CONR$^{10}$R$^{10}$, —OC(O)NR$^{10}$R$^{10}$, CH$_2$NR$^{10}$R$^{10}$ or —C(O)R$^9$;

wherein R$^9$ is aralkyl, C$_{1-6}$-alkyl or aryl, each optionally substituted with one, two or three substituents independently selected from halogen, —NO$_2$, —CN, —OR$^x$, —SR$^x$ or —NR$^x$SOR$^{10}$;

wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds; R$^x$ is selected from C$_{1-3}$-alkyl optionally substituted with one or more halogens, up to and including perhalo, and wherein said C$_{1-6}$-alkyl, C$_{2-6}$-alkenyl or C$_{2-6}$-alkynyl is optionally substituted with one, two or three substituents independently selected from halogen, —CN, —CF$_3$, —OCHF$_2$, —OCF$_3$, —NO$_2$, —OR$^9$ or C$_{1-6}$-alkyl.

In another embodiment, D is a substituted group selected from phenyl, pyridyl, pyrimidinyl, benzimidazolyl, benzoxazolyl, benzofuranyl, or benzothiazolyl, wherein said group is substituted with L and, optionally, one or more additional substituents independently selected from halogen, —CN, —CF$_3$, —OR$^9$, —SR$^9$, —C(O)R$^9$, —C$_{1-4}$-alkyl, —C$_{2-4}$-alkenyl, —C$_{2-6}$-alkynyl, —C$_{1-4}$-alkoxy-, —CH$_2$CN, —CHF$_2$, —CF$_3$, —CH$_2$CF$_3$, —C$_{3-6}$-alkyl-CF$_3$, —C$_{2-3}$-perfluoroalkyl, —OCF$_3$, —OCH$_2$CF$_3$, —O—C$_{3-6}$-alkyl-CF$_3$, —OC$_{2-3}$-perfluoroalkyl, —CH$_2$OR$^9$, —CH$_2$NR$^9$R$^{10}$, —CH$_2$CONR$^9$R$^{10}$ or —OCH$_2$CONR$^9$R$^{10}$;

wherein said heteroaryl contains one or two heteroatoms independently selected from nitrogen, oxygen or sulfur;

wherein R$^9$ is aralkyl, C$_{1-6}$-alkyl or aryl, each optionally substituted with halogen, —CN, —O—C$_{1-3}$-alkyl or —S—C$_{1-3}$-alkyl; wherein said C$_{1-3}$-alkyl of —O—C$_{1-3}$-alkyl or —S—C$_{1-3}$-alkyl is optionally substituted with one or more halogens, up to and including perhalo; and, wherein R$^{10}$ is selected from hydrogen, optionally substituted C$_{1-6}$-alkyl or optionally substituted aryl.

In another embodiment, D is a substituted group selected from phenyl, pyridyl, pyrimidinyl, benzimidazolyl, benzoxazolyl, benzofuranyl or benzothiazolyl, wherein said group is substituted with L and, optionally, one or more additional substituents independently selected from halogen, —CF$_3$, —CN, optionally substituted C$_{1-6}$-alkyl or optionally substituted C$_{1-6}$-alkoxy-.

In another embodiment, D is a substituted group selected from phenyl, pyridyl, pyrimidinyl, benzimidazolyl, benzoxazolyl, benzofuranyl or benzothiazolyl, wherein said group is substituted with L and, optionally, one or more additional substituents independently selected from halogen, —CF$_3$, —CN, C$_{1-6}$-haloalkyl, C$_{1-6}$-alkyl, C$_{1-6}$-haloalkoxy or C$_{1-6}$-alkoxy-.

In another embodiment, D is a substituted group selected from phenyl, pyridyl, pyrimidinyl, benzimidazolyl, benzoxazolyl, benzofuranyl or benzothiazolyl, wherein said group is substituted with L and, optionally, one or more additional substituents independently selected from F—, Cl—, Br—, —CN, C$_{1-6}$-alkyl, —CF$_3$, —CH$_2$—CF$_3$, O—CF$_3$, —O—CH$_2$—CF$_3$ or C$_{1-6}$-alkoxy-.

In any embodiment discussed above, D may be substituted with L and 1, 2, 3 or 4 additional substituents. Other embodiments provide compounds where D is only substituted with L.

In one embodiment, L is a group selected from hydrogen, CF$_3$, phenyl, phenyl-oxy-, phenyl-C$_{1-6}$-alkyl-oxy-, phenyl-C(O)—, phenyl-C$_{1-6}$-alkyl-C(O)—, phenyl-N(R$^{12}$)—, fiveor six-membered heterocyclic monoaryl, five- or six-membered heterocyclic monoaryl-oxy-, five- or six-membered heterocyclic monoaryl-$C_{1-6}$-alkyl-oxy-, five- or six-membered heterocyclic monoarylketyl-, five- or six-membered heterocyclic monoaryl-$C_{1-6}$-alkyl-C(O)—, five- or six-membered heterocyclic monoaryl-N($R^{12}$)—, nine- or ten-membered carbocyclic bicyclic aryl, nine- or ten-membered carbocyclic bicyclic aryl-oxy-, nine- or ten-membered carbocyclic bicyclic aryl-$C_{1-6}$-alkyl-oxy-, nine- or ten-membered carbocyclic bicyclic aryl-C(O)—, nine- or ten-membered carbocyclic bicyclic aryl-$C_{1-6}$-alkyl-C(O)—, nine- or ten-membered carbocyclic bicyclic aryl-N($R^{12}$)—, nine- or ten-membered bicyclic heteroaryl, nine- or ten-membered bicyclic heteroaryl-oxy-, nine- or ten-membered bicyclic heteroaryl-$C_{1-6}$-alkyl-oxy-, nine- or ten-membered bicyclic heteroaryl-C(O)—, nine- or ten-membered bicyclic heteroaryl-$C_{1-6}$-alkyl-C(O)—, nine- or ten-membered bicyclic heteroaryl-N($R^{12}$)—, five-, six-, seven- or eight-membered cycloalkyl, five- or six-membered cycloalkyl-oxy-, five-, six-, seven- or eight-membered cycloalkyl-$C_{1-6}$-alkyl-oxy-, five-, six-, seven- or eight-membered cycloalkyl-C(O)—, five-, six-, seven- or eight-membered cycloalkyl-$C_{1-6}$-alkyl-C(O)—, five-, six-, seven- or eight-membered cycloalkyl-N($R^{12}$)—, five-, six-, seven- or eight-membered heterocyclyl, five-, six-, seven- or eight-membered heterocyclyl-oxy-, five-, six-, seven-, eight-membered heterocyclyl-$C_{1-6}$-alkyl-oxy- or -five-, six-, seven-, eight-membered heterocyclyl-$C_{1-6}$-alkyl-N($R^{12}$)—;

wherein $R^{12}$ is selected from hydrogen or $C_{1-3}$-alkyl; and,
wherein each of said group, excluding hydrogen, is optionally substituted.

In another embodiment, L is a group selected from hydrogen, $CF_3$, phenyl, phenyl-oxy-, phenyl-$C_{1-6}$-alkyl-oxy-, phenyl-C(O)—, phenyl-$C_{1-6}$-alkyl-C(O)—, phenyl-N($R^{12}$)—, five- or six-membered heterocyclic monoaryl, five- or six-membered heterocyclic monoaryl-oxy-, five- or six-membered heterocyclic monoaryl-$C_{1-6}$-alkyl-oxy-, five- or six-membered heterocyclic monoarylketyl-, five- or six-membered heterocyclic monoaryl-$C_{1-6}$-alkyl-C(O)—, five- or six-membered heterocyclic monoaryl-N($R^{12}$)—, nine- or ten-membered carbocyclic bicyclic aryl, nine- or ten-membered carbocyclic bicyclic aryl-oxy-, nine- or ten-membered carbocyclic bicyclic aryl-$C_{1-6}$-alkyl-oxy-, nine- or ten-membered carbocyclic bicyclic aryl-C(O)—, nine- or ten-membered carbocyclic bicyclic aryl-$C_{1-6}$-alkyl-C(O)—, nine- or ten-membered carbocyclic bicyclic aryl-N($R^{12}$)—, nine- or ten-membered bicyclic heteroaryl, nine- or ten-membered bicyclic heteroaryl-oxy-, nine- or ten-membered bicyclic heteroaryl-$C_{1-6}$-alkyl-oxy-, nine- or ten-membered bicyclic heteroaryl-C(O)—, nine- or ten-membered bicyclic heteroaryl-$C_{1-6}$-alkyl-C(O)—, nine- or ten-membered bicyclic heteroaryl-N($R^{12}$)—, five-, six-, seven- or eight-membered cycloalkyl, five- or six-membered cycloalkyl-oxy-, five-, six-, seven- or eight-membered cycloalkyl-$C_{1-6}$-alkyl-oxy-, five-, six-, seven- or eight-membered cycloalkyl-C(O)—, five-, six-, seven- or eight-membered cycloalkyl-$C_{1-6}$-alkyl-C(O)—, five-, six-, seven- or eight-membered cycloalkyl-N($R^{12}$)—, five-, six-, seven- or eight-membered heterocyclyl, five-, six-, seven- or eight-membered heterocyclyl-oxy-, five-, six-, seven-, eight-membered heterocyclyl-$C_{1-6}$-alkyl-oxy- or -five-, six-, seven-, eight-membered heterocyclyl-$C_{1-6}$-alkyl-N($R^{12}$)—;

wherein said group, excluding hydrogen, is substituted with one, two or three groups selected from halogen, hydroxy, amido, optionally substituted $C_{1-6}$-alkyl, optionally substituted $C_{2-6}$-alkenyl, optionally substituted $C_{2-6}$-alkynyl, optionally substituted $C_{3-6}$-cycloalkyl, optionally substituted $C_{4-8}$-cycloalkenyl, optionally substituted $C_{1-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$NO_2$, —$CF_3$, —CN, —$NR^{10}R^{10}$, —$OR^9$, —$SR^9$, —$S(O)R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —OC(O)$NR^{10}R^{10}$, —$CH_2NR^{10}R^{10}$, —OC(O)$R^9$, —C(O)$R^9$, —$COOR^9$, phenyl, phenyl-oxy- or phenyl-$C_{1-6}$-alkyl-oxy-;

wherein $R^9$ is independently selected from hydrogen, optionally substituted aralkyl or optionally substituted $C_{1-6}$-alkyl;

wherein $R^{12}$ is selected from hydrogen or $C_{1-3}$-alkyl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, L is a first group selected from hydrogen, $CF_3$, phenyl, phenyl-oxy-, phenyl-$C_{1-6}$-alkyl-oxy-, phenyl-C(O)—, phenyl-$C_{1-6}$-alkyl-C(O)—, phenyl-N($R^{12}$)—, indenyl, five- or six-membered heterocyclic monoaryl, five- or six-membered heterocyclic monoaryl-oxy-, five- or six-membered heterocyclic monoaryl-$C_{1-6}$-alkyl-oxy-, five- or six-membered heterocyclic monoarylketyl-, five-, six-membered heterocyclic monoaryl-$C_{1-6}$-alkyl-C(O)— or five- or six-membered heterocyclic monoaryl-N($R^{12}$)—, nine- or ten-membered bicyclic heteroaryl, nine- or ten-membered bicyclic heteroaryl-oxy-, nine- or ten-membered bicyclic heteroaryl-$C_{1-6}$-alkyl-oxy-;

wherein said first group is substituted with a second group —$(CR^{11}R^{11})_a$—O—$(CR^{11}R^{11})_c$—O— to form a third group; wherein said —$(CR^{11}R^{11})_a$—O—$(CR^{11}R^{11})_c$—O— is attached at two adjacent positions on D to form a 5- or 6-membered ring; wherein a is 0 or 1; wherein c is 1 or 2; and wherein each $R^{11}$ is independently selected from hydrogen, $C_{1-6}$-alkyl or fluoro;

wherein said third group is optionally substituted with one, two, three or four substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{1-6}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$NO_2$, $CF_3$, —CN, —$NR^{10}R^{10}$, —$OR^9$, —$SR^9$, —$S(O)R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —OC(O)$NR^{10}R^{10}$, —$CH_2NR^{10}R^{10}$, —OC(O)$R^9$, —C(O)$R^9$ or —$COOR^9$;

wherein $R^{12}$ is selected from hydrogen or $C_{1-3}$-alkyl;

wherein, $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, L is a group selected from hydrogen, $CF_3$, phenyl, phenyl-oxy-, phenyl-$C_{1-6}$-alkyl-oxy-, phenyl-C(O)—, phenyl-$C_{1-6}$-alkyl-C(O)—, phenyl-N($R^{12}$)—, indenyl, five- or six-membered heterocyclic monoaryl, five- or six-membered heterocyclic monoaryl-oxy-, five- or six-membered heterocyclic monoaryl-$C_{1-6}$-alkyl-oxy-, five- or six-membered heterocyclic monoarylketyl-, five- or six-membered heterocyclic monoaryl-$C_{1-6}$-alkyl-C(O)—, five- or six-membered heterocyclic monoaryl-N($R^{12}$)—, nine- or ten-membered carbocyclic bicyclic aryl, nine- or ten-membered carbocyclic bicyclic aryl-oxy-, nine- or ten-membered carbocyclic bicyclic aryl-$C_{1-6}$-alkyl-oxy-, nine- or ten-membered carbocyclic bicyclic aryl-C(O)—, nine- or ten-membered carbocyclic bicyclic aryl-$C_{1-6}$-alkyl-C(O)—, nine- or ten-membered carbocyclic bicyclic aryl-N($R^{12}$)—, nine- or ten-membered bicyclic heteroaryl, nine- or ten-membered bicyclic heteroaryl-oxy-, nine- or ten-membered bicyclic heteroaryl-$C_{1-6}$-alkyl-oxy-, nine- or ten-membered bicyclic heteroaryl-C(O)—, nine- or ten-membered bicyclic heteroaryl-$C_{1-6}$-alkyl-C(O)—, nine- or ten-membered bicyclic heteroaryl-N($R^{12}$)—, five-, six-, seven- or eight-membered cycloalkyl, five-, six-, seven- or eight-membered cycloalkyl-oxy-, five-, six-, seven- or eight-membered cycloalkyl-$C_{1-6}$-alkyl-oxy-, five-, six-, seven- or eight-membered cycloalkyl-C(O)—, five-, six-, seven- or eight-membered cycloalkyl-$C_{1-6}$-alkyl-C(O)—, five-, six-, seven- or eight-membered cycloalkyl-N($R^{12}$)—, five-, six-, seven- or eight-membered heterocyclyl, five-, six-, seven- or eight-membered heterocyclyl-oxy-, five-, six-, seven-, eight-membered heterocyclyl-$C_{1-6}$-alkyl-oxy- or -five-, six-, seven-, eight-membered heterocyclyl-$C_{1-6}$-alkyl-N($R^{12}$)—;

wherein said group, excluding hydrogen, is optionally substituted with one, two or three groups selected from halogen, $CF_3$, hydroxy, amido, optionally substituted $C_{1-6}$-alkyl, optionally substituted $C_{2-6}$-alkenyl, optionally substituted $C_{2-6}$-alkynyl, optionally substituted $C_{3-6}$-cycloalkyl, optionally substituted $C_{4-8}$-cycloalkenyl, optionally substituted $C_{1-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, —$NO_2$, —CN, —$NR^{10}R^{10}$, —$OR^9$, —$SR^9$, —S(O)$R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —$OC(O)NR^{10}R^{10}$, —$CH_2NR^{10}R^{10}$, —OC(O)$R^9$, —C(O)$R^9$ or —$COOR^9$;

wherein $R^{12}$ is selected from hydrogen or $C_{1-3}$-alkyl;

wherein $R^9$ is independently selected from hydrogen, optionally substituted aralkyl or optionally substituted $C_{1-6}$-alkyl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, L is a group selected from hydrogen, $CF_3$, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinylquinolinyl, isoquinolinyl, quinazolinyl, quinoxalinyl, thiophenyl-oxy-, phenyl-oxy-, pyridyl-oxy-, pyrimidinyl-oxy-, benzofuranyl-oxy-, benzothiophenyl-oxy-, benzimidazolyl-oxy-, furanyl-oxy-, thiophenyl-oxy-, oxazolyl-oxy-, thiazolyl-oxy-, phenyl-N($R^{12}$)—, pyridyl-N($R^{12}$)—, pyrimidinyl-N($R^{12}$)—, benzofuranyl-N($R^{12}$)—, benzothiophenyl-N($R^{12}$)—, benzimidazolyl-N($R^{12}$)—, benzoxazolyl-N($R^{12}$)—, $C_3$-cycloalkyloxy, $C_4$-cycloalkyloxy, $C_5$-cycloalkyloxy, $C_6$-cycloalkyloxy, $C_7$-cycloalkyloxy, $C_8$-cycloalkyloxy, $C_4$-cycloalkenyloxy, $C_5$-cycloalkenyloxy, $C_6$-cycloalkenyloxy, $C_7$-cycloalkenyloxy, $C_8$-cycloalkenyloxy, $C_3$-cycloalkyl-N($R^{12}$)—, $C_4$-cycloalkyl-N($R^{12}$)—, $C_5$-cycloalkyl-N($R^{12}$)—, $C_6$-cycloalkyl-N($R^{12}$)—, $C_7$-cycloalkyl-N($R^{12}$)—, $C_8$-cycloalkyl-N($R^{12}$)—, $C_4$-cycloalkenyl-N($R^{12}$), $C_5$-cycloalkenyl-N($R^{12}$)—, $C_6$-cycloalkenyl-N($R^{12}$)—, $C_7$-cycloalkenyl-N($R^{12}$)—, $C_8$-cycloalkenyl-N($R^{12}$)—, $C_3$-cycloalkyl-$C_1$-alkoxy, $C_3$-cycloalkyl-$C_2$-alkoxy, $C_3$-cycloalkyl-$C_3$-alkoxy, $C_3$-cycloalkyl-$C_4$-alkoxy, $C_3$-cycloalkyl-$C_5$-alkoxy, $C_3$-cycloalkyl-$C_6$-alkoxy, $C_4$-cycloalkyl-$C_1$-alkoxy, $C_4$-cycloalkyl-$C_2$-alkoxy, $C_4$-cycloalkyl-$C_3$-alkoxy, $C_4$-cycloalkyl-$C_4$-alkoxy, $C_4$-cycloalkyl-$C_5$-alkoxy, $C_4$-cycloalkyl-$C_6$-alkoxy, $C_5$-cycloalkyl-$C_1$-alkoxy, $C_5$-cycloalkyl-$C_2$-alkoxy, $C_5$-cycloalkyl-$C_3$-alkoxy, $C_5$-cycloalkyl-$C_4$-alkoxy, $C_5$-cycloalkyl-$C_5$-alkoxy, $C_5$-cycloalkyl-$C_6$-alkoxy, $C_6$-cycloalkyl-$C_1$-alkoxy, $C_6$-cycloalkyl-$C_2$-alkoxy, $C_6$-cycloalkyl-$C_3$-alkoxy, $C_6$-cycloalkyl-$C_4$-alkoxy, $C_6$-cycloalkyl-$C_5$-alkoxy, $C_6$-cycloalkyl-$C_6$-alkoxy, $C_7$-cycloalkyl-$C_1$-alkoxy, $C_7$-cycloalkyl-$C_2$-alkoxy, $C_7$-cycloalkyl-$C_3$-alkoxy, $C_7$-cycloalkyl-$C_4$-alkoxy, $C_7$-cycloalkyl-$C_5$-alkoxy, $C_7$-cycloalkyl-$C_6$-alkoxy, $C_8$-cycloalkyl-$C_1$-alkoxy, $C_8$-cycloalkyl-$C_2$-alkoxy, $C_8$-cycloalkyl-$C_3$-alkoxy, $C_8$-cycloalkyl-$C_4$-alkoxy, $C_8$-cycloalkyl-$C_5$-alkoxy, $C_8$-cycloalkyl-$C_6$-alkoxy, $C_4$-cycloalkenyloxy, $C_5$-cycloalkenyloxy, $C_6$-cycloalkenyloxy, $C_7$-cycloalkenyloxy, $C_8$-cycloalkenyloxy, $C_4$-cycloalkenyl-$C_1$-alkoxy, $C_4$-cycloalkenyl-$C_2$-alkoxy, $C_4$-cycloalkenyl-$C_3$-alkoxy, $C_4$-cycloalkenyl-$C_4$-alkoxy, $C_4$-cycloalkenyl-$C_5$-alkoxy, $C_4$-cycloalkenyl-$C_6$-alkoxy, $C_5$-cycloalkenyl-$C_1$-alkoxy, $C_5$-cycloalkenyl-$C_2$-alkoxy, $C_5$-cycloalkenyl-$C_3$-alkoxy, $C_5$-cycloalkenyl-$C_4$-alkoxy, $C_5$-cycloalkenyl-$C_5$-alkoxy, $C_5$-cycloalkenyl-$C_6$-alkoxy, $C_6$-cycloalkenyl-$C_1$-alkoxy, $C_6$-cycloalkenyl-$C_2$-alkoxy, $C_6$-cycloalkenyl-$C_3$-alkoxy, $C_6$-cycloalkenyl-$C_4$-alkoxy, $C_6$-cycloalkenyl-$C_5$-alkoxy, $C_6$-cycloalkenyl-$C_6$-alkoxy, $C_7$-cycloalkenyl-$C_1$-alkoxy, $C_7$-cycloalkenyl-$C_2$-alkoxy, $C_7$-cycloalkenyl-$C_3$-alkoxy, $C_7$-cycloalkenyl-$C_4$-alkoxy, $C_7$-cycloalkenyl-$C_5$-alkoxy, $C_7$-cycloalkenyl-$C_6$-alkoxy, $C_8$-cycloalkenyl-$C_1$-alkoxy, $C_8$-cycloalkenyl-$C_2$-alkoxy, $C_8$-cycloalkenyl-$C_3$-alkoxy, $C_8$-cycloalkenyl-$C_4$-alkoxy, $C_8$-cycloalkenyl-$C_5$-alkoxy, $C_8$-cycloalkenyl-$C_6$-alkoxy, $C_1$-alkoxy, $C_2$-alkoxy, $C_3$-alkoxy, $C_4$-alkoxy, $C_5$-alkoxy, $C_6$-alkoxy, wherein $R^{12}$ is selected from hydrogen or $C_{1-3}$-alkyl;

wherein said group, excluding hydrogen, is optionally substituted with one, two or three groups selected from halogen, hydroxy, amido, optionally substituted $C_{1-6}$-alkyl, optionally substituted $C_{2-6}$-alkenyl, optionally substituted $C_{2-6}$-alkynyl, optionally substituted $C_{3-6}$-cycloalkyl, optionally substituted $C_{4-8}$-cycloalkenyl, optionally substituted $C_{1-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$NO_2$, —CN, —$NR^{10}R^{10}$, —$OR^9$, —$SR^9$, —S(O)$R^9$, —$SO_2R^9$, —$NR^9SOR^{10}$, —$NR^9SO_2R^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein said C$_{1-4}$-alkyl, C$_{2-4}$-alkenyl or C$_{2-6}$-alkynyl is optionally substituted with one, two or three substituents independently selected from halogen, —CN, —CF$_3$, —OCHF$_2$, —OCF$_3$, —NO$_2$, —OR$^9$ or C$_{1-6}$-alkyl;

wherein R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, L is a group selected from hydrogen, CF$_3$, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinyl, furanyl-oxy-, thiophenyl-oxy-, oxazolyl-oxy-, thiazolyl-oxy-, phenyl-oxy-, pyridyl-oxy-, pyrimidinyl-oxy-, benzofuranyl-oxy-, benzothiophenyl-oxy-, benzimidazolyl-oxy-, phenyl-N(R$^{12}$)—, pyridyl-N(R$^{12}$)—, pyrimidinyl-N(R$^{12}$)—, benzofuranyl-N(R$^{12}$)—, benzothiophenyl-N(R$^{12}$)—, benzimidazolyl-N(R$^{12}$)—, C$_3$-cycloalkyloxy, C$_4$-cycloalkyloxy, C$_5$-cycloalkyloxy, C$_6$-cycloalkyloxy, C$_7$-cycloalkyloxy, C$_8$-cycloalkyloxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_1$-alkoxy, C$_2$-alkoxy, C$_3$-alkoxy, C$_4$-alkoxy, C$_5$-alkoxy, C$_6$-alkoxy, C$_3$-cycloalkyl-N(R$^{12}$)—, C$_4$-cycloalkyl-N(R$^{12}$)—, C$_5$-cycloalkyl-N(R$^{12}$)—, C$_6$-cycloalkyl-N(R$^{12}$)—, C$_7$-cycloalkyl-N(R$^{12}$)—, C$_8$-cycloalkyl-N(R$^{12}$)—, C$_4$-cycloalkenyl-N(R$^{12}$)—, C$_5$-cycloalkenyl-N(R$^{12}$)—, C$_6$-cycloalkenyl-N(R$^{12}$)—, C$_7$-cycloalkenyl-N(R$^{12}$)—, C$_8$-cycloalkenyl-N(R$^{12}$)—;

wherein R$^{12}$ is selected from hydrogen or C$_{1-3}$-alkyl;

wherein said group, excluding hydrogen, is optionally substituted with one, two or three groups selected from halogen, CF$_3$, hydroxy, NR$^w{}_2$—C(O)—, NR$^w{}_2$—S(=O)—, NR$^w{}_2$S(=O)$_2$—, —NR$^w$—C(O)—C$_{1-6}$-alkyl, —NR$^w$—S(=O)—C$_{1-6}$-alkyl and —NR$^w$S(=O)$_2$—C$_{1-6}$-alkyl, C$_{1-6}$-alkyl, C$_{2-6}$-alkenyl, C$_{2-6}$-alkynyl, C$_{2-6}$-alkynyl, C$_{3-6}$-cycloalkyl, C$_{4-8}$-cycloalkenyl, C$_{1-8}$-alkoxy, C$_{3-8}$-alkylthio-, C$_{3-8}$-cycloalkylalkoxy, C$_{3-8}$-cycloalkylalkylthio-, C$_{3-8}$-cycloalkyloxy, C$_{3-8}$-cycloalkylthio, —NO$_2$, —CN, —NR$^9$R$^9$, —OC(O)NR$^9$R$^9$, —CH$_2$NR$^9$R$^9$, —OC(O)CR$^9$, —C(O)R$^9$ or —COOR$^9$;

wherein R$^w$ is selected from —H or C$_{1-6}$-alkyl;

wherein said substitutents C$_{1-6}$-alkyl, C$_{2-4}$-alkenyl or C$_{2-6}$-alkynyl is optionally substituted with one, two or three substituents independently selected from halogen, —CN, —CF$_3$, —OCHF$_2$, —OCF$_3$, —NO$_2$, —OR$^9$ or C$_{1-6}$-alkyl; and, wherein R$^9$ is independently selected from hydrogen or C$_{1-6}$-alkyl optionally substituted with one, two or three substituents independently selected from halogen, —CN, —CF$_3$, —OCHF$_2$, —OCF$_3$, —NO$_2$, —OR$^9$ or C$_{1-6}$-alkyl.

In another embodiment, L is a group selected from hydrogen, CF$_3$, halo, phenyl, benzofuranyl, benzoxazolyl, benzothiazolyl, indenyl, indolyl, phenyl-oxy-, C$_3$-cycloalkyl, C$_6$-cycloalkyl-C$_1$-alkoxy, C$_3$-cycloalkyl-, C$_6$-cycloalkenyl, perfluoromethoxy, perfluoromethylthio;

wherein said phenyl, benzofuranyl, benzoxazolyl, benzothiazolyl, indenyl, phenyl-oxy-, C$_3$-cycloalkyl, C$_6$-cycloalkyl-C$_1$-alkoxy, cyclopropyl-, C$_6$-cycloalkenyl, is optionally substituted with one, two or three groups selected from Cl—, F—, Br—, I—, CF$_3$—, CF$_3$S—, CF$_3$O—, N(CH$_3$)$_2$S(=O)$_2$—, N(CH$_3$)$_2$C(O)—, benzyl-oxy-, —OH, CH$_3$O—, CH$_3$—, cyclopropyl-, cyclohexenyl, —NH—S(=O)$_2$—CH$_3$ or —CN.

In another embodiment, L is a group selected from hydrogen, CF$_3$, halo, phenyl, benzofuranyl, benzoxazolyl, benzimidazolyl, quinolinyl, isoquinolinyl, quinazolinyl, quinoxalinyl, thiophenyl-oxy-, benzothiazolyl, indenyl, indolyl, phenoxy-, C$_3$-cycloalkyl, C$_6$-cycloalkyl-C$_1$-alkoxy, C$_3$-cycloalky-, C$_6$-cycloalkenyl, perfluoromethoxy or perfluoromethylthio;

wherein said phenyl, benzofuranyl, benzimidazolyl, quinolinyl, isoquinolinyl, quinazolinyl, quinoxalinyl, thiophenyl-oxy-, benzoxazolyl, benzothiazolyl, indenyl, phenyl-oxy-, C$_3$-cycloalkyl, C$_6$-cycloalkyl-C$_1$-alkoxy, cyclopropyl-, C$_6$-cycloalkenyl, is optionally substituted with one or two groups selected from Cl—, F—, Br—, I—, CF$_3$—, CF$_3$S—, CF$_3$O—, N(CH$_3$)$_2$S(=O)$_2$—, N(CH$_3$)$_2$C(O)—, benzyloxy-, —OH, CH$_3$O—, CH$_3$—, cyclopropyl-, cyclohexenyl, —NH—S(=O)$_2$—CH$_3$ or —CN.

In another embodiment, L is a group selected from —H, CF$_3$, phenyl, CF$_3$O—, CF$_3$S—, C$_6$-cycloalkyl-C$_1$-alkoxy, benzofuranyl, benzimidazolyl, benzoxazolyl, benzothiazolyl, indenyl, Br—, phenoxy-, phenoxy disubstituted with Cl—, cyclohexenyl, benzyl or benzyl disubstituted with Cl—.

In another embodiment, L is phenyl substituted with one or more groups selected from methyl, Cl—, F—, Br—, I—, CF$_3$—, N(CH$_3$)$_2$C(O)—, N(CH$_3$)$_2$S(=O)$_2$—, C$_6$-cycloalkyl-C$_1$-alkoxy, CF$_3$O—, CF$_3$S—, —OH, —NHS(=O)$_2$ CH$_3$, Br—, methoxy-, —CN or cyclopropyl.

In another embodiment, L is phenyl disubstituted with one or more groups selected from Cl—, F—, Cl— and F—, benzyloxy- and F—, —OH and F—, CF$_3$— and CF$_3$—, F— and CF$_3$—, Cl— and CF$_3$—, methoxy- and F—, —CN and F—, —CF$_3$ and —CH$_3$, —CH$_3$ and —Cl, or CH$_3$— and F—.

In another embodiment, L is phenyl substituted with methoxy- and disubstituted with fluoro.

In another embodiment, L is —H.

In one embodiment, Z is isoxazol-3,5-diyl.

In another embodiment, Z is isoxazol-3,5-diyl wherein, D is attached at position 5 of said isoxazol-3,5-diyl.

In another embodiment, Z is isoxazol-3,5-diyl wherein, D is attached at position 3 of said isoxazol-3,5-diyl.

In another embodiment, Z is —C(O)N(R$^2$)—; wherein said R$^2$ is hydrogen or C$_{1-3}$-alkyl.

In another embodiment, Z is —C(O)NH—.

In another embodiment, Z is —C(O)NCH$_3$—.

In another embodiment, Z is —C(O)NCH$_2$CH$_3$—.

In another embodiment, Z is —C(O)NCH$_2$CH$_2$CH$_3$—.

In one embodiment, R$^1$ is hydrogen, —F or optionally substituted C$_{1-3}$-alkyl.

In another embodiment, R$^1$ is —H.

In another embodiment, R$^1$ is —CH$_3$.

In another embodiment, R$^1$ is —CH$_2$CH$_3$.

In another embodiment, R$^1$ is —CH$_2$CH$_2$CH$_3$.

In another embodiment, R$^1$ is cyclopropyl.

In another embodiment, R$^1$ is —CF$_3$.

In another embodiment, R$^1$ is —CH$_2$CF$_3$.

In another embodiment, R$^1$ is —F.

In one embodiment, E is a group selected from a phenyl-C$_{2-6}$-alkenyl-, phenyl-C$_{2-6}$-alkynyl-, phenyl-C$_{3-8}$-cycloalkyl-, phenyl-$C_{3-8}$-cycloalkenyl-, biphenyl, heteroaryl-$C_{2-6}$-alkenyl-, heteroaryl-$C_{2-6}$-alkynyl-phenyl-, $C_{2-6}$-alkenyl-phenyl-, $C_{2-6}$-alkynyl-heteroaryl-, $C_{2-6}$-alkenyl-, $C_{2-6}$-alkynyl-heteroaryl-t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, or benzyl-, each optionally substituted; wherein each of said heteroaryl is a five- or six-membered heteroaryl.

In another embodiment, E is a group selected from phenyl, five- or six-membered heteroaryl, nine- or ten-membered bicyclic carbocyclic aryl, nine- or ten-membered bicyclic heteroaryl, t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, $C_{1-12}$-alkyl, $C_{2-12}$-alkenyl, $C_{2-12}$-alkynyl, $C_{3-8}$-cycloalkyl or $C_{4-8}$-cycloalkenyl; wherein said group is optionally substituted with one to six groups independently selected from halogen, —CN, —$C_{1-6}$-alkyl, halogen, —CHF$_2$, —CF$_3$, —OCF$_3$, —OCHF$_2$, —OCH$_2$CF$_3$, —OCF$_2$CHF$_2$, —SCF$_3$, —OR$^9$, —NR$^{10}$R$^{10}$, —SR$^9$, —S(O)R$^9$, —S(O)$_2$R$^9$, —C(O)NR$^{10}$R$^{10}$, —OC(O)NR$^{10}$R$^{10}$, —NR$^9$C(O)R$^9$, —OCH$_2$C(O)NR$^{10}$R$^{10}$, —C(O)R$^9$ or —C(O)OR$^9$, $C_{3-8}$-cycloalkyl, $C_{4-8}$-cycloalkenyl, optionally substituted phenyl or optionally substituted five- or six-membered heteroaryl; wherein, R$^9$ is independently selected from hydrogen, optionally substituted $C_{1-6}$-alkyl or optionally substituted aryl; wherein each R$^{10}$ is independently selected from hydrogen, optionally substituted $C_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, $C_{1-12}$-alkyl, $C_{2-12}$-alkenyl, $C_{2-12}$-alkynyl, $C_{3-8}$-cycloalkyl, $C_{4-8}$-cycloalkenyl or benzyl; wherein each group is optionally substituted with one to three groups independently selected from halogen, —CN, —$C_{1-6}$-alkyl, halogen, —CHF$_2$, —CF$_3$, —OCF$_3$, —OCHF$_2$, —OCH$_2$CF$_3$, —OCF$_2$CHF$_2$, —OR$^9$, —NR$^{10}$R$^{10}$, optionally substituted $C_{3-8}$-cycloalkyl, optionally substituted $C_{4-8}$-cycloalkenyl, optionally substituted phenyl, or optionally substituted five- or six-membered heteroaryl; wherein, R$^9$ is independently selected from hydrogen, optionally substituted $C_{1-6}$-alkyl or optionally substituted aryl; wherein each R$^{10}$ is independently selected from hydrogen, optionally substituted $C_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, phenyl-$C_{2-6}$-alkenyl-, phenyl-$C_{2-6}$-alkynyl-, phenyl-$C_{3-8}$-cycloalkyl, phenyl-$C_{5-8}$-cycloalkenyl-, heteroaryl-$C_{2-6}$-alkenyl-, heteroaryl-$C_{2-6}$-alkynyl-phenyl-, $C_{2-6}$-alkenyl-phenyl-, $C_{2-6}$-alkynyl-heteroaryl-, $C_{2-6}$-alkenyl-, $C_{2-6}$-alkynyl-heteroaryl-, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, or benzyl, each optionally substituted; wherein each of said heteroaryl is a five- or six-membered heteroaryl; wherein said group is substituted with one to six substituents independently selected from —$C_{1-6}$-alkyl, halogen, —CHF$_2$, —CF$_3$, —OCF$_3$, —OCHF$_2$, —OCH$_2$CF$_3$, —OCF$_2$CHF$_2$, —SCF$_3$, —OR$^9$, —NR$^{10}$R$^{10}$, —SR$^9$, —S(O)R$^9$, —S(O)$_2$R$^9$, —C(O)NR$^{10}$R$^{10}$, —OC(O)NR$^{10}$R$^{10}$, —NR$^9$C(O)R$^9$, —OCH$_2$C(O)NR$^{10}$R$^{10}$, —C(O)R$^9$ or —C(O)OR$^9$; wherein, R$^9$ is independently selected from hydrogen, optionally substituted $C_{1-6}$-alkyl or optionally substituted aryl; each R$^{10}$ is independently selected from hydrogen, optionally substituted $C_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl, biphenyl, naphthyl, benzothiophenyl, benzoisoxazolyl, pyridyl, pyrimidinyl, cyclohexenyl, isoxazolyl, $C_3$-$C_6$-cycloalkyl-alkyl-, alkyl, or benzyl; wherein said group is substituted with one to six substituents independently selected from $C_{1-6}$-alkyl, $C_{3-6}$-cycloalkyl, $C_3$-$C_6$-cycloalkyl-$C_1$-$C_6$-alkyl-, $C_{5-6}$-cycloalkenyl, phenyl, halogen, —CHF$_2$, —CF$_3$, —OCF$_3$, —OCHF$_2$, —OCH$_2$CF$_3$, —OCF$_2$CHF$_2$, —SCF$_3$, —OR$^9$, —NR$^{10}$R$^{10}$, —SR$^9$, —S(O)R$^9$, —S(O)$_2$R$^9$, —C(O)NR$^{10}$R$^{10}$, —OC(O)NR$^{10}$R$^{10}$, —NR$^9$C(O)R$^9$, —OCH$_2$C(O)NR$^{10}$R$^{10}$, —C(O)R$^9$ or —C(O)OR$^9$; wherein, R$^9$ is independently selected from hydrogen, optionally substituted $C_{1-6}$-alkyl or optionally substituted aryl; each R$^{10}$ is independently selected from hydrogen, optionally substituted $C_{1-6}$-alkyl, optionally substituted aryl or R$^{10}$R$^{10}$ together with the N to which they are attached form a 3 to 8 membered optionally substituted heterocyclic ring optionally containing one or two further heteroatoms independently selected from nitrogen, oxygen and sulfur, and optionally containing 0, 1 or 2 double bonds.

In another embodiment, E is a group selected from t-butylvinylphenyl, (S)-4-t-butylcyclohexenylphenyl, (R)-4-t-butylcyclohexenylphenyl, 4,4-dimethylcyclohexadienyl-phenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl, methyl-phenyl-, ethyl-phenyl-, n-propyl-phenyl-, isopropyl-phenyl-, cyclopropyl-phenyl-, cyclopropyl-methyl-phenyl-, cyclopropyl-ethyl-phenyl-, cyclopropyl-propyl-phenyl-, cyclopropyl-butyl-phenyl-, n-butyl-phenyl-, sec-butyl-phenyl-, t-butyl-phenyl-, cyclobutyl-phenyl-, cyclobutyl-methyl-phenyl-, cyclobutyl-ethyl-phenyl-, cyclobutyl-propyl-phenyl-, n-pentyl-phenyl-, neopentyl-phenyl-, isopentyl-phenyl-, cyclopentyl-phenyl-, cyclopentyl-methyl-phenyl-, cyclopentyl-ethyl-phenyl-, hexyl-phenyl-methyl-pentyl-phenyl-, ethyl-butyl-phenyl-cyclohexyl-phenyl-, ethenyl-phenyl-, n-propenyl-phenyl-, isopropenyl-phenyl-, n-butenyl-phenyl-, sec-butenyl-phenyl-, t-butenyl-phenyl-, cyclobutenyl-phenyl-, n-pentenyl-phenyl-, neopentenyl-phenyl-, isopentenyl-phenyl-, cyclopentenyl-phenyl-, hexenyl-phenyl-, cyclohexenyl-phenyl-, ethynyl-phenyl-, n-propynyl-phenyl-, isopropynyl-phenyl-, n-butynyl-phenyl-, sec-butynyl-phenyl-, t-butynyl-phenyl-, n-pentynyl and n-hexynyl-phenyl-; benzyl, methyl-benzyl-, ethyl-benzyl-, n-propyl-benzyl-, isopropyl-benzyl-, cyclopropyl-benzyl-, cyclopropyl-methyl-benzyl-, cyclopropyl-ethyl-benzyl-, cyclopropyl-propyl-benzyl-, cyclopropyl-butyl-benzyl-, n-butyl-benzyl-, sec-butyl-benzyl-, t-butyl-benzyl-, cyclobutyl-benzyl-, cyclobutyl-methyl-benzyl-, cyclobutyl-ethyl-benzyl-, cyclobutyl-propyl-benzyl-, n-pentyl-benzyl-, neopentyl-benzyl-, isopentyl-benzyl-, cyclopentyl-benzyl-, cyclopentyl-methyl-benzyl-, cyclopentyl-ethyl-benzyl-, hexyl-benzyl-, methyl-pentyl-benzyl-, ethyl-butyl-benzyl-cyclohexyl-benzyl-, ethenyl-benzyl-, n-propenyl-benzyl-, isopropenyl-benzyl-, n-butenyl-benzyl-, sec-butenyl-benzyl-, t-butenyl-benzyl-, cyclobutenyl-benzyl-, n-pentenyl-benzyl-, neopentenyl-benzyl-, isopentenyl-benzyl-, cyclopentenyl-benzyl-, hexenyl-benzyl-, cyclohexenyl-benzyl-, ethynyl-benzyl-, n-propynyl-benzyl-, isopropynyl-benzyl-, n-butynyl-benzyl-, sec-butynyl-benzyl-, t-butynyl-benzyl-, n-pentynyl and n-hexynyl-benzyl-;

wherein each group is optionally substituted with one to six groups independently selected from halogen, —CN, —$C_{1-6}$-alkyl, halogen, —$CHF_2$, —$CF_3$, —$OCF_3$, —$OCHF_2$, —$OCH_2CF_3$, —$OCF_2CHF_2$, —$SCF_3$, —$OR^9$, —$NR^{10}R^{10}$, —$SR^9$, —$S(O)R^9$, —$S(O)_2R^9$, —C(O)$NR^{10}R^{10}$, —OC(O)$NR^{10}R^{10}$, —$NR^9C(O)R^9$, —$OCH_2C(O)$$NR^{10}R^{10}$, —C(O)$R^9$ or —C(O)O$R^9$, $C_{3-8}$-cycloalkyl, $C_{4-8}$-cycloalkenyl, optionally substituted phenyl or optionally substituted five- or six-membered heteroaryl; wherein, $R^9$ is independently selected from hydrogen, optionally substituted $C_{1-6}$-alkyl or optionally substituted aryl; wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

In another embodiment, E is a group selected from t-butylvinylphenyl, (S)-4-t-butylcyclohexenylphenyl, (R)-4-t-butylcyclohexenylphenyl, 4,4-dimethylcyclohexadienyl-phenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, trifluoromethyl-phenyl-, trifluoromethoxy-phenyl-, trifluoromethylthio-phenyl-, halophenyl-, biphenyl-, cyclopropyl-phenyl-, cyclopropyl-propyl-phenyl-, t-butyl-phenyl-, cyclopentenyl-phenyl-, cyclohexyl-phenyl-, propenyl-phenyl-, cyclohexenyl-phenyl-, 3,3-dimethyl-but-1-enyl-phenyl-, 4,4-dimethyl-pent-1-enyl-phenyl-, 4,4-dimethyl-pent-2-enyl-phenyl-, n-hexyl-phenyl-, n-hexenyl-phenyl-, 3-methyl-benzothiophen-2-yl-, 3,5-dimethyl-isoxazol-4-yl-phenyl, 4-t-butyl-cyclohexen-1-yl-phenyl-, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, or 5,5-dimethyl-cyclohexa-1,3-dien-2-yl-phenyl-.

In another embodiment, E is a group selected from t-butylvinylphenyl, (S)-4-t-butylcyclohexenylphenyl, (R)-4-t-butylcyclohexenylphenyl, 4,4-dimethylcyclohexadienyl-phenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluoromethyl-thio-benzyl-, halobenzyl-, phenyl-benzyl-, cylcopropyl-benzyl-, cyclopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent-2-enyl-benzyl-, n-hexyl-benzyl-, n-hexenyl-benzyl- or dimethyl-isoxazol-4-yl-benzyl-.

In one embodiment, Y is —O—, —$CR^{26}R^{27}$— or —$CF_2$—; wherein $R^{26}$ is hydrogen or $C_{1-3}$-alkyl and wherein $R^{27}$ is hydrogen, $C_{1-3}$-alkyl, hydroxyl or fluoro.

In another embodiment, Y is —O— or —$CR^{26}R^{27}$—; wherein, $R^{27}$ is hydrogen or $C_{1-3}$-alkyl.

In another embodiment, Y is —O—.
In another embodiment, Y is —$CH_2$—.
In another embodiment, Y is —$CH(CH_3)$—.
In another embodiment, Y is —$CH(CH_2CH_3)$—.
In another embodiment, Y is —$CH(CH(CH_3)_2)$—.
In another embodiment, Y is —$C(CH_3)_2$—.
In another embodiment, Y is —$C(CH_3)(CH_2CH_3)$—.
In another embodiment, Y is —$C(CH_2CH_3)(CH_2CH_3)$—.
In another embodiment, Y is —$CF_2$—.
In another embodiment, Y is —CHF—.
In another embodiment, Y is —$CH(CF_3)$—.
In another embodiment, Y is —CH(OH)—.
In another embodiment, Y is —$C(CH_3)(OH)$—.
In another embodiment, Y is —$C(CF_3)(CH_3)$—.

In one embodiment, X is a group selected from phenylene, heterocyclic monoarylene, $C_{5-8}$-cycloalkylene or $C_{5-8}$-cycloalkenylene;

wherein said group is optionally substituted with one or two groups independently selected from halogen, —CN, —CF$_3$, —OCF$_3$, —OCHF$_2$, —NO$_2$, —OR$^{30}$, C$_{1-6}$-alkyl, C$_{2-6}$-alkenyl or C$_{1-6}$-alkynyl; wherein, R$^{30}$ is hydrogen or C$_{1-6}$-alkyl.

In another embodiment, X is a group selected from a phenylene, five- or six-membered heterocyclic mono-arylene, C$_{5-8}$-cycloalkylene or C$_{5-8}$-cycloalkenylene;

wherein said group is optionally substituted with one or two groups independently selected from halogen, —CN, —CF$_3$, —OCF$_3$, —OCHF$_2$, —OCH$_2$CF$_3$, —NO$_2$, —OH, —OCH$_3$, —OCH$_2$CH$_3$, —OCH$_2$CH$_2$CH$_3$, —CH$_3$, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl, C$_6$-alkenyl, C$_1$-alkynyl, C$_2$-alkynyl, C$_3$-alkynyl, C$_4$-alkynyl or C$_5$-alkynyl C$_6$-alkynyl.

In another embodiment, X is a group selected from phenylene, five- or six-membered heterocyclic mono-arylene, C$_{5-8}$-cycloalkylene or C$_{5-8}$-cycloalkenylene;

wherein said group is optionally substituted with one or two groups independently selected from halogen, —CN, —CF$_3$, —OCF$_3$, —OCHF$_2$, —OCH$_2$CF$_3$, —OH, —OCH$_3$, —OCH$_2$CH$_3$, —OCH$_2$CH$_2$CH$_3$, —CH$_3$, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl, C$_6$-alkenyl.

In another embodiment, X is a group selected from furanylene, thiophenylene, oxazolylene, thiazolylene, phenylene, pyridylene or pyrimidinylene;

wherein said group is optionally substituted with one or two groups independently selected from halogen, —CN, —CF$_3$, —OCF$_3$, —OCHF$_2$, —OCH$_2$CF$_3$, —OH, —OCH$_3$, —OCH$_2$CH$_3$, —OCH$_2$CH$_2$CH$_3$, —CH$_3$, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl, C$_6$-alkenyl.

In another embodiment, X is phenylene;

wherein said phenyl is optionally substituted with one or two groups independently selected from halogen, —CN, —CF$_3$, —OCF$_3$, —OCHF$_2$, —OCH$_2$CF$_3$, —OH, —OCH$_3$, —OCH$_2$CH$_3$, —OCH$_2$CH$_2$CH$_3$, —CH$_3$, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl, C$_6$-alkenyl.

In another embodiment, X is phenylene.

In one embodiment M is —NHC(O)—.
In another embodiment M is —N(CH$_3$)C(O)—.
In another embodiment M is —N(CH$_2$CH$_3$)C(O)—.
In another embodiment M is —N(CH$_2$CH$_2$CH$_3$)C(O)—.
In another embodiment M is —N(C$_{4-8}$-alkyl)C(O)—.
In another embodiment M is —C(O)NH—.
In another embodiment M is —C(O)N(CH$_3$)—.
In another embodiment M is —C(O)N(CH$_2$CH$_3$)—.
In another embodiment M is —C(O)N(CH$_2$CH$_2$CH$_3$)—.
In another embodiment M is —C(O)N(C$_{4-6}$-alkyl)-.
In another embodiment M is —NHS(O)$_2$—.
In another embodiment M is —N(CH$_3$)S(O)$_2$—.
In another embodiment M is —N(CH$_2$CH$_3$)S(O)$_2$—.
In another embodiment M is —N(CH$_2$CH$_2$CH$_3$)S(O)$_2$—.
In another embodiment M is —N(C$_{4-6}$-alkyl)S(O)$_2$—.
In another embodiment M is —S(O)$_2$NH—.
In another embodiment M is —S(O)$_2$N(CH$_3$)—.
In another embodiment M is —S(O)$_2$N(CH$_2$CH$_3$)—.
In another embodiment M is —S(O)$_2$N(CH$_2$CH$_2$CH$_3$)—.
In another embodiment M is —S(O)$_2$N(C$_{4-6}$-alkyl)-.
In another embodiment M is —NHC(S)—.
In another embodiment M is —N(CH$_3$)C(S)—.
In another embodiment M is —N(CH$_2$CH$_3$)C(S)—.
In another embodiment M is —N(CH$_2$CH$_2$CH$_3$)C(S)—.
In another embodiment M is —N(C$_{4-6}$-alkyl)C(S)—.
In another embodiment M is —C(S)NH—.
In another embodiment M is —C(S)N(CH$_3$)—.
In another embodiment M is —C(S)N(CH$_2$CH$_3$)—.
In another embodiment M is —C(S)N(CH$_2$CH$_2$CH$_3$)—.
In another embodiment M is —C(S)N(C$_{4-6}$-alkyl)-.
In another embodiment M is —O—.
In another embodiment M is —S—.
In another embodiment M is —S(O)$_2$—.

In one embodiment, T is absent and A is connected directly to M.

In another embodiment, T is —CHR$^{30}$—, wherein R$^{30}$ is —H or C$_{1-3}$-alkyl.
In another embodiment, T is —CHR$^{30}$CHR$^{30}$—, wherein R$^{30}$ is —H or C$_{1-3}$-alkyl.
In another embodiment, T is —CHR$^{30}$CHR$^{30}$CHR$^{30}$—, wherein R$^{30}$ is —H or C$_{1-3}$-alkyl.
In another embodiment, T is —CHR$^{30}$CHR$^{30}$CHR$^{30}$—, wherein R$^{30}$ is —H or —CH$_3$.
In another embodiment, T is —CH$_2$—.
In another embodiment, T is —CH$_2$CH$_2$—.
In another embodiment, T is —CH$_2$CH$_2$CH$_2$—.
In another embodiment, T is —C(CH$_3$)H—.
In another embodiment, T is —C(CF$_3$)H—.
In another embodiment, T is —C(CH$_3$)HCH$_2$—.
In another embodiment, T is —C(CF$_3$)HCH$_2$—.
In another embodiment, T is —C(CH$_3$)HCH$_2$CH$_2$—.
In another embodiment, T is —C(CF$_3$)HCH$_2$CH$_2$—.
In another embodiment, T is —CH$_2$C(CH$_3$)H—.
In another embodiment, T is —CH$_2$C(CF$_3$)H—.
In another embodiment, T is —CH$_2$C(CH$_3$)HCH$_2$—.
In another embodiment, T is —CH$_2$CH$_2$C(CH$_3$)H—.
In another embodiment, T is —CH(CH$_3$)CH(CH$_3$)—.
In another embodiment, T is —CH(CH$_3$)CH(CH$_3$)CH$_2$—.
In another embodiment, T is —CH(CH$_3$)CH$_2$CH(CH$_3$)—.
In another embodiment, T is —CH$_2$C(CH$_3$)HC(CH$_3$)H—.
In another embodiment, T is —CH(CH$_2$CH$_3$)CH$_2$—.
In another embodiment, T is —C(CH$_2$CH$_3$)H—.
In another embodiment, T is —C(CH$_2$CH$_2$CH$_3$)H—.
In another embodiment, T is —C(CH$_2$CH$_2$CH$_3$)HCH$_2$—.
In another embodiment, T is —CH$_2$C(CH$_2$CH$_3$)H—.
In another embodiment, T is —CH$_2$C(CH$_2$CH$_2$CH$_3$)H—.

In another embodiment, T is a phenylene or a five- or a six-membered heterocyclic monoarylene ring.
In another embodiment, T is oxazolylene.
In another embodiment, T is phenylene.
In another embodiment, T is pyridylene.
In another embodiment, T is pyrimidinylene.

In one embodiment, A is —(CHR$^{36}$)$_m$R$^5$; wherein, R$^5$ is —P(O)(OH)$_2$, —P(O)[—O-alk-SC(O)R$^{53}$]$_2$, —P(O)[—OCR$^z_2$OC(O)R$^y$]$_2$, —P(O)[—OCR$^z_2$OC(O)OR$^y$]$_2$, —P(O)[—N(H)CR$^z_2$C(O)OR$^y$]$_2$, —P(O)[—N(H)CR$^z_2$C(O)OR$^y$][-GR$^{21}$], —P(O)[—OCH(V)CH$_2$CH$_2$O—], —P(O)(OH)(GR$^{21}$), —P(O)(OR$^e$)(OR$^e$), —P(O)[—OCR$^z_2$OC(O)R$^y$](OR$^e$), —P(O)[—OCR$^z_2$OC(O)OR$^y$](OR$^e$), or —P(O)[—N(H)CR$^z_2$C(O)OR$^y$](OR$^e$); V is aryl or heteroaryl, each optionally substituted; R$^e$ is —C$_1$-C$_{12}$ alkyl, —C$_2$-C$_{12}$ alkenyl, —C$_2$-C$_{12}$ alkynyl, —(CR$^{57}_2$)$_n$aryl, —(CR$^{57}_2$)$_n$cycloalkyl, or —(CR$^{57}_2$)$_n$heterocycloalkyl, each optionally substituted; G is —O— or —NR$^v$—; when G is —O—, R$^{21}$ attached to —O— is independently selected from —H, alkyl, optionally substituted aryl, optionally substituted heterocycloalkyl, optionally substituted —CH$_2$-heterocycloakyl wherein the cyclic moiety contains a carbonate or thiocarbonate, optionally substituted -alkylaryl, —C(R$^z$)$_2$OC(O)NR$^z_2$, —NR$^z$—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—

C(O)R$^y$, -alkyl-S—S-alkylhydroxy, and -alkyl-S—S—S-alkylhydroxy; or when G is —NR$^v$—, then R$^{21}$ attached to —NR$^v$— is independently selected from —H, —[C(R$^z$)$_2$]$_r$, —COOR$^y$, —C(R$^x$)$_2$COOR$^y$, —[C(R$^z$)$_2$]$_r$—C(O)SR$^y$, and -cycloalkylene-COOR$^y$; and R$^v$ is —H, lower alkyl, acyloxyalkyl, alkoxycarbonyloxyalkyl, lower acyl, C$_{1-6}$-perfluoroalkyl or NH(CR$^{43}$R$^{43}$)$_f$CH$_3$;

each R$^{57}$ is independently selected from the group consisting of hydrogen, optionally substituted —C$_1$-C$_4$ alkyl, halogen, optionally substituted —O—C$_1$-C$_4$ alkyl, —OCF$_3$, optionally substituted —S—C$_1$-C$_4$ alkyl, —NR$^{58}$R$^{59}$, optionally substituted —C$_2$-C$_4$ alkenyl, and optionally substituted —C$_2$-C$_4$ alkynyl; wherein, when one R$^{57}$ is attached to C through an O, S, or N atom, then the other R$^{57}$ attached to the same C is a hydrogen, or attached via a carbon atom;

R$^{58}$ is selected from hydrogen and optionally substituted —C$_1$-C$_4$ alkyl; and, R$^{59}$ is selected from the group consisting of hydrogen and optionally substituted —C$_1$-C$_4$ alkyl, optionally substituted —C(O)—C$_1$-C$_4$ alkyl and —C(O)H.

In another embodiment, A is —(CHR$^{36}$)$_m$R$^5$; R$^5$ is —PO$_3$H$_2$, —P(O)[—OCR$^z$$_2$OC(O)R$^y$]$_2$, —P(O)[—OCR$^z$$_2$OC(O)OR$^y$]$_2$, —P(O)[—N(H)CR$^z$$_2$C(O)OR$^y$]$_2$, —P(O)[—N(H)CR$^z$$_2$C(O)OR$^y$][—OR$^6$], —P(O)[—OCH(V)CH$_2$CH$_2$O—], —P(O)(OR$^e$)(OR$^e$), —P(O)[—OCR$^z$$_2$OC(O)R$^y$](OR$^e$), —P(O)[—OCR$^z$$_2$OC(O)OR$^y$](OR$^e$), —P(O)[—N(H)CR$^z$$_2$C(O)OR$^y$](OR$^e$) or —P(O)(OH)(NH$_2$); V is aryl or heteroaryl, each optionally substituted; R$^e$ is —C$_1$-C$_{12}$ alkyl, —C$_2$-C$_{12}$ alkenyl, —C$_2$-C$_{12}$ alkynyl, —(CR$^a$$_2$)$_n$aryl, —(CR$^a$$_2$)$_n$cycloalkyl, or —(CR$^a$$_2$)$_n$heterocycloalkyl, each optionally substituted; R$^6$ is alkyl, aryl, —OH, —NH$_2$ or —OR$^7$; and R$^7$ is alkyl, aryl, alicyclic or aralkyl.

In another embodiment, A is —(CHR$^{36}$)$_m$R$^5$; and R$^5$ is —P(O)(OH)$_2$, —P(O)[—OCH$_2$OC(O)-t-butyl]$_2$, —P(O)[—OCH$_2$OC(O)O-i-propyl]$_2$, —P(O)[—N(H)CH(CH$_3$)C(O)OCH$_2$CH$_3$]$_2$, —P(O)[—N(H)C(CH$_3$)$_2$C(O)OCH$_2$CH$_3$]$_2$, —P(O)[—N(H)CH(CH$_3$)C(O)OCH$_2$CH$_3$][3,4-methylenedioxyphenyl], —P(O)[—N(H)C(CH$_3$)$_2$C(O)OCH$_2$CH$_3$][3,4-methylenedioxyphenyl], —P(O)[—OCH(3-chlorophenyl)CH$_2$CH$_2$O—], —P(O)[—OCH(pyrid-4-yl)CH$_2$CH$_2$O—], —P(O)[—OCH$_2$OC(O)-t-butyl](OCH$_3$), —P(O)[—OCH$_2$OC(O)O-i-propyl](OCH$_3$), —P(O)[—OCH(CH$_3$)OC(O)-t-butyl](OCH$_3$), —P(O)[—OCH(CH$_3$)OC(O)O-i-propyl](OCH$_3$), —P(O)[—N(H)CH(CH$_3$)C(O)OCH$_2$CH$_3$](OCH$_3$), —P(O)[—N(H)C(CH$_3$)$_2$C(O)OCH$_2$CH$_3$](OCH$_3$) or —P(O)(OH)(NH$_2$).

In another embodiment, A is —(CHR$^{36}$)$_m$R$^5$; G and G' are each independently selected from —O— and —NR$^v$—; and together R$^{21}$ and R$^{21}$ are the group

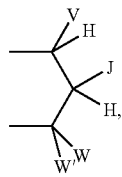

wherein, V is substituted aryl or substituted heteroaryl.

In a further embodiment, J is —H, W is —H, and W' is —H.

In a further embodiment, V is 3-chlorophenyl, 4-chlorophenyl, 3-bromophenyl, 3-fluorophenyl, pyrid-4-yl, pyrid-3-yl or 3,5-dichlorophenyl.

In a further embodiment, the relative stereochemistry between the V-group substituent and the carbon attached to the P atom of R$^5$ is cis.

In a further embodiment, the relative stereochemistry between the V-group substituent and the carbon attached to the P atom of R$^5$ is trans.

In a further embodiment, said compound has R stereochemistry at the carbon where the V-group is attached.

In a further embodiment, the compound has S stereochemistry at the carbon where the V-group is attached.

In another embodiment, A is —(CHR$^{36}$)$_m$ SO$_2$OR$^{40}$, wherein R$^{40}$ is nitrophenyl.

In another embodiment, A is —(CHR$^{36}$)$_m$ SO$_3$H, —(CHR$^{36}$)$_m$ QSO$_2$R$^{39}$ or —(CHR$^{36}$)$_q$ tetrazol-5-yl; m is 1, 2 or 3; q is 0, 1, 2 or 3; R$^{36}$ is hydrogen, hydroxyl, —OR$^{38}$, fluoro or —(CH$_2$)$_p$OR$^{38}$; Q is oxygen or NH; wherein R$^{38}$ is C$_{1-3}$-alkyl, CF$_3$, CHF$_2$, CH$_2$CF$_3$ or C$_{2-3}$-perfluoroalkyl and R$^{39}$ is OH or NH$_2$.

In another embodiment, A is —(CHR$^{36}$)$_m$SO$_3$H, —(CHR$^{36}$)$_m$QSO$_3$H or —(CHR)$_q$tetrazol-5-yl; m is 1 or 2; q is 0 or 1; R$^{36}$ is hydrogen or hydroxyl; and Q is oxygen.

In another embodiment, A is —(CH$_2$)$_m$SO$_3$H, —(CH$_2$)$_m$QSO$_3$H or —(CH$_2$)$_q$ tetrazol-5-yl; T is absent; R$^{36}$ is —H, C$_{1-6}$-alkyl or —(CH$_2$)$_p$OR$^{38}$, m is 1 or 2; q is 0 or 1; and Q is —NH; wherein R$^{38}$ is C$_{1-3}$-alkyl, CF$_3$, CHF$_2$, CH$_2$CF$_3$ or C$_{2-3}$-perfluoroalkyl.

In another embodiment, A is —(CH$_2$)$_m$CO$_2$H.

In another embodiment, T is absent and A is a group selected from —(CHR$^{36}$)$_m$CO$_2$H, —(CHR$^{36}$)$_m$SO$_3$H, —(CHR$^{36}$)$_m$QSO$_2$R$^{39}$ or —(CHR$^{36}$)$_q$ tetrazol-5-yl.

In another embodiment, T is absent and A is —CHR$^{13}$CO$_2$H; wherein R$^{13}$ is a group selected from hydrogen, C$_{1-3}$-alkyl, C$_{1-3}$-haloalkyl, hydroxyl, chloro or fluoro.

In another embodiment, T is absent and A is —(CHR$^{13}$)$_2$CO$_2$H; wherein R$^{13}$ is a group selected from hydrogen, C$_{1-3}$-alkyl, C$_{1-3}$-haloalkyl, hydroxyl, chloro or fluoro.

In another embodiment, T is absent and A is —(CHR$^{13}$)$_3$CO$_2$H; wherein R$^{13}$ is a group selected from hydrogen, C$_{1-3}$-alkyl, C$_{1-3}$-haloalkyl, hydroxyl, chloro or fluoro.

In another embodiment, T is absent and A is —CHR$^{13}$SO$_3$H; wherein R$^{13}$ is a group selected from hydrogen, C$_{1-3}$-alkyl, C$_{1-3}$-haloalkyl, hydroxyl, chloro or fluoro.

In another embodiment, T is absent and A is —(CHR$^{13}$)$_2$SO$_3$H; wherein R$^{13}$ is a group selected from hydrogen, C$_{1-3}$-alkyl, C$_{1-3}$-haloalkyl, hydroxyl, chloro or fluoro.

In another embodiment, T is absent and A is —(CHR$^{13}$)$_3$SO$_3$H; wherein R$^{13}$ is a group selected from hydrogen, C$_{1-3}$-alkyl, C$_{1-3}$-haloalkyl, hydroxyl, chloro or fluoro.

In another embodiment, T is absent and A is —CHR$^{13}$SO$_3$H; wherein R$^{13}$ is a group selected from hydrogen, C$_1$-alkyl, C$_1$-haloalkyl, hydroxyl, chloro or fluoro.

In another embodiment, T is absent and A is —(CHR$^{13}$)$_2$SO$_3$H; wherein R$^{13}$ is a group selected from hydrogen, C$_1$-alkyl, C$_1$-haloalkyl, hydroxyl, chloro or fluoro.

In another embodiment, T is absent and A is —(CHR$^{13}$)$_3$SO$_3$H; wherein R$^{13}$ is a group selected from hydrogen, C$_1$-alkyl, C$_1$-haloalkyl, hydroxyl, chloro or fluoro.

In another embodiment, T is absent and A is —(CHR$^{13}$)$_2$SO$_3$H; wherein R$^{13}$ is a group selected from hydrogen, C$_{1-3}$-alkyl, chloro or fluoro.

In another embodiment, T is absent and A is —(CHR$^{13}$)$_2$SO$_3$H; wherein R$^{13}$ is a group selected from hydrogen, C$_{1-3}$-alkyl or C$_{1-3}$-haloalkyl.

In another embodiment, T is absent and A is —(CHR$^{13}$)$_2$SO$_3$H; wherein R$^{13}$ is a group selected from hydrogen, C$_{1-3}$-alkyl, C$_{1-3}$-haloalkyl, hydroxyl.

In another embodiment, T is absent and A is —(CHR$^{13}$)$_2$SO$_3$H; wherein R$^{13}$ is a group selected from hydrogen, C$_{1-3}$-alkyl hydroxyl.

In another embodiment, T is absent and A is —(CHR$^{13}$)$_2$SO$_3$H; wherein R$^{13}$ is a group selected from hydrogen C$_{1-3}$-haloalkyl, hydroxyl, chloro or fluoro.

In another embodiment, T is absent and A is —(CHR$^{13}$)$_2$SO$_3$H; wherein R$^{13}$ is a group selected from hydrogen or hydroxyl.

In another embodiment, T is absent and A is —(CHR$^{13}$)$_2$SO$_3$H; wherein R$^{13}$ is a group selected from hydrogen, hydroxyl, chloro or fluoro.

In another embodiment, T is absent and A is —(CHR$^{13}$)$_2$SO$_3$H; wherein R$^{13}$ is a group selected from hydrogen chloro or fluoro.

In another embodiment, T is absent and A is —CHR$^{13}$SO$_3$H; wherein R$^{13}$ is a group selected from hydrogen, C$_{1-3}$-alkyl, chloro or fluoro.

In another embodiment, T is absent and A is —CHR$^{13}$SO$_3$H; wherein R$^{13}$ is a group selected from hydrogen, C$_{1-3}$-alkyl or C$_{1-3}$-haloalkyl.

In another embodiment, T is absent and A is —CHR$^{13}$SO$_3$H; wherein R$^{13}$ is a group selected from hydrogen, C$_{1-3}$-alkyl, C$_{1-3}$-haloalkyl, hydroxyl.

In another embodiment, T is absent and A is —CHR$^{13}$SO$_3$H; wherein R$^{13}$ is a group selected from hydrogen, C$_{1-3}$-alkyl hydroxyl.

In another embodiment, T is absent and A is —CHR$^{13}$SO$_3$H; wherein R$^{13}$ is a group selected from hydrogen C$_{1-3}$-haloalkyl, hydroxyl, chloro or fluoro.

In another embodiment, T is absent and A is —CHR$^{13}$SO$_3$H; wherein R$^{13}$ is a group selected from hydrogen hydroxyl.

In another embodiment, T is absent and A is —CHR$^{13}$SO$_3$H; wherein R$^{13}$ is a group selected from hydrogen hydroxyl.

In another embodiment, T is absent and A is —CHR$^{13}$SO$_3$H; wherein R$^{13}$ is a group selected from hydrogen chloro or fluoro.

In another embodiment, A is —(CHR$^{36}$)$_m$CO$_2$H, wherein R$^{36}$ is R$^{36}$ is —H, C$_{1-6}$-alkyl or —(CH$_2$)$_p$OR$^{38}$, m is 1 or 2; q is 0 or 1; and Q is —NH; wherein R$^{38}$ is C$_{1-3}$-alkyl, CF$_3$, CHF$_2$, CH$_2$CF$_3$, or C$_{2-3}$-perfluoroalkyl.

In another embodiment, A is —CO$_2$H.

In another embodiment, T is absent and A is —CO$_2$H.

In another embodiment, T is absent and A is —CH$_2$CO$_2$H.

In another embodiment, T is absent and A is —CH$_2$CH$_2$CO$_2$H.

In another embodiment, T is absent and A is —CH$_2$CH(OH)CO$_2$H.

In another embodiment, T is absent and A is —CH$_2$CH$_2$CH$_2$CO$_2$H.

In another embodiment, T is absent and A is —C(CH$_3$)HCO$_2$H.

In another embodiment, T is absent and A is —C(CF$_3$)HCO$_2$H.

In another embodiment, T is absent and A is —C(CH$_3$)HCH$_2$CO$_2$H.

In another embodiment, T is absent and A is —C(CF$_3$)HCH$_2$CO$_2$H.

In another embodiment, T is absent and A is —C(CH$_3$)HCH$_2$CH$_2$CO$_2$H.

In another embodiment, T is absent and A is —C(CF$_3$)HCH$_2$CH$_2$CO$_2$H.

In another embodiment, T is absent and A is —CH$_2$C(CH$_3$)HCO$_2$H.

In another embodiment, T is absent and A is —CH$_2$C(CF$_3$)HCO$_2$H.

In another embodiment, T is absent and A is —CH$_2$C(CH$_3$)HCH$_2$CO$_2$H.

In another embodiment, T is absent and A is —CH$_2$CH$_2$C(CH$_3$)HCO$_2$H.

In another embodiment, T is absent and A is —CH(CH$_3$)CH(CH$_3$)CO$_2$H.

In another embodiment, T is absent and A is —CH(CH$_3$)CH$_2$CO$_2$H.

In another embodiment, T is absent and A is —CH(CH$_3$)CH(CH$_3$)CO$_2$H.

In another embodiment, T is absent and A is —CH$_2$C(CH$_3$)HC(CH$_3$)HCO$_2$H.

In another embodiment, T is absent and A is —CH(CH$_2$CH$_3$)CH$_2$CO$_2$H.

In another embodiment, T is absent and A is —C(CH$_2$CH$_3$)HCO$_2$H.

In another embodiment, T is absent and A is —C(CH$_2$CH$_2$CH$_3$)HCO$_2$H.

In another embodiment, T is absent and A is —C(CH$_2$CH$_2$CH$_3$)HCH$_2$CO$_2$H.

In another embodiment, T is absent and A is —CH$_2$C(CH$_2$CH$_3$)HCO$_2$H.

In another embodiment, T is absent and A is —CH$_2$C(CH$_2$CH$_2$CH$_3$)HCO$_2$H.

In another embodiment, Z is isoxazolyl, A is —(CHR$^{36}$)$_m$CO$_2$H, wherein R$^{36}$ is —H, C$_{1-6}$-alkyl or —(CH$_2$)$_p$OR$^{38}$, m is 1 or 2; q is 0 or 1; and Q is —NH; wherein R$^{38}$ is C$_{1-3}$-alkyl, CF$_3$, CHF$_2$, CH$_2$CF$_3$ or C$_{2-3}$-perfluoroalkyl.

In another embodiment, Z is isoxazolyl, A is —CO$_2$H.

In another embodiment, Z is isoxazolyl, T is absent and A is —CO$_2$H.

In another embodiment, Z is isoxazolyl, T is absent and A is —CH$_2$CO$_2$H.

In another embodiment, Z is isoxazolyl, T is absent and A is —CH$_2$CH$_2$CO$_2$H.

In another embodiment, Z is isoxazolyl. T is absent and A is —CH$_2$CH(OH)CO$_2$H.

In another embodiment, Z is isoxazolyl, T is absent and A is —CH$_2$CH$_2$CH$_2$CO$_2$H.

In another embodiment, Z is isoxazolyl, T is absent and A is —C(CH$_3$)HCO$_2$H.

In another embodiment, Z is isoxazolyl, T is absent and A is —C(CF$_3$)HCO$_2$H.

In another embodiment, Z is isoxazolyl, T is absent and A is —C(CH$_3$)HCH$_2$CO$_2$H.

In another embodiment, Z is isoxazolyl, T is absent and A is —C(CF$_3$)HCH$_2$CO$_2$H.

In another embodiment, Z is isoxazolyl, T is absent and A is —C(CH$_3$)HCH$_2$CH$_2$CO$_2$H.

In another embodiment, Z is isoxazolyl, T is absent and A is —C(CF$_3$)HCH$_2$CH$_2$CO$_2$H.

In another embodiment, Z is isoxazolyl, T is absent and A is —CH$_2$C(CH$_3$)HCO$_2$H.

In another embodiment, Z is isoxazolyl, T is absent and A is —CH$_2$C(CF$_3$)HCO$_2$H.

In another embodiment, Z is isoxazolyl, T is absent and A is —CH$_2$C(CH$_3$)HCH$_2$CO$_2$H.

In another embodiment, Z is isoxazolyl, T is absent and A is —CH$_2$CH$_2$C(CH$_3$)HCO$_2$H.

In another embodiment, Z is isoxazolyl, T is absent and A is —CH(CH$_3$)CH(CH$_3$)CO$_2$H.

In another embodiment, Z is isoxazolyl, T is absent and A is —CH(CH$_3$)CH(CH$_3$)CH$_2$CO$_2$H.

In another embodiment, Z is isoxazolyl, T is absent and A is —CH(CH$_3$)CH$_2$CH(CH$_3$)CO$_2$H.

In another embodiment, Z is isoxazolyl, T is absent and A is —CH$_2$CH(CH$_3$)CH(CH$_3$)CO$_2$H.
In another embodiment, Z is isoxazolyl, T is absent and A is —CH(CH$_2$CH$_3$)CH$_2$CO$_2$H.
In another embodiment, Z is isoxazolyl, T is absent and A is —CH(CH$_2$CH$_3$)CO$_2$H.
In another embodiment, Z is isoxazolyl, T is absent and A is —CH(CH$_2$CH$_2$CH$_3$)CO$_2$H.
In another embodiment, Z is isoxazolyl, T is absent and A is —CH(CH$_2$CH$_2$CH$_3$)CH$_2$CO$_2$H.
In another embodiment, Z is isoxazolyl, T is absent and A is —CH$_2$CH(CH$_2$CH$_3$)CO$_2$H.
In another embodiment, Z is isoxazolyl, T is absent and A is —CH$_2$CH(CH$_2$CH$_2$CH$_3$)CO$_2$H.
In another embodiment, A is —(CHR$^{36}$)$_m$SO$_3$H.
In another embodiment, A is —SO$_3$H.
In another embodiment, T is absent and A is —SO$_3$H.
In another embodiment, T is absent and A is —CH$_2$SO$_3$H.
In another embodiment, T is absent and A is —CH$_2$CH$_2$SO$_3$H.
In another embodiment, T is absent and A is —CH$_2$CH$_2$CH$_2$SO$_3$H.
In another embodiment, T is absent and A is —C(CH$_3$)HSO$_3$H.
In another embodiment, T is absent and A is —C(CF$_3$)HSO$_3$H.
In another embodiment, T is absent and A is —C(CH$_3$)HCH$_2$SO$_3$H.
In another embodiment, T is absent and A is —C(CF$_3$)HCH$_2$SO$_3$H.
In another embodiment, T is absent and A is —C(CH$_3$)HCH$_2$CH$_2$SO$_3$H.
In another embodiment, T is absent and A is —C(CF$_3$)HCH$_2$CH$_2$SO$_3$H.
In another embodiment, T is absent and A is —CH$_2$C(CH$_3$)HSO$_3$H.
In another embodiment, T is absent and A is —CH$_2$C(CF$_3$)HSO$_3$H.
In another embodiment, T is absent and A is —CH$_2$C(CH$_3$)HCH$_2$SO$_3$H.
In another embodiment, T is absent and A is —CH$_2$CH$_2$C(CH$_3$)HSO$_3$H.
In another embodiment, T is absent and A is —CH(CH$_3$)CH(CH$_3$)SO$_3$H.
In another embodiment, T is absent and A is —CH(CH$_3$)CH(CH$_3$)CH$_2$SO$_3$H.
In another embodiment, T is absent and A is —CH(CH$_3$)CH$_2$CH(CH$_3$)SO$_3$H.
In another embodiment, T is absent and A is —CH$_2$C(CH$_3$)HC(CH$_3$)HSO$_3$H.
In another embodiment, T is absent and A is —CH(CH$_2$CH$_3$)CH$_2$SO$_3$H.
In another embodiment, T is absent and A is —C(CH$_2$CH$_3$)HSO$_3$H.
In another embodiment, T is absent and A is —C(CH$_2$CH$_2$CH$_3$)HSO$_3$H.
In another embodiment, T is absent and A is —C(CH$_2$CH$_2$CH$_3$)H, —CH$_2$SO$_3$H.
In another embodiment, T is absent and A is —CH$_2$C(CH$_2$CH$_3$)HSO$_3$H.
In another embodiment, T is absent and A is —CH$_2$C(CH$_2$CH$_2$CH$_3$)HSO$_3$H.
In another embodiment, T is absent and A is —(CHR$^{36}$)$_m$QSO$_2$R$^{39}$.
In another embodiment, T is absent and A is —CHR$^{36}$QSO$_2$R$^{39}$.
In another embodiment, T is absent and A is —(CHR$^{36}$)$_2$QSO$_2$R$^{39}$.
In another embodiment, T is absent and A is —(CHR$^{36}$)$_3$QSO$_2$R$^{39}$.
In another embodiment, T is absent and A is —(CHR$^{36}$)$_m$OSO$_2$R$^{39}$.
In another embodiment, T is absent and A is —(CHR$^{36}$)$_m$OSO$_2$OH.
In another embodiment, T is absent and A is —(CHR$^{36}$)$_m$OSO$_2$NHOH.
In another embodiment, T is absent and A is —(CHR$^{36}$)$_m$OSO$_2$NH$_2$.
In another embodiment, T is absent and A is —(CHR$^{36}$)$_m$NR$^{43}$SO$_2$R$^{39}$.
In another embodiment, T is absent and A is —(CHR$^{36}$)$_m$N(C$_{1-3}$-alkyl)HSO$_2$R$^{39}$.
In another embodiment, T is absent and A is —(CHR$^{36}$)$_m$N(C$_{1-3}$-alkyl)$_2$SO$_2$R$^{39}$.
In another embodiment, T is absent and A is —(CHR$^{36}$)$_m$NR$^{43}$SO$_2$OH.
In another embodiment, T is absent and A is —(CHR$^{36}$)$_m$N(C$_{1-3}$-alkyl)HSO$_2$OH.
In another embodiment, T is absent and A is —(CHR$^{36}$)$_m$N(C$_{1-3}$-alkyl)$_2$SO$_2$OH.
In another embodiment, T is absent and A is —(CHR$^{36}$)$_m$NR$^{43}$SO$_2$NHOH.
In another embodiment, T is absent and A is —(CHR$^{36}$)$_m$N(C$_{1-3}$-alkyl)HSO$_2$NHOH.
In another embodiment, T is absent and A is —(CHR$^{36}$)$_m$N(C$_{1-3}$-alkyl)$_2$SO$_2$NHOH.
In another embodiment, T is absent and A is —(CHR$^{36}$)$_m$NR$^{43}$SO$_2$NH$_2$.
In another embodiment, T is absent and A is —(CHR$^{36}$)$_m$N(C$_{1-3}$-alkyl)HSO$_2$NH$_2$.
In another embodiment, T is absent and A is —(CHR$^{36}$)$_m$N(C$_{1-3}$-alkyl)$_2$SO$_2$NH$_2$.
In another embodiment, T is absent and A is —(CHR$^{36}$)$_q$tetrazol-5-yl.
In another embodiment, T is absent and A is -tetrazol-5-yl.
In another embodiment, T is absent and A is —CHR$^{36}$-tetrazol-5-yl.
In another embodiment, T is absent and A is —(CHR$^{36}$)$_2$tetrazol-5-yl.
In another embodiment, T is absent and A is —(CHR$^{36}$)$_3$tetrazol-5-yl.
In another embodiment, T is absent and A is —CH(C$_{1-6}$-alkyl)-tetrazol-5-yl.
In another embodiment, T is absent and A is —CH(C$_{1-3}$-alkyl)-tetrazol-5-yl.
In another embodiment, T is absent and A is —CH(OH)-tetrazol-5-yl.
In another embodiment, T is absent and A is —CH(OC$_{1-3}$-alkyl)-tetrazol-5-yl.
In another embodiment, T is absent and A is —CH(CH$_2$OC$_{1-3}$-alkyl)-tetrazol-5-yl.
In another embodiment, T is absent and A is —CH(OH)-tetrazol-5-yl.
In another embodiment, T is absent and A is —CH(CH$_2$OH)-tetrazol-5-yl.
In another embodiment, T is absent and A is —CHF-tetrazol-5-yl.
In another embodiment, Z is isoxazolyl T is absent and A is —(CHR$^{36}$)$_q$tetrazol-5-yl.
In another embodiment, Z is isoxazolyl T is absent and A is -tetrazol-5-yl.
In another embodiment, Z is isoxazolyl T is absent and A is —CHR$^{36}$-tetrazol-5-yl.

In another embodiment, Z is isoxazolyl T is absent and A is —(CHR$^{36}$)$_2$ tetrazol-5-yl.

In another embodiment, Z is isoxazolyl T is absent and A is —(CHR$^{36}$)$_3$ tetrazol-5-yl.

In another embodiment, Z is isoxazolyl T is absent and A is —CH(C$_{1-6}$-alkyl)-tetrazol-5-yl.

In another embodiment, Z is isoxazolyl T is absent and A is —CH(C$_{1-3}$-alkyl)-tetrazol-5-yl.

In another embodiment, Z is isoxazolyl T is absent and A is —CH(OH)-tetrazol-5-yl.

In another embodiment, Z is isoxazolyl T is absent and A is —CH(OC$_{1-3}$-alkyl)-tetrazol-5-yl.

In another embodiment, Z is isoxazolyl T is absent and A is —CH(CH$_2$OC$_{1-3}$-alkyl)-tetrazol-5-yl.

In another embodiment, Z is isoxazolyl T is absent and A is —CH(OH)-tetrazol-5-yl.

In another embodiment, Z is isoxazolyl T is absent and A is —CH(CH$_2$OH)-tetrazol-5-yl.

In another embodiment, Z is isoxazolyl T is absent and A is —CHF-tetrazol-5-yl.

In another embodiment, T is absent and A is —CH(C$_{1-6}$-alkyl)-tetrazol-5-yl.

In another embodiment, T is absent and A is —CHR$^{36}$CH(C$_{1-3}$-alkyl)-tetrazol-5-yl.

In another embodiment, T is absent and A is —CHR$^{36}$CH(OH)-tetrazol-5-yl.

In another embodiment, T is absent and A is —CHR$^{36}$CH(OC$_{1-3}$-alkyl)-tetrazol-5-yl.

In another embodiment, T is absent and A is —CHR$^{36}$CH(CH$_2$OC$_{1-3}$-alkyl)-tetrazol-5-yl.

In another embodiment, T is absent and A is —CHR$^{36}$CH(OH)-tetrazol-5-yl.

In another embodiment, T is absent and A is —CHR$^{36}$CH(CH$_2$OH)-tetrazol-5-yl.

In another embodiment, T is absent and A is —CHR$^{36}$CHF-tetrazol-5-yl.

In another embodiment, T is absent and A is —CH(C$_{1-6}$-alkyl) CHR$^{36}$-tetrazol-5-yl.

In another embodiment, T is absent and A is —CH(C$_{1-3}$-alkyl) CHR$^{36}$-tetrazol-5-yl.

In another embodiment, T is absent and A is —CH(OH) CHR$^{36}$-tetrazol-5-yl.

In another embodiment, T is absent and A is —CH(OC$_{1-3}$-alkyl) CHR$^{36}$-tetrazol-5-yl.

In another embodiment, T is absent and A is —CH(CH$_2$OC$_{1-3}$-alkyl) CHR$^{36}$-tetrazol-5-yl.

In another embodiment, T is absent and A is —CH(OH) CHR$^{36}$-tetrazol-5-yl.

In another embodiment, T is absent and A is —CH(CH$_2$OH) CHR$^{36}$-tetrazol-5-yl.

In another embodiment, T is absent and A is —CHF CHR$^{36}$-tetrazol-5-yl.

In another embodiment, the present invention provides compounds of general formula (I) wherein:

L is a group selected from hydrogen, phenyl, phenyl-oxy-, phenyl-C$_{1-6}$-alkyl-oxy-, phenyl-C(O)—, phenyl-C$_{1-6}$-alkyl-C(O)—, phenyl-N(R$^{12}$)—, five- or six-membered heterocyclic monoaryl, five- or six-membered heterocyclic monoaryl-oxy-, five- or six-membered heterocyclic monoaryl-C$_{1-6}$-alkyl-oxy-, five- or six-membered heterocyclic monoarylketyl-, five- or six-membered heterocyclic monoaryl-C$_{1-6}$-alkyl-C(O)—, five- or six-membered heterocyclic monoaryl-N(R$^{12}$)—, nine- or ten-membered carbocyclic bicyclic aryl, nine- or ten-membered carbocyclic bicyclic aryl-oxy-, nine- or ten-membered carbocyclic bicyclic aryl-C$_{1-6}$-alkyl-oxy-, nine- or ten-membered carbocyclic bicyclic aryl-C(O)—, nine- or ten-membered carbocyclic bicyclic aryl-C$_{1-6}$-alkyl-C(O)—, nine- or ten-membered carbocyclic bicyclic aryl-N(R$^{12}$)—, nine- or ten-membered bicyclic heteroaryl, nine- or ten-membered bicyclic heteroaryl-oxy-, nine- or ten-membered bicyclic heteroaryl-C$_{1-6}$-alkyl-oxy-, nine- or ten-membered bicyclic heteroaryl-C(O)—, nine- or ten-membered bicyclic heteroaryl-C$_{1-6}$-alkyl-C(O)—, nine- or ten-membered bicyclic heteroaryl-N(R$^{12}$)—, five-, six-, seven- or eight-membered cycloalkyl, five- or six-membered cycloalkyl-oxy-, five-, six-, seven- or eight-membered cycloalkyl-C$_{1-6}$-alkyl-oxy-, five-, six-, seven- or eight-membered cycloalkyl-C(O)—, five-, six-, seven- or eight-membered cycloalkyl-C$_{1-6}$-alkyl-C(O)—, five-, six-, seven- or eight-membered cycloalkyl-N(R$^{12}$)—, five-, six-, seven- or eight-membered heterocyclyl, five-, six-, seven- or eight-membered heterocyclyl-oxy-, five-, six-, seven-, eight-membered heterocyclyl-C$_{1-6}$-alkyl-oxy- or -five-, six-, seven-, eight-membered heterocyclyl-C$_{1-6}$-alkyl-N(R$^{12}$)—;

wherein R$^{12}$ is selected from hydrogen or C$_{1-3}$-alkyl; and, wherein each of said group, excluding hydrogen, is optionally substituted;

D is a substituted group selected from carbocyclic aryl, heteroaryl, cycloalkyl or heterocyclyl, wherein said group is substituted with L and is substituted with one, two, three or four substituents independently selected from optionally substituted C$_{1-6}$-alkyl, optionally substituted C$_{2-6}$-alkenyl, optionally substituted C$_{2-6}$-alkynyl, optionally substituted C$_{3-4}$-cycloalkyl, optionally substituted C$_{4-8}$-cycloalkenyl, optionally substituted C$_{3-8}$-alkoxy, optionally substituted C$_{3-8}$-alkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —CF$_3$, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds; Z is a group selected from isoxazol-3,5-diyl, —C(O)N(R$^2$)—; wherein said R$^2$ is hydrogen or C$_{1-3}$-alkyl;

R$^1$ is a group selected from hydrogen, —F or optionally substituted C$_{1-3}$-alkyl;

E is a group selected from a phenyl-C$_{2-6}$-alkenyl-, phenyl-C$_{2-6}$-alkynyl-, phenyl-C$_{3-8}$-cycloalkyl-, phenyl-C$_{4-8}$-cycloalkenyl-, heteroaryl-C$_{2-6}$-alkenyl-, heteroaryl-C$_{2-6}$-alkynyl-phenyl-, C$_{2-6}$-alkenyl-phenyl-, C$_{2-6}$-alkynyl-heteroaryl-, C$_{2-6}$-alkenyl-, C$_{2-6}$-alkynyl-heteroaryl-, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, or benzyl-, each optionally substituted; wherein each of said heteroaryl is a five- or six-membered heteroaryl;

Y is a group selected from —O—, —CR$^{26}$R$^{27}$— or —CF$_2$—; wherein R$^{26}$ is hydrogen or C$_{1-3}$-alkyl and wherein R$^{27}$ is hydrogen, C$_{1-3}$-alkyl, hydroxyl or fluoro;

X is a group selected from phenylene, heterocyclic monoarylene, C$_{5-8}$-cycloalkylene or C$_{5-8}$-cycloalkenylene;

wherein X is optionally substituted with one or two groups independently selected from halogen, —CN, —CF$_3$—OCF$_3$, —OCHF$_2$, —NO$_2$, —OR$^{30}$, C$_{1-6}$-alkyl, C$_{2-6}$-alkenyl or C$_{1-6}$-alkynyl; wherein, R$^{30}$ is hydrogen or C$_{1-6}$-alkyl;

M is a group selected from —NHC(O)—, —N(CH$_3$)C(O)—, —N(CH$_2$CH$_3$)C(O)—, —N(CH$_2$CH$_2$CH$_3$)C(O)—, —N(C$_{4-6}$-alkyl)C(O)—, —C(O)NH—, —C(O)N(CH$_3$)—, —C(O)N(CH$_2$CH$_3$)—, —C(O)N(CH$_2$CH$_2$CH$_3$)—, —C(O)N(C$_{4-6}$-alkyl)-, —NHS(O)$_2$—, —N(CH$_3$)S(O)$_2$—, —N(CH$_2$CH$_3$)S(O)$_2$—, —N(CH$_2$CH$_2$CH$_3$)S(O)$_2$—, —N(C$_{4-6}$-alkyl)S(O)$_2$—, —S(O)$_2$NH—, —S(O)$_2$N(CH$_3$)—, —S(O)$_2$N(CH$_2$CH$_3$)—, —S(O)$_2$N(CH$_2$CH$_2$CH$_3$)—, —S(O)$_2$N(C$_{4-6}$-alkyl)-, —NHC(S)—, —N(CH$_3$)C(S)—, —N(CH$_2$CH$_3$)C(S)—, —N(CH$_2$CH$_2$CH$_3$)C(S)—, —N(C$_{4-6}$-alkyl)C(S)—, —C(S)NH—, —C(S)N(CH$_3$)—, —C(S)N(CH$_2$CH$_3$)—, —C(S)N(CH$_2$CH$_2$CH$_3$)—, —C(S)N(C$_{4-6}$-alkyl)-, —O—, —S— or —S(O)$_2$—;

T is absent or is a group selected from —CHR$^{30}$— (wherein R$^{30}$ is —H or C$_{1-3}$-alkyl), —CHR$^{30}$CHR$^{30}$— (wherein R$^{30}$ is —H or C$_{1-3}$-alkyl), —CHR$^{30}$CHR$^{30}$CHR$^{30}$— (wherein R$^{30}$ is —H or C$_{1-3}$-alkyl), —CHR$^{30}$CHR$^{30}$CHR$^{30}$— (wherein R$^{30}$ is —H or —CH$_3$), —CH$_2$—, —CH$_2$CH$_2$—, —CH$_2$CH$_2$CH$_2$—, —C(CH$_3$)H—, —C(CF$_3$)H—, —C(CH$_3$)HCH$_2$—, —C(CF$_3$)HCH$_2$—, —C(CH$_3$)HCH$_2$CH$_2$—, —C(CF$_3$)HCH$_2$CH$_2$—, —CH$_2$C(CH$_3$)H—, —CH$_2$C(CF$_3$)H—, —CH$_2$C(CH$_3$)HCH$_2$—, —CH$_2$CH$_2$C(CH$_3$)H—, —CH(CH$_3$)CH(CH$_3$)—, —CH(CH$_3$)CH(CH$_3$)CH$_2$—, —CH(CH$_3$)CH$_2$CH(CH$_3$)—, —CH$_2$C(CH$_3$)HC(CH$_3$)H—, —CH(CH$_2$CH$_3$)CH$_2$—, —C(CH$_2$CH$_3$)H—, —C(CH$_2$CH$_2$CH$_3$)H—, —C(CH$_2$CH$_2$CH$_3$)HCH$_2$—, —CH$_2$C(CH$_2$CH$_3$)H—, —CH$_2$C(CH$_2$CH$_2$CH$_3$)H—, phenylene, five- or six-membered heterocyclic monoarylene ring, oxazolylene, phenylene, pyridylene, or pyrimidinylene; and A is a group selected from —CO$_2$H, —CH$_2$CO$_2$H, —CH$_2$CH$_2$CO$_2$H, —CH$_2$CH(OH)CO$_2$H, —CH$_2$CH$_2$CH$_2$CO$_2$H, —C(CH$_3$)HCO$_2$H, —C(CF$_3$)HCO$_2$H, —C(CH$_3$)HCH$_2$CO$_2$H, —C(CF$_3$)HCH$_2$CO$_2$H, —C(CH$_3$)HCH$_2$CH$_2$CO$_2$H, —C(CF$_3$)HCH$_2$CH$_2$CO$_2$H, —CH$_2$C(CH$_3$)HCO$_2$H, —CH$_2$C(CF$_3$)HCO$_2$H, —CH$_2$C(CH$_3$)HCH$_2$CO$_2$H, —CH$_2$CH$_2$C(CH$_3$)HCO$_2$H, —CH(CH$_3$)CH(CH$_3$)CO$_2$H, —CH(CH$_3$)CH(CH$_3$)CH$_2$CO$_2$H, —CH(CH$_3$)CH$_2$CH(CH$_3$)CO$_2$H, —CH$_2$C(CH$_3$)HC(CH$_3$)HCO$_2$H, —CH(CH$_2$CH$_3$)CH$_2$CO$_2$H, —C(CH$_2$CH$_3$)HCO$_2$H, —C(CH$_2$CH$_2$CH$_3$)HCO$_2$H, —C(CH$_2$CH$_2$CH$_3$)HCH$_2$CO$_2$H, —CH$_2$C(CH$_2$CH$_3$)HCO$_2$H, —CH$_2$C(CH$_2$CH$_2$CH$_3$)HCO$_2$H, —SO$_3$H, —CH$_2$SO$_3$H, —CH$_2$CH$_2$SO$_3$H, —CH$_2$CH$_2$CH$_2$SO$_3$H, —C(CH$_3$)HSO$_3$H, —C(CF$_3$)HSO$_3$H, —C(CH$_3$)HCH$_2$SO$_3$H, —C(CF$_3$)HCH$_2$SO$_3$H, —C(CH$_3$)HCH$_2$CH$_2$SO$_3$H, —C(CF$_3$)HCH$_2$CH$_2$SO$_3$H, —CH$_2$C(CH$_3$)HSO$_3$H, —CH$_2$C(CF$_3$)HSO$_3$H, —CH$_2$C(CH$_3$)HCH$_2$SO$_3$H, —CH$_2$CH$_2$C(CH$_3$)HSO$_3$H, —CH(CH$_3$)CH(CH$_3$)SO$_3$H, —CH(CH$_3$)CH(CH$_3$)CH$_2$SO$_3$H, —CH(CH$_3$)CH$_2$CH(CH$_3$)SO$_3$H, —CH$_2$C(CH$_3$)HC(CH$_3$)HSO$_3$H, —CH(CH$_2$CH$_3$)CH$_2$SO$_3$H, —C(CH$_2$CH$_3$)HSO$_3$H, —C(CH$_2$CH$_2$CH$_3$)HSO$_3$H, —C(CH$_2$CH$_2$CH$_3$)H, —CH$_2$SO$_3$H, —CH$_2$C(CH$_2$CH$_3$)HSO$_3$H, —CH$_2$C(CH$_2$CH$_2$CH$_3$)HSO$_3$H, —(CHR$^{36}$)$_m$QSO$_2$R$^{39}$, —CHR$^{36}$QSO$_2$R$^{39}$, —(CHR$^{36}$)$_2$QSO$_2$R$^{39}$, —(CHR$^{36}$)$_3$QSO$_2$R$^{39}$, —(CHR$^{36}$)$_m$OSO$_2$R$^{39}$, —(CHR$^{36}$)$_m$OSO$_2$OH, —(CHR$^{36}$)$_m$OSO$_2$NHOH, —(CHR$^{36}$)$_m$OSO$_2$ NH$_2$, —(CHR$^{36}$)$_m$ NR$^{43}$SO$_2$R$^{39}$, —(CHR$^{36}$)$_m$ N(C$_{1-3}$-alkyl)HSO$_2$R$^{39}$, —(CHR$^{36}$)$_m$ N(C$_{1-3}$-alkyl)$_2$SO$_2$R$^{39}$, —(CHR$^{36}$)$_m$ NR$^{43}$SO$_2$OH, —(CHR$^{36}$)$_m$ N(C$_{1-3}$-alkyl)HSO$_2$OH, —(CHR$^{36}$)$_m$ N(C$_{1-3}$-alkyl)$_2$SO$_2$OH, —(CHR$^{36}$)$_m$ NR$^{43}$SO$_2$NHOH, —(CHR$^{36}$)$_m$ N(C$_{1-3}$-alkyl)HSO$_2$NHOH, —(CHR$^{36}$)$_m$ N(C$_{1-3}$-alkyl)$_2$SO$_2$NHOH, —(CHR$^{36}$)$_m$ NR$^{43}$SO$_2$NH$_2$, —(CHR$^{36}$)$_m$ N (C$_{1-3}$-alkyl)HSO$_2$NH$_2$, —(CHR$^{36}$)$_m$ N(C$_{1-3}$-alkyl)$_2$SO$_2$NH$_2$, —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$-alkyl)-tetrazol-5-yl, —CH(CH$_2$OC$_{1-3}$-alkyl)-tetrazol-5-yl, —CH(OH)-tetrazol-5-yl, —CH(CH$_2$OH)-tetrazol-5-yl, —CHF-tetrazol-5-yl, —CH(C$_{1-6}$-alkyl)-tetrazol-5-yl, —CHR$^{36}$CH(C$_{1-3}$-alkyl)-tetrazol-5-yl, —CHR$^{36}$CH(OH)-tetrazol-5-yl, —CHR$^{36}$CH(OC$_{1-3}$-alkyl)-tetrazol-5-yl, —CHR$^{36}$CH(CH$_2$C$_{1-3}$-alkyl)-tetrazol-5-yl, —CHR$^{36}$CH(OH)-tetrazol-5-yl, —CHR$^{36}$CH(CH$_2$OH)-tetrazol-5-yl, —CHR$^{36}$CHF-tetrazol-5-yl, —CH(C$_{1-6}$-alkyl) CHR$^{36}$-tetrazol-5-yl, —CH(C$_{1-3}$-alkyl) CHR$^{36}$-tetrazol-5-yl, —CH (OH) CHR$^{36}$-tetrazol-5-yl, —CH(OC$_{1-3}$-alkyl) CHR$^{36}$-tetrazol-5-yl, —CH(CH$_2$OC$_{1-3}$-alkyl) CHR$^{36}$-tetrazol-5-yl, —CH(OH) CHR$^{36}$-tetrazol-5-yl, —CH(CH$_2$OH) CHR$^{36}$-tetrazol-5-yl or —CHF CHR$^{36}$-tetrazol-5-yl.

In another embodiment, the present invention provides compounds of general formula (I) wherein:

L is a group selected from hydrogen, phenyl, phenyl-oxy-, phenyl-C$_{1-6}$-alkyl-oxy-, phenyl-C(O)—, phenyl-C$_{1-6}$-alkyl-C(O)—, phenyl-N(R$^{12}$)—, five- or six-membered heterocyclic monoaryl, five- or six-membered heterocyclic monoaryl-oxy-, five- or six-membered heterocyclic monoaryl-C$_{1-6}$-alkyl-oxy-, five- or six-membered heterocyclic monoarylketyl-, five- or six-membered heterocyclic monoaryl-C$_{1-6}$-alkyl-C(O)—, five- or six-membered heterocyclic monoaryl-N(R$^{12}$)—, nine- or ten-membered carbocyclic bicyclic aryl, nine- or ten-membered carbocyclic bicyclic aryl-oxy-, nine- or ten-membered carbocyclic bicyclic aryl-C$_{1-6}$-alkyl-oxy-, nine- or ten-membered carbocyclic bicyclic aryl-C(O)—, nine- or ten-membered carbocyclic bicyclic aryl-C$_{1-6}$-alkyl-C(O)—, nine- or ten-membered carbocyclic bicyclic aryl-N(R$^{12}$)—, nine- or ten-membered bicyclic heteroaryl, nine- or ten-membered bicyclic heteroaryl-oxy-, nine- or ten-membered bicyclic heteroaryl-C$_{1-6}$-alkyl-oxy-, nine- or ten-membered bicyclic heteroaryl-C(O)—, nine- or ten-membered bicyclic heteroaryl-C$_{1-6}$-alkyl-C(O)—, nine- or ten-membered bicyclic heteroaryl-N(R$^{12}$)—, five-, six-, seven- or eight-membered cycloalkyl, five- or six-membered cycloalkyl-oxy-, five-, six-, seven- or eight-membered cycloalkyl-C$_{1-6}$-alkyl-oxy-, five-, six-, seven- or eight-membered cycloalkyl-C(O)—, five-, six-, seven- or eight-membered cycloalkyl-C$_{1-6}$-alkyl-C(O)—, five-, six-, seven- or eight-membered cycloalkyl-N(R$^{12}$)—, five-, six-, seven- or eight-membered heterocyclyl, five-, six-, seven- or eight-membered heterocyclyl-oxy-, five-, six-, seven-, eight-membered heterocyclyl-C$_{1-6}$-alkyl-oxy- or -five-, six-, seven-, eight-membered heterocyclyl-C$_{1-6}$-alkyl-N(R$^{12}$)—;

wherein R$^{12}$ is selected from hydrogen or C$_{1-3}$-alkyl; and, wherein each of said group, excluding hydrogen, is optionally substituted;

D is a substituted group selected from carbocyclic aryl, heteroaryl, cycloalkyl or heterocyclyl, wherein said group is substituted with L and is substituted with one, two, three or four substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{3-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, $-NO_2$, $-CF_3$, $-CN$, $-NR^{10}R^{10}$, $-OR^9$, $-SR^9$, $-S(O)R^9$, $-SO_2R^9$, $-NR^9SOR^{10}$, $-NR^9SO_2R^{10}$, $-SO_2NR^{10}R^{10}$, $-CONR^{10}R^{10}$, $-NR^9COR^{10}$, $-OC(O)NR^{10}R^{10}$, $-CH_2NR^{10}R^{10}$, $-OC(O)R^9$, $-C(O)R^9$ or $-COOR^9$;

wherein $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Z is a group selected from isoxazol-3,5-diyl, $-C(O)N(R^2)-$; wherein said $R^2$ is hydrogen or $C_{1-3}$-alkyl;

$R^1$ is a group selected from hydrogen, $-F$ or optionally substituted $C_{1-3}$-alkyl;

E is a group selected from phenyl, five- or six-membered heteroaryl, nine- or ten-membered bycyclic carbocyclic aryl, nine- or ten-membered bycyclic heteroaryl, $C_{1-12}$-alkyl, $C_{2-12}$-alkenyl, $C_{2-12}$-alkynyl, $C_{3-8}$-cycloalkyl t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, or $C_{4-8}$-cycloalkenyl; wherein each group is optionally substituted with one to six groups independently selected from halogen, $-CN$, $-C_{1-6}$-alkyl, halogen, $-CHF_2$, $-CF_3$, $-OCF_3$, $-OCHF_2$, $-OCH_2CF_3$, $-OCF_2CHF_2$, $-SCF_3$, $-OR^9$, $-NR^{10}R^{10}$, $-SR^9$, $-S(O)R^9$, $-S(O)_2R^9$, $-C(O)NR^{10}R^{10}$, $-OC(O)NR^{10}R^{10}$, $-NR^9C(O)R^9$, $-OCH_2C(O)NR^{10}R^{10}$, $-C(O)R^9$ or $-C(O)OR^9$, $C_{3-8}$-cycloalkyl, $C_{4-8}$-cycloalkenyl, optionally substituted phenyl or optionally substituted five- or six-membered heteroaryl; wherein, $R^9$ is independently selected from hydrogen, optionally substituted $C_{1-6}$-alkyl or optionally substituted aryl; wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Y is a group selected from $-O-$, $-CR^{26}R^{27}-$ or $-CF_2-$; wherein $R^{26}$ is hydrogen or $C_{1-3}$-alkyl and wherein $R^{27}$ is hydrogen, $C_{1-3}$-alkyl, hydroxyl or fluoro;

X is a group selected from phenylene, heterocyclic monoarylene, $C_{5-8}$-cycloalkylene or $C_{5-8}$-cycloalkenylene;

wherein X is optionally substituted with one or two groups independently selected from halogen, $-CN$, $-CF_3$, $-OCF_3$, $-OCHF_2$, $-NO_2$, $-OR^{30}$, $C_{1-6}$-alkyl, $C_{2-6}$-alkenyl or $C_{1-6}$-alkynyl; wherein, $R^{30}$ is hydrogen or $C_{1-6}$-alkyl;

M is a group selected from $-NHC(O)-$, $-N(CH_3)C(O)-$, $-N(CH_2CH_3)C(O)-$, $-N(CH_2CH_2CH_3)C(O)-$, $-N(C_{4-6}\text{-alkyl})C(O)-$, $-C(O)NH-$, $-C(O)N(CH_3)-$, $-C(O)N(CH_2CH_3)-$, $-C(O)N(CH_2CH_2CH_3)-$, $-C(O)N(C_{4-6}\text{-alkyl})-$, $-NHS(O)_2-$, $-N(CH_3)S(O)_2-$, $-N(CH_2CH_3)S(O)_2-$, $-N(CH_2CH_2CH_3)S(O)_2-$, $-N(C_{4-6}\text{-alkyl})S(O)_2-$, $-S(O)_2NH-$, $-S(O)_2N(CH_3)-$, $-S(O)_2N(CH_2CH_3)-$, $-S(O)_2N(CH_2CH_2CH_3)-$, $-S(O)_2N(C_{4-6}\text{-alkyl})-$, $-NHC(S)-$, $-N(CH_3)C(S)-$, $-N(CH_2CH_3)C(S)-$, $-N(CH_2CH_2CH_3)C(S)-$, $-N(C_{4-6}\text{-alkyl})C(S)-$, $-C(S)NH-$, $-C(S)N(CH_3)-$, $-C(S)N(CH_2CH_3)-$, $-C(S)N(CH_2CH_2CH_3)-$, $-C(S)N(C_{4-6}\text{-alkyl})-$, $-O-$, $-S-$ or $-S(O)_2-$;

T is absent or is a group selected from, $-CHR^{30}-$ (wherein $R^{30}$ is $-H$ or $C_{1-3}$-alkyl), $-CHR^{30}CHR^{30}-$ (wherein $R^{30}$ is $-H$ or $C_{1-3}$-alkyl), $-CHR^{30}CHR^{30}CHR^{30}-$ (wherein $R^{30}$ is $-H$ or $C_{1-3}$-alkyl), $-CHR^{30}CHR^{30}CHR^{30}-$ (wherein $R^{30}$ is $-H$ or $-CH_3$), $-CH_2-$, $-CH_2CH_2-$, $-CH_2CH_2CH_2-$, $-C(CH_3)H-$, $-C(CF_3)H-$, $-C(CH_3)HCH_2-$, $-C(CF_3)HCH_2-$, $-C(CH_3)HCH_2CH_2-$, $-C(CF_3)HCH_2CH_2-$, $-CH_2C(CH_3)H-$, $-CH_2C(CF_3)H-$, $-CH_2C(CH_3)HCH_2-$, $-CH_2CH_2C(CH_3)H-$, $-CH(CH_3)CH(CH_3)-$, $-CH(CH_3)CH(CH_3)CH_2-$, $-CH(CH_3)CH_2CH(CH_3)-$, $-CH_2C(CH_3)HC(CH_3)H-$, $-CH(CH_2CH_3)CH_2-$, $-C(CH_2CH_3)H-$, $-C(CH_2CH_2CH_3)H-$, $-C(CH_2CH_2CH_3)HCH_2-$, $-CH_2C(CH_2CH_3)H-$, $-CH_2C(CH_2CH_2CH_3)H-$, phenylene, five- or six-membered heterocyclic monoarylene ring, oxazolylene, phenylene, pyridylene or pyrimidinylene;

A is a group selected from $-CO_2H-$, $-CH_2CO_2H$, $-CH_2CH_2CO_2H$, $-CH_2CH(OH)CO_2H$, $-CH_2CH_2CH_2CO_2H$, $-C(CH_3)HCO_2H$, $-C(CF_3)HCO_2H$, $-C(CH_3)HCH_2CO_2H$, $-C(CF_3)HCH_2CO_2$, $-C(CH_3)HCH_2CH_2CO_2H$, $-C(CF_3)HCH_2CH_2CO_2H$, $-CH_2C(CH_3)HCO_2H$, $-CH_2C(CF_3)HCO_2H$, $-CH_2C(CH_3)HCH_2CO_2H$, $-CH_2CH_2C(CH_3)HCO_2H$, $-CH(CH_3)CH(CH_3)CO_2H$, $-CH(CH_3)CH(CH_3)CH_2CO_2H$, $-CH(CH_3)CH_2CH(CH_3)CO_2H$, $-CH_2C(CH_3)HC(CH_3)HCO_2H$, $-CH(CH_2CH_3)CH_2CO_2H$, $-C(CH_2CH_3)HCO_2H$, $-C(CH_2CH_3)HCH_2CO_2H$, $-C(CH_2CH_2CH_3)HCO_2H$, $-CH_2C(CH_2CH_3)HCO_2H$, $-CH_2C(CH_2CH_2CH_3)HCO_2H$, $-SO_3H$, $-CH_2SO_3H$, $-CH_2CH_2SO_3H$, $-CH_2CH_2CH_2SO_3H$, $-C(CH_3)HSO_3H$, $-C(CF_3)HSO_3H$, $-C(CH_3)HCH_2SO_3H$, $-C(CF_3)HCH_2SO_3H$, $-C(CH_3)HCH_2CH_2SO_3H$, $-C(CF_3)HCH_2CH_2SO_3H$, $-CH_2C(CH_3)HSO_3H$, $-CH_2C(CF_3)HSO_3H$, $-CH_2C(CH_3)HCH_2SO_3H$, $-CH_2CH_2C(CH_3)HSO_3H$, $-CH(CH_3)CH(CH_3)SO_3H$, $-CH(CH_3)CH(CH_3)CH_2SO_3H$, $-CH(CH_3)CH_2CH(CH_3)SO_3H$, $-CH_2C(CH_3)HC(CH_3)HSO_3H$, $-CH(CH_2CH_3)CH_2SO_3H$, $-C(CH_2CH_3)HSO_3H$, $-C(CH_2CH_2CH_3)HSO_3H$, $-C(CH_2CH_2CH_3)H$, $-CH_2SO_3H$, $-CH_2C(CH_2CH_3)HSO_3H$, $-CH_2C(CH_2CH_2CH_3)HSO_3H$, $-(CHR^{36})_m QSO_2R^{39}$, $-CHR^{36}QSO_2R^{39}$, $-(CHR^{36})_2QSO_2R^{39}$, $-(CHR^{36})_3QSO_2R^{39}$, $-(CHR^{36})_m OSO_2R^{39}$, $-(CHR^{36})_m OSO_2OH$, $-(CHR^{36})_m OSO_2NHOH$, $-(CHR^{36})_m OSO_2NH_2$, $-(CHR^{36})_m NR^{43}SO_2R^{39}$, $-(CHR^{36})_m N(C_{1-3}\text{alkyl})HSO_2R^{39}$, $-(CHR^{36})_m N(C_{1-3}\text{-alkyl})_2SO_2R^{39}$, $-(CHR^{36})_m NR^{43}SO_2OH$, $-(CHR^{36})_m N(C_{1-3}\text{-alkyl})HSO_2OH$, $-(CHR^{36})_m N(C_{1-3}\text{-alkyl})_2SO_2OH$, $-(CHR^{36})_m NR^{43}SO_2NHOH$, $-(CHR^{36})_m N(C_{1-3}\text{-alkyl})HSO_2NHOH$, $-(CHR^{36})_m N(C_{1-3}\text{-alkyl})_2SO_2NHOH$, $-(CHR^{36})_m NR^{43}SO_2NH_2$, $-(CHR^{36})_m N(C_{1-3}\text{-alkyl})HSO_2NH_2$, $-(CHR^{36})_m N(C_{1-3}\text{-alkyl})_2SO_2NH_2$, $-(CHR^{36})_q$ tetrazol-5-yl, -tetrazol-5-yl, $-CHR^{36}$-tetrazol-5-yl, $-(CHR^{36})_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$-alkyl)-tetrazol-5-yl, —CH(CH$_2$OC$_{1-3}$-alkyl)-tetrazol-5-yl, —CH(OH)-tetrazol-5-yl, —CH(CH$_2$OH)-tetrazol-5-yl, —CHF-tetrazol-5-yl, —CH(C$_{1-6}$-alkyl)-tetrazol-5-yl, —CHR$^{36}$CH(C$_{1-3}$-alkyl)-tetrazol-5-yl, —CHR$^{36}$CH(OH)-tetrazol-5-yl, —CHR$^{36}$CH(OC$_{1-3}$-alkyl)-tetrazol-5-yl, —CHR$^{36}$CH(CH$_2$OC$_{1-3}$-alkyl)-tetrazol-5-yl, —CHR$^{36}$CH(OH)-tetrazol-5-yl, —CHR$^{36}$CH(CH$_2$OH)-tetrazol-5-yl, —CHR$^{36}$CHF-tetrazol-5-yl, —CH(C$_{1-6}$-alkyl) CHR$^{36}$-tetrazol-5-yl, —CH(C$_{1-3}$-alkyl) CHR$^{36}$-tetrazol-5-yl, —CH(OH) CHR$^{36}$-tetrazol-5-yl, —CH(OC$_{1-3}$-alkyl) CHR$^{36}$-tetrazol-5-yl, —CH(CH$_2$OC$_{1-3}$-alkyl) CHR$^{36}$-tetrazol-5-yl, —CH(OH) CHR$^{36}$-tetrazol-5-yl, —CH(CH$_2$OH) CHR$^{36}$-tetrazol-5-yl or —CHFCHR$^{36}$-tetrazol-5-yl.

In another embodiment, of the present invention provides compounds of general formula (I) wherein:

L is a group selected from hydrogen, phenyl, phenyl-oxy-, phenyl-C$_{1-6}$-alkyl-oxy-, phenyl-C(O)—, phenyl-C$_{1-6}$-alkyl-C(O)—, phenyl-N(R$^{12}$)—, five- or six-membered heterocyclic monoaryl, five- or six-membered heterocyclic monoaryl-oxy-, five- or six-membered heterocyclic monoaryl-C$_{1-6}$-alkyl-oxy-, five- or six-membered heterocyclic monoarylketyl-, five- or six-membered heterocyclic monoaryl-C$_{1-6}$-alkyl-C(O)—, five- or six-membered heterocyclic monoaryl-N(R$^{12}$)—, nine- or ten-membered carbocyclic bicyclic aryl, nine- or ten-membered carbocyclic bicyclic aryl-oxy-, nine- or ten-membered carbocyclic bicyclic aryl-C$_{1-6}$-alkyl-oxy-, nine- or ten-membered carbocyclic bicyclic aryl-C(O)—, nine- or ten-membered carbocyclic bicyclic aryl-C$_{1-6}$-alkyl-C(O)—, nine- or ten-membered carbocyclic bicyclic aryl-N(R$^{12}$)—, nine- or ten-membered bicyclic heteroaryl, nine- or ten-membered bicyclic heteroaryl-oxy-, nine- or ten-membered bicyclic heteroaryl-C$_{1-6}$-alkyl-oxy-, nine- or ten-membered bicyclic heteroaryl-C(O)—, nine- or ten-membered bicyclic heteroaryl-C$_{1-6}$-alkyl-C(O)—, nine- or ten-membered bicyclic heteroaryl-N(R$^{12}$)—, five-, six-, seven- or eight-membered cycloalkyl, five- or six-membered cycloalkyl-oxy-, five-, six-, seven- or eight-membered cycloalkyl-C$_{1-6}$-alkyl-oxy-, five-, six-, seven- or eight-membered cycloalkyl-C(O)—, five-, six-, seven- or eight-membered cycloalkyl-C$_{1-6}$-alkyl-C(O)—, five-, six-, seven- or eight-membered cycloalkyl-N(R$^{12}$)—, five-, six-, seven- or eight-membered heterocyclyl, five-, six-, seven- or eight-membered heterocyclyl-oxy-, five-, six-, seven-, eight-membered heterocyclyl-C$_{1-6}$-alkyl-oxy- or -five-, six-, seven-, eight-membered heterocyclyl-C$_{1-6}$-alkyl-N(R$^{12}$)—;

wherein R$^{12}$ is selected from hydrogen or C$_{1-3}$-alkyl; and, wherein each of said group, excluding hydrogen, is optionally substituted;

D is a substituted group selected from carbocyclic aryl, heteroaryl, cycloalkyl or heterocyclyl, wherein said group is substituted with L and is substituted with one, two, three or four substituents independently selected from optionally substituted C$_{1-6}$-alkyl, optionally substituted C$_{2-6}$-alkenyl, optionally substituted C$_{2-6}$-alkynyl, optionally substituted C$_{3-4}$-cycloalkyl, optionally substituted C$_{4-8}$-cycloalkenyl, optionally substituted C$_{3-8}$-alkoxy, optionally substituted C$_{3-8}$-alkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —NO$_2$, —CN, —CF$_3$, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Z is a group selected from isoxazol-3,5-diyl, —C(O)N(R$^2$)—; wherein said R$^2$ is hydrogen or C$_{1-3}$-alkyl;

R$^1$ is a group selected from hydrogen, —F or optionally substituted C$_{1-3}$-alkyl;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, C$_{1-12}$-alkyl, C$_{2-12}$-alkenyl, C$_{2-12}$-alkynyl, C$_{3-8}$-cycloalkyl, C$_{4-8}$-cycloalkenyl or benzyl; wherein each group is optionally substituted with one to three groups independently selected from halogen, —CN, —C$_{1-6}$-alkyl, halogen, —CHF$_2$, —CF$_3$, —OCF$_3$, —OCHF$_2$, —OCH$_2$CF$_3$, —OCF$_2$CHF$_2$, —OR$^9$, —NR$^{10}$R$^{10}$, optionally substituted C$_{3-8}$-cycloalkyl, optionally substituted C$_{4-8}$-cycloalkenyl, optionally substituted phenyl or optionally substituted five- or six-membered heteroaryl; wherein, R$^9$ is independently selected from hydrogen, optionally substituted C$_{1-6}$-alkyl or optionally substituted aryl; wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Y is a group selected from —O—, —CR$^{26}$R$^{27}$— or —CF$_2$—; wherein R$^{26}$ is hydrogen or C$_{1-3}$-alkyl and wherein R$^{27}$ is hydrogen, C$_{1-3}$-alkyl, hydroxyl or fluoro;

X is a group selected from phenylene, heterocyclic monoarylene, C$_{5-8}$-cycloalkylene or C$_{5-8}$-cycloalkenylene;

wherein X is optionally substituted with one or two groups independently selected from halogen, —CN, —CF$_3$, —OCF$_3$, —OCHF$_2$, —NO$_2$, —OR$^{30}$, C$_{1-6}$-alkyl, C$_{2-6}$-alkenyl or C$_{1-6}$-alkynyl; wherein, R$^{30}$ is hydrogen or C$_{1-6}$-alkyl;

M is a group selected from —NHC(O)—, —N(CH$_3$)C(O)—, —N(CH$_2$CH$_3$)C(O)—, —N(CH$_2$CH$_2$CH$_3$)C(O)—, —N(C$_{4-8}$-alkyl)C(O)—, —C(O)NH—, —C(O)N(CH$_3$)—, —C(O)N(CH$_2$CH$_3$)—, —C(O)N(CH$_2$CH$_2$CH$_3$)—, —C(O)N(C$_{4-6}$-alkyl)-, —NHS(O)$_2$—, —N(CH$_3$)S(O)$_2$—, —N(CH$_2$CH$_3$)S(O)$_2$—, —N(CH$_2$CH$_2$CH$_3$)S(O)$_2$—, —N(C$_{4-6}$-alkyl)S(O)$_2$—, —S(O)$_2$NH—, —S(O)$_2$N(CH$_3$)—, —S(O)$_2$N(CH$_2$CH$_3$)—, —S(O)$_2$N(CH$_2$CH$_2$CH$_3$)—, —S(O)$_2$N(C$_{4-8}$-alkyl)-, —NHC(S)—, —N(CH$_3$)C(S)—, —N(CH$_2$CH$_3$)C(S)—, —N(CH$_2$CH$_2$CH$_3$)C(S)—, —N(C$_{4-8}$-alkyl)C(S)—, —C(S)

NH—, —C(S)N(CH$_3$)—, —C(S)N(CH$_2$CH$_3$)—, —C(S)N(CH$_2$CH$_2$CH$_3$)—, —C(S)N(C$_{4-6}$-alkyl)-, —O—, —S—, —S(O)$_2$—;

T is absent or is a group selected from, —CHR$^{30}$— (wherein R$^{30}$ is —H or C$_{1-3}$-alkyl), —CHR$^{30}$CHR$^{30}$— (wherein R$^{30}$ is —H or C$_{1-3}$-alkyl), —CHR$^{30}$CHR$^{30}$CHR$^{30}$— (wherein R$^{30}$ is —H or C$_{1-3}$-alkyl), —CHR$^{30}$CHR$^{30}$CHR$^{30}$— (wherein R$^{30}$ is —H or —CH$_3$), —CH$_2$—, —CH$_2$CH$_2$—, —CH$_2$CH$_2$CH$_2$—, —C(CH$_3$)H—, —C(CF$_3$)H—, —C(CH$_3$)HCH$_2$—, —C(CF$_3$)HCH$_2$—, —C(CH$_3$)HCH$_2$CH$_2$—, —C(CF$_3$)HCH$_2$CH$_2$—, —CH$_2$C(CH$_3$)H—, —CH$_2$C(CF$_3$)H—, —CH$_2$C(CH$_3$)HCH$_2$—, —CH$_2$CH$_2$C(CH$_3$)H—, —CH(CH$_3$)CH(CH$_3$)—, —CH(CH$_3$)CH(CH$_3$)CH$_2$—, —CH(CH$_3$)CH$_2$CH(CH$_3$)—, —CH$_2$C(CH$_3$)HC(CH$_3$)H—, —CH(CH$_2$CH$_3$)CH$_2$—, —C(CH$_2$CH$_3$)H—, —C(CH$_2$CH$_2$CH$_3$)H—, —C(CH$_2$CH$_2$CH$_3$)HCH$_2$—, —CH$_2$C(CH$_2$CH$_3$)H—, —CH$_2$C(CH$_2$CH$_2$CH$_3$)H—, phenylene five- or six-membered heterocyclic monoarylene ring, oxazolylene, phenylene, pyridylene, or pyrimidinylene; and A is a group selected from —CO$_2$H, —CH$_2$CO$_2$H, —CH$_2$CH$_2$CO$_2$H, —CH$_2$CH(OH)CO$_2$H, —CH$_2$CH$_2$CH$_2$CO$_2$H, —C(CH$_3$)HCO$_2$H, —C(CF$_3$)HCO$_2$H, —C(CH$_3$)HCH$_2$CO$_2$H—, —C(CF$_3$)HCH$_2$CO$_2$H, —C(CH$_3$)HCH$_2$CH$_2$CO$_2$H, —C(CF$_3$)HCH$_2$CH$_2$CO$_2$H, —CH$_2$C(CH$_3$)HCO$_2$H, —CH$_2$C(CF$_3$)HCO$_2$H, —CH$_2$C(CH$_3$)HCH$_2$CO$_2$H, —CH$_2$CH$_2$C(CH$_3$)HCO$_2$H, —CH(CH$_3$)CH(CH$_3$)CO$_2$H, —CH(CH$_3$)CH(CH$_3$)CH$_2$CO$_2$H, —CH(CH$_3$)CH$_2$CH(CH$_3$)CO$_2$H, —CH$_2$C(CH$_3$)HC(CH$_3$)HCO$_2$H, —CH(CH$_2$CH$_3$)CH$_2$CO$_2$H, —C(CH$_2$CH$_3$)HCO$_2$H, —C(CH$_2$CH$_2$CH$_3$)HCO$_2$H, —C(CH$_2$CH$_2$CH$_3$)HCH$_2$CO$_2$H, —CH$_2$C(CH$_2$CH$_3$)HCO$_2$H, —CH$_2$C(CH$_2$CH$_2$CH$_3$)HCO$_2$H, —SO$_3$H, —CH$_2$SO$_3$H, —CH$_2$CH$_2$SO$_3$H, —CH$_2$CH$_2$CH$_2$SO$_3$H, —C(CH$_3$)HSO$_3$H, —C(CF$_3$)HSO$_3$H, —C(CH$_3$)HCH$_2$SO$_3$H, —C(CF$_3$)HCH$_2$SO$_3$H, —C(CH$_3$)HCH$_2$CH$_2$SO$_3$H, —C(CF$_3$)HCH$_2$CH$_2$SO$_3$H, —CH$_2$C(CH$_3$)HSO$_3$H, —CH$_2$C(CF$_3$)HSO$_3$H, —CH$_2$C(CH$_3$)HCH$_2$SO$_3$H, —CH$_2$CH$_2$C(CH$_3$)HSO$_3$H, —CH(CH$_3$)CH(CH$_3$)SO$_3$H, —CH(CH$_3$)CH(CH$_3$)CH$_2$SO$_3$H, —CH(CH$_3$)CH$_2$CH(CH$_3$)SO$_3$H, —CH$_2$C(CH$_3$)HC(CH$_3$)HSO$_3$H, —CH(CH$_2$CH$_3$)CH$_2$SO$_3$H, —C(CH$_2$CH$_3$)HSO$_3$H, —C(CH$_2$CH$_2$CH$_3$)HSO$_3$H, —C(CH$_2$CH$_2$CH$_3$)H, —CH$_2$SO$_3$H, —CH$_2$C(CH$_2$CH$_3$)HSO$_3$H, —CH$_2$C(CH$_2$CH$_2$CH$_3$)HSO$_3$H, —(CHR$^{36}$)$_m$QSO$_2$R$^{39}$, —CHR$^{36}$QSO$_2$R$^{39}$, —(CHR$^{36}$)$_2$QSO$_2$R$^{39}$, —(CHR$^{36}$)$_3$QSO$_2$R$^{39}$, —(CHR$^{36}$)$_m$OSO$_2$R$^{39}$, —(CHR$^{36}$)$_m$OSO$_2$OH, —(CHR$^{36}$)$_m$OSO$_2$NHOH, —(CHR$^{36}$)$_m$OSO$_2$NH$_2$, —(CHR$^{36}$)$_m$NR$^{43}$SO$_2$R$^{39}$, —(CHR$^{36}$)$_m$N(C$_{1-3}$-alkyl)HSO$_2$R$^{39}$, —(CHR$^{36}$)$_m$N(C$_{1-3}$-alkyl)$_2$SO$_2$R$^{39}$, —(CHR$^{36}$)$_m$NR$^{43}$SO$_2$OH, —(CHR$^{36}$)$_m$N(C$_{1-3}$-alkyl)HSO$_2$OH, —(CHR$^{36}$)$_m$N(C$_{1-3}$-alkyl)$_2$SO$_2$OH, —(CHR$^{36}$)$_m$NR$^{43}$SO$_2$NHOH, —(CHR$^{36}$)$_m$N(C$_{1-3}$-alkyl)HSO$_2$NHOH, —(CHR$^{36}$)$_m$N(C$_{1-3}$-alkyl)$_2$SO$_2$NHOH, —(CHR$^{36}$)$_m$NR$^{43}$SO$_2$NH$_2$, —(CHR$^{36}$)$_m$N(C$_{1-3}$ alkyl)HSO$_2$NH$_2$, —(CHR$^{36}$)$_m$N(C$_{1-3}$-alkyl)$_2$SO$_2$NH$_2$, —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$alkyl)-tetrazol-5-yl, —CH(CH$_2$OC$_{1-3}$-alkyl)-tetrazol-5-yl, —CH(OH)-tetrazol-5-yl, —CH(CH$_2$OH)-tetrazol-5-yl, —CHF-tetrazol-5-yl, —CH(C$_{1-6}$-alkyl)-tetrazol-5-yl, —CHR$^{36}$CH(C$_{1-3}$-alkyl)-tetrazol-5-yl, —CHR$^{36}$CH(OH)-tetrazol-5-yl, —CHR$^{36}$CH(OC$_{1-3}$alkyl)-tetrazol-5-yl, —CHR$^{36}$CH(CH$_2$OC$_{1-3}$-alkyl)-tetrazol-5-yl, —CHR$^{36}$CH(OH)-tetrazol-5-yl, —CHR$^{36}$CH(CH$_2$OH)-tetrazol-5-yl, —CHR$^{36}$CHF-tetrazol-5-yl, —CH(C$_{1-6}$-alkyl) CHR$^{36}$-tetrazol-5-yl, —CH(C$_{1-3}$-alkyl) CHR$^{36}$-tetrazol-5-yl, —CH(OH) CHR$^{36}$-tetrazol-5-yl, —CH(OC$_{1-3}$-alkyl) CHR$^{36}$-tetrazol-5-yl, —CH(CH$_2$OC$_{1-3}$-alkyl) CHR$^{36}$-tetrazol-5-yl, —CH(OH) CHR$^{36}$-tetrazol-5-yl, —CH(CH$_2$OH) CHR$^{36}$-tetrazol-5-yl or —CHFCHR$^{36}$-tetrazol-5-yl.

In another embodiment, of the present invention provides compounds of general formula (I) wherein:

L is a group selected from hydrogen, phenyl, phenyl-oxy-, phenyl-C$_{1-6}$-alkyl-oxy-, -phenyl-C(O)—, phenyl-C$_{1-6}$-alkyl-C(O)—, phenyl-N(R$^{12}$)—, five- or six-membered heterocyclic monoaryl, five- or six-membered heterocyclic monoaryl-oxy-, five- or six-membered heterocyclic monoaryl-C$_{1-6}$-alkyl-oxy-, five- or six-membered heterocyclic monoarylketyl-, five- or six-membered heterocyclic monoaryl-C$_{1-6}$-alkyl-C(O)—, five- or six-membered heterocyclic monoaryl-N(R$^{12}$)—, nine- or ten-membered carbocyclic bicyclic aryl, nine- or ten-membered carbocyclic bicyclic aryl-oxy-, nine- or ten-membered carbocyclic bicyclic aryl-C$_{1-6}$-alkyl-oxy-, nine- or ten-membered carbocyclic bicyclic aryl-C(O)—, nine- or ten-membered carbocyclic bicyclic aryl-C$_{1-6}$-alkyl-C(O)—, nine- or ten-membered carbocyclic bicyclic aryl-N(R$^{12}$)—, nine- or ten-membered bicyclic heteroaryl, nine- or ten-membered bicyclic heteroaryl-oxy-, nine- or ten-membered bicyclic heteroaryl-C$_{1-6}$-alkyl-oxy-, nine- or ten-membered bicyclic heteroaryl-C(O)—, nine- or ten-membered bicyclic heteroaryl-C$_{1-6}$-alkyl-C(O)—, nine- or ten-membered bicyclic heteroaryl-N(R$^{12}$)—, five-, six-, seven- or eight-membered cycloalkyl, five- or six-membered cycloalkyl-oxy-, five-, six-, seven- or eight-membered cycloalkyl-C$_{1-6}$-alkyl-oxy-, five-, six-, seven- or eight-membered cycloalkyl-C(O)—, five-, six-, seven- or eight-membered cycloalkyl-C$_{1-6}$-alkyl-C(O)—, five-, six-, seven- or eight-membered cycloalkyl-N(R$^{12}$)—, five-, six-, seven- or eight-membered heterocyclyl, five-, six-, seven- or eight-membered heterocyclyl-oxy-, five-, six-, seven-, eight-membered heterocyclyl-C$_{1-6}$-alkyl-oxy- or -five-, six-, seven-, eight-membered heterocyclyl-C$_{1-6}$-alkyl-N(R$^{12}$)—;

wherein L, excluding hydrogen, is substituted with one, two or three groups selected from halogen, hydroxy, amido, optionally substituted C$_{1-6}$-alkyl, optionally substituted C$_{2-6}$-alkenyl, optionally substituted C$_{2-6}$-alkynyl, optionally substituted C$_{3-6}$-cycloalkyl, optionally substituted C$_{4-8}$-cycloalkenyl, optionally substituted C$_{1-8}$-alkoxy, optionally substituted C$_{3-8}$-alkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$, phenyl, phenyl-oxy-, phenyl-C$_{1-6}$-alkyl-oxy-, wherein R$^9$ is independently selected from hydrogen, optionally substituted aralkyl, C$_{1-6}$-alkyl or optionally substituted aryl;

wherein R$^{12}$ is selected from hydrogen or C$_{1-3}$-alkyl;

wherein, R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

D is a substituted group selected from carbocyclic aryl, heteroaryl, cycloalkyl or heterocyclyl, wherein said group is substituted with L and is substituted with one, two, three or four substituents independently selected from optionally substituted $C_{1-4}$-alkyl, optionally substituted $C_{2-4}$-alkenyl or optionally substituted $C_{2-6}$-alkynyl, optionally substituted $C_{1-4}$-alkoxy-, optionally substituted $C_{3-8}$-cycloalkyl, optionally substituted $C_{4-8}$-cycloalkenyl, optionally substituted $C_{3-8}$-cycloalkyloxy, optionally substituted $C_{3-8}$-cycloalkylthio, halogen, —$CF_3$, —$NO_2$, —CN, —$NR^{10}R^{10}$, —$OR^9$, —$SR^9$, —$NR^9SOR^{10}$, —$SO_2NR^{10}R^{10}$, —$CONR^{10}R^{10}$, —$OC(O)NR^{10}R^{10}$, —$CH_2NR^{10}R^{10}$ or —$C(O)R^9$;

wherein said heterocyclyl or heteroaryl independently contain one, two, three or four heteroatoms independently selected from nitrogen, oxygen and sulfur;

wherein $R^9$ is aralkyl, $C_{1-6}$-alkyl or aryl, each optionally substituted with one, two or three substituents independently selected from halogen, —$NO_2$, —CN, —$OR^x$, —$SR^x$ or —$NR^xSOR^{10}$:

wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

wherein $R^x$ is selected from $C_{1-3}$-alkyl optionally substituted with one or more halogens, up to and including perhalo; and, wherein said $C_{1-4}$-alkyl, $C_{2-4}$-alkenyl or $C_{2-6}$-alkynyl is optionally substituted with one, two or three substituents independently selected from halogen, —CN, —$CF_3$, —$OCHF_2$, —$OCF_3$, —$NO_2$, —$OR^9$ or $C_{1-6}$-alkyl;

Z is a group selected from isoxazol-3,5-diyl (wherein D is attached at position 5 of said isoxazol-3,5-diyl), isoxazol-3,5-diyl wherein, D is attached at position 3 of said isoxazol-3,5-diyl, —C(O)NH—, —$C(O)NCH_3$—, —$C(O)NCH_2CH_3$— or —$C(O)NCH_2CH_2CH_3$—;

$R^1$ is a group selected from —H, —$CH_3$, —$CH_2CH_3$, —$CH_2CH_2CH_3$, cyclopropyl, —$CF_3$, —$CH_2CF_3$ or —F;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl-$C_{2-6}$-alkenyl-, phenyl-$C_{2-6}$-alkynyl-, heteroaryl-$C_{2-6}$-alkenyl-, heteroaryl-$C_{2-6}$-alkynyl-phenyl-, $C_{2-6}$-alkenyl-phenyl-, $C_{2-6}$-alkynyl-heteroaryl-, $C_{2-6}$-alkenyl-, $C_{2-6}$-alkynyl-heteroaryl-, or benzyl, each optionally substituted; wherein each of said heteroaryl is a five- or six-membered heteroaryl; wherein said group is substituted with one to six substituents independently selected from —$C_{1-6}$-alkyl, halogen, —$CHF_2$, —$CF_3$, —$OCF_3$, —$OCHF_2$, —$OCH_2CF_3$, —$OCF_2CHF_2$, —$SCF_3$, —$OR^9$, —$NR^{10}R^{10}$, —$SR^9$, —$S(O)R^9$, —$S(O)_2R^9$, —$C(O)NR^{10}R^{10}$, —$OC(O)NR^{10}R^{10}$, —$NR^9C(O)R^9$, —$OCH_2C(O)NR^{10}R^{10}$, —$C(O)R^9$ or —$C(O)OR^9$; wherein, $R^9$ is independently selected from hydrogen, optionally substituted $C_{1-6}$-alkyl or optionally substituted aryl; each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Y is a group selected from —O— or —$CR^{26}R^{27}$—; wherein, $R^{27}$ is hydrogen or $C_{1-3}$-alkyl;

X is a group selected from a phenylene, five- or six-membered heterocyclic monoarylene, $C_{5-8}$-cycloalkylene or $C_{5-8}$-cycloalkenylene;

wherein X optionally substituted with one or two groups independently selected from halogen, —CN, —$CF_3$, —$OCF_3$, —$OCHF_2$, —$OCH_2CF_3$, —$NO_2$, —OH, —$OCH_3$, —$OCH_2CH_3$, —$OCH_2CH_2CH_3$, —$CH_3$, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl, $C_6$-alkenyl, $C_1$-alkynyl, $C_2$-alkeynyl, $C_3$-alkynyl, $C_4$-alkynyl or $C_5$-alkynyl $C_6$-alkynyl;

M is a group selected from —NHC(O)—, —C(O)NH—, —O—, —S—, —$S(O)_2$—;

T is absent or is a group selected from —$CHR^{30}CHR^{30}CHR^{30}$— (wherein $R^{30}$ is —H or —$CH_3$), —$CH_2$—, —$CH_2CH_2$—, —$CH_2CH_2CH_2$—, —$C(CH_3)H$—, T is —$C(CF_3)H$—, —$C(CH_3)HCH_2$—, T is —$C(CF_3)HCH_2$—, —$C(CH_3)HCH_2CH_2$—, —$C(CF_3)HCH_2CH_2$—, —$CH_2C(CH_3)H$—, $CH_2C(CF_3)H$—, —$CH_2C(CH_3)HCH_2$—, —$CH_2CH_2C(CH_3)H$—, —$CH(CH_3)CH(CH_3)$—, —$CH(CH_3)CH(CH_3)CH_2$—, —$CH(CH_3)CH_2CH(CH_3)$—, —$CH_2C(CH_3)HC(CH_3)H$—, —$CH(CH_2CH_3)CH_2$—, —$C(CH_2CH_3)H$—, —$C(CH_2CH_2CH_3)H$—, —$C(CH_2CH_3)HCH_2$—, —$CH_2C(CH_2CH_3)H$—, —$CH_2C(CH_2CH_2CH_3)H$—, oxazolylene, phenylene, pyridylene or pyrimidinylene; and A is a group selected from —$CO_2H$, —$CH_2CO_2H$, —$CH_2CH_2CO_2H$, —$CH_2CH(OH)CO_2H$, —$CH_2CH_2CH_2CO_2H$, —$C(CH_3)HCO_2H$, —$C(CF_3)HCO_2H$, —$C(CH_3)HCH_2CO_2H$, —$C(CF_3)HCH_2CO_2H$, —$C(CH_3)HCH_2CH_2CO_2H$, —$C(CF_3)HCH_2CH_2CO_2H$, —$CH_2C(CH_3)HCO_2H$, —$CH_2C(CF_3)HCO_2H$, —$CH_2C(CH_3)HCH_2CO_2H$, —$CH_2C(CH_3)HCO_2H$, —CH($CH_3$)CH($CH_3$)$CO_2H$—, —CH($CH_3$)CH($CH_3$)$CH_2CO_2H$, —CH($CH_3$)$CH_2CH(CH_3)CO_2H$, —$CH_2C(CH_3)HC(CH_3)HCO_2H$, —CH($CH_2CH_3$)$CH_2CO_2H$, —$C(CH_2CH_3)HCO_2H$, —$C(CH_2CH_2CH_3)HCO_2H$, —$C(CH_2CH_3)HCH_2CO_2H$, —$CH_2C(CH_2CH_3)HCO_2H$, —$CH_2C(CH_2CH_3)HCO_2H$, —$SO_3H$, —$CH_2SO_3H$, —$CH_2CH_2SO_3H$, —$CH_2CH_2CH_2SO_3H$, —$C(CH_3)HSO_3H$, —$C(CF_3)HSO_3H$, —$C(CH_3)HCH_2SO_3H$, —$C(CF_3)HCH_2SO_3H$, —$C(CH_3)HCH_2SO_3H$, —$C(CF_3)HCH_2CH_2SO_3H$, —$CH_2C(CH_3)HSO_3H$, —$CH_2C(CF_3)HSO_3H$, —$CH_2C(CH_3)HCH_2SO_3H$, —$CH_2CH_2C(CH_3)HSO_3H$, —CH($CH_3$)CH($CH_3$)$SO_3H$, —CH($CH_3$)CH($CH_3$)$CH_2SO_3H$, —CH($CH_3$)$CH_2CH(CH_3)SO_3H$, —$CH_2C(CH_3)HC(CH_3)HSO_3H$, —CH($CH_2CH_3$)$CH_2SO_3H$, —$C(CH_2CH_3)HSO_3H$, —$C(CH_2CH_2CH_3)HSO_3H$, —$C(CH_2CH_2CH_3)H$, —$CH_2SO_3H$, —$CH_2C(CH_2CH_3)HSO_3H$, —$CH_2C(CH_2CH_2CH_3)HSO_3H$, —$(CHR^{36})_mQSO_2R^{39}$, —$CHR^{36}QSO_2R^{39}$, —$(CHR^{36})_2QSO_2R^{39}$, —$(CHR^{36})_3QSO_2R^{39}$, —$(CHR^{36})_mOSO_2R^{39}$, —$(CHR^{36})_mOSO_2OH$, —$(CHR^{36})_mOSO_2NHOH$, —$(CHR^{36})_mOSO_2NH_2$, —$(CHR^{36})_mNR^{43}SO_2R^{39}$, —$(CHR^{36})_mN(C_{1-3}$-alkyl)$HSO_2R^{39}$, —$(CHR^{36})_mN(C_{1-3}$-alkyl)$_2SO_2R^{39}$, —$(CHR^{36})_mNR^{43}SO_2OH$, —$(CHR^{36})_m$ N($C_{1-3}$-alkyl)$HSO_2OH$, —(CHR$^{36}$) N(C$_{1-3}$-alkyl)$_2$SO$_2$OH, —(CHR$^{36}$)$_m$ NR$^{43}$SO$_2$NHOH, —(CHR$^{36}$)$_m$ N(C$_{1-3}$-alkyl)HSO$_2$NHOH, —(CHR$^{36}$)$_m$ N(C$_{1-3}$-alkyl)$_2$SO$_2$NHOH, —(CHR$^{36}$)$_m$ NR$^{43}$SO$_2$NH$_2$, —(CHR$^{36}$)$_m$ N(C$_{1-3}$-alkyl)HSO$_2$NH$_2$, —(CHR$^{36}$)$_m$ N(C$_{1-3}$-alkyl)$_2$SO$_2$NH$_2$, —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$-alkyl)-tetrazol-5-yl, —CH (CH$_2$OC$_{1-3}$-alkyl)-tetrazol-5-yl, —CH(OH)-tetrazol-5-yl, —CH(CH$_2$OH)-tetrazol-5-yl, —CHF-tetrazol-5-yl, —CH (C$_{1-6}$-alkyl)-tetrazol-5-yl, —CHR$^{36}$CH(C$_{1-3}$-alkyl)-tetrazol-5-yl, —CHR$^{36}$CH(OH)-tetrazol-5-yl, —CHR$^{36}$CH (OC$_{1-3}$-alkyl)-tetrazol-5-yl, —CHR$^{36}$CH(CH$_2$OC$_{1-3}$-alkyl)-tetrazol-5-yl, —CHR$^{36}$CH(OH)-tetrazol-5-yl, —CHR$^{36}$CH (CH$_2$OH)-tetrazol-5-yl, —CHR$^{36}$CHF-tetrazol-5-yl, —CH (C$_{1-6}$-alkyl) CHR$^{36}$-tetrazol-5-yl, —CH(C$_{1-3}$-alkyl) CHR$^{36}$-tetrazol-5-yl, —CH(OH) CHR$^{36}$-tetrazol-5-yl, —CH (OC$_{1-3}$-alkyl) CHR$^{36}$-tetrazol-5-yl, —CH(CH$_2$OC$_{1-3}$-alkyl) CHR$^{36}$-tetrazol-5-yl, —CH(OH) CHR$^{36}$-tetrazol-5-yl, —CH(CH$_2$OH) CHR$^{36}$-tetrazol-5-yl or —CHFCHR$^{36}$-tetrazol-5-yl.

In another embodiment, of the present invention provides compounds of general formula (I) wherein:

L is a first group selected from hydrogen, phenyl, phenyl-oxy-, phenyl-C$_{1-6}$-alkyl-oxy-, phenyl-C(O)—, phenyl-C$_{1-6}$-alkyl-C(O)—, phenyl-N(R$^{12}$)—, indenyl, five- or six-membered heterocyclic monoaryl, five- or six-membered heterocyclic monoaryl-oxy-, five- or six-membered heterocyclic monoaryl-C$_{1-6}$-alkyl-oxy-, five- or six-membered heterocyclic monoarylketyl-, five-, six-membered heterocyclic monoaryl-C$_{1-6}$-alkyl-C(O)— or five- or six-membered heterocyclic monoaryl-N(R$^{12}$)—, nine- or ten-membered bicyclic heteroaryl, nine- or ten-membered bicyclic heteroaryl-oxy-, nine- or ten-membered bicyclic heteroaryl-C$_{1-6}$-alkyl-oxy-;

wherein said first group is substituted with a second group —(CR$^{11}$R$^{11}$)$_a$—O—(CR$^{11}$R$^{11}$)$_c$—O— to form a third group; wherein said —(CR$^{11}$R$^{11}$)$_a$—O—(CR$^{11}$R$^{11}$)$_c$—O— is attached at two adjacent positions on D to form a 5- or 6-membered ring; wherein a is 0 or 1; wherein c is 1 or 2; and wherein each R$^{11}$ is independently selected from hydrogen, C$_{1-6}$-alkyl or fluoro;

wherein said third group is optionally substituted with one, two, three or four substituents independently selected from optionally substituted C$_{1-6}$-alkyl, optionally substituted C$_{2-6}$-alkenyl, optionally substituted C$_{2-6}$-alkynyl, optionally substituted C$_{3-4}$-cycloalkyl, optionally substituted C$_{4-8}$-cycloalkenyl, optionally substituted C$_{1-6}$-alkoxy, optionally substituted C$_{3-8}$-cycloalkylalkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O) NR$^{10}$R$^{10}$, —CH$_2$NR$^{10}$R$^{10}$, —OC(O)R$^9$, —C(O)R$^9$ or —COOR$^9$;

wherein R$^{12}$ is selected from hydrogen or C$_{1-3}$-alkyl;

wherein, R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

D is a substituted first group selected from phenyl or heteroaryl;

wherein said first group is substituted with L and is further substituted with a second group —(CR$^{11}$R$^{11}$)$_a$—O—(CR$^{11}$R$^{11}$)$_c$—O— to form a third group; wherein said —(CR$^{11}$R$^{11}$)$_a$—O—(CR$^{11}$R$^{11}$)$_c$—O— is attached at two adjacent positions on D to form a 5- or 6-membered ring; wherein a is 0 or 1; wherein c is 1 or 2; and wherein each R$^{11}$ is independently selected from hydrogen, C$_{1-6}$-alkyl or fluoro;

wherein said third group is optionally substituted with one, two, three or four substituents independently selected from optionally substituted C$_{1-6}$-alkyl, optionally substituted C$_{2-6}$-alkenyl, optionally substituted C$_{2-6}$-alkynyl, optionally substituted C$_{3-4}$-cycloalkyl, optionally substituted C$_{4-8}$-cycloalkenyl, optionally substituted C$_{1-6}$-alkoxy, optionally substituted C$_{3-8}$-alkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein, R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Z is a group selected from isoxazol-3,5-diyl (wherein D is attached at position 5 of said isoxazol-3,5-diyl), isoxazol-3,5-diyl (wherein D is attached at position 3 of said isoxazol-3,5-diyl), —C(O)NH—, —C(O)NCH$_3$—, —C(O) NCH$_2$CH$_3$— or —C(O)NCH$_2$CH$_2$CH$_3$—;

R$^1$ is a group selected from —H, —CH$_3$, —CH$_2$CH$_3$, —CH$_2$CH$_2$CH$_3$, cyclopropyl, —CF$_3$, —CH$_2$CF$_3$ or —F;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl, biphenyl, naphthyl, benzothiophenyl, benzoisoxazolyl, pyridyl, pyrimidinyl, cyclohexenyl, isoxazolyl, C$_3$-C$_6$-cycloalkylalkyl-, alkyl, or benzyl; wherein said group is substituted with one to six substituents independently selected from C$_{1-6}$-alkyl, C$_{3-6}$-cycloalkyl, C$_3$-C$_6$-cycloalkyl-C$_1$-C$_6$-alkyl-, C$_{5-6}$-cycloalkenyl, phenyl, halogen, —CHF$_2$, —CF$_3$, —OCF$_3$, —OCHF$_2$, —OCH$_2$CF$_3$, —OCF$_2$CHF$_2$, —SCF$_3$, —OR$^9$, —NR$^{10}$R$^{10}$, —SR$^9$, —S(O)R$^9$, —S(O)$_2$R$^9$, —C(O)

NR$^{10}$R$^{10}$, —OC(O)NR$^{10}$R$^{10}$, —NR$^9$C(O)R$^9$, —OCH$_2$C(O)NR$^{10}$R$^{10}$, —C(O)R$^9$ or —C(O)OR$^9$; wherein, R$^9$ is independently selected from hydrogen, optionally substituted C$_{1-6}$-alkyl or optionally substituted aryl; each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring optionally containing one or two further heteroatoms independently selected from nitrogen, oxygen and sulfur, and optionally containing 0, 1 or 2 double bonds;

Y is a group selected from —O— or —CR$^{26}$R$^{27}$—; wherein, R$^{27}$ is hydrogen or C$_{1-3}$-alkyl;

X is a group selected from a phenylene, five- or six-membered heterocyclic monoarylene, C$_{5-8}$-cycloalkylene or C$_{5-8}$-cycloalkenylene;

wherein X is optionally substituted with one or two groups independently selected from halogen, —CN, —CF$_3$, —OCF$_3$, —OCHF$_2$, —OCH$_2$CF$_3$, —NO$_2$, —OH, —OCH$_3$, —OCH$_2$CH$_3$, —OCH$_2$CH$_2$CH$_3$, —CH$_3$, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl, C$_6$-alkenyl, C$_1$-alkynyl, C$_2$-alkynyl, C$_3$-alkynyl, C$_4$-alkynyl, C$_5$-alkynyl or C$_6$-alkynyl;

M is a group selected from —NHC(O)—, —C(O)NH—, —O—, —S— or —S(O)$_2$—;

T is absent, or is a group selected from —CHR$^{30}$CHR$^{30}$CHR$^{30}$— (wherein R$^{30}$ is —H or —CH$_3$), —CH$_2$—, —CH$_2$CH$_2$—, —CH$_2$CH$_2$CH$_2$—, —C(CH$_3$)H—, —C(CF$_3$)H—, —C(CH$_3$)HCH$_2$—, —C(CF$_3$)HCH$_2$—, —C(CH$_3$)HCH$_2$CH$_2$—, —C(CF$_3$)HCH$_2$CH$_2$—, —CH$_2$C(CH$_3$)H—, —CH$_2$C(CF$_3$)H—, —CH$_2$C(CH$_3$)HCH$_2$—, —CH$_2$CH$_2$C(CH$_3$)H—, —CH(CH$_3$)CH(CH$_3$)—, —CH(CH$_3$)CH(CH$_3$)CH$_2$—, —CH(CH$_3$)CH(CH$_3$)—, —CH$_2$C(CH$_3$)HC(CH$_3$)H—, —CH(CH$_2$CH$_3$)CH$_2$—, —C(CH$_2$CH$_3$)H—, —C(CH$_2$CH$_2$CH$_3$)H—, —C(CH$_2$CH$_2$CH$_3$)HCH$_2$—, —CH$_2$C(CH$_2$CH$_3$)H—, —CH$_2$C(CH$_2$CH$_2$CH$_3$)H—, oxazolylene, phenylene, pyridylene or pyrimidinylene; and A is a group selected from —CO$_2$H, —CH$_2$CO$_2$H, —CH$_2$CH$_2$CO$_2$H, —CH$_2$CH(OH)CO$_2$H, —CH$_2$CH$_2$CH$_2$CO$_2$H, —C(CH$_3$)HCO$_2$H, —C(CF$_3$)HCO$_2$H, —C(CH$_3$)HCH$_2$CO$_2$H, —C(CF$_3$)HCH$_2$CO$_2$H, —C(CH$_3$)HCH$_2$CH$_2$CO$_2$H, —C(CF$_3$)HCH$_2$CH$_2$CO$_2$H, —CH$_2$C(CH$_3$)HCO$_2$H, —CH$_2$C(CF$_3$)HCO$_2$H, —CH$_2$C(CH$_3$)HCH$_2$CO$_2$H, —CH$_2$CH$_2$C(CH$_3$)HCO$_2$H, —CH(CH$_3$)CH(CH$_3$)CO$_2$H, —CH(CH$_3$)CH(CH$_3$)CH$_2$CO$_2$H, —CH(CH$_3$)CH$_2$CH(CH$_3$)CO$_2$H, —CH$_2$C(CH$_3$)HC(CH$_3$)HCO$_2$H, —CH(CH$_2$CH$_3$)CH$_2$CO$_2$H, —C(CH$_2$CH$_3$)HCH$_2$CO$_2$H, —C(CH$_2$CH$_2$CH$_3$)HCO$_2$H, —C(CH$_2$CH$_3$)HCH$_2$CO$_2$H, —CH$_2$C(CH$_2$CH$_3$)HCO$_2$H, —CH$_2$C(CH$_2$CH$_2$CH$_3$)HCO$_2$H, —SO$_3$H, —CH$_2$SO$_3$H, —CH$_2$CH$_2$SO$_3$H, —CH$_2$CH$_2$CH$_2$SO$_3$H, —C(CH$_3$)HSO$_3$H, —C(CF$_3$)HSO$_3$H—, —C(CH$_3$)HCH$_2$SO$_3$H—, —C(CF$_3$)HCH$_2$SO$_3$H, —C(CH$_3$)HCH$_2$CH$_2$SO$_3$H, —C(CF$_3$)HCH$_2$CH$_2$SO$_3$H, —CH$_2$C(CH$_3$)HSO$_3$H, —CH$_2$C(CF$_3$)HSO$_3$H, —CH$_2$C(CH$_3$)HCH$_2$SO$_3$H, —CH$_2$CH$_2$C(CH$_3$)HSO$_3$H, —CH(CH$_3$)CH(CH$_3$)SO$_3$H, —CH(CH$_3$)CH(CH$_3$)CH$_2$SO$_3$H, —CH(CH$_3$)CH$_2$CH(CH$_3$)SO$_3$H, —CH$_2$C(CH$_3$)HC(CH$_3$)HSO$_3$H, —CH(CH$_2$CH$_3$)CH$_2$SO$_3$H, —C(CH$_2$CH$_3$)HSO$_3$H, —C(CH$_2$CH$_2$CH$_3$)HSO$_3$H, —C(CH$_2$CH$_2$CH$_3$)H, —CH$_2$SO$_3$H, —CH$_2$C(CH$_2$CH$_3$)HSO$_3$H, —CH$_2$C(CH$_2$CH$_2$CH$_3$)HSO$_3$H, —(CHR$^{36}$)$_m$QSO$_2$R$^{39}$, —CHR$^{36}$QSO$_2$R$^{39}$, —(CHR$^{36}$)$_2$QSO$_2$R$^{39}$, —(CHR$^{36}$)$_3$QSO$_2$R$^{39}$, —(CHR$^{36}$)$_m$OSO$_2$R$^{39}$, —(CHR$^{36}$)$_m$OSO$_2$OH, —(CHR$^{36}$)$_m$OSO$_2$NH$_2$, —(CHR$^{36}$)$_m$NR$^{43}$SO$_2$R$^{39}$, —(CHR$^{36}$)$_m$N(C$_{1-3}$-alkyl)HSO$_2$R$^{39}$, —(CHR$^{36}$)$_m$N(C$_{1-3}$-alkyl)$_2$SO$_2$R$^{39}$, —(CHR$^{36}$)$_m$NR$^{43}$SO$_2$OH, —(CHR$^{36}$)$_m$N(C$_{1-3}$-alkyl)HSO$_2$OH, —(CHR$^{36}$)$_m$N(C$_{1-3}$-alkyl)$_2$SO$_2$OH, —(CHR$^{36}$)$_m$NR$^{43}$SO$_2$NHOH, —(CHR$^{36}$)$_m$N(C$_{1-3}$-alkyl)HSO$_2$NHOH, —(CHR$^{36}$)$_m$N(C$_{1-3}$-alkyl)$_2$SO$_2$NHOH, —(CHR$^{36}$)$_m$NR$^{43}$SO$_2$NH$_2$, —(CHR$^{36}$)$_m$N(C$_{1-3}$-alkyl)HSO$_2$NH$_2$, —(CHR$^{36}$)$_m$N(C$_{1-3}$-alkyl)$_2$SO$_2$NH$_2$, —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$-alkyl)-tetrazol-5-yl, —CH(CH$_2$OC$_{1-3}$-alkyl)-tetrazol-5-yl, —CH(OH)-tetrazol-5-yl, —CH(CH$_2$OH)-tetrazol-5-yl, —CHF-tetrazol-5-yl, —CH(C$_{1-6}$-alkyl)-tetrazol-5-yl, —CHR$^{36}$CH(C$_{1-3}$-alkyl)-tetrazol-5-yl, —CHR$^{36}$CH(OH)-tetrazol-5-yl, —CHR$^{36}$CH(OC$_{1-3}$-alkyl)-tetrazol-5-yl, —CHR$^{36}$CH(CH$_2$OC$_{1-3}$-alkyl)-tetrazol-5-yl, —CHR$^{36}$CH(OH)-tetrazol-5-yl, —CHR$^{36}$CH(CH$_2$OH)-tetrazol-5-yl, —CHR$^{36}$CHF-tetrazol-5-yl, —CH(C$_{1-6}$-alkyl) CHR$^{36}$-tetrazol-5-yl, —CH(C$_{1-3}$-alkyl) CHR$^{36}$-tetrazol-5-yl, —CH(OH) CHR$^{36}$-tetrazol-5-yl, —CH(OC$_{1-3}$-alkyl) CHR$^{36}$-tetrazol-5-yl, —CH(CH$_2$OC$_{1-3}$-alkyl) CHR$^{36}$-tetrazol-5-yl, —CH(OH) CHR$^{36}$-tetrazol-5-yl, —CH(CH$_2$OH) CHR$^{36}$-tetrazol-5-yl or —CHFCHR$^{36}$-tetrazol-5-yl.

In another embodiment, of the present invention provides compounds of general formula (I) wherein:

L is a group selected from hydrogen, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinyl, thiophenyl-oxy-, phenyl-oxy-, pyridyl-oxy-, pyrimidinyl-oxy-, benzofuranyl-oxy-, benzothiophenyl-oxy-, benzimidazolyl-oxy-, furanyl-oxy-, thiophenyl-oxy-, oxazolyl-oxy-, thiazolyl-oxy-, phenyl-N(R$^{12}$)—, pyridyl-N(R$^{12}$)—, pyrimidinyl-N(R$^{12}$)—, benzofuranyl-N(R$^{12}$)—, benzothiophenyl-N(R$^{12}$)—, benzimidazolyl-N(R$^{12}$)—, benzoxazolyl-N(R$^{12}$)—, C$_3$-cycloalkyloxy, C$_4$-cycloalkyloxy, C$_5$-cycloalkyloxy, C$_6$-cycloalkyloxy, C$_7$-cycloalkyloxy, C$_8$-cycloalkyloxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_3$-cycloalkyl-N(R$^{12}$)—, C$_4$-cycloalkyl-N(R$^{12}$)—, C$_5$-cycloalkyl-N(R$^{12}$)—, C$_6$-cycloalkyl-N(R$^{12}$)—, C$_7$-cycloalkyl-N(R$^{12}$)—, C$_8$-cycloalkyl-N(R$^{12}$)—, C$_4$-cycloalkenyl-N(R$^{12}$)—, C$_5$-cycloalkenyl-N(R$^{12}$)—, C$_6$-cycloalkenyl-N(R$^{12}$)—, C$_7$-cycloalkenyl-N(R$^{12}$)—, C$_8$-cycloalkenyl-N(R$^{12}$)—, C$_3$-cycloalkyl-C$_1$-alkoxy, C$_3$-cycloalkyl-C$_2$-alkoxy, C$_3$-cycloalkyl-C$_3$-alkoxy, C$_3$-cycloalkyl-C$_4$-alkoxy, C$_3$-cycloalkyl-C$_5$-alkoxy, C$_3$-cycloalkyl-C$_6$-alkoxy, C$_4$-cycloalkyl-C$_1$-alkoxy, C$_4$-cycloalkyl-C$_2$-alkoxy, C$_4$-cycloalkyl-C$_3$-alkoxy, C$_4$-cycloalkyl-C$_4$-alkoxy, C$_4$-cycloalkyl-C$_5$-alkoxy, C$_4$-cycloalkyl-C$_6$-alkoxy, C$_5$-cycloalkyl-C$_1$-alkoxy, C$_5$-cycloalkyl-C$_2$-alkoxy, C$_5$-cycloalkyl-C$_3$-alkoxy, C$_5$-cycloalkyl-C$_4$-alkoxy, C$_5$-cycloalkyl-C$_5$-alkoxy, C$_5$-cycloalkyl-C$_6$-alkoxy, C$_6$-cycloalkyl-C$_1$-alkoxy, C$_6$-cycloalkyl-C$_2$-alkoxy, C$_6$-cycloalkyl-C$_3$-alkoxy, C$_6$-cycloalkyl-C$_4$-alkoxy, C$_6$-cycloalkyl-C$_5$-alkoxy, C$_6$-cycloalkyl-C$_6$-alkoxy, C$_7$-cycloalkyl-C$_1$-alkoxy, C$_7$-cycloalkyl-C$_2$-alkoxy, C$_7$-cycloalkyl-C$_3$-alkoxy, C$_7$-cycloalkyl-C$_4$-alkoxy, C$_7$-cycloalkyl-C$_5$-alkoxy, C$_7$-cycloalkyl-C$_6$-alkoxy, C$_8$-cycloalkyl-C$_1$-alkoxy, C$_8$-cycloalkyl-C$_2$-alkoxy, C$_8$-cycloalkyl-C$_3$-alkoxy, C$_8$-cycloalkyl-C$_4$-alkoxy, C$_8$-cycloalkyl-C$_5$-alkoxy, C$_8$-cycloalkyl-C$_6$-alkoxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_4$-cycloalkenyl-C$_1$-alkoxy, C$_4$-cycloalkenyl-C$_2$-alkoxy, C$_4$-cycloalkenyl-C$_3$-alkoxy, C$_4$-cycloalkenyl-C$_4$-alkoxy, $C_4$-cycloalkenyl-$C_5$-alkoxy, $C_4$-cycloalkenyl-$C_6$-alkoxy, $C_5$-cycloalkenyl-$C_1$-alkoxy, $C_5$-cycloalkenyl-$C_2$-alkoxy, $C_5$-cycloalkenyl-$C_3$-alkoxy, $C_5$-cycloalkenyl-$C_4$-alkoxy, $C_5$-cycloalkenyl-$C_5$-alkoxy, $C_5$-cycloalkenyl-$C_6$-alkoxy, $C_6$-cycloalkenyl-$C_1$-alkoxy, $C_6$-cycloalkenyl-$C_2$-alkoxy, $C_6$-cycloalkenyl-$C_3$-alkoxy, $C_6$-cycloalkenyl-$C_4$-alkoxy, $C_6$-cycloalkenyl-$C_5$-alkoxy, $C_6$-cycloalkenyl-$C_6$-alkoxy, $C_7$-cycloalkenyl-$C_1$-alkoxy, $C_7$-cycloalkenyl-$C_2$-alkoxy, $C_7$-cycloalkenyl-$C_3$-alkoxy, $C_7$-cycloalkenyl-$C_4$-alkoxy, $C_7$-cycloalkenyl-$C_5$-alkoxy, $C_7$-cycloalkenyl-$C_6$-alkoxy, $C_8$-cycloalkenyl-$C_1$-alkoxy, $C_8$-cycloalkenyl-$C_2$-alkoxy, $C_8$-cycloalkenyl-$C_3$-alkoxy, $C_8$-cycloalkenyl-$C_4$-alkoxy, $C_8$-cycloalkenyl-$C_5$-alkoxy, $C_8$-cycloalkenyl-$C_6$-alkoxy, $C_1$-alkoxy, $C_2$-alkoxy, $C_3$-alkoxy, $C_4$-alkoxy, $C_5$-alkoxy or $C_6$-alkoxy;

wherein $R^{12}$ is selected from hydrogen or $C_{1-3}$-alkyl;

wherein L, excluding hydrogen, is optionally substituted with one, two or three groups selected from halogen, hydroxy, amido, optionally substituted $C_{1-6}$-alkyl, optionally substituted $C_{2-6}$-alkenyl, optionally substituted $C_{2-6}$-alkynyl, optionally substituted $C_{3-6}$-cycloalkyl, optionally substituted $C_{4-8}$-cycloalkenyl, optionally substituted $C_{1-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$NO_2$, —CN, —$NR^{10}R^{10}$, —$OR^9$, —$SR^9$, —$S(O)R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —$OC(O)NR^{10}R^{10}$, —$CH_2NR^{10}R^{10}$, —$OC(O)R^9$, —$C(O)R^9$ or —$COOR^9$;

wherein said $C_{1-4}$-alkyl, $C_{2-4}$-alkenyl or $C_{2-6}$-alkynyl is optionally substituted with one, two or three substituents independently selected from halogen, —CN, —$CF_3$, —$OCHF_2$, —$OCF_3$, —$NO_2$, —$OR^9$ or $C_{1-6}$-alkyl;

wherein $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

D is a substituted group selected from phenyl or heteroaryl;

wherein said group is substituted with L and further substituted with one, two, three or four substituents independently selected from halogen, —CN, —$OR^9$, —$SR^9$, —$C(O)R^9$, —$C_{1-4}$-alkyl, —$C_{2-4}$-alkenyl, —$C_{2-6}$-alkynyl, —$C_{1-4}$-alkoxy-, —$CH_2CN$, —$CHF_2$, —$CF_3$, —$CH_2CF_3$, —$C_{3-6}$-alkyl-$CF_3$, —$C_{2-3}$-perfluoroalkyl, —$OCF_3$, —$OCH_2CF_3$, —O—$C_{3-6}$-alkyl-$CF_3$, —$OC_{2-3}$-perfluoroalkyl, —$CH_2OR^9$, —$CH_2NR^9R^{10}$, —$CH_2CONR^9R^{10}$ or —$OCH_2CONR^9R^{10}$;

wherein said heteroaryl contains one or two heteroatoms independently selected from nitrogen, oxygen or sulfur;

wherein $R^9$ is selected from aralkyl, $C_{1-6}$-alkyl or aryl, each optionally substituted with halogen, —CN, —O—$C_{1-3}$-alkyl or —S—$C_{1-3}$-alkyl; wherein said $C_{1-3}$-alkyl of —O—$C_{1-3}$-alkyl or —S—$C_{1-3}$-alkyl is optionally substituted with one or more halogens, up to and including perhalo; and, wherein $R^{10}$ is selected from hydrogen, optionally substituted $C_{1-6}$-alkyl or optionally substituted aryl;

Z is a group selected from isoxazol-3,5-diyl (wherein D is attached at position 5 of said isoxazol-3,5-diyl), isoxazol-3,5-diyl (wherein D is attached at position 3 of said isoxazol-3,5-diyl), —C(O)NH—, —$C(O)NCH_3$—, —C(O)$NCH_2CH_3$— or —C(O)$NCH_2CH_2CH_3$—;

$R^1$ is a group selected from —H, —$CH_3$, or —F;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl, methylphenyl-, ethyl-phenyl-, n-propyl-phenyl-, isopropyl-phenyl-, cyclopropyl-phenyl-, cyclopropyl-methyl-phenyl-, cyclopropyl-ethyl-phenyl-, cyclopropyl-propyl-phenyl-, cyclopropyl-butyl-phenyl-, n-butyl-phenyl-, sec-butyl-phenyl-, t-butyl-phenyl-, cyclobutyl-phenyl-, cyclobutyl-methyl-phenyl-, cyclobutyl-ethyl-phenyl-, cyclobutyl-propyl-phenyl-, n-pentyl-phenyl-, neopentyl-phenyl-, isopentyl-phenyl-, cyclopentyl-phenyl-, cyclopentyl-methyl-phenyl-, cyclopentyl-ethyl-phenyl-, hexyl-phenyl-, methyl-pentyl-phenyl-, ethyl-butyl-phenyl-cyclohexyl-phenyl-, ethenyl-phenyl-, n-propenyl-phenyl-, isopropenyl-phenyl-, n-butenyl-phenyl-, sec-butenyl-phenyl-, t-butenyl-phenyl-, cyclobutenyl-phenyl-, n-pentenyl-phenyl-, neopentenyl-phenyl-, isopentenyl-phenyl-, cyclopentenyl-phenyl-, hexenyl-phenyl-, cyclohexenyl-phenyl-, ethynyl-phenyl-, n-propynyl-phenyl-, isopropynyl-phenyl-, n-butynyl-phenyl-, sec-butynyl-phenyl-, t-butynyl-phenyl-, n-pentynyl and n-hexynyl-phenyl-; benzyl, methyl-benzyl-, ethyl-benzyl-, n-propyl-benzyl-, isopropyl-benzyl-, cyclopropyl-benzyl-, cyclopropyl-methyl-benzyl-, cyclopropyl-ethyl-benzyl-, cyclopropyl-propyl-benzyl-, cyclopropyl-butyl-benzyl-, n-butyl-benzyl-, sec-butyl-benzyl-, t-butyl-benzyl-, cyclobutyl-benzyl-, cyclobutyl-methyl-benzyl-, cyclobutyl-ethyl-benzyl-, cyclobutyl-propyl-benzyl-, n-pentyl-benzyl-, neopentyl-benzyl-, isopentyl-benzyl-, cyclopentyl-benzyl-, cyclopentyl-methyl-benzyl-, cyclopentyl-ethyl-benzyl-, hexyl-benzyl-, methyl-pentyl-benzyl-, ethyl-butyl-benzyl-cyclohexyl-benzyl-, ethenyl-benzyl-, n-propenyl-benzyl-, isopropenyl-benzyl-, n-butenyl-benzyl-, sec-butenyl-benzyl-, t-butenyl-benzyl-, cyclobutenyl-benzyl-, n-pentenyl-benzyl-, neopentenyl-benzyl-, isopentenyl-benzyl-, cyclopentenyl-benzyl-, hexenyl-benzyl-, cyclohexenyl-benzyl-, ethynyl-benzyl-, n-propynyl-benzyl-, isopropynyl-benzyl-, n-butynyl-benzyl-, sec-butynyl-benzyl-, t-butynyl-benzyl-, n-pentynyl and n-hexynyl-benzyl-;

wherein E is optionally substituted with one to six groups independently selected from halogen, —CN, —$C_{1-6}$-alkyl, halogen, —$CHF_2$, —$CF_3$, —$OCF_3$, —$OCHF_2$, —$OCH_2CF_3$, —$OCF_2CHF_2$, —$SCF_3$, —$OR^9$, —$NR^{10}R^{10}$, —$SR^9$, —$S(O)R^9$, —$S(O)_2R^9$, —$C(O)NR^{10}R^{10}$, —OC(O)$NR^{10}R^{10}$, —$NR^9C(O)R^9$, —$OCH_2C(O)NR^{10}R^{10}$, —$C(O)R^9$ or —$C(O)OR^9$, $C_{3-8}$-cycloalkyl, $C_{4-8}$-cycloalkenyl, optionally substituted phenyl or optionally substituted five- or six-membered heteroaryl; wherein, $R^9$ is independently selected from hydrogen, optionally substituted $C_{1-6}$-alkyl or optionally substituted aryl; wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Y is a group selected from —O—, —CH$_2$—, —CH(CH$_3$)—, —CH(CH$_2$CH$_3$)—, —CH(CH(CH$_3$)$_2$, —C(CH$_3$)$_2$—, —C(CH$_3$)(CH$_2$CH$_3$)—, —C(CH$_2$CH$_3$)(CH$_2$CH$_3$)—, —CF$_2$—, —CHF—, —CH(CF$_3$)—, —CH(OH)—, —C(CH$_3$)(OH)— or —C(CF$_3$)(CH$_3$)—;

X is a group selected from phenylene, five- or six-membered heterocyclic monoarylene, C$_{5-8}$-cycloalkylene or C$_{5-8}$-cycloalkenylene;

wherein X is optionally substituted with one or two groups independently selected from halogen, —CN, —CF$_3$, —OCF$_3$, —OCHF$_2$, —OCH$_2$CF$_3$, —OH, —OCH$_3$, —OCH$_2$CH$_3$, —OCH$_2$CH$_2$CH$_3$, —CH$_3$, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl, C$_6$-alkenyl;

M is a group selected from —NHC(O)—, —C(O)NH—, —O—, —S— or —S(O)$_2$—;

T is absent; and

A is a group selected from —CO$_2$H, —CH$_2$CO$_2$H, —CH$_2$CH$_2$CO$_2$H, —CH$_2$CH(OH)CO$_2$H, —CH$_2$CH$_2$CH$_2$CO$_2$H, —C(CH$_3$)HCO$_2$H, —C(CF$_3$)HCO$_2$H, —C(CH$_3$)HCH$_2$CO$_2$H, —C(CF$_3$)HCH$_2$CO$_2$H, —C(CH$_3$)HCH$_2$CH$_2$CO$_2$H, —C(CF$_3$)HCH$_2$CH$_2$CO$_2$H, —CH$_2$C(CH$_3$)HCO$_2$H, —CH$_2$C(CF$_3$)HCO$_2$H, —CH$_2$C(CH$_3$)HCH$_2$CO$_2$H, —CH$_2$CH$_2$C(CH$_3$)HCO$_2$H, —CH(CH$_3$)CH(CH$_3$)CO$_2$H, —CH(CH$_3$)CH(CH$_3$)CH$_2$CO$_2$H, —CH(CH$_3$)CH$_2$CH(CH$_3$)CO$_2$H, —CH$_2$C(CH$_3$)HC(CH$_3$)HCO$_2$H, —CH(CH$_2$CH$_3$)CH$_2$CO$_2$H, —C(CH$_2$CH$_3$)HCO$_2$H, —C(CH$_2$CH$_2$CH$_3$)HCO$_2$H, —C(CH$_2$CH$_3$)HCH$_2$CO$_2$H, —CH$_2$C(CH$_2$CH$_3$)HCO$_2$H, —CH$_2$C(CH$_2$CH$_2$CH$_3$)HCO$_2$H, —SO$_3$H, —CH$_2$SO$_3$H, —CH$_2$CH$_2$SO$_3$H, —CH$_2$CH$_2$CH$_2$SO$_3$H, —C(CH$_3$)HSO$_3$H, —C(CF$_3$)HSO$_3$H, —C(CH$_3$)HCH$_2$SO$_3$H, —C(CF$_3$)HCH$_2$SO$_3$H, —C(CH$_3$)HCH$_2$CH$_2$SO$_3$H, —C(CF$_3$)HCH$_2$CH$_2$SO$_3$H, —CH$_2$C(CH$_3$)HSO$_3$H, —CH$_2$C(CF$_3$)HSO$_3$H, —CH$_2$C(CH$_3$)HCH$_2$SO$_3$H, —CH$_2$CH$_2$C(CH$_3$)HSO$_3$H, —CH(CH$_3$)CH(CH$_3$)SO$_3$H, —CH(CH$_3$)CH(CH$_3$)CH$_2$SO$_3$H, —CH(CH$_3$)CH$_2$CH(CH$_3$)SO$_3$H, —CH$_2$C(CH$_3$)HC(CH$_3$)HSO$_3$H—, —CH(CH$_2$CH$_3$)CH$_2$SO$_3$H—, —C(CH$_2$CH$_3$)HSO$_3$H, —C(CH$_2$CH$_2$CH$_3$)HSO$_3$H, —C(CH$_2$CH$_2$CH$_3$)H, —CH$_2$SO$_3$H, —CH$_2$C(CH$_2$CH$_3$)HSO$_3$H, —CH$_2$C(CH$_2$CH$_2$CH$_3$)HSO$_3$H, —(CHR$^{36}$)$_m$QSO$_2$R$^{39}$, —CHR$^{36}$QSO$_2$R$^{39}$, —(CHR$^{36}$)$_2$QSO$_2$R$^{39}$, —(CHR$^{36}$)$_3$QSO$_2$R$^{39}$, —(CHR$^{36}$)$_m$OSO$_2$R$^{39}$, —(CHR$^{36}$)$_m$OSO$_2$OH, —(CHR$^{36}$)$_m$OSO$_2$NHOH, —(CHR$^{36}$)$_m$OSO$_2$NH$_2$, —(CHR$^{36}$)$_m$NR$^{43}$SO$_2$R$^{39}$, —(CHR$^{36}$)$_m$N(C$_{1-3}$alkyl)HSO$_2$R$^{39}$, —(CHR$^{36}$)$_m$N(C$_{1-3}$-alkyl)$_2$SO$_2$R$^{39}$, —(CHR$^{36}$)$_m$NR$^{43}$SO$_2$OH, —(CHR$^{36}$)$_m$N(C$_{1-3}$-alkyl)HSO$_2$OH, —(CHR$^{36}$)$_m$N(C$_{1-3}$-alkyl)$_2$SO$_2$OH, —(CHR$^{36}$)$_m$NR$^{43}$SO$_2$NHOH, —(CHR$^{36}$)$_m$N(C$_{1-3}$-alkyl)HSO$_2$NHOH, —(CHR$^{36}$)$_m$N(C$_{1-3}$-alkyl)$_2$SO$_2$NHOH, —(CHR$^{36}$)$_m$NR$^{43}$SO$_2$NH$_2$, —(CHR$^{36}$)$_m$N(C$_{1-3}$-alkyl)HSO$_2$NH$_2$, —(CHR$^{36}$)$_m$N(C$_{1-3}$-alkyl)$_2$SO$_2$NH$_2$, —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$-alkyl)-tetrazol-5-yl, —CH(CH$_2$OC$_{1-3}$-alkyl)-tetrazol-5-yl, —CH(CH$_2$OH)-tetrazol-5-yl, —CHF-tetrazol-5-yl, —CH(C$_{1-6}$-alkyl)-tetrazol-5-yl, —CHR$^{36}$CH(C$_{1-3}$-alkyl)-tetrazol-5-yl, —CHR$^{36}$CH(OH)-tetrazol-5-yl, —CHR$^{36}$CH(OC$_{1-3}$-alkyl)-tetrazol-5-yl, —CHR$^6$CH(CH$_2$OC$_{1-3}$-alkyl)-tetrazol-5-yl, —CHR$^{36}$CH(OH)-tetrazol-5-yl, —CHR$^{36}$CH(CH$_2$OH)-tetrazol-5-yl, —CHR$^{36}$CHF-tetrazol-5-yl, —CH(C$_{1-6}$-alkyl) CHR$^{36}$-tetrazol-5-yl, —CH(C$_{1-3}$-alkyl) CHR$^{36}$-tetrazol-5-yl, —CH(OH) CHR$^{36}$-tetrazol-5-yl, —CH(OC$_{1-3}$-alkyl) CHR$^{36}$-tetrazol-5-yl, —CH(CH$_2$OC$_{1-3}$-alkyl) CHR$^{36}$-tetrazol-5-yl, —CH(OH) CHR$^{36}$-tetrazol-5-yl, —CH(CH$_2$OH) CHR$^{36}$-tetrazol-5-yl or —CHFCHR$^{36}$-tetrazol-5-yl.

In another embodiment, of the present invention provides compounds of general formula (I) wherein:

L is a group selected from hydrogen, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinyl, thiophenyl-oxy-, phenyl-oxy-, pyridyl-oxy-, pyrimidinyl-oxy-, benzofuranyl-oxy-, benzothiophenyl-oxy-, benzimidazolyl-oxy-, furanyl-oxy-, thiophenyl-oxy-, oxazolyl-oxy-, thiazolyl-oxy-, phenyl-N(R$^{12}$)—, pyridyl-N(R$^{12}$)—, pyrimidinyl-N(R$^{12}$)—, benzofuranyl-N(R$^{12}$)—, benzothiophenyl-N(R$^{12}$)—, benzimidazolyl-N(R$^{12}$)—, benzoxazolyl-N(R$^{12}$)—, C$_3$-cycloalkyloxy, C$_4$-cycloalkyloxy, C$_5$-cycloalkyloxy, C$_6$-cycloalkyloxy, C$_7$-cycloalkyloxy, C$_8$-cycloalkyloxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_3$-cycloalkyl-N(R$^{12}$)—, C$_4$-cycloalkyl-N(R$^{12}$)—, C$_5$-cycloalkyl-N(R$^{12}$)—, C$_6$-cycloalkyl-N(R$^{12}$)—, C$_7$-cycloalkyl-N(R$^{12}$)—, C$_8$-cycloalkyl-N(R$^{12}$)—, C$_4$-cycloalkenyl-N(R$^{12}$)—, C$_5$-cycloalkenyl-N(R$^{12}$)—, C$_6$-cycloalkenyl-N(R$^{12}$)—, C$_7$-cycloalkenyl-N(R$^{12}$)—, C$_8$-cycloalkenyl-N(R$^{12}$)—, C$_3$-cycloalkyl-C$_1$-alkoxy, C$_3$-cycloalkyl-C$_2$-alkoxy, C$_3$-cycloalkyl-C$_3$-alkoxy, C$_3$-cycloalkyl-C$_4$-alkoxy, C$_3$-cycloalkyl-C$_5$-alkoxy, C$_3$-cycloalkyl-C$_6$-alkoxy, C$_4$-cycloalkyl-C$_1$-alkoxy, C$_4$-cycloalkyl-C$_2$-alkoxy, C$_4$-cycloalkyl-C$_3$-alkoxy, C$_4$-cycloalkyl-C$_4$-alkoxy, C$_4$-cycloalkyl-C$_5$-alkoxy, C$_4$-cycloalkyl-C$_6$-alkoxy, C$_5$-cycloalkyl-C$_1$-alkoxy, C$_5$-cycloalkyl-C$_2$-alkoxy, C$_5$-cycloalkyl-C$_3$-alkoxy, C$_5$-cycloalkyl-C$_4$-alkoxy, C$_5$-cycloalkyl-C$_5$-alkoxy, C$_5$-cycloalkyl-C$_6$-alkoxy, C$_6$-cycloalkyl-C$_1$-alkoxy, C$_6$-cycloalkyl-C$_2$-alkoxy, C$_6$-cycloalkyl-C$_3$-alkoxy, C$_6$-cycloalkyl-C$_4$-alkoxy, C$_6$-cycloalkyl-C$_5$-alkoxy, C$_6$-cycloalkyl-C$_6$-alkoxy, C$_7$-cycloalkyl-C$_1$-alkoxy, C$_7$-cycloalkyl-C$_2$-alkoxy, C$_7$-cycloalkyl-C$_3$-alkoxy, C$_7$-cycloalkyl-C$_4$-alkoxy, C$_7$-cycloalkyl-C$_5$-alkoxy, C$_7$-cycloalkyl-C$_6$-alkoxy, C$_8$-cycloalkyl-C$_1$-alkoxy, C$_8$-cycloalkyl-C$_2$-alkoxy, C$_8$-cycloalkyl-C$_3$-alkoxy, C$_8$-cycloalkyl-C$_4$-alkoxy, C$_8$-cycloalkyl-C$_5$-alkoxy, C$_8$-cycloalkyl-C$_6$-alkoxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_4$-cycloalkenyl-C$_1$-alkoxy, C$_4$-cycloalkenyl-C$_2$-alkoxy, C$_4$-cycloalkenyl-C$_3$-alkoxy, C$_4$-cycloalkenyl-C$_4$-alkoxy, C$_4$-cycloalkenyl-C$_5$-alkoxy, C$_4$-cycloalkenyl-C$_6$-alkoxy, C$_5$-cycloalkenyl-C$_1$-alkoxy, C$_5$-cycloalkenyl-C$_2$-alkoxy, C$_5$-cycloalkenyl-C$_3$-alkoxy, C$_5$-cycloalkenyl-C$_4$-alkoxy, C$_5$-cycloalkenyl-C$_5$-alkoxy, C$_5$-cycloalkenyl-C$_6$-alkoxy, C$_6$-cycloalkenyl-C$_1$-alkoxy, C$_6$-cycloalkenyl-C$_2$-alkoxy, C$_6$-cycloalkenyl-C$_3$-alkoxy, C$_6$-cycloalkenyl-C$_4$-alkoxy, C$_6$-cycloalkenyl-C$_5$-alkoxy, C$_6$-cycloalkenyl-C$_6$-alkoxy, C$_7$-cycloalkenyl-C$_1$-alkoxy, C$_7$-cycloalkenyl-C$_2$-alkoxy, C$_7$-cycloalkenyl-C$_3$-alkoxy, C$_7$-cycloalkenyl-C$_4$-alkoxy, C$_7$-cycloalkenyl-C$_5$-alkoxy, C$_7$-cycloalkenyl-C$_6$-alkoxy, C$_8$-cycloalkenyl-C$_1$-alkoxy, C$_8$-cycloalkenyl-C$_2$-alkoxy, C$_8$-cycloalkenyl-C$_3$-alkoxy, C$_8$-cycloalkenyl-C$_4$-alkoxy, $C_8$-cycloalkenyl-$C_5$-alkoxy, $C_8$-cycloalkenyl-$C_6$-alkoxy, $C_1$-alkoxy, $C_2$-alkoxy, $C_3$-alkoxy, $C_4$-alkoxy, $C_5$-alkoxy or $C_6$-alkoxy;

wherein $R^{12}$ is selected from hydrogen or $C_{1-3}$-alkyl;

wherein L, excluding hydrogen, is optionally substituted with one, two or three groups selected from halogen, hydroxy, amido, optionally substituted $C_{1-6}$-alkyl, optionally substituted $C_{2-6}$-alkenyl, optionally substituted $C_{2-6}$-alkynyl, optionally substituted $C_{3-6}$-cycloalkyl, optionally substituted $C_{4-8}$-cycloalkenyl, optionally substituted $C_{1-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$NO_2$, —CN, —$NR^{10}R^{10}$, —$OR^9$, —$SR^9$, —$S(O)R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —OC(O)$NR^{10}R^{10}$, —$CH_2NR^{10}R^{10}$, —OC(O)$R^9$, —C(O)$R^9$ or —$COOR^9$;

wherein said $C_{1-4}$-alkyl, $C_{2-4}$-alkenyl or $C_{2-6}$-alkynyl is optionally substituted with one, two or three substituents independently selected from halogen, —CN, —$CF_3$, —$OCHF_2$, —$OCF_3$, —$NO_2$, —$OR^9$ or $C_{1-6}$-alkyl;

wherein $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

D is a substituted group selected from phenyl, five- or six-membered heterocyclic monoaryl, nine- or ten-membered, carbocyclic bicyclic aryl, nine- or ten-membered bicyclic heteroaryl, five- or six-membered cycloalkyl or five- or six-membered heterocyclyl;

wherein said group is substituted with L and is further substituted with one, two, three or four substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{3-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$NO_2$, —$CF_3$, —CN, —$NR^{10}R^{10}$, —$OR^9$, —$SR^9$, —$S(O)R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —OC(O)$NR^{10}R^{10}$, —$CH_2NR^{10}R^{10}$, —OC(O)$R^9$, —C(O)$R^9$ or —$COOR^9$;

wherein, $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Z is a group selected from isoxazol-3,5-diyl (wherein D is attached at position 5 of said isoxazol-3,5-diyl), isoxazol-3,5-diyl (wherein D is attached at position 3 of said isoxazol-3,5-diyl), —C(O)NH—, —C(O)$NCH_3$—, —C(O)$NCH_2CH_3$— or —C(O)$NCH_2CH_2CH_3$—;

$R^1$ is a group selected from —H, —$CH_3$, or —F;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-phenyl-, trifluorometh-oxy-phenyl-, trifluoromethylthio-phenyl-, halophenyl-, biphenyl-, cyclopropyl-phenyl-, cyclopropyl-propyl-phenyl-, t-butyl-phenyl-, cyclopentenyl-phenyl-, cyclohexyl-phenyl-, propenyl-phenyl-, cyclohexenyl-phenyl-, 3,3-dimethyl-but-1-enyl-phenyl-, 4,4-dimethyl-pent-1-enyl-phenyl-, 4,4-dimethyl-pent-2-enyl-phenyl-, n-hexyl-phenyl-, n-hexenyl-phenyl-, 3-methyl-benzothiophen-2-yl-, 3,5-dimethyl-isoxazol-4-yl-phenyl-, 4-t-butyl-cyclohexen-1-yl-phenyl- or 5,5-dimethyl-cyclohexa-1,3-dien-2-yl-phenyl-;

Y is a group selected from —O—, —$CH_2$—, —CH($CH_3$)—, —CH($CH_2CH_3$)—, —CH(CH($CH_3$)$_2$)—, —C($CH_3$)$_2$—, —C($CH_3$)($CH_2CH_3$)—, —C($CH_2CH_3$)($CH_2CH_3$)—, —$CF_2$—, —CHF—, —CH($CF_3$)—, —CH(OH)—, —C($CH_3$)(OH)— or —C($CF_3$)($CH_3$)—;

X is a group selected from phenylene, five- or six-membered heterocyclic monoarylene, $C_{5-8}$-cycloalkylene or $C_{5-8}$-cycloalkenylene;

wherein X is optionally substituted with one or two groups independently selected from halogen, —CN, —$CF_3$, —$OCF_3$, —$OCHF_2$, —$OCH_2CF_3$, —OH, —$OCH_3$, —$OCH_2CH_3$, —$OCH_2CH_2CH_3$, —$CH_3$, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl, $C_6$-alkenyl;

M is a group selected from —NHC(O)—, —C(O)NH—, —O—, —S— or —S(O)$_2$—;

T is absent; and

A is a group selected from —$CO_2H$, —$CH_2CO_2H$, —$CH_2CH_2CO_2H$, —$CH_2CH(OH)CO_2H$, —$CH_2CH_2CH_2CO_2H$, —C($CH_3$)$HCO_2H$, —C($CF_3$)$HCO_2H$, —C($CH_3$)$HCH_2CO_2H$, —C($CF_3$)$HCH_2CO_2H$, —C($CH_3$)$HCH_2CH_2CO_2H$, —C($CF_3$)$HCH_2CH_2CO_2H$, —$CH_2C$($CH_3$)$HCO_2H$, —$CH_2C$($CF_3$)$HCO_2H$, —$CH_2C$($CH_3$)$HCH_2CO_2H$, —$CH_2CH_2C$($CH_3$)$HCO_2H$, —CH($CH_3$)CH($CH_3$)$CO_2H$, —CH($CH_3$)CH($CH_3$)$CH_2CO_2H$, —CH($CH_3$)$CH_2CH$($CH_3$)$CO_2H$, —$CH_2C$($CH_3$)HC($CH_3$)$HCO_2H$—, —CH($CH_2CH_3$)$CH_2CO_2H$, —C($CH_2CH_3$)$HCO_2H$, —C($CH_2CH_2CH_3$)$HCO_2H$, —C($CH_2CH_2CH_3$)$HCH_2CO_2H$, —$CH_2C$($CH_2CH_3$)$HCO_2H$, —$CH_2C$($CH_2CH_2CH_3$)$HCO_2H$, —$SO_3H$, —$CH_2SO_3H$, —$CH_2CH_2SO_3H$, —$CH_2CH_2CH_2SO_3H$, —C($CH_3$)$HSO_3H$, —C($CF_3$)$HSO_3H$, —C($CH_3$)$HCH_2SO_3H$, —C($CF_3$)$HCH_2SO_3H$, —C($CH_3$)$HCH_2CH_2SO_3H$, —C($CF_3$)$HCH_2CH_2SO_3H$, —$CH_2C$($CH_3$)$HSO_3H$, —$CH_2C$($CF_3$)$HSO_3H$, —$CH_2C$($CH_3$)$HCH_2SO_3H$, —$CH_2CH_2C$($CH_3$)$HSO_3H$, —CH($CH_3$)CH($CH_3$)$SO_3H$, —CH($CH_3$)CH($CH_3$)$CH_2SO_3H$, —CH($CH_3$)$CH_2CH$($CH_3$)$SO_3H$, —$CH_2C$($CH_3$)HC($CH_3$)$HSO_3H$, —CH($CH_2CH_3$)$CH_2SO_3H$, —C($CH_2CH_3$)$HSO_3H$, —C($CH_2CH_2CH_3$)$HSO_3H$, —C($CH_2CH_2CH_3$)H, —$CH_2SO_3H$, —$CH_2C$($CH_2CH_3$)

HSO$_3$H, —CH$_2$C(CH$_2$CH$_2$CH$_3$)HSO$_3$H, —(CHR$^{36}$)$_m$QSO$_2$R$^{39}$, —CHR$^{36}$QSO$_2$R$^{39}$, —(CHR$^{36}$)$_2$QSO$_2$R$^{39}$, —(CHR$^{36}$)$_3$QSO$_2$R$^{39}$, —(CHR$^{36}$)$_m$OSO$_2$R$^{39}$, —(CHR$^{36}$)$_m$OSO$_2$OH, —(CHR$^{36}$)$_m$OSO$_2$NHOH, —(CHR$^{36}$)$_m$OSO$_2$NH$_2$, —(CHR$^{36}$)$_m$NR$^{43}$SO$_2$R$^{39}$, —(CHR$^{36}$)$_m$N(C$_{1-3}$-alkyl)HSO$_2$R$^{39}$, —(CHR$^{36}$)$_m$N(C$_{1-3}$-alkyl)$_2$SO$_2$R$^{39}$, —(CHR$^{36}$)$_m$NR$^{43}$SO$_2$OH, —(CHR$^{36}$)$_m$N(C$_{1-3}$-alkyl)HSO$_2$OH, —(CHR$^{36}$)$_m$N(C$_{1-3}$-alkyl)$_2$SO$_2$OH, —(CHR$^{36}$)$_m$NR$^{43}$SO$_2$NHOH, (CHR$^{36}$)$_m$N(C$_{1-3}$-alkyl)HSO$_2$NHOH, —(CHR$^{36}$)$_m$N(C$_{1-3}$-alkyl)$_2$SO$_2$NHOH, —(CHR$^{36}$)$_m$NR$^{43}$SO$_2$NH$_2$, —(CHR$^{36}$)$_m$N(C$_{1-3}$ alkyl)HSO$_2$NH$_2$, —(CHR$^{36}$)$_m$N(C$_{1-3}$-alkyl)$_2$SO$_2$NH$_2$, —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$-alkyl)-tetrazol-5-yl, —CH(CH$_2$OC$_{1-3}$-alkyl)-tetrazol-5-yl, —CH(OH)-tetrazol-5-yl, —CH(CH$_2$OH)— tetrazol-5-yl, —CHR$^{36}$CH(OH)-tetrazol-5-yl, —CHR$^{36}$CH(OC$_{1-3}$-alkyl)-tetrazol-5-yl, —CHR$^{36}$CH(CH$_2$OC$_{1-3}$-alkyl)-tetrazol-5-yl, —CHR$^{36}$CH(OH)-tetrazol-5-yl, —CHR$^{36}$CH(CH$_2$OH)-tetrazol-5-yl, —CHR$^{36}$CHF-tetrazol-5-yl, —CH(C$_{1-6}$-alkyl) CHR$^{36}$-tetrazol-5-yl, —CH (C$_{1-3}$-alkyl) CHR$^{36}$-tetrazol-5-yl, —CH(OH) CHR$^{36}$-tetrazol-5-yl, —CH(OC$_{1-3}$-alkyl) CHR$^{36}$-tetrazol-5-yl, —CH(CH$_2$OC$_{1-3}$-alkyl) CHR$^{36}$-tetrazol-5-yl, —CH(OH) CHR$^{36}$-tetrazol-5-yl, —CH(CH$_2$OH) CHR$^{36}$-tetrazol-5-yl or —CHFCHR$^{36}$-tetrazol-5-yl.

In another embodiment, of the present invention provides compounds of general formula (I) wherein:

L is a group selected from hydrogen, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinyl, thiophenyl-oxy-, phenyl-oxy-, pyridyl-oxy-, pyrimidinyl-oxy-, benzofuranyl-oxy-, benzothiophenyl-oxy-, benzimidazolyl-oxy-, furanyl-oxy-, thiophenyl-oxy-, oxazolyl-oxy-, thiazolyl-oxy-, phenyl-N(R$^{12}$)—, pyridyl-N(R$^{12}$)—, pyrimidinyl-N(R$^{12}$)—, benzofuranyl-N(R$^{12}$)—, benzothiophenyl-N(R$^{12}$)—, benzimidazolyl-N(R$^{12}$)—, benzoxazolyl-N(R$^{12}$)—, C$_3$-cycloalkyloxy, C$_4$-cycloalkyloxy, C$_5$-cycloalkyloxy, C$_6$-cycloalkyloxy, C$_7$-cycloalkyloxy, C$_8$-cycloalkyloxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_3$-cycloalkyl-N(R$^{12}$)—, C$_4$-cycloalkyl-N(R$^{12}$)—, C$_5$-cycloalkyl-N(R$^{12}$)—, C$_6$-cycloalkyl-N(R$^{12}$)—, C$_7$-cycloalkyl-N(R$^{12}$)—, C$_8$-cycloalkyl-N(R$^{12}$)—, C$_4$-cycloalkenyl-N(R$^{12}$)—, C$_5$-cycloalkenyl-N(R$^{12}$)—, C$_6$-cycloalkenyl-N(R$^{12}$)—, C$_7$-cycloalkenyl-N(R$^{12}$)—, C$_8$-cycloalkenyl-N(R$^{12}$)—, C$_3$-cycloalkyl-C$_1$-alkoxy, C$_3$-cycloalkyl-C$_2$-alkoxy, C$_3$-cycloalkyl-C$_3$-alkoxy, C$_3$-cycloalkyl-C$_4$-alkoxy, C$_3$-cycloalkyl-C$_5$-alkoxy, C$_3$-cycloalkyl-C$_6$-alkoxy, C$_4$-cycloalkyl-C$_1$-alkoxy, C$_4$-cycloalkyl-C$_2$-alkoxy, C$_4$-cycloalkyl-C$_3$-alkoxy, C$_4$-cycloalkyl-C$_4$-alkoxy, C$_4$-cycloalkyl-C$_5$-alkoxy. C$_4$-cycloalkyl-C$_6$-alkoxy. C$_5$-cycloalkyl-C$_1$-alkoxy, C$_5$-cycloalkyl-C$_2$-alkoxy, C$_5$-cycloalkyl-C$_3$-alkoxy, C$_5$-cycloalkyl-C$_4$-alkoxy, C$_5$-cycloalkyl-C$_5$-alkoxy, C$_5$-cycloalkyl-C$_6$-alkoxy, C$_6$-cycloalkyl-C$_1$-alkoxy, C$_6$-cycloalkyl-C$_2$-alkoxy, C$_6$-cycloalkyl-C$_3$-alkoxy, C$_6$-cycloalkyl-C$_4$-alkoxy, C$_6$-cycloalkyl-C$_5$-alkoxy, C$_6$-cycloalkyl-C$_6$-alkoxy, C$_7$-cycloalkyl-C$_1$-alkoxy, C$_7$-cycloalkyl-C$_2$-alkoxy, C$_7$-cycloalkyl-C$_3$-alkoxy, C$_7$-cycloalkyl-C$_4$-alkoxy, C$_7$-cycloalkyl-C$_5$-alkoxy, C$_7$-cycloalkyl-C$_6$-alkoxy, C$_8$-cycloalkyl-C$_1$-alkoxy, C$_8$-cycloalkyl-C$_2$-alkoxy, C$_8$-cycloalkyl-C$_3$-alkoxy, C$_8$-cycloalkyl-C$_4$-alkoxy, C$_8$-cycloalkyl-C$_5$-alkoxy, C$_8$-cycloalkyl-C$_6$-alkoxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_4$-cycloalkenyl-C$_1$-alkoxy, C$_4$-cycloalkenyl-C$_2$-alkoxy, C$_4$-cycloalkenyl-C$_3$-alkoxy, C$_4$-cycloalkenyl-C$_4$-alkoxy, C$_4$-cycloalkenyl-C$_5$-alkoxy, C$_4$-cycloalkenyl-C$_6$-alkoxy, C$_5$-cycloalkenyl-C$_1$-alkoxy, C$_5$-cycloalkenyl-C$_2$-alkoxy, C$_5$-cycloalkenyl-C$_3$-alkoxy, C$_5$-cycloalkenyl-C$_4$-alkoxy, C$_5$-cycloalkenyl-C$_5$-alkoxy, C$_5$-cycloalkenyl-C$_6$-alkoxy, C$_6$-cycloalkenyl-C$_1$-alkoxy, C$_6$-cycloalkenyl-C$_2$-alkoxy, C$_6$-cycloalkenyl-C$_3$-alkoxy, C$_6$-cycloalkenyl-C$_4$-alkoxy, C$_6$-cycloalkenyl-C$_5$-alkoxy, C$_6$-cycloalkenyl-C$_6$-alkoxy, C$_7$-cycloalkenyl-C$_1$-alkoxy, C$_7$-cycloalkenyl-C$_2$-alkoxy, C$_7$-cycloalkenyl-C$_3$-alkoxy, C$_7$-cycloalkenyl-C$_4$-alkoxy, C$_7$-cycloalkenyl-C$_5$-alkoxy, C$_7$-cycloalkenyl-C$_6$-alkoxy, C$_8$-cycloalkenyl-C$_1$-alkoxy, C$_8$-cycloalkenyl-C$_2$-alkoxy, C$_8$-cycloalkenyl-C$_3$-alkoxy, C$_8$-cycloalkenyl-C$_4$-alkoxy, C$_8$-cycloalkenyl-C$_5$-alkoxy, C$_8$-cycloalkenyl-C$_6$-alkoxy, C$_1$-alkoxy, C$_2$-alkoxy, C$_3$-alkoxy, C$_4$-alkoxy, C$_5$-alkoxy, C$_6$-alkoxy;

wherein R$^{12}$ is selected from hydrogen or C$_{1-3}$-alkyl;

wherein said group, excluding hydrogen, is optionally substituted with one, two or three groups selected from halogen, hydroxy, amido, optionally substituted C$_{1-6}$-alkyl, optionally substituted C$_{2-6}$-alkenyl, optionally substituted C$_{2-6}$-alkynyl, optionally substituted C$_{3-6}$-cycloalkyl, optionally substituted C$_{4-8}$-cycloalkenyl, optionally substituted C$_{1-8}$-alkoxy, optionally substituted C$_{3-8}$-alkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein said C$_{1-4}$-alkyl, C$_{2-4}$-alkenyl or C$_{2-6}$-alkynyl is optionally substituted with one, two or three substituents independently selected from halogen, —CN, —CF$_3$, —OCHF$_2$, —OCF$_3$, —NO$_2$, —OR$^9$ or C$_{1-6}$-alkyl;

wherein R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

D is a substituted group selected from phenyl, five- or six-membered heterocyclic monoaryl, nine- or ten-membered carbocyclic bicyclic aryl, nine- or ten-membered bicyclic heteroaryl, five- or six-membered cycloalkyl or five- or six-membered heterocyclyl;

wherein said group is substituted with L and is further substituted with one, two, three or four substituents independently selected from optionally substituted C$_{1-6}$-alkyl, optionally substituted C$_{2-6}$-alkenyl, optionally substituted C$_{2-6}$-alkynyl, optionally substituted C$_{3-8}$-cycloalkyl, optionally substituted C$_{4-8}$-cycloalkenyl, optionally substituted C$_{3-8}$-alkoxy, optionally substituted C$_{3-8}$-cycloalkylalkoxy, optionally substituted C$_{3-8}$-cycloalkyloxy, optionally substituted C$_{3-8}$-cycloalkylthio, halogen, —CF$_3$, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein R$^9$ is aralkyl, C$_{1-6}$-alkyl or aryl, each optionally substituted with one, two or three substituents independently selected from halogen, —NO$_2$, —CN, —OR$^x$, —SR$^x$ or —NR$^x$SOR$^{10}$;

wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

wherein said C$_{1-6}$-alkyl, C$_{2-6}$-alkenyl or C$_{2-6}$-alkynyl is optionally substituted with one, two or three substituents independently selected from halogen, —CN, —CF$_3$, —OCHF$_2$, —OCF$_3$, —NO$_2$, —OR$^9$ or C$_{1-6}$-alkyl;

Z is a group selected from isoxazol-3,5-diyl wherein, D is attached at position 5 of said isoxazol-3,5-diyl, isoxazol-3,5-diyl wherein, D is attached at position 3 of said isoxazol-3,5-diyl, —C(O)NH—, —C(O)NCH$_3$—, —C(O)NCH$_2$CH$_3$— or —C(O)NCH$_2$CH$_2$CH$_3$—;

R$^1$ is —H, —CH$_3$ or —F;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluoromethylthio-benzyl-, halobenzyl-, phenyl-benzyl-, cylcopropyl-benzyl-, cylcopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent-2-enyl-benzyl-, n-hexyl-benzyl-, n-hexenyl-benzyl- or dimethyl-isoxazol-4-yl-benzyl-;

Y is a group selected from —O—, —CH$_2$—, —CH(CH$_3$)—, —CH(CH$_2$CH$_3$)—, —CH(CH(CH$_3$)$_2$, —C(CH$_3$)$_2$—, —C(CH$_3$)(CH$_2$CH$_3$)—, —C(CH$_2$CH$_3$)(CH$_2$CH$_3$)—, —CF$_2$—, —CHF—, —CH(CF$_3$)—, —CH(OH)—, —C(CH$_3$)(OH)— or —C(CF$_3$)(CH$_3$)—;

X is a group selected from phenylene, five- or six-membered heterocyclic monoarylene, C$_{5-8}$-cycloalkylene or C$_{5-8}$-cycloalkenylene;

wherein X is optionally substituted with one or two groups independently selected from halogen, —CN, —CF$_3$, —OCF$_3$, —OCHF$_2$, —OCH$_2$CF$_3$, —OH, —OCH$_3$, —OCH$_2$CH$_3$, —OCH$_2$CH$_2$CH$_3$, —CH$_3$, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl or C$_6$-alkenyl;

M is a group selected from —NHC(O)—, —C(O)NH—, —O—, —S— or —S(O)$_2$—;

T is absent; and

A is a group selected from —CO$_2$H, —CH$_2$CO$_2$H, —CH$_2$CH$_2$CO$_2$H, —CH$_2$CH(OH)CO$_2$H, —CH$_2$CH$_2$CH$_2$CO$_2$H, —C(CH$_3$)HCO$_2$H, —C(CF$_3$) HCO$_2$H, —C(CH$_3$)HCH$_2$CO$_2$H, —C(CF$_3$)HCH$_2$CO$_2$H, —C(CH$_3$)HCH$_2$CH$_2$CO$_2$H, —C(CF$_3$)HCH$_2$CH$_2$CO$_2$H, —CH$_2$C(CH$_3$)HCO$_2$H, —CH$_2$C(CF$_3$)HCO$_2$H, —CH$_2$C(CH$_3$)HCH$_2$CO$_2$H, —CH$_2$CH$_2$C(CH$_3$)HCO$_2$H, —CH(CH$_3$)CH(CH$_3$)CO$_2$H, —CH(CH$_3$)CH(CH$_3$)CH$_2$CO$_2$H, —CH(CH$_3$)CH$_2$CH(CH$_3$)CO$_2$H, —CH$_2$C(CH$_3$)HC(CH$_3$)HCO$_2$H, —CH(CH$_2$CH$_3$)CH$_2$CO$_2$H, —C(CH$_2$CH$_3$)HCO$_2$H, —C(CH$_2$CH$_2$CH$_3$)HCO$_2$H, —C(CH$_2$CH$_2$CH$_3$)HCH$_2$CO$_2$H, —CH$_2$C(CH$_2$CH$_3$)HCO$_2$H, —CH$_2$C(CH$_2$CH$_2$CH$_3$)HCO$_2$H, —SO$_3$H, —CH$_2$SO$_3$H, —CH$_2$CH$_2$SO$_3$H, —CH$_2$CH$_2$CH$_2$SO$_3$H, —C(CH$_3$)HSO$_3$H, —C(CF$_3$)HSO$_3$H, —C(CH$_3$)HCH$_2$SO$_3$H, —C(CF$_3$)HCH$_2$SO$_3$H, —C(CH$_3$)HCH$_2$SO$_3$H, —C(CF$_3$)HCH$_2$CH$_2$SO$_3$H, —CH$_2$C(CH$_3$)HSO$_3$H, —CH$_2$C(CF$_3$)HSO$_3$H, —CH$_2$C(CH$_3$)HCH$_2$SO$_3$H, —CH$_2$CH$_2$C(CH$_3$)HSO$_3$H, —CH(CH$_3$)CH(CH$_3$)SO$_3$H, —CH(CH$_3$)CH(CH$_3$)CH$_2$SO$_3$H, —CH(CH$_3$)CH$_2$CH(CH$_3$)SO$_3$H, —CH$_2$C(CH$_3$)HC(CH$_3$)HSO$_3$H, —CH(CH$_2$CH$_3$)CH$_2$SO$_3$H, —C(CH$_2$CH$_3$)HSO$_3$H, —C(CH$_2$CH$_2$CH$_3$)HSO$_3$H, —C(CH$_2$CH$_2$CH$_3$)H, —CH$_2$SO$_3$H, —CH$_2$C(CH$_2$CH$_3$)HSO$_3$H, —CH$_2$C(CH$_2$CH$_2$CH$_3$)HSO$_3$H, —(CHR$^{36}$)$_m$ QSO$_2$R$^{39}$, —CHR$^{36}$QSO$_2$R$^{39}$, —(CHR$^{36}$)$_2$QSO$_2$R$^{39}$, —(CHR$^{36}$)$_3$QSO$_2$R$^{39}$, —(CHR$^{36}$)$_m$OSO$_2$R$^{39}$, —(CHR$^{36}$)$_m$OSO$_2$OH, —(CHR$^{36}$)$_m$OSO$_2$NHOH, —(CHR$^{36}$)$_m$OSO$_2$NH$_2$, —(CHR$^{36}$)$_m$NR$^{43}$SO$_2$R$^{39}$, —(CHR$^{36}$)$_m$N(C$_{1-3}$-alkyl)HSO$_2$R$^{39}$, —(CHR$^{36}$)$_m$N(C$_{1-3}$-alkyl)$_2$SO$_2$R$^{39}$, —(CHR$^{36}$)$_m$NR$^{43}$SO$_2$OH, —(CHR$^{36}$)$_m$N(C$_{1-3}$-alkyl)HSO$_2$OH, —(CHR$^{36}$)$_m$N(C$_{1-3}$-alkyl)$_2$SO$_2$OH, —(CHR$^{36}$)$_m$NR$^{43}$SO$_2$NHOH, —(CHR$^{36}$)$_m$N(C$_{1-3}$-alkyl)HSO$_2$NHOH, —(CHR$^{36}$)$_m$N(C$_{1-3}$-alkyl)$_2$SO$_2$NHOH, —(CHR$^{36}$)$_m$NR$^{43}$SO$_2$NH$_2$, —(CHR$^{36}$)$_m$N(C$_{1-3}$-alkyl)HSO$_2$NH$_2$, —(CHR$^{36}$)$_m$N(C$_{1-3}$-alkyl)$_2$SO$_2$NH$_2$, —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OH$_{1-3}$-alkyl)-tetrazol-5-yl, —CH(CH$_2$OC$_{1-3}$-alkyl)-tetrazol-5-yl, —CH(OH)-tetrazol-5-yl, —CH(CH$_2$OH)-tetrazol-5-yl, —CHF-tetrazol-5-yl, —CH(C$_{1-6}$-alkyl)-tetrazol-5-yl, —CHR$^{36}$CH(C$_{1-3}$-alkyl)-tetrazol-5-yl, —CHR$^{36}$CH(OH)-tetrazol-5-yl, —CHR$^{36}$CH(OC$_{1-3}$-alkyl)-tetrazol-5-yl, —CHR$^{36}$CH(CH$_2$OC$_{1-3}$alkyl) tetrazol-5-yl, —CHR$^{36}$CH(OH)-tetrazol-5-yl, —CHR$^{36}$CH(CH$_2$OH)-tetrazol-5-yl, —CHR$^{36}$CHF-tetrazol-5-yl, —CH(C$_{1-6}$-alkyl) CHR$^{36}$-tetrazol-5-yl, —CH(C$_{1-3}$-alkyl) CHR$^{36}$-tetrazol-5-yl, —CH(OH) CHR$^{36}$-tetrazol-5-yl, —CH(OC$_{1-3}$-alkyl) CHR$^{36}$-tetrazol-5-yl, —CH(CH$_2$OC$_{1-3}$-alkyl) CHR$^{36}$-tetrazol-5-yl, —CH(OH) CHR$^{36}$-tetrazol-5-yl, —CH(CH$_2$OH) CHR$^{36}$-tetrazol-5-yl or —CHFCHR$^{36}$-tetrazol-5-yl.

In another embodiment, of the present invention provides compounds of general formula (I) wherein:

L is a group selected from hydrogen, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinyl, furanyl-oxy-, thiophenyl-oxy-, oxazolyl-oxy-, thiazolyl-oxy-, phenyl-oxy-, pyridyl-oxy-, pyrimidinyl-oxy-, benzofuranyl-oxy-, benzothiophenyl-oxy-, benzimidazolyl-oxy-, phenyl-N(R$^{12}$)—, pyridyl-N(R$^{12}$)—, pyrimidinyl-N(R$^{12}$)—, benzofuranyl-N(R$^{12}$)—, benzothiophenyl-N(R$^{12}$)—, benzimidazolyl-N(R$^{12}$)—, C$_3$-cycloalkyloxy, C$_4$-cycloalkyloxy, C$_5$-cycloalkyloxy, C$_6$-cycloalkyloxy, C$_7$-cycloalkyloxy, C$_8$-cycloalkyloxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_1$-alkoxy, C$_2$-alkoxy, C$_3$-alkoxy, C$_4$-alkoxy, C$_5$-alkoxy, C$_6$-alkoxy, C$_3$-cycloalkyl-N(R$^{12}$)—, C$_4$-cycloalkyl-N(R$^{12}$)—, C$_5$-cycloalkyl-N(R$^{12}$)—, C$_6$-cycloalkyl-N(R$^{12}$)—, C$_7$-cycloalkyl-N(R$^{12}$)—, C$_8$-cycloalkyl-N(R$^{12}$)—, C$_4$-cycloalkenyl-N ($R^{12}$)—, $C_5$-cycloalkenyl-N($R^{12}$)—, $C_6$-cycloalkenyl-N($R^{12}$)—, $C_7$-cycloalkenyl-N($R^{12}$)— or $C_8$-cycloalkenyl-N($R^{12}$)—;

wherein $R^{12}$ is selected from hydrogen or $C_{1-3}$-alkyl;

wherein L, excluding hydrogen, is optionally substituted with one, two or three groups selected from halogen, hydroxy, $NR^w_2$—C(O)—, $NR^w_2$—S(=O)—, $NR^w_2S(O)_2$—, —$NR^w$—C(O)—$C_{1-6}$-alkyl, —$NR^w$—S(=O)—$C_{1-6}$-alkyl and —$NR^wS(=O)_2$—$C_{1-6}$-alkyl, $C_{1-6}$-alkyl, $C_{2-6}$-alkenyl, $C_{2-6}$-alkynyl, $C_{2-6}$-alkynyl, $C_{3-6}$-cycloalkyl, $C_{4-8}$-cycloalkenyl, $C_{1-8}$-alkoxy, $C_{3-8}$-alkylthio-, $C_{3-8}$-cycloalkylalkoxy, $C_{3-8}$-cycloalkylalkylthio-, $C_{3-8}$-cycloalkyloxy, $C_{3-8}$-cycloalkylthio, halogen, —$NO_2$, —CN, —$NR^9R^9$, —OC(O)$NR^9R^9$, —$CH_2NR^9R^9$, —OC(O)$CR^9$, —C(O)$R^9$ or —COO$R^9$;

wherein $R^w$ is selected from —H or $C_{1-6}$-alkyl;

wherein said substitutents $C_{1-6}$-alkyl, $C_{2-4}$-alkenyl or $C_{2-6}$-alkynyl is optionally substituted with one, two or three substituents independently selected from halogen, —CN, —$CF_3$, —$OCHF_2$, —$OCF_3$, —$NO_2$, —$OR^9$ or $C_{1-6}$-alkyl; and, wherein $R^9$ is independently selected from hydrogen or $C_{1-6}$-alkyl optionally substituted with one, two or three substituents independently selected from halogen, —CN, —$CF_3$, —$OCHF_2$, —$OCF_3$, —$NO_2$, —$OR^9$ or $C_{1-6}$-alkyl;

D is a substituted group selected from phenyl or heteroaryl;

wherein said group is substituted with L and is further substituted with one, two or three substituents independently selected from halogen, —$CF_3$, —CN, $C_{1-6}$-haloalkyl, $C_{1-6}$-alkyl, $C_{1-6}$-haloalkoxy or $C_{1-6}$-alkoxy-;

Z is a group selected from —C(O)NH—;

$R^1$ is a group selected from —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl, methylphenyl-, ethyl-phenyl-, n-propyl-phenyl-, isopropyl-phenyl-, cyclopropyl-phenyl-, cyclopropyl-methyl-phenyl-, cyclopropyl-ethyl-phenyl-, cyclopropyl-propyl-phenyl-, cyclopropyl-butyl-phenyl-, n-butyl-phenyl-, sec-butyl-phenyl-, t-butyl-phenyl-, cyclobutyl-phenyl-, cyclobutyl-methyl-phenyl-, cyclobutyl-ethyl-phenyl-, cyclobutyl-propyl-phenyl-, n-pentyl-phenyl-, neopentyl-phenyl-, isopentyl-phenyl-, cyclopentyl-phenyl-, cyclopentyl-methyl-phenyl-, cyclopentyl-ethyl-phenyl-, hexyl-phenyl-, methyl-pentyl-phenyl-, ethyl-butyl-phenyl-cyclohexyl-phenyl-, ethenyl-phenyl-, n-propenyl-phenyl-, isopropenyl-phenyl-, n-butenyl-phenyl-, sec-butenyl-phenyl-, t-butenyl-phenyl-, cyclobutenyl-phenyl-, n-pentenyl-phenyl-, neopentenyl-phenyl-, isopentenyl-phenyl-, cyclopentenyl-phenyl-, hexenyl-phenyl-, cyclohexenyl-phenyl-, ethynyl-phenyl-, n-propynyl-phenyl-, isopropynyl-phenyl-, n-butynyl-phenyl-, sec-butynyl-phenyl-, t-butynyl-phenyl-, n-pentynyl and n-hexynyl-phenyl-; benzyl, methyl-benzyl-, ethyl-benzyl-, n-propyl-benzyl-, isopropyl-benzyl-, cyclopropyl-benzyl-, cyclopropyl-methyl-benzyl-, cyclopropyl-ethyl-benzyl-, cyclopropyl-propyl-benzyl-, cyclopropyl-butyl-benzyl-, n-butyl-benzyl-, sec-butyl-benzyl-, t-butyl-benzyl-, cyclobutyl-benzyl-, cyclobutyl-methyl-benzyl-, cyclobutyl-ethyl-benzyl-, cyclobutyl-propyl-benzyl-, n-pentyl-benzyl-, neopentyl-benzyl-, isopentyl-benzyl-, cyclopentyl-benzyl-, cyclopentyl-methyl-benzyl-, cyclopentyl-ethyl-benzyl-, hexyl-benzyl-, methyl-pentyl-benzyl-, ethyl-butyl-benzyl-cyclohexyl-benzyl-, ethenyl-benzyl-, n-propenyl-benzyl-, isopropenyl-benzyl-, n-butenyl-benzyl-, sec-butenyl-benzyl-, t-butenyl-benzyl-, cyclobutenyl-benzyl-, n-pentenyl-benzyl-, neopentenyl-benzyl-, isopentenyl-benzyl-, cyclopentenyl-benzyl-, hexenyl-benzyl-, cyclohexenyl-benzyl-, ethynyl-benzyl-, n-propynyl-benzyl-, isopropynyl-benzyl-, n-butynyl-benzyl-, sec-butynyl-benzyl-, t-butynyl-benzyl-, n-pentynyl or n-hexynyl-benzyl-;

wherein each group is optionally substituted with one to six groups independently selected from halogen, —CN, —$C_{1-6}$-alkyl, halogen, —$CHF_2$, —$CF_3$, —$OCF_3$, —$OCHF_2$, —$OCH_2CF_3$, —$OCF_2CHF_2$, —$SCF_3$, —$OR^9$, —$NR^{10}R^{10}$, —$SR^9$, —S(O)$R^9$, —S(O)$_2R^9$, —C(O)$NR^{10}R^{10}$, —OC(O)$NR^{10}R^{10}$, —$NR^9C(O)R^9$, —$OCH_2C(O)NR^{10}R^{10}$, —C(O)$R^9$ or —C(O)$OR^9$, $C_{3-8}$-cycloalkyl, $C_{4-8}$-cycloalkenyl, optionally substituted phenyl or optionally substituted five- or six-membered heteroaryl; wherein, $R^9$ is independently selected from hydrogen, optionally substituted $C_{1-6}$-alkyl or optionally substituted aryl; wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Y is a group selected from —O—, —$CH_2$—, —CH($CH_3$)—, —CH($CH_2CH_3$)—, —C($CH_3$)$_2$— or —CHF—;

X is a group selected from furanylene, thiophenylene, oxazolylene, thiazolylene, phenylene, pyridylene or pyrimidinylene;

wherein X is optionally substituted with one or two groups independently selected from halogen, —CN, —$CF_3$, —$OCF_3$, —$OCHF_2$, —$OCH_2CF_3$, —OH, —$OCH_3$, —$OCH_2CH_3$, —$OCH_2CH_2CH_3$, —$CH_3$, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl or $C_6$-alkenyl;

M is a group selected from —NHC(O)—, —C(O)NH— or —O—;

T is absent or is a group selected from —$CH_2$—; and

A is a group selected from —$CO_2H$, —$CH_2CO_2H$, —$CH_2CH_2CO_2H$, —$CH_2CH(OH)CO_2H$, —$CH_2CH_2CH_2CO_2H$, —C($CH_3$)$HCO_2H$, —C($CF_3$)$HCO_2H$, —C($CH_3$)$HCH_2CO_2H$, —C($CF_3$)$HCH_2CO_2H$, —C($CH_3$)$HCH_2CH_2CO_2H$, —C($CF_3$)$HCH_2CH_2CO_2H$, —$CH_2C$($CH_3$)$HCO_2H$, —$CH_2C$($CF_3$)$HCO_2H$, —$CH_2C$($CH_3$)$HCH_2CO_2H$, —$CH_2CH_2C$($CH_3$)$HCO_2H$, —CH($CH_3$)CH($CH_3$)$CO_2H$, —CH($CH_3$)CH($CH_3$)$CH_2CO_2H$, —CH($CH_3$)$CH_2$CH($CH_3$)$CO_2H$, —$CH_2C$($CH_3$)HC($CH_3$)$HCO_2H$, —CH($CH_2CH_3$)$CH_2CO_2H$, —C($CH_2CH_3$)$HCO_2H$, —C($CH_2CH_2CH_3$)$HCO_2H$, —C($CH_2CH_2CH_3$)$HCH_2CO_2H$, —$CH_2C$($CH_2CH_3$)$HCO_2H$, —$CH_2C$($CH_2CH_2CH_3$)$HCO_2H$, —$SO_3H$, —$CH_2SO_3H$, —$CH_2CH_2SO_3H$, —$CH_2CH_2CH_2SO_3H$, —C($CH_3$)$HSO_3H$, —C($CF_3$)$HSO_3H$, —C($CH_3$)$HCH_2SO_3H$, —C($CF_3$)$HCH_2SO_3H$, —C($CH_3$)$HCH_2SO_3H$, —C($CF_3$)$HCH_2CH_2SO_3H$, —$CH_2C$($CH_3$)$HSO_3H$, —$CH_2C$($CF_3$)$HSO_3H$, —$CH_2C$($CH_3$)$HCH_2SO_3H$, —$CH_2CH_2C$($CH_3$)$HSO_3H$, —CH($CH_3$)CH($CH_3$)$SO_3H$, —CH($CH_3$)CH($CH_3$)$CH_2SO_3H$, —CH($CH_3$)$CH_2$CH($CH_3$)$SO_3H$, —$CH_2C$($CH_3$)HC($CH_3$)$HSO_3H$, —CH($CH_2CH_3$)$CH_2SO_3H$, —C(CH$_2$CH$_3$)HSO$_3$H, —C(CH$_2$CH$_2$CH$_3$)HSO$_3$H, —C(CH$_2$CH$_2$CH$_3$)H, —CH$_2$SO$_3$H, —CH$_2$C(CH$_2$CH$_3$)HSO$_3$H, —CH$_2$C(CH$_2$CH$_2$CH$_3$)HSO$_3$H, —(CHR$^{36}$)$_m$QSO$_2$R$^{39}$, —CHR$^{36}$QSO$_2$R$^{39}$, —(CHR$^{36}$)$_2$QSO$_2$R$^{39}$, —(CHR$^{36}$)$_3$QSO$_2$R$^{39}$, —(CHR$^{36}$)$_m$OSO$_2$R$^{39}$, —(CHR$^{36}$)$_m$OSO$_2$OH, —(CHR$^{36}$)$_m$OSO$_2$ NHOH, —(CHR$^{36}$)$_m$OSO$_2$NH$_2$, —(CHR$^{36}$)$_m$NR$^{43}$SO$_2$R$^{39}$, —(CHR$^{36}$)$_m$N(C$_{1-3}$-alkyl)HSO$_2$R$^{39}$, —(CHR$^{36}$)$_m$N(C$_{1-3}$-alkyl)$_2$SO$_2$R$^{39}$, —(CHR$^{36}$)$_m$NR$^{43}$SO$_2$OH, —(CHR$^{36}$)$_m$ N(C$_{1-3}$-alkyl)HSO$_2$OH, —(CHR$^{36}$)$_m$ N(C$_{1-3}$-alkyl)$_2$SO$_2$OH, —(CHR$^{36}$)$_m$NR$^{43}$SO$_2$NHOH, —(CHR$^{36}$)$_m$ N(C$_{1-3}$-alkyl)HSO$_2$NHOH, —(CHR$^{36}$)$_m$ N(C$_{1-3}$-alkyl)$_2$SO$_2$NHOH, —(CHR$^{36}$)$_m$NR$^{43}$SO$_2$NH$_2$, —(CHR$^{36}$)$_m$ N(C$_{1-3}$-alkyl)HSO$_2$NH$_2$, —(CHR$^{36}$)$_m$ N(C$_{1-3}$-alkyl)$_2$SO$_2$NH$_2$, —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$-alkyl)-tetrazol-5-yl, —CH(CH$_2$OC$_{1-3}$-alkyl)-tetrazol-5-yl, —CH(OH)-tetrazol-5-yl, —CH(CH$_2$OH)-tetrazol-5-yl, —CHF-tetrazol-5-yl, —CH(C$_{1-6}$-alkyl)-tetrazol-5-yl, —CHR$^{36}$CH(C$_{1-3}$-alkyl)-tetrazol-5-yl, —CHR$^{36}$CH(OH)-tetrazol-5-yl, —CHR$^{36}$CH(OC$_{1-3}$-alkyl)-tetrazol-5-yl, —CHR$^{36}$CH(CH$_2$OC$_{1-3}$-alkyl)-tetrazol-5-yl, —CHR$^{36}$CH(OH)-tetrazol-5-yl, —CHR$^{36}$CH(CH$_2$OH)-tetrazol-5-yl, —CHR$^{36}$CHF-tetrazol-5-yl, —CH(C$_{1-6}$-alkyl) CHR$^{36}$-tetrazol-5-yl, —CH(C$_{1-3}$-alkyl) CHR$^{36}$-tetrazol-5-yl, —CH(OH) CHR$^{36}$-tetrazol-5-yl, —CH(OC$_{1-3}$-alkyl) CHR$^{36}$-tetrazol-5-yl, —CH(CH$_2$OC$_{1-3}$-alkyl) CHR$^{36}$-tetrazol-5-yl, —CH(OH) CHR$^{36}$-tetrazol-5-yl, —CH(CH$_2$OH) CHR$^{36}$-tetrazol-5-yl or —CHFCHR$^{36}$-tetrazol-5-yl.

In another embodiment, of the present invention provides compounds of general formula (I) wherein:

L is a group selected from hydrogen, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinyl, furanyl-oxy-, thiophenyl-oxy-, oxazolyl-oxy-, thiazolyl-oxy-, phenyl-oxy-, pyridyl-oxy-, pyrimidinyl-oxy-, benzofuranyl-oxy-, benzothiophenyl-oxy-, benzimidazolyl-oxy-, phenyl-N(R$^{12}$)—, pyridyl-N(R$^{12}$)—, pyrimidinyl-N(R$^{12}$)—, benzofuranyl-N(R$^{12}$)—, benzothiophenyl-N(R$^{12}$)—, benzimidazolyl-N(R$^{12}$)—, C$_3$-cycloalkyloxy, C$_4$-cycloalkyloxy, C$_5$-cycloalkyloxy, C$_6$-cycloalkyloxy, C$_7$-cycloalkyloxy, C$_8$-cycloalkyloxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_1$-alkoxy, C$_2$-alkoxy, C$_3$-alkoxy, C$_4$-alkoxy, C$_5$-alkoxy, C$_6$-alkoxy, C$_3$-cycloalkyl-N(R$^{12}$)—, C$_4$-cycloalkyl-N(R$^{12}$)—, C$_5$-cycloalkyl-N(R$^{12}$)—, C$_6$-cycloalkyl-N(R$^{12}$)—, C$_7$-cycloalkyl-N(R$^{12}$)—, C$_8$-cycloalkyl-N(R$^{12}$)—, C$_4$-cycloalkenyl-N(R$^{12}$)—, C$_5$-cycloalkenyl-N(R$^{12}$)—, C$_6$-cycloalkenyl-N(R$^{12}$)—, C$_7$-cycloalkenyl-N(R$^{12}$)— or C$_8$-cycloalkenyl-N(R$^{12}$)—;

wherein R$^{12}$ is selected from hydrogen or C$_{1-3}$-alkyl;

wherein L, excluding hydrogen, is optionally substituted with one, two or three groups selected from halogen, hydroxy, NR$^w{}_2$—C(O)—, NR$^w{}_2$—S(=O)—, NR$^w{}_2$S(=O)$_2$—, —NR$^w$—C(O)—C$_{1-6}$-alkyl, —NR$^w$—S(=O)—C$_{1-6}$-alkyl and —NR$^w$S(=O)$_2$—C$_{1-6}$-alkyl, C$_{1-6}$-alkyl, C$_{2-6}$-alkenyl, C$_{2-6}$-alkynyl, C$_{2-6}$-alkynyl, C$_{3-6}$-cycloalkyl, C$_{4-8}$-cycloalkenyl, C$_{1-8}$-alkoxy, C$_{3-8}$-alkylthio-, C$_{3-8}$-cycloalkylalkoxy, C$_{3-8}$-cycloalkylalkylthio-, C$_{3-8}$-cycloalkyloxy, C$_{3-8}$-cycloalkylthio, halogen, —NO$_2$, —CN, —NR$^9$R$^9$, —OC(O)NR$^9$R$^9$, —CH$_2$NR$^9$R$^9$, —OC(O)CR$^9$, —OC(O)R$^9$ or —COOR$^9$;

wherein R$^w$ is selected from —H or C$_{1-6}$-alkyl;

wherein said substitutents C$_{1-6}$-alkyl, C$_{2-4}$-alkenyl or C$_{2-6}$-alkynyl is optionally substituted with one, two or three substituents independently selected from halogen, —CN, —CF$_3$, —OCHF$_2$, —OCF$_3$, —NO$_2$, —OR$^9$ or C$_{1-6}$-alkyl; and, wherein R$^9$ is independently selected from hydrogen or C$_{1-6}$-alkyl optionally substituted with one, two or three substituents independently selected from halogen, —CN, —CF$_3$, —OCHF$_2$, —OCF$_3$, —NO$_2$, —OR$^9$ or C$_{1-6}$-alkyl;

D is a substituted group selected from phenyl or heteroaryl;

wherein said group is substituted with L and is further substituted with one, two or three substituents independently selected from halogen, —CN, —CF$_3$, C$_{1-6}$-haloalkyl, C$_{1-6}$-alkyl, C$_{1-6}$-haloalkoxy or C$_{1-6}$-alkoxy-;

Z is isoxazol-3,5-diyl;

R$^1$ is a group selected from —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl, methyl-phenyl-, ethyl-phenyl-, n-propyl-phenyl-, isopropyl-phenyl-, cyclopropyl-phenyl-, cyclopropyl-methyl-phenyl-, cyclopropyl-ethyl-phenyl-, cyclopropyl-propyl-phenyl-, cyclopropyl-butyl-phenyl-, n-butyl-phenyl-, sec-butyl-phenyl-, t-butyl-phenyl-, cyclobutyl-phenyl-, cyclobutyl-methyl-phenyl-, cyclobutyl-ethyl-phenyl-, cyclobutyl-propyl-phenyl-, n-pentyl-phenyl-, neopentyl-phenyl-, isopentyl-phenyl-, cyclopentyl-phenyl-, cyclopentyl-methyl-phenyl-, cyclopentyl-ethyl-phenyl-, hexyl-phenyl-, methyl-pentyl-phenyl-, ethyl-butyl-phenyl-cyclohexyl-phenyl-, ethenyl-phenyl-, n-propenyl-phenyl-, isopropenyl-phenyl-, n-butenyl-phenyl-, sec-butenyl-phenyl-, t-butenyl-phenyl-, cyclobutenyl-phenyl-, n-pentenyl-phenyl-, neopentenyl-phenyl-, isopentenyl-phenyl-, cyclopentenyl-phenyl-, hexenyl-phenyl-, cyclohexenyl-phenyl-, ethynyl-phenyl-, n-propynyl-phenyl-, isopropynyl-phenyl-, n-butynyl-phenyl-, sec-butynyl-phenyl-, t-butynyl-phenyl-, n-pentynyl and n-hexynyl-phenyl-; benzyl, methyl-benzyl-, ethyl-benzyl-, n-propyl-benzyl-, isopropyl-benzyl-, cyclopropyl-benzyl-, cyclopropyl-methyl-benzyl-, cyclopropyl-ethyl-benzyl-, cyclopropyl-propyl-benzyl-, cyclopropyl-butyl-benzyl-, n-butyl-benzyl-, sec-butyl-benzyl-, t-butyl-benzyl-, cyclobutyl-benzyl-, cyclobutyl-methyl-benzyl-, cyclobutyl-ethyl-benzyl-, cyclobutyl-propyl-benzyl-, n-pentyl-benzyl-, neopentyl-benzyl-, isopentyl-benzyl-, cyclopentyl-benzyl-, cyclopentyl-methyl-benzyl-, cyclopentyl-ethyl-benzyl-, hexyl-benzyl-, methyl-pentyl-benzyl-, ethyl-butyl-benzyl-cyclohexyl-benzyl-, ethenyl-benzyl-, n-propenyl-benzyl-, isopropenyl-benzyl-, n-butenyl-benzyl-, sec-butenyl-benzyl-, t-butenyl-benzyl-, cyclobutenyl-benzyl-, n-pentenyl-benzyl-, neopentenyl-benzyl-, isopentenyl-benzyl-, cyclopentenyl-benzyl-, hexenyl-benzyl-, cyclohexenyl-benzyl-, ethynyl-benzyl-, n-propynyl-benzyl-, isopropynyl-benzyl-, n-butynyl-benzyl-, sec-butynyl-benzyl-, t-butynyl-benzyl-, n-pentynyl or n-hexynyl-benzyl-;

wherein each group is optionally substituted with one to six groups independently selected from halogen, —CN, —C$_{1-6}$-alkyl, halogen, —CHF$_2$, —CF$_3$, —OCF$_3$, —OCHF$_2$, —OCH$_2$CF$_3$, —OCF$_2$CHF$_2$, —SCF$_3$, —OR$^9$, —NR$^{10}$R$^{10}$, —SR$^9$, —S(O)R$^9$, —S(O)?R$^9$, —C(O)NR$^{10}$R$^{10}$, —OC(O)NR$^{10}$R$^{10}$, —NR$^9$C(O)R$^9$, —OCH$_2$C(O)NR$^{10}$R$^{10}$, —C(O)R$^9$ or —C(O)OR$^9$, C$_{3-8}$-cycloalkyl, C$_{4-8}$-cycloalkenyl, optionally substituted phenyl or optionally substituted five- or six-membered heteroaryl; wherein, R$^9$ is independently selected from hydrogen, optionally substituted C$_{1-6}$-alkyl or optionally substituted aryl; wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom;

wherein said heterocyclic ring optionally contains one or two further heteroatoms independently selected from nitrogen, oxygen and sulfur; and wherein said heterocyclic ring optionally contains 0, 1 or 2 double bonds;

Y is a group selected from —O—, —CH$_2$—, —CH(CH$_3$)—, —CH(CH$_2$CH$_3$)—, —C(CH$_3$)$_2$— or —CHF—;

X is a group selected from furanylene, thiophenylene, oxazolylene, thiazolylene, phenylene, pyridylene or pyrimidinylene;

wherein X is optionally substituted with one or two groups independently selected from halogen, —CN, —CF$_3$, —OCF$_3$, —OCHF$_2$, —OCH$_2$CF$_3$, —OH, —OCH$_3$, —OCH$_2$CH$_3$, —OCH$_2$CH$_2$CH$_3$, —CH$_3$, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl or C$_6$-alkenyl;

M is a group selected from —NHC(O)—, —C(O)NH— or —O—;

T is absent; and

A is a group selected from —CO$_2$H, —CH$_2$CO$_2$H, —CH$_2$CH$_2$CO$_2$H, —CH$_2$CH(OH)CO$_2$H, —CH$_2$CH$_2$CH$_2$CO$_2$H, —C(CH$_3$)HCO$_2$H, —C(CF$_3$)HCO$_2$H, —C(CH$_3$)HCH$_2$CO$_2$H, —C(CF$_3$)HCH$_2$CO$_2$H, —C(CH$_3$)HCH$_2$CH$_2$CO$_2$H, —C(CF$_3$)HCH$_2$CH$_2$CO$_2$H, —CH$_2$C(CH$_3$)HCO$_2$H, —CH$_2$C(CF$_3$)HCO$_2$H, —CH$_2$C(CH$_3$)HCH$_2$CO$_2$H, —CH$_2$CH$_2$C(CH$_3$)HCO$_2$H, —CH(CH$_3$)CH(CH$_3$)CO$_2$H, —CH(CH$_3$)CH(CH$_3$)CH$_2$CO$_2$H, —CH(CH$_3$)CH$_2$CH(CH$_3$)CO$_2$H, —CH$_2$CH(CH$_3$)CH(CH$_3$)CO$_2$H, —CH(CH$_2$CH$_3$)CH$_2$CO$_2$H, —CH(CH$_2$CH$_3$)CO$_2$H, —CH(CH$_2$CH$_2$CH$_3$)CO$_2$H, —CH(CH$_2$CH$_2$CH$_3$)CH$_2$CO$_2$H, —CH$_2$CH(CH$_2$CH$_3$)CO$_2$H, —CH$_2$CH(CH$_2$CH$_2$CH$_3$)CO$_2$H, —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$-alkyl)-tetrazol-5-yl, —CH(CH$_2$OC$_{1-3}$-alkyl)-tetrazol-5-yl, —CH(OH)-tetrazol-5-yl, —CH(CH$_2$OH)-tetrazol-5-yl or —CHF-tetrazol-5-yl, In another embodiment, of the present invention provides compounds of general formula (I) wherein:

L is a group selected from hydrogen, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinyl, furanyl-oxy-, thiophenyl-oxy-, oxazolyl-oxy-, thiazolyl-oxy-, phenyl-oxy-, pyridyl-oxy-, pyrimidinyl-oxy-, benzofuranyl-oxy-, benzothiophenyl-oxy-, benzimidazolyl-oxy-, phenyl-N(R$^{12}$)—, pyridyl-N(R$^{12}$)—, pyrimidinyl-N(R$^{12}$)—, benzofuranyl-N(R$^{12}$)—, benzothiophenyl-N(R$^{12}$)—, benzimidazolyl-N(R$^{12}$)—, C$_3$-cycloalkyloxy, C$_4$-cycloalkyloxy, C$_5$-cycloalkyloxy, C$_6$-cycloalkyloxy, C$_7$-cycloalkyloxy, C$_8$-cycloalkyloxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_1$-alkoxy, C$_2$-alkoxy, C$_3$-alkoxy, C$_4$-alkoxy, C$_5$-alkoxy, C$_6$-alkoxy, C$_3$-cycloalkyl-N(R$^{12}$)—, C$_4$-cycloalkyl-N(R$^{12}$)—, C$_5$-cycloalkyl-N(R$^{12}$)—, C$_6$-cycloalkyl-N(R$^{12}$)—, C$_7$-cycloalkyl-N(R$^{12}$)—, C$_8$-cycloalkyl-N(R$^{12}$)—, C$_4$-cycloalkenyl-N(R$^{12}$)—, C$_5$-cycloalkenyl-N(R$^{12}$)—, C$_6$-cycloalkenyl-N(R$^{12}$)—, C$_7$-cycloalkenyl-N(R$^{12}$)— or C$_8$-cycloalkenyl-N(R$^{12}$)—;

wherein R$^{12}$ is selected from hydrogen or C$_{1-3}$-alkyl;

wherein said group, excluding hydrogen, is optionally substituted with one, two or three groups selected from halogen, hydroxy, NR$^w$$_2$—C(O)—, NR$^w$$_2$—S(=O)—, NR$^w$$_2$S(=O)$_2$—, —NR$^w$—C(O)—C$_{1-6}$-alkyl, —NR$^w$—S(=O)—C$_{1-6}$-alkyl and —NR$^w$S(=O)$_2$—C$_{1-6}$-alkyl, C$_{1-6}$-alkyl, C$_{2-6}$-alkenyl, C$_{2-6}$-alkynyl, C$_{2-6}$-alkynyl, C$_{3-6}$-cycloalkyl, C$_{4-8}$-cycloalkenyl, C$_{1-8}$-alkoxy, C$_{3-8}$-alkylthio-, C$_{3-8}$-cycloalkylalkoxy, C$_{3-8}$-cycloalkylalkylthio-, C$_{3-8}$-cycloalkyloxy, C$_{3-8}$-cycloalkylthio, halogen, —NO$_2$, —CN, —NR$^9$R$^9$, —OC(O)NR$^9$R$^9$, —CH$_2$NR$^9$R$^9$, —OC(O)CR$^9$, —C(O)R$^9$ or —COOR$^9$;

wherein R$^w$ is selected from —H or C$_{1-6}$-alkyl;

wherein said substitutents C$_{1-6}$-alkyl, C$_{2-4}$-alkenyl or C$_{2-6}$-alkynyl is optionally substituted with one, two or three substituents independently selected from halogen, —CN, —CF$_3$, —OCHF$_2$, —OCF$_3$, —NO$_2$, —OR$^9$ or C$_{1-6}$-alkyl; and, wherein R$^9$ is independently selected from hydrogen or C$_{1-6}$-alkyl optionally substituted with one, two or three substituents independently selected from halogen, —CN, —CF$_3$, —OCHF$_2$, —OCF$_3$, —NO$_2$, —OR$^9$ or C$_{1-6}$-alkyl;

D is a substituted group selected from a phenyl, five- or six-membered heterocyclic monoaryl, nine- or ten-membered carbocyclic bicyclic aryl, nine- or ten-membered bicyclic heteroaryl, five- or six-membered cycloalkyl or five- or six-membered heterocyclyl; wherein said group is substituted with L and is optionally further substituted;

Z is —C(O)NH—;

R$^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl, methyl-phenyl-, ethyl-phenyl-, n-propyl-phenyl-, isopropyl-phenyl-, cyclopropyl-phenyl-, cyclopropyl-methyl-phenyl-, cyclopropyl-ethyl-phenyl-, cyclopropyl-propyl-phenyl-, cyclopropyl-butyl-phenyl-, n-butyl-phenyl-, sec-butyl-phenyl-, t-butyl-phenyl-, cyclobutyl-phenyl-, cyclobutyl-methyl-phenyl-, cyclobutyl-ethyl-phenyl-, cyclobutyl-propyl-phenyl-, n-pentyl-phenyl-, neopentyl-phenyl-, isopentyl-phenyl-, cyclopentyl-phenyl-, cyclopentyl-methyl-phenyl-, cyclopentyl-ethyl-phenyl-, hexyl-phenyl-, methyl-pentyl-phenyl-, ethyl-butyl-phenyl-cyclohexyl-phenyl-, ethenyl-phenyl-, n-propenyl-phenyl-, isopropenyl-phenyl-, n-butenyl-phenyl-, sec-butenyl-phenyl-, t-butenyl-phenyl-, cyclobutenyl-phenyl-, n-pentenyl-phenyl-, neopentenyl-phenyl-, isopentenyl-phenyl-, cyclopentenyl-phenyl-, hexenyl-phenyl-, cyclohexenyl-phenyl-, ethynyl-phenyl-, n-propynyl-phenyl-, isopropynyl-phenyl-, n-butynyl-phenyl-, sec-butynyl-phenyl-, t-butynyl-phenyl-, n-pentynyl and n-hexynyl-phenyl-; benzyl, methyl-benzyl-, ethyl-benzyl-, n-propyl-benzyl-, isopropyl-benzyl-, cyclopropyl-benzyl-, cyclopropyl-methyl-benzyl-, cyclopropylethyl-benzyl-, cyclopropyl-propyl-benzyl-, cyclopropyl-butyl-benzyl-, n-butyl-benzyl-, sec-butyl-benzyl-, t-butyl-benzyl-, cyclobutyl-benzyl-, cyclobutyl-methyl-benzyl-, cyclobutyl-ethyl-benzyl-, cyclobutyl-propyl-benzyl-, n-pentyl-benzyl-, neopentyl-benzyl-, isopentyl-benzyl-, cyclopentyl-benzyl-, cyclopentyl-methyl-benzyl-, cyclopentyl-ethyl-benzyl-, hexyl-benzyl-, methyl-pentyl-benzyl-, ethyl-butyl-benzyl-cyclohexyl-benzyl-, ethenyl-benzyl-, n-propenyl-benzyl-, isopropenyl-benzyl-, n-butenyl-benzyl-, sec-butenyl-benzyl-, t-butenyl-benzyl-, cyclobutenyl-benzyl-, n-pentenyl-benzyl-, neopentenyl-benzyl-, isopentenyl-benzyl-, cyclopentenyl-benzyl-, hexenyl-benzyl-, cyclohexenyl-benzyl-, ethynyl-benzyl-, n-propynyl-benzyl-, isopropynyl-benzyl-, n-butynyl-benzyl-, sec-butynyl-benzyl-, t-butynyl-benzyl-, n-pentynyl and n-hexynyl-benzyl-;

wherein each group is optionally substituted with one to six groups independently selected from halogen, —CN, —$C_{1-6}$-alkyl, halogen, —$CHF_2$, —$CF_3$, —$OCF_3$, —$OCHF_2$, —$OCH_2CF_3$, —$OCF_2CHF_2$, —$SCF_3$, —$OR^9$, —$NR^{10}R^{10}$, —$SR^9$, —$S(O)R^9$, —$S(O)_2R^9$, —$C(O)NR^{10}R^{10}$, —$OC(O)NR^{10}R^{10}$, —$NR^9C(O)R^9$, —$OCH_2C(O)NR^{10}R^{10}$, —$C(O)R^9$ or —$C(O)OR^9$, $C_{3-8}$-cycloalkyl, $C_{4-8}$-cycloalkenyl, optionally substituted phenyl or optionally substituted five- or six-membered heteroaryl; wherein; $R^9$ is independently selected from hydrogen, optionally substituted $C_{1-6}$-alkyl or optionally substituted aryl; wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Y is a group selected from —O—, —$CH_2$—, —CH($CH_3$)—, —$CH(CH_2CH_3)$—, —$C(CH_3)_2$— or —CHF—;

X is a group selected from furanylene, thiophenylene, oxazolylene, thiazolylene, phenylene, pyridylene or pyrimidinylene;

wherein X is optionally substituted with one or two groups independently selected from halogen, —CN, —$CF_3$, —$OCF_3$, —$OCHF_2$, —$OCH_2CF_3$, —OH, —$OCH_3$, —$OCH_2CH_3$, —$OCH_2CH_2CH_3$, —$CH_3$, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl or $C_6$-alkenyl;

M is a group selected from —NHC(O)—, —C(O)NH— or —O—;

T is absent; and

A is a group selected from —$CO_2H$, —$CH_2CO_2H$, —$CH_2CH_2CO_2H$, —$CH_2CH(OH)CO_2H$, —$CH_2CH_2CH_2CO_2H$, —$C(CH_3)HCO_2H$, —$C(CF_3)HCO_2H$, —$C(CH_3)HCH_2CO_2H$, —$C(CF_3)HCH_2CO_2H$, —$C(CH_3)HCH_2CH_2CO_2H$, —$C(CF_3)HCH_2CH_2CO_2H$, —$CH_2C(CH_3)HCO_2H$, —$CH_2C(CF_3)HCO_2H$, —$CH_2C(CH_3)HCH_2CO_2H$, —$CH_2CH_2C(CH_3)HCO_2H$, —$CH(CH_3)CH(CH_3)CO_2H$, —$CH(CH_3)CH(CH_3)CH_2CO_2H$, —$CH(CH_3)CH_2CH(CH_3)CO_2H$, —$CH_2C(CH_3)HC(CH_3)HCO_2H$, —$CH(CH_2CH_3)CH_2CO_2H$, —$C(CH_2CH_3)HCO_2H$, —$C(CH_2CH_2CH_3)HCO_2H$, —$C(CH_2CH_2CH_3)HCH_2CO_2H$, —$CH_2C(CH_2CH_3)HCO_2H$, —$CH_2C(CH_2CH_2CH_3)HCO_2H$, —$SO_3H$, —$CH_2SO_3H$, —$CH_2CH_2SO_3H$, —$CH_2CH_2CH_2SO_3H$, —$C(CH_3)HSO_3H$, —$C(CF_3)HSO_3H$, —$C(CH_3)HCH_2SO_3H$, —$C(CF_3)HCH_2SO_3H$, —$C(CH_3)HCH_2CH_2SO_3H$, —$C(CF_3)HCH_2CH_2SO_3H$, —$CH_2C(CH_3)HSO_3H$, —$CH_2C(CF_3)HSO_3H$, —$CH_2C(CH_3)HCH_2SO_3H$, —$CH_2CH_2C(CH_3)HSO_3H$, —$CH(CH_3)CH(CH_3)SO_3H$, —$CH(CH_3)CH(CH_3)CH_2SO_3H$, —$CH(CH_3)CH_2CH(CH_3)SO_3H$, —$CH_2C(CH_3)HC(CH_3)HSO_3H$, —$CH(CH_2CH_3)CH_2SO_3H$, —$C(CH_2CH_3)HSO_3H$, —$C(CH_2CH_2CH_3)HSO_3H$, —$C(CH_2CH_2CH_3)H$, —$CH_2SO_3H$, —$CH_2C(CH_2CH_3)HSO_3H$, —$CH_2C(CH_2CH_2CH_3)HSO_3H$, —$(CHR^{36})_m QSO_2R^{39}$, —$CHR^{36}QSO_2R^{99}$, —$(CHR^{36})_2QSO_2R^{39}$, —$(CHR^{36})_3QSO_2R^{39}$, —$(CHR^{36})_m OSO_2R^{39}$, —$(CHR^{36})_m OSO_2OH$, —$(CHR^{36})_m OSO_2NHOH$, —$(CHR^{36})_m OSO_2NH_2$, —$(CHR^{36})_m NR^{43}SO_2R^{39}$, —$(CHR^{36})_m N(C_{1-3}\text{-alkyl})HSO_2R^{39}$, —$(CHR^{36})_m N(C_{1-3}\text{-alkyl})_2SO_2R^{39}$, —$(CHR^{36})_m NR^{43}SO_2OH$, —$(CHR^{36})_m N(C_{1-3}\text{-alkyl})HSO_2OH$, —$(CHR^{36})_m N(C_{1-3}\text{-alkyl})_2SO_2OH$, —$(CHR^{36})_m NR^{43}SO_2NHOH$, —$(CHR^{36})_m N(C_{1-3}\text{-alkyl})HSO_2NHOH$, —$(CHR^{36})_m N(C_{1-3}\text{-alkyl})_2SO_2NHOH$, —$(CHR^{36})_m NR^{43}SO_2NH_2$, —$(CHR^{36})_m N(C_{1-3}\text{-alkyl})HSO_2NH_2$, —$(CHR^{36})_m N(C_{1-3}\text{-alkyl})_2SO_2NH_2$, —$(CHR^{36})_q$ tetrazol-5-yl, -tetrazol-5-yl, —$CHR^{36}$-tetrazol-5-yl, —$(CHR^{36})_2$ tetrazol-5-yl, —$(CHR^{36})_3$ tetrazol-5-yl, —$CH(C_{1-6}\text{-alkyl})$-tetrazol-5-yl, —$CH(C_{1-3}\text{-alkyl})$-tetrazol-5-yl, —CH(OH)-tetrazol-5-yl, —$CH(OC_{1-3}\text{-alkyl})$-tetrazol-5-yl, —$CH(CH_2OC_{1-3}\text{-alkyl})$-tetrazol-5-yl, —CH(OH)-tetrazol-5-yl, —$CH(CH_2OH)$-tetrazol-5-yl, —CHF-tetrazol-5-yl, —$C(C_{1-6}\text{-alkyl})$-tetrazol-5-yl, —$CHR^{36}CH(C_{1-3}\text{-alkyl})$-tetrazol-5-yl, —$CHR^{36}CH(OH)$-tetrazol-5-yl, —$CHR^{36}CH(OC_{1-3}\text{-alkyl})$-tetrazol-5-yl, —$CHR^{36}CH(CH_2OC_{1-3}\text{-alkyl})$-tetrazol-5-yl, —$CHR^{36}CH(OH)$-tetrazol-5-yl, —$CHR^{36}CH(CH_2OH)$-tetrazol-5-yl, —$CHR^{36}CHF$-tetrazol-5-yl, —$CH(C_{1-6}\text{-alkyl}) CHR^{36}$-tetrazol-5-yl, —$CH(C_{1-3}\text{-alkyl}) CHR^{36}$-tetrazol-5-yl, —CH(OH) $CHR^{36}$-tetrazol-5-yl, —CH($OC_{1-3}$-alkyl) $CHR^{36}$-tetrazol-5-yl, —$CH(CH_2OC_{1-3}\text{-alkyl}) CHR^{36}$-tetrazol-5-yl, —CH(OH) $CHR^{36}$-tetrazol-5-yl, —$CH(CH_2OH) CHR^{36}$-tetrazol-5-yl or —$CHFCHR^{36}$-tetrazol-5-yl.

In another embodiment, of the present invention provides compounds of general formula (I) wherein:

L is a group selected from hydrogen, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinyl, furanyl-oxy-, thiophenyl-oxy-, oxazolyl-oxy-, thiazolyl-oxy-, phenyl-oxy-, pyridyl-oxy-, pyrimidinyl-oxy-, benzofuranyl-oxy-, benzothiophenyl-oxy-, benzimidazolyl-oxy-, phenyl-N($R^{12}$)—, pyridyl-N($R^{12}$)—, pyrimidinyl-N($R^{12}$)—, benzofuranyl-N($R^{12}$)—, benzothiophenyl-N($R^{12}$)—, benzimidazolyl-N($R^{12}$)—, $C_3$-cycloalkyloxy, $C_4$-cycloalkyloxy, $C_5$-cycloalkyloxy, $C_6$-cycloalkyloxy, $C_7$-cycloalkyloxy, $C_8$-cycloalkyloxy, $C_4$-cycloalkenyloxy, $C_5$-cycloalkenyloxy, $C_6$-cycloalkenyloxy, $C_7$-cycloalkenyloxy, $C_8$-cycloalkenyloxy, $C_1$-alkoxy, $C_2$-alkoxy, $C_3$-alkoxy, $C_4$-alkoxy, $C_5$-alkoxy, $C_6$-alkoxy, $C_3$-cycloalkyl-N($R^{12}$)—, $C_4$-cycloalkyl-N($R^{12}$)—, $C_5$-cycloalkyl-N($R^{12}$)—, $C_6$-cycloalkyl-N($R^{12}$)—, $C_7$-cycloalkyl-N($R^{12}$)—, $C_8$-cycloalkyl-N($R^{12}$)—, $C_4$-cycloalkenyl-N($R^{12}$)—, $C_5$-cycloalkenyl-N($R^{12}$)—, $C_6$-cycloalkenyl-N($R^{12}$)—, $C_7$-cycloalkenyl-N($R^{12}$)— or $C_8$-cycloalkenyl-N($R^{12}$)—;

wherein $R^{12}$ is selected from hydrogen or $C_{1-3}$-alkyl;

wherein said group, excluding hydrogen, is optionally substituted with one, two or three groups selected from halogen, hydroxy, $NR^w_2$—C(O)—, $NR^w_2$—S(=O)—, $NR^w_2S(=O)_2$—, —$NR^w$—C(O)—$C_{1-6}$-alkyl, —$NR^w$—S(=O)—$C_{1-6}$-alkyl and —$NR^wS(=O)_2$—$C_{1-6}$-alkyl, $C_{1-6}$-alkyl, $C_{2-6}$-alkenyl, $C_{2-6}$-alkynyl, $C_{2-6}$-alkynyl, $C_{3-6}$-cycloalkyl, $C_{4-8}$-cycloalkenyl, $C_{1-8}$-alkoxy, $C_{3-8}$-alkylthio-, $C_{3-8}$-cycloalkylalkoxy, $C_{3-8}$-cycloalkylalkylthio-, $C_{3-8}$-cycloalkyloxy, $C_{3-8}$-cycloalkylthio, halogen, —$NO_2$, —CN, —$NR^9R^9$, —OC(O)$NR^9R^9$, —$CH_2NR^9R^9$, —OC(O)$CR^9$, —C(O)$R^9$ or —COO$R^9$;

wherein $R^w$ is selected from —H or $C_{1-6}$-alkyl;

wherein said substituents $C_{1-6}$-alkyl, $C_{2-4}$-alkenyl or $C_{2-6}$-alkynyl is optionally substituted with one, two or three substituents independently selected from halogen, —CN, —$CF_3$, —$OCHF_2$, —$OCF_3$, —$NO_2$, —$OR^9$ or $C_{1-6}$-alkyl; and, wherein $R^9$ is independently selected from hydrogen or $C_{1-6}$-alkyl optionally substituted with one, two or three substituents independently selected from halogen, —CN, —$CF_3$, —$OCHF_2$, —$OCF_3$, —$NO_2$, —$OR^9$ or $C_{1-6}$-alkyl;

D is a substituted group selected from a phenyl, five- or six-membered heterocyclic monoaryl, nine- or ten-membered carbocyclic bicyclic aryl, nine- or ten-membered bicyclic heteroaryl, five- or six-membered cycloalkyl or five- or six-membered heterocyclyl; wherein said group is substituted with L and is optionally further substituted;

Z is isoxazol-3,5-diyl;

$R^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl, methyl-phenyl-, ethyl-phenyl-, n-propyl-phenyl-, isopropyl-phenyl-, cyclopropyl-phenyl-, cyclopropyl-methyl-phenyl-, cyclopropyl-ethyl-phenyl-, cyclopropyl-propyl-phenyl-, cyclopropyl-butyl-phenyl-, n-butyl-phenyl-, sec-butyl-phenyl-, t-butyl-phenyl-, cyclobutyl-phenyl-, cyclobutyl-methyl-phenyl-, cyclobutyl-ethyl-phenyl-, cyclobutyl-propyl-phenyl-, n-pentyl-phenyl-, neopentyl-phenyl-, isopentyl-phenyl-, cyclopentyl-phenyl-, cyclopentyl-methyl-phenyl-, cyclopentyl-ethyl-phenyl-, hexyl-phenyl-, methyl-pentyl-phenyl-, ethyl-butyl-phenyl-cyclohexyl-phenyl-, ethenyl-phenyl-, n-propenyl-phenyl-, isopropenyl-phenyl-, n-butenyl-phenyl-, sec-butenyl-phenyl-, t-butenyl-phenyl-, cyclobutenyl-phenyl-, n-pentenyl-phenyl-, neopentenyl-phenyl-, isopentenyl-phenyl-, cyclopentenyl-phenyl-, hexenyl-phenyl-, cyclohexenyl-phenyl-, ethynyl-phenyl-, n-propynyl-phenyl-, isopropynyl-phenyl-, n-butynyl-phenyl-, sec-butynyl-phenyl-, t-butynyl-phenyl-, n-pentynyl and n-hexynyl-phenyl-; benzyl, methyl-benzyl-, ethyl-benzyl-, n-propyl-benzyl-, isopropyl-benzyl-, cyclopropyl-benzyl-, cyclopropyl-methyl-benzyl-, cyclopropyl-ethyl-benzyl-, cyclopropyl-propyl-benzyl-, cyclopropyl-butyl-benzyl-, n-butyl-benzyl-, sec-butyl-benzyl-, t-butyl-benzyl-, cyclobutyl-benzyl-, cyclobutyl-methyl-benzyl-, cyclobutyl-ethyl-benzyl-, cyclobutyl-propyl-benzyl-, n-pentyl-benzyl-, neopentyl-benzyl-, isopentyl-benzyl-, cyclopentyl-benzyl-, cyclopentyl-methyl-benzyl-, cyclopentyl-ethyl-benzyl-, hexyl-benzyl-, methyl-pentyl-benzyl-, ethyl-butyl-benzyl-cyclohexyl-benzyl-, ethenyl-benzyl-, n-propenyl-benzyl-, isopropenyl-benzyl-, n-butenyl-benzyl-, sec-butenyl-benzyl-, t-butenyl-benzyl-, cyclobutenyl-benzyl-, n-pentenyl-benzyl-, neopentenyl-benzyl-, isopentenyl-benzyl-, cyclopentenyl-benzyl-, hexenyl-benzyl-, cyclohexenyl-benzyl-, ethynyl-benzyl-, n-propynyl-benzyl-, isopropynyl-benzyl-, n-butynyl-benzyl-, sec-butynyl-benzyl-, t-butynyl-benzyl-, n-pentynyl and n-hexynyl-benzyl-;

wherein each group is optionally substituted with one to six groups independently selected from halogen, —CN, —$C_{1-6}$-alkyl, halogen, —$CHF_2$, —$CF_3$, —$OCF_3$, —$OCHF_2$, —$OCH_2CF_3$, —$OCF_2CHF_2$, —$SCF_3$, —$OR^9$, —$NR^{10}R^{10}$, —$SR^9$, —S(O)$R^9$, —S(O)$_2R^9$, —C(O)$NR^{10}R^{10}$, —OC(O)$NR^{10}R^{10}$, —$NR^9$C(O)$R^9$, —$OCH_2$C(O)$NR^{10}R^{10}$, —C(O)$R^9$ or —C(O)O$R^9$, $C_{3-8}$-cycloalkyl, $C_{4-8}$-cycloalkenyl, optionally substituted phenyl or optionally substituted five- or six-membered heteroaryl; wherein, $R^9$ is independently selected from hydrogen, optionally substituted $C_{1-6}$-alkyl or optionally substituted aryl; wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Y is a group selected from —O—, —$CH_2$—, —CH($CH_3$)—, —CH($CH_2CH_3$)—, —C($CH_3$)$_2$— or —CHF—;

X is a group selected from furanylene, thiophenylene, oxazolylene, thiazolylene, phenylene, pyridylene or pyrimidinylene;

wherein X is optionally substituted with one or two groups independently selected from halogen, —CN, —$CF_3$, —$OCF_3$, —$OCHF_2$, —$OCH_2CF_3$, —OH, —$OCH_3$, —$OCH_2CH_3$, —$OCH_2CH_2CH_3$, —$CH_3$, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl or $C_6$-alkenyl;

M is a group selected from —NHC(O)—, —C(O)NH— or —O—;

T is absent; and

A is a group selected from —$CO_2H$, —$CH_2CO_2H$, —$CH_2CH_2CO_2H$ —$CH_2CH(OH)CO_2H$, —$CH_2CH_2CH_2CO_2H$, —C($CH_3$)$HCO_2H$, —C($CF_3$)$HCO_2H$, —C($CH_3$)$HCH_2CO_2H$, —C($CF_3$)$HCH_2CO_2H$, —C($CH_3$)$HCH_2CH_2CO_2H$, —C($CF_3$)$HCH_2CH_2CO_2H$, —$CH_2$C($CH_3$)$HCO_2H$, —$CH_2$C($CF_3$)$HCO_2H$, —$CH_2$C($CH_3$)$HCH_2CO_2H$, —$CH_2CH_2$C($CH_3$)$HCO_2H$, —CH($CH_3$)CH($CH_3$)$CO_2H$, —CH($CH_3$)CH($CH_3$)$CH_2CO_2H$, —CH($CH_3$)$CH_2$CH($CH_3$)$CO_2H$, —$CH_2$CH($CH_3$)CH($CH_3$)$CO_2H$, —CH($CH_2CH_3$)$CH_2CO_2H$, —CH($CH_2CH_3$)$CO_2H$, —CH($CH_2CH_3$CH_2CH_3$)$CO_2H$, —CH($CH_2CH_3$)$CH_2CO_2H$, —$CH_2$CH($CH_2CH_2CH_3$)$CO_2H$ —(CH$R^{36}$)$_q$ tetrazol-5-yl, -tetrazol-5-yl, —CH$R^{36}$-tetrazol-5-yl, —(CH$R^{36}$)$_2$ tetrazol-5-yl, —(CH$R^{36}$)$_3$ tetrazol-5-yl, —CH($C_{1-6}$-alkyl)-tetrazol-5-yl, —CH($C_{1-3}$-alkyl)-tetrazol-5-yl, —CH(OH)-tetrazol-5-yl, —CH(O$C_{1-3}$-alkyl)-tetrazol-5-yl, —CH($CH_2$O$C_{1-3}$-alkyl)-tetrazol-5-yl, —CH(OH)-tetrazol-5-yl, —CH($CH_2$OH)-tetrazol-5-yl or —CHF-tetrazol-5-yl.

In another embodiment, of the present invention provides compounds of general formula (I) wherein:

L is a group selected from hydrogen, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinyl, furanyl-oxy-, thiophenyl-oxy-, oxazolyl-oxy-, thiazolyl-oxy-, phenyl-oxy-, pyridyl-oxy-, pyrimidinyl-oxy-, benzofuranyl-oxy-, benzothiophenyl-oxy-, benzimidazolyl-oxy-, phenyl-N($R^{12}$)—, pyridyl-N($R^{12}$)—, pyrimidinyl-N($R^{12}$)—, benzofuranyl-N($R^{12}$)—, benzothiophenyl-N($R^{12}$)—, benzimidazolyl-N($R^{12}$)—, $C_3$-cycloalkyloxy, $C_4$-cycloalkyloxy, $C_5$-cycloalkyloxy, $C_6$-cycloalkyloxy, $C_7$-cycloalkyloxy, $C_8$-cycloalkyloxy, $C_4$-cycloalkenyloxy, $C_5$-cycloalkenyloxy, $C_6$-cycloalkenyloxy, $C_7$-cycloalkenyloxy, $C_8$-cycloalkenyloxy, $C_1$-alkoxy, $C_2$-alkoxy, $C_3$-alkoxy, $C_4$-alkoxy, $C_5$-alkoxy, $C_6$-alkoxy, $C_3$-cycloalkyl-N($R^{12}$)—, $C_4$-cycloalkyl-N($R^{12}$)—, $C_5$-cycloalkyl-N($R^{12}$)—, $C_6$-cycloalkyl-N($R^{12}$)—, $C_7$-cycloalkyl-N($R^{12}$)—, $C_8$-cycloalkyl-N($R^{12}$)—, $C_4$-cycloalkenyl-N($R^{12}$)—, $C_5$-cycloalkenyl-N($R^{12}$)—, $C_6$-cycloalkenyl-N($R^{12}$)—, $C_7$-cycloalkenyl-N($R^{12}$)— or $C_8$-cycloalkenyl-N($R^{12}$)—;

wherein $R^{12}$ is selected from hydrogen or $C_{1-3}$-alkyl;

wherein said group, excluding hydrogen, is optionally substituted with one, two or three groups selected from halogen, hydroxy, $NR^w{}_2$—C(O)—, $NR^w{}_2$—S(=O)—, $NR^w{}_2S(=O)_2$—, —$NR^w$—C(O)—$C_{1-6}$-alkyl, —$NR^w$—S(=O)—$C_{1-6}$-alkyl and —$NR^wS(=O)_2$—$C_{1-6}$-alkyl, $C_{1-6}$-alkyl, $C_{2-6}$-alkenyl, $C_{2-6}$-alkynyl, $C_{2-6}$-alkynyl, $C_{3-6}$-cycloalkyl, $C_{4-8}$-cycloalkenyl, $C_{1-8}$-alkoxy, $C_{3-8}$-alkylthio-, $C_{3-8}$-cycloalkylalkoxy, $C_{3-8}$-cycloalkylalkylthio-, $C_{3-8}$-cycloalkyloxy, $C_{3-8}$-cycloalkylthio, halogen, —$NO_2$, —CN, —$NR^9R^9$, —OC(O)$NR^9R^9$, —$CH_2NR^9R^9$, —OC(O)$CR^9$, —C(O)$R^9$ or —COO$R^9$;

wherein $R^w$ is selected from —H or $C_{1-6}$-alkyl;

wherein said substituents $C_{1-6}$-alkyl, $C_{2-4}$-alkenyl or $C_{2-6}$-alkynyl is optionally substituted with one, two or three substituents independently selected from halogen, —CN, —$CF_3$, —$OCHF_2$, —$OCF_3$, —$NO_2$, —$OR^9$ or $C_{1-6}$-alkyl; and, wherein $R^9$ is independently selected from hydrogen or $C_{1-6}$-alkyl optionally substituted with one, two or three substituents independently selected from halogen, —CN, —$CF_3$, —$OCHF_2$, —$OCF_3$, —$NO_2$, —$OR^9$ or $C_{1-6}$-alkyl;

D is a substituted first group selected from phenyl, five- or six-membered heterocyclic monoaryl, nine- or ten-membered, carbocyclic bicyclic aryl, nine- or ten-membered bicyclic heteroaryl, five- or six-membered cycloalkyl or five- or six-membered heterocyclyl;

wherein said first group is substituted with L and is further substituted with a second group, —$(CR^{11}R^{11})_a$—O—$(CR^{11}R^{11})_c$—O—, to form a third group; wherein said —$(CR^{11}R^{11})_a$—O—$(CR^{11}R^{11})_c$—O— is attached at two adjacent positions on D to form a 5- or 6-membered ring; wherein a is 0 or 1; wherein c is 1 or 2; and wherein each $R^{11}$ is independently selected from hydrogen, $C_{1-6}$-alkyl or fluoro;

wherein said third group is optionally substituted with one, two, three or four substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{1-6}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$NO_2$, —CN, —$NR^{10}R^{10}$, —$OR^9$, —$SR^9$, —S(O)$R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —OC(O)$NR^{10}R^{10}$, —$CH_2NR^{10}R^{10}$, —OC(O)$R^9$, —C(O)$R^9$ or —COO$R^9$;

wherein, $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Z is —C(O)NH—;

$R^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl, methyl-phenyl-, ethyl-phenyl-, n-propyl-phenyl-, isopropyl-phenyl-, cyclopropyl-phenyl-, cyclopropyl-methyl-phenyl-, cyclopropyl-ethyl-phenyl-, cyclopropyl-propyl-phenyl-, cyclopropyl-butyl-phenyl-, n-butyl-phenyl-, sec-butyl-phenyl-, t-butyl-phenyl-, cyclobutyl-phenyl-, cyclobutyl-methyl-phenyl-, cyclobutyl-ethyl-phenyl-, cyclobutyl-propyl-phenyl-, n-pentyl-phenyl-, neopentyl-phenyl-, isopentyl-phenyl-, cyclopentyl-phenyl-, cyclopentyl-methyl-phenyl-, cyclopentyl-ethyl-phenyl-, hexyl-phenyl-, methyl-pentyl-phenyl-, ethyl-butyl-phenyl-cyclohexyl-phenyl-, ethenyl-phenyl-, n-propenyl-phenyl-, isopropenyl-phenyl-, n-butenyl-phenyl-, sec-butenyl-phenyl-, t-butenyl-phenyl-, cyclobutenyl-phenyl-, n-pentenyl-phenyl-, neopentenyl-phenyl-, isopentenyl-phenyl-, cyclopentenyl-phenyl-, hexenyl-phenyl-, cyclohexenyl-phenyl-, ethynyl-phenyl-, n-propynyl-phenyl-, isopropynyl-phenyl-, n-butynyl-phenyl-, sec-butynyl-phenyl-, t-butynyl-phenyl-, n-pentynyl and n-hexynyl-phenyl-; benzyl, methyl-benzyl-, ethyl-benzyl-, n-propyl-benzyl-, isopropyl-benzyl-, cyclopropyl-benzyl-, cyclopropyl-methyl-benzyl-, cyclopropyl-ethyl-benzyl-, cyclopropyl-propyl-benzyl-, cyclopropyl-butyl-benzyl-, n-butyl-benzyl-, sec-butyl-benzyl-, t-butyl-benzyl-, cyclobutyl-benzyl-, cyclobutyl-methyl-benzyl-, cyclobutyl-ethyl-benzyl-, cyclobutyl-propyl-benzyl-, n-pentyl-benzyl-, neopentyl-benzyl-, isopentyl-benzyl-, cyclopentyl-benzyl-, cyclopentyl-methyl-benzyl-, cyclopentyl-ethyl-benzyl-, hexyl-benzyl-, methyl-pentyl-benzyl-, ethyl-butyl-benzyl-cyclohexyl-benzyl-, ethenyl-benzyl-, n-propenyl-benzyl-, isopropenyl-benzyl-, n-butenyl-benzyl-, sec-butenyl-benzyl-, t-butenyl-benzyl-, cyclobutenyl-benzyl-, n-pentenyl-benzyl-, neopentenyl-benzyl-, isopentenyl-benzyl-, cyclopentenyl-benzyl-, hexenyl-benzyl-, cyclohexenyl-benzyl-, ethynyl-benzyl-, n-propynyl-benzyl-, isopropynyl-benzyl-, n-butynyl-benzyl-, sec-butynyl-benzyl-, t-butynyl-benzyl-, n-pentynyl and n-hexynyl-benzyl-;

wherein each group is optionally substituted with one to six groups independently selected from halogen, —CN, —$C_{1-6}$-alkyl, halogen, —$CHF_2$, —$CF_3$, —$OCF_3$, —$OCHF_2$, —$OCH_2CF_3$, —$OCF_2CHF_2$, —$SCF_3$, —$OR^9$, —$NR^{10}R^{10}$, —$SR^9$, —S(O)$R^9$, —$S(O)_2R^9$, —C(O)$NR^{10}R^{10}$, —OC(O)$NR^{10}R^{10}$, —$NR^9C(O)R^9$, —$OCH_2C(O)NR^{10}R^{10}$, —C(O)$R^9$ or —C(O)O$R^9$, $C_{3-8}$-cycloalkyl, $C_{4-8}$-cycloalkenyl, optionally substituted phenyl or optionally substituted five- or six-membered heteroaryl; wherein, $R^9$ is independently selected from hydrogen, optionally substituted $C_{1-6}$-alkyl or optionally substituted aryl; wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom;

wherein said heterocyclic ring optionally contains one or two further heteroatoms independently selected from nitrogen, oxygen and sulfur; and wherein said heterocyclic ring optionally contains 0, 1 or 2 double bonds;

Y is a group selected from —O—, —CH$_2$—, —CH(CH$_3$)—, —CH(CH$_2$CH$_3$)—, —C(CH$_3$)$_2$— or —CHF—;

X is a group selected from furanylene, thiophenylene, oxazolylene, thiazolylene, phenylene, pyridylene or pyrimidinylene;

wherein X is optionally substituted with one or two groups independently selected from halogen, —CN, —CF$_3$, —OCF$_3$, —OCHF$_2$, —OCH$_2$CF$_3$, —OH, —OCH$_3$, —OCH$_2$CH$_3$, —OCH$_2$CH$_2$CH$_3$, —CH$_3$, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl or C$_6$-alkenyl;

M is a group selected from —NHC(O)—, —C(O)NH— or —O—;

T is absent; and

A is a group selected from —CO$_2$H, —CH$_2$CO$_2$H, —CH$_2$CH$_2$CO$_2$H, —CH$_2$CH(OH)CO$_2$H, —CH$_2$CH$_2$CH$_2$CO$_2$H, —C(CH$_3$)HCO$_2$H, —C(CF$_3$)HCO$_2$H, —C(CH$_3$)HCH$_2$CO$_2$H, —C(CF$_3$)HCH$_2$CO$_2$H, —C(CH$_3$)HCH$_2$CH$_2$CO$_2$H, —C(CF$_3$)HCH$_2$CH$_2$CO$_2$H, —CH$_2$C(CH$_3$)HCO$_2$H, —CH$_2$C(CF$_3$)HCO$_2$H, —CH$_2$C(CH$_3$)HCH$_2$CO$_2$H, —CH$_2$C(CF$_3$)HCO$_2$H, —CH(CH$_3$)C(CH$_3$)CO$_2$H, —CH(CH$_3$)CH(CH$_3$)C$_2$CO$_2$H, —CH(CH$_3$)CH$_2$CH(CH$_3$)CO$_2$H, —CH$_2$C(CH$_3$)HC(CH$_3$)HCO$_2$H, —CH(CH$_2$CH$_3$)CH$_2$CO$_2$H, —C(CH$_2$CH$_3$)HCO$_2$H, —C(CH$_2$CH$_2$CH$_3$)HCO$_2$H, —C(CH$_2$CH$_3$)HCH$_2$CO$_2$H, —CH$_2$C(CH$_2$CH$_3$)HCO$_2$H, —CH$_2$C(CH$_2$CH$_2$CH$_3$)HCO$_2$H, —SO$_3$H, —CH$_2$SO$_3$H, —CH$_2$CH$_2$SO$_3$H, —CH$_2$CH$_2$CH$_2$SO$_3$H, —C(CH$_3$)HSO$_3$H, —C(CF$_3$)HSO$_3$H, —C(CH$_3$)HCH$_2$SO$_3$H, —C(CF$_3$)HCH$_2$SO$_3$H, —C(CH$_3$)HCH$_2$CH$_2$SO$_3$H, —C(CF$_3$)HCH$_2$CH$_2$SO$_3$H, —CH$_2$C(CH$_3$)HSO$_3$H, —CH$_2$C(CF$_3$)HSO$_3$H, —CH$_2$C(CH$_3$)HCH$_2$SO$_3$H, —CH$_2$CH$_2$C(CH$_3$)HSO$_3$H, —CH(CH$_3$)CH(CH$_3$)SO$_3$H, —CH(CH$_3$)CH(CH$_3$)CH$_2$SO$_3$H, —CH(CH$_3$)CH$_2$CH(CH$_3$)SO$_3$H, —CH$_2$C(CH$_3$)HC(CH$_3$)HSO$_3$H, —CH(CH$_2$CH$_3$)CH$_2$SO$_3$H, —C(CH$_2$CH$_3$)HSO$_3$H, —C(CH$_2$CH$_2$CH$_3$)HSO$_3$H, —C(CH$_2$CH$_2$CH$_3$)H, —CH$_2$SO$_3$H, —CH$_2$C(CH$_2$CH$_3$)HSO$_3$H, —CH$_2$C(CH$_2$CH$_2$CH$_3$)HSO$_3$H, —(CHR$^{36}$)$_m$QSO$_2$R$^{39}$, —CHR$^{36}$QSO$_2$R$^{39}$, —(CHR$^{36}$)$_2$QSO$_2$R$^{39}$, —(CHR$^{36}$)$_3$QSO$_2$R$^{39}$, —(CHR$^{36}$)$_m$OSO$_2$R$^{39}$, —(CHR$^{36}$)$_m$OSO$_2$OH, —(CHR$^{36}$)$_m$OSO$_2$NHOH, —(CHR$^{36}$)$_m$OSO$_2$NH$_2$, —(CHR$^{36}$)$_m$NR$^{43}$SO$_2$R$^{39}$, —(CHR$^{36}$)$_m$N(C$_{1-3}$-alkyl)HSO$_2$R$^{39}$, —(CHR$^{36}$)$_m$N(C$_{1-3}$-alkyl)$_2$SO$_2$R$^{39}$, —(CHR$^{36}$)$_m$NR$^{43}$SO$_2$OH, —(CHR$^{36}$)$_m$N(C$_{1-3}$-alkyl)HSO$_2$OH, —(CHR$^{36}$)$_m$N(C$_{1-3}$-alkyl)$_2$SO$_2$OH, —(CHR$^{36}$)$_m$NR$^{43}$SO$_2$NHOH, —(CHR$^{36}$)$_m$N(C$_{1-3}$-alkyl)HSO$_2$NHOH, —(CHR$^{36}$)$_m$N(C$_{1-3}$-alkyl)$_2$SO$_2$NHOH, —(CHR$^{36}$)$_m$NR$^{43}$SO$_2$NH$_2$, —(CHR$^{36}$)$_m$N(C$_{1-3}$-alkyl)HSO$_2$NH$_2$, —(CHR$^{36}$)$_m$N(C$_{1-3}$-alkyl)$_2$SO$_2$NH$_2$, —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$-alkyl)-tetrazol-5-yl, —CH(CH$_2$OC$_{1-3}$-alkyl)-tetrazol-5-yl, —CH(OH)-tetrazol-5-yl, —CH(CH$_2$OH)-tetrazol-5-yl, —CHF-tetrazol-5-yl, —CH(C$_{1-6}$-alkyl)-tetrazol-5-yl, —CHR$^{36}$CH(C$_{1-3}$-alkyl)-tetrazol-5-yl, —CHR$^{36}$CH(OH)-tetrazol-5-yl, —CHR$^{36}$CH(OC$_{1-3}$-alkyl)-tetrazol-5-yl, —CHR$^{36}$CH(CH$_2$OC$_{1-3}$-alkyl)-tetrazol-5-yl, —CHR$^{36}$CH(OH)-tetrazol-5-yl, —CHR$^{36}$CH(CH$_2$OH)-tetrazol-5-yl, —CHR$^{36}$CHF-tetrazol-5-yl, —CH(C$_{1-6}$-alkyl) CHR$^{36}$-tetrazol-5-yl, —CH(C$_{1-3}$-alkyl) CHR$^{36}$-tetrazol-5-yl, —CH(OH) CHR$^{36}$-tetrazol-5-yl, —CH(OC$_{1-3}$-alkyl) CHR$^{36}$-tetrazol-5-yl, —CH(CH$_2$OC$_{1-3}$-alkyl) CHR$^{36}$-tetrazol-5-yl, —CH(OH) CHR$^{36}$-tetrazol-5-yl, —CH(CH$_2$OH) CHR$^{36}$-tetrazol-5-yl or —CHFCHR$^{36}$-tetrazol-5-yl.

In another embodiment, of the present invention provides compounds of general formula (I) wherein:

L is a group selected from hydrogen, furanyl, thiophenyl, oxazolyl, thiazolyl, phenyl, indenyl, pyridyl, pyrimidinyl, benzofuranyl, indolyl, benzoxazolyl, benzothiazolyl, benzothiophenyl, benzimidazolyl, quinolinyl, isoquinolinyl, quinazolinyl, quinoxalinyl, furanyl-oxy-, thiophenyl-oxy-, oxazolyl-oxy-, thiazolyl-oxy-, phenyl-oxy-, pyridyl-oxy-, pyrimidinyl-oxy-, benzofuranyl-oxy-, benzothiophenyl-oxy-, benzimidazolyl-oxy-, phenyl-N(R$^{12}$)—, pyridyl-N(R$^{12}$)—, pyrimidinyl-N(R$^{12}$)—, benzofuranyl-N(R$^{12}$)—, benzothiophenyl-N(R$^{12}$)—, benzimidazolyl-N(R$^{12}$)—, C$_3$-cycloalkyloxy, C$_4$-cycloalkyloxy, C$_5$-cycloalkyloxy, C$_6$-cycloalkyloxy, C$_7$-cycloalkyloxy, C$_8$-cycloalkyloxy, C$_4$-cycloalkenyloxy, C$_5$-cycloalkenyloxy, C$_6$-cycloalkenyloxy, C$_7$-cycloalkenyloxy, C$_8$-cycloalkenyloxy, C$_1$-alkoxy, C$_2$-alkoxy, C$_3$-alkoxy, C$_4$-alkoxy, C$_5$-alkoxy, C$_6$-alkoxy, C$_3$-cycloalkyl-N(R$^{12}$)—, C$_4$-cycloalkyl-N(R$^{12}$)—, C$_5$-cycloalkyl-N(R$^{12}$)—, C$_6$-cycloalkyl-N(R$^{12}$)—, C$_7$-cycloalkyl-N(R$^{12}$)—, C$_8$-cycloalkyl-N(R$^{12}$)—, C$_4$-cycloalkenyl-N(R$^{12}$)—, C$_5$-cycloalkenyl-N(R$^{12}$)—, C$_6$-cycloalkenyl-N(R$^{12}$)—, C$_7$-cycloalkenyl-N(R$^{12}$)— or C$_8$-cycloalkenyl-N(R$^{12}$)—;

wherein R$^{12}$ is selected from hydrogen or C$_{1-3}$-alkyl;

wherein said group, excluding hydrogen, is optionally substituted with one, two or three groups selected from halogen, hydroxy, NR$^w$$_2$—C(O)—, NR$^w$$_2$—S(=O)—, NR$^w$$_2$S(=O)$_2$—, —NR$^w$—C(O)—C$_{1-6}$-alkyl, —NR$^w$—S(=O)—C$_{1-6}$-alkyl and —NR$^w$S(=O)$_2$—C$_{1-6}$-alkyl, C$_{1-6}$-alkyl, C$_{2-6}$-alkenyl, C$_{2-6}$-alkynyl, C$_{2-6}$-alkynyl, C$_{3-6}$-cycloalkyl, C$_{4-8}$-cycloalkenyl, C$_{1-8}$-alkoxy, C$_{3-8}$-alkylthio-, C$_{3-8}$-cycloalkylalkoxy, C$_{3-8}$-cycloalkylalkylthio-, C$_{3-8}$-cycloalkyloxy, C$_{3-8}$-cycloalkylthio, halogen, —NO$_2$, —CN, —NR$^9$R$^9$, —OC(O)NR$^9$R$^9$, —CH$_2$NR$^9$R$^9$. —OC(O)CR$^9$, —C(O)R$^9$ or —COOR$^9$;

wherein R$^w$ is selected from —H or C$_{1-6}$-alkyl;

wherein said substitutents C$_{1-6}$-alkyl, C$_{2-4}$-alkenyl or C$_{2-6}$-alkynyl is optionally substituted with one, two or three substituents independently selected from halogen, —CN, —CF$_3$, —OCHF$_2$, —OCF$_3$, —NO$_2$, —OR$^9$ or C$_{1-6}$-alkyl; and, wherein R$^9$ is independently selected from hydrogen or C$_{1-6}$-alkyl optionally substituted with one, two or three substituents independently selected from halogen, —CN, —CF$_3$, —OCHF$_2$, —OCF$_3$, —NO$_2$, —OR$^9$ or C$_{1-6}$-alkyl;

D is a substituted first group selected from phenyl, five- or six-membered heterocyclic monoaryl, nine- or ten-membered, carbocyclic bicyclic aryl, nine- or ten-membered bicyclic heteroaryl, five- or six-membered cycloalkyl or five- or six-membered heterocyclyl;

wherein said first group is substituted with L and is further substituted with a second group, —(CR$^{11}$R$^{11}$)$_a$—O—(CR$^{11}$R$^{11}$)$_c$—O—, to form a third group; wherein said —(CR$^{11}$R$^{11}$)$_a$—O—(CR$^{11}$R$^{11}$)$_c$—O— is attached at two adjacent positions on D to form a 5- or 6-membered ring; wherein a is 0 or 1; wherein c is 1 or 2; and wherein each R$^{11}$ is independently selected from hydrogen, C$_{1-6}$-alkyl or fluoro;

wherein said third group is optionally substituted with one, two, three or four substituents independently selected from optionally substituted C$_{1-6}$-alkyl, optionally substituted C$_{2-6}$-alkenyl, optionally substituted C$_{2-6}$-alkynyl, optionally substituted C$_{3-4}$-cycloalkyl, optionally substituted C$_{4-8}$-cycloalkenyl, optionally substituted C$_{1-6}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$NO_2$, —CN, —$NR^{10}R^{10}$, —$OR^9$, —$SR^9$, —$S(O)R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —$OC(O)NR^{10}R^{10}$, —$CH_2NR^{10}R^{10}$, —$OC(O)R^9$, —$C(O)R^9$ or —$COOR^9$;

wherein, $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Z is isoxazol-3,5-diyl;

$R^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, phenyl, methyl-phenyl-, ethyl-phenyl-, n-propyl-phenyl-, isopropyl-phenyl-, cyclopropyl-phenyl-, cyclopropyl-methyl-phenyl-, cyclopropyl-ethyl-phenyl-, cyclopropyl-propyl-phenyl-, cyclopropyl-butyl-phenyl-, n-butyl-phenyl-, sec-butyl-phenyl-, t-butyl-phenyl-, cyclobutyl-phenyl-, cyclobutyl-methyl-phenyl-, cyclobutyl-ethyl-phenyl-, cyclobutyl-propyl-phenyl-, n-pentyl-phenyl-, neopentyl-phenyl-, isopentyl-phenyl-, cyclopentyl-phenyl-, cyclopentyl-methyl-phenyl-, cyclopentyl-ethyl-phenyl-, hexyl-phenyl-, methyl-pentyl-phenyl-, ethyl-butyl-phenyl-cyclohexyl-phenyl-, ethenyl-phenyl-, n-propenyl-phenyl-, isopropenyl-phenyl-, n-butenyl-phenyl-, sec-butenyl-phenyl-, t-butenyl-phenyl-, cyclobutenyl-phenyl-, n-pentenyl-phenyl-, neopentenyl-phenyl-, isopentenyl-phenyl-, cyclopentenyl-phenyl-, hexenyl-phenyl-, cyclohexenyl-phenyl-, ethynyl-phenyl-, n-propynyl-phenyl-, isopropynyl-phenyl-, n-butynyl-phenyl-, sec-butynyl-phenyl-, t-butynyl-phenyl-, n-pentynyl and n-hexynyl-phenyl-; benzyl, methyl-benzyl-, ethyl-benzyl-, n-propyl-benzyl-, isopropyl-benzyl-, cyclopropyl-benzyl-, cyclopropyl-methyl-benzyl-, cyclopropyl-ethyl-benzyl-, cyclopropyl-propyl-benzyl-, cyclopropyl-butyl-benzyl-, n-butyl-benzyl-, sec-butyl-benzyl-, t-butyl-benzyl-, cyclobutyl-benzyl-, cyclobutyl-methyl-benzyl-, cyclobutyl-ethyl-benzyl-, cyclobutyl-propyl-benzyl-, n-pentyl-benzyl-, neopentyl-benzyl-, isopentyl-benzyl-, cyclopentyl-benzyl-, cyclopentyl-methyl-benzyl-, cyclopentyl-ethyl-benzyl-, hexyl-benzyl-, methyl-pentyl-benzyl-, ethyl-butyl-benzyl-cyclohexyl-benzyl-, ethenyl-benzyl-, n-propenyl-benzyl-, isopropenyl-benzyl-, n-butenyl-benzyl-, sec-butenyl-benzyl-, t-butenyl-benzyl-, cyclobutenyl-benzyl-, n-pentenyl-benzyl-, neopentenyl-benzyl-, isopentenyl-benzyl-, cyclopentenyl-benzyl-, hexenyl-benzyl-, cyclohexenyl-benzyl-, ethynyl-benzyl-, n-propynyl-benzyl-, isopropynyl-benzyl-, n-butynyl-benzyl-, sec-butynyl-benzyl-, t-butynyl-benzyl-, n-pentynyl and n-hexynyl-benzyl-;

wherein each group is optionally substituted with one to six groups independently selected from halogen, —CN, —$C_{1-6}$-alkyl, halogen, —$CHF_2$, —$CF_3$, —$OCF_3$, —$OCHF_2$, —$OCH_2CF_3$, —$OCF_2CHF_2$, —$SCF_3$, —$OR^9$, —$NR^{10}R^{10}$, —$SR^9$, —$S(O)R^9$, —$S(O)_2R^9$, —$C(O)NR^{10}R^{10}$, —$OC(O)NR^{10}R^{10}$, —$NR^9C(O)R^9$, —$OCH_2C(O)NR^{10}R^{10}$, —$C(O)R^9$ or —$C(O)OR^9$, $C_{3-8}$-cycloalkyl, $C_{4-8}$-cycloalkenyl, optionally substituted phenyl or optionally substituted five- or six-membered heteroaryl; wherein, $R^9$ is independently selected from hydrogen, optionally substituted $C_{1-6}$-alkyl or optionally substituted aryl; wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Y is a group selected from —O—, —$CH_2$—, —CH($CH_3$)—, —CH($CH_2CH_3$)—, —C($CH_3$)$_2$— or —CHF—;

X is a group selected from furanylene, thiophenylene, oxazolylene, thiazolylene, phenylene, pyridylene or pyrimidinylene;

wherein X is optionally substituted with one or two groups independently selected from halogen, —CN, —$CF_3$, —$OCF_3$, —$OCHF_2$, —$OCH_2CF_3$, —OH, —$OCH_3$, —$OCH_2CH_3$, —$OCH_2CH_2CH_3$, —$CH_3$, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl or $C_6$-alkenyl;

M is a group selected from —NHC(O)—, —C(O)NH— or —O—;

T is absent; and

A is a group selected from —$CO_2H$, —$CH_2CO_2H$, —$CH_2CH_2CO_2H$ —$CH_2CH(OH)CO_2H$, —$CH_2CH_2CH_2CO_2H$, —$C(CH_2)HCO_2H$, —$C(CF_3)HCO_2H$, —$C(CH_3)HCH_2CO_2H$, —$C(CF_3)HCH_2CO_2H$, —$C(CH_3)HCH_2CH_2CO_2H$, —$C(CF_3)HCH_2CH_2CO_2H$, —$CH_2C(CH_2)HCO_2H$, —$CH_2C(CF_3)HCO_2H$, —$CH_2C(CH_3)HCH_2CO_2H$, —$CH_2CH_2C(CH_3)HCO_2H$, —CH($CH_3$)CH($CH_3$)$CO_2H$, —CH($CH_3$)CH($CH_3$)$CH_2CO_2H$, —CH($CH_3$)$CH_2$CH($CH_3$)$CO_2H$, —$CH_2$CH($CH_3$)CH($CH_3$)$CO_2H$, —CH($CH_2CH_3$)$CH_2CO_2H$, —CH($CH_2CH_3$)$CO_2H$, —CH($CH_2CH_2CH_3$)$CO_2H$, —CH($CH_2CH_2CH_3$)$CH_2CO_2H$, —$CH_2$CH($CH_2CH_3$)$CO_2H$, —$CH_2$CH($CH_2CH_2CH_3$)$CO_2H$ —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH($C_{1-6}$-alkyl)-tetrazol-5-yl, —CH($C_{1-3}$-alkyl)-tetrazol-5-yl, —CH(OH)-tetrazol-5-yl, —CH($OC_{1-3}$-alkyl)-tetrazol-5-yl, —CH($CH_2OC_{1-3}$-alkyl)-tetrazol-5-yl, —CH(OH)-tetrazol-5-yl, —CH($CH_2OH$)-tetrazol-5-yl or —CHF-tetrazol-5-yl.

In another embodiment, of the present invention provides compounds of general formula (I) wherein:

L is a group selected from hydrogen, halo, phenyl, benzofuranyl, benzoxazolyl, benzothiazolyl, indenyl, indolyl, phenoxy-, $C_3$-cycloalkyl, $C_6$-cycloalkyl-$C_1$-alkoxy, $C_3$-cycloalky-, $C_6$-cycloalkenyl, perfluoromethoxy or perfluoromethylthio;

wherein said phenyl, benzofuranyl, benzoxazolyl, benzothiazolyl, indenyl, phenyl-oxy-, $C_3$-cycloalkyl, $C_6$-cycloalkyl-$C_1$-alkoxy, cyclopropyl-, $C_6$-cycloalkenyl, is optionally substituted with one, two or three groups selected from Cl—, F—, Br—, I—, $CF_3$—, $CF_3S$—, $CF_3O$—, $N(CH_3)_2S(=O)_2$—, $N(CH_3)_2C(O)$—, benzyloxy-, —OH, $CH_3O$—, $CH_3$—, cyclopropyl-, cyclohexenyl, —NH—S$(=O)_2$—$CH_3$ or —CN;

D is a substituted group selected from carbocyclic aryl or heteroaryl;

wherein said group is substituted with L and is further substituted with one, two or three substituents independently selected from halogen, —$CF_3$, —CN, optionally substituted $C_{1-6}$-alkyl or optionally substituted $C_{1-6}$-alkoxy-;

Z is a group selected from —C(O)NH—;

$R^1$ is a group selected from —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-phenyl-, trifluorometh-oxy-phenyl-, trifluoromethyl-thio-phenyl-, halophenyl-, biphenyl-, cyclopropyl-phenyl-, cyclopropyl-propyl-phenyl-, t-butyl-phenyl-, cyclopentenyl-phenyl-, cyclohexyl-phenyl-, propenyl-phenyl-, cyclohexenyl-phenyl-, 3,3-dimethyl-but-1-enyl-phenyl-, 4,4-dimethyl-pent-1-enyl-phenyl-, 4,4-dimethyl-pent-2-enyl-phenyl-, n-hexyl-phenyl-, n-hexenyl-phenyl-, 3-methyl-benzothiophen-2-yl-, 3,5-dimethyl-isoxazol-4-yl-phenyl-, 4-t-butyl-cyclohexen-1-yl-phenyl-, or 5,5-dimethyl-cyclohexa-1,3-dien-2-yl-phenyl;

Y is a group selected from —$CH_2$— or —$CH(CH_3)$—;

X is phenylene;

wherein said phenylene is optionally substituted with one or two groups independently selected from halogen, —CN, —$CF_3$, —$OCF_3$, —$OCHF_2$, —$OCH_2CF_3$, —OH, —$OCH_3$, —$OCH_2CH_3$, —$OCH_2CH_2CH_3$, —$CH_3$, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl or $C_6$-alkenyl;

M is a group selected from —NHC(O)—, —C(O)NH— or —O—;

T is absent; and

A is a group selected from —$CO_2H$, —$CH_2CO_2H$, —$CH_2CH_2CO_2H$, —$CH_2CH(OH)CO_2H$, —$CH_2CH_2CH_2CO_2H$, —$C(CH_3)HCO_2H$, —$C(CF_3)HCO_2H$, —$C(CH_3)HCH_2CO_2H$, —$C(CF_3)HCH_2CO_2H$, —$C(CH)HCH_2CH_2CO_2H$, —$C(CF_3)HCH_2CH_2CO_2H$, —$CH_2C(CH_3)HCO_2H$, —$CH_2C(CF_3)HCO_2H$, —$CH_2C(CH_3)HCH_2CO_2H$, —$CH_2CH_2C(CH_3)HCO_2H$, —$CH(CH_3)CH(CH_3)CO_2$, —$CH(CH_3)CH(CH_3)H_2CO_2H$, —$CH(CH_3)CH_2CH(CH_3)CO_2H$, —$CH_2C(CH_3)HC(CH_3)HCO_2H$, —$CH(CH_2CH_3)CH_2CO_2H$, —$C(CH_2CH_3)HCO_2H$, —$C(CH_2CH_2CH_3)HCO_2H$, —$C(CH_2CH_3)HCH_2CO_2H$, —$CH_2C(CH_2CH_3)HCO_2H$, —$CH_2C(CH_2CH_2CH_3)HCO_2H$, —$SO_3H$, —$CH_2SO_3H$, —$CH_2CH_2SO_3H$, —$CH_2CH_2CH_2SO_3H$, —$C(CH_3)HSO_3H$, —$C(CF_3)HSO_3H$, —$C(CH_3)HCH_2SO_3H$, —$C(CF_3)HCH_2SO_3H$, —$C(CH_3)HCH_2CH_2SO_3H$, —$C(CF_3)HCH_2CH_2SO_3H$, —$CH_2C(CH_3)HSO_3H$, —$CH_2C(CF_3)HSO_3H$, —$CH_2C(CH_3)HCH_2SO_3H$, —$CH_2CH_2C(CH_3)HSO_3H$—, —$CH(CH_3)CH(CH_3)SO_3H$, —$CH(CH_3)CH(CH_3)CH_2SO_3H$, —$CH(CH_3)CH_2CH(CH_3)SO_3H$, —$CH_2C(CH_3)HC(CH_3)HSO_3H$, —$CH(CH_2CH_3)CH_2SO_3H$, —$C(CH_2CH_3)HSO_3H$, —$C(CH_2CH_2CH_3)HSO_3H$, —$CH_2SO_3H$, —$CH_2C(CH_2CH_3)H$, —$CH_2SO_3H$, —$CH_2C(CH_2CH_3)HSO_3H$—, —$CH_2C(CH_2CH_2CH_3)HSO_3H$, —$(CHR^{36})_mQSO_2R^{39}$, —$CHR^{36}QSO_2R^{39}$, —$(CHR^{36})_2QSO_2R^{39}$, —$(CHR^{36})_3QSO_2R^{39}$, —$(CHR^{36})_mOSO_2R^{39}$, —$(CHR^{36})_mOSO_2OH$, —$(CHR^{36})_mOSO_2NHOH$, —$(CHR^{36})_mOSO_2NH_2$, —$(CHR^{36})_m NR^{43}SO_2R^{39}$, —$(CHR^{36})_m N(C_{1-3}alkyl)HSO_2R^{39}$, —$(CHR^{36})_m N(C_{1-3}alkyl)_2SO_2R^{39}$, —$(CHR^{36})_m NR^{43}SO_2OH$, —$(CHR^{36})_m N(C_{1-3}\text{-alkyl})HSO_2OH$, —$(CHR^{36})_m N^*(C_{1-3}\text{-alkyl})_2SO_2OH$, —$(CHR^{36})_m NR^{43}SO_2NHOH$, —$(CHR^{36})_m N(C_{1-3}\text{-alkyl})HSO_2NHOH$, —$(CHR^{36})_m N(C_{1-3}\text{-alkyl})_2SO_2NHOH$, —$(CHR^{36})_m NR^{43}SO_2NH_2$, —$(CHR^{36})_m N(C_{1-3} \text{ alkyl})HSO_2NH_2$, —$(CHR^{36})_m N(C_{1-3}\text{-alkyl})_2SO_2NH_2$, —$(CHR^{36})_q$ tetrazol-5-yl, -tetrazol-5-yl, —$CHR^{36}$-tetrazol-5-yl, —$(CHR^{36})_2$ tetrazol-5-yl, —$(CHR^{36})_3$ tetrazol-5-yl, —$CH(C_{1-6}\text{-alkyl})$-tetrazol-5-yl, —$CH(C_{1-3}\text{-alkyl})$-tetrazol-5-yl, —$CH(OH)$-tetrazol-5-yl, —$CH(OC_{1-3}\text{-alkyl})$-tetrazol-5-yl, —$CH(CH_2OC_{1-3}\text{-alkyl})$-tetrazol-5-yl, —$CH(OH)$-tetrazol-5-yl, —$CH(CH_2OH)$-tetrazol-5-yl, —CHF-tetrazol-5-yl, —$CH(C_{1-6}\text{-alkyl})$-tetrazol-5-yl, —$CHR^{36}CH(C_{1-3}\text{-alkyl})$-tetrazol-5-yl, —$CHR^{36}CH(OH)$-tetrazol-5-yl, —$CHR^{36}CH(OC_{1-3}\text{-alkyl})$-tetrazol-5-yl, —$CHR^{36}CH(CH_2OC_{1-3}\text{-alkyl})$-tetrazol-5-yl, —$CHR^{36}CH(OH)$-tetrazol-5-yl, —$CHR^{36}CH(CH_2OH)$-tetrazol-5-yl, —$CHR^{36}CHF$-tetrazol-5-yl, —$CH(C_{1-6}\text{-alkyl}) CHR^{36}$-tetrazol-5-yl, —$CH(C_{1-3}\text{-alkyl}) CHR^{36}$-tetrazol-5-yl, —$CH(OH) CHR^{36}$-tetrazol-5-yl, —$CH(OC_{1-3}\text{-alkyl}) CHR^{36}$-tetrazol-5-yl, —$CH(CH_2OC_{1-3}\text{-alkyl}) CHR^{36}$-tetrazol-5-yl, —$CH(OH) CHR^{36}$-tetrazol-5-yl, —$CH(CH_2OH) CHR^{36}$-tetrazol-5-yl or —$CHFCHR^{36}$-tetrazol-5-yl.

In another embodiment, of the present invention provides compounds of general formula (I) wherein:

L is a group selected from hydrogen, halo, phenyl, benzofuranyl, benzoxazolyl, benzothiazolyl, indenyl, indolyl, phenoxy-, $C_3$-cycloalkyl, $C_6$-cycloalkyl-$C_1$-alkoxy, $C_3$-cycloalky-, $C_6$-cycloalkenyl, perfluoromethoxy or perfluoromethylthio;

wherein said phenyl, benzofuranyl, benzoxazolyl, benzothiazolyl, indenyl, phenyl-oxy-, $C_3$-cycloalkyl, $C_6$-cycloalkyl-$C_1$-alkoxy, cyclopropyl-, $C_6$-cycloalkenyl, is optionally substituted with one, two or three groups selected from Cl—, F—, Br—, I—, $CF_3$—, $CF_3S$—, $CF_3O$—, $N(CH_3)_2S(=O)_2$—, $N(CH_3)_2C(O)$—, benzyloxy-, —OH, $CH_3O$—, $CH_3$—, cyclopropyl-, cyclohexenyl, —NH—S$(=O)_2$—$CH_3$ or —CN;

D is a substituted group selected from carbocyclic aryl or heteroaryl;

wherein said group is substituted with L and is further substituted with one, two or three substituents independently selected from halogen, —$CF_3$, —CN, optionally substituted $C_{1-6}$-alkyl or optionally substituted $C_{1-6}$-alkoxy-;

Z is isoxazol-3,5-diyl;

$R^1$ is a group selected from —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-phenyl-, trifluorometh-oxy-phenyl-, trifluoromethyl-thio-phenyl-, halophenyl-, biphenyl-, cyclopropyl-phenyl-, cyclopropyl-propyl-phenyl-, t-butyl-phenyl-, cyclopentenyl-phenyl-, cyclohexyl-phenyl-, propenyl-phenyl-, cyclohexenyl-phenyl-, 3,3-dimethyl-but-1-enyl-phenyl-, 4,4-dimethyl-pent-1-enyl-phenyl-, 4,4-dimethyl-pent-2-enyl-phenyl-, n-hexyl-phenyl-, n-hexenyl-phenyl-, 3-methyl-benzothiophen-2-yl-, 3,5-dimethyl-isoxazol-4-yl-phenyl-, 4-t-butyl-cyclohexen-1-yl-phenyl-, or 5,5-dimethyl-cyclohexa-1,3-dien-2-yl-phenyl;

Y is a group selected from —$CH_2$— or —$CH(CH_3)$—;

X is phenylene;

wherein said phenylene is optionally substituted with one or two groups independently selected from halogen, —CN, —$CF_3$, —$OCF_3$, —$OCHF_2$, —$OCH_2CF_3$, —OH, —$OCH_3$, —$OCH_2CH_3$, —$OCH_2CH_2CH_3$, —$CH_3$, $C_2$-alkyl, $C_3$-alkyl, $C_4$-alkyl, $C_8$-alkyl, $C_6$-alkyl, $C_2$-alkenyl, $C_3$-alkenyl, $C_4$-alkenyl, $C_5$-alkenyl or $C_6$-alkenyl;

M is a group selected from —NHC(O)—, —C(O)NH— or —O—;

T is absent; and

A is a group selected from —$CO_2H$, —$CH_2CO_2H$, —$CH_2CH_2CO_2H$ —$CH_2CH(OH)CO_2H$, —$CH_2CH_2CH_2CO_2H$, —$C(CH_3)HCO_2H$, —$C(CF_3)HCO_2H$, —$C(CH_3)HCH_2CO_2H$, —$C(CF_3)HCH_2CO_2H$, —$C(CH_3)HCH_2CH_2CO_2H$, —$C(CF_3)HCH_2CH_2CO_2H$, —$CH_2C(CH_3)HCO_2H$, —$CH_2C(CF_3)HCO_2H$, —$CH_2C(CH_3)HCH_2CO_2H$, —$CH_2C(CH_3)HCH_2CO_2H$, —$CH_2C(CH_3)HCO_2H$, —$CH(CH_3)CH_2CO_2H$, —$CH(CH_3)CH(CH_3)CH_2CO_2H$, —$CH(CH_3)CH_2CH(CH_3)CO_2H$, —$CH_2CH(CH_3)CH(CH_3)CO_2H$, —$CH(CH_2CH_3)CH_2CO_2H$, —$CH(CH_2CH_3)CO_2H$, —$CH(CH_2CH_2CH_3)CO_2H$, —$CH(CH_2CH_2CH_3)CH_2CO_2H$, —$CH_2CH(CH_2CH_3)CO_2H$, —$CH_2CH(CH_2CH_2CH_3)CO_2H$ —$(CHR^{36})_q$ tetrazol-5-yl, -tetrazol-5-yl, —$CHR^{36}$-tetrazol-5-yl, —$(CHR^{36})_2$ tetrazol-5-yl, —$(CHR^{36})_3$ tetrazol-5-yl, —$CH(C_{1-6}$-alkyl)-tetrazol-5-yl, —$CH(C_{1-3}$-alkyl)-tetrazol-5-yl, —CH(OH)-tetrazol-5-yl, —$CH(OC_{1-3}$-alkyl)-tetrazol-5-yl, —$CH(CH_2OC_{1-3}$-alkyl)-tetrazol-5-yl, —CH(OH)-tetrazol-5-yl, —$CH(CH_2OH)$-tetrazol-5-yl or —CHF-tetrazol-5-yl.

In another embodiment, of the present invention provides compounds of general formula (I) wherein:

L is a group selected from hydrogen, halo, phenyl, benzofuranyl, benzimidazolyl, quinolinyl, isoquinolinyl, quinazolinyl, quinoxalinyl, benzoxazolyl, benzothiazolyl, indenyl, indolyl, phenoxy-, $C_3$-cycloalkyl, $C_6$-cycloalkyl-$C_1$-alkoxy, $C_3$-cycloalky-, $C_6$-cycloalkenyl, perfluoromethoxy, perfluoromethylthio;

wherein said phenyl, benzofuranyl, benzimidazolyl, quinolinyl, isoquinolinyl, quinazolinyl, quinoxalinyl, benzoxazolyl, benzothiazolyl, indenyl, phenyl-oxy-, $C_3$-cycloalkyl, $C_6$-cycloalkyl-$C_1$-alkoxy, cyclopropyl-, $C_6$-cycloalkenyl, is optionally substituted with one or two groups selected from Cl—, F—, Br—, I—, $CF_3$—, $CF_3S$—, $CF_3O$—, $N(CH_3)_2S$(=O)$_2$—, $N(CH_3)_2C(O)$—, benzyloxy-, —OH, $CH_3O$—, $CH_3$—, cyclopropyl-, cyclohexenyl, —NH—S(=O)$_2$—$CH_3$ or —CN;

D is a substituted group selected from phenyl, five- or six-membered heterocyclic monoaryl, nine- or ten-membered, carbocyclic bicyclic aryl, nine- or ten-membered bicyclic heteroaryl, five- or six-membered cycloalkyl or five- or six-membered heterocyclyl;

wherein said group is substituted with L and is further substituted with one, two, three or four substituents independently selected from halogen, —CN, —$OR^9$, —$SR^9$, —$C(O)R^9$, —$C_{1-4}$-alkyl, —$C_{2-4}$-alkenyl, —$C_{2-6}$-alkynyl, —$C_{1-4}$-alkoxy-, —$CH_2CN$, —$CHF_2$, —$CF_3$, —$CH_2CF_3$, —$C_{3-6}$-alkyl-$CF_3$, —$C_{2-3}$-perfluoroalkyl, —$OCF_3$, —$OCH_2CF_3$, —O—$C_{3-6}$-alkyl-$CF_3$, —$OC_{2-3}$-perfluoroalkyl, —$CH_2OR^9$, —$CH_2NR^9R^{10}$, —$CH_2CONR^9R^{10}$ or —$OCH_2CONR^9R^{10}$;

wherein said heteroaryl or heterocyclyl contains one or two heteroatoms independently selected from nitrogen, oxygen or sulfur;

wherein $R^9$ is selected from aralkyl, $C_{1-6}$-alkyl or aryl, each optionally substituted with halogen, —CN, —O—$C_{1-3}$-alkyl or —S—$C_{1-3}$-alkyl; wherein said $C_{1-3}$-alkyl of —O—$C_{1-3}$-alkyl or —S—$C_{1-3}$-alkyl is optionally substituted with one or more halogens, up to and including perhalo; and, wherein each $R^{10}$ is independently selected from hydrogen, optionally substituted $C_{1-6}$-alkyl or optionally substituted aryl; and, wherein $R^x$ is selected from $C_{1-3}$-alkyl optionally substituted with one or more halogens, up to and including perhalo;

Z is —C(O)NH—;

$R^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-phenyl-, trifluorometh-oxy-phenyl-, trifluoromethylthio-phenyl-, halophenyl-, biphenyl-, cyclopropyl-phenyl-, cyclopropyl-propyl-phenyl-, t-butyl-phenyl-, cyclopentenyl-phenyl-, cyclohexyl-phenyl-, propenyl-phenyl-, cyclohexenyl-phenyl-, 3,3-dimethyl-but-1-enyl-phenyl-, 4,4-dimethyl-pent-1-enyl-phenyl-, 4,4-dimethyl-pent-2-enyl-phenyl-, n-hexyl-phenyl-, n-hexenyl-phenyl-, 3-methyl-benzothiophen-2-yl-, 3,5-dimethyl-isoxazol-4-yl-phenyl-, 4-t-butyl-cyclohexen-1-yl-phenyl-, or 5,5-dimethyl-cyclohexa-1,3-dien-2-yl-phenyl;

Y is a group selected from —$CH_2$— or —$CH(CH_3)$—;

X is phenylene;

wherein said phenylene is optionally substituted with one or two groups independently selected from halogen, —CN, —$CF_3$, —$OCF_3$, —$OCHF_2$, —$OCH_2CF_3$, —OH, —$OCH_3$, —$OCH_2CH_3$, —$OCH_2CH_2CH_3$, —$CH_3$, $C_2$-alkyl, $C_3$-alkyl, $C_4$-alkyl, $C_5$-alkyl, $C_6$-alkyl, $C_2$-alkenyl, $C_3$-alkenyl, $C_4$-alkenyl, $C_5$-alkenyl, $C_6$-alkenyl;

M is a group selected from —NHC(O)—, —C(O)NH— or —O—;

T is absent; and

A is a group selected from —$SO_1H$, —$CH_2SO_3H$, —$CH_2CH_2SO_3H$, —$CH_2CH_2CH_2SO_3H$, —$C(CH_3)HSO_3H$, —$C(CF_3)HSO_3H$, —$C(CH_3)HCH_2SO_3H$, —$C(CF_3)HCH_2SO_3H$, —$C(CH_3)HCH_2SO_3H$, —$C(CF_3)HCH_2CH_2SO_3H$, —$CH_2C(CH_3)HSO_3H$, —$CH_2C(CF_3)HSO_3H$, —$CH_2C(CH_3)HCH_2SO_3H$, —$CH_2CH_2C(CH_3)HSO_3H$, —$CH(CH_3)CH(CH_3)SO_3H$, —$CH(CH_3)CH(CH_3)CH_2SO_3H$, —$CH(CH_3)CH_2CH(CH_3)SO_3H$, —$CH_2C(CH_3)HC(CH_3)HSO_3H$, —$CH(CH_2CH_3)CH_2SO_3H$, —$C(CH_2CH_3)HSO_3H$, —$C(CH_2CH_2CH_3)HSO_3H$, —$C(CH_2CH_2CH_3)H$, —$CH_2SO_3H$, —$CH_2C(CH_2CH_3)HSO_3H$, —$CH_2C(C_2CH_2CH_3)HSO_3H$, —$(CHR^{26})_mQSO_2R^{39}$, —$CHR^{36}QSO_2R^{39}$, —$(CHR^{36})_2QSO_2R^{39}$, —$(CHR^{36})_3QSO_2R^{39}$, —$(CHR^{36})_mOSO_2R^{39}$, —$(CHR^{36})_mOSO_2OH$, —$(CHR^{36})_mOSO_2$ NHOH, —$(CHR^{36})_mOSO_2$ $NH_2$, —$(CHR^{36})_m$ $NR^{43}SO_2R^{39}$, —$(CHR^{36})_m$ $N(C_{1-3}$-alkyl)$HSO_2R^{39}$, —$(CHR^{36})_m$ $N(C_{1-3}$-alkyl)$_2SO_2R^{39}$, —$(CHR^{36})_m$ $NR^{43}SO_2OH$, —$(CHR^{36})_m$ $N(C_{1-3}$-alkyl)$HSO_2OH$, —(CHR$^{36}$)$_m$ N(C$_{1-3}$-alkyl)$_2$SO$_2$OH, —(CHR$^{36}$)$_m$ NR$^{43}$SO$_2$NHOH, —(CHR$^{36}$)$_m$ N(C$_{1-3}$-alkyl)HSO$_2$NHOH, —(CHR$^{36}$)$_m$ N(C$_{1-3}$-alkyl)$_2$SO$_2$NHOH, —(CHR$^{36}$)$_m$ NR$^{43}$SO$_2$NH$_2$, —(CHR$^{36}$)$_m$ N(C$_{1-3}$-alkyl)HSO$_2$NH$_2$ or —(CHR$^{36}$)$_m$ N(C$_{1-3}$-alkyl)$_2$SO$_2$NH$_2$.

In another embodiment, of the present invention provides compounds of general formula (I) wherein:

L is a group selected from hydrogen, halo, phenyl, benzofuranyl, benzimidazolyl, quinolinyl, isoquinolinyl, quinazolinyl, quinoxalinyl, benzoxazolyl, benzothiazolyl, indenyl, indolyl, phenoxy-, C$_3$-cycloalkyl, C$_6$-cycloalkyl-C$_1$-alkoxy, C$_3$-cycloalky-, C$_6$-cycloalkenyl, perfluoromethoxy, perfluoromethylthio;

wherein said phenyl, benzofuranyl, benzimidazolyl, quinolinyl, isoquinolinyl, quinazolinyl, quinoxalinyl, benzoxazolyl, benzothiazolyl, indenyl, phenyl-oxy-, C$_3$-cycloalkyl, C$_6$-cycloalkyl-C$_1$-alkoxy, cyclopropyl-, C$_6$-cycloalkenyl, is optionally substituted with one or two groups selected from Cl—, F—, Br—, I—, CF$_3$—, CF$_3$S—, CF$_3$O—, N(CH$_3$)$_2$S(═O)$_2$—, N(CH$_3$)$_2$C(O)—, benzyloxy-, —OH, CH$_3$O—, CH$_3$—, cyclopropyl-, cyclohexenyl, —NH—S(═O)$_2$—CH$_3$ or —CN;

D is a substituted group selected from phenyl, five- or six-membered heterocyclic monoaryl, nine- or ten-membered, carbocyclic bicyclic aryl, nine- or ten-membered bicyclic heteroaryl, five- or six-membered cycloalkyl or five- or six-membered heterocyclyl;

wherein said group is substituted with L and is further substituted with one, two, three or four substituents independently selected from halogen, —CN, —OR$^9$, —SR$^9$, —C(O)R$^9$, —C$_{1-4}$-alkyl, —C$_{2-4}$-alkenyl, —C$_{2-6}$-alkynyl, —C$_{1-4}$-alkoxy-, —CH$_2$CN, —CHF$_2$, —CF$_3$, —CH$_2$CF$_3$, —C$_{3-6}$-alkyl-CF$_3$, —C$_{2-3}$-perfluoroalkyl, —OCF$_3$, —OCH$_2$CF$_3$, —O—C$_{3-6}$-alkyl-CF$_3$, —OC$_{2-3}$-perfluoroalkyl, —CH$_2$OR$^9$, —CH$_2$NR$^9$R$^{10}$, —CH$_2$CONR$^9$R$^{10}$ or —OCH$_2$CONR$^9$R$^{10}$;

wherein said heteroaryl or heterocyclyl contains one or two heteroatoms independently selected from nitrogen, oxygen or sulfur;

wherein R$^9$ is selected from aralkyl, C$_{1-6}$-alkyl or aryl, each optionally substituted with halogen, —CN, —O—C$_{1-3}$-alkyl or —S—C$_{1-3}$-alkyl; wherein said C$_{1-3}$-alkyl of —O—C$_{1-3}$-alkyl or —S—C$_{1-3}$-alkyl is optionally substituted with one or more halogens, up to and including perhalo; and, wherein each R$^{10}$ is independently selected from hydrogen, optionally substituted C$_{1-6}$-alkyl or optionally substituted aryl; and, wherein R$^x$ is selected from C$_{1-3}$-alkyl optionally substituted with one or more halogens, up to and including perhalo;

Z is isoxazol-3,5-diyl;

R$^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-phenyl-, trifluorometh-oxy-phenyl-, trifluorometh-thio-phenyl-, halophenyl-, biphenyl-, cyclopropyl-phenyl-, cyclopropyl-propyl-phenyl-, t-butyl-phenyl-, cyclopentenyl-phenyl-, cyclohexyl-phenyl-, propenyl-phenyl-, cyclohexenyl-phenyl-, 3,3-dimethyl-but-1-enyl-phenyl-, 4,4-dimethyl-pent-1-enyl-phenyl-, 4,4-dimethyl-pent-2-enyl-phenyl-, n-hexyl-phenyl-, n-hexenyl-phenyl-, 3-methyl-benzothiophen-2-yl-, 3,5-dimethyl-isoxazol-4-yl-phenyl-, 4-t-butyl-cyclohexen-1-yl-phenyl-, or 5,5-dimethyl-cyclohexa-1,3-dien-2-yl-phenyl;

Y is a group selected from —CH$_2$— or —CH(CH$_3$)—;

X is phenylene;

wherein said phenylene is optionally substituted with one or two groups independently selected from halogen, —CN, —CF$_3$, —OCF$_3$, —OCHF$_2$, —OCH$_2$CF$_3$, —OH, —OCH$_3$, —OCH$_2$CH$_3$, —OCH$_2$CH$_2$CH$_3$, —CH$_3$, C$_2$-alkyl, C$_3$-alkyl, C$_4$-alkyl, C$_5$-alkyl, C$_6$-alkyl, C$_2$-alkenyl, C$_3$-alkenyl, C$_4$-alkenyl, C$_5$-alkenyl, C$_6$-alkenyl;

M is a group selected from —NHC(O)—, —C(O)NH— or —O—;

T is absent; and

A is a group selected from —CO$_2$H, —CH$_2$CO$_2$H, —CH$_2$CH$_2$CO$_2$H, —CH$_2$CH(OH)CO$_2$H, —CH$_2$CH$_2$CH$_2$CO$_2$H, —C(CH$_3$)HCO$_2$H, —C(CF$_3$)HCO$_2$H, —C(CH$_3$)HCH$_2$CO$_2$H, —C(CF$_3$)HCH$_2$CO$_2$H, —C(CH$_3$)HCH$_2$CH$_2$CO$_2$H, —C(CF$_3$)HCH$_2$CH$_2$CO$_2$H, —CH$_2$C(CH$_3$)HCO$_2$H, —CH$_2$C(CF$_3$)HCO$_2$H, —CH$_2$C(CH$_3$)HCH$_2$CO$_2$H, —CH$_2$CH$_2$C(CH$_3$)HCO$_2$H, —CH(CH$_3$)C(CH$_3$)$_2$CO$_2$H, —CH(CH$_3$)CH(CH$_3$)C$_2$CO$_2$H, —CH(CH$_3$)CH$_2$CH(CH$_3$)CO$_2$H, —CH$_2$CH(CH$_3$)CH(CH$_3$)CO$_2$H, —CH(CH$_2$CH$_3$)CH$_2$CO$_2$H, —CH(CH$_2$CH$_3$)CO$_2$H, —CH(CH$_2$CH$_2$CH$_3$)CO$_2$H, —CH(CH$_2$CH$_2$CH$_3$)CH$_2$CO$_2$H, —CH$_2$CH(CH$_2$CH$_3$)CO$_2$H, —CH$_2$CH(CH$_2$CH$_2$CH$_3$)CO$_2$H —(CHR$^{36}$)$_q$ tetrazol-5-yl, -tetrazol-5-yl, —CHR$^{36}$-tetrazol-5-yl, —(CHR$^{36}$)$_2$ tetrazol-5-yl, —(CHR$^{36}$)$_3$ tetrazol-5-yl, —CH(C$_{1-6}$-alkyl)-tetrazol-5-yl, —CH(C$_{1-3}$-alkyl)-tetrazol-5-yl, —CH(OH)-tetrazol-5-yl, —CH(OC$_{1-3}$-alkyl)-tetrazol-5-yl, —CH(CH$_2$OC$_{1-3}$-alkyl)-tetrazol-5-yl, —CH(OH)-tetrazol-5-yl, —CH(CH$_2$OH)-tetrazol-5-yl or —CHF-tetrazol-5-yl.

In another embodiment, of the present invention provides compounds of general formula (I) wherein:

L is a) a group selected from —H, phenyl, CF$_3$O—, CF$_3$S—, C$_6$-cycloalkyl-C$_1$-alkoxy, benzofuranyl, benzimidazolyl, benzoxazolyl, benzothiazolyl, indenyl, Br—, phenoxy-, phenoxy disubstituted with Cl—, cyclohexenyl, benzyl or benzyl disubstituted with Cl—, b) phenyl substituted with a group selected from Cl—, F—, Br—, I—, CF$_3$—, N(CH$_3$)$_2$C(O)—, N(CH$_3$)$_2$S(═O)$_2$—, C$_6$-cycloalkyl-C$_1$-alkoxy, CF$_3$O—, CF$_3$S—, —OH, —NHS(═O)$_2$CH$_3$, Br—, methoxy-, —CN or cyclopropyl, c) phenyl disubstituted with a group(s) selected from Cl—, F—, Cl— and F—, benzyloxy- and F—, —OH and F—, CF$_3$— and CF$_3$—, F— and CF$_3$—, Cl— and CF$_3$—, methoxy- and F—, —CN and F— or CH$_3$— and F— or d) phenyl substituted methoxy- and disubstituted with F—;

D is a substituted group selected from carbocyclic aryl or heteroaryl;

wherein said group is substituted with L and is further substituted with one, two or three substituents independently selected from F—, Cl—, Br—, —CN, C$_{1-6}$-alkyl, —CF$_3$, —CH$_2$—CF$_3$, O—CF$_3$, —O—CH$_2$—CF$_3$ or C$_{1-6}$-alkoxy-;

Z is —C(O)NH—;

R$^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t- butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluoromeththio-benzyl-, halobenzyl-, phenyl-benzyl-, cylcopropyl-benzyl-, cylcopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent-2-enyl-benzyl-, n-hexyl-benzyl-, n-hexenyl-benzyl- or dimethyl-isoxazol-4-yl-benzyl-;

Y is a group selected from —$CH_2$— or —$CH(CH_3)$—;

X is phenylene;

M is a group selected from —NHC(O)—, —C(O)NH— or —O—;

T is absent; and

A is a group selected from —$SO_3H$, —$CH_2SO_3H$, —$CH_2CH_2SO_3H$, —$CH_2CH_2CH_2SO_3H$, —$C(CH_3)HSO_3H$, —$C(CF_3)HSO_3H$, —$C(CH_3)HCH_2SO_3H$, —$C(CF_3)HCH_2SO_3H$, —$C(CH_3)HCH_2CH_2SO_3H$, —$C(CF_3)HCH_2CH_2SO_3H$, —$CH_2C(CF_3)HSO_3H$, —$CH_2C(CH_3)HCH_2SO_3H$, —$CH_2CH_2C(CH_3)HSO_3H$, —$CH(CH_3)CH(CH_3)SO_3H$, —$CH(CH_3)CH(CH_3)CH_2SO_3H$, —$CH(CH_3)CH_2CH(CH_3)SO_3H$, —$CH_2C(CH_3)HC(CH_3)HSO_3H$, —$CH(CH_2CH_3)CH_2SO_3H$, —$C(CH_2CH_3)HSO_3H$, —$C(CH_2CH_2CH_3)HSO_3H$, —$C(CH_2CH_2CH_3)H$, —$CH_2SO_3H$, —$CH_2C(CH_2CH_3)HSO_3H$, —$CH_2C(CH_2CH_2CH_3)HSO_3H$, —$(CHR^{36})_m QSO_2R^{39}$, —$CHR^{36}QSO_2R^{39}$, —$(CHR^{36})_2QSO_2R^{39}$, —$(CHR^{36})_3QSO_2R^{39}$, —$(CHR^{36})_m OSO_2R^{39}$, —$(CHR^{36})_m OSO_2OH$, —$(CHR^{36})_m OSO_2NHOH$, —$(CHR^{36})_m OSO_2NH_2$, —$(CHR^{36})_m NR^{43}SO_2R^{39}$, —$(CHR^{36})_m N(C_{1-3}\text{-alkyl})HSO_2R^{39}$, —$(CHR^{36})_m N(C_{1-3}\text{-alkyl})_2SO_2R^{39}$, —$(CHR^{36})_m NR^{43}SO_2OH$, —$(CHR^{36})_m N(C_{1-3}\text{-alkyl})HSO_2OH$, —$(CHR^{36})_m N(C_{1-3}\text{-alkyl})_2SO_2OH$, —$(CHR^{36})_m NR^{43}SO_2NHOH$, —$(CHR^{36})_m N(C_{1-3}\text{-alkyl})HSO_2NHOH$, —$(CHR^{36})_m N(C_{1-3}\text{-alkyl})_2SO_2NHOH$, —$(CHR^{36})_m NR^{43}SO_2NH_2$, —$(CHR^{36})_m N(C_{1-3}\text{-alkyl})HSO_2NH_2$ or —$(CHR^{36})_m N(C_{1-3}\text{-alkyl})_2SO_2NH_2$.

In another embodiment, of the present invention provides compounds of general formula (I) wherein:

L is a) a group selected from —H, phenyl, $CF_3O$—, $CF_3S$—, $C_6$-cycloalkyl-$C_1$-alkoxy, benzofuranyl, benzimidazolyl, benzoxazolyl, benzothiazolyl, indenyl, Br—, phenoxy-, phenoxy disubstituted with Cl—, cyclohexenyl, benzyl or benzyl disubstituted with Cl—, b) phenyl substituted with a group selected from Cl—, F—, Br—, I—, $CF_3$—, $N(CH_3)_2C(O)$—, $N(CH_3)_2S(=O)_2$—, $C_6$-cycloalkyl-$C_1$-alkoxy, $CF_3O$—, $CF_3S$—, —OH, —$NHS(=O)_2CH_3$, Br—, methoxy-, —CN or cyclopropyl, c) phenyl disubstituted with a group(s) selected from Cl—, F—, Cl— and F—, benzyloxy- and F—, —OH and F—, $CF_3$— and $CF_3$—, F— and $CF_3$—, Cl— and $CF_3$—, methoxy- and F—, —CN and F— or $CH_3$— and F— or d) phenyl substituted methoxy- and disubstituted with F—;

D is a substituted group selected from a substituted phenyl or a substituted five- or six-membered heterocyclic monoaryl;

wherein said group is substituted with L and is further substituted with one, two or three substituents independently selected from halogen, —CF$_3$, —CN, optionally substituted $C_{1-6}$-alkyl or optionally substituted $C_{1-6}$-alkoxy-;

Z is —C(O)NH—;

$R^1$—H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluoromeththio-benzyl-, halobenzyl-, phenyl-benzyl-, cylcopropyl-benzyl-, cylcopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent-2-enyl-benzyl-, n-hexyl-benzyl-, n-hexenyl-benzyl- or dimethyl-isoxazol-4-yl-benzyl-;

Y is a group selected from —$CH_2$— or —$CH(CH_3)$—;

X is phenylene;

M is a group selected from —NHC(O)—, —C(O)NH— or —O—;

T is absent; and

A is —$CH_2CH_2SO_3H$.

In another embodiment, of the present invention provides compounds of general formula (I) wherein:

L is a) a group selected from —H, phenyl, $CF_3O$—, $CF_3S$—, $C_6$-cycloalkyl-$C_1$-alkoxy, benzofuranyl, benzimidazolyl, benzoxazolyl, benzothiazolyl, indenyl, Br—, phenoxy-, phenoxy disubstituted with Cl—, cyclohexenyl, benzyl or benzyl disubstituted with Cl—, b) phenyl substituted with a group selected from Cl—, F—, Br—, I—, $CF_3$—, $N(CH_3)_2C(O)$—, $N(CH_3)_2S(=O)_2$—, $C_6$-cycloalkyl-$C_1$-alkoxy, $CF_3O$—, $CF_3S$—, —OH, —$NHS(=O)_2CH_3$, Br—, methoxy-, —CN or cyclopropyl, c) phenyl disubstituted with a group(s) selected from Cl—, F—, Cl— and F—, benzyloxy- and F—, —OH and F—, $CF_3$— and $CF_3$—, F— and $CF_3$—, Cl— and $CF_3$—, methoxy- and F—, —CN and F— or $CH_3$— and F— or d) phenyl substituted methoxy- and disubstituted with F—;

D is a substituted group selected from a substituted phenyl or a substituted five- or six-membered heterocyclic monoaryl;

wherein said group is substituted with L and is further substituted with one, two or three substituents independently selected from halogen, —CN, —$CF_3$, $C_{1-6}$-haloalkyl, $C_{1-6}$-alkyl, $C_{1-6}$-haloalkoxy or $C_{1-6}$-alkoxy-;

Z is —C(O)NH—;

$R^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluoromeththio-benzyl-, halobenzyl-, phenyl-benzyl-, cylcopropyl-benzyl-, cylcopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent- 2-enyl-benzyl-, n-hexyl-benzyl-, n-hexenyl-benzyl- or dimethyl-isoxazol-4-yl-benzyl-;

Y is a group selected from —CH$_2$—, or —CH(CH$_3$)—;

X is phenylene;

M is a group selected from —NHC(O)—, —C(O)NH— or —O—;

T is absent; and

A is —CH$_2$CH$_2$SO$_3$H.

In another embodiment, of the present invention provides compounds of general formula (I) wherein:

L is a) a group selected from —H, phenyl, CF$_3$O—, CF$_3$S—, C$_6$-cycloalkyl-C$_1$-alkoxy, benzofuranyl, benzimidazolyl, benzoxazolyl, benzothiazolyl, indenyl, Br—, phenoxy-, phenoxy disubstituted with Cl—, cyclohexenyl, benzyl or benzyl disubstituted with Cl—, b) phenyl substituted with a group selected from Cl—, F—, Br—, I—, CF$_3$—, N(CH$_3$)$_2$C(O)—, N(CH$_3$)$_2$S(=O)$_2$—, C$_6$-cycloalkyl-C$_1$-alkoxy, CF$_3$O—, CF$_3$S—, —OH, —NHS(=O)$_2$CH$_3$, Br—, methoxy-, —CN or cyclopropyl, c) phenyl disubstituted with a group(s) selected from Cl—, F—, Cl— and F—, benzyloxy- and F—, —OH and F—, CF$_3$— and CF$_3$—, F— and CF$_3$—, Cl— and CF$_3$—, methoxy- and F—, —CN and F— or CH$_3$— and F— or d) phenyl substituted methoxy- and disubstituted with F—;

D is a substituted group selected from phenyl, pyridyl, pyrimidinyl, benzimidazolyl, benzoxazolyl, benzofuranyl, or benzothiazolyl; wherein said group is substituted with L and is optionally further substituted;

Z is —C(O)NH—;

R$^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluoromethylthio-benzyl-, halobenzyl-, phenyl-benzyl-, cylcopropyl-benzyl-, cylcopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent-2-enyl-benzyl-, n-hexyl-benzyl-, n-hexenyl-benzyl- or dimethyl-isoxazol-4-yl-benzyl-;

Y is a group selected from —CH$_2$— or —CH(CH$_3$)—;

X is phenylene

M is a group selected from —NHC(O)—, —C(O)NH— or —O—;

T is absent; and

A is —CH$_2$CH$_2$SO$_3$H.

In another embodiment, of the present invention provides compounds of general formula (I) wherein:

L is a) a group selected from —H, phenyl, CF$_3$O—, CF$_3$S—, C$_6$-cycloalkyl-C$_1$-alkoxy, benzofuranyl, benzimidazolyl, benzoxazolyl, benzothiazolyl, indenyl, Br—, phenoxy-, phenoxy disubstituted with Cl—, cyclohexenyl, benzyl or benzyl disubstituted with Cl—, b) phenyl substituted with a group selected from Cl—, F—, Br—, I—, CF$_3$—, N(CH$_3$)$_2$C(O)—, N(CH$_3$)$_2$S(=O)$_2$—, C$_6$-cycloalkyl-C$_1$-alkoxy, CF$_3$O—, CF$_3$S—, —OH, —NHS(=O)$_2$CH$_3$, Br—, methoxy-, —CN or cyclopropyl, c) phenyl disubstituted with a group(s) selected from Cl—, F—, Cl— and F—, benzyloxy- and F—, —OH and F—, CF$_3$— and CF$_3$—, F— and CF$_3$—, Cl— and CF$_3$—, methoxy- and F—, —CN and F— or CH$_3$— and F— or d) phenyl substituted methoxy- and disubstituted with F—;

D is a substituted group selected from a substituted phenyl or a substituted five- or six-membered heterocyclic monoaryl;

wherein said group is substituted with L and is further substituted with one, two or three substituents independently selected from F—, Cl—, Br—, —CN, C$_{1-6}$-alkyl, —CF$_3$, —CH$_2$—CF$_3$, O—CF$_3$, —O—CH$_2$—CF$_3$ or C$_{1-6}$-alkoxy-;

Z is —C(O)NH—;

R$^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluoromethylthio-benzyl-, halobenzyl-, phenyl-benzyl-, cylcopropyl-benzyl-, cylcopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent-2-enyl-benzyl-, n-hexyl-benzyl-, n-hexenyl-benzyl- or dimethyl-isoxazol-4-yl-benzyl-;

Y is —CH$_2$—;

X is phenylene;

M is a group selected from —NHC(O)—, —C(O)NH— or —O—;

T is absent; and

A is —CH$_2$CH$_2$SO$_3$H.

In another embodiment, of the present invention provides compounds of general formula (I) wherein:

L is a) a group selected from —H, phenyl, CF$_3$O—, CF$_3$S—, C$_6$-cycloalkyl-C$_1$-alkoxy, benzofuranyl, benzimidazolyl, benzoxazolyl, benzothiazolyl, indenyl, Br—, phenoxy-, phenoxy disubstituted with Cl—, cyclohexenyl, benzyl or benzyl disubstituted with Cl—, b) phenyl substituted with a group selected from Cl—, F—, Br—, I—, CF$_3$—, N(CH$_3$)$_2$C(O)—, N(CH$_3$)$_2$S(=O)$_2$—, C$_6$-cycloalkyl-C$_1$-alkoxy, CF$_3$O—, CF$_3$S—, —OH, —NHS(O)$_2$CH$_3$, Br—, methoxy-, —CN or cyclopropyl, c) phenyl disubstituted with a group(s) selected from Cl—, F—, Cl— and F—, benzyloxy- and F—, —OH and F—, CF$_3$— and CF$_3$—, F— and CF$_3$—, Cl— and CF$_3$—, methoxy- and F—, —CN and F— or CH$_3$— and F— or d) phenyl substituted methoxy- and disubstituted with F—;

D is a substituted group selected from phenyl, pyridyl, pyrimidinyl, benzimidazolyl, benzoxazolyl, benzofuranyl or benzothiazolyl;

wherein said group is substituted with L and is further substituted with one, two, three or four substituents independently selected from optionally substituted C$_{1-6}$-alkyl, optionally substituted C$_{2-6}$-alkenyl, optionally substituted C$_{2-6}$-alkynyl, optionally substituted C$_{3-4}$-cycloalkyl, optionally substituted C$_{4-8}$-cycloalkenyl, optionally substituted C$_{3-8}$-alkoxy, optionally substituted C$_{3-8}$-alkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —CF$_3$, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{11}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein, R$^9$ is independently selected from hydrogen, optionally substituted aralkyl, C1-6-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Z is —C(O)NH—;

R$^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluoromethio-benzyl-, halobenzyl-, phenyl-benzyl-, cylcopropyl-benzyl-, cylcopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent-2-enyl-benzyl-, n-hexyl-benzyl-, n-hexenyl-benzyl- or dimethyl-isoxazol-4-yl-benzyl-.

Y is —CH$_2$—;

X is phenylene;

M is a group selected from —NHC(O)—, —C(O)NH— or —O—;

T is absent; and

A is —CH$_2$CH$_2$SO$_3$H.

In another embodiment of the present invention provides compounds of general formula (I) wherein:

L is a) a group selected from —H, phenyl, CF$_3$O—, CF$_3$S—, C$_6$-cycloalkyl-C$_1$-alkoxy, benzofuranyl, benzimidazolyl, benzoxazolyl, benzothiazolyl, indenyl, Br—, phenoxy-, phenoxy disubstituted with Cl—, cyclohexenyl, benzyl or benzyl disubstituted with Cl—, b) phenyl substituted with a group selected from Cl—, F—, Br—, I—, CF$_3$—, N(CH$_3$)$_2$C(O)—, N(CH$_3$)$_2$S(=O)$_2$—, C$_6$-cycloalkyl-C$_1$-alkoxy, CF$_3$O—, CF$_3$S—, —OH, —NHS(=O)$_2$CH$_3$, Br—, methoxy-, —CN or cyclopropyl, c) phenyl disubstituted with a group(s) selected from Cl—, F—, Cl— and F—, benzyloxy- and F—, —OH and F—, CF$_3$— and CF$_3$—, F— and CF$_3$—, Cl— and CF$_3$—, methoxy- and F—, —CN and F— or CH$_3$— and F— or d) phenyl substituted methoxy- and disubstituted with F—;

D is a phenyl group substituted with L and further substituted with a second group —(CR$^{11}$R$^{11}$)$_a$—O—(CR$^{11}$R$^{11}$)$_c$—O— to form a third group; wherein said —(CR$^{11}$R$^{11}$)$_a$—O—(CR$^{11}$R$^{11}$)$_c$—O— is attached at two adjacent positions on D to form a 5- or 6-membered ring; wherein a is 0 or 1; wherein c is 1 or 2; and wherein each R$^{11}$ is independently selected from hydrogen, C$_{1-6}$-alkyl or fluoro;

wherein said third group is optionally substituted with one, two, three or four substituents independently selected from optionally substituted C$_{1-6}$-alkyl, optionally substituted C$_{2-6}$-alkenyl, optionally substituted C$_{2-6}$-alkynyl, optionally substituted C$_{3-4}$-cycloalkyl, optionally substituted C$_{4-8}$-cycloalkenyl, optionally substituted C$_{1-6}$-alkoxy, optionally substituted C$_{3-8}$-alkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein, R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

Z is —C(O)NH—;

R$^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluoromethio-benzyl-, halobenzyl-, phenyl-benzyl-, cylcopropyl-benzyl-, cylcopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent-2-enyl-benzyl-, n-hexyl-benzyl-, n-hexenyl-benzyl- or dimethyl-isoxazol-4-yl-benzyl-;

Y is —CH$_2$—;

X is phenylene;

M is a group selected from —NHC(O)—, —C(O)NH— or —O—;

T is absent;

A is —CH$_2$CH$_2$SO$_3$H.

In another embodiment, of the present invention provides compounds of general formula (I) wherein:

L is a) a group selected from —H, phenyl, CF$_3$O—, CF$_3$S—, C$_6$-cycloalkyl-C$_1$-alkoxy, benzofuranyl, benzimidazolyl, benzoxazolyl, benzothiazolyl, indenyl, Br—, phenoxy-, phenoxy disubstituted with Cl—, cyclohexenyl, benzyl or benzyl disubstituted with Cl—, b) phenyl substituted with a group selected from Cl—, F—, Br—, I—, CF$_3$—, N(CH$_3$)$_2$C(O)—, N(CH$_3$)$_2$S(=O)$_2$—, C$_6$-cycloalkyl-C$_1$-alkoxy, CF$_3$O—, CF$_3$S—, —OH, —NHS(=O)$_2$CH$_3$, Br—, methoxy-, —CN or cyclopropyl, c) phenyl disubstituted with a group(s) selected from Cl—, F—, Cl— and F—, benzyloxy- and F—, —OH and F—, $CF_3$— and $CF_3$—, F— and $CF_3$—, Cl— and $CF_3$—, methoxy- and F—, —CN and F— or $CH_3$— and F— or d) phenyl substituted methoxy- and disubstituted with F—;

D is a substituted group selected from phenyl, pyridyl, pyrimidinyl, benzimidazolyl, benzoxazolyl, benzofuranyl, or benzothiazolyl;

wherein said group is substituted with L and is further substituted with one, two, three or four substituents independently selected from optionally substituted $C_{1-6}$-alkyl, optionally substituted $C_{2-6}$-alkenyl, optionally substituted $C_{2-6}$-alkynyl, optionally substituted $C_{3-8}$-cycloalkyl, optionally substituted $C_{4-8}$-cycloalkenyl, optionally substituted $C_{3-8}$-cycloalkyloxy, optionally substituted $C_{3-8}$-cycloalkyl-thio, halogen, —$CF_3$, —$NO_2$, —CN, —$NR^{10}R^{10}$, —$OR^9$, —$SR^9$, —$NR^9SOR^{10}$, —$SO_2NR^{10}R^{10}$, —$CONR^{10}R^{10}$, —$OC(O)NR^{10}R^{10}$, $CH_2NR^{10}R^{10}$ or —$C(O)R^9$; wherein $R^9$ is aralkyl, $C_{1-6}$-alkyl or aryl, each optionally substituted with one, two or three substituents independently selected from halogen, —$NO_2$, —CN, —$OR^x$, —$SR^x$ or —$NR^xSOR^{10}$;

wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds; $R^x$ is selected from $C_{1-3}$-alkyl optionally substituted with one or more halogens, up to and including perhalo, and wherein said $C_{1-6}$-alkyl, $C_{2-6}$-alkenyl or $C_{2-6}$-alkynyl is optionally substituted with one, two or three substituents independently selected from halogen, —CN, —$CF_3$, —$OCHF_2$, —$OCF_3$, —$NO_2$, —$OR^9$ or $C_{1-6}$-alkyl;

Z is —C(O)NH—;

$R^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluorometh-thio-benzyl-, halobenzyl-, phenyl-benzyl-, cylcopropyl-benzyl-, cylcopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent-2-enyl-benzyl-, n-hexyl-benzyl-, n-hexenyl-benzyl- or dimethyl-isoxazol-4-yl-benzyl-;

Y is —$CH_2$—;

X is phenylene;

M is a group selected from —NHC(O)—, —C(O)NH—, —O—;

T is absent; and

A is —$CH_2CH_2SO_3H$.

In another embodiment, of the present invention provides compounds of general formula (I) wherein:

L is a) a group selected from —H, phenyl, $CF_3O$—, $CF_3S$—, $C_6$-cycloalkyl-$C_1$-alkoxy, benzofuranyl, benzimidazolyl, benzoxazolyl, benzothiazolyl, indenyl, Br—, phenoxy-, phenoxy disubstituted with Cl—, cyclohexenyl, benzyl or benzyl disubstituted with Cl—, b) phenyl substituted with a group selected from Cl—, F—, Br—, I—, $CF_3$—, $N(CH_3)_2C(O)$—, $N(CH_3)_2S(=O)_2$—, $C_6$-cycloalkyl-$C_1$-alkoxy, $CF_3O$—, $CF_3S$—, —OH, —$NHS(=O)_2CH_3$, Br—, methoxy-, —CN or cyclopropyl, c) phenyl disubstituted with a group(s) selected from Cl—, F—, Cl— and F—, benzyloxy- and F—, —OH and F—, $CF_3$— and $CF_3$—, F— and $CF_3$—, Cl— and $CF_3$—, methoxy- and F—, —CN and F— or $CH_3$— and F— or d) phenyl substituted methoxy- and disubstituted with F—;

D is a substituted group selected from phenyl, pyridyl, pyrimidinyl, benzimidazolyl, benzoxazolyl, benzofuranyl, or benzothiazolyl;

wherein said group is substituted with L and is further substituted with one, two, three or four substituents independently selected from optionally substituted $C_{1-6}$-alkyl, optionally substituted $C_{2-6}$-alkenyl, optionally substituted $C_{2-6}$-alkynyl, optionally substituted $C_{3-8}$-cycloalkyl, optionally substituted $C_{4-8}$-cycloalkenyl, optionally substituted $C_{3-8}$-cycloalkyloxy, optionally substituted $C_{3-8}$-cycloalkyl-thio, halogen, —$NO_2$, —$CF_3$, —CN, —$NR^{10}R^{10}$, —$OR^9$, —$SR^9$, —$NR^9SOR^{10}$, —$SO_2NR^{10}R^{10}$, —$CONR^{10}R^{10}$, —$OC(O)NR^{10}R^{10}$, $CH_2NR^{10}R^{10}$ or —$C(O)R^9$;

wherein $R^9$ is aralkyl, $C_{1-6}$-alkyl or aryl, each optionally substituted with one, two or three substituents independently selected from halogen, —$NO_2$, —CN, —$OR^x$, —$SR^x$ or —$NR^xSOR^{10}$;

wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds;

$R^x$ is selected from $C_{1-3}$-alkyl optionally substituted with one or more halogens, up to and including perhalo, and wherein said $C_{1-6}$-alkyl, $C_{2-6}$-alkenyl or $C_{2-6}$-alkynyl is optionally substituted with one, two or three substituents independently selected from halogen, —CN, —$CF_3$, —$OCHF_2$, —$OCF_3$, —$NO_2$, —$OR^9$ or $C_{1-6}$-alkyl;

Z is —C(O)NH—;

$R^1$ is —H;

E is a group selected from t-butylvinylphenyl, (S)-4-t-butylcyclohexenylphenyl, (R)-4-t-butylcyclohexenylphenyl, 4,4-dimethylcyclohexadienylphenyl, 4,4-dimethylcyclohexenylphenyl, cyclohexenylphenyl, 4,4-diethylcyclohexenylphenyl, 4,4-dipropylcyclohexenylphenyl, cis-4-t-butylcyclohexylphenyl, trans-4-t-butylcyclohexylphenyl, 4-t-butylphenylphenyl, methoxyphenyl-, ethoxyphenyl-, propyloxyphenyl-, isopropyloxyphenyl-, butyloxyphenyl-, t-butyloxyphenyl-, iso-butyloxyphenyl-, pentyloxyphenyl-, isopentyloxyphenyl-, neopentyloxyphenyl-, trifluoromethyl-benzyl-, trifluorometh-oxy-benzyl-, trifluorometh-thio-benzyl-, halobenzyl-, phenyl-benzyl-, cylcopropyl-benzyl-, cylcopropyl-propyl-benzyl-, t-butyl-benzyl-, cyclopentenyl-phenyl-, cyclohexyl-phenyl-, propenyl-phenyl-, cyclohexenyl-benzyl-, 3,3-dimethyl-but-1-enyl-benzyl-, 4,4-dimethyl-pent-1-enyl-benzyl-, 4,4-dimethyl-pent-2-enyl-benzyl-, n-hexyl-benzyl-, n-hexenyl-benzyl- or dimethyl-isoxazol-4-yl-benzyl-;

Y is —$CH_2$—;

X is phenylene;

M is a group selected from —NHC(O)—, —C(O)NH— or —O—;

T is absent; and

A is —CH$_2$CH$_2$SO$_3$H.

Certain aspects of the invention provide for compounds of the following formulae:

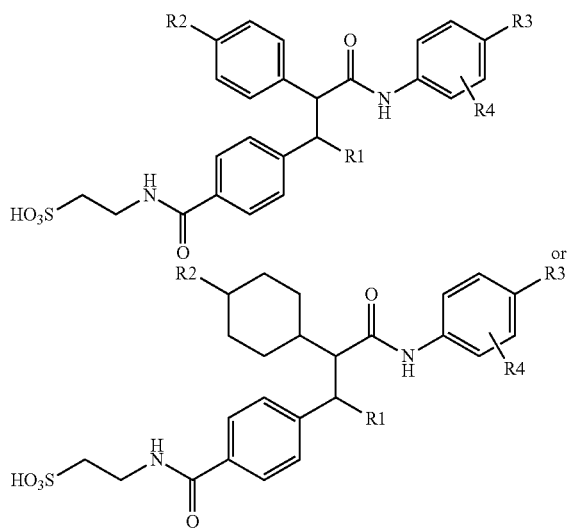

wherein:

R1 is H, CH$_3$ or CH$_3$CH$_2$

R2 is C1-C6 alkyl, alkenyl or alkoxy

R3 is phenyl, benzofuran-2-yl or benzoxazol-2-yl, optionally substituted with one or more substituents; and R4 is H, F, Cl, CH$_3$, CF$_3$, OCF$_3$ and CN.

Various embodiments of these compounds provide compounds where R3 is substituted with one or more substituents independently selected from H, F, Cl, CH$_3$, CF$_3$, OCF$_3$ or CN. Other aspects provide for R3 to be substituted with one or more substituents independently selected from optionally substituted C$_{1-6}$-alkyl, optionally substituted C$_{2-6}$-alkenyl, optionally substituted C$_{2-6}$-alkynyl, optionally substituted C$_{3-4}$-cycloalkyl, optionally substituted C$_{4-8}$-cycloalkenyl, optionally substituted C$_{3-8}$-alkoxy, optionally substituted C$_{3-8}$-alkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$ or —COOR$^9$;

wherein R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

Yet other embodiments provide compounds where R2 is selected from (CH$_3$)$_3$C—, (CH$_3$)$_3$CCH═CH— or (CH$_3$)$_3$CCH$_2$O—. Another embodiment provides for compounds wherein R2 is selected from (CH$_3$)$_3$C—, (CH$_3$)$_3$CCH═CH— or (CH$_3$)$_3$CCH$_2$O— and R3 is substituted with one or more substituents independently selected from H, F, Cl, CH$_3$, CF$_3$, OCF$_3$ or CN.

Further aspects of the invention provide for compounds where R2 is selected from (CH$_3$)$_3$C—, (CH$_3$)$_3$CCH═CH— or (CH$_3$)$_3$CCH$_2$O— and R3 is substituted with one or more substituents independently selected from optionally substituted C$_{1-6}$-alkyl, optionally substituted C$_{2-6}$-alkenyl, optionally substituted C$_{2-6}$-alkynyl, optionally substituted C$_{3-4}$-cycloalkyl, optionally substituted C$_{4-8}$-cycloalkenyl, optionally substituted C$_{3-8}$-alkoxy, optionally substituted C$_{3-8}$-alkylthio-, optionally substituted C$_{3-8}$-cycloalkylalkoxy, optionally substituted C$_{3-8}$-cycloalkylalkylthio-, optionally substituted C$_{3-8}$-cycloalkyloxy, optionally substituted C$_{3-8}$-cycloalkylthio, halogen, —NO$_2$, —CN, —NR$^{10}$R$^{10}$, —OR$^9$, —SR$^9$, —S(O)R$^9$, —SO$_2$R$^9$, —NR$^9$SOR$^{10}$, —NR$^9$SO$_2$R$^{10}$, —SO$_2$NR$^{10}$R$^{10}$, —CONR$^{10}$R$^{10}$, —NR$^9$COR$^{10}$, —OC(O)NR$^{10}$R$^{10}$, —CH$_2$NR$^{10}$R$^{10}$, —OC(O)R$^9$, —C(O)R$^9$, —CF$_3$, or —COOR$^9$;

wherein R$^9$ is independently selected from hydrogen, optionally substituted aralkyl, C$_{1-6}$-alkyl or optionally substituted aryl; and, wherein each R$^{10}$ is independently selected from hydrogen, optionally substituted C$_{1-6}$-alkyl, optionally substituted aryl or R$^{10}$R$^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds.

Certain aspects of the invention provide for compounds, prodrugs thereof, and compositions comprising the compounds or prodrugs thereof wherein the compound is:

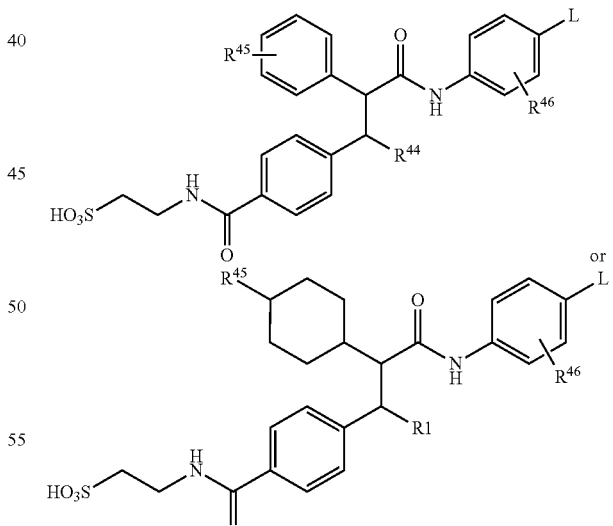

wherein:

R$^{44}$ is H, CH$_3$ or CH$_3$CH$_2$; R$^{45}$ is optionally substituted, is located at any position on the aryl ring and is C$_1$-C$_6$ alkyl, alkenyl or alkoxy, C$_{3-6}$ cycloalkyl, or C$_{4-8}$ cycloalkenyl; L is phenyl, indenyl, benzofuran-2-yl or benzoxazol-2-yl, optionally substituted with one or more substituents; and R$^{46}$ is H, F, Cl, CH$_3$, CF$_3$, OCF$_3$ and CN. In certain embodiments, $R^{45}$ is located at the 3 or 4 position of the aryl ring. Other aspects of the invention provide for L to be substituted with one or more substituents independently selected from H, F, Cl, $CH_3$, $CF_3$, $OCF_3$ or CN. Alternatively, L can be substituted with one or more substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{3-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$NO_2$, —CN, —$CF_3$, —$NR^{10}R^{10}$, —$OR^9$, —$SR^9$, —$S(O)R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —$OC(O)NR^{10}R^{10}$, —$CH_2NR^{10}R^{10}$, —$OC(O)R^9$, —$C(O)R^9$ or —$COOR^9$; wherein $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds. Certain other aspects of the compounds provide for $R^{45}$ to be optionally substituted and selected from $(CH_3)_3C$—, $(CH_3)_3CCH=CH$—, t-butylcycloalkenyl-, or $(CH_3)_3CCH_2O$—. Various other aspects provide for $R^{45}$ to be optionally substituted and selected from $(CH_3)_3C$—, $(CH_3)_3CCH=CH$—, t-butylcycloalkenyl-, or $(CH_3)_3CCH_2O$— and L is substituted with one or more substituents independently selected from H, F, Cl, $CH_3$, $CF_3$, $OCF_3$ or CN. Other aspects of the invention provide for $R^{45}$ to be selected from $(CH_3)_3C$—, $(CH_3)_3CCH=CH$— or $(CH_3)_3CCH_2O$— and L is substituted with one or more substituents independently selected from optionally substituted $C_{1-6}$-alkyl, optionally substituted $C_{2-6}$-alkenyl, optionally substituted $C_{2-6}$-alkynyl, optionally substituted $C_{3-4}$-cycloalkyl, optionally substituted $C_{4-8}$-cycloalkenyl, optionally substituted $C_{3-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$NO_2$, —CN, —$NR^{10}R^{10}$, —$OR^9$, —$SR^9$, —$S(O)R^9$, —$SO_2R^9$, —$NR^9SOR^{10}$, —$NR^9SO_2R^{10}$, —$SO_2NR^{10}R^{10}$, —$CONR^{10}R^{10}$, —$NR^9COR^{10}$, —$OC(O)NR^{10}R^{10}$, —$CH_2NR^{10}R^{10}$, —$OC(O)R^9$, —$C(O)R^9$ or —$COOR^9$; wherein $R^9$ is independently selected from hydrogen, optionally substituted aralkyl, $C_{1-6}$-alkyl or optionally substituted aryl; and, wherein each $R^{10}$ is independently selected from hydrogen, optionally substituted $C_{1-6}$-alkyl, optionally substituted aryl or $R^{10}R^{10}$ together with the N to which they are attached form a 3 to 8 membered optionally substituted heterocyclic ring; wherein said heterocyclic ring contains at least one C atom; wherein said heterocyclic ring optionally contains one or two further heteroatoms independently selected from nitrogen, oxygen and sulfur; and wherein said heterocyclic ring optionally contains 0, 1 or 2 double bonds. In some embodiments where $R^{45}$ is substituted, $R^{45}$ can be substituted with $C_1$-$C_4$ alkyl.

The following compounds of formula I wherein Y is —$CHR26$-, X is -1,4-Ph-, M is —HN—CO—, T is —$CH_2$—, and A is —$CH_2$—$SO_3H$, and pharmaceutically acceptable salts and prodrugs thereof are preferred. These preferred compounds are shown in Formula I* below:

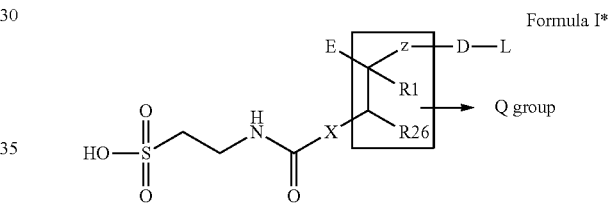

Formula I*

The preferred compounds are listed in Table 1 by designated numbers assigned to E, Q, D and L moieties in the above formula according to the following convention: E.Q.D.L. For each moiety, structures are assigned to a number shown in the following tables for E, Q, D, and L.

Variable E represents the substituent that is connected to the carbon atom which is connected to Z and R1 as shown in formula I, and it is divided into five Groups, each listing six different substituents.

The Group 1 substituents for variable E are assigned the following numbers:

| # | 1 | 2 |
|---|---|---|
| E | | |

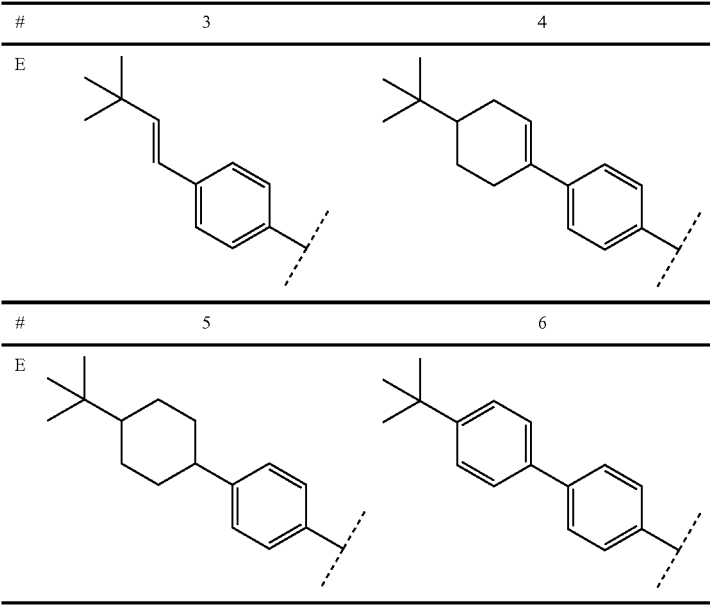
The Group 2 substituents for variable E are assigned the following numbers:
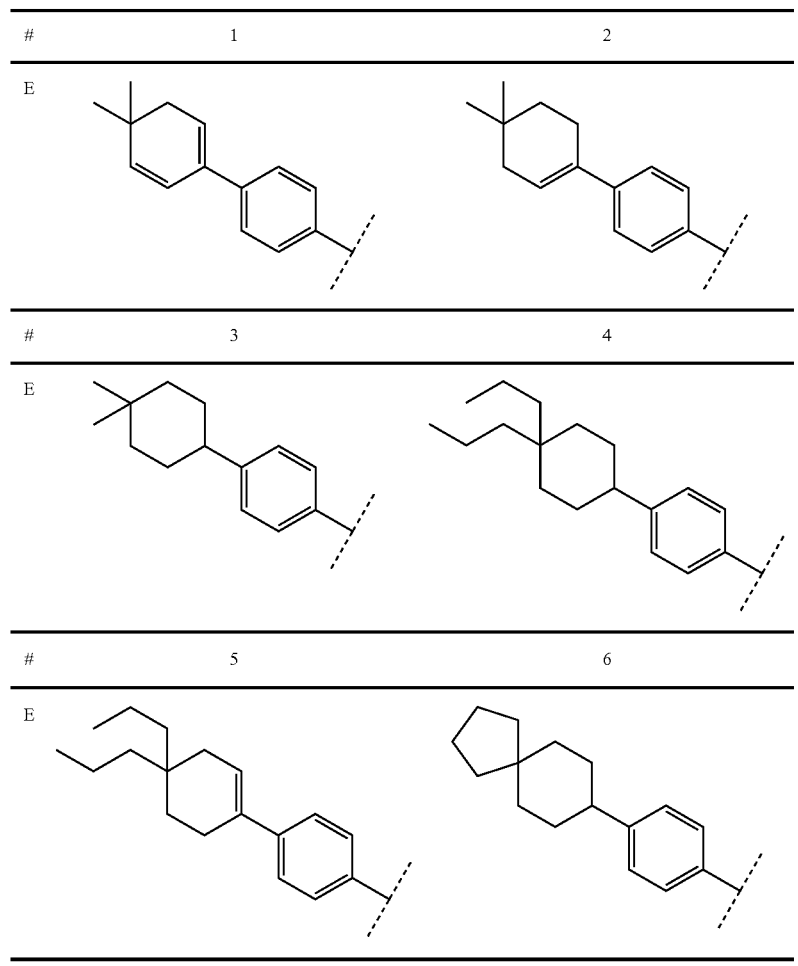

The Group 3 substituents for variable E are assigned the following numbers:
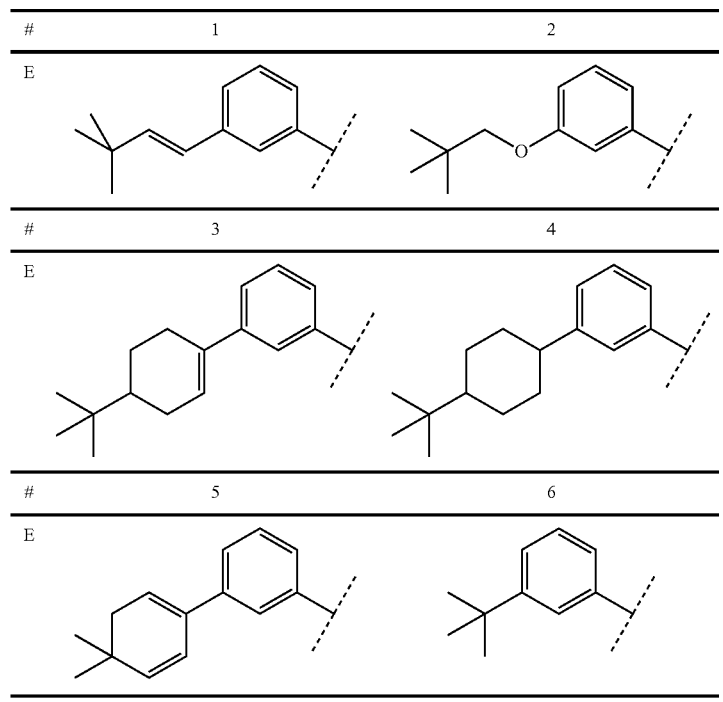
The Group 4 substituents for variable E are assigned the following numbers:
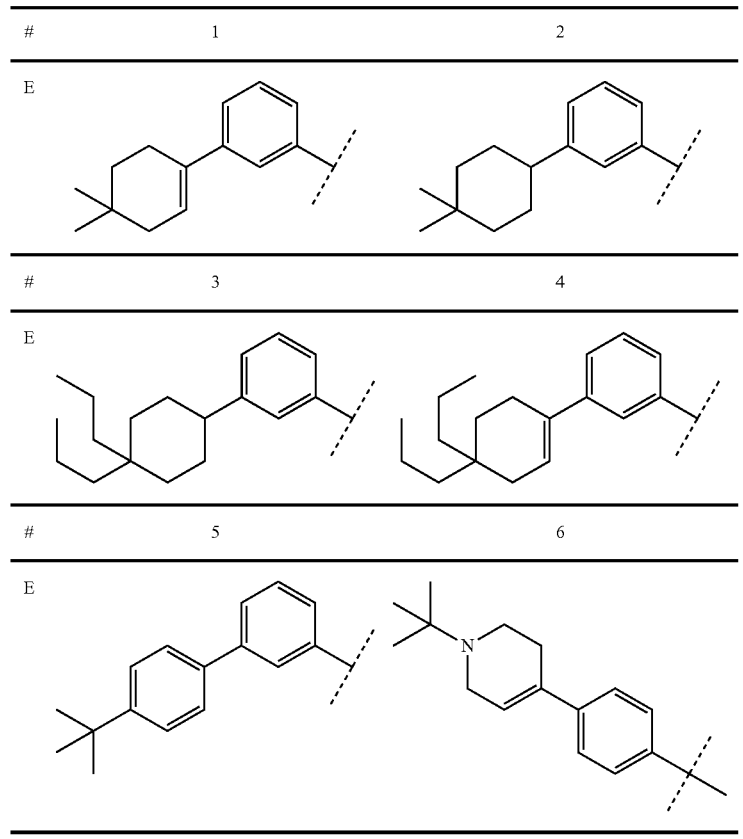

The Group 5 substituents for variable E are assigned the following numbers:

| # | 1 | 2 |
|---|---|---|
| E | [4,4-dimethylcyclohex-2-enyl-phenyl-CH₂- structure] | [4,4-di-n-propyl-cyclohexenyl-phenyl-CH₂- structure] |

| # | 3 | 4 |
|---|---|---|
| E | [cyclohexenyl-1,4-phenyl-CH₂- structure] | [cyclohexenyl-1,3-phenyl-CH₂- structure] |

| # | 5 | 6 |
|---|---|---|
| E | [4,4-di-n-propyl-cyclohexenyl-1,3-phenyl-CH₂- structure] | [4,4-dimethyl-cyclohexenyl-1,3-phenyl-CH₂- structure] |

Variable Q represents the moiety containing Z, R1 and CHR26 as shown in Formula I* and it is connected to E, D, and X (wherein X is a -1,4-phenylene-) as shown in the above configuration. Variable Q is divided into five Groups, each listing six different moieties.

The Group 1 moieties for variable Q are assigned the following numbers:

| # | 1 | 2 | 3 |
|---|---|---|---|
| Q | E-CHH-C(O)-NH-D with X-CH-H | E-C(Me)H-C(O)-NH-D with X-CH-H | E-CFH-C(O)-NH-D with X-CH-H |

| # | 4 | 5 | 6 |
|---|---|---|---|
| Q | E-CHH-C(O)-NH-D with X-CH-Me | E-C(Me)H-C(O)-NH-D with X-CH-Me | E-CFH-C(O)-NH-D with X-CH-Me |

The Group 2 moieties for variable Q are assigned the following numbers:

| # | 1 | 2 |
|---|---|---|
| Q | E-CHH-(isoxazole)-D with X-CH-H | E-C(Me)H-(isoxazole)-D with X-CH-H |

| # | 3 | 4 |
|---|---|---|
| Q | E-CFH-(isoxazole)-D with X-CH-H | E-CHH-(isoxazole)-D with X-CH-Me |

| # | 5 | 6 |
|---|---|---|
| Q | E-CFH-(isoxazole)-D with X-CH-Me | E-C(Me)H-(isoxazole)-D with X-CH-Me |

The Group 3 moieties for variable Q are assigned the following numbers:

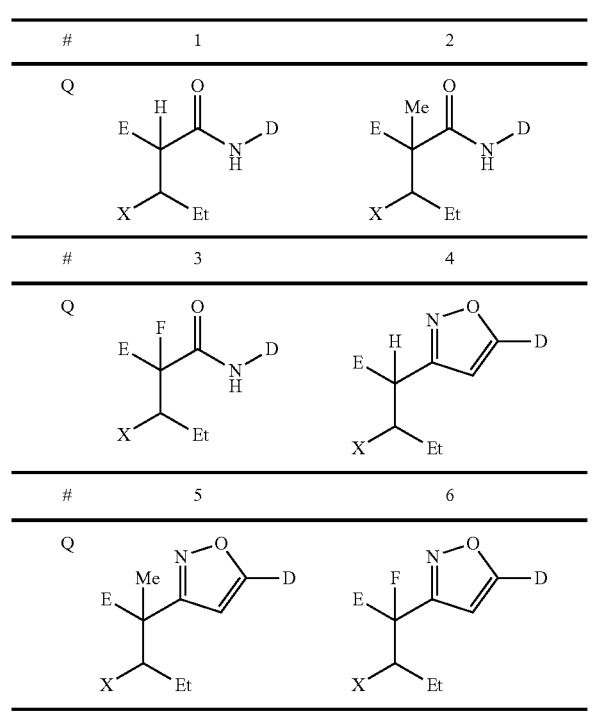

The Group 4 moieties for variable Q are assigned the following numbers:

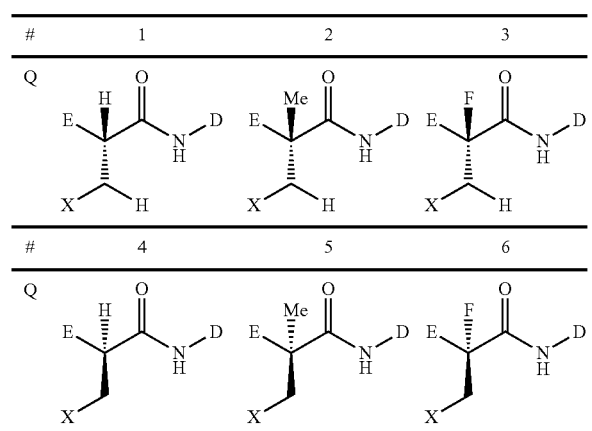

The Group 5 moieties for variable Q are assigned the following numbers:

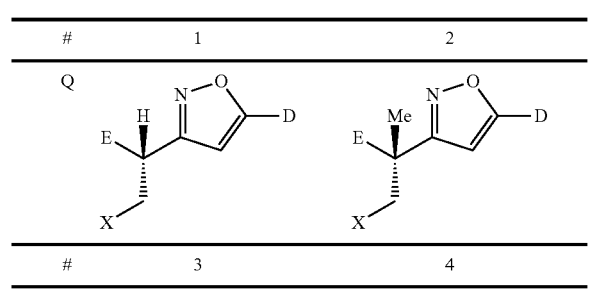

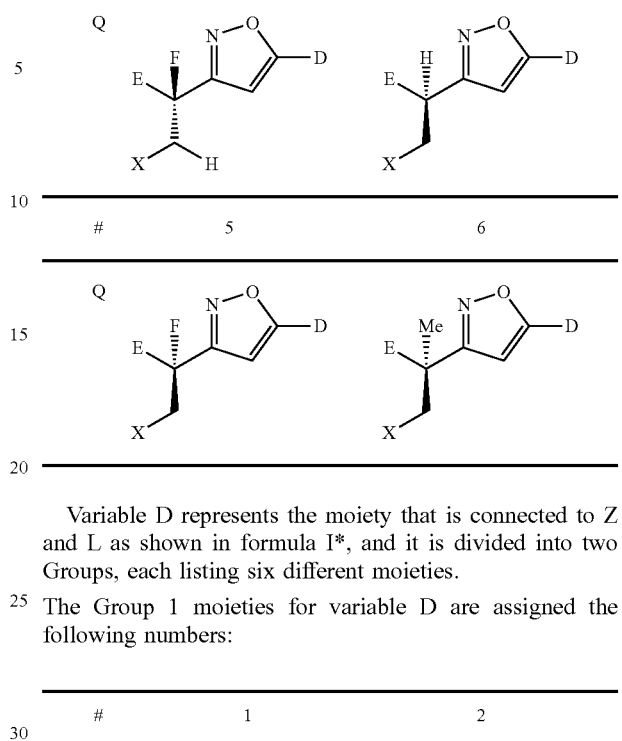

Variable D represents the moiety that is connected to Z and L as shown in formula I*, and it is divided into two Groups, each listing six different moieties.

The Group 1 moieties for variable D are assigned the following numbers:

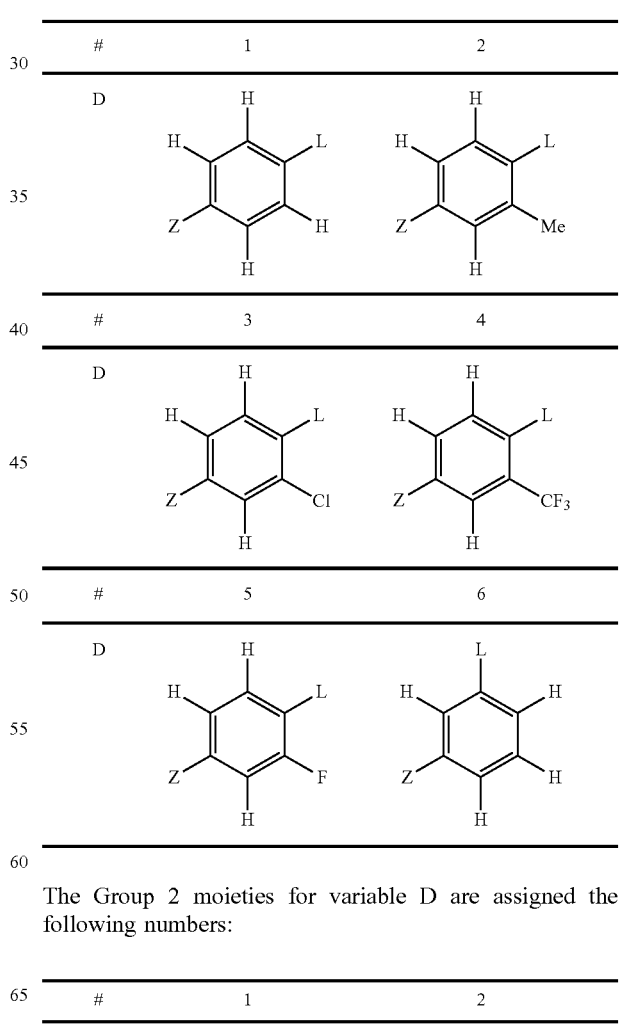

The Group 2 moieties for variable D are assigned the following numbers:

| # | 1 | 2 |
|---|---|---|

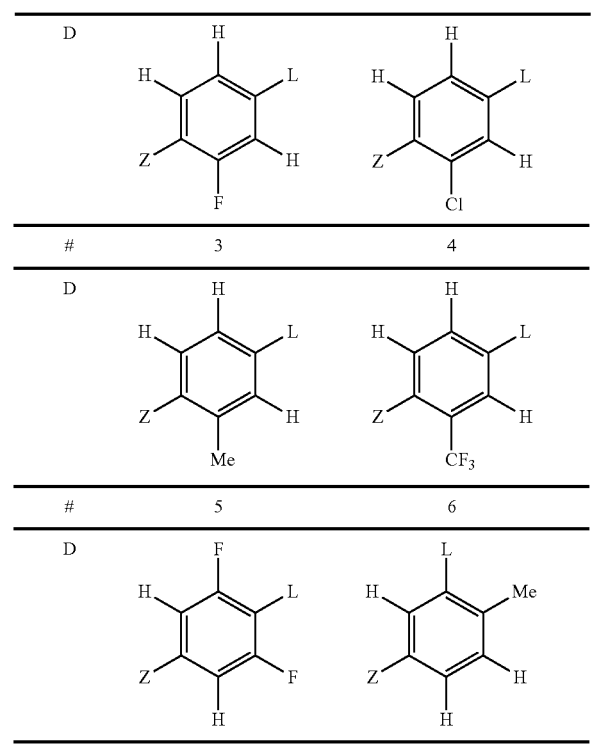

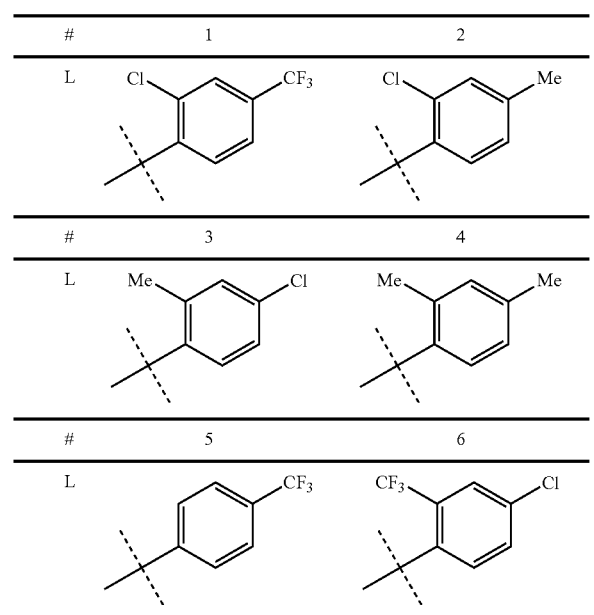

Variable L represents the substituent that is connected to D as shown in formula I*, and it is divided into five Groups, each listing six different substituents.

The Group 1 substituents for variable L are assigned the following numbers:

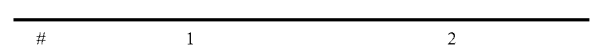

The Group 2 substituents for variable L are assigned the following numbers:

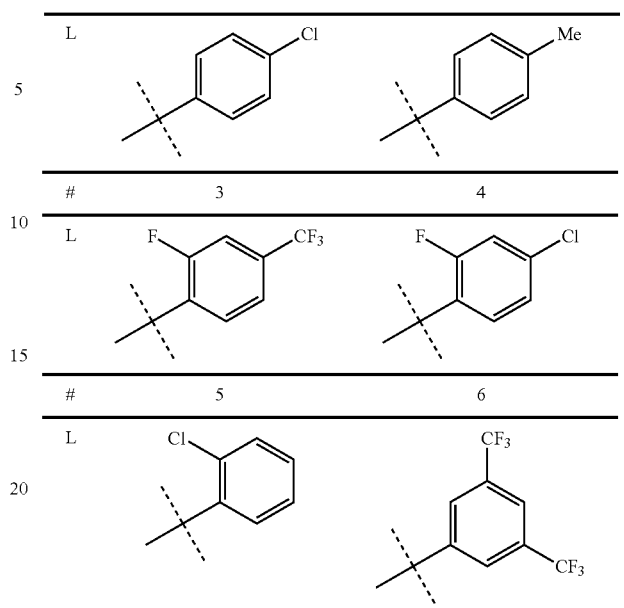

The Group 3 substituents for variable L are assigned the following numbers:

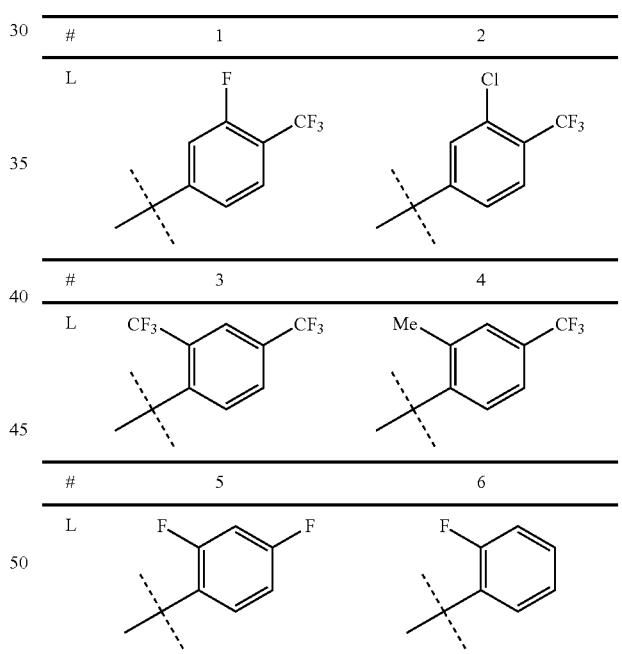

The Group 4 substituents for variable L are assigned the following numbers:

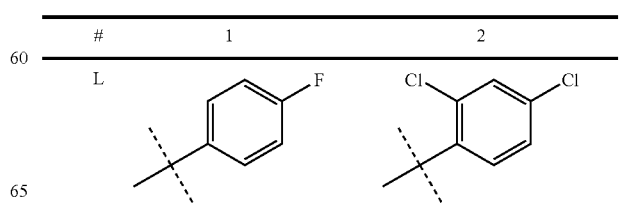

| # | 3 | 4 |
|---|---|---|
| L | 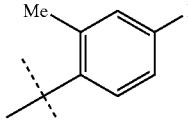 | 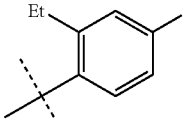 |
| # | 5 | 6 |
|---|---|---|
| L | 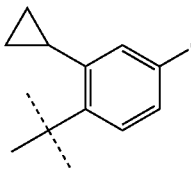 | 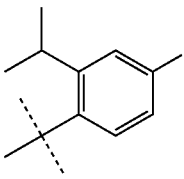 |
The Group 5 substituents for variable L are assigned the following numbers:
| # | 1 | 2 | 3 |
|---|---|---|---|
| L | 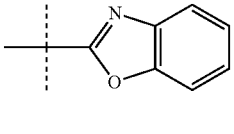 | 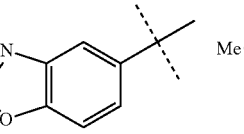 | 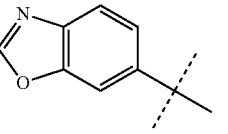 |
| # | 4 | 5 | 6 |
|---|---|---|---|
| L | 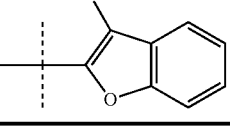 | 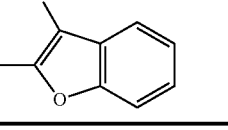 | 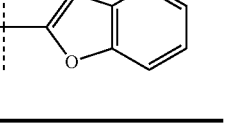 |
TABLE 1
1.1.1.1
1.1.1.2
1.1.1.3
1.1.1.4
1.1.1.5
1.1.1.6
1.1.2.1
1.1.2.2
1.1.2.3
1.1.2.4
1.1.2.5
1.1.2.6
1.1.3.1
1.1.3.2
1.1.3.3
1.1.3.4
1.1.3.5
1.1.3.6
1.1.4.1
1.1.4.2
1.1.4.3
1.1.4.4
1.1.4.5
1.1.4.6
1.1.5.1
1.1.5.2
1.1.5.3
1.1.5.4
1.1.5.5
1.1.5.6
1.1.6.1
TABLE 1-continued
1.1.6.2
1.1.6.3
1.1.6.4
1.1.6.5
1.1.6.6
1.2.1.1
1.2.1.2
1.2.1.3
1.2.1.4
1.2.1.5
1.2.1.6
1.2.2.1
1.2.2.2
1.2.2.3
1.2.2.4
1.2.2.5
1.2.2.6
1.2.3.1
1.2.3.2
1.2.3.3
1.2.3.4
1.2.3.5
TABLE 1-continued
1.2.3.6
1.2.4.1
1.2.4.2
1.2.4.3
1.2.4.4
1.2.4.5
1.2.4.6
1.2.5.1
1.2.5.2
1.2.5.3
1.2.5.4
1.2.5.5
1.2.5.6
1.2.6.1
1.2.6.2
1.2.6.3
1.2.6.4
1.2.6.5
1.2.6.6
1.3.1.1
1.3.1.2
1.3.1.3
1.3.1.4
1.3.1.5
1.3.1.6
1.3.2.1
1.3.2.2
1.3.2.3
1.3.2.4
1.3.2.5
1.3.2.6

TABLE 1-continued

| |
|---|
| 1.3.3.1 |
| 1.3.3.2 |
| 1.3.3.3 |
| 1.3.3.4 |
| 1.3.3.5 |
| 1.3.3.6 |
| 1.3.4.1 |
| 1.3.4.2 |
| 1.3.4.3 |
| 1.3.4.4 |
| 1.3.4.5 |
| 1.3.4.6 |
| 1.3.5.1 |
| 1.3.5.2 |
| 1.3.5.3 |
| 1.3.5.4 |
| 1.3.5.5 |
| 1.3.5.6 |
| 1.3.6.1 |
| 1.3.6.2 |
| 1.3.6.3 |
| 1.3.6.4 |
| 1.3.6.5 |
| 1.3.6.6 |
| 1.4.1.1 |
| 1.4.1.2 |
| 1.4.1.3 |
| 1.4.1.4 |
| 1.4.1.5 |
| 1.4.1.6 |
| 1.4.2.1 |
| 1.4.2.2 |
| 1.4.2.3 |
| 1.4.2.4 |
| 1.4.2.5 |
| 1.4.2.6 |
| 1.4.3.1 |
| 1.4.3.2 |
| 1.4.3.3 |
| 1.4.3.4 |
| 1.4.3.5 |
| 1.4.3.6 |
| 1.4.4.1 |
| 1.4.4.2 |
| 1.4.4.3 |
| 1.4.4.4 |
| 1.4.4.5 |
| 1.4.4.6 |
| 1.4.5.1 |
| 1.4.5.2 |
| 1.4.5.3 |
| 1.4.5.4 |
| 1.4.5.5 |
| 1.4.5.6 |
| 1.4.6.1 |
| 1.4.6.2 |
| 1.4.6.3 |
| 1.4.6.4 |
| 1.4.6.5 |
| 1.4.6.6 |
| 1.5.1.1 |
| 1.5.1.2 |
| 1.5.1.3 |
| 1.5.1.4 |
| 1.5.1.5 |
| 1.5.1.6 |
| 1.5.2.1 |
| 1.5.2.2 |
| 1.5.2.3 |
| 1.5.2.4 |
| 1.5.2.5 |
| 1.5.2.6 |
| 1.5.3.1 |
| 1.5.3.2 |
| 1.5.3.3 |
| 1.5.3.4 |
| 1.5.3.5 |
| 1.5.3.6 |
| 1.5.4.1 |
| 1.5.4.2 |

TABLE 1-continued

| |
|---|
| 1.5.4.3 |
| 1.5.4.4 |
| 1.5.4.5 |
| 1.5.4.6 |
| 1.5.5.1 |
| 1.5.5.2 |
| 1.5.5.3 |
| 1.5.5.4 |
| 1.5.5.5 |
| 1.5.5.6 |
| 1.5.6.1 |
| 1.5.6.2 |
| 1.5.6.3 |
| 1.5.6.4 |
| 1.5.6.5 |
| 1.5.6.6 |
| 1.6.1.1 |
| 1.6.1.2 |
| 1.6.1.3 |
| 1.6.1.4 |
| 1.6.1.5 |
| 1.6.1.6 |
| 1.6.2.1 |
| 1.6.2.2 |
| 1.6.2.3 |
| 1.6.2.4 |
| 1.6.2.5 |
| 1.6.2.6 |
| 1.6.3.1 |
| 1.6.3.2 |
| 1.6.3.3 |
| 1.6.3.4 |
| 1.6.3.5 |
| 1.6.3.6 |
| 1.6.4.1 |
| 1.6.4.2 |
| 1.6.4.3 |
| 1.6.4.4 |
| 1.6.4.5 |
| 1.6.4.6 |
| 1.6.5.1 |
| 1.6.5.2 |
| 1.6.5.3 |
| 1.6.5.4 |
| 1.6.5.5 |
| 1.6.5.6 |
| 1.6.6.1 |
| 1.6.6.2 |
| 1.6.6.3 |
| 1.6.6.4 |
| 1.6.6.5 |
| 1.6.6.6 |
| 2.1.1.1 |
| 2.1.1.2 |
| 2.1.1.3 |
| 2.1.1.4 |
| 2.1.1.5 |
| 2.1.1.6 |
| 2.1.2.1 |
| 2.1.2.2 |
| 2.1.2.3 |
| 2.1.2.4 |
| 2.1.2.5 |
| 2.1.2.6 |
| 2.1.3.1 |
| 2.1.3.2 |
| 2.1.3.3 |
| 2.1.3.4 |
| 2.1.3.5 |
| 2.1.3.6 |
| 2.1.4.1 |
| 2.1.4.2 |
| 2.1.4.3 |
| 2.1.4.4 |
| 2.1.4.5 |
| 2.1.4.6 |
| 2.1.5.1 |
| 2.1.5.2 |
| 2.1.5.3 |
| 2.1.5.4 |

TABLE 1-continued 2.1.5.5
2.1.5.6
2.1.6.1
2.1.6.2
2.1.6.3
2.1.6.4
2.1.6.5
2.1.6.6
2.2.1.1
2.2.1.2
2.2.1.3
2.2.1.4
2.2.1.5
2.2.1.6
2.2.2.1
2.2.2.2
2.2.2.3
2.2.2.4
2.2.2.5
2.2.2.6
2.2.3.1
2.2.3.2
2.2.3.3
2.2.3.4
2.2.3.5
2.2.3.6
2.2.4.1
2.2.4.2
2.2.4.3
2.2.4.4
2.2.4.5
2.2.4.6
2.2.5.1
2.2.5.2
2.2.5.3
2.2.5.4
2.2.5.5
2.2.5.6
2.2.6.1
2.2.6.2
2.2.6.3
2.2.6.4
2.2.6.5
2.2.6.6
2.3.1.1
2.3.1.2
2.3.1.3
2.3.1.4
2.3.1.5
2.3.1.6
2.3.2.1
2.3.2.2
2.3.2.3
2.3.2.4
2.3.2.5
2.3.2.6
2.3.3.1
2.3.3.2
2.3.3.3
2.3.3.4
2.3.3.5
2.3.3.6
2.3.4.1
2.3.4.2
2.3.4.3
2.3.4.4
2.3.4.5
2.3.4.6
2.3.5.1
2.3.5.2
2.3.5.3
2.3.5.4
2.3.5.5
2.3.5.6
2.3.6.1
2.3.6.2
2.3.6.3
2.3.6.4
2.3.6.5
2.3.6.6

TABLE 1-continued 2.4.1.1
2.4.1.2
2.4.1.3
2.4.1.4
2.4.1.5
2.4.1.6
2.4.2.1
2.4.2.2
2.4.2.3
2.4.2.4
2.4.2.5
2.4.2.6
2.4.3.1
2.4.3.2
2.4.3.3
2.4.3.4
2.4.3.5
2.4.3.6
2.4.4.1
2.4.4.2
2.4.4.3
2.4.4.4
2.4.4.5
2.4.4.6
2.4.5.1
2.4.5.2
2.4.5.3
2.4.5.4
2.4.5.5
2.4.5.6
2.4.6.1
2.4.6.2
2.4.6.3
2.4.6.4
2.4.6.5
2.4.6.6
2.5.1.1
2.5.1.2
2.5.1.3
2.5.1.4
2.5.1.5
2.5.1.6
2.5.2.1
2.5.2.2
2.5.2.3
2.5.2.4
2.5.2.5
2.5.2.6
2.5.3.1
2.5.3.2
2.5.3.3
2.5.3.4
2.5.3.5
2.5.3.6
2.5.4.1
2.5.4.2
2.5.4.3
2.5.4.4
2.5.4.5
2.5.4.6
2.5.5.1
2.5.5.2
2.5.5.3
2.5.5.4
2.5.5.5
2.5.5.6
2.5.6.1
2.5.6.2
2.5.6.3
2.5.6.4
2.5.6.5
2.5.6.6
2.6.1.1
2.6.1.2
2.6.1.3
2.6.1.4
2.6.1.5
2.6.1.6
2.6.2.1
2.6.2.2

TABLE 1-continued

| | |
|---|---|
| 2.6.2.3 | 3.2.3.5 |
| 2.6.2.4 | 3.2.3.6 |
| 2.6.2.5 | 3.2.4.1 |
| 2.6.2.6 | 3.2.4.2 |
| 2.6.3.1 | 3.2.4.3 |
| 2.6.3.2 | 3.2.4.4 |
| 2.6.3.3 | 3.2.4.5 |
| 2.6.3.4 | 3.2.4.6 |
| 2.6.3.5 | 3.2.5.1 |
| 2.6.3.6 | 3.2.5.2 |
| 2.6.4.1 | 3.2.5.3 |
| 2.6.4.2 | 3.2.5.4 |
| 2.6.4.3 | 3.2.5.5 |
| 2.6.4.4 | 3.2.5.6 |
| 2.6.4.5 | 3.2.6.1 |
| 2.6.4.6 | 3.2.6.2 |
| 2.6.5.1 | 3.2.6.3 |
| 2.6.5.2 | 3.2.6.4 |
| 2.6.5.3 | 3.2.6.5 |
| 2.6.5.4 | 3.2.6.6 |
| 2.6.5.5 | 3.3.1.1 |
| 2.6.5.6 | 3.3.1.2 |
| 2.6.6.1 | 3.3.1.3 |
| 2.6.6.2 | 3.3.1.4 |
| 2.6.6.3 | 3.3.1.5 |
| 2.6.6.4 | 3.3.1.6 |
| 2.6.6.5 | 3.3.2.1 |
| 2.6.6.6 | 3.3.2.2 |
| 3.1.1.1 | 3.3.2.3 |
| 3.1.1.2 | 3.3.2.4 |
| 3.1.1.3 | 3.3.2.5 |
| 3.1.1.4 | 3.3.2.6 |
| 3.1.1.5 | 3.3.3.1 |
| 3.1.1.6 | 3.3.3.2 |
| 3.1.2.1 | 3.3.3.3 |
| 3.1.2.2 | 3.3.3.4 |
| 3.1.2.3 | 3.3.3.5 |
| 3.1.2.4 | 3.3.3.6 |
| 3.1.2.5 | 3.3.4.1 |
| 3.1.2.6 | 3.3.4.2 |
| 3.1.3.1 | 3.3.4.3 |
| 3.1.3.2 | 3.3.4.4 |
| 3.1.3.3 | 3.3.4.5 |
| 3.1.3.4 | 3.3.4.6 |
| 3.1.3.5 | 3.3.5.1 |
| 3.1.3.6 | 3.3.5.2 |
| 3.1.4.1 | 3.3.5.3 |
| 3.1.4.2 | 3.3.5.4 |
| 3.1.4.3 | 3.3.5.5 |
| 3.1.4.4 | 3.3.5.6 |
| 3.1.4.5 | 3.3.6.1 |
| 3.1.4.6 | 3.3.6.2 |
| 3.1.5.1 | 3.3.6.3 |
| 3.1.5.2 | 3.3.6.4 |
| 3.1.5.3 | 3.3.6.5 |
| 3.1.5.4 | 3.3.6.6 |
| 3.1.5.5 | 3.4.1.1 |
| 3.1.5.6 | 3.4.1.2 |
| 3.1.6.1 | 3.4.1.3 |
| 3.1.6.2 | 3.4.1.4 |
| 3.1.6.3 | 3.4.1.5 |
| 3.1.6.4 | 3.4.1.6 |
| 3.1.6.5 | 3.4.2.1 |
| 3.1.6.6 | 3.4.2.2 |
| 3.2.1.1 | 3.4.2.3 |
| 3.2.1.2 | 3.4.2.4 |
| 3.2.1.3 | 3.4.2.5 |
| 3.2.1.4 | 3.4.2.6 |
| 3.2.1.5 | 3.4.3.1 |
| 3.2.1.6 | 3.4.3.2 |
| 3.2.2.1 | 3.4.3.3 |
| 3.2.2.2 | 3.4.3.4 |
| 3.2.2.3 | 3.4.3.5 |
| 3.2.2.4 | 3.4.3.6 |
| 3.2.2.5 | 3.4.4.1 |
| 3.2.2.6 | 3.4.4.2 |
| 3.2.3.1 | 3.4.4.3 |
| 3.2.3.2 | 3.4.4.4 |
| 3.2.3.3 | 3.4.4.5 |
| 3.2.3.4 | 3.4.4.6 |

TABLE 1-continued

| | |
|---|---|
| 3.4.5.1 | 3.6.6.3 |
| 3.4.5.2 | 3.6.6.4 |
| 3.4.5.3 | 3.6.6.5 |
| 3.4.5.4 | 3.6.6.6 |
| 3.4.5.5 | 4.1.1.1 |
| 3.4.5.6 | 4.1.1.2 |
| 3.4.6.1 | 4.1.1.3 |
| 3.4.6.2 | 4.1.1.4 |
| 3.4.6.3 | 4.1.1.5 |
| 3.4.6.4 | 4.1.1.6 |
| 3.4.6.5 | 4.1.2.1 |
| 3.4.6.6 | 4.1.2.2 |
| 3.5.1.1 | 4.1.2.3 |
| 3.5.1.2 | 4.1.2.4 |
| 3.5.1.3 | 4.1.2.5 |
| 3.5.1.4 | 4.1.2.6 |
| 3.5.1.5 | 4.1.3.1 |
| 3.5.1.6 | 4.1.3.2 |
| 3.5.2.1 | 4.1.3.3 |
| 3.5.2.2 | 4.1.3.4 |
| 3.5.2.3 | 4.1.3.5 |
| 3.5.2.4 | 4.1.3.6 |
| 3.5.2.5 | 4.1.4.1 |
| 3.5.2.6 | 4.1.4.2 |
| 3.5.3.1 | 4.1.4.3 |
| 3.5.3.2 | 4.1.4.4 |
| 3.5.3.3 | 4.1.4.5 |
| 3.5.3.4 | 4.1.4.6 |
| 3.5.3.5 | 4.1.5.1 |
| 3.5.3.6 | 4.1.5.2 |
| 3.5.4.1 | 4.1.5.3 |
| 3.5.4.2 | 4.1.5.4 |
| 3.5.4.3 | 4.1.5.5 |
| 3.5.4.4 | 4.1.5.6 |
| 3.5.4.5 | 4.1.6.1 |
| 3.5.4.6 | 4.1.6.2 |
| 3.5.5.1 | 4.1.6.3 |
| 3.5.5.2 | 4.1.6.4 |
| 3.5.5.3 | 4.1.6.5 |
| 3.5.5.4 | 4.1.6.6 |
| 3.5.5.5 | 4.2.1.1 |
| 3.5.5.6 | 4.2.1.2 |
| 3.5.6.1 | 4.2.1.3 |
| 3.5.6.2 | 4.2.1.4 |
| 3.5.6.3 | 4.2.1.5 |
| 3.5.6.4 | 4.2.1.6 |
| 3.5.6.5 | 4.2.2.1 |
| 3.5.6.6 | 4.2.2.2 |
| 3.6.1.1 | 4.2.2.3 |
| 3.6.1.2 | 4.2.2.4 |
| 3.6.1.3 | 4.2.2.5 |
| 3.6.1.4 | 4.2.2.6 |
| 3.6.1.5 | 4.2.3.1 |
| 3.6.1.6 | 4.2.3.2 |
| 3.6.2.1 | 4.2.3.3 |
| 3.6.2.2 | 4.2.3.4 |
| 3.6.2.3 | 4.2.3.5 |
| 3.6.2.4 | 4.2.3.6 |
| 3.6.2.5 | 4.2.4.1 |
| 3.6.2.6 | 4.2.4.2 |
| 3.6.3.1 | 4.2.4.3 |
| 3.6.3.2 | 4.2.4.4 |
| 3.6.3.3 | 4.2.4.5 |
| 3.6.3.4 | 4.2.4.6 |
| 3.6.3.5 | 4.2.5.1 |
| 3.6.3.6 | 4.2.5.2 |
| 3.6.4.1 | 4.2.5.3 |
| 3.6.4.2 | 4.2.5.4 |
| 3.6.4.3 | 4.2.5.5 |
| 3.6.4.4 | 4.2.5.6 |
| 3.6.4.5 | 4.2.6.1 |
| 3.6.4.6 | 4.2.6.2 |
| 3.6.5.1 | 4.2.6.3 |
| 3.6.5.2 | 4.2.6.4 |
| 3.6.5.3 | 4.2.6.5 |
| 3.6.5.4 | 4.2.6.6 |
| 3.6.5.5 | 4.3.1.1 |
| 3.6.5.6 | 4.3.1.2 |
| 3.6.6.1 | 4.3.1.3 |
| 3.6.6.2 | 4.3.1.4 |

TABLE 1-continued 4.3.1.5
4.3.1.6
4.3.2.1
4.3.2.2
4.3.2.3
4.3.2.4
4.3.2.5
4.3.2.6
4.3.3.1
4.3.3.2
4.3.3.3
4.3.3.4
4.3.3.5
4.3.3.6
4.3.4.1
4.3.4.2
4.3.4.3
4.3.4.4
4.3.4.5
4.3.4.6
4.3.5.1
4.3.5.2
4.3.5.3
4.3.5.4
4.3.5.5
4.3.5.6
4.3.6.1
4.3.6.2
4.3.6.3
4.3.6.4
4.3.6.5
4.3.6.6
4.4.1.1
4.4.1.2
4.4.1.3
4.4.1.4
4.4.1.5
4.4.1.6
4.4.2.1
4.4.2.2
4.4.2.3
4.4.2.4
4.4.2.5
4.4.2.6
4.4.3.1
4.4.3.2
4.4.3.3
4.4.3.4
4.4.3.5
4.4.3.6
4.4.4.1
4.4.4.2
4.4.4.3
4.4.4.4
4.4.4.5
4.4.4.6
4.4.5.1
4.4.5.2
4.4.5.3
4.4.5.4
4.4.5.5
4.4.5.6
4.4.6.1
4.4.6.2
4.4.6.3
4.4.6.4
4.4.6.5
4.4.6.6
4.5.1.1
4.5.1.2
4.5.1.3
4.5.1.4
4.5.1.5
4.5.1.6
4.5.2.1
4.5.2.2
4.5.2.3
4.5.2.4
4.5.2.5
4.5.2.6

TABLE 1-continued 4.5.3.1
4.5.3.2
4.5.3.3
4.5.3.4
4.5.3.5
4.5.3.6
4.5.4.1
4.5.4.2
4.5.4.3
4.5.4.4
4.5.4.5
4.5.4.6
4.5.5.1
4.5.5.2
4.5.5.3
4.5.5.4
4.5.5.5
4.5.5.6
4.5.6.1
4.5.6.2
4.5.6.3
4.5.6.4
4.5.6.5
4.5.6.6
4.6.1.1
4.6.1.2
4.6.1.3
4.6.1.4
4.6.1.5
4.6.1.6
4.6.2.1
4.6.2.2
4.6.2.3
4.6.2.4
4.6.2.5
4.6.2.6
4.6.3.1
4.6.3.2
4.6.3.3
4.6.3.4
4.6.3.5
4.6.3.6
4.6.4.1
4.6.4.2
4.6.4.3
4.6.4.4
4.6.4.5
4.6.4.6
4.6.5.1
4.6.5.2
4.6.5.3
4.6.5.4
4.6.5.5
4.6.5.6
4.6.6.1
4.6.6.2
4.6.6.3
4.6.6.4
4.6.6.5
4.6.6.6
5.1.1.1
5.1.1.2
5.1.1.3
5.1.1.4
5.1.1.5
5.1.1.6
5.1.2.1
5.1.2.2
5.1.2.3
5.1.2.4
5.1.2.5
5.1.2.6
5.1.3.1
5.1.3.2
5.1.3.3
5.1.3.4
5.1.3.5
5.1.3.6
5.1.4.1
5.1.4.2

TABLE 1-continued

| |
|---|
| 5.1.4.3 |
| 5.1.4.4 |
| 5.1.4.5 |
| 5.1.4.6 |
| 5.1.5.1 |
| 5.1.5.2 |
| 5.1.5.3 |
| 5.1.5.4 |
| 5.1.5.5 |
| 5.1.5.6 |
| 5.1.6.1 |
| 5.1.6.2 |
| 5.1.6.3 |
| 5.1.6.4 |
| 5.1.6.5 |
| 5.1.6.6 |
| 5.2.1.1 |
| 5.2.1.2 |
| 5.2.1.3 |
| 5.2.1.4 |
| 5.2.1.5 |
| 5.2.1.6 |
| 5.2.2.1 |
| 5.2.2.2 |
| 5.2.2.3 |
| 5.2.2.4 |
| 5.2.2.5 |
| 5.2.2.6 |
| 5.2.3.1 |
| 5.2.3.2 |
| 5.2.3.3 |
| 5.2.3.4 |
| 5.2.3.5 |
| 5.2.3.6 |
| 5.2.4.1 |
| 5.2.4.2 |
| 5.2.4.3 |
| 5.2.4.4 |
| 5.2.4.5 |
| 5.2.4.6 |
| 5.2.5.1 |
| 5.2.5.2 |
| 5.2.5.3 |
| 5.2.5.4 |
| 5.2.5.5 |
| 5.2.5.6 |
| 5.2.6.1 |
| 5.2.6.2 |
| 5.2.6.3 |
| 5.2.6.4 |
| 5.2.6.5 |
| 5.2.6.6 |
| 5.3.1.1 |
| 5.3.1.2 |
| 5.3.1.3 |
| 5.3.1.4 |
| 5.3.1.5 |
| 5.3.1.6 |
| 5.3.2.1 |
| 5.3.2.2 |
| 5.3.2.3 |
| 5.3.2.4 |
| 5.3.2.5 |
| 5.3.2.6 |
| 5.3.3.1 |
| 5.3.3.2 |
| 5.3.3.3 |
| 5.3.3.4 |
| 5.3.3.5 |
| 5.3.3.6 |
| 5.3.4.1 |
| 5.3.4.2 |
| 5.3.4.3 |
| 5.3.4.4 |
| 5.3.4.5 |
| 5.3.4.6 |
| 5.3.5.1 |
| 5.3.5.2 |
| 5.3.5.3 |
| 5.3.5.4 |
| 5.3.5.5 |
| 5.3.5.6 |
| 5.3.6.1 |
| 5.3.6.2 |
| 5.3.6.3 |
| 5.3.6.4 |
| 5.3.6.5 |
| 5.3.6.6 |
| 5.4.1.1 |
| 5.4.1.2 |
| 5.4.1.3 |
| 5.4.1.4 |
| 5.4.1.5 |
| 5.4.1.6 |
| 5.4.2.1 |
| 5.4.2.2 |
| 5.4.2.3 |
| 5.4.2.4 |
| 5.4.2.5 |
| 5.4.2.6 |
| 5.4.3.1 |
| 5.4.3.2 |
| 5.4.3.3 |
| 5.4.3.4 |
| 5.4.3.5 |
| 5.4.3.6 |
| 5.4.4.1 |
| 5.4.4.2 |
| 5.4.4.3 |
| 5.4.4.4 |
| 5.4.4.5 |
| 5.4.4.6 |
| 5.4.5.1 |
| 5.4.5.2 |
| 5.4.5.3 |
| 5.4.5.4 |
| 5.4.5.5 |
| 5.4.5.6 |
| 5.4.6.1 |
| 5.4.6.2 |
| 5.4.6.3 |
| 5.4.6.4 |
| 5.4.6.5 |
| 5.4.6.6 |
| 5.5.1.1 |
| 5.5.1.2 |
| 5.5.1.3 |
| 5.5.1.4 |
| 5.5.1.5 |
| 5.5.1.6 |
| 5.5.2.1 |
| 5.5.2.2 |
| 5.5.2.3 |
| 5.5.2.4 |
| 5.5.2.5 |
| 5.5.2.6 |
| 5.5.3.1 |
| 5.5.3.2 |
| 5.5.3.3 |
| 5.5.3.4 |
| 5.5.3.5 |
| 5.5.3.6 |
| 5.5.4.1 |
| 5.5.4.2 |
| 5.5.4.3 |
| 5.5.4.4 |
| 5.5.4.5 |
| 5.5.4.6 |
| 5.5.5.1 |
| 5.5.5.2 |
| 5.5.5.3 |
| 5.5.5.4 |
| 5.5.5.5 |
| 5.5.5.6 |
| 5.5.6.1 |
| 5.5.6.2 |
| 5.5.6.3 |
| 5.5.6.4 |
| 5.5.6.5 |
| 5.5.6.6 |

TABLE 1-continued

| | |
|---|---|
| 5.6.1.1 | 6.2.2.3 |
| 5.6.1.2 | 6.2.2.4 |
| 5.6.1.3 | 6.2.2.5 |
| 5.6.1.4 | 6.2.2.6 |
| 5.6.1.5 | 6.2.3.1 |
| 5.6.1.6 | 6.2.3.2 |
| 5.6.2.1 | 6.2.3.3 |
| 5.6.2.2 | 6.2.3.4 |
| 5.6.2.3 | 6.2.3.5 |
| 5.6.2.4 | 6.2.3.6 |
| 5.6.2.5 | 6.2.4.1 |
| 5.6.2.6 | 6.2.4.2 |
| 5.6.3.1 | 6.2.4.3 |
| 5.6.3.2 | 6.2.4.4 |
| 5.6.3.3 | 6.2.4.5 |
| 5.6.3.4 | 6.2.4.6 |
| 5.6.3.5 | 6.2.5.1 |
| 5.6.3.6 | 6.2.5.2 |
| 5.6.4.1 | 6.2.5.3 |
| 5.6.4.2 | 6.2.5.4 |
| 5.6.4.3 | 6.2.5.5 |
| 5.6.4.4 | 6.2.5.6 |
| 5.6.4.5 | 6.2.6.1 |
| 5.6.4.6 | 6.2.6.2 |
| 5.6.5.1 | 6.2.6.3 |
| 5.6.5.2 | 6.2.6.4 |
| 5.6.5.3 | 6.2.6.5 |
| 5.6.5.4 | 6.2.6.6 |
| 5.6.5.5 | 6.3.1.1 |
| 5.6.5.6 | 6.3.1.2 |
| 5.6.6.1 | 6.3.1.3 |
| 5.6.6.2 | 6.3.1.4 |
| 5.6.6.3 | 6.3.1.5 |
| 5.6.6.4 | 6.3.1.6 |
| 5.6.6.5 | 6.3.2.1 |
| 5.6.6.6 | 6.3.2.2 |
| 6.1.1.1 | 6.3.2.3 |
| 6.1.1.2 | 6.3.2.4 |
| 6.1.1.3 | 6.3.2.5 |
| 6.1.1.4 | 6.3.2.6 |
| 6.1.1.5 | 6.3.3.1 |
| 6.1.1.6 | 6.3.3.2 |
| 6.1.2.1 | 6.3.3.3 |
| 6.1.2.2 | 6.3.3.4 |
| 6.1.2.3 | 6.3.3.5 |
| 6.1.2.4 | 6.3.3.6 |
| 6.1.2.5 | 6.3.4.1 |
| 6.1.2.6 | 6.3.4.2 |
| 6.1.3.1 | 6.3.4.3 |
| 6.1.3.2 | 6.3.4.4 |
| 6.1.3.3 | 6.3.4.5 |
| 6.1.3.4 | 6.3.4.6 |
| 6.1.3.5 | 6.3.5.1 |
| 6.1.3.6 | 6.3.5.2 |
| 6.1.4.1 | 6.3.5.3 |
| 6.1.4.2 | 6.3.5.4 |
| 6.1.4.3 | 6.3.5.5 |
| 6.1.4.4 | 6.3.5.6 |
| 6.1.4.5 | 6.3.6.1 |
| 6.1.4.6 | 6.3.6.2 |
| 6.1.5.1 | 6.3.6.3 |
| 6.1.5.2 | 6.3.6.4 |
| 6.1.5.3 | 6.3.6.5 |
| 6.1.5.4 | 6.3.6.6 |
| 6.1.5.5 | 6.4.1.1 |
| 6.1.5.6 | 6.4.1.2 |
| 6.1.6.1 | 6.4.1.3 |
| 6.1.6.2 | 6.4.1.4 |
| 6.1.6.3 | 6.4.1.5 |
| 6.1.6.4 | 6.4.1.6 |
| 6.1.6.5 | 6.4.2.1 |
| 6.1.6.6 | 6.4.2.2 |
| 6.2.1.1 | 6.4.2.3 |
| 6.2.1.2 | 6.4.2.4 |
| 6.2.1.3 | 6.4.2.5 |
| 6.2.1.4 | 6.4.2.6 |
| 6.2.1.5 | 6.4.3.1 |
| 6.2.1.6 | 6.4.3.2 |
| 6.2.2.1 | 6.4.3.3 |
| 6.2.2.2 | 6.4.3.4 |

TABLE 1-continued 6.4.3.5
6.4.3.6
6.4.4.1
6.4.4.2
6.4.4.3
6.4.4.4
6.4.4.5
6.4.4.6
6.4.5.1
6.4.5.2
6.4.5.3
6.4.5.4
6.4.5.5
6.4.5.6
6.4.6.1
6.4.6.2
6.4.6.3
6.4.6.4
6.4.6.5
6.4.6.6
6.5.1.1
6.5.1.2
6.5.1.3
6.5.1.4
6.5.1.5
6.5.1.6
6.5.2.1
6.5.2.2
6.5.2.3
6.5.2.4
6.5.2.5
6.5.2.6
6.5.3.1
6.5.3.2
6.5.3.3
6.5.3.4
6.5.3.5
6.5.3.6
6.5.4.1
6.5.4.2
6.5.4.3
6.5.4.4
6.5.4.5
6.5.4.6
6.5.5.1
6.5.5.2
6.5.5.3
6.5.5.4
6.5.5.5
6.5.5.6
6.5.6.1
6.5.6.2
6.5.6.3
6.5.6.4
6.5.6.5
6.5.6.6
6.6.1.1
6.6.1.2
6.6.1.3
6.6.1.4
6.6.1.5
6.6.1.6
6.6.2.1
6.6.2.2
6.6.2.3
6.6.2.4
6.6.2.5
6.6.2.6
6.6.3.1
6.6.3.2
6.6.3.3
6.6.3.4
6.6.3.5
6.6.3.6
6.6.4.1
6.6.4.2
6.6.4.3
6.6.4.4
6.6.4.5
6.6.4.6

TABLE 1-continued 6.6.5.1
6.6.5.2
6.6.5.3
6.6.5.4
6.6.5.5
6.6.5.6
6.6.6.1
6.6.6.2
6.6.6.3
6.6.6.4
6.6.6.5
6.6.6.6

Therefore, compounds specifically named in Table 1 of formula I* are represented by each number. For example, using Group 1 for variable Q, using Group 1 for variable E, using Group 1 for variable D, and using Group 5 for variable L the compound named by 1.1.1.6 is:

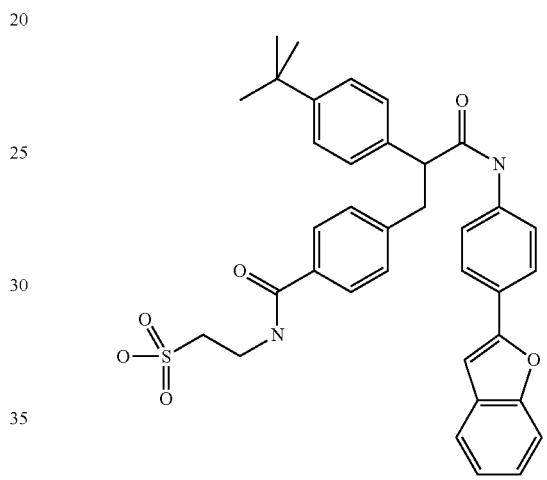

This compound is shown in Example 1.002.

Analogously, using Group 2 for variable Q, using Group 1 for variable E, using Group 1 for variable D, and using Group 5 for variable L the compound named by 1.1.6.6 is:

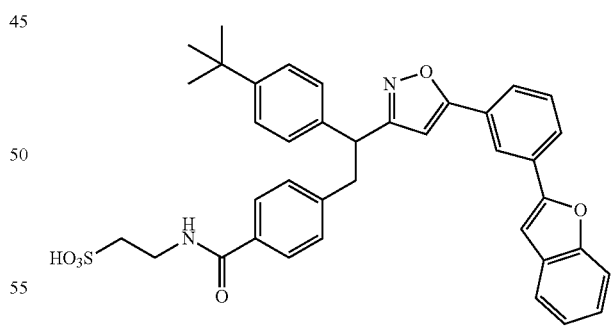

This compound is shown in Example 2.037

It is noted that each numerical identifier E.Q.D.L appearing in Table 1 represents a set of compounds rather than a single compound. For a particular numerical designation E.Q.D.L, there are 5 possible Groups for E, 5 possible Groups for Q, 2 possible Groups for D, and 5 possible Groups for L. Thus, a particular numerical designation E.Q.D.L represents a set of 5×5×2×5=250 individual compounds.

Another aspect of the present invention are pharmaceutical compositions comprising a compound as disclosed herein.

Another aspect of the present invention are single enantiomers or diasteromers of a compound as disclosed herein.

Another aspect of the present invention are enantiomerically enriched compositions comprising an enantiomer of a compound of the present invention. In one embodiment, a single enantiomer is >60%, >70%, >80%, >85%, >90%, >91%, >92%, >93%, >94%, >95%, >96%, >97%, >98% or >99% enriched as compared to the total percentage of all other enantiomers of the same compound present in the composition.

Another aspect provides for salts, including pharmaceutically acceptable salts, of compounds of the present invention and pharmaceutical compositions comprising a pharmaceutically acceptable salt of the present invention. Salts of compounds of the present invention include an inorganic base addition salt such as sodium, potassium, lithium, calcium, magnesium, ammonium, aluminum salts or organic base addition salts, or an inorganic acid addition salt such as HBr, HCl, sulfuric, nitric, or phosphoric acid addition salts or an organic acid addition salt such as acetic, propionic, pyruvic, malanic, succinic, malic, maleic, fumaric, tartaric, citric, benzoic, methanesulfonic, ethanesulforic, stearic or lactic acid addition salt.

Another aspect provides for anhydrates, hydrates and solvates of compounds of the present invention and pharmaceutical compositions comprising a pharmaceutically acceptable anhydrates, hydrates and solvates of the present invention. Included are an anhydrate, hydrate or solvate of a free form or salt of a compound of the present invention. Hydrates include, for example, a hemihydrate, monohydrate, dihydrate, trihydrate, quadrahydrate, pentahydrate, sesquihydrate.

Another aspect provides for the use of a compound of the present invention for the manufacture of a medicament for treating, preventing, delaying the time to onset or reducing the risk for the development or progression of a disease or condition for which one or more glucagon receptor antagonist or inverse agonist is indicated.

Another aspect provides for the use of a compound of the invention for the manufacture of a medicament for treating, preventing, delaying the time to onset or reducing the risk for the development or progression of a disease or condition responsive to decreased hepatic glucose production or responsive to lowered blood glucose levels, the method comprising the step of administering to an animal a therapeutically effective amount a compound of the invention, or a pharmaceutically acceptable salt or prodrugs thereof.

Another aspect provides for methods of treating, preventing, delaying the time to onset or reducing the risk for the development or progression of a disease or condition for which one or more glucagon receptor antagonist or inverse agonist is indicated.

Another aspect provides for methods of treating, preventing, delaying the time to onset or reducing the risk for the development or progression of a disease or condition responsive to decreased hepatic glucose production or responsive to lowered blood glucose levels, the method comprising the step of administering to an animal a therapeutically effective amount a compound of the invention, or a pharmaceutically acceptable salt or prodrugs thereof.

Another aspect provides for methods for treating, preventing, delaying the time to onset or reducing the risk for the development or progression of Type 1 diabetes, the method comprising the step of administering to an animal a therapeutically effective amount a compound of the invention.

Another aspect provides for methods for treating, preventing, delaying the time to onset or reducing the risk for the development or progression of Type II diabetes, the method comprising the step of administering to an animal a therapeutically effective amount a compound of the invention.

Another aspect provides for methods for treating, preventing, delaying the time to onset or reducing the risk for the development or progression of impaired glucose tolerance, the method comprising the step of administering to an animal a therapeutically effective amount a compound of the invention.

Another aspect provides for methods for treating, preventing, delaying the time to onset or reducing the risk for the development or progression of insulin resistance, the method comprising the step of administering to an animal a therapeutically effective amount a compound of the invention.

Another aspect provides for methods for treating, preventing, delaying the time to onset or reducing the risk for the development or progression of hyperglycemia, the method comprising the step of administering to an animal a therapeutically effective amount a compound of the invention. In one embodiment, the hyperglycemia is postprandial hyperglycemia. In another embodiment, the hyperglycemia is fasting hyperglycemia.

Another aspect provides for methods for treating, preventing, delaying the time to onset of or reducing the risk for the development or progression of accelerated gluconeogenesis, the method comprising the step of administering to an animal a therapeutically effective amount a compound of the invention.

Another aspect provides for methods for treating, preventing, delaying the time to onset of or reducing the risk for the development or progression of increased or excessive (greater than normal levels) hepatic glucose output, the method comprising the step of administering to an animal a therapeutically effective amount a compound of the invention.

Another aspect provides for methods for treating, preventing, delaying the time to onset of or reducing the risk for the development or progression of hyperinsulinemia, the method comprising the step of administering to an animal a therapeutically effective amount a compound of the invention.

Another aspect provides for methods for treating, preventing, delaying the time to onset of or reducing the risk for the development or progression of hyperlipidemia, the method comprising the step of administering to an animal a therapeutically effective amount a compound of the invention.

Another aspect provides for methods for treating, preventing, delaying the time to onset of or reducing the risk for the development or progression of dyslipidemia, the method comprising the step of administering to an animal a therapeutically effective amount a compound of the invention.

Another aspect provides for methods for treating, preventing, delaying the time to onset of or reducing the risk for the development or progression of hypercholesterolemia, the method comprising the step of administering to an animal a therapeutically effective amount a compound of the invention.

Another aspect provides for methods for treating, preventing, delaying the time to onset of or reducing the risk for the development or progression of atherosclerosis, the method comprising the step of administering to an animal a therapeutically effective amount a compound of the invention.

Another aspect provides for methods for treating, preventing, delaying the time to onset of or reducing the risk for the development or progression of obesity, the method comprising the step of administering to an animal a therapeutically effective amount a compound of the invention.

Another aspect provides for methods for treating, preventing, delaying the time to onset of or reducing the risk for the development or progression of Metabolic Syndrome X, the method comprising the step of administering to an animal a therapeutically effective amount a compound of the invention.

Formulations

In one aspect, compounds of the invention are administered in a total daily dose of 0.01 to 2500 mg. In one aspect the range is about 1 mg to about 1000 mg. In one aspect the range is about 1 mg to about 500 mg. In one aspect the range is about 10 mg to about 500 mg. The dose may be administered in as many divided doses as is convenient or necessary.

In another aspect, compounds of the invention are administered in a unit dose of a range between 0.01 to 1000 mg. In one aspect the range is about 0.1 mg to about 500 mg. In one aspect the range is about 0.1 mg to about 100 mg. In one aspect the range is about 1 mg to about 1000 mg. In one aspect the range is about 1 mg to about 500 mg. In one aspect the range is about 1 mg to about 100 mg. In one aspect the range is about 1 mg to about 10 mg. In one aspect the range is about 10 mg to about 1000 mg. In one aspect the range is about 10 mg to about 500 mg. In one aspect the range is about 10 mg to about 100 mg. In one aspect, the unit dose is 10 mg. In one aspect, the unit dose is 25 mg. In one aspect, the unit dose is 50 mg. In one aspect, the unit dose is 75 mg. In one aspect, the unit dose is 100 mg. In one aspect, the unit dose is 150 mg. In one aspect, the unit dose is 200 mg. In one aspect, the unit dose is 250 mg. In one aspect, the unit dose is 300 mg. In one aspect, the unit dose is 400 mg. In one aspect, the unit dose is 500 mg. In one aspect, the unit dose is 600 mg. In one aspect, the unit dose is 700 mg. In one aspect, the unit dose is 800 mg. In one aspect, the unit dose is 900 mg. In one aspect, the unit dose is 1000 mg.

In one aspect the compound is administered QD (once a day). In another aspect the compound is administered BID (twice a day). In another aspect the compound is administered TID (three times a day). In another aspect the compound is administered QID (four times a day). In one aspect the compound is administered before a meal. In one aspect the compound is administered after a meal. In one aspect the compound is administered in the morning hours. In one aspect the compound is administered upon awaking in the morning. In one aspect the compound is administered in the evening hours. In one aspect the compound is administered at bedtime in the evening.

Compounds of this invention may be used in combination with other pharmaceutical agents. The compounds may be administered as a daily dose or an appropriate fraction of the daily dose (e.g., bid). Administration of the compound may occur at or near the time in which the other pharmaceutical agent is administered or at a different time. The compounds of this invention may be used in a multidrug regimen, also known as combination or 'cocktail' therapy, wherein, multiple agents may be administered together, may be administered separately at the same time or at different intervals, or administered sequentially. The compounds of this invention may be administered after a course of treatment by another agent, during a course of therapy with another agent, administered as part of a therapeutic regimen, or may be administered prior to therapy by another agent in a treatment program.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Intravenous administration is generally preferred.

Pharmaceutically acceptable salts include acetate, adipate, besylate, bromide, camsylate, chloride, citrate, edisylate, estolate, fumarate, gluceptate, gluconate, glucoranate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, terphthalate, tosylate, and triethiodide.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. One aspect relates to the administration of a pharmaceutically acceptable composition of the present invention by controlled- or delayed-release means. Controlled-release pharmaceutical products have a common goal of improving drug therapy over that achieved by their non-controlled release counterparts.

A variety of known controlled- or extended-release dosage forms, formulations, and devices can be adapted for use with the crystalline forms of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185; each of which is incorporated herein by reference.

These dosage forms can be used to provide delayed or controlled-release of one or more active ingredients using, for example, hydroxypropylmethyl cellulose, other polymer matrices, gels, permeable membranes, osmotic systems (such as OROS, Alza Corporation, Mountain View, Calif. USA), multilayer coatings, microparticles, liposomes, or microspheres or a combination thereof to provide the desired release profile in varying proportions. Additionally, ion exchange materials can be used to prepare immobilized, adsorbed co-crystals and thus effect controlled delivery of the drug. Examples of specific anion exchangers include, but are not limited to, Duolite A568 and Duolite AP143 (Rohm & Haas, Spring House, Pa., USA).

One aspect of the invention encompasses a unit dosage form which comprises a pharmaceutically acceptable composition comprising a crystalline form of a compound of the present invention and one or more pharmaceutically acceptable excipients or diluents, wherein the pharmaceutical composition, medicament or dosage forms is formulated for controlled-release. In another aspect, the dosage form utilizes an osmotic drug delivery system.

A particular and well-known osmotic drug delivery system is referred to as OROS (Alza Corporation, Mountain View, Calif. USA). This technology can readily be adapted for the delivery of compounds and compositions of the invention. Various aspects of the technology are disclosed in U.S. Pat. Nos. 6,375,978; 6,368,626; 6,342,249; 6,333,050; 6,287,295; 6,283,953; 6,270,787; 6,245,357; and 6,132,420; each of which is incorporated herein by reference. Specific adaptations of OROS that can be used to administer compounds and compositions of the invention include, but are not limited to, the OROS; Push-Pull, Delayed Push-Pull, Multi-Layer Push-Pull, and Push-Stick Systems, all of which are well known. See, e.g., www.alza.com. Additional OROS systems that can be used for the controlled oral delivery of compounds and compositions of the invention include OROS-CT and L-OROS (Id.; see also, Delivery Times, vol. II, issue II (Alza Corporation).

Conventional OROS oral dosage forms are made by compressing a drug powder (e.g. a crystalline form selected from Forms A-D) into a hard tablet, coating the tablet with cellulose derivatives to form a semi-permeable membrane, and then drilling an orifice in the coating (e.g., with a laser). Kim, Cherug-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS drug delivery systems cannot be used to effectively deliver drugs with low water solubility. Id. at 234.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a crystalline form of a compound of the present invention. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a crystalline form of a compound of the present invention. See U.S. Pat. No. 6,342,249, the entirety of which is incorporated herein by reference.

In another aspect, a pharmaceutical composition or medicament comprising a crystalline form of a compound of the present invention is administered transdermally. Such a transdermal (TD) delivery can avoid first-pass metabolism. Additionally, a "pill-and-patch" strategy can be taken, where only a fraction of the daily dose is delivered through the skin to generate basal systemic levels, onto which oral therapy is added.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, ethylcellulose, hydroxypropylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachid oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachid oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of Formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Formulations suitable for parenteral administration may be administered in a continuous infusion manner via an indwelling pump or via a hospital bag. Continuous infusion includes the infusion by an external pump. The infusions may be done through a Hickman or PICC or any other suitable means of administering a formulation either parenterally or i.v.

Preferred unit dosage formulations are those containing a daily dose or unit, daily sub-dose, or an appropriate fraction thereof, of a drug.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

EXAMPLES: SYNTHESIS OF COMPOUNDS OF FORMULA I

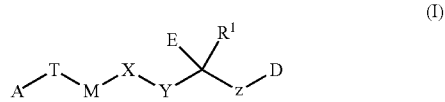

(I)

Compounds of Formula I can be prepared according to the methodology outlined in the following general synthetic schemes or with modifications of these schemes that will be evident to persons skilled in the art.

Synthesis of Various Building Blocks:

The carboxylic acids A1c can be generated using standard methods. As shown below, an ester can be alkylated by reaction with a base (such as lithium diisopropylamide or lithium hexamethyldisilylamide) in a suitable solvent (such as THF or DME) followed by reaction with an aralkyl halide. It is preferred that Ra and Rb groups are adequately chosen so that liberation of the carboxylic acid to generate A1c can take place selectively. For example, a standard Rb group can be a methyl or ethyl group while the Ra group can be a benzyl, t-butyl, 2-trimethylsilylethyl group or other groups that can be selectively removed under conditions where the other ester group Rb would remain intact.

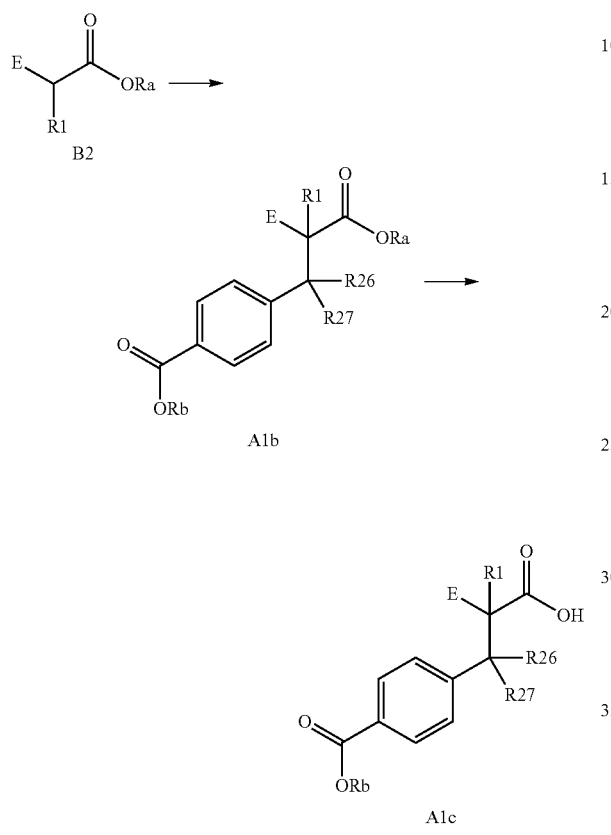

An alternative route for the synthesis of this particular building block can involve condensation of an acetic acid derivative with an aldehyde or a ketone leading to the α,β-unsaturated ester intermediate A1a. The esters A1a can be hydrogenated under conditions that are well-documented in the literature (for example, hydrogen atmosphere and palladium on carbon as a catalyst in a solvent such as ethanol) to generate the carboxylate esters A1b (where R1 and R27 are both hydrogen). 1,4-Addition of an alkyl group can take place by reaction with a suitable carbon nucleophile (e.g. copper mediated reaction of alkyl lithium or alkyl Grignard reagent) to yield compounds A1b wherein R27 is alkyl. Other methods for the incorporation of R27 include the reaction with dilakylzinc halides with or without the presence of metal catalysts. The group R1 can be incorporated into A1b by quenching the anions generated in the above reactions with a suitable electrophile (e.g. R1-Hal where Hal is a halogen or a trifluoromethanesulfonate ester or other suitable leaving group). On the other hand, the above discussed reaction can be quenched with a suitable proton source (e.g. aqueous ammonium chloride or dilute aqueous hydrochloric acid) to give compounds A1b wherein R1 is H. Alternatively, the R1 group can also be incorporated from A1b (R1=H) by enolization followed by reaction with a suitable electrophile R1-Hal.

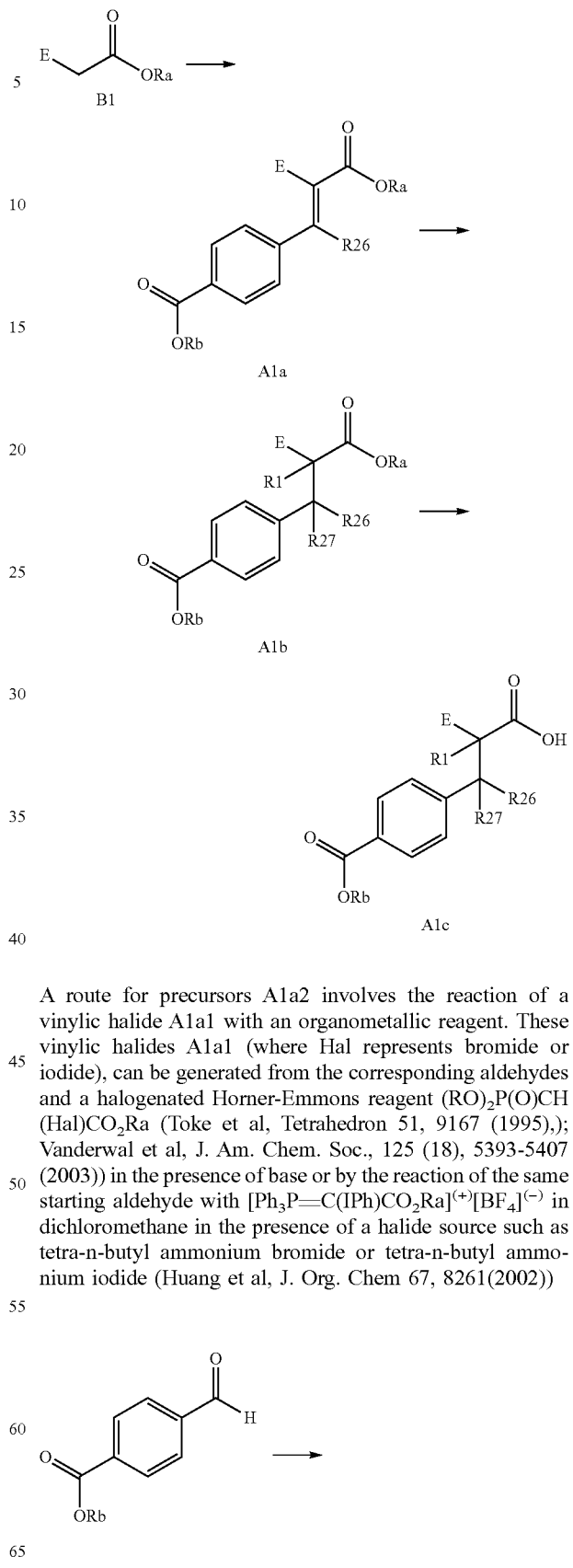

A route for precursors A1a2 involves the reaction of a vinylic halide A1a1 with an organometallic reagent. These vinylic halides A1a1 (where Hal represents bromide or iodide), can be generated from the corresponding aldehydes and a halogenated Horner-Emmons reagent $(RO)_2P(O)CH(Hal)CO_2Ra$ (Toke et al, Tetrahedron 51, 9167 (1995),); Vanderwal et al, J. Am. Chem. Soc., 125 (18), 5393-5407 (2003)) in the presence of base or by the reaction of the same starting aldehyde with $[Ph_3P=C(IPh)CO_2Ra]^{(+)}[BF_4]^{(-)}$ in dichloromethane in the presence of a halide source such as tetra-n-butyl ammonium bromide or tetra-n-butyl ammonium iodide (Huang et al, J. Org. Chem 67, 8261(2002))

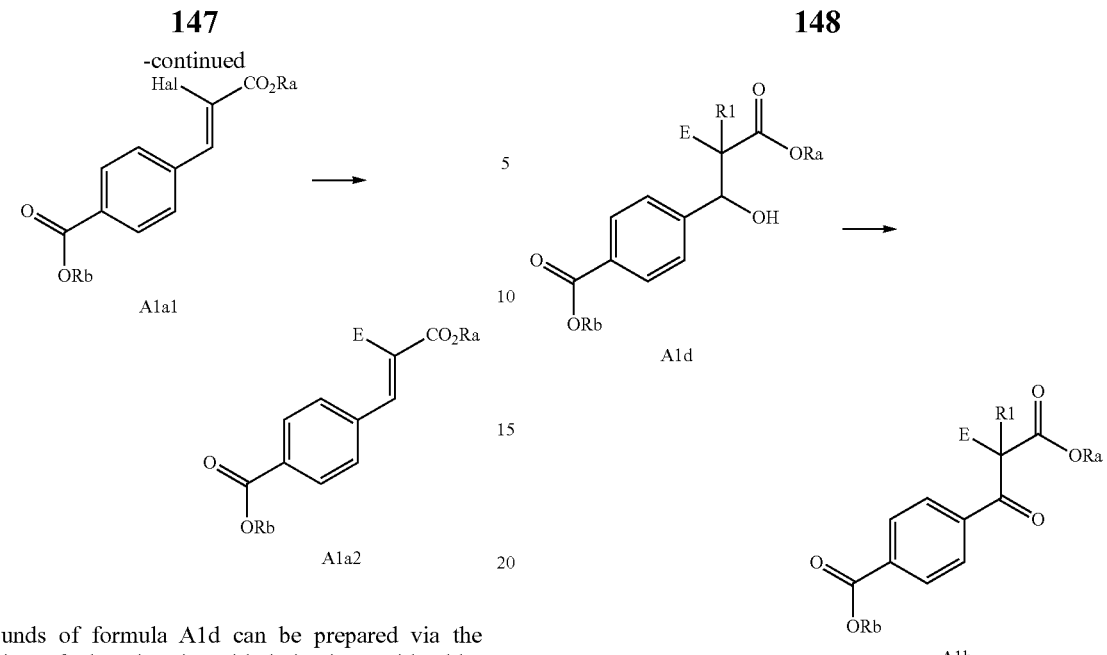

Compounds of formula A1d can be prepared via the condensation of phenylacetic acid derivatives with aldehydes or ketones, which is performed in a manner such that dehydration does not take place. Examples of methods for this conversion would be the deprotonation of a phenylacetic acid ester derivative with a suitable base followed by addition of an aromatic aldehyde or ketone. This hydroxyl group can be manipulated to afford a fluoride analog A1e by a variety of established methods. The reaction of alcohols with fluorinating agents (such as $Et_2NSF_3$, $(PhSO_2)_2NF$, etc.) is known to directly yield the corresponding fluorides. Alternatively, the alcohol can be converted into a good leaving group such as a mesylate and treated with a fluoride source such as CsF or KF.

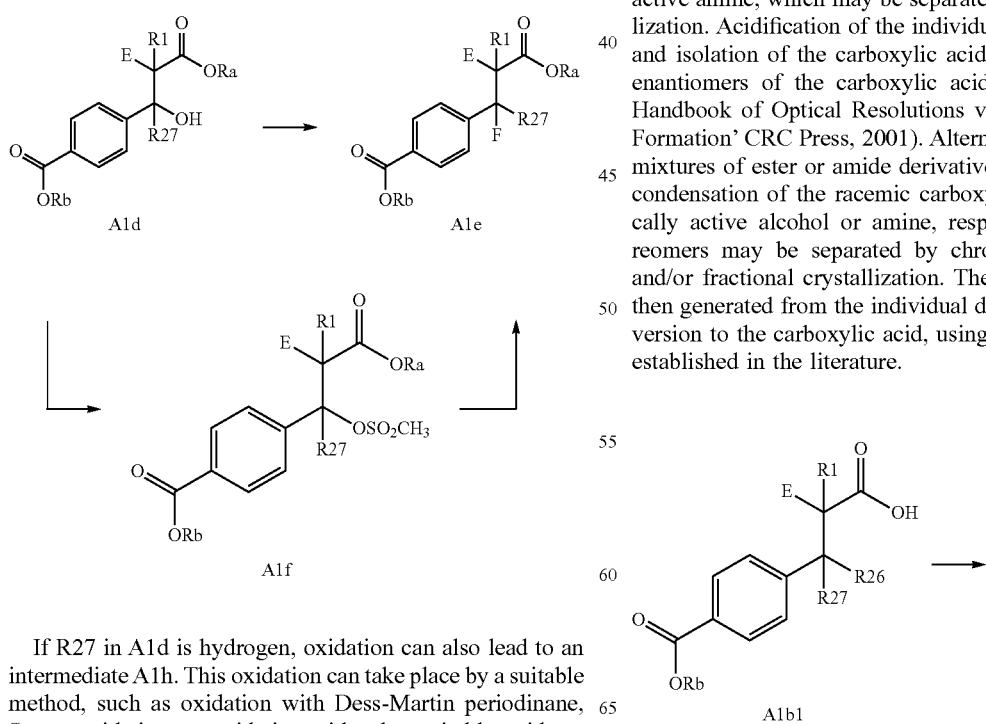

If R27 in A1d is hydrogen, oxidation can also lead to an intermediate A1h. This oxidation can take place by a suitable method, such as oxidation with Dess-Martin periodinane, Swern oxidation, or oxidation with other suitable oxidants such as PCC, PDC, or like reagents.

It is recognized that the carbon atom to which E, Z and Y are attached is an asymmetric center. The synthesis of compounds of the invention in enantiomerically pure form can be achieved by utilization of the methods described above if the starting material A1b1 exists in enantiomerically pure form. An optically pure precursor A1b1*, can be generated by resolution of racemic A1b1 or by use of synthetic methods that generate the asymmetric center in an enantioselective manner.

Resolution methods include the generation of a diastereomeric mixture of carboxylate salts with an optically active amine, which may be separated by fractional crystallization. Acidification of the individual diastereomeric salts and isolation of the carboxylic acid affords the individual enantiomers of the carboxylic acid (D. Kozma: 'CRCC Handbook of Optical Resolutions via Diastereomeric Salt Formation' CRC Press, 2001). Alternatively, diastereomeric mixtures of ester or amide derivatives may be prepared by condensation of the racemic carboxylic acid with an optically active alcohol or amine, respectively; these diastereomers may be separated by chromatographic methods and/or fractional crystallization. The pure enantiomers are then generated from the individual diastereomers by reconversion to the carboxylic acid, using methods that are well established in the literature.

-continued

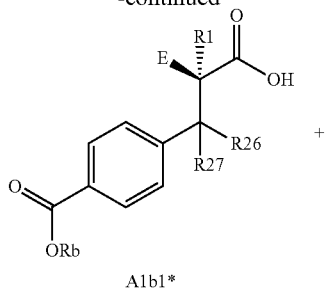
A1b1*

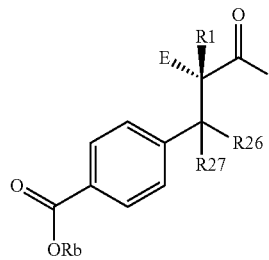
A1b1**

Methods that generate the chiral center in an enantioselective manner include, but are not limited to, the alkylation of precursors containing a chiral auxiliary Xc. This should generate an unequal amount of two diastereomers, which may be separated by fractional crystallization or chromatography. After the separation of the diastereomers, they can be converted into the corresponding enantiomerically enriched acids by known procedures and further elaborated into the compounds of the invention as described in the Examples below.

Asymmetric centers may be present in other positions of the molecule. As an example, substitution on a cyclohexenyl group generates a new chiral center in compound 1.267. This center can be fixed in an appropriately functionalized precursor prior to construction of the target molecule. A potential route to this chiral precursor involves the desymmetrization of a racemic ketone. The reaction of 4-t-butylcyclohexanone with a chiral amide base has been reported to generate the corresponding chiral enolate in an enantioselective manner [Busch-Petersen and Corey, Tetrahedron Letters 41, 6941(2000), Lyapkalo et al, Synlett 1292(2001)]. Conversion of the enolate into a trifluoromethanesulfonate or a nonafluorobutanesulfonate [Busch-Petersen and Corey, Tetrahedron Letters 41, 6941(2000), Lyapkalo et al, Synlett 1292(2001)], leads to a chiral precursor that may be used in subsequent steps (A specific enantiomer is shown below, but it should be understood that either enantiomer can be synthesized by modifications of this method). The precursor B2a1 so obtained can then be elaborated into the single enantiomer as described above.

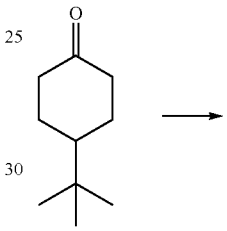

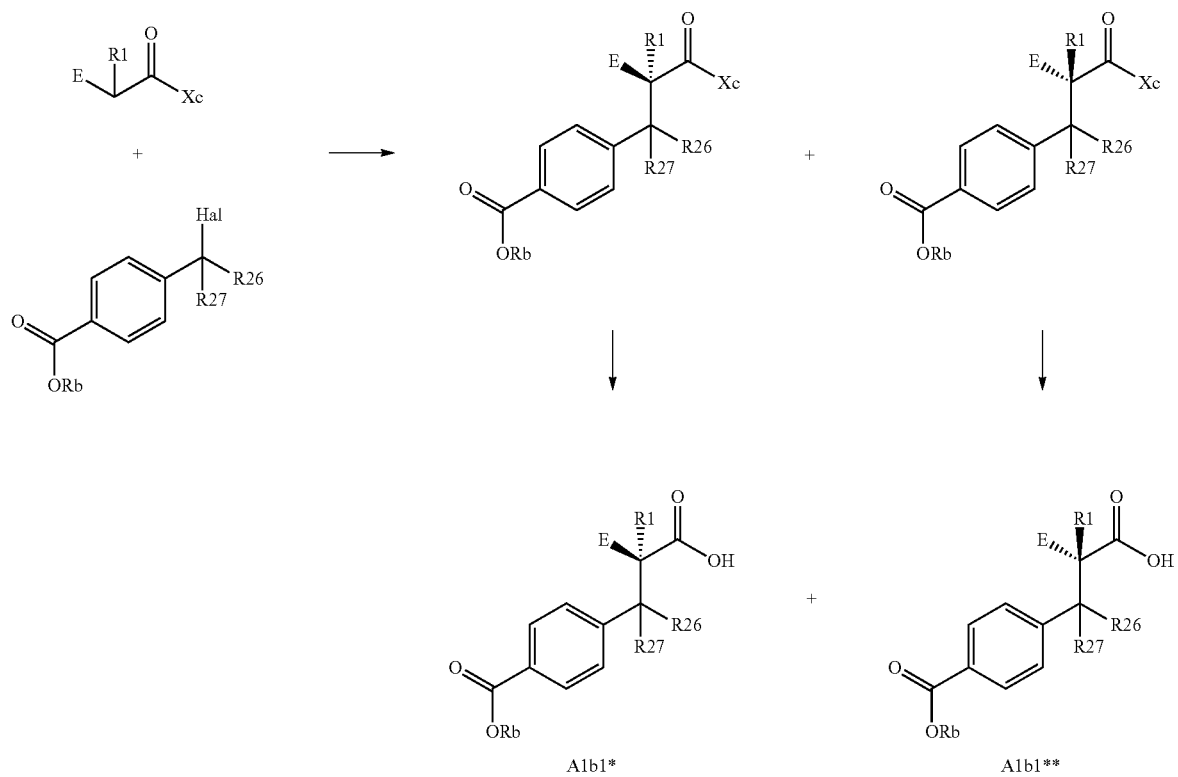

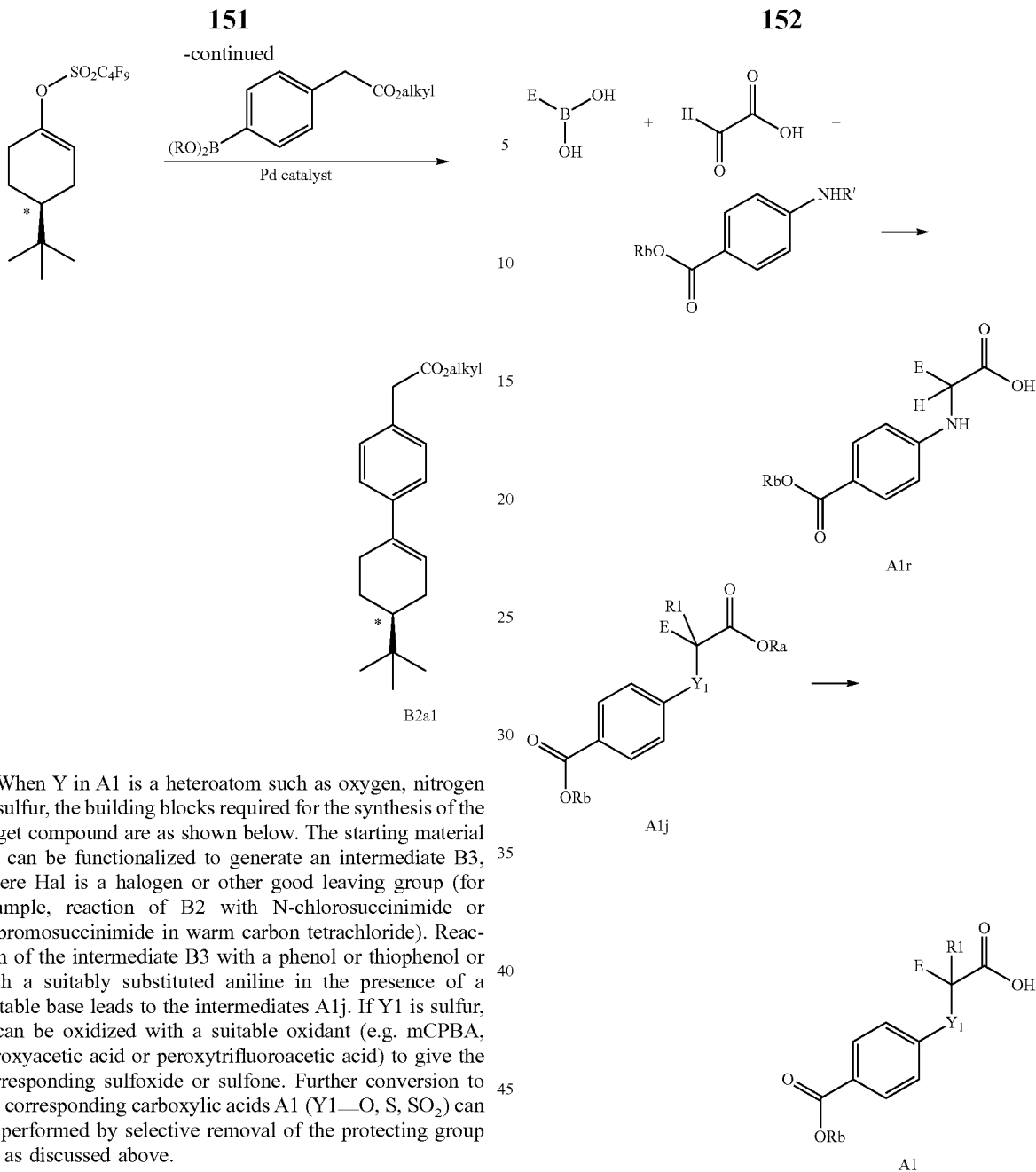

When Y in A1 is a heteroatom such as oxygen, nitrogen or sulfur, the building blocks required for the synthesis of the target compound are as shown below. The starting material B2 can be functionalized to generate an intermediate B3, where Hal is a halogen or other good leaving group (for example, reaction of B2 with N-chlorosuccinimide or N-bromosuccinimide in warm carbon tetrachloride). Reaction of the intermediate B3 with a phenol or thiophenol or with a suitably substituted aniline in the presence of a suitable base leads to the intermediates A1j. If Y1 is sulfur, it can be oxidized with a suitable oxidant (e.g. mCPBA, peroxyacetic acid or peroxytrifluoroacetic acid) to give the corresponding sulfoxide or sulfone. Further conversion to the corresponding carboxylic acids A1 (Y1=O, S, SO$_2$) can be performed by selective removal of the protecting group Ra as discussed above.

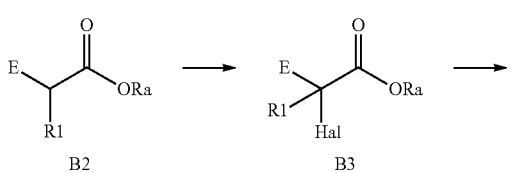

A method for the synthesis of precursors with the general structure A1r involves an adaptation of the Petasis boronic acid Mannich reaction (Kurti, L., Czako, B. *Strategic Applications of Named Reactions in Organic Synthesis*, Elsvier, 2005, 340-342; Petasis, N. A., Akritopoulou, I. *Tetrahedron Lett.* 1993, 34, 583-586). In this case, a boronic acid E-B(OH)$_2$, a functionalized aniline and glyoxylic acid are mixed in equimolar ratios in dichloromethane, resulting in the formation of precursors A1r.

An alternative route to A1j where Y1 is nitrogen involves the reductive amination of an α-ketoester with a suitably substituted aniline. On the other hand, if the 'Hal' group in B3 is hydroxyl, a Mitsunobu coupling reaction can be used to generate the intermediate A1j where Y1 is oxygen or sulfur.

The methods shown in the schemes above can be modified to allow access to compounds where X is different from a 2,4-disubstituted phenyl. For example reaction of B2 (R1=H) with an aldehyde can lead to compound A1m, where the X group can be a substituted cycloalkyl, cycloalkenyl, heteroary, alkynyl or alkenyl group. In a similar fashion, reaction of B2 with a halogenated precursor can lead to an analog A1k. Further modifications of these intermediates as illustrated above could lead to compounds of the invention.

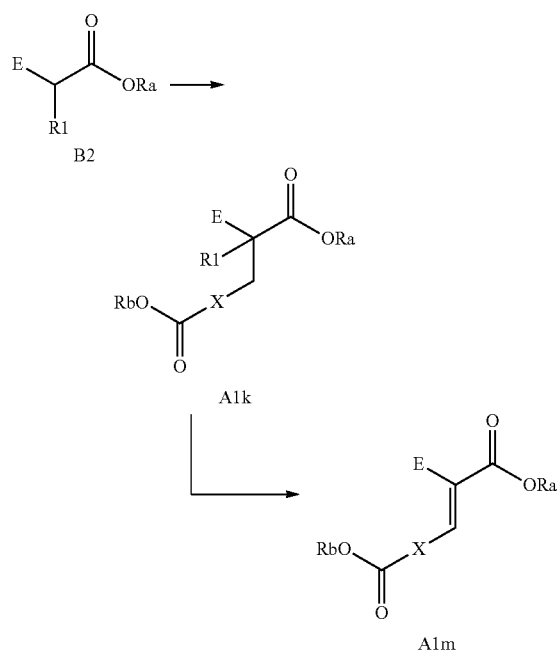

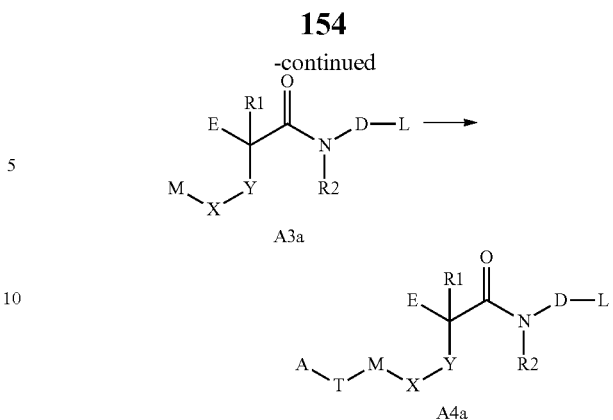

A route to the synthesis of the isoxazole core is exemplified in the sequence below. The carboxylate A1 can be converted to the aldehyde A2b by methods known in the literature, including methods where the carboxylate is reduced to the alcohol stage followed by reoxidation to the aldehyde. The resulting aldehyde A2b is converted into the chloro-oxime A3b by a two-step sequence: (i) oxime formation (e.g. treatment with hydroxylamine hydrochloride in the presence of sodium acetate or other suitable base followed by) (ii) chlorination of the oxime (for example, using N-chlorosuccinimide in a suitable solvent such as DMF). A [3+2] cycloaddition reaction of A3 with substituted terminal acetylene derivatives (Yao et al, Tetrahedron 1998, 54(5/6), 791-822,) leads to isoxazoles with the general structure A4b.

At this stage modification can be made on D, in order to reach the desired pattern of substitution on this fragment as illustrated in the Examples. Modification on the fragment M leads to generation of compounds of Formula I as will be described below.

A method that can be used to synthesize compounds of formula I (where Z is —C(O)NR²—) is exemplified below. The carboxylic acids A1 are converted to the corresponding amides by methods known for amide bond formation reactions. As an example, generation of an acid chloride A2a from A1 takes place under standard conditions (e.g. thionyl chloride in toluene or oxalyl chloride and catalytic DMF in dichloromethane). Treatment of acid chloride A2a with amines or anilines generates the desired amides A3a. Alternatively, amines can be directly coupled with the carboxylic acid A1 by use of an activating agent (for example, DCC or EDCI with or without a catalyst such as DMAP) to generate the amides A3a. When D is an aromatic group, then aryl amides A3a with an appropriate substituent (e.g. a halo group such as bromo or iodo group on the aryl ring D) can be further functionalized through metal-mediated (e.g. Palladium) C—C bond coupling reactions to give further functionalized amides A3a. Hydrolysis of the ester group of A3a (e.g. M=—CO₂CH₃) results in a carboxylic acid A3a (wherein M=—CO₂H), which can then be coupled with taurine or amine containing carboxylic acids or aminoalkyl phosph(i/o)nic acids using standard amide bond forming reactions to generate the targeted compounds A4a (M=—NHCO—).

The amide bond in the last step can also be formed by other reported methods known for amide bond formation, for example, reaction of an N-hydroxysuccinimidyl ester and taurine gives the target taurine amide derivative A4a. Other activated esters (e.g. pentafluorophenyl esters) can also be used to effect the amide bond formation.

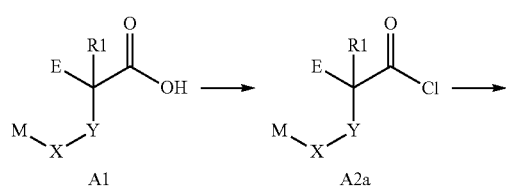

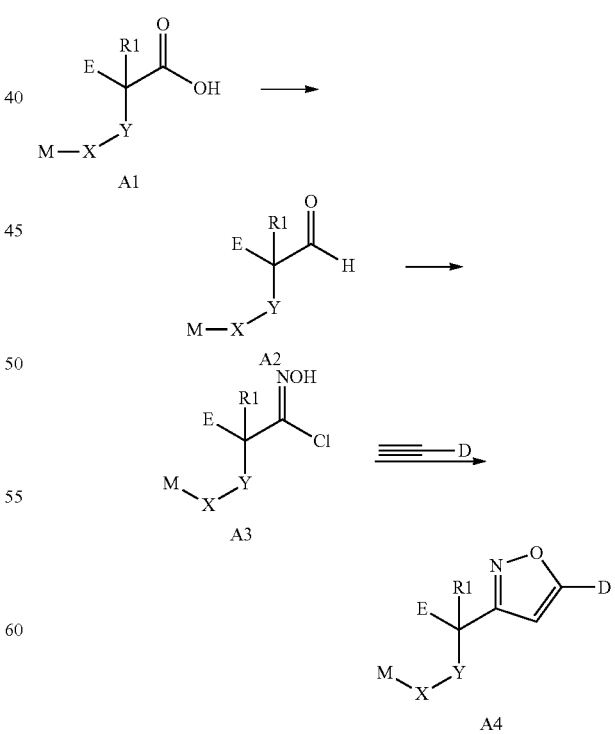

Another potential approach to the construction of the isoxazole core starts with reaction of the ketone A5 (which can be generated from the carboxylic acid A1 or a synthetic equivalent) with hydroxylamine hydrochloride or an O-protected hydroxylamine derivative in the presence of a suitable base. Deprotonation of the resulting oxime derivative A6 and reaction with a precursor D1 (Singh et al, Chem. Pharm. Bull. 1999, 47(10), 1501-1505) (wherein LG is a leaving group such as —OEt, —NMe(OMe), —Cl, etc.) will lead to an intermediate A7 which cyclizes spontaneously or under dehydrating conditions to generate A4b.

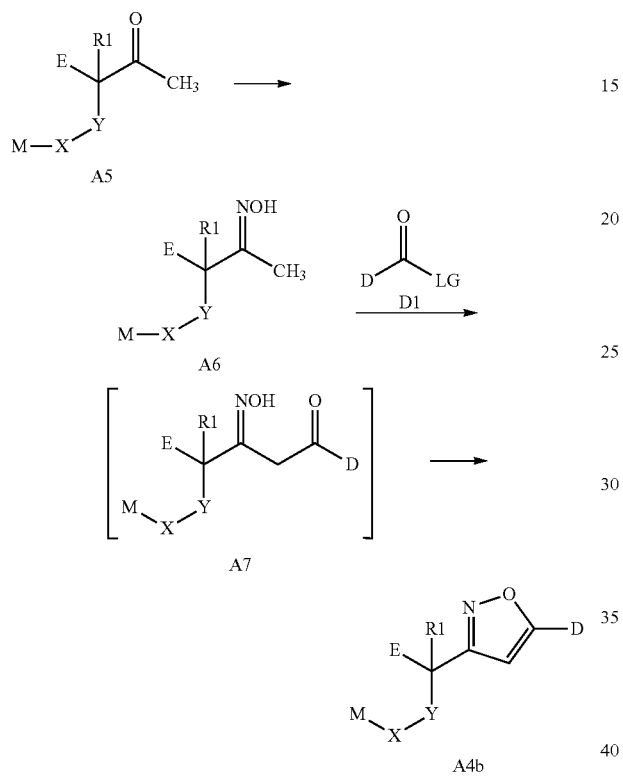

The synthesis of isoxazoles can also take place from nitro compounds A8, which undergo [3+2] cycloaddition reactions with acetylene derivatives (Cereda et al, Tetrahedron Lett. 2001, 42(30) 4951) to generate isoxazoles A4b.

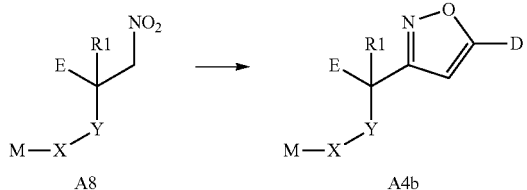

In another route, the precursor A3 can be reacted with 1-tributylstannylacetylene (Lee et al, Bioorg. Med. Chem. Lett. 2003, 13(22) 4117-4120) to generate an intermediate A9. This stannane can be coupled with an aryl halide or triflate in the presence of a metal catalyst to generate a precursor A4b. Alternatively, iodination of A9 generates A10, which can then be coupled with a metallated precursor D-Met to generate A4b. In this case, Met is a metal such as MgBr, MgCl, MgI, Sn(n-Bu)$_3$, ZnCl, B(OH)$_2$, etc.

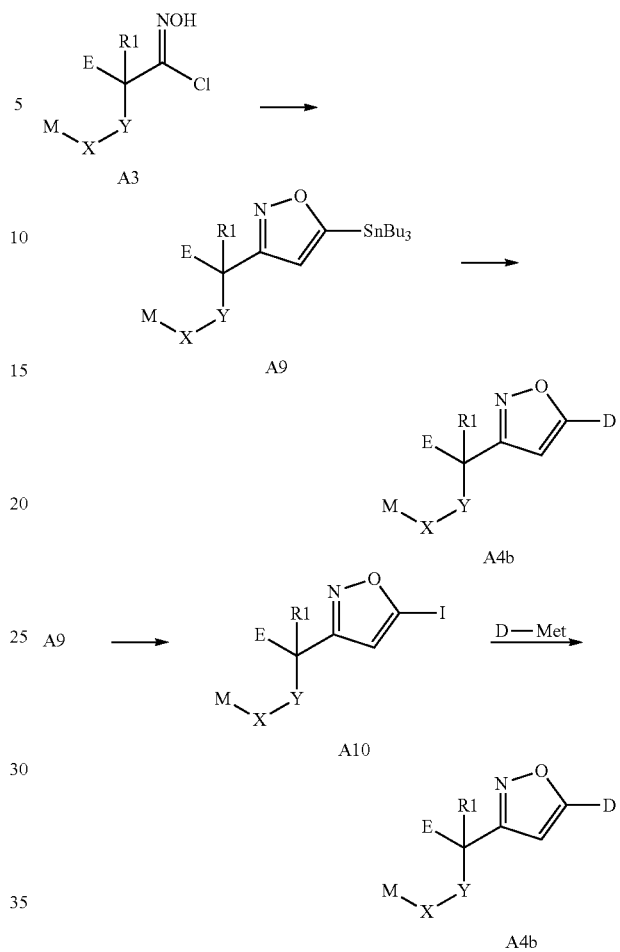

Modifications of the substituents at the 3-position of an isoxazole intermediate are also envisioned to give the desired compounds. For example, the commercially available chloro-oxime A11 can undergo a [3+2] cycloaddition reaction with an alkyne to generate the intermediate A12. The ester in A12 or a synthetic equivalent accessible from it such as an acid chloride, activated ester or an amide, can be used in reactions with organometallic reagents E-Met to generate ketones A13. In this case, Met is a metal such as Li, MgBr, MgCl, MgI, Sn(n-Bu)$_3$, ZnCl, etc. and E is aryl, alkyl or cycloalkyl, cycloalkenyl, heteroaryl, etc as defined above.

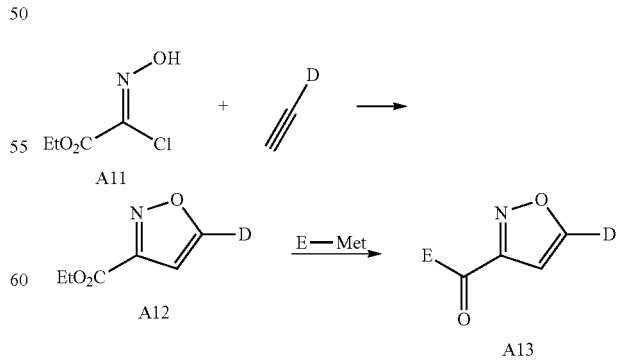

The intermediate ketones A13 can be the starting materials for multiple transformations. For example, the addition of organometallic reagents R1-Met to A13 results in the generation of alcohols A14. In this case, Met is a metal such as Li, MgBr, MgCl, MgI, Sn(n-Bu)$_3$, ZnCl, etc. The intermediate alcohol A14 can in turn be converted into halo-substituted A15 (wherein Hal is F, Cl, Br, I, OSO$_2$aryl, OSO$_2$CF$_3$ or other suitable leaving group). Reduction of the keto group in A13 to the methylene-containing A16 can be carried out using conventional chemistry, which provides a precursor for A17. A13 can also be a substrate for olefination reactions leading to intermediates A18 that can be further modified to give A19.

2004, pp 276-282). Amino alcohols with appropriate substituents can be protected with a group such as CO$_2$CH$_2$Ph to yield intermediates like T2, as exemplified below. The resulting alcohol is then treated with thioacetic acid under Mitsunobu conditions (e.g. triphenyl phosphine and diethylazodicarboxylate) in a solvent such as THF to generate a thioacetate ester T3. Oxidation to the sulfonic acid with hydrogen peroxide in formic acid leads to the aminosulfonic acid T4. These aminosulfonic acid fragments can be coupled

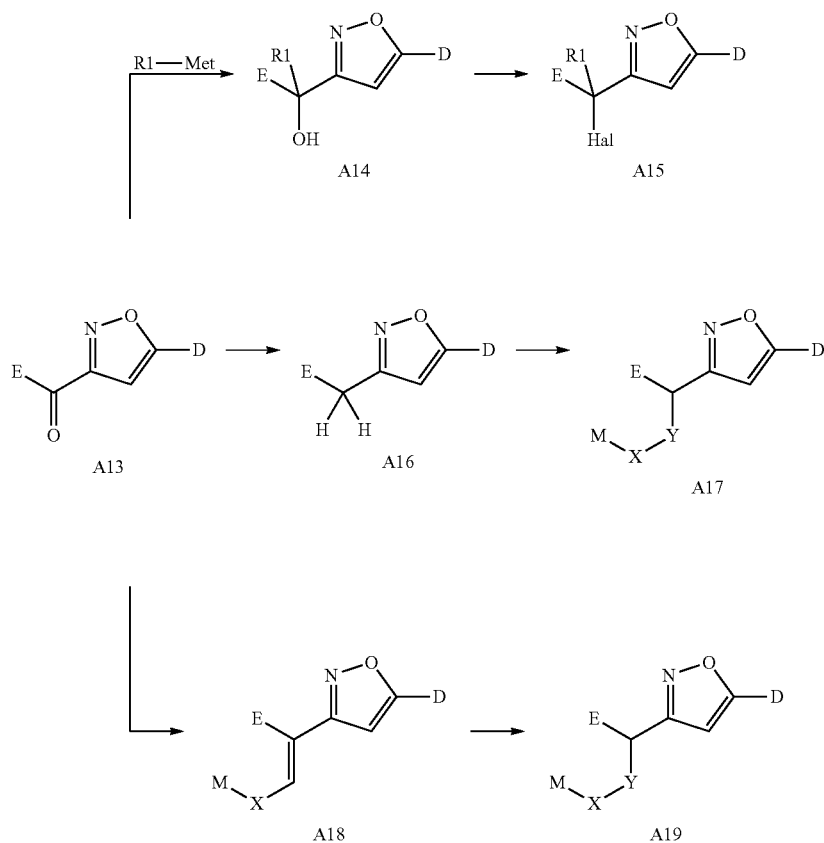

Similar methods can be used for the synthesis of analogs where Y is O, N, etc as described above.

The desired A-T-M fragments can be introduced at various points of the synthesis as a preformed unit. Alternatively, modifications of a precursor intermediate at the A-T-M region can also lead to the desired A-T-M configurations. To provide examples, the following section describes some of the many viable synthetic routes for the modification of the A-T-M fragments, which can either be used to prepare the desired A-T-M fragments to be incorporated into a synthetic route at various points or to modify a precursor intermediate.

Examples for the A-T-M fragments include amino sulfonic acids, aminophosphonic acids and aminophosphinic acids. Many synthetic routes to these compounds can be envisioned and a few examples are discussed in the following section.

Taurine analogs can be synthesized from aminoalcohols using existing methods (for example: Xu and Xu, Synthesis with carboxylic acids directly under usual conditions (e.g. DCC, EDCI, etc.) or reacted with suitably activated carboxylic acid derivatives (e.g. pentafluorophenol esters, N-hydroxylsuccimide esters) to generate the target compounds T7.

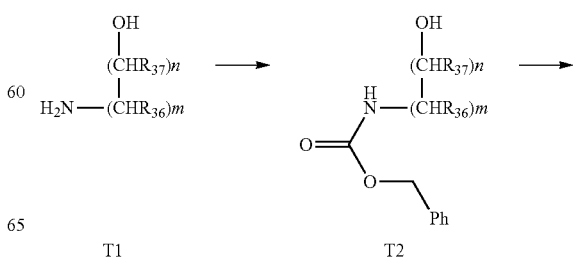

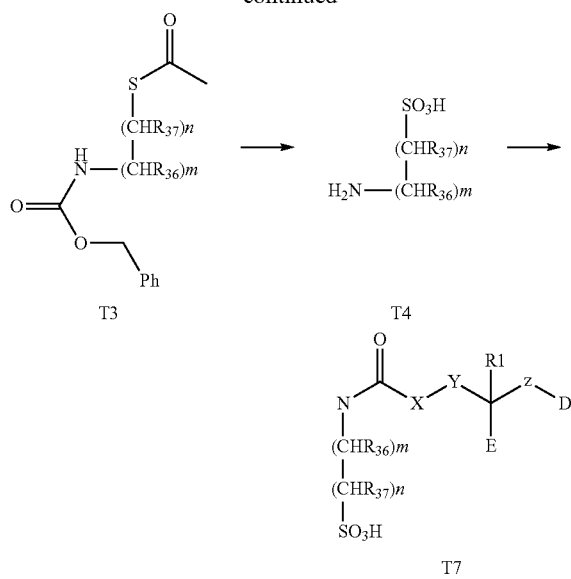

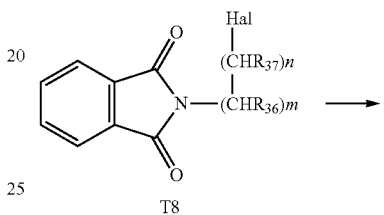

In an alternative route, the amino alcohols T1 can be coupled with a carboxylic acid precursor to give compounds of formula T5 and the alcohol group in T5 can then be converted into a sulfonic acid T7 by a sequence similar to the one shown above:

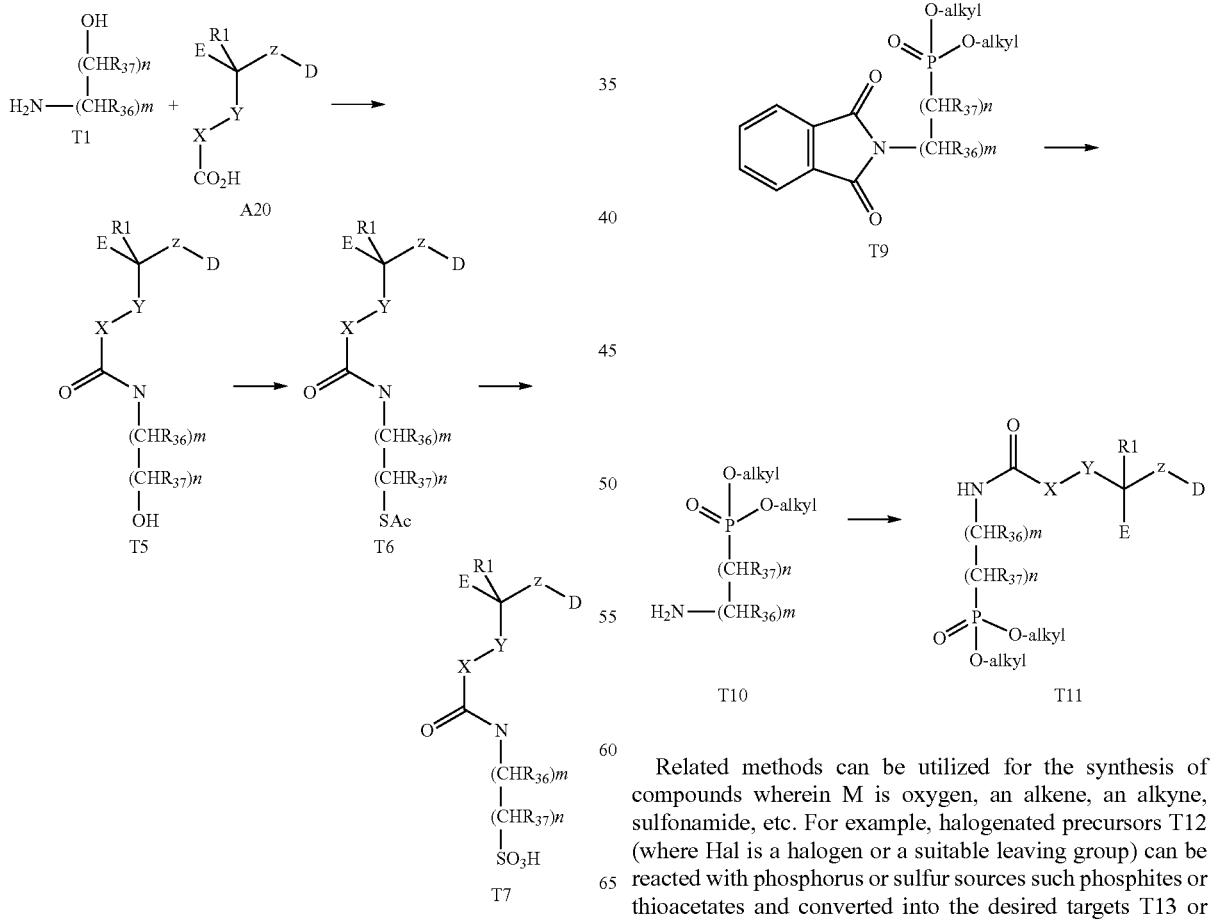

Aminophosphonic and aminophosphinic acids can be prepared by known methods. As shown below, Arbuzov reaction of suitably protected haloalkyl amines T8 with a phosphite (e.g. (alkylO)$_3$P) or a hydrogen phosphonate (e.g. (alkylO)$_2$POH) or an equivalent reagent results in the formation of a phosphonate ester T9. The amine protecting group is then selectively removed and the resulting aminophosphonate T10 is coupled with a carboxylic acid to generate a protected version of the target compound T11. Removal of the alkyl groups of the phosphonate ester is achieved under well known conditions (e.g. reaction with bromo- or iodo-trimethylsilane in a suitable solvent such as dichloromethane). A similar sequence can be employed for the synthesis of aminophosphinic acids, except that (alkyl)P(O-alkyl')$_2$ is used in the initial Arbuzov reaction.

Related methods can be utilized for the synthesis of compounds wherein M is oxygen, an alkene, an alkyne, sulfonamide, etc. For example, halogenated precursors T12 (where Hal is a halogen or a suitable leaving group) can be reacted with phosphorus or sulfur sources such phosphites or thioacetates and converted into the desired targets T13 or T14 by methods similar to those described above.

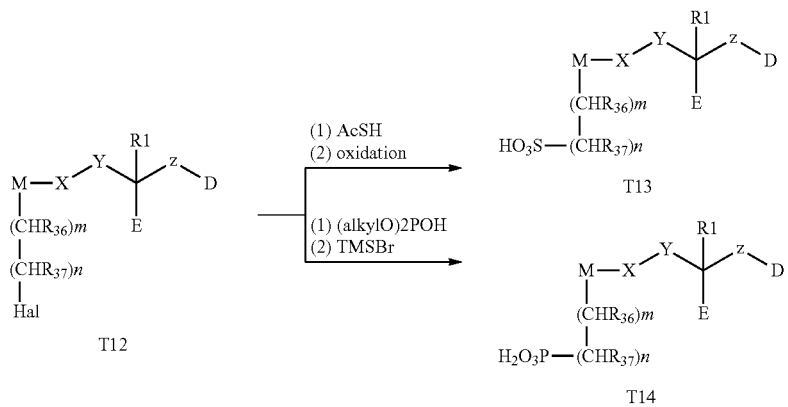

In the route below, the amino group attached to X is functionalized to generate a derivative T16 where M₃ is a carbonyl or an SO₂ group and Hal is a halogen or other suitable leaving group. Replacement of this halogen by a phosphonate, phosphinate or sulfonate following the methods described earlier will give compounds wherein A is a phosphonate, phosphinate or a sulfonate group.

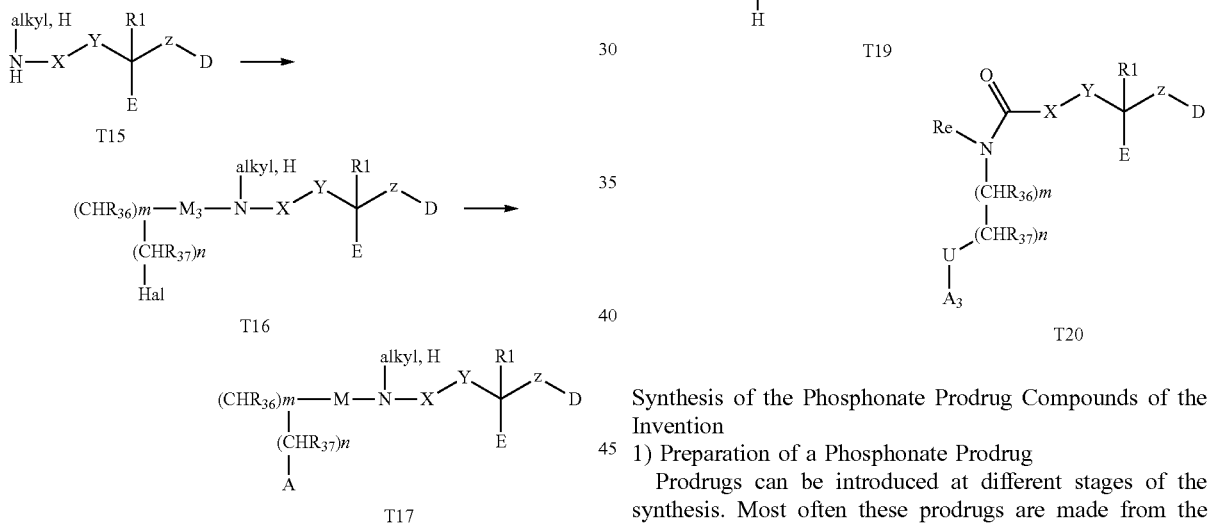

The reaction of diamines or amino alcohols with carboxylic acids T18 (or activated esters derived from it) generates amides T19, wherein Re is hydrogen or $C_{1-6}$ alkyl and U is oxygen or NRg, where Rg is hydrogen or $C_{1-6}$ alkyl. Conversion of T19 into the corresponding sulfamates or sulfates T20 ($A_3$=HO₃S—) can take place by reaction with PhOSO₂Cl in a suitable solvent such as dichloromethane and in the presence of a suitable base such as triethylamine, followed by hydrolysis.

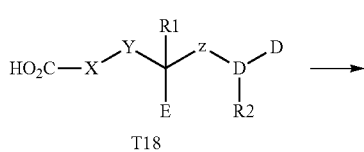

Synthesis of the Phosphonate Prodrug Compounds of the Invention

1) Preparation of a Phosphonate Prodrug

Prodrugs can be introduced at different stages of the synthesis. Most often these prodrugs are made from the phosphonic acids of Formula I because of their lability.

Phosphonic acids of Formula I can be alkylated with electrophiles such as alkyl halides and alkyl sulfonates under nucleophilic substitution conditions to give phosphonate esters. For example, compounds of Formula I wherein $GR^{21}$ is an acyloxyalkyl group can be prepared by direct alkylation of compounds of Formula I with an appropriate acyloxyalkyl halide (e.g., Cl, Br, I; *Phosphorus Sulfur* 54:143 (1990); *Synthesis* 62 (1988)) in the presence of a suitable base (e.g., pyridine, TEA, diisopropylethylamine) in suitable solvents such as DMF (*J. Med. Chem.* 37:1875 (1994)). The carboxylate component of these acyloxyalkyl halides includes but is not limited to acetate, propionate, isobutyrate, pivalate, benzoate, carbonate and other carboxylates. Dimethylformamide dialkyl acetals can also be used for the alkylation of phosphonic acids (*Collect. Czech Chem. Commu.* 59:1853 (1994)). Compounds of Formula I wherein $GR^{21}$ is a cyclic carbonate, a lactone or a phthalidyl group can also be synthesized by direct alkylation of the free phosphonic acids with appropriate halides in the presence of a suitable base such as NaH or diisopropylethylamine (*J. Med. Chem.* 38:1372 (1995); *J. Med. Chem.* 37:1857 (1994); *J. Pharm. Sci.* 76:180 (1987)).

Alternatively, these phosphonate prodrugs can be synthesized by the reactions of the corresponding dichlorophosphonates and an alcohol (*Collect Czech Chem. Commun.* 59:1853 (1994)). For example, a dichlorophosphonate is reacted with substituted phenols and arylalkyl alcohols in the presence of a base such as pyridine or TEA to give the compounds of Formula I wherein $GR^{21}$ is an aryl group (*J. Med. Chem.* 39:4109 (1996); *J. Med. Chem.* 38:1372 (1995); *J. Med. Chem.* 37:498 (1994)) or an arylalkyl group (*J. Chem. Soc. Perkin Trans.* 1 38:2345 (1992)). The disulfide-containing prodrugs (*Antiviral Res.* 22:155 (1993)) can be prepared from a dichlorophosphonate and 2-hydroxyethyl-disulfide under standard conditions. Dichlorophosphonates are also useful for the preparation of various phosphonamides as prodrugs. For example, treatment of a dichlorophosphonate with ammonia gives both a monophosphonamide and a diphosphonamide; treatment of a dichlorophosphonate with 1-amino-3-propanol gives a cyclic 1,3-propylphosphonamide; treatment of a chlorophosphonate monophenyl ester with an amino acid ester in the presence of a suitable base gives a substituted monophenyl monophosphonamidate.

Such reactive dichlorophosphonates can be generated from the corresponding phosphonic acids with a chlorinating agent (e.g., thionyl chloride, *J. Med. Chem.* 1857 (1994); oxalyl chloride, *Tetrahedron Lett.* 31:3261 (1990); phosphorous pentachloride, *Synthesis* 490 (1974)). Alternatively, a dichlorophosphonate can be generated from its corresponding disilyl phosphonate esters (*Synth. Commu.* 17:1071 (1987)) or dialkyl phosphonate esters (*Tetrahedron Lett.* 24:4405 (1983); *Bull. Soc. Chim.* 130:485 (1993)).

The compounds of Formula I can be mixed phosphonate ester (e.g., phenyl and benzyl esters, or phenyl and acyloxyalkyl esters) including the chemically combined mixed esters such as phenyl and benzyl combined prodrugs reported in *Bioorg. Med. Chem. Lett.* 7:99 (1997).

Dichlorophosphonates are also useful for the preparation of various phosphonamides as prodrugs. For example, treatment of a dichlorophosphonate with an amine (e.g. an amino acid alkyl ester such as L-alanine ethyl ester) in the presence of a suitable base (e.g. triethylamine, pyridine, etc.) gives the corresponding bisphosphonamide; treatment of a dichlorophosphonate with 1-amino-3-propanol gives a cyclic 1,3-propylphosphonamide; treatment of a chlorophosphonate monophenyl ester with an amino acid ester in the presence of a suitable base gives a substituted monophenyl monophosphonamidate. Direct couplings of a phosphonic acid with an amine (e.g. an amino acid alkyl ester such as L-alanine ethyl ester) are also reported to give the corresponding bisamidates under Mukaiyama conditions (*J. Am. Chem. Soc.*, 94:8528 (1972)).

The SATE (S-acetyl thioethyl) prodrugs can be synthesized by the coupling reaction of the phosphonic acids of Formula I and S-acyl-2-thioethanol in the presence of DCC, EDCI or PyBOP (*J. Med. Chem.* 39:1981 (1996)).

Cyclic phosphonate esters of substituted 1,3-propane diols can be synthesized by either reactions of the corresponding dichlorophosphonate with a substituted 1,3-propanediol or coupling reactions using suitable coupling reagents (e.g., DCC, EDCI, PyBOP; *Synthesis* 62 (1988)). The reactive dichlorophosphonate intermediates can be prepared from the corresponding acids and chlorinating agents such as thionyl chloride (*J. Med. Chem.* 1857 (1994)), oxalyl chloride (*Tetrahedron Lett.* 31:3261 (1990)) and phosphorus pentachloride (*Synthesis* 490 (1974)). Alternatively, these dichlorophosphonates can also be generated from disilyl esters (*Synth. Commun.* 17:1071 (1987)) and dialkyl esters (*Tetrahedron Lett.* 24:4405 (1983); *Bull. Soc. Chim. Fr.,* 130:485 (1993)).

Alternatively, these cyclic phosphonate esters of substituted 1,3-propane diols are prepared from phosphonic acids by coupling with diols under Mitsunobu reaction conditions (*Synthesis* 1 (1981); *J. Org. Chem.* 52:6331 (1992)), and other acid coupling reagents including, but not limited to, carbodiimides (*Collect. Czech. Chem. Commun.* 59:1853 (1994); *Bioorg. Med. Chem. Lett.* 2:145 (1992); *Tetrahedron Lett.* 29:1189 (1988)), and benzotriazolyloxytris-(dimethylamino) phosphonium salts (*Tetrahedron Lett.* 34:6743 (1993)).

Phosphonic acids also undergo cyclic prodrug formation with cyclic acetals or cyclic ortho esters of substituted propane-1,3-diols to provide prodrugs as in the case of carboxylic acid esters (*Helv. Chim. Acta.* 48:1746 (1965)). Alternatively, more reactive cyclic sulfites or sulfates are also suitable coupling precursors to react with phosphonic acid salts. These precursors can be made from the corresponding diols as described in the literature.

Alternatively, cyclic phosphonate esters of substituted 1,3-propane diols can be synthesized by trans esterification reaction with substituted 1,3-propane diol under suitable conditions. Mixed anhydrides of parent phosphonic acids generated in situ under appropriate conditions react with diols to give prodrugs as in the case of carboxylic acid esters (*Bull. Chem. Soc. Jpn.* 52:1989 (1979)). Aryl esters of phosphonates are also known to undergo transesterification with alkoxy intermediates (*Tetrahedron Lett.* 38:2597 (1997); *Synthesis* 968 (1993)).

One aspect of the present invention provides methods to synthesize and isolate single isomers of prodrugs of phosphonic acids of Formula 1. Because phosphorus is a stereogenic atom, formation of a prodrug with a substituted-1,3-propane-diol will produce a mixture of isomers. For example, formation of a prodrug with a racemic 1-(V)-substituted-1,3-propane diol gives a racemic mixture of cis-prodrugs and a racemic mixture of trans-prodrugs. In an other aspect, the use of the enantioenriched substituted-1,3-propane diol with the R-configuration gives enantioenriched R-cis- and R-trans-prodrugs. These compounds can be separated by a combination of column chromatography and/or fractional crystallization.

The compounds of Formula I can be mixed phosphonate esters (e.g. phenyl benzyl phosphonate esters, phenyl acyloxyalkyl phosphonate esters, phenyl aminoacid esters etc). For example, the chemically combined phenyl-benzyl prodrugs are reported by Meier, et al. *Bioorg. Med. Chem. Lett.,* 1997, 7: 99.

The substituted cyclic propyl phosphonate esters of Formula I, can be synthesized by reaction of the corresponding dichlorophosphonate and the substituted 1,3-propane diol. The following are non-limiting methods to prepare the substituted 1,3-propane diols.

Synthesis of the 1,3-Propane Diols Used in the Preparation of Certain Prodrugs

The discussion of this step includes various synthetic methods for the preparation of the following types of propane-1,3-diols: i) 1-substituted; ii) 2-substituted; and iii) 1,2- or 1,3-annulated. Different groups on the prodrug part of the molecule i.e., on the propane diol moiety can be introduced or modified either during the synthesis of the diols or after the synthesis of the prodrugs.

i) 1-Substituted 1,3-Propane Diols

Propane-1,3-diols can be synthesized by several well known methods in the literature. Aryl Grignard additions to 1-hydroxypropan-3-al gives 1-aryl-substituted propane-1,3-diols (path a). This method will enable conversion of various substituted aryl halides to 1-arylsubstituted-1,3-propane diols (Coppi, et. al., *J. Org. Chem.*, 1988, 53, 911). Aryl halides can also be used to synthesize 1-substituted propanediols by Heck coupling of 1,3-diox-4-ene followed by reduction and hydrolysis (Sakamoto, et. al., *Tetrahedron Lett.*, 1992, 33, 6845). A variety of aromatic aldehydes can be converted to I-substituted-1,3-propane diols by vinyl Grignard addition followed by hydroboration (path b). Substituted aromatic aldehydes are also useful for lithium-t-butylacetate addition followed by ester reduction (path e) (Turner., *J. Org. Chem.*, 1990, 55 4744). In another method, commercially available cinnamyl alcohols can be converted to epoxy alcohols under catalytic asymmetric epoxidation conditions. These epoxy alcohols are reduced by Red-Al to result in enantiomerically pure propane-1,3-diols (path c). Alternatively, enantiomerically pure 1,3-diols can be obtained by chiral borane reduction of hydroxyethyl aryl ketone derivatives (Ramachandran, et. al., *Tetrahedron Lett.*, 1997, 38 761). Pyridyl, quinoline, and isoquinoline propan-3-ol derivatives can be oxygenated to 1-substituted propan-1,3-diols by N-oxide formation followed by rearrangement under acetic anhydride conditions (path d) (Yamamoto, et. al., *Tetrahedron*, 1981, 37, 1871).

diol. Triethyl methanetricarboxylate can be converted to the triol by complete reduction (path a) or diol-monocarboxylic acid derivatives can be obtained by partial hydrolysis and diester reduction (Larock, *Comprehensive Organic Transformations*, VCH, New York, 1989). Nitrotriol is also known to give the triol by reductive elimination (path b) (Latour, et. al., *Synthesis,* 1987, 8, 742). The triol can be derivatized as a mono acetate or carbonate by treatment with alkanoyl chloride, or alkylchloroformate, respectively (path d) (Greene and Wuts, *Protective Groups in Organic Synthesis*, John Wiley, New York, 1990). Aryl substitution effected by oxidation to the aldehyde followed by aryl Grignard additions (path c) and the aldehyde can also be converted to substituted amines by reductive amination reactions (path e).

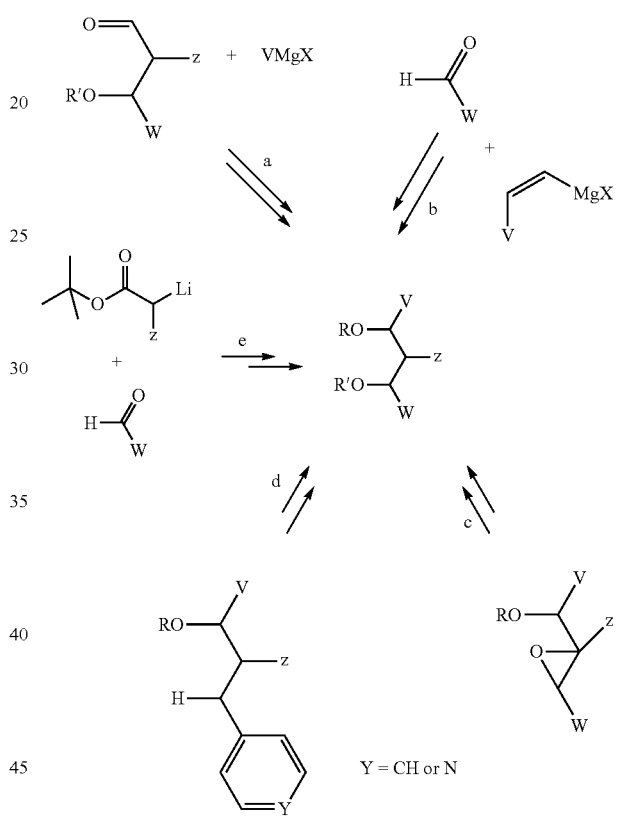

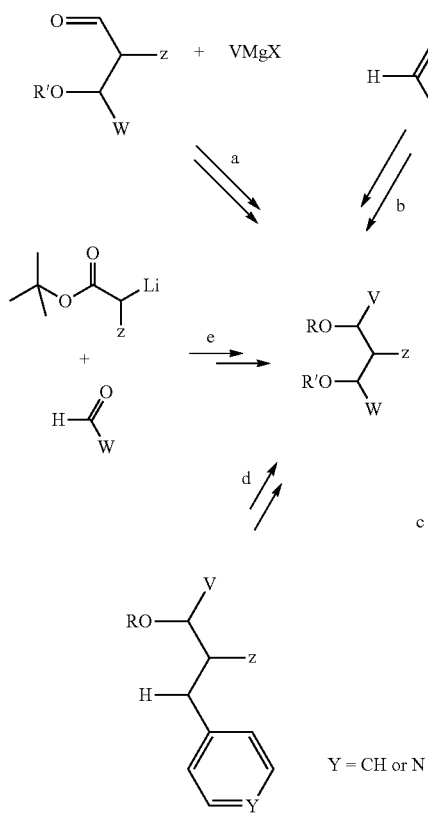

ii) 2-Substituted 1,3-Propane Diols:

Various 2-substituted propane-1,3-diols can be made from commercially available 2-(hydroxymethyl)-1,3-propane iii) Annulated 1,3-Propane Diols:

Prodrugs of Formula I where V-Z or V-W are fused by three carbons are made from cyclohexane diol derivatives. Commercially available cis, cis-1,3,5-cyclohexane triol can be used for prodrug formation. This cyclohexanetriol can also be modified as described in the case of 2-substituted propan-1,3-diols to give various analogues. These modifications can either be made before or after formation of prodrugs. Various 1,3-cyclohexane diols can be made by Diels-Alder methodology using pyrone as the diene (Posner, et. al., *Tetrahedron Lett.,* 1991, 32, 5295). Cyclohexyl diol derivatives are also made by nitrile oxide olefin-additions (Curran, et. al., *J. Am. Chem. Soc.,* 1985, 107, 6023). Alternatively, cyclohexyl precursors can be made from quinic acid (Rao, et. al., *Tetrahedron Lett.,* 1991, 32, 547.)

2) Phosphonate Deprotection

Select compounds may be prepared from phosphonate esters using known phosphate and phosphonate ester cleavage conditions. In general, silyl halides have been used to cleave the various phosphonate esters, followed by mild hydrolysis of the resulting silyl phosphonate esters to give the desired phosphonic acids. Depending on the stability of the products, these reactions are usually accomplished in the presence of acid scavengers such as 1,1,1,3,3,3-hexamethyldisilazane, 2,6-lutidine, etc. Such silyl halides include, chlorotrimethylsilane (Rabinowitz, *J. Org. Chem.*, 1963, 28: 2975), bromotrimethylsilane (McKenna, et al, *Tetrahedron Lett.*, 1977, 155), iodotrimethylsilane (Blackburn, et al, *J. Chem. Soc., Chem. Commun.*, 1978, 870). Alternately, phosphonate esters can be cleaved under strong acid conditions, (e.g HBr, HCl, etc.) in polar solvents, preferably acetic acid (Moffatt, et al, U.S. Pat. No. 3,524,846, 1970) or water. These esters can also be cleaved via dichlorophosphonates, prepared by treating the esters with halogenating agents e.g. phosphorus pentachloride, thionyl chloride, $BBr_3$, etc. (Pelchowicz, et al, *J. Chem. Soc.*, 1961, 238) followed by aqueous hydrolysis to give phosphonic acids. Aryl and benzyl phosphonate esters can be cleaved under hydrogenolysis conditions (Lejczak, et al, *Synthesis*, 1982, 412; Elliott, et al, *J. Med. Chem.*, 1985, 28: 1208; Baddiley, et al, *Nature*, 1953, 171: 76) or dissolving metal reduction conditions (Shafer, et al, *J. Am. Chem. Soc.*, 1977, 99: 5118). Electrochemical (Shono, et al, *J. Org. Chem.*, 1979, 44: 4508) and pyrolysis (Gupta, et al, *Synth. Commun.*, 1980, 10: 299) conditions have also been used to cleave various phosphonate esters.

The following examples are provided so that the invention can be more fully understood. They should not be construed as limiting the invention in any way Example 1.001

Sodium: 2-{4-[2-(4-tert-butyl-phenyl)-2-(2',4'-dichloro-biphenyl-4-yl -carbamoyl)-ethyl]-benzoylamino}-ethanesulfonate Step A Thionyl chloride (1.8 mL) was added to 3.137 g of the starting carboxylic acid (prepared as reported in Bioorg. Med. Chem Lett. 2004, 14, 2047-2050) in 25 mL of toluene and the reaction mixture was heated to reflux for a period of 1 h. The volatiles were removed under reduced pressure. The crude acid chloride, obtained as a yellow oil, was used immediately.

A sample of 1.672 g of the above acid chloride in toluene (25 mL) was treated with 4-iodoaniline (1.547 g) and N,N-diisopropyl-ethylamine (1.54 mL). The resulting mixture was heated at 100° C. for 2 h, cooled to room temperature and diluted with ethyl acetate. The organic phase was washed with 1M aqueous hydrochloric acid and saturated sodium chloride. After drying over magnesium sulfate and chromatography on silica gel (ethyl acetate-hexanes gradient) obtained the iodoanilide (1.179 g)

LCMS (m/z): 542.6 $(M+H)^+$

Step B

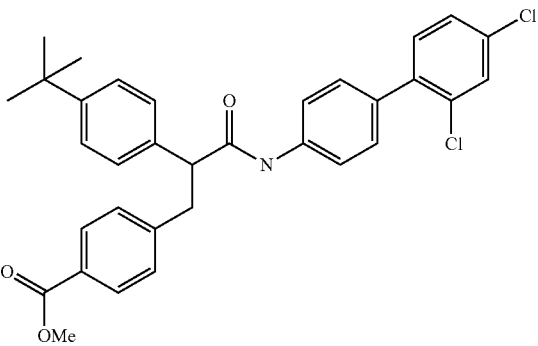 [SMILES: COC(=O)c1ccc(CC(C(=O)Nc2ccc(-c3ccc(Cl)cc3Cl)cc2)c2ccc(C(C)(C)C)cc2)cc1]

A mixture of the aryl iodide from Step A above (659 mg) in THF:ethanol:water (6 mL:3 mL:2 mL) was placed in a glass vial and treated with 2,4-dichlorophenyl boronic acid (1.137 g), 96 mg of palladium dichloride bis(tri(o-tolyl) phosphine) and sodium carbonate (659 mg). The flask was sealed and the reaction mixture was heated in a microwave reactor at 125° C. for a period of 6 min. To the resulting mixture added an excess of 1M aqueous hydrochloric acid and ethyl acetate. The heterogeneous mixture was filtered through a pad of celite. The organic phase was separated, washed with water and saturated sodium chloride and dried over magnesium sulfate. Chromatography on silica gel using an ethyl acetate-hexanes gradient afforded the biphenylamide (442 mg)

LCMS (m/z): 560.4 $(M+H)^+$

Step C

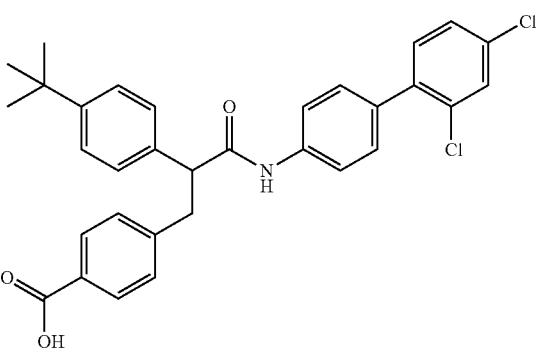 [SMILES: CC(C)(C)c1ccc(C(Cc2ccc(C(=O)O)cc2)C(=O)Nc2ccc(-c3ccc(Cl)cc3Cl)cc2)cc1]

To a solution of the methyl ester obtained in Step B above (442 mg) in THF:methanol:water (30 mL:20 mL:10 mL) was added sodium hydroxide (347 mg) and the reaction stirred at room temperature for a 15 h period. The THF and methanol were removed under reduced pressure. The residue was treated with an excess of 1M aqueous HCl and extracted with ethyl acetate. The organic phase was washed (water, saturated sodium chloride), dried over magnesium sulfate and concentrated to leave the crude carboxylic acid that was used without further purification in the following step.

LCMS (m/z): 546.6 $(M+H)^+$

Step D

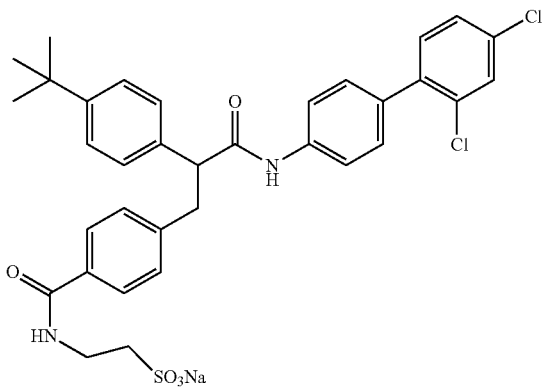

To the crude carboxylic acid derived from 442 mg of the corresponding methyl ester (Step C, above) in DMF (5 mL) added HOBt-H$_2$O (130 mg), EDCI (183 mg), taurine (129 mg) and N,N-diisopropyl ethylamine (0.194 mL). The reaction mixture was stirred at room temperature for 21 h. Added a solution of sodium carbonate (541 mg in water and loaded the crude mixture on top of a reverse phase (C18) silica gel column. The column was eluted with a gradient of acetonitrile and water. The product-containing fractions were concentrated and coevaporated with a mixture of acetonitrile and toluene. The title compound was obtained as a white solid.

LCMS: (m/z): 653.6 (M+H)$^+$. Elemental Analysis calculated for C34H35N2O5Cl2SNa+4H2O: C: 54.62, H: 5.53, N: 3.75. Found: C:54.38, H: 5.28, N: 3.77.

Example 1.002

Sodium: 2-{4-[2-(4-benzofuran-2-yl-phenylcarbamoyl)-2-(4-tert-butyl-phenyl-ethyl]-benzoylamino}-ethanesulfonate

Step A

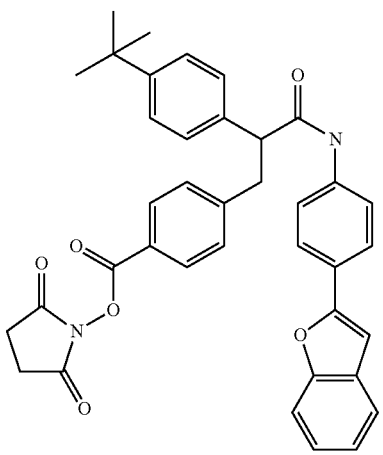 [SMILES: CC(C)(C)c1ccc(C(Cc2ccc(C(=O)ON3C(=O)CCC3=O)cc2)C(=O)Nc2ccc(-c3cc4ccccc4o3)cc2)cc1]

A mixture of 200 mg of 4-[2-(4-Benzofuran-2-yl-phenylcarbamoyl)-2-(4-tert-butyl-phenyl)-ethyl]-benzoic acid (prepared as in Example 1.001, Steps A-C, except that benzofuran-2-yl boronic acid was used instead of 2,4-dichlorophenyl boronic acid in Step B), 65 mg of N-hydroxysuccinimide and 91 mg of DCC was stirred in THF at room temperature for a 16 h period. The white precipitate formed was removed by filtration and rinsed with THF. The filtrate was concentrated and chromatographed on silica gel using an ethyl acetate-hexanes mixture. The product N-hydroxysuccinyl ester was obtained as a white foam (230 mg)

$^1$H NMR (DMSO-d6): δ 10.28 (1H, s), 7.98-8.00 (2H, d, J=8.2 Hz), 7.80-7.83 (2H, d, J=8.8 Hz), 7.65-7.68 (2H, d, J=8.8 Hz), 7.59-7.63 (2H, m), 7.51-7.53 (2H, d, J=8.5 Hz), 7.37-7.38 (4H, d, J=2.0 Hz), 7.23-7.29 (3H, m), 4.01-4.06 (1H, m), 3.50-3.60 (1H, m), 3.10-3.14 (1H, m), 2.87 (4H, s), 1.25 (9H, s).

Step B

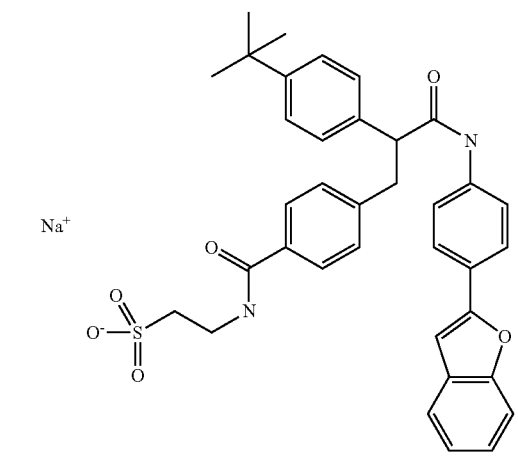 [SMILES: [Na+] ; CC(C)(C)c1ccc(C(Cc2ccc(C(=O)NCCS(=O)(=O)[O-])cc2)C(=O)Nc2ccc(-c3cc4ccccc4o3)cc2)cc1]

A mixture of the above obtained N-hydroxysuccinyl ester (230 mg), taurine (91 mg) and triethylamine (0.2 mL) in a mixture of ethanol (2 mL) and water (1 mL) was heated in a microwave reactor at 125° C. for a 6 min period. The crude mixture was treated with an excess of aqueous sodium hydroxide and loaded on top of a reverse phase silica gel column. The product was eluted with an acetonitrile-water gradient. The product containing fractions were concentrated to afford the title compound.

$^1$H NMR (MeOH-d4): δ 7.78-7.81 (2H, d, J=8.8 Hz), 7.69-7.72 (2H, d, J=7.9 Hz), 7.55-7.58 (2H, d, J=8.8 Hz), 7.47-7.50 (2H, d, J=8.5 Hz), 7.38 (4H, s), 7.31-7.34 (2H, d, J=8.3 Hz), 7.17-7.27 (2H, m), 7.08 (1H, s), 3.94-3.99 (1H, m), 3.75-3.79 (2H, m), 3.49-3.57 (1H, m), 3.04-3.08 (3H, m), 1.31 (9H, s).

Example 1.003

4-[2-(4-Benzofuran-2-yl-phenylcarbamoyl)-2-(4-cyclohex-1-enyl-phenyl)-ethyl]-benzoyl amino-ethane sulfonic acid sodium salt

Step A

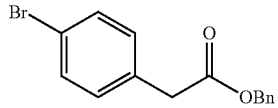 [SMILES: O=C(Cc1ccc(Br)cc1)OCc1ccccc1]

To a stirred solution of 4-bromophenyl acetic acid (7.5 g, 35.0 mmol) in DMF (60 mL) at rt were added Cs₂CO₃ (12.41 g, 38.15 mmol) and benzyl bromide (6.77 g, 39.6 mmol). The reaction mixture was stirred overnight at room temperature, and then at 100° C. for 1 h and cooled to rt. The solvent was removed under reduced pressure and poured into cold 1 N HCl (50 mL). The mixture was extracted with ethyl acetate (2×100 mL) and the combined organic layers were washed with brine, dried over Na₂SO₄, filtered and concentrated under reduced pressure. The crude product was recrystallized from hexanes to afford (4-bromo-phenyl) acetic acid benzyl ester as a white solid. (10.65 g, 100%): $^1$H NMR (300 MHz, CDCl₃): δ 7.42 (d, J=8.4 Hz, 2H), 7.25-7.34 m, 5H), 7.14 (d, J=8.4 Hz, 2H), 5.12 (s, 2H), 3.61 (s, 2H); TLC conditions: Uniplate silica gel, 250 microns; mobile phase=ethyl acetate-hexanes (1:5); $R_f$=0.8.

Step B

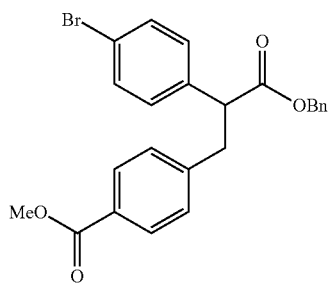 [SMILES: COC(=O)c1ccc(CC(C(=O)OCc2ccccc2)c2ccc(Br)cc2)cc1]

To a stirred solution of (4-bromo-phenyl) acetic acid benzyl ester (14.7 g, 48.3 mmol) in anhydrous THF (15 mL) was added LiHMDS (50.7 mL, 50.7 mmol, 1.0 M solution in toluene) at −78° C. The reaction mixture was stirred for 1.5 h at −78° C., and then methyl-4-bromo methyl benzoate (11.6 g, 50.7 mmol, in THF 3.0 mL) was added dropwise, stirred for 2 h at −78° C. and then allowed to warm to rt for 1 h. After completion, the reaction was quenched with saturated NH₄Cl solution (20 mL) and stirred for 10 min. The reaction mixture was extracted with ethyl acetate (100 mL) and the organic layer was washed with brine, dried over Na₂SO₄ and concentrated under reduced pressure. The crude product was recrystallized from a minimum amount of EtOAc and hexane at room temperature to afford 4-[2-benzyloxycarbonyl-2-(4-bromo-phenyl)-ethyl]-benzoic acid methyl ester as a white solid (14.2 g, 90%): $^1$H NMR (300 MHz, CDCl₃): δ 7.87 (d, J=8.4 Hz, 2H), 7.41 (d, J=8.4 Hz, 2H), 7.25-7.28 (m, 3H), 7.11-7.15 (m, 6H), 5.06 (dd, J=12.3, 28.5 Hz, 2H), 3.89 (s, 3H), 3.83 (d, J=7.5 Hz, 1H), 3.41 (dd, J=8.4, 13.8 Hz, 1H), 3.05 (dd, J=7.2, 13.5 Hz, 1H); TLC conditions: Uniplate silica gel, 250 microns; mobile phase=ethyl acetate-hexanes (1:4); $R_f$=0.6.

Step C

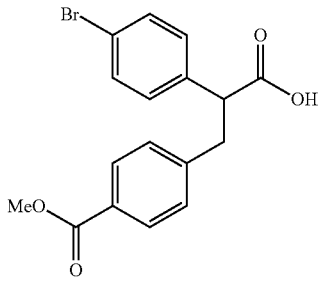 [SMILES: COC(=O)c1ccc(CC(C(=O)O)c2ccc(Br)cc2)cc1]

To a stirred solution of 4-[2-benzyloxycarbonyl-2-(4-bromo-phenyl)-ethyl]-benzoic acid methyl ester (0.7 g, 1.54 mmol) in EtOH (25 mL) at rt, was added platinum (IV) oxide (0.1 g) and the reaction mixture was stirred at room temperature for 3 h under H₂ gas (1 atm). The reaction mixture was filtered through a celite plug, washed with ethyl acetate (50 mL) and concentrated under reduced pressure. The crude product was dried under vacuum for 3 h to afford 4-[2-(4-bromo-phenyl)-2-carboxy-ethyl]-benzoic acid methyl ester (0.51 g, 91%): $^1$H NMR (300 MHz, DMSO-d₆): δ 12.52 (s, 1H), 7.77 (d, J=8.4 Hz, 2H), 7.48 (d, J=8.7 Hz, 2H), 7.28 (d, J=8.4 Hz, 2H), 7.22 (d, J=8.4 Hz, 2H), 3.93 (t, J=7.8 Hz, 1H), 3.79 (s, 3H), 3.30 (dd, J=8.4, 13.8 Hz, 1H), 3.0 (dd, J=8.1, 13.8 Hz, 1H).

Step D

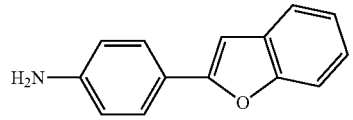 [SMILES: Nc1ccc(-c2cc3ccccc3o2)cc1]

A mixture of 4-iodo-aniline (25.0 g, 114.1 mmol), 2-benzofuran-boronic acid (27.7 g, 171.2 mmol), PdCl₂(O-tolylphosphine) (11.66 g, 14.8 mmol), and Na₂CO₃ (60.49 g, 570.7 mmol) in DME/EtOH/H2O (4:2:1)(700 mL) was heated at 125° C. for 2 h. The reaction mixture was cooled to room temperature, filtered and washed. The solvent was removed under reduced pressure. The residue was partitioned (ethyl acetate/water) and the organic layer was washed with brine, dried over Na₂SO₄ and concentrated under reduced pressure. The resulting crude was purified by column chromatography on silica gel, eluting with dichloromethane to afford 4-benzofuran-2-yl-phenylamine (11) as a pale yellow solid (23.78 g, 99.5%): $^1$H NMR (300 MHz, CDCl₃): δ 7.66 (d, J=9.0 Hz, 2H), 7.51-7.55 (m, 2H), 7.20-7.23 (m, 2H), 6.81 (s, 1H), 6.73 (d, J=9.0 Hz, 2H), 3.83 (bs, 2H) TLC conditions: Uniplate silica gel, 250 microns; mobile phase=ethyl acetate/hexanes (2:1); $R_f$=0.45.

Step E

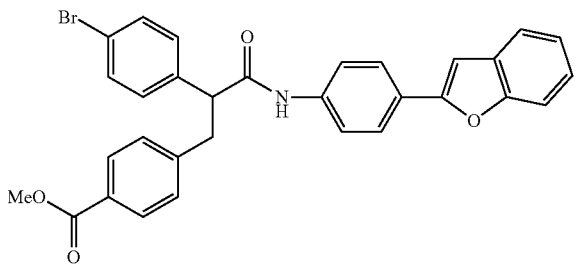 [SMILES: COC(=O)c1ccc(CC(C(=O)Nc2ccc(-c3cc4ccccc4o3)cc2)c2ccc(Br)cc2)cc1]

To a stirred suspension of 4-[2-(4-bromo-phenyl)-2-carboxy-ethyl]-benzoic acid methyl ester (0.4 g, 1.10 mmol) in anhydrous $CH_2Cl_2$ (10 mL), was added oxalyl chloride (0.28 g, 2.7 mmol) at room temperature. The reaction mixture was stirred for 14 h, concentrated under reduced pressure and coevaporated with $CH_2Cl_2$ (2×10 mL. The crude material was dried under vacuum for 3 h. The crude acid chloride (0.4 g, 1.04 mmol) was treated with 4-benzofuran phenyl amine (Step E above, 0.26 g, 1.25 mmol) and N,N-diispropylethylamine (0.6 mL, 3.12 mmol) in $CH_2Cl_2$ at 0° C. The resulting mixture was stirred for 14 h at room temperature and concentrated under reduced pressure. The residue was treated with MeOH t and the precipitate was filtered and washed with cold MeOH to give 4-[2-(4-benzofuran-2yl-phenylcarbamoyl)-2-(4-bromo-phenyl)-ethyl]-benzoic acid methyl ester as a brownish solid (0.4 g, 69%): $^1$H NMR (300 MHz, $CDCl_3$): δ 7.82 (d, J=8.1 Hz, 2H), 7.68 (d, J=8.7 Hz, 2H), 7.38-7.47 (m, 5H), 7.09-7.20 (m, 7H), 6.87 (s, 1H), 3.81 (s, 3H), 3.53-3.64 (m, 2H), 3.0 (dd, J=6.6, 12.9 Hz, 1H); LC-MS m/z=554 $[C_{31}H_{42}NBrO_4+H]^+$; TLC conditions: Uniplate silica gel, 250 microns; mobile phase=ethyl acetate/hexanes (2:1); $R_f$=0.4.

Step F

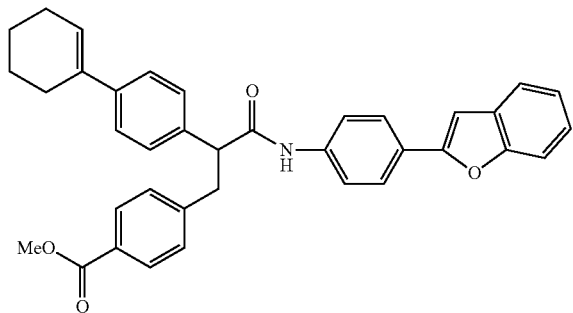 [SMILES: COC(=O)c1ccc(CC(C(=O)Nc2ccc(-c3cc4ccccc4o3)cc2)c2ccc(C3=CCCCC3)cc2)cc1]

A mixture of 4-[2-(4-benzofuran-2yl-phenylcarbamoyl)-2-(4-bromo-phenyl)-ethyl]-benzoic acid methyl ester (0.4 g, 0.74 mmol), cyclohexen-2-ylboronic acid (0.23 g, 1.85 mmol), $PdCl_2$(o-tolylphosphine) (75 mg, 0.096 mmol), and $Na_2CO_3$ (390 mg, 3.70 mmol) in DME/EtOH/H2O (4:2:1) (17.5 mL) was heated in an oil bath at 130° C. for 2 h, cooled to rt, filtered and washed with EtOAc (20 mL). The solvent was removed under reduced pressure. The crude mixture was extracted with ethyl acetate (100 mL) and the organic layer was washed with brine, dried over $Na_2SO_4$ and concentrated under reduced pressure. The resulting crude was purified by column chromatography on silica gel, eluting with ethyl acetate:hexanes (3:2) to afford 4-[2-(4-benzofuran-2-yl-phenylcarbamoyl)-2-(4-cyclohex-1-enyl-phenyl)-ethyl]-benzoic acid methyl ester as a white solid (0.42 g). $^1$H NMR (300 MHz, $CDCl_3$): δ 10.23 (s, 1H), 7.81 (d, J=8.4 Hz, 2H), 7.54-7.65 (m, 4H), 7.21-7.34 (m, 8H), 6.10 (bt, 1H), 4.02 (m, 1H), 3.78 (s, 3H), 3.45 (dd, J=8.7, 13.5 Hz, 1H), 3.04 (dd, J=6.6, 13.5 Hz, 1H), 2.25-2.40 (m, 2H), 2.10-2.20 (m, 2H), 1.64-1.72 (m, 2H), 1.54-1.59 (m, 2H); LC-MS m/z=556 $[C_{37}H_{33}NO_4+H]^+$; TLC conditions: Uniplate silica gel, 250 microns; mobile phase=ethyl acetate/hexanes (2:1); $R_f$=0.45.

Step G

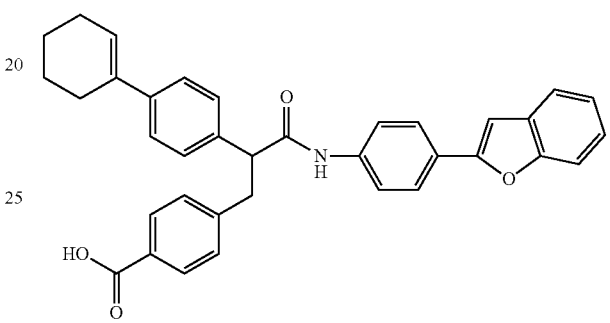

To a stirred solution of 4-[2-(4-benzofuran-2-yl-phenylcarbamoyl)-2-(4-cyclohex-1-enyl-phenyl)-ethyl]-benzoic acid methylester (6) (0.42 g, 0.75 mmol) in EtOH/THF/$H_2O$ (4:2:1) (20 mL) at rt, was added aq. 40% NaOH (2.5 ml). The reaction mixture was stirred overnight. After completion of the reaction, the solvent was removed under reduced pressure and the crude was acidified with 4N HCl (pH=2). The resulting mixture was extracted with ethyl acetate, the organic layer was dried over $MgSO_4$ and concentrated. The resulting compound was dried under vacuum to afford 4-[2-(4-benzofuran-2yl-phenylcarbamoyl)-2-(4-cyclohex-1-enyl-phenyl)-ethyl]-benzoic acid as a solid (0.35 g): $^1$H NMR (300 MHz, $CD_3OD$): 10.23 (s, 1H), 7.78 (d, J=8.7 Hz, 4H), 7.55-7.66 (m, 4H), 7.20-7.40 (m, 9H), 6.10 (bt, 1H), 4.03 (t, J=7.2 Hz, 1H), 3.45 (dd, J=5.0, 9.0 Hz, 1H), 3.03 (dd, J=5.7, 12.9 Hz, 1H), 2.20-2.40 (m, 2H), 2.10-2.15 (m, 2H), 1.65-1.75 (m, 2H), 1.50-1.60 (m, 2H); LC-MS m/z=541 $[C_{37}H_{34}NO_3+H]^+$.

Step H

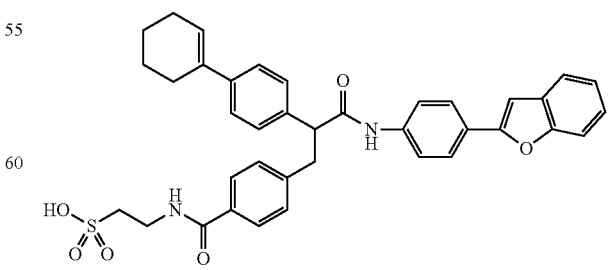

To a mixture of 4-[2-(4-benzofuran-2yl-phenylcarbamoyl)-2-(4-cyclohex-1-enyl-phenyl)-ethyl]-benzoic acid (7)

(0.23 g, 0.42 mmol), EDCI (0.162 g, 0.85 mmol), HOBt (130 mg, 0.85 mmol and N,N-diisopropylethylamine (0.31 mL, 2.75 mmol) in DMF (15 mL) was added taurine (106 mg, 0.85 mmol). After stirring for 14 h the solvent was removed under reduced pressure. The residue was treated with an excess of sodium hydroxide and loaded on a C18 reverse phase column. Elution with H$_2$O/acctonitrile 40% afforded 4-[2-(4-benzofuran-2-yl-phenylcarbamoyl)-2-(4-cyclohex-1-enyl-phenyl)-ethyl]-benzoyl amino-ethane sulfonic acid sodium salt (8) as a white solid. (0.11 g, 40%): $^1$H NMR (300 MHz, DMSO-d$_6$): 10.24 (s, 1H), 8.39 (t, J=5.7 Hz, 1H), 7.78 (d, J=8.7 Hz, 2H), 7.50-7.66 (m, 6H), 7.21-7.40 (m, 9H), 6.10 (bt, 1H), 4.0 (t, J=7.2 Hz, 1H), 3.30-3.50 (m, 3H), 3.03 (dd, J=6.6, 13.2 Hz, 1H), 2.60 (t, J=8.1 Hz, 2H), 2.25-2.40 (m, 2H), 2.10-2.15 (m, 2H), 1.65-1.75 (m, 2H), 1.55-1.60 (m, 2H); LC-MS m/z=671 [C$_{38}$H$_{35}$N$_2$O$_6$SNa+H]$^+$; HPLC conditions: Waters Atlantis C-18 OBD 4.6×150 mm; mobile phase=ACN/(H$_2$O:0.1 TFA) flow rate=1.0 mL/min; detection=UV@254, 220 nm retention time in min: 23.08; Anal Calcd: (MF: C$_{38}$H$_{35}$N$_2$O$_6$SNa+1.9H$_2$O) Calcd: C:64.74, H:5.55, N:3.97. Found: C: 64.73, H:5.49, N:4.35.

Example 1.004

4-[2-(4-Benzofuran-2-yl-phenylcarbamoyl)-2-(4-cyclohexyl-phenyl)-ethyl]-benzoyl amino-ethane sulfonic acid sodium salt Step A

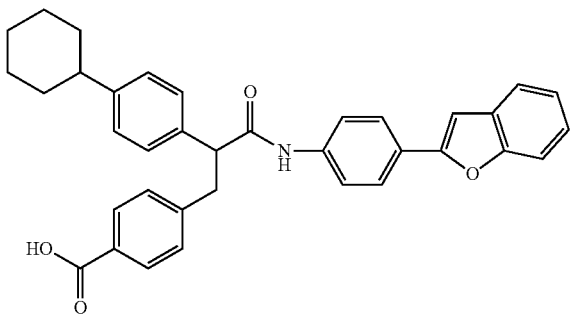 [SMILES: O=C(O)c1ccc(CC(C(=O)Nc2ccc(-c3cc4ccccc4o3)cc2)c2ccc(C3CCCCC3)cc2)cc1]

To a stirred solution of 4-[2-(4-benzofuran-2yl-phenylcarbamoyl)-2-(4-cyclohex-1-enyl-phenyl)-ethyl]-benzoic acid (Example 1.003, Step F) (0.23 g, 0.42 mmol) in EtOH (15 mL) at room temperature, was added 10% Pd/C (30 mg) and hydrogenated under 1 atm. H$_2$ (gas) for a 3 h period. The reaction mixture was filtered through a celite plug, washed with ethyl acetate (2×50 mL) and concentrated under reduced pressure. The resulting compound was dried under vacuum to afford 4-[2-(4-benzofuran-2yl-phenylcarbamoyl)-2-(4-cyclohexyl-phenyl)-ethyl]-benzoic acid (9) (0.21 g, 92%), $^1$H NMR (300 MHz, CD$_3$OD): 7.85 (d, J=8.1 Hz, 2H), 7.70 (d, J=8.7 Hz, 2H), 7.50 (d, J=9.0 Hz, 2H), 7.16-7.45 (m, 8H), 7.07 (s, 1H), 3.95 (dd, J=6.0, 9.3 Hz, 1H), 3.51 (dd, J=9.3, 12.0 Hz, 1H), 3.06 (dd, J=5.7, 10.8 Hz, 1H), 2.42-2.48 (m, 1H), 1.72-1.90 (m, 5H), 1.35-1.46 (m, 5H); LC-MS m/z=543 [C$_{37}$H$_{36}$NO$_3$+H]$^+$ Step B

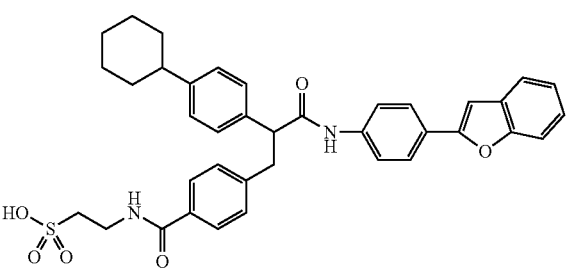 [SMILES: O=C(NCCS(=O)(=O)O)c1ccc(CC(C(=O)Nc2ccc(-c3cc4ccccc4o3)cc2)c2ccc(C3CCCCC3)cc2)cc1]

To a mixture of 4-[2-(4-benzofuran-2yl-phenylcarbamoyl)-2-(4-cyclohexyl-phenyl)-ethyl]-benzoic acid (9) (0.21 g, 0.38 mmol), EDCI (148 g, 1.11 mmol), HOBt (118 mg, 0.77 mmol) and N,N-diisopropylethylamine (0.2 g, 1.54 mmol) in DMF (15 mL) was added taurine (97 mg, 0.77 mmol). After stirring for 14 h the solvent was removed under reduced pressure. The residue was treated with an excess of sodium hydroxide and loaded on a C18 reverse phase column. Eluted with H$_2$O/acetonitrile 40% to afford 4-[2-(4-benzofuran-2-yl-phenylcarbamoyl)-2-(4-cyclohexyl-phenyl)-ethyl]-benzoyl amino-ethane sulfonic acid sodium salt (10) (124 mg, 50%), as a white solid. $^1$H NMR (300 MHz, DMSO-d$_6$): 10.25 (s, 1H), 8.42 (t, J=4.8 Hz, 1H), 7.81 (d, J=8.7 Hz, 2H), 7.55-7.70 (m, 6H), 7.18-7.40 (m, 9H), 4.0 (dd, J=6.0, 13.5 Hz, 1H), 3.45-3.55 (m, 3H), 3.01 (dd, J=7.8, 14.1 Hz, 1H), 2.63 (t, J=6.9 Hz, 2H), 2.30-2.46 (m, 1H), 1.65-1.80 (m, 5H), 1.24-1.45 (m, 5H); LC-MS m/z=673 [C$_{38}$H$_{37}$N$_2$O$_6$SNa+H]$^+$; HPLC conditions: Waters Atlantis C-18 OBD 4.6×150 mm; mobile phase=ACN/(H$_2$O: 0.1TFA) flow rate=1.0 mL/min; detection=UV@254, 220 nm retention time in min: 19.42; Anal Calcd: (MF: C$_{38}$H$_{37}$N$_2$O$_6$SNa+1.9H$_2$O) Calcd: C:64.07, H:5.86, N:3.93. Found: C: 63.87, H:5.78, N:3.94.

The following compounds were prepared by the methods described above with modifications evident to an individual skilled in the art:

| Example | STRUCTURE | MASS SPECT. (MODE) | Formula CHN (Calcd) CHN (Found) |
|---|---|---|---|
| 1.005 | 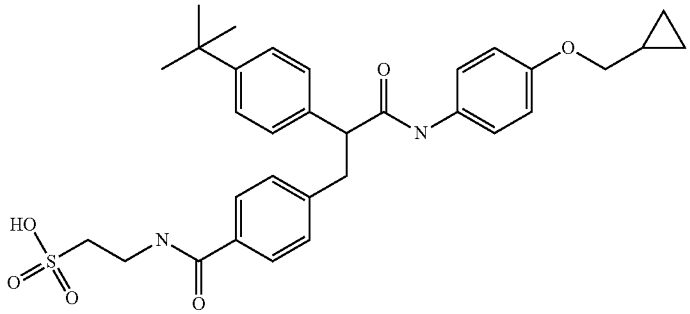 [SMILES: CC(C)(C)c1ccc(C(Cc2ccc(C(=O)NCCS(=O)(=O)O)cc2)C(=O)Nc2ccc(OCC3CC3)cc2)cc1] | 579.3 (+) | C32H38N2O6S + 0.8 H2O<br>C: 61.58 H: 6.40 N: 4.49<br>C: 61.87 H: 7.03 N: 4.80 |
| 1.006 | 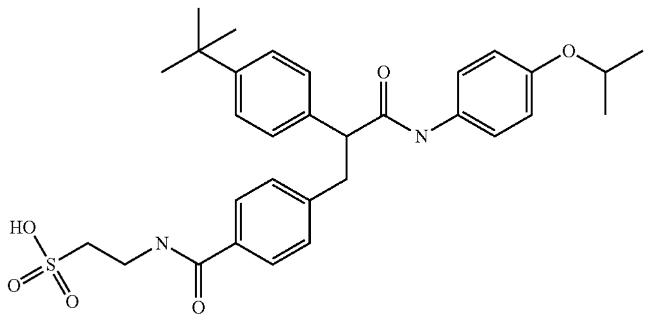 [SMILES: CC(C)Oc1ccc(NC(=O)C(Cc2ccc(C(=O)NCCS(=O)(=O)O)cc2)c2ccc(C(C)(C)C)cc2)cc1] | 567.3 (+) | C31H38N2O6S + 1.5 H2O<br>C: 62.71 H: 6.96 N: 4.72<br>C: 62.89 H: 6.88 N: 5.14 |
| 1.007 | 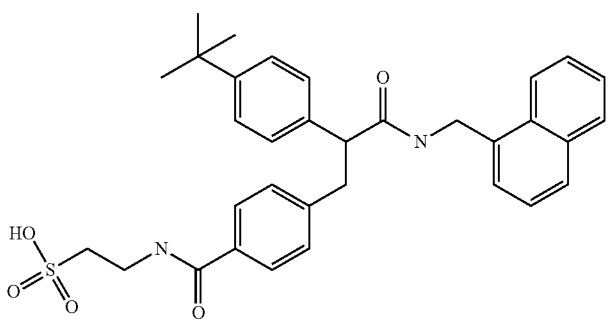 [SMILES: CC(C)(C)c1ccc(C(Cc2ccc(C(=O)NCCS(=O)(=O)O)cc2)C(=O)NCc2cccc3ccccc23)cc1] | 571.5 (−) | C33H36N2O6S + 1 H2O + 0.2 TFA<br>C: 65.39 H: 6.28 N: 4.57<br>C: 65.21 H: 6.43 N: 4.81 |
| 1.008 | 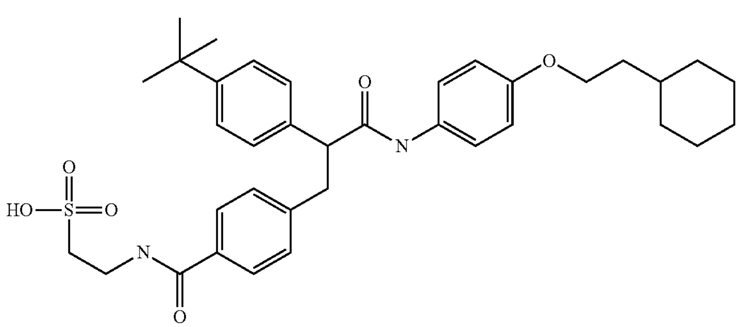 [SMILES: CC(C)(C)c1ccc(C(Cc2ccc(C(=O)NCCS(=O)(=O)O)cc2)C(=O)Nc2ccc(OCCC3CCCCC3)cc2)cc1] | 633.3 (−) | C36H46N2O6S + 2.25 H2O<br>C: 64.02 H: 7.54 N: 4.15<br>C: 64.29 H: 8.04 N: 4.31 |

-continued
| Example | STRUCTURE | MASS SPECT. (MODE) | Formula CHN (Calcd) CHN (Found) |
|---|---|---|---|
| 1.009 | 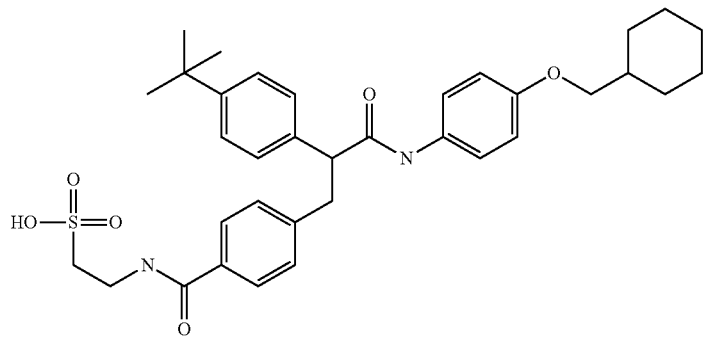 [SMILES: CC(C)(C)c1ccc(C(Cc2ccc(C(=O)NCCS(=O)(=O)O)cc2)C(=O)Nc2ccc(OCC3CCCCC3)cc2)cc1] | 619.5 (−) | C35H44N2O6S + 3 H2O C: 62.29 H: 7.47 N: 4.15 C: 64.64 H: 7.85 N: 4.15 |
| 1.010 | 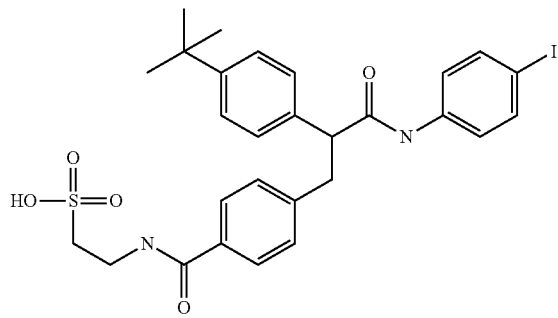 [SMILES: CC(C)(C)c1ccc(C(Cc2ccc(C(=O)NCCS(=O)(=O)O)cc2)C(=O)Nc2ccc(I)cc2)cc1] | 633.0 (−) | C28H31IN2O5S + 2 H2O C: 50.15 H: 5.26 N: 4.18 C: 50.28 H: 5.53 N: 5.49 |
| 1.011 | 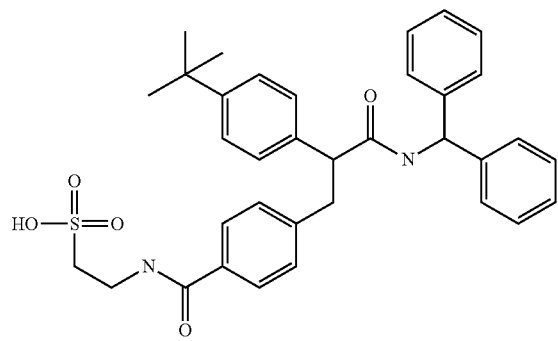 [SMILES: CC(C)(C)c1ccc(C(Cc2ccc(C(=O)NCCS(=O)(=O)O)cc2)C(=O)NC(c2ccccc2)c2ccccc2)cc1] | 597.3 (−) | C35H38N2O6S + 2.75 H2O C: 64.84 H: 6.76 N: 4.32 C: 64.85 H: 6.86 N: 4.31 |
| 1.012 | 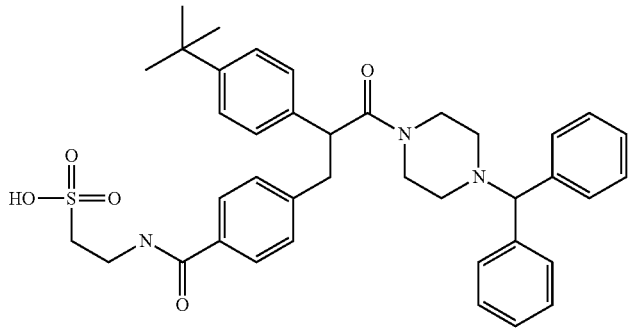 [SMILES: CC(C)(C)c1ccc(C(Cc2ccc(C(=O)NCCS(=O)(=O)O)cc2)C(=O)N2CCN(C(c3ccccc3)c3ccccc3)CC2)cc1] | 666.5 (−) | C39H45N3O6S + 1.75 H2O C: 66.98 H: 6.99 N: 6.01 C: 67.10 H: 7.31 N: 5.98 |

| Example | STRUCTURE | MASS SPECT. (MODE) | Formula CHN (Calcd) CHN (Found) |
|---|---|---|---|
| 1.013 | 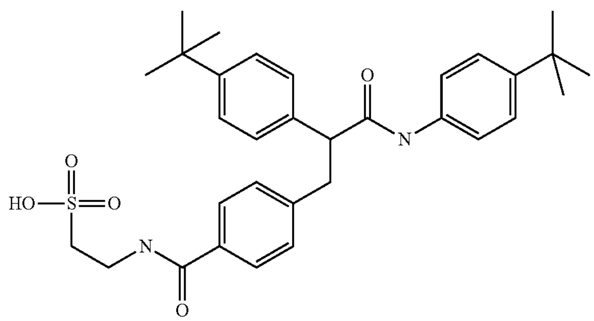 [SMILES: CC(C)(C)c1ccc(NC(=O)C(Cc2ccc(C(=O)NCCS(=O)(=O)O)cc2)c2ccc(C(C)(C)C)cc2)cc1] | 565.5 (+) | C32H40N2O5S + 2.75 H2O<br>C: 62.57 H: 7.47 N: 4.56<br>C: 62.57 H: 7.62 N: 5.80 |
| 1.014 | 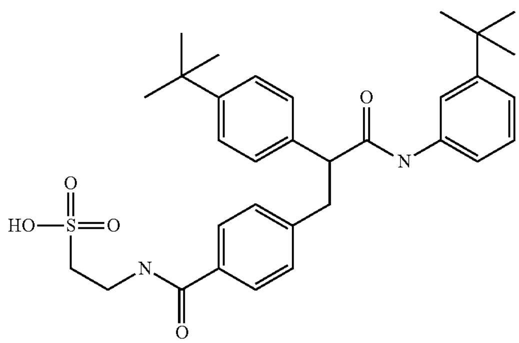 [SMILES: CC(C)(C)c1ccc(C(Cc2ccc(C(=O)NCCS(=O)(=O)O)cc2)C(=O)Nc2cccc(C(C)(C)C)c2)cc1] | 565.5 (+) | C32H40N2O5S + 2.75 H2O<br>C: 62.57 H: 7.47 N: 4.56<br>C: 62.59 H: 7.30 N: 5.21 |
| 1.015 | 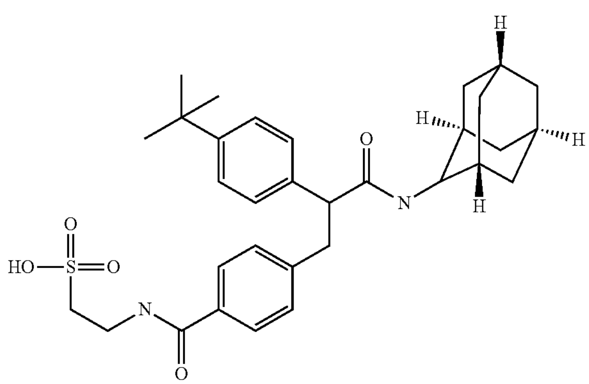 [SMILES: CC(C)(C)c1ccc(C(Cc2ccc(C(=O)NCCS(=O)(=O)O)cc2)C(=O)NC2[C@H]3C[C@@H]4C[C@@H](C[C@H]2C4)C3)cc1] | 567.9 (+) | C32H42N2O5S + 2.75 H2O<br>C: 62.36 H: 7.77 N: 4.55<br>C: 62.01 H: 7.56 N: 5.41 |
| 1.016 | 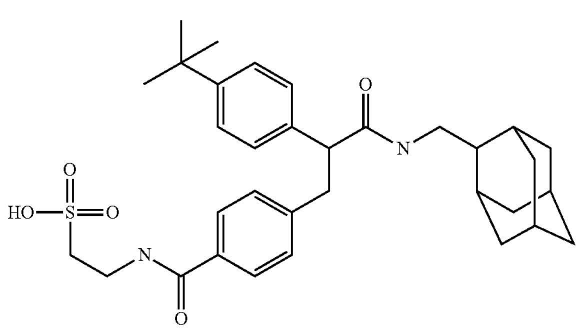 [SMILES: CC(C)(C)c1ccc(C(Cc2ccc(C(=O)NCCS(=O)(=O)O)cc2)C(=O)NCC2C3CC4CC(C3)CC2C4)cc1] | 579.3 (−) | C33H44N2O5S + 2.75 H2O<br>C: 62.88 H: 7.92 N: 4.44<br>C: 62.57 H: 7.73 N: 5.06 |

-continued
| Example | STRUCTURE | MASS SPECT. (MODE) | Formula CHN (Calcd) CHN (Found) |
|---|---|---|---|
| 1.017 | 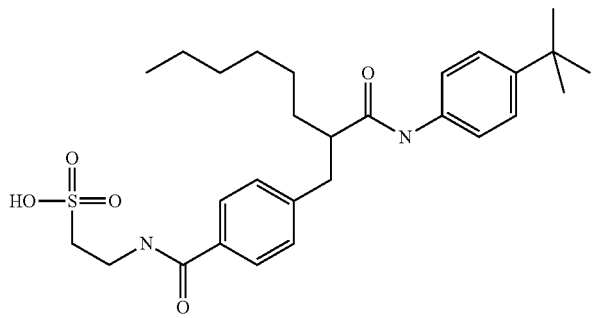 [SMILES: CCCCCCC(Cc1ccc(C(=O)NCCS(=O)(=O)O)cc1)C(=O)Nc1ccc(C(C)(C)C)cc1] | 515.3 (−) | C28H40N2O5S + 2.25 H2O<br>C: 60.35 H: 8.05 N: 5.03<br>C: 60.01 H: 8.09 N: 6.13 |
| 1.018 | 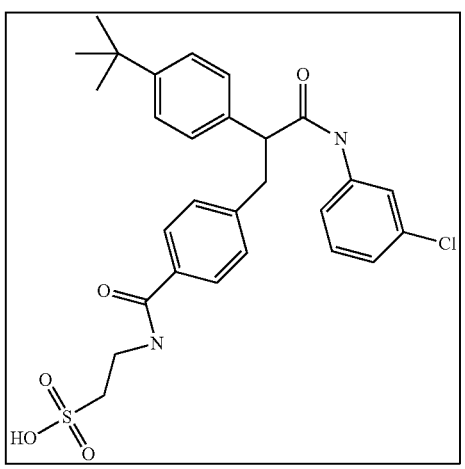 [SMILES: CC(C)(C)c1ccc(C(Cc2ccc(C(=O)NCCS(=O)(=O)O)cc2)C(=O)Nc2cccc(Cl)c2)cc1] | 544 | C28H31N2O5ClS + 3H2O<br>56.32 6.25 4.69<br>56.17 5.10 4.77 |
| 1.019 | 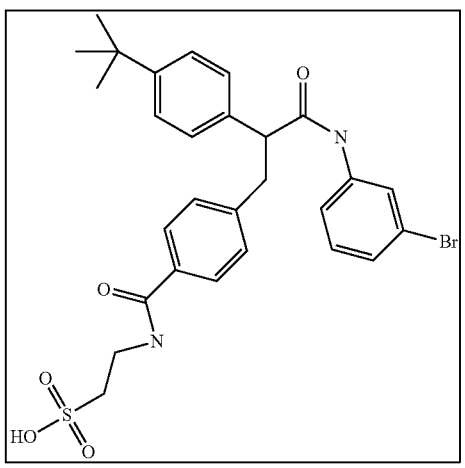 [SMILES: CC(C)(C)c1ccc(C(Cc2ccc(C(=O)NCCS(=O)(=O)O)cc2)C(=O)Nc2cccc(Br)c2)cc1] | 588 | C28H31N2O5BrS + 3.7H2O<br>51.41 5.92 4.28<br>51.04 5.53 4.38 |

-continued
| Example | STRUCTURE | MASS SPECT. (MODE) | Formula CHN (Calcd) CHN (Found) |
|---|---|---|---|
| 1.020 | 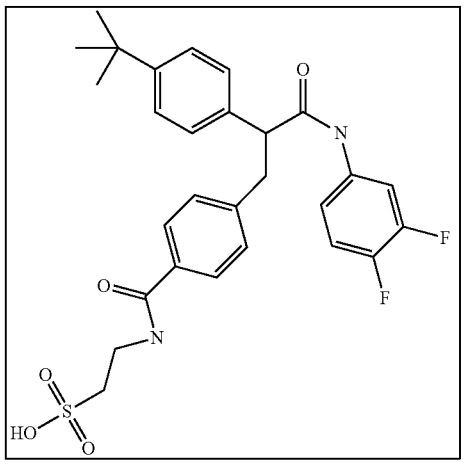 [SMILES: CC(C)(C)c1ccc(C(Cc2ccc(C(=O)NCCS(=O)(=O)O)cc2)C(=O)Nc2ccc(F)c(F)c2)cc1] | 545 | C28H30N2O5F2S + 3.6H2O<br>55.09 6.31 4.59<br>54.75 5.36 4.80 |
| 1.021 | 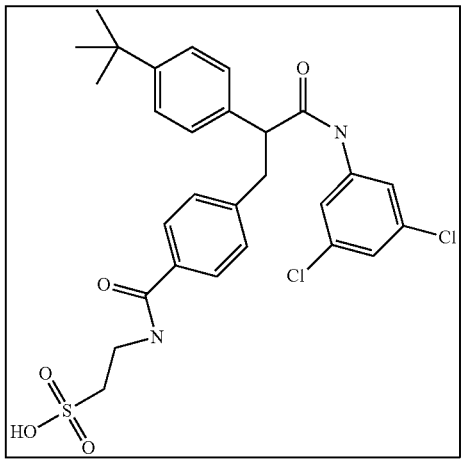 [SMILES: CC(C)(C)c1ccc(C(Cc2ccc(C(=O)NCCS(=O)(=O)O)cc2)C(=O)Nc2cc(Cl)cc(Cl)c2)cc1] | 578 | C28H30N2O5Cl2S +<br>1.5H2O + 0.3 Taurine<br>53.50 5.51 5.02<br>53.45 5.23 5.33 |
| 1.022 | 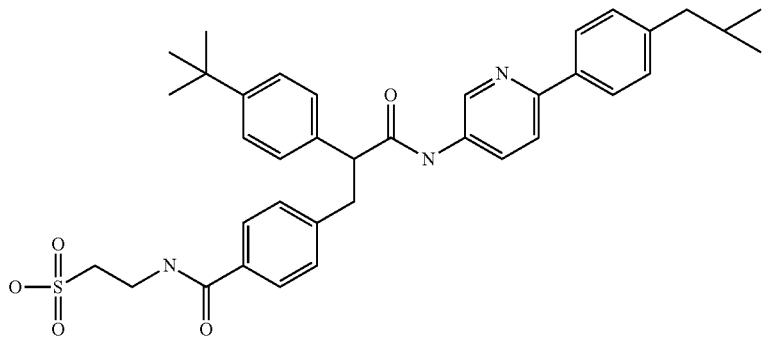 [SMILES: CC(C)Cc1ccc(-c2ccc(NC(=O)C(Cc3ccc(C(=O)NCCS(=O)(=O)O)cc3)c3ccc(C(C)(C)C)cc3)cn2)cc1] | 642.6 (+) | C37H43N3O5S + 1.0<br>H2O + 0.5 TFA<br>63.67 6.40 5.86<br>63.51 6.69 5.93 |

-continued
| Example | STRUCTURE | MASS SPECT. (MODE) | Formula CHN (Calcd) CHN (Found) |
|---|---|---|---|
| 1.023 | 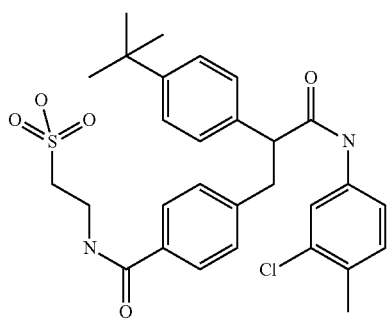 [SMILES: Cc1ccc(NC(=O)C(Cc2ccc(C(=O)NCCS(=O)(=O)O)cc2)c2ccc(C(C)(C)C)cc2)cc1Cl] | 557.3 (+) | C29H33ClN2O5S + 2.1H₂O<br>58.55 6.30 4.71<br>58.15 6.15 5.10 |
| 1.024 | 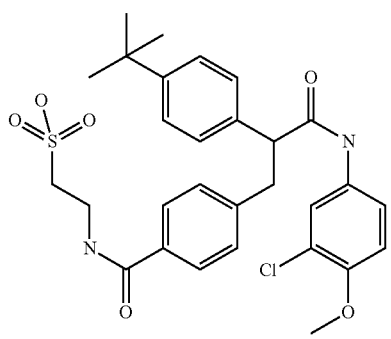 [SMILES: COc1ccc(NC(=O)C(Cc2ccc(C(=O)NCCS(=O)(=O)O)cc2)c2ccc(C(C)(C)C)cc2)cc1Cl] | 573.3 (+) | C29H33ClN2O6S + 3H₂O<br>55.54 6.27 4.47<br>55.39 6.05 4.84. |
| 1.025 | 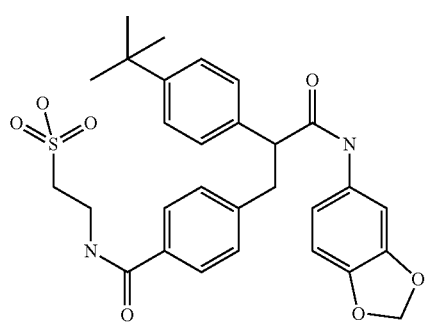 [SMILES: CC(C)(C)c1ccc(C(Cc2ccc(C(=O)NCCS(=O)(=O)O)cc2)C(=O)Nc2ccc3c(c2)OCO3)cc1] | 533.5 (+) | C29H32N2O7S + 3.3H₂O<br>56.91 6.36 4.58<br>56.66 5.41 4.49. |
| 1.026 | 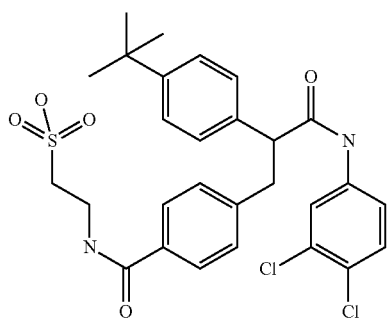 [SMILES: CC(C)(C)c1ccc(C(Cc2ccc(C(=O)NCCS(=O)(=O)O)cc2)C(=O)Nc2ccc(Cl)c(Cl)c2)cc1] | 577.3 (+) | C28H30Cl2N2O5S + 3.8H₂O<br>52.06 5.87 4.34<br>52.07 4.87 3.97. |

| Example | STRUCTURE | MASS SPECT. (MODE) | Formula CHN (Calcd) CHN (Found) |
|---|---|---|---|
| 1.027 | 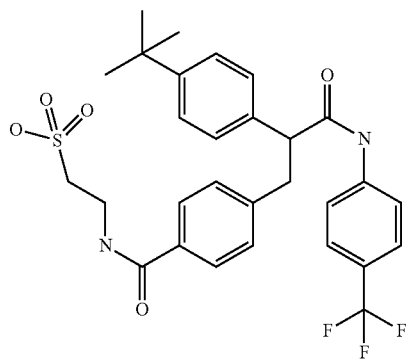 [SMILES: CC(C)(C)c1ccc(C(Cc2ccc(C(=O)NCCS(=O)(=O)O)cc2)C(=O)Nc2ccc(C(F)(F)F)cc2)cc1] | 577.3 (+) | C29H31F3N2O5S + 3H2O 55.23 5.91 4.44. 54.75 5.37 4.50 |
| 1.028 | 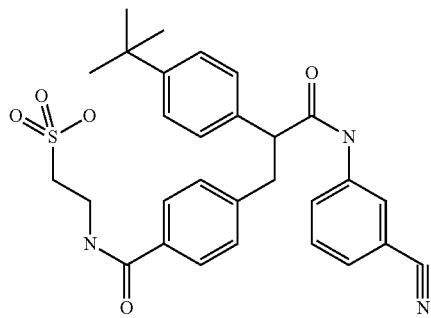 [SMILES: CC(C)(C)c1ccc(C(Cc2ccc(C(=O)NCCS(=O)(=O)O)cc2)C(=O)Nc2cccc(C#N)c2)cc1] | 534.3 (+) | C29H31N3O5S + 3H2O 59.27 6.35 7.15. 59.26 5.30 6.81. |
| 1.029 | 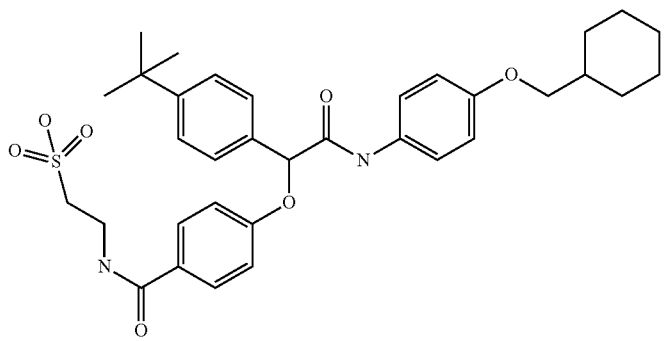 [SMILES: CC(C)(C)c1ccc(C(Oc2ccc(C(=O)NCCS(=O)(=O)O)cc2)C(=O)Nc2ccc(OCC3CCCCC3)cc2)cc1] | 621.3 (−) | C34H42N2O7S + 3H2O 60.34 7.05 4.14 60.11 7.20; 4.54 |
| 1.030 | 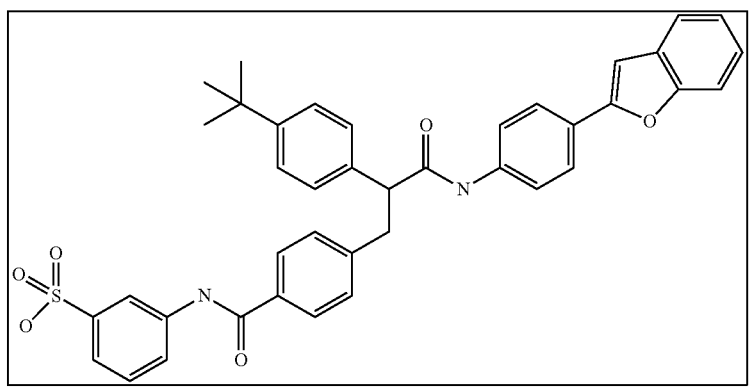 [SMILES: CC(C)(C)c1ccc(C(Cc2ccc(C(=O)Nc3cccc(S(=O)(=O)O)c3)cc2)C(=O)Nc2ccc(-c3cc4ccccc4o3)cc2)cc1] | 673.6 (+) | C40H36N2O6S + 2.2 H2O + 0.6 TFA C: 63.37, H: 5.29, N: 3.59 C: 63.70, H: 5.68, N: 3.96 |

-continued

| Example | STRUCTURE | MASS SPECT. (MODE) | Formula CHN (Calcd) CHN (Found) |
|---|---|---|---|
| 1.031 | 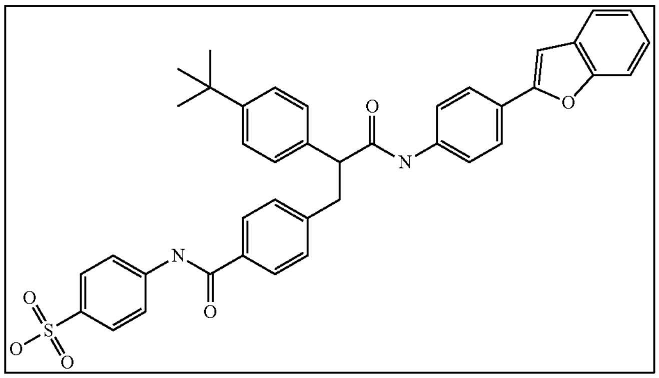 [SMILES: CC(C)(C)c1ccc(C(Cc2ccc(C(=O)Nc3ccc(S(=O)(=O)O)cc3)cc2)C(=O)Nc2ccc(-c3cc4ccccc4o3)cc2)cc1] | 673.6 (+) | C40H36N2O6S + 1.5 H2O<br>C: 68.65, H: 5.62, N: 4.00<br>C: 69.03, H: 6.09, N: 4.18 |
| 1.032 | 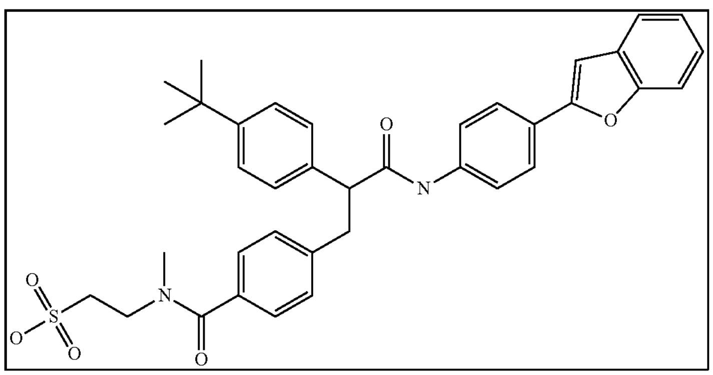 [SMILES: CN(CCS(=O)(=O)O)C(=O)c1ccc(CC(C(=O)Nc2ccc(-c3cc4ccccc4o3)cc2)c2ccc(C(C)(C)C)cc2)cc1] | 637.9 (+) | C37H38N2O6S + 2.0 H2O + 0.2 CF3CO2H<br>C: 64.39, H: 6.10, N: 4.02<br>C: 64.39, H: 6.00, N: 4.01 |
| 1.033 | 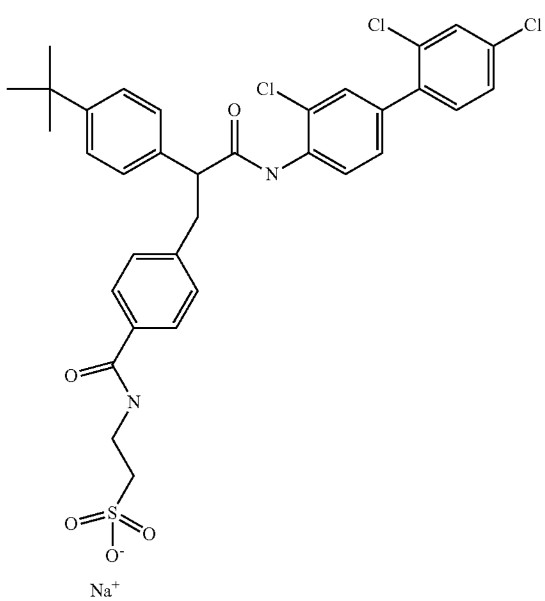 [SMILES: CC(C)(C)c1ccc(C(Cc2ccc(C(=O)NCCS(=O)(=O)[O-])cc2)C(=O)Nc2ccc(-c3ccc(Cl)cc3Cl)cc2Cl)cc1 ; [Na+]] | 687.6 (−) | C34H32N2O5Cl3SNa + 0.6 H2O<br>56.65 4.64 3.89<br>56.30 4.40 3.91 |

-continued
| Example | STRUCTURE | MASS SPECT. (MODE) | Formula CHN (Calcd) CHN (Found) |
|---|---|---|---|
| 1.034 | 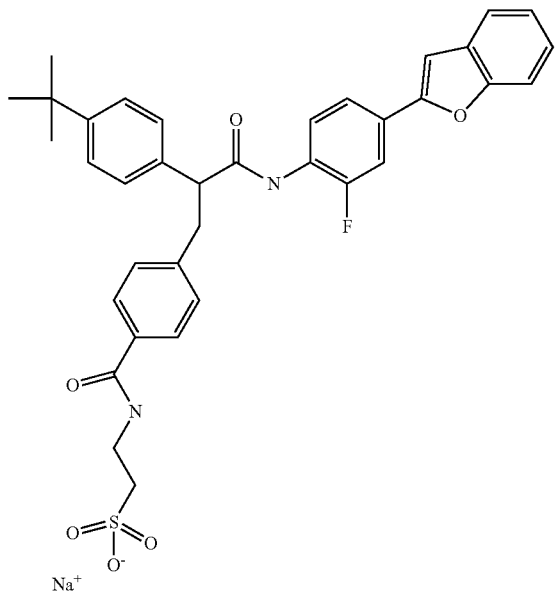 [SMILES: CC(C)(C)c1ccc(C(Cc2ccc(C(=O)NCCS(=O)(=O)[O-])cc2)C(=O)Nc2ccc(-c3cc4ccccc4o3)cc2F)cc1 ; [Na+]] | 657.4 | C36H35N2O6ClS + 2.5 H2O + 0.3CF3COOH 59.53 5.50 3.79 59.26 5.87 4.02 |
| 1.035 | 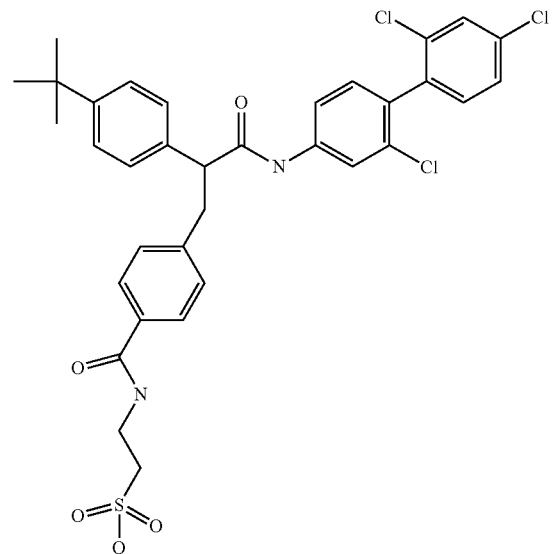 [SMILES: CC(C)(C)c1ccc(C(Cc2ccc(C(=O)NCCS(=O)(=O)O)cc2)C(=O)Nc2ccc(-c3ccc(Cl)cc3Cl)c(Cl)c2)cc1] | 687.6 (−) | C34H33N2O5Cl3S + 1 H2O + 0.6CF3COOH 54.59 4.63 3.62 54.31 4.42 3.50 |

| Example | STRUCTURE | MASS SPECT. .(MODE) | Formula CHN (Calcd) CHN (Found) |
|---|---|---|---|
| 1.036 | 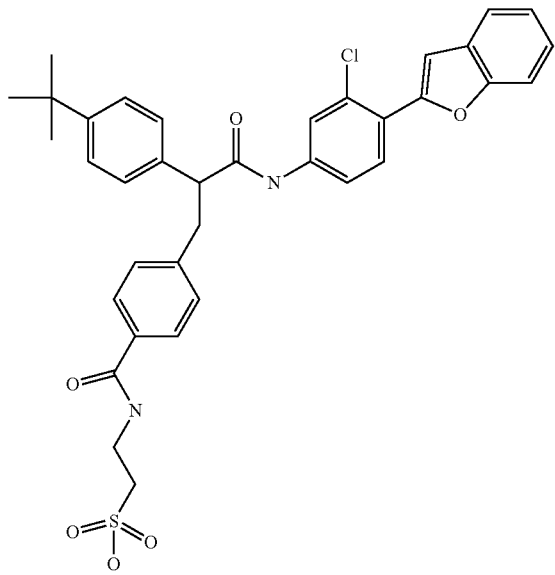 [SMILES: CC(C)(C)c1ccc(C(Cc2ccc(C(=O)NCCS(=O)(=O)O)cc2)C(=O)Nc2ccc(-c3cc4ccccc4o3)c(Cl)c2)cc1] | 657.4 (−) | C36H35N2O6ClS + 1 H2O + 0.4CF3COOH 61.15 5.22 3.88 61.13 4.92 3.82 |
| 1.037 | 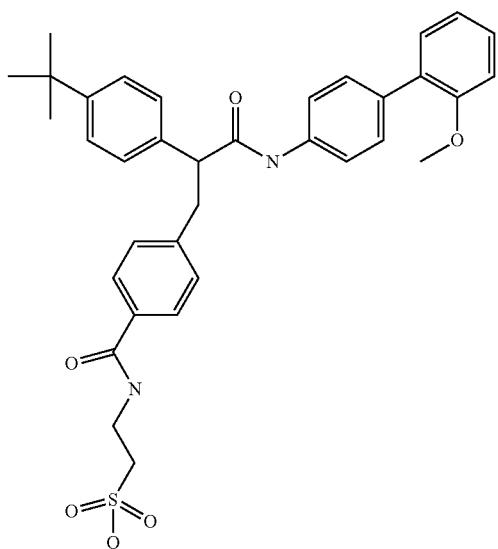 [SMILES: COc1ccccc1-c1ccc(NC(=O)C(Cc2ccc(C(=O)NCCS(=O)(=O)O)cc2)c2ccc(C(C)(C)C)cc2)cc1] | 613.4 (−) | C35H38N2O6S + 2 H2O + 0.5CF3COOH 61.09 6.05 3.96 60.78 6.23 4.24 |

| Example | STRUCTURE | MASS SPECT. (MODE) | Formula CHN (Calcd) CHN (Found) |
|---|---|---|---|
| 1.038 | 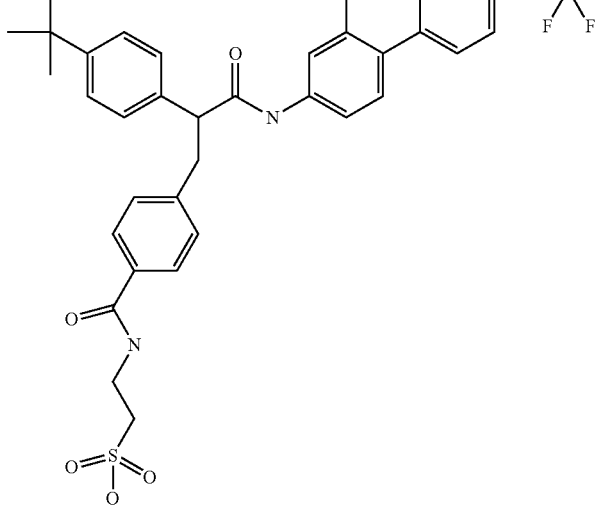 | 701.4 (−) | C35H34N2O6F3ClS + 3 H2O<br>55.52 5.32 3.70<br>55.82 5.29 3.57 |
| 1.039 | 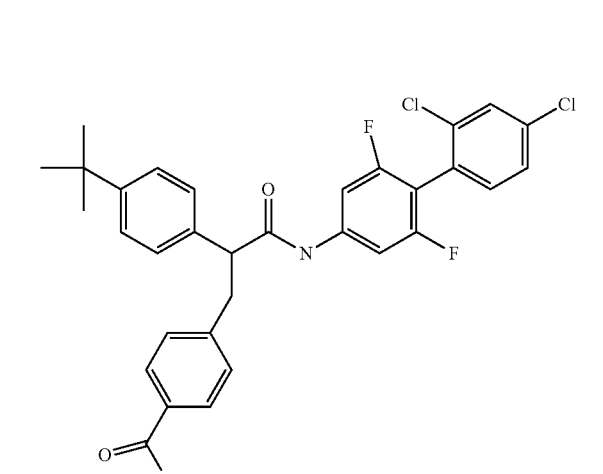 | 687.6 (−) | C34H32N2O5F2Cl2S + 0.8 CF3COOH<br>54.76 4.23 3.59<br>54.72 4.23 3.63 |

-continued
| Example | STRUCTURE | MASS SPECT. (MODE) | Formula CHN (Calcd) CHN (Found) |
|---|---|---|---|
| 1.040 | 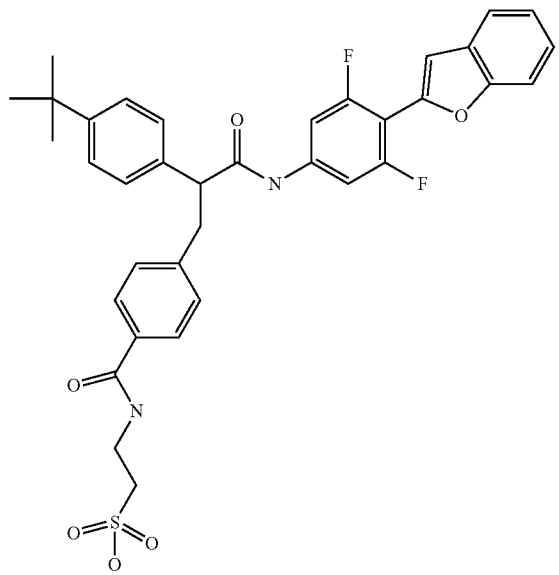 [SMILES: CC(C)(C)c1ccc(C(Cc2ccc(C(=O)NCCS(=O)(=O)O)cc2)C(=O)Nc2cc(F)c(-c3cc4ccccc4o3)c(F)c2)cc1] | 659.6 (−) | C36H34N2O6F2S + 0.1 H2O + 0.6 CF3COOH 61.13 4.80 3.83 60.78 4.99 4.19 |
| 1.041 | 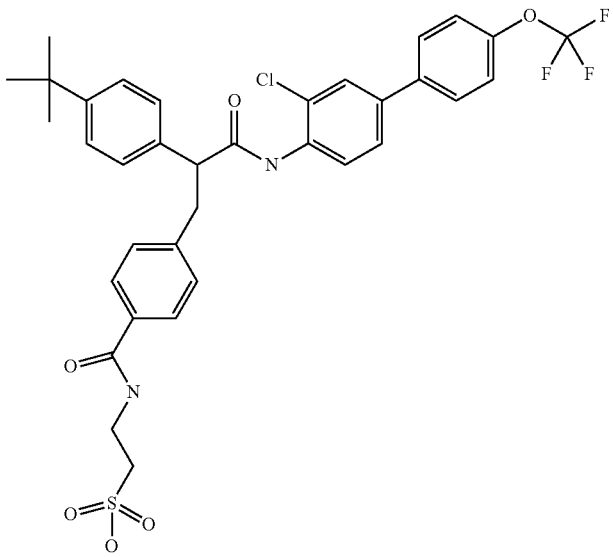 [SMILES: CC(C)(C)c1ccc(C(Cc2ccc(C(=O)NCCS(=O)(=O)O)cc2)C(=O)Nc2ccc(-c3ccc(OC(F)(F)F)cc3)cc2Cl)cc1] | 701.4 (−) | C35H34N2O6F3ClS + 0.7 CF3COOH 55.84 4.47 3.58 56.11 4.08 3.44 |
| 1.042 | 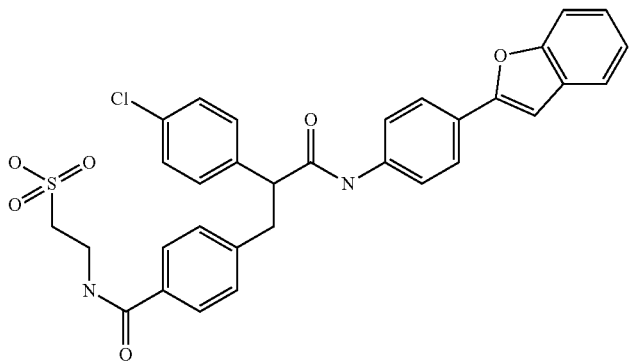 [SMILES: O=C(NCCS(=O)(=O)O)c1ccc(CC(C(=O)Nc2ccc(-c3cc4ccccc4o3)cc2)c2ccc(Cl)cc2)cc1] | 603.4 (−) | C32H27N2O6ClS + H2O C: 61.88 H: 4.71 N: 4.51 C: 61.55 H: 4.60 N: 4.82 |

| Example | STRUCTURE | MASS SPECT. (MODE) | Formula CHN (Calcd) CHN (Found) |
|---|---|---|---|
| 1.043 | 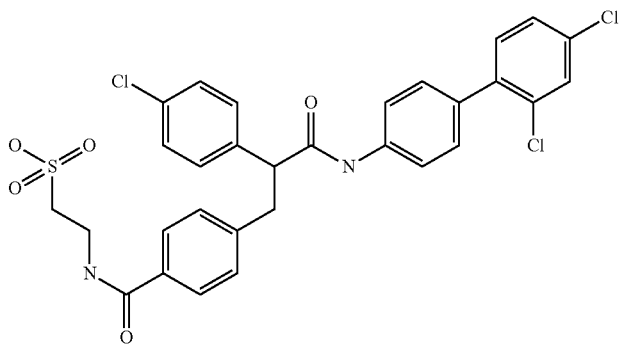 [SMILES: O=C(NCCS(=O)(=O)O)c1ccc(CC(C(=O)Nc2ccc(-c3ccc(Cl)cc3Cl)cc2)c2ccc(Cl)cc2)cc1] | 603.9 (−) | C30H25N2O5Cl3S + 0.4 H2O<br>C: 56.37 H: 4.07 N: 4.38<br>C: 56.61 H: 4.15 N: 4.36 |
| 1.044 | 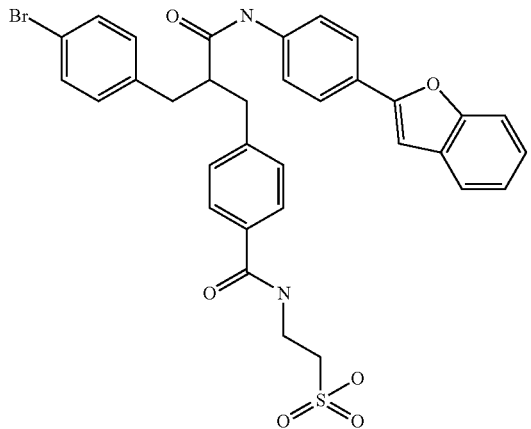 [SMILES: O=C(NCCS(=O)(=O)O)c1ccc(CC(Cc2ccc(Br)cc2)C(=O)Nc2ccc(-c3cc4ccccc4o3)cc2)cc1] | 661.6 (−) | C33H29N2O6BrS + 2H2O<br>C: 56.82 H: 4.77 N: 4.02<br>C: 56.79 H: 4.76 N: 4.07 |
| 1.045 | 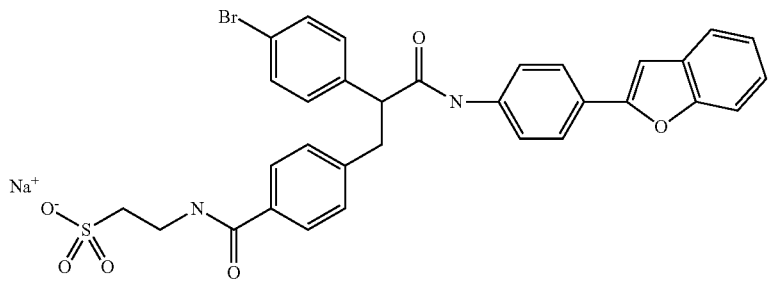 [SMILES: [Na+] ; O=C(NCCS(=O)(=O)[O-])c1ccc(CC(C(=O)Nc2ccc(-c3cc4ccccc4o3)cc2)c2ccc(Br)cc2)cc1] | 649 (+) | C35H31N2O6SN + 1.2H2O<br>C: 64.35, H: 5.31, N: 4.29<br>C: 64.10, H: 4.77, N: 4.46 |
| 1.046 | 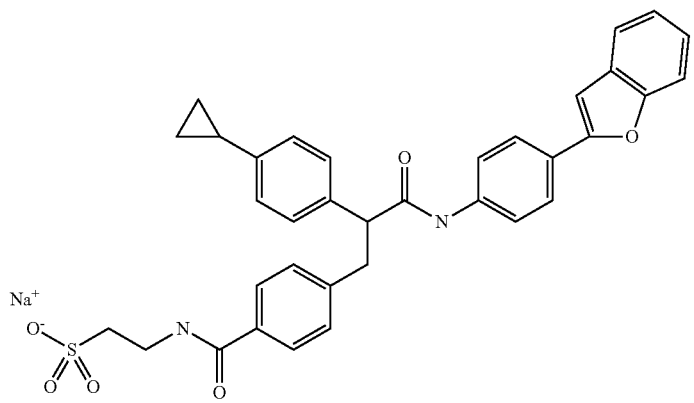 [SMILES: [Na+] ; O=C(NCCS(=O)(=O)[O-])c1ccc(CC(C(=O)Nc2ccc(-c3cc4ccccc4o3)cc2)c2ccc(C3CC3)cc2)cc1] | 609 (+) | C35H31N2O6SNa + 1.2H2O<br>C: 64.35, H: 5.31, N: 4.29<br>C: 64.10, H: 4.77, N: 4.46 |

-continued
| Example | STRUCTURE | MASS SPECT. (MODE) | Formula CHN (Calcd) CHN (Found) |
|---|---|---|---|
| 1.047 | 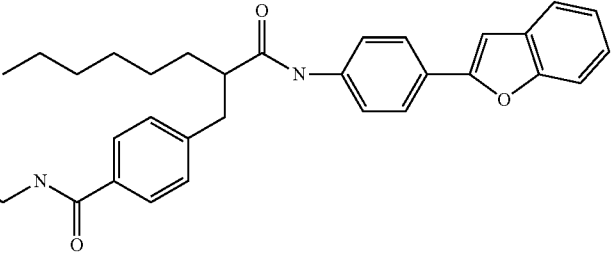 | 577 (+) | C32H36N2O6SNa + 0.4 CH2Cl2 C: 61.41, H: 5.85, N: 4.42 C: 61.15 H: 5.57, N: 4.19 |
| 1.048 | 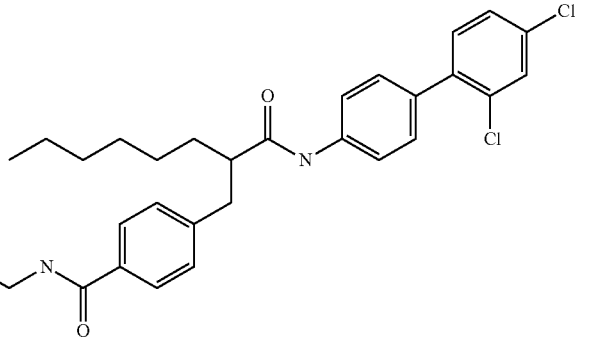 | 605 (+) | C30H34N2O6SNa + 0.8 NaCl C: 61.41, H: 5.85, N: 4.42: C: 55.26 H: 5.07, N: 3.99 |
| 1.049 | 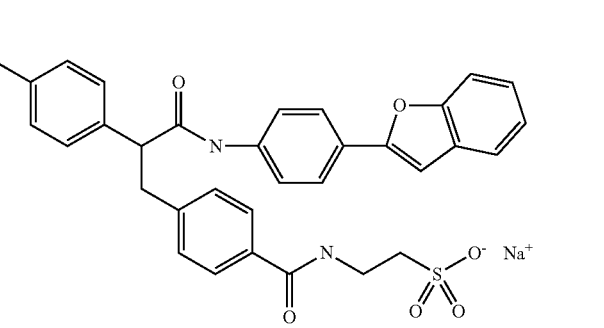 | 635 (+) | C37H33N2O6SNa + 4.0H2O C: 60.89, H: 5.80, N: 3.84 C: 60.50, H: 5.45, N: 4.08 (C37H33N2O6SNa + 4.0 H2O) |
| 1.050 | 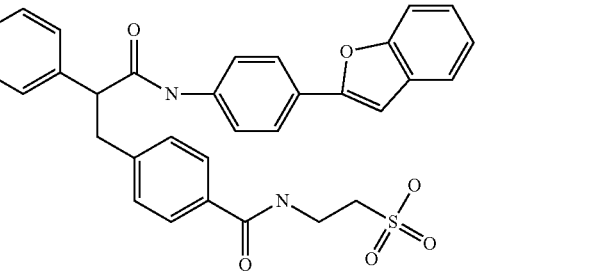 | 569 (+) | C32H28N2O6S + 2.5H2O + 0.1CH3CN C: 62.70, H: 5.28, N: 4.77 C: 62.70, H: 5.50, N: 4.99 |
| 1.051 | 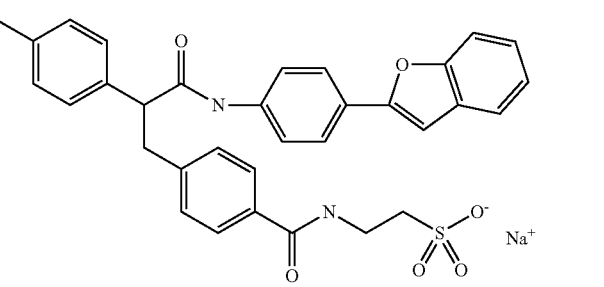 | 632 (+) | C35H31N2O6SNa + 2.0 H2O C: 62.96, H: 5.43, N: 4.20 C: 62.97, H: 5.63, N: 4.53 (C35H31N2O6SNa + 2.0H2O) |

| Example | STRUCTURE | MASS SPECT. (MODE) | Formula CHN (Calcd) CHN (Found) |
|---|---|---|---|
| 1.052 | 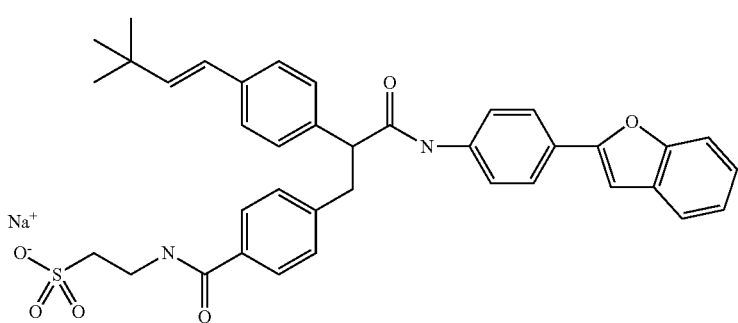 [SMILES: [Na+] ; CC(C)(C)/C=C/c1ccc(C(Cc2ccc(C(=O)NCCS(=O)(=O)[O-])cc2)C(=O)Nc2ccc(-c3cc4ccccc4o3)cc2)cc1] | 651 (+) | C38H37N2O6SNa + 2.0 H2O C: 64.39, H: 5.83, N: 3.95 C: 64.28, H: 5.86, N: 4.12 |
| 1.053 | 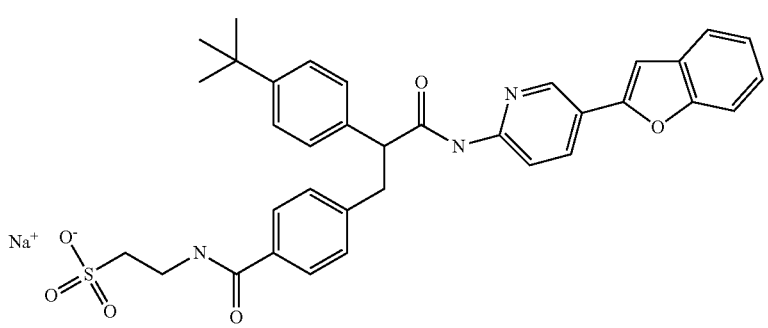 [SMILES: [Na+] ; CC(C)(C)c1ccc(C(Cc2ccc(C(=O)NCCS(=O)(=O)[O-])cc2)C(=O)Nc2ccc(-c3cc4ccccc4o3)cn2)cc1] | 626.6 (+) | $C_{35}H_{34}N_3O_6SNa$ + 6.0 H$_2$O C: 55.62, H: 6.13, N: 5.56; C: 55.32, H: 5.71, N: 5.36. |
| 1.054 | 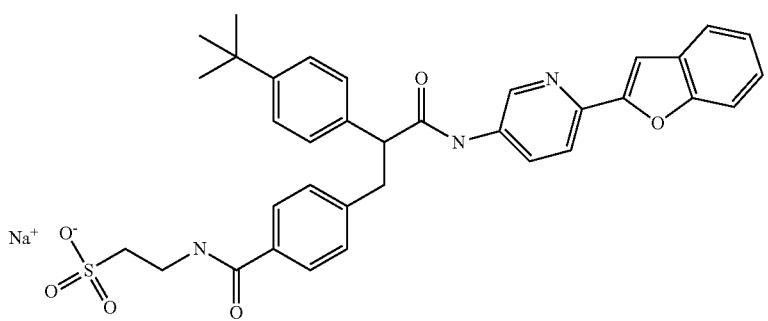 [SMILES: [Na+] ; CC(C)(C)c1ccc(C(Cc2ccc(C(=O)NCCS(=O)(=O)[O-])cc2)C(=O)Nc2ccc(-c3cc4ccccc4o3)nc2)cc1] | 626.6 (+) | $C_{35}H_{34}N_3O_6SNa$ + 2.5 H$_2$O) C: 60.68, H: 5.67, N: 6.07; C: 60.79, H: 5.40, N: 6.02 |
| 1.055 | 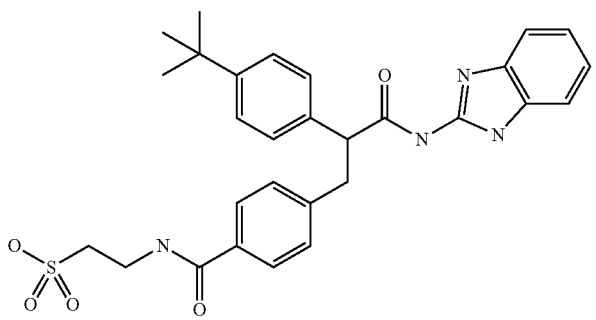 [SMILES: CC(C)(C)c1ccc(C(Cc2ccc(C(=O)NCCS(=O)(=O)O)cc2)C(=O)Nc2nc3ccccc3[nH]2)cc1] | 539.4 (+) | $C_{29}H_{32}N_4O_5S$ + 0.2 TFA C: 61.79, H: 5.68, N: 9.80; C: 61.56, H: 5.41, N: 9.84 |

-continued
| Example | STRUCTURE | MASS SPECT. (MODE) | Formula CHN (Calcd) CHN (Found) |
|---|---|---|---|
| 1.056 | 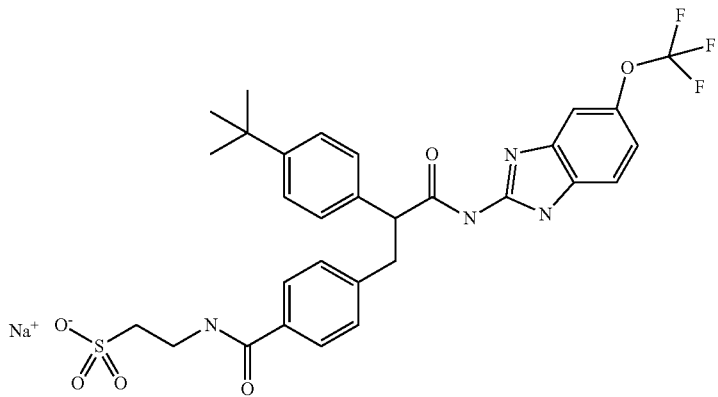 [SMILES: [Na+] ; CC(C)(C)c1ccc(C(Cc2ccc(C(=O)NCCS(=O)(=O)[O-])cc2)C(=O)Nc2nc3cc(OC(F)(F)F)ccc3[nH]2)cc1] | 633.6 (+) | C$_{30}$H$_{30}$F$_3$N$_4$O$_6$SNa + 3.6 H$_2$O) C: 50.08, H: 5.21, N: 7.79; C: 49.95, H: 4.88, N: 7.40. |
| 1.057 | 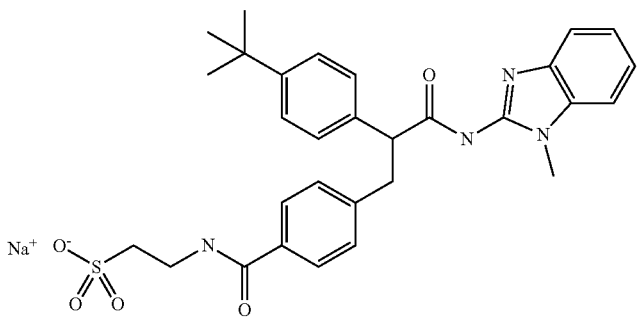 [SMILES: [Na+] ; Cn1c(NC(=O)C(Cc2ccc(C(=O)NCCS(=O)(=O)[O-])cc2)c2ccc(C(C)(C)C)cc2)nc2ccccc21] | 563.4 (+) | C$_{30}$H$_{33}$N$_4$O$_5$SNa + 4.2 H$_2$O C: 54.57, H: 6.32, N: 8.48; C: 54.58, H: 5.59, N: 8.41. |
| 1.058 | 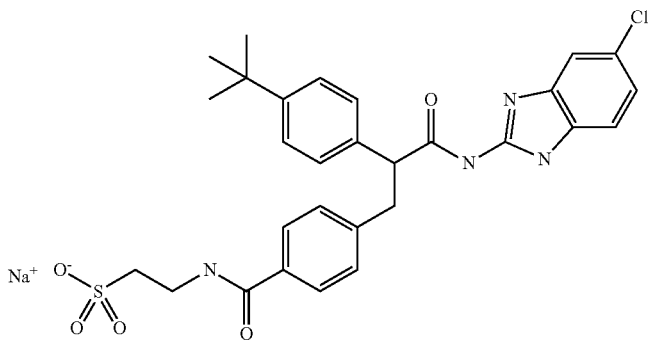 [SMILES: [Na+] ; CC(C)(C)c1ccc(C(Cc2ccc(C(=O)NCCS(=O)(=O)[O-])cc2)C(=O)Nc2nc3cc(Cl)ccc3[nH]2)cc1] | 583.1 (+) | C$_{29}$H$_{30}$ClN$_4$O$_5$SNa + 1.8 H$_2$O C: 54.64, H: 5.31, N: 8.79; C: 54.59, H: 5.28, N: 8.68. |
| 1.059 | 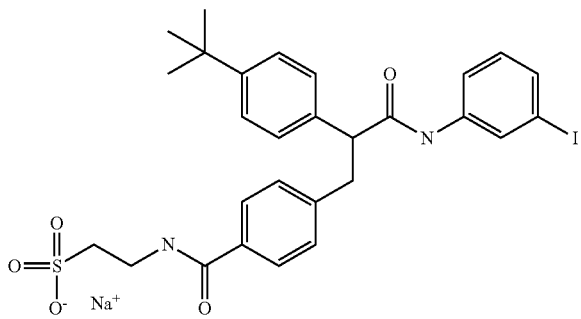 [SMILES: CC(C)(C)c1ccc(C(Cc2ccc(C(=O)NCCS(=O)(=O)[O-])cc2)C(=O)Nc2cccc(I)c2)cc1 ; [Na+]] | 633.6 (−) | C28H30N2O5SINa + (0.5) H2O C: 50.53, H: 4.69, N: 4.21 C: 50.64, H: 4.64, N: 4.33 |

-continued

| Example | STRUCTURE | MASS SPECT. .(MODE) | Formula CHN (Calcd) CHN (Found) |
|---|---|---|---|
| 1.060 | 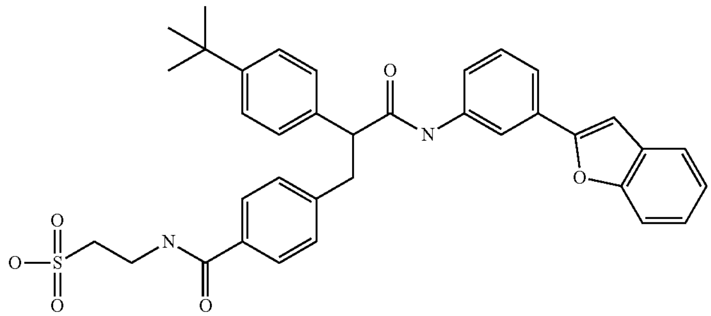 [SMILES: CC(C)(C)c1ccc(C(Cc2ccc(C(=O)NCCS(=O)(=O)O)cc2)C(=O)Nc2cccc(-c3cc4ccccc4o3)c2)cc1] | 623.6 (−) | C36H36N2O6S + (1.9) H2O C: 65.62, H: 6.09, N: 4.25 C: 65.31, H: 5.68, N: 4.15 |
| 1.061 | 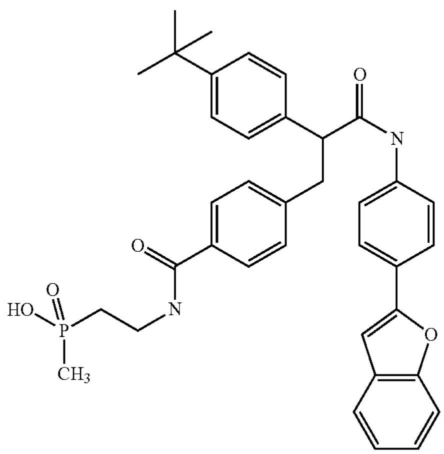 [SMILES: CC(C)(C)c1ccc(C(Cc2ccc(C(=O)NCCP(C)(=O)O)cc2)C(=O)Nc2ccc(-c3cc4ccccc4o3)cc2)cc1] | 623.9 (+) | C37H39N2O5P C: 71.37, H: 6.31; N: 4.50 C: 64.86; H: 5.75; N: 4.04 |
| 1.062 | 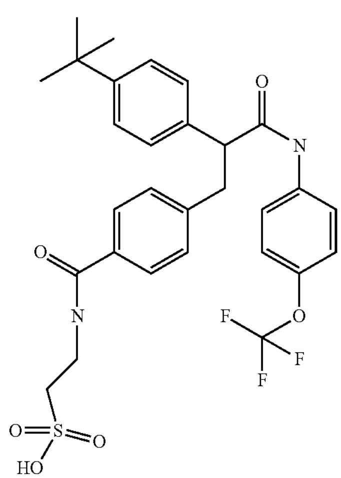 [SMILES: CC(C)(C)c1ccc(C(Cc2ccc(C(=O)NCCS(=O)(=O)O)cc2)C(=O)Nc2ccc(OC(F)(F)F)cc2)cc1] | 593.6 (+) | C29H31F3N2O6S 58.77 5.27 4.73 57.66 6.54 6.00 |

| Example | STRUCTURE | MASS SPECT. (MODE) | Formula CHN (Calcd) CHN (Found) |
|---|---|---|---|
| 1.063 | 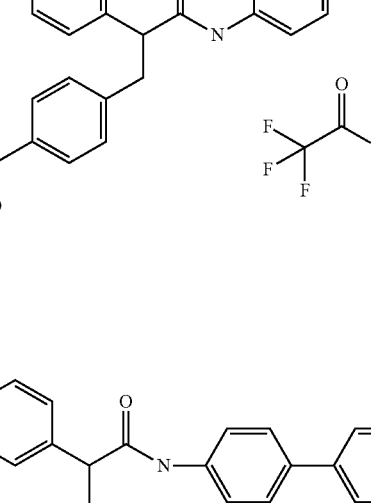 | 586.3 (+) | C35H35N3O5S + 1.5H2O + 1.1CF3CO2H<br>C: 57.27; H: 5.34; N: 5.69<br>C: 57.07; H: 5.52; N: 5.78 |
| 1.064 | 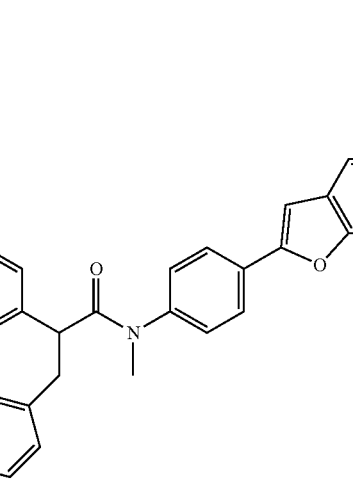 | 584.6 (−) | C33H34N3O5SNa + 2.5H2O<br>C: 60.72; H: 6.02; N: 6.44<br>C: 60.56; H: 5.73; N: 6.41 |
| 1.065 | 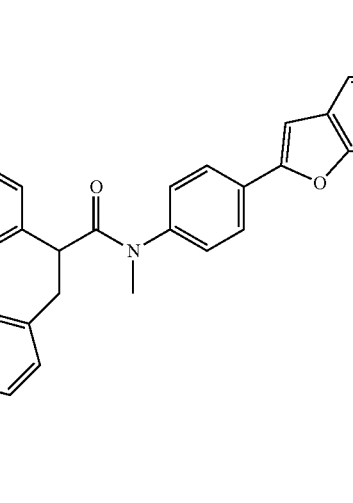 | 639.6 (+) | C37H37N2O6SNa<br>C: 67.26 H: 5.64; N: 4.24<br>Not measured |

-continued
| Example | STRUCTURE | MASS SPECT. (MODE) | Formula CHN (Calcd) CHN (Found) |
|---|---|---|---|
| 1.066 | 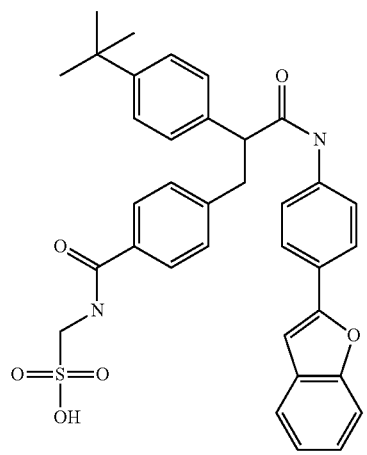 [SMILES: CC(C)(C)c1ccc(C(Cc2ccc(C(=O)NCS(=O)(=O)O)cc2)C(=O)Nc2ccc(-c3cc4ccccc4o3)cc2)cc1] | 611.6 (+) | C35H33N2O6S + 0.5Na + 0.5 HTEA + 1H2O 66.12 6.28 5.07 65.75 6.51 5.27 |
| 1.067 | 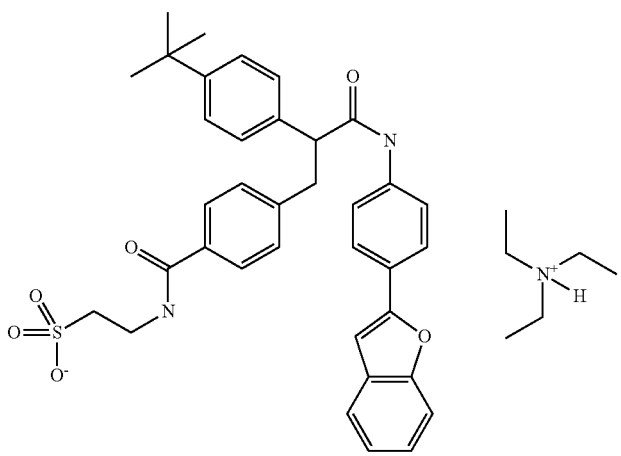 | 625.3 (+) | C36H35N2O6S + 0.8 H2O + C6H16N 68.14 7.16 5.68 68.00 7.30 5.81 |
| 1.068 | 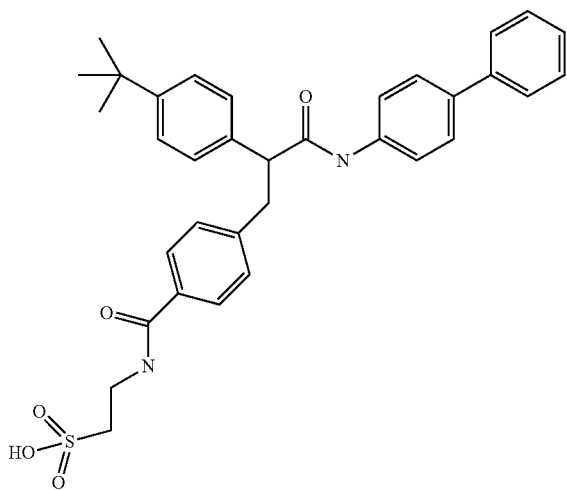 [SMILES: CC(C)(C)c1ccc(C(Cc2ccc(C(=O)NCCS(=O)(=O)O)cc2)C(=O)Nc2ccc(-c3ccccc3)cc2)cc1] | 585.3 (+) | C34H36N2O5S + 3H2O C: 63.93; H: 6.63; N: 4.39 C: 63.63; H: 6.17; N: 4.49 |

-continued
| Example | STRUCTURE | MASS SPECT. (MODE) | Formula CHN (Calcd) CHN (Found) |
|---|---|---|---|
| 1.069 | 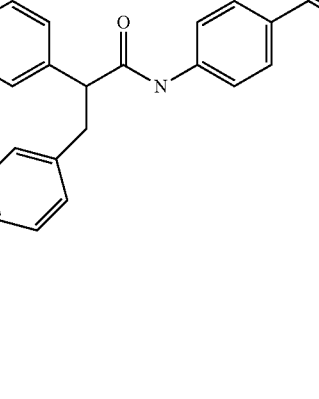 | 631.2 (+) | C36H36N2O4Cl2<br>C: 68.46 H: 5.75 N: 4.44<br>C: 68.59 H: 5.87 N: 4.32 |
| 1.070 | 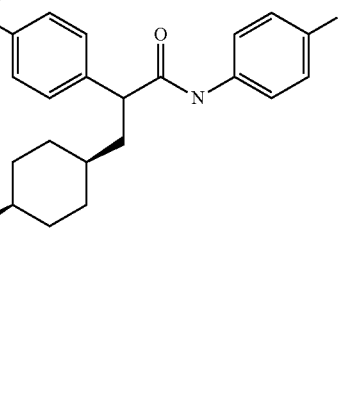 | 625.3 (−) | C35 H50 N2 O6 S +<br>1.2 H2O<br>C: 64.83 H: 8.14 N: 4.32<br>C: 64.73 H: 7.39 N: 4.74 |
| 1.071 | 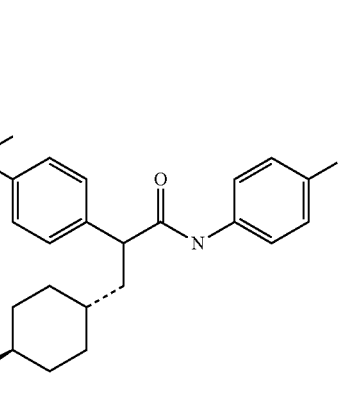 | 625.3 (−) | C35 H50 N2 O6 S +<br>3 H2O<br>C: 61.74 H: 8.29 N: 4.11<br>C: 61.97 H: 8.56 N: 4.39 |

-continued
| Example | STRUCTURE | MASS SPECT. (MODE) | Formula CHN (Calcd) CHN (Found) |
|---|---|---|---|
| 1.072 | 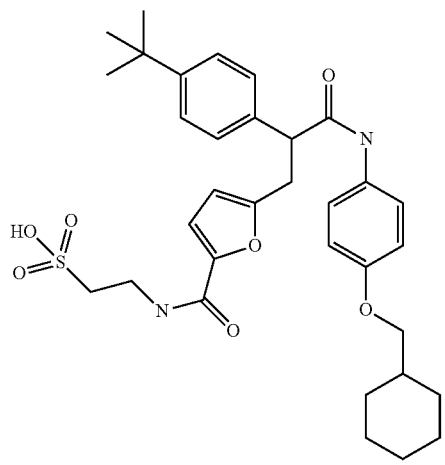 [SMILES: CC(C)(C)c1ccc(C(Cc2ccc(C(=O)NCCS(=O)(=O)O)o2)C(=O)Nc2ccc(OCC3CCCCC3)cc2)cc1] | 611.3 (+) | C30H36N2O5S + 2.5H2O + 0.16DMF C: 61.69; H: 7.15; N: 5.10 C: 61.41; H: 7.43; N: 5.49 |
| 1.073 | 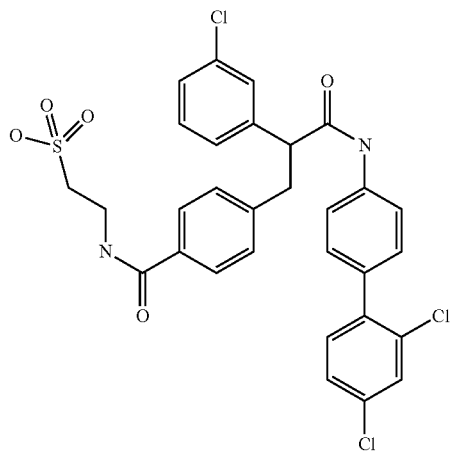 [SMILES: O=C(NCCS(=O)(=O)O)c1ccc(CC(C(=O)Nc2ccc(-c3ccc(Cl)cc3Cl)cc2)c2cccc(Cl)c2)cc1] | 631.4 (−) | C30H25Cl3N2O5S + 1.7H2O C: 54.38, H: 4.32, N: 4.23 C: 54.04, H: 4.07, N: 4.34 |
| 1.074 | 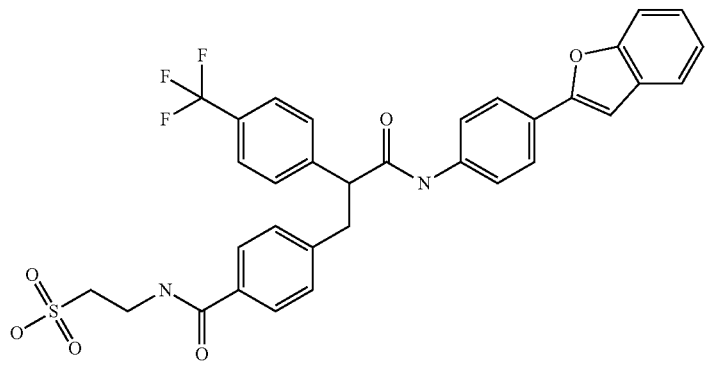 [SMILES: O=C(NCCS(=O)(=O)O)c1ccc(CC(C(=O)Nc2ccc(-c3cc4ccccc4o3)cc2)c2ccc(C(F)(F)F)cc2)cc1] | 637.3 (+) | C33H27N2O6F3S + 2.6 H2O + 0.1 TFA C: 57.39, H: 4.69, N: 4.03 C: 57.67, H: 5.20, N: 4.20 |

-continued

| Example | STRUCTURE | MASS SPECT. (MODE) | Formula CHN (Calcd) CHN (Found) |
|---|---|---|---|
| 1.075 | 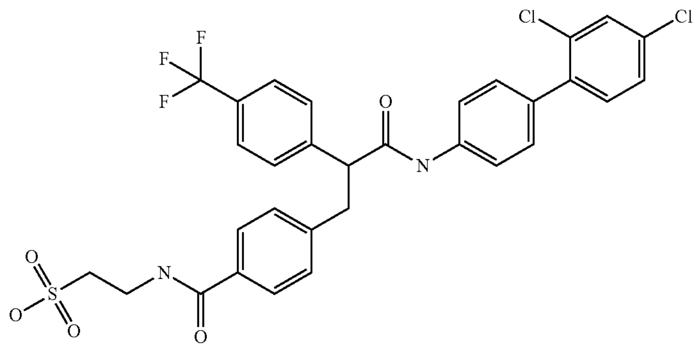 [SMILES: O=C(NCCS(=O)(=O)O)c1ccc(CC(C(=O)Nc2ccc(-c3ccc(Cl)cc3Cl)cc2)c2ccc(C(F)(F)F)cc2)cc1] | 665.2 (+) | C31H25N2O5F3Cl2S + 1.4 H2O + 0.1 TFA<br>C: 53.37, H: 4.01, N: 3.99<br>C: 53.15, H: 4.53, N: 4.39 |
| 1.076 | 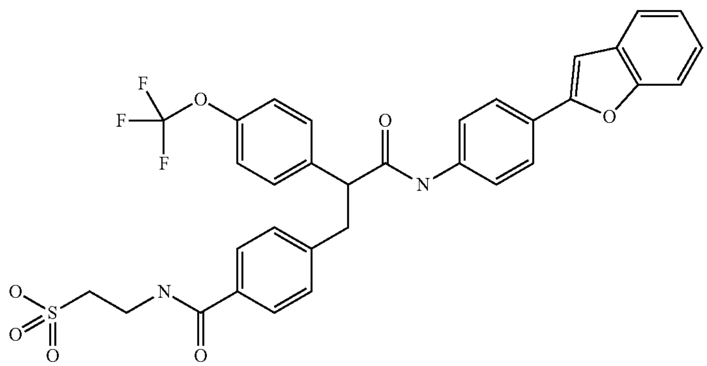 [SMILES: O=C(NCCS(=O)(=O)O)c1ccc(CC(C(=O)Nc2ccc(-c3cc4ccccc4o3)cc2)c2ccc(OC(F)(F)F)cc2)cc1] | 653.6 (+) | C33H27F3N2O7S + 0.8 H2O + 0.1 TFA<br>C: 58.77, H: 4.26, N: 4.13<br>C: 58.37, H: 4.16, N: 4.55 |
| 1.077 | 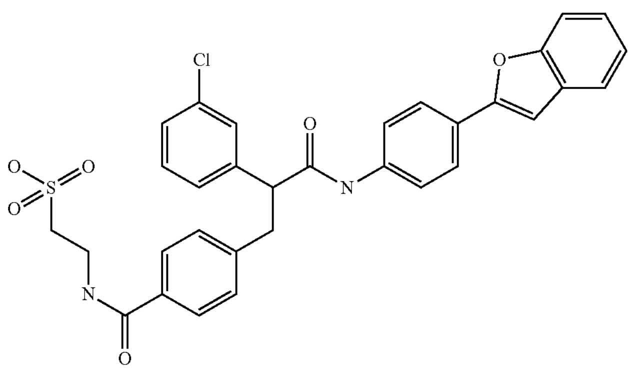 [SMILES: O=C(NCCS(=O)(=O)O)c1ccc(CC(C(=O)Nc2ccc(-c3cc4ccccc4o3)cc2)c2cccc(Cl)c2)cc1] | 601.6 (−) | C32H27ClN2O6S + 1.3H2O<br>C: 61.35, H: 4.76, N: 4.47<br>C: 61.07, H: 4.79, N: 4.68 |
| 1.078 | 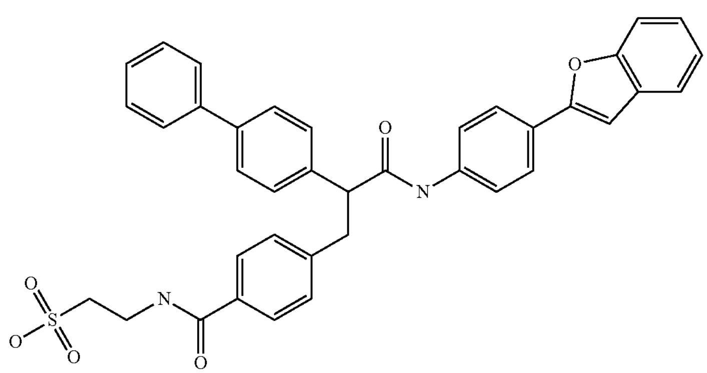 [SMILES: O=C(NCCS(=O)(=O)O)c1ccc(CC(C(=O)Nc2ccc(-c3cc4ccccc4o3)cc2)c2ccc(-c3ccccc3)cc2)cc1] | 645.4 (+) | C38H32N2O6S + 2.6 H2O + 0.3 DMF<br>C: 65.48, H: 5.55, N: 4.52<br>C: 65.88, H: 5.98, N: 4.22 |

| Example | STRUCTURE | MASS SPECT. (MODE) | Formula CHN (Calcd) CHN (Found) |
|---|---|---|---|
| 1.079 | 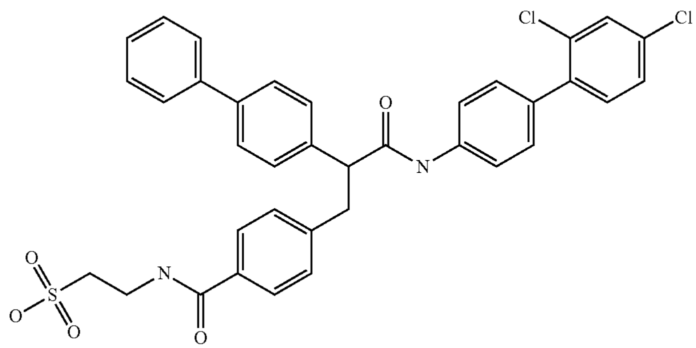 [SMILES: O=C(NCCS(=O)(=O)O)c1ccc(CC(C(=O)Nc2ccc(-c3ccc(Cl)cc3Cl)cc2)c2ccc(-c3ccccc3)cc2)cc1] | 673.4 (+) | C36H30N2O5Cl2S + 2.6 H2O + 0.6 DMF<br>C: 59.40, H: 5.20, N: 4.76<br>C: 59.29, H: 5.55, N: 4.78 |
| 1.080 | 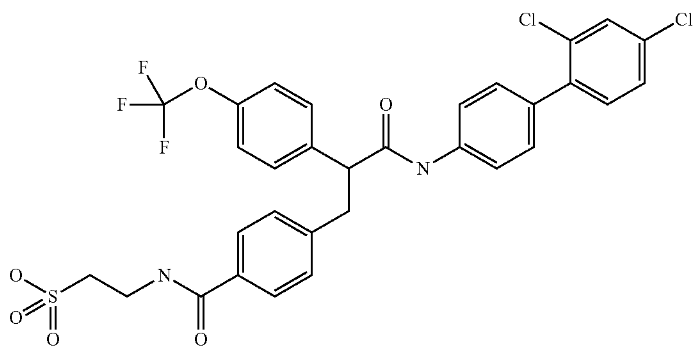 [SMILES: O=C(NCCS(=O)(=O)O)c1ccc(CC(C(=O)Nc2ccc(-c3ccc(Cl)cc3Cl)cc2)c2ccc(OC(F)(F)F)cc2)cc1] | 681.4 (+) | C31H25Cl2F3N2O6S + 1 H2O + 0.1 TFA<br>C: 52.55, H: 3.84, N: 3.94<br>C: 52.33, H: 4.21, N: 3.95 |
| 1.081 | 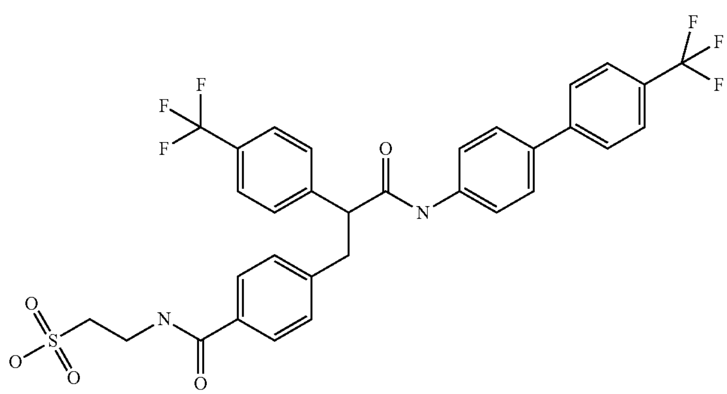 [SMILES: O=C(NCCS(=O)(=O)O)c1ccc(CC(C(=O)Nc2ccc(-c3ccc(C(F)(F)F)cc3)cc2)c2ccc(C(F)(F)F)cc2)cc1] | 665.6 (+) | C32H26N2O5F6S + 2.7 H2O + 0.3 TFA<br>C: 52.38, H: 4.27, N: 3.75<br>C: 52.21, H: 4.58, N: 4.10 |
| 1.082 | 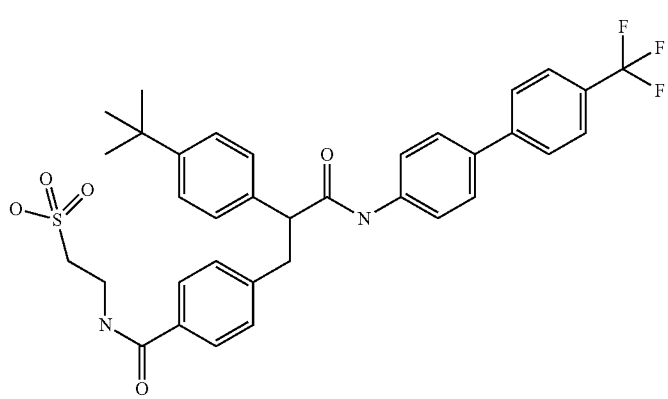 [SMILES: CC(C)(C)c1ccc(C(Cc2ccc(C(=O)NCCS(=O)(=O)O)cc2)C(=O)Nc2ccc(-c3ccc(C(F)(F)F)cc3)cc2)cc1] | 651.6 (−) | C35H35F3N2O5S + 2.1H2O<br>C: 60.88, H: 5.72, N: 4.06<br>C: 61.26, H: 6.20, N: 4.37 |

-continued

| Example | STRUCTURE | MASS SPECT. (MODE) | Formula CHN (Calcd) CHN (Found) |
|---|---|---|---|
| 1.083 | 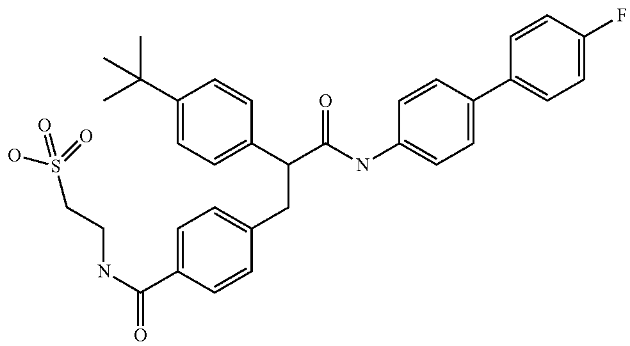 [SMILES: CC(C)(C)c1ccc(C(Cc2ccc(C(=O)NCCS(=O)(=O)O)cc2)C(=O)Nc2ccc(-c3ccc(F)cc3)cc2)cc1] | 601.6 (−) | C34H35FN2O5S + 1.9H2O<br>C: 64.11, H: 6.14, N: 4.40<br>C: 64.27, H: 5.94, N: 4.60 |
| 1.084 | 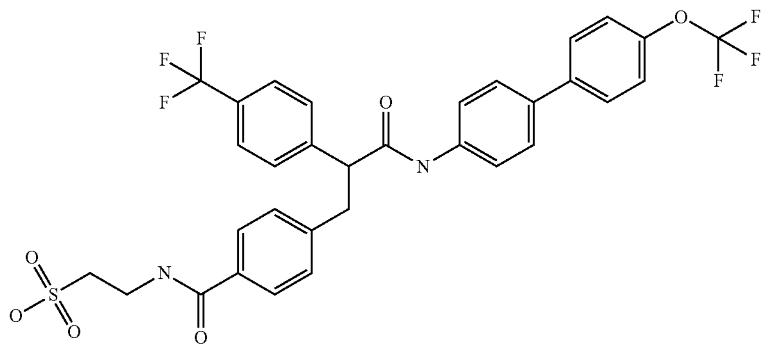 [SMILES: O=C(NCCS(=O)(=O)O)c1ccc(CC(C(=O)Nc2ccc(-c3ccc(OC(F)(F)F)cc3)cc2)c2ccc(C(F)(F)F)cc2)cc1] | 681.4 (+) | C32H26N2O6F6S + 1.2 H2O + 0.2 TFA<br>C: 53.67, H: 3.98, N: 3.86<br>C: 53.64, H: 4.02, N: 4.11 |
| 1.085 | 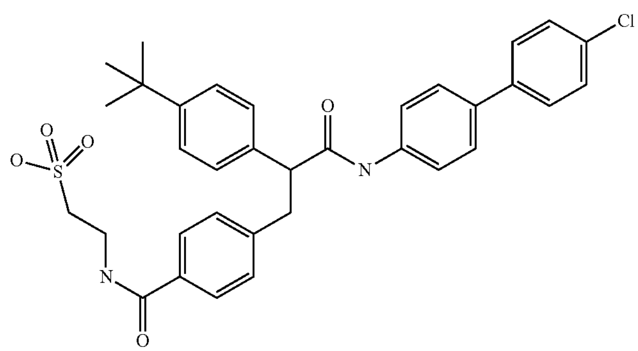 [SMILES: CC(C)(C)c1ccc(C(Cc2ccc(C(=O)NCCS(=O)(=O)O)cc2)C(=O)Nc2ccc(-c3ccc(Cl)cc3)cc2)cc1] | 617.4 (−) | C34H35ClN2O5S + 1.7H2O + 0.1TFA<br>C: 62.12, H: 5.87, N: 4.24<br>C: 61.84, H: 6.20, N: 4.14 |
| 1.086 | 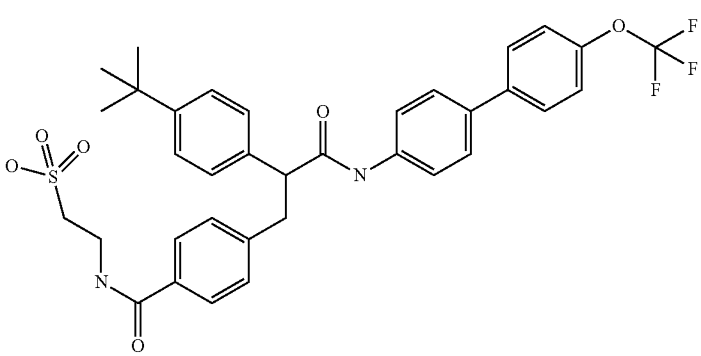 [SMILES: CC(C)(C)c1ccc(C(Cc2ccc(C(=O)NCCS(=O)(=O)O)cc2)C(=O)Nc2ccc(-c3ccc(OC(F)(F)F)cc3)cc2)cc1] | 667.4 (−) | C35H35F3N2O6S + 2.0H2O<br>C: 59.65, H: 5.58, N: 3.97<br>C: 59.38, H: 4.94, N: 3.96 |

-continued

| Example | STRUCTURE | MASS SPECT. (MODE) | Formula CHN (Calcd) CHN (Found) |
|---|---|---|---|
| 1.087 | 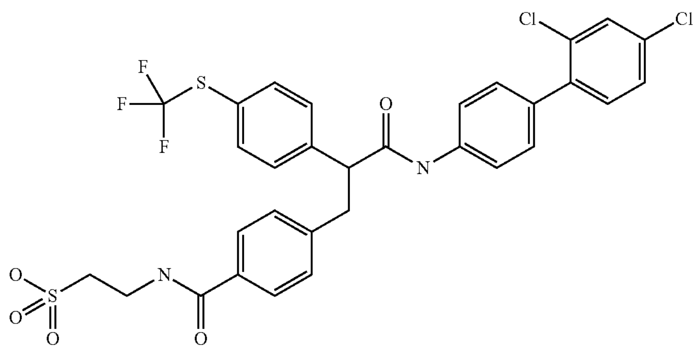 [SMILES: O=C(NCCS(=O)(=O)O)c1ccc(CC(C(=O)Nc2ccc(-c3ccc(Cl)cc3Cl)cc2)c2ccc(SC(F)(F)F)cc2)cc1] | 699.1 (+) | C31H25Cl2F3N2O5S + 1.8 H2O<br>C: 51.00, H: 3.95, N: 3.84<br>C: 50.89, H: 3.57, N: 3.75 |
| 1.088 | 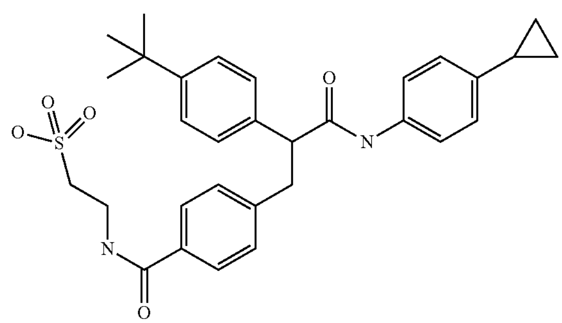 [SMILES: CC(C)(C)c1ccc(C(Cc2ccc(C(=O)NCCS(=O)(=O)O)cc2)C(=O)Nc2ccc(C3CC3)cc2)cc1] | 547.6 (−) | C31H36N2O5S + 2.3H2O<br>C: 63.09, H: 6.93, N: 4.75<br>C: 62.93, H: 7.19, N: 4.77 |
| 1.089 | 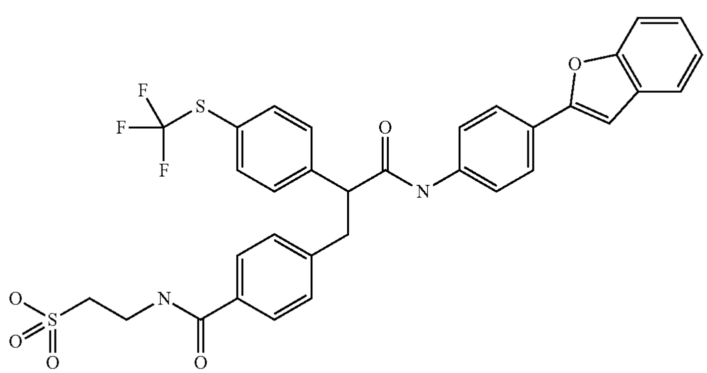 [SMILES: O=C(NCCS(=O)(=O)O)c1ccc(CC(C(=O)Nc2ccc(-c3cc4ccccc4o3)cc2)c2ccc(SC(F)(F)F)cc2)cc1] | 669.4 (+) | C33H27F3N2O6S2 + 1.5 H2O<br>C: 56.97, H: 4.35, N: 4.03<br>C: 56.81, H: 3.99, N: 4.25 |
| 1.090 | 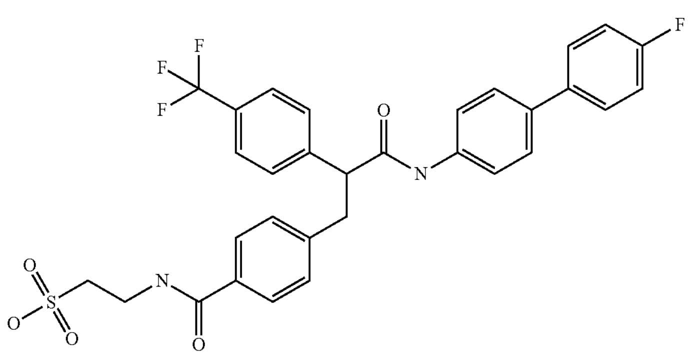 [SMILES: O=C(NCCS(=O)(=O)O)c1ccc(CC(C(=O)Nc2ccc(-c3ccc(F)cc3)cc2)c2ccc(C(F)(F)F)cc2)cc1] | 615.4 (+) | C31H26N2O5F4S + 0.9 H2O + 0.3 TFA<br>C: 57.07, H: 4.26, N: 4.21<br>C: 56.76, H: 3.83, N: 4.64 |

-continued

| Example | STRUCTURE | MASS SPECT. (MODE) | Formula CHN (Calcd) CHN (Found) |
|---|---|---|---|
| 1.091 | 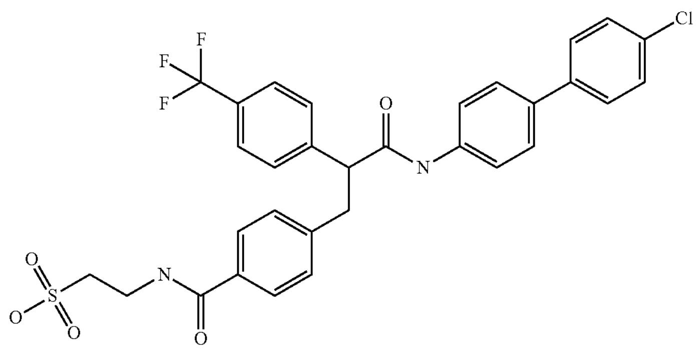 [SMILES: O=C(NCCS(=O)(=O)O)c1ccc(CC(C(=O)Nc2ccc(-c3ccc(Cl)cc3)cc2)c2ccc(C(F)(F)F)cc2)cc1] | 631.6 (+) | C31H26N2O5F3ClS + 2.6 H2O + 0.1 TFA<br>C: 54.36, H: 4.58, N: 4.06<br>C: 54.53, H: 4.88, N: 4.43 |
| 1.092 | 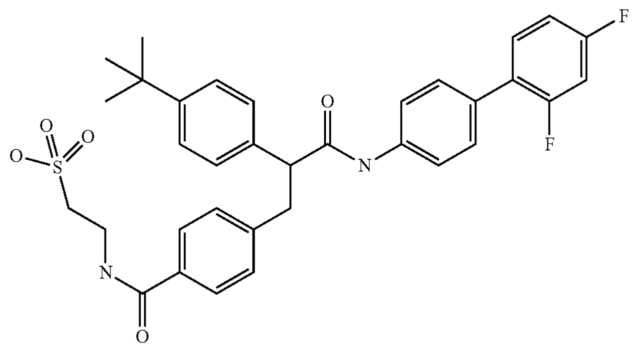 [SMILES: CC(C)(C)c1ccc(C(Cc2ccc(C(=O)NCCS(=O)(=O)O)cc2)C(=O)Nc2ccc(-c3ccc(F)cc3F)cc2)cc1] | 619.4 (−) | C34H34F2N2O5S + 1.6H2O<br>C: 62.87, H: 5.77, N: 4.31<br>C: 62.60, H: 5.62, N: 4.50 |
| 1.093 | 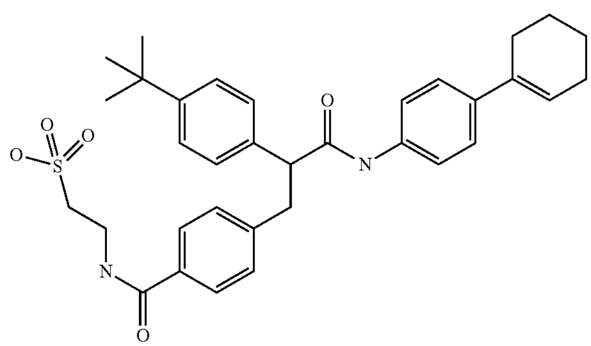 [SMILES: CC(C)(C)c1ccc(C(Cc2ccc(C(=O)NCCS(=O)(=O)O)cc2)C(=O)Nc2ccc(C3=CCCCC3)cc2)cc1] | 587.4 (−) | C34H40N2O5S + 2.5H2O<br>C: 64.43, H: 7.16, N: 4.42<br>C: 64.10, H: 6.43, N: 4.34 |
| 1.094 | 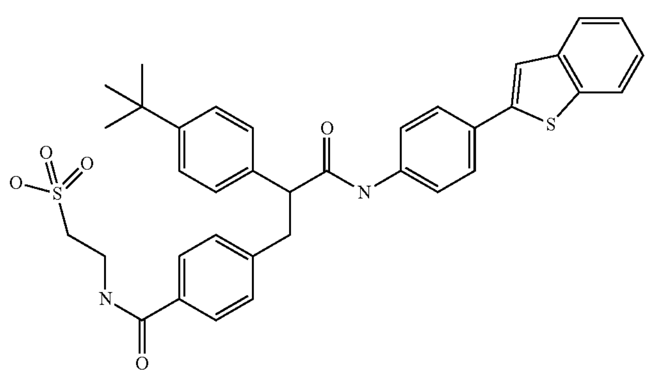 [SMILES: CC(C)(C)c1ccc(C(Cc2ccc(C(=O)NCCS(=O)(=O)O)cc2)C(=O)Nc2ccc(-c3cc4ccccc4s3)cc2)cc1] | 639.6 (−) | C36H36N2O5S2 + 1.8H2O<br>C: 64.23, H: 5.93, N: 4.16<br>C: 64.06, H: 5.73, N: 4.14 |

-continued

| Example | STRUCTURE | MASS SPECT. (MODE) | Formula CHN (Calcd) CHN (Found) |
|---|---|---|---|
| 1.095 | 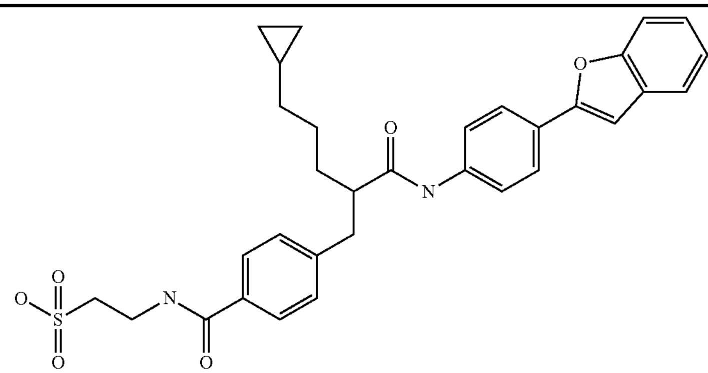 | 573.7 (−) | C 32 H34 N2 O6 S + 3 H2O C: 61.13 H: 6.41 N: 4.46 C: 53.75 H: 4.41 N: 6.91 |
| 1.096 | 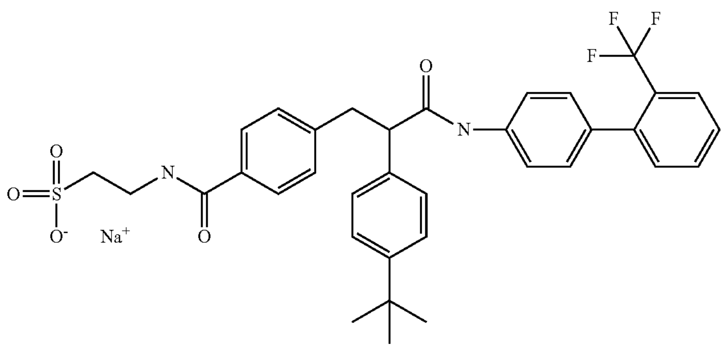 [SMILES: CC(C)(C)c1ccc(C(Cc2ccc(C(=O)NCCS(=O)(=O)[O-])cc2)C(=O)Nc2ccc(-c3ccccc3C(F)(F)F)cc2)cc1 ; [Na+]] | 651.19 (−) | C35H34N2O5SF3Na + (2.2) H2O C: 58.85, H: 5.42, N: 3.92 C: 58.52, H: 5.03, N: 4.03 |
| 1.097 | 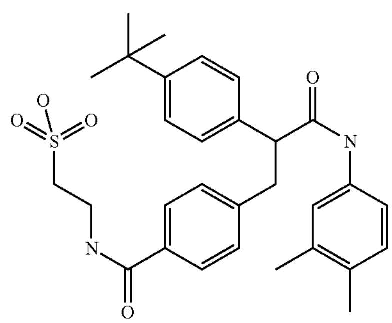 [SMILES: Cc1ccc(NC(=O)C(Cc2ccc(C(=O)NCCS(=O)(=O)O)cc2)c2ccc(C(C)(C)C)cc2)cc1C] | 537.3 (+) | C30H36N2O5S + 2.5H2O + 0.16DMF C: 61.69, H: 7.15, N: 5.10 C: 61.41, H: 7.43, N: 5.49 |

Example 1.098

Precursor 1:

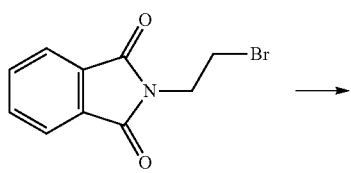

→

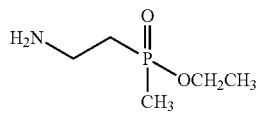

A mixture of 2.372 g of the commercially available N-(2-bromoethyl)phthalimide and 5.00 g of diethylmethylphosphonite was heated at 140° C. for a 21 h period. The volatiles were removed under reduced pressure and the residue purified by chromatography on silica gel (methanol-dichloromethane gradient). The product was obtained as a yellow oil. HNMR (300 MHz, DMSO-$d_6$): 7.8 (4H, m), 3.83 (6H, m), 2.10 (2H, m), 1.46 (3H, d, J=13.9 Hz), 1.10 (3H, t, J=7.0 Hz).

The oil obtained in the previous step (2.454 g) in 7 mL of ethanol was treated with 2.12 mL of hydrazine hydrate. The resulting mixture was heated to reflux for a 2 h period and allowed to cool to room temperature. The white precipitate formed was removed by filtration and the solution concentrated under reduced pressure to afford Precursor 1 as a yellow oil HNMR (300 MHz, DMSO-$d_6$): 3.90 (4H, m), 2.75 (2H, m), 2.60 (2H, broad), 1.80 (2H, m), 1.38 (3H, d, J=13.8 Hz), 1.20 (3H, t, J=7.0 Hz)

Step A

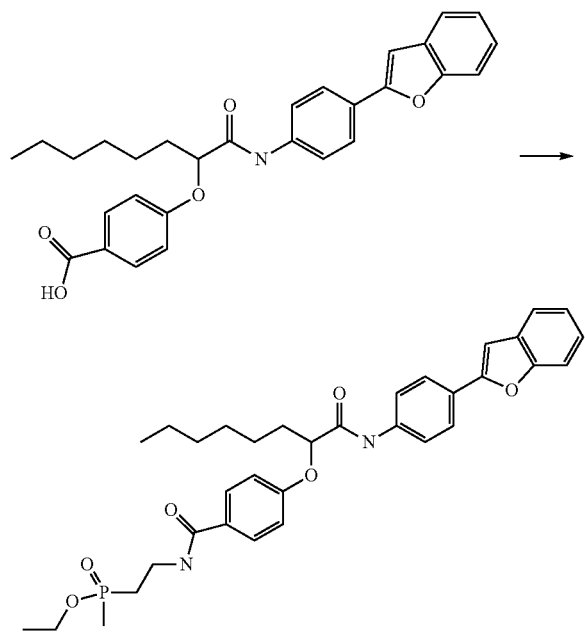

4-[1-(4-Benzofuran-2-yl-phenylcarbamoyl)-heptyloxy]-benzoic acid was prepared as described in Bioorganic & Medicinal Chemistry Letters 14 (2004) 2047-2050. To a solution of 200 mg of the starting carboxylic acid (prepared as described in Bioorganic & Medicinal Chemistry Letters 2004, 14, 2047-2050) in THF was added carbonyl diimidazole (85 mg) and the solution stirred at room temperature for 1 h. Precursor 1 (77 mg) was added in one portion and the reaction mixture was stirred for a further 1 h period. The mixture was then diluted with ethyl acetate and washed with water. After drying over magnesium sulfate and concentration, the crude product was chromatographed on silica gel using an ethyl acetate-hexanes gradient.

$^1$H NMR (CDCl$_3$): δ 8.30 (1H, s), 7.80-7.87 (4H, m), 7.72 (1H, m), 7.63-7.66 (2H, d, J=8.8 Hz), 7.52-7.58 (2H, m), 7.20-7.29 (2H, m), 7.00-7.03 (2H, d, J=8.8 Hz), 6.97 (1H, s), 4.71-4.75 (1H, t, J=5.7 Hz), 4.06-4.19 (2H, m), 3.74-3.82 (2H, m), 2.01-2.11 (2H, m), 1.51-1.55 (3H, d, J=13.5 Hz), 1.45-1.52 (2H, m), 1.20-1.35 (11H, m), 0.86-0.90 (3H, t, J=6.7 Hz).

Step B

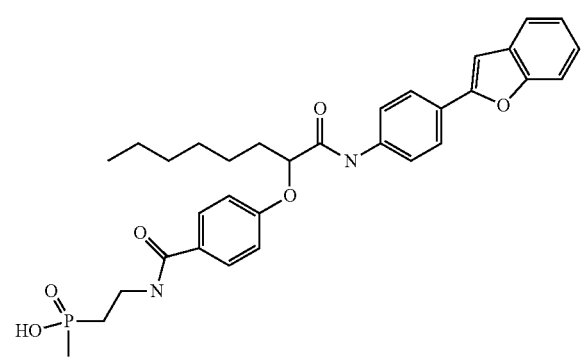 [SMILES: CCCCCCC(Oc1ccc(C(=O)NCCP(C)(=O)O)cc1)C(=O)Nc1ccc(-c2cc3ccccc3o2)cc1]

A solution of 70 mg of phosphinic ester (from Step A above) in dichloromethane was treated with 0.174 mL of bromotrimethylsilane. The mixture was stirred at room temperature for 3 days. The reaction mixture was diluted with water and acetonitrile (1:1) and stirred at room temperature for a further 0.5 h. The mixture was evaporated under reduced pressure and partitioned between ethyl acetate and water. The organic phase was washed with water and saturated sodium chloride and dried over magnesium sulfate. Chromatography on reverse phase silica gel using an acetonitrile-water gradient yielded the product as a white solid.

$^1$H NMR (DMSO-d6): δ 8.53 (1H, s), 8.47-8.49 (1H, t, J=5.3 Hz), 7.74-7.80 (2H, d, J=9.3 Hz), 7.54-7.55 (2H, d, J=8.8 Hz), 7.31-7.35 (2H, d, J=7.7 Hz), 7.21-7.23 (2H, d, J=9.1 Hz), 4.61 (2H, s), 4.06 (1H, m), 3.45 (2H, m), 1.69-1.89 (2H, m), 1.64-1.75 (4H, m), 1.31-1.34 (3H, d, J=14 Hz), 1.36-1.41 (2H, m), 1.06-1.11 (2H, m), 0.84-0.87 (1H, m), 0.81 (9H, s).

Example 1.099: 2-{4-[2-(4-tert-Butylphenyl)-2-(4-cyclohexylmethoxyphenylcarbamoyl)-ethyl]-phenoxy}-ethanesulfonic acid Step A

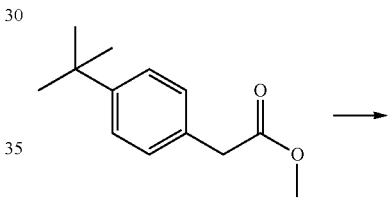

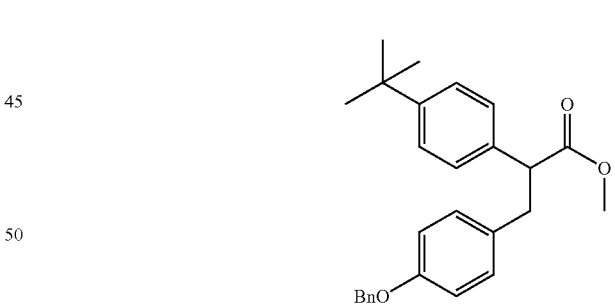

To a 2M solution of LDA in THF (5.4 mL, 10.8 mmol) in 300 mL THF cooled to −78° C. was slowly added 4-tertbutylphenyl acetic acid methyl ester (2 g, 9.8 mmol). After stirring for 1 hr at −78° C. a solution of 2.7 g of 1-benzyloxy-4-bromomethylbenzene (Chow and Mak, J. Org. Chem 1997, 62(15), 5116) in THF (10 mL) was added. The mixture was allowed to warm to room temperature overnight. Saturated ammonium chloride was added and the solution extracted with ethyl acetate. The solution was washed with brine, dried over sodium sulfate and concentrated to afford 3-(4-Benzyloxyphenyl)-2-(4-tert-butylphenyl)-propionic acid methyl ester as a yellow oil. TLC: R$_f$=0.42 hexane/ethyl acetate (8:1). The crude was carried on as is for the next step.

Step B

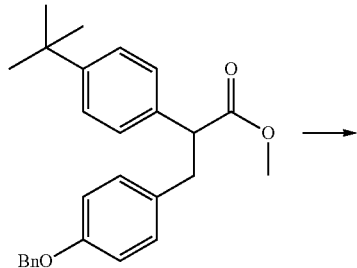

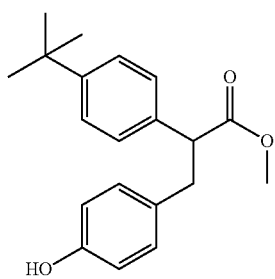

The mixture of crude 3-(4-Benzyloxyphenyl)-2-(4-tert-butylphenyl)-propionic acid methyl ester from step A and 10% Pd/C (200 mg) in methanol (75 mL) was stirred under an atmosphere of $H_2$ overnight. The mixture was filtered through celite and concentrated under vacuum to afford 2-(4-tert-Butylphenyl)-3-(4-hydroxyphenyl)-propionic acid methyl ester as a light yellow oil. TLC: $R_f$=0.15 hexane/ethyl acetate (7:1).

Step C: Precursor 2

To 2-Benzyloxyethanol (1.1 g, 7.3 mmol) and N,N-diisopropyl ethylamine (1.3 mL, 8.1 mmol) in dichloromethane (30 mL) at 0-4° C. was added trifluoromethane sulfonic anhydride (1.4 mL, 8.1 mmol). The solution was stirred for 1 hr then quenched with water. The mixture was partitioned and the organic portion washed with brine, dried over sodium sulfate then concentrated to afford trifluoromethanesulfonic acid 2-benzyloxy-ether ester as a dark colored oil (1.74 g, 83%). $^1$H NMR (300 MHz, DMSO-d6): 7.41 (m, 5H), 4.60 (s, 2H), 4.35 (m, 2H), 3.75 (m, 2H).

Step D

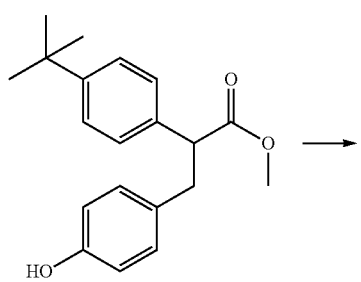

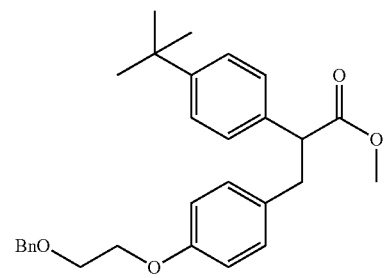

To a solution of 2-(4-tert-Butylphenyl)-3-(4-hydroxyphenyl)-propionic acid methyl ester (419 mg, 1.3 mmol) in anhydrous DMF (8 mL) was added NaH (54 mg, 1.3 mmol, 60%). After $H_2$ evolution had ceased, precursor 2 was added and the resulting mixture was allowed to stir at rt overnight. The reaction mixture was quenched with 1N HCl then extracted with diethyl ether. The organic portion was washed with brine, dried over $Na_2SO_4$ then concentrated to afford 3-[4-(2-Benzyloxyethoxy)-phenyl]-2-(4-tert-butylphenyl)-propionic acid methyl ester as an amber colored oil. TLC: $R_f$=0.48 hexane/ethyl acetate (4:1). The crude product was carried into the next step without further pruifications.

Step E

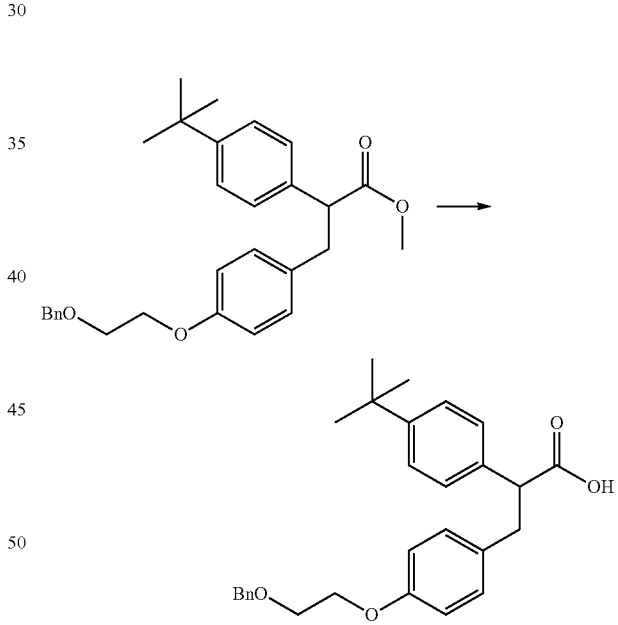

To the crude 3-[4-(2-Benzyloxyethoxy)-phenyl]-2-(4-tert-butylphenyl)-propionic acid methyl ester from step d dissolved in 20 mL of THF/MeOH/$H_2O$ (3:1:1) was added lithium hydroxide (270 mg, 6.5 mmol) After stirring for 5 hrs at rt, the organic solvents were removed under vacuum and the reaction residue diluted further with water (25 mL). The aqueous mixture was extracted with diethyl ether, made acidic with 1 N HCl and extracted again with ethyl acetate. The ethyl acetate portion was then dried over $Na_2SO_4$ and concentrated under vacuum to afford 3-[4-(2-Benzyloxyethoxy)-phenyl]-2-(4-tert-butylphenyl)-propionic acid as a semi-solid mass. (456 mg, 81% over 2 steps)

Step F

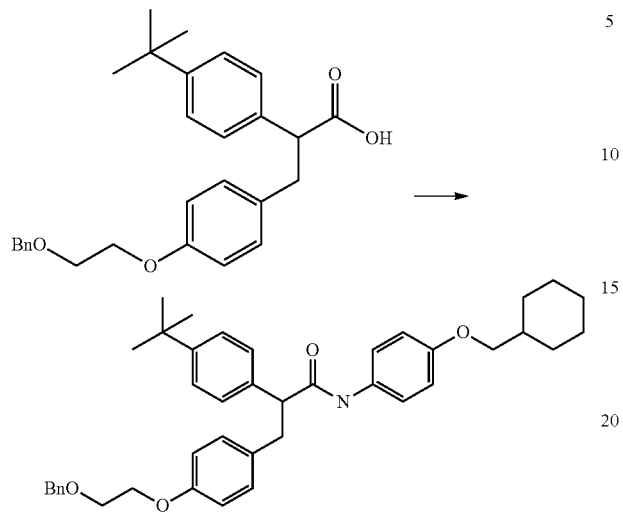

The compound 3-[4-(2-Benzyloxyethoxy)-phenyl]-2-(4-tert-butylphenyl)-N-(4-cyclohexylmethoxyphenyl)-propionamide was prepared from 3-[4-(2-Benzyloxyethoxy)-phenyl]-2-(4-tert-butylphenyl)-propionic acid according to the procedure described for the synthesis of Example 1.001, Step A. The crude was purified by chromatography on silica gel eluting with a gradient of ethyl acetate in hexane to afford the desired product. LC-MS m/z=619 [C$_{41}$H$_{49}$NO$_4$+H]$^+$.

Step G

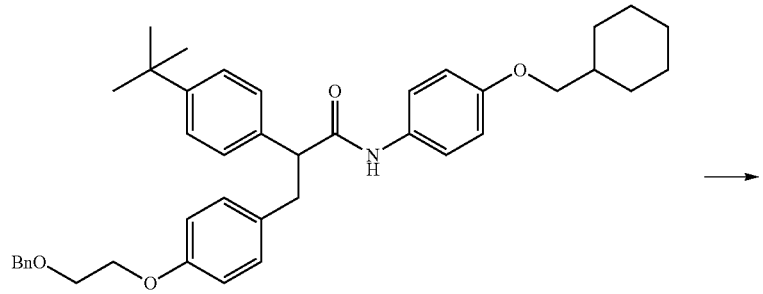

A mixture of 3-[4-(2-Benzyloxyethoxy)-phenyl]-2-(4-tert-butylphenyl)-N-(4-cyclohexylmethoxyphenyl)-propionamide (200 mg, 0.32 mmol) and 10% Pd/C (20 mg) in a solution of methanol/ethyl acetate (60 mL, 4:1) was stirred under an atmosphere of H$_2$ overnight. The mixture was filtered through celite and concentrated under vacuum. The crude was purified by chromatography on silica gel (ISCO cartridge, 40 g), eluting with dichloromethane over 20 minutes to afford 2-(4-tert-Butylphenyl)-N-(4-cyclohexylmethoxyphenyl)-3-[4-(2-hydroxy ethoxy)-phenyl]-propionamide (126 mg, 74%). LC-MS m/z=530 [C$_{34}$H$_{43}$NO$_4$+H]$^+$.

Step H

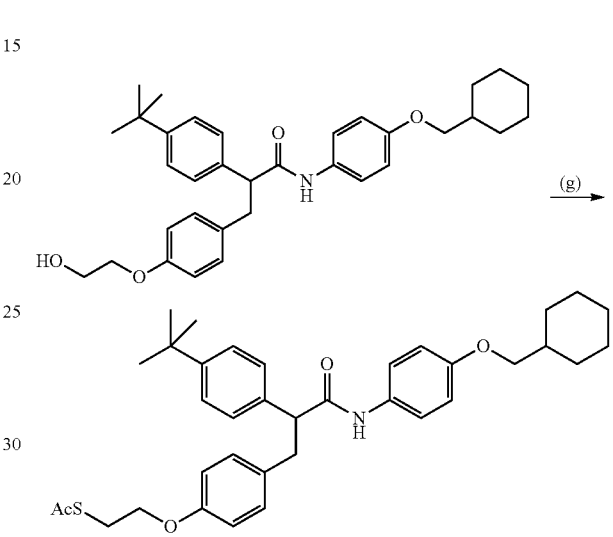

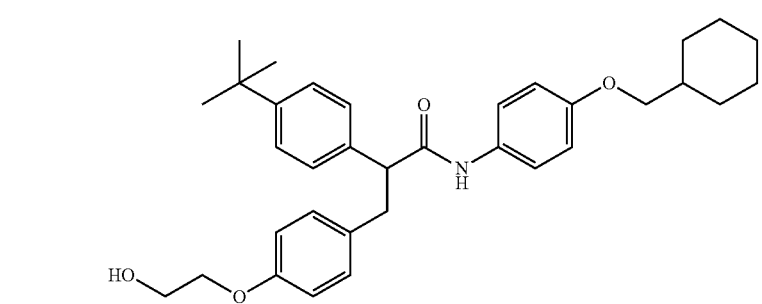

To a solution of triphenylphosphine (125 mg, 0.48 mmol) in anhydrous THF (5 mL) at 0° C. was added diisopropylazodicarboxylate (94 uL, 0.48 mmol). After stirring for 30 min. a solution consisting of thioacetic acid (34 uL, 0.48 mmol) and 2-(4-tert-Butylphenyl)-N-(4-cyclohexyl-methoxyphenyl)-3-[4-(2-hydroxyethoxy)-phenyl]-propionamide (126 mg, 0.23 mmol) was added. The resulting solution was allowed to warm to rt overnight. The mixture was partitioned between ethyl acetate and H₂O and the organic portion concentrated under vacuum. Purification of the crude by preparative TLC (SiO₂, 2 mm) using hexane/ethyl acetate (4:1) as eluant afforded Thioacetic acid S-(2-{4-[2-(4-tert-Butylphenyl)-2-(4-cyclohexylmethoxyphenyl carbamoyl)-ethyl]-phenoxy}-ethyl) ester (102 mg, 73%). TLC: $R_f$=0.38 hexane/ethyl acetate (4:1).

Step I

To a solution of Thioacetic acid S-(2-{4-[2-(4-tert-Butyl-phenyl)-2-(4-cyclohexyl methoxyphenylcarbamoyl)-ethyl]-phenoxy}-ethyl) ester (102 mg, 0.17 mmol) from Step H in formic acid (3 mL, 88%) chilled at 0° C. was added performic acid (1 mL) pre-chilled to 0° C. prior to addition. The resulting mixture was stirred at 0° C. for 2 hrs and allowed to warm to rt overnight. The reaction mixture was carefully concentrated under vacuum and the crude material purified by preparatory HPLC on a Shimadzu modular HPLC system using a Waters Atlantis dC18 30×150 mm preparatory column and running a gradient from 40% to 100% acetonitrile over 13 minutes. TFA was used as an ionizer and was present in 0.05% (v/v). Detection was accomplished using an in-line UV detector running at 254 nm. Rotary evaporation of the solvated compound provided the title compound (7.6 mg): ¹H NMR (500 MHz, CD3OD):

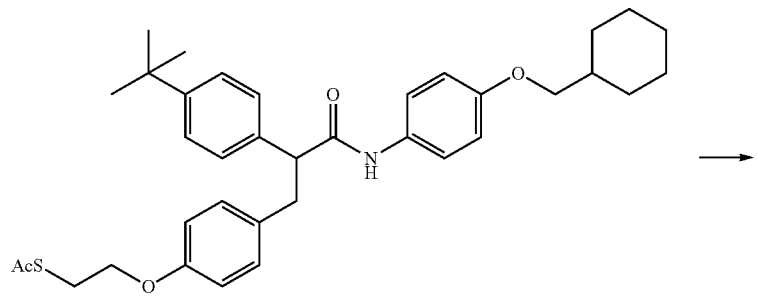

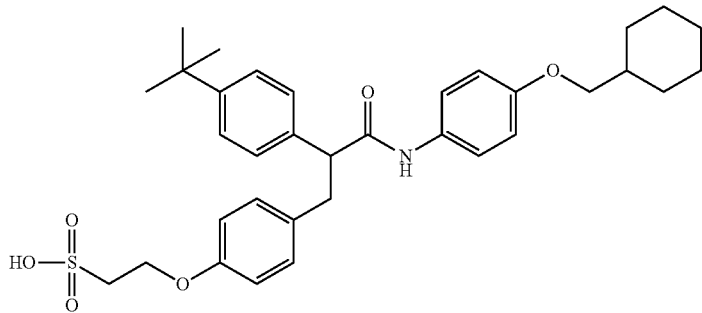

δ 7.35 (s, 4H), 7.25 (d, J=9.0 Hz, 2H), 7.12 (d, J=8.5 Hz, 2H), 6.83 (d, J=9.0 Hz, 2H), 6.79 (d, J=8.5 Hz, 2H), 4.32 (t, J=7.0 Hz, 2H), 3.83 (dd, J=10.0 Hz, J=9.5 Hz, 1H), 3.71 (d, J=6.5 Hz, 2H), 3.24 (t, J=7.0 Hz, 2H), 2.93 (dd, J=10.0 Hz, J=9.5 Hz, 1H), 1.85-1.69 (m, 6H), 1.35-1.21 (m, 11H), 1.10-1.03 (m, 3H). LC-MS m/z=592 $[C_{34}H_{43}N_2O_6S+H]^-$.

Example 1.100: 2-{4-[2-(4-tert-Butylphenyl)-2-(4-cyclohexylmethoxyphenylcarbamoyl-propyl]-phenoxy}-ethanesulfonic acid

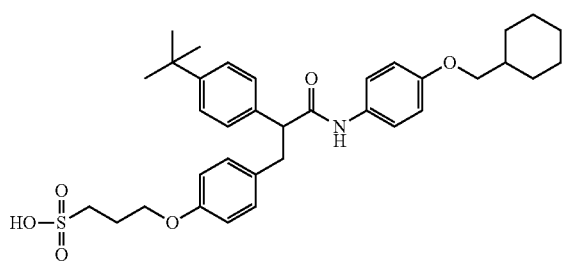 [SMILES: CC(C)(C)c1ccc(C(Cc2ccc(OCCCS(=O)(=O)O)cc2)C(=O)Nc2ccc(OCC3CCCCC3)cc2)cc1]

Precursor 3

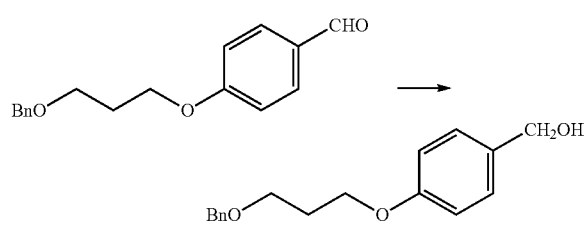

To a solution of 4-(3-Benzyloxypropoxy)-benzaldehyde (1.9 g, 6.9 mmol) in methanol (30 mL) chilled to 0° C. was added portionwise NaBH$_4$ (523 mg, 13.8 mmol). The resulting mixture was stirred for 1 hr before being quenched with water. After extracting with EtOAc the organic portion was washed with brine, dried over Na$_2$SO$_4$ and concentrated under vacuum to afford 4-(3-Benzyloxypropoxy)-methanol as a colorless oil (1.86 g, 99%). TLC: R$_f$=0.21 hexane/ethyl acetate (4:1).

To a solution of 4-(3-Benzyloxypropoxy)-methanol (1.86 g, 6.8 mmol) in diethyl ether chilled to 0° C. was slowly added PBr$_3$ (1.9 mL, 20.4 mmol). After stirring for 2 hrs the reaction was carefully quenched by addition of ice and then water. The mixture was partitioned and the organic portion washed with brine, dried over Na$_2$SO$_4$ and concentrated under vacuum to afford 1-(3-Benzyloxypropoxy)-4-bromomethylbenzene as a colorless oil.

Step A

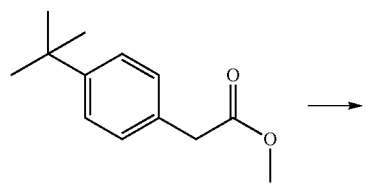

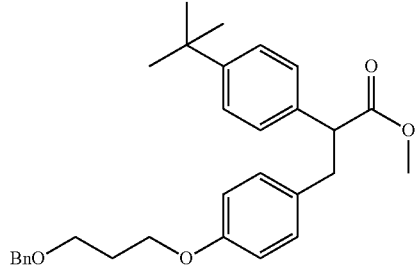

The compound 3-[4-(3-Benzyloxypropoxy)-phenyl]-2-(4-tert-butylphenyl)-propionic acid methyl ester was prepared from 4-tertbutylphenyl acetic acid methyl ester according to the procedure described for the synthesis of Example 1.099, step A. TLC: R$_f$=0.55 hexane/ethyl acetate (4:1).

Step B

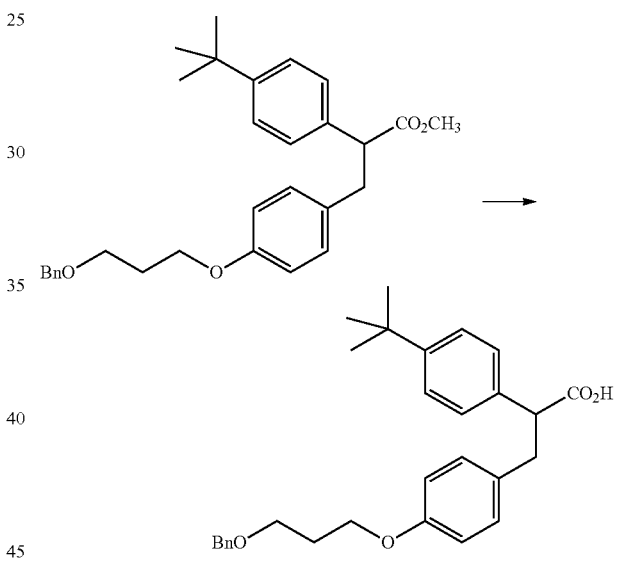

The compound 3-[4-(3-Benzyloxypropoxy)-phenyl]-2-(4-tert-butylphenyl)-propionic acid was prepared from the corresponding methyl ester according to the procedure described for the synthesis of Example 1.099), step E.

Step C

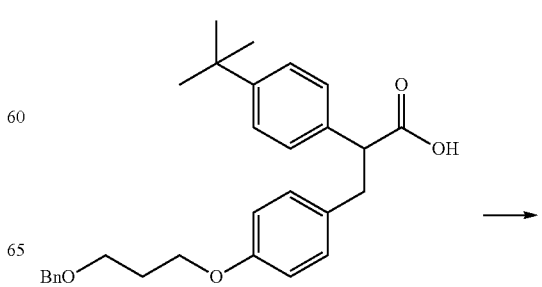

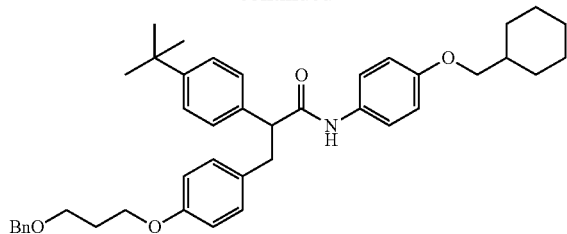

The compound 3-[4-(3-Benzyloxypropoxy)-phenyl]-2-(4-tert-butylphenyl)-N-(4-cyclohexylmethoxyphenyl)-propionamide was prepared from [4-(3-Benzyloxypropoxy)-phenyl]-2-(4-tert-butylphenyl)-propionic acid according to the procedure described for the synthesis of Example 1.099 step F. The crude was purified by chromatography on silica gel eluting with a gradient of ethyl acetate in hexanes. TLC: $R_f$=0.42 hexane/ethyl acetate (4:1).

Step D

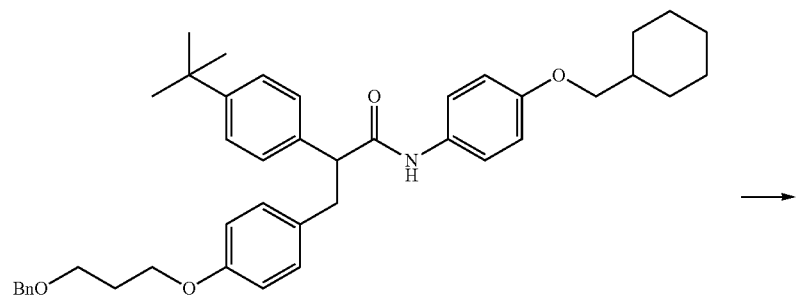

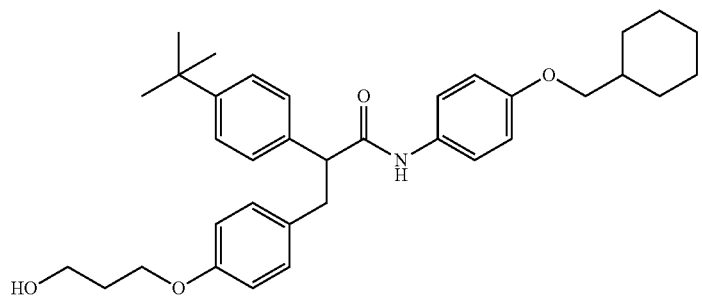

The compound 2-(4-tert-Butylphenyl)-N-(4-cyclohexylmethoxyphenyl)-3-[4-(3-hydroxypropoxy)phenyl]-propionamide was prepared from 3-[4-(3-Benzyloxypropoxy)-phenyl]-2-(4-tert-butylphenyl)-N-(4-cyclohexylmethoxyphenyl)-propionamide according to the procedure described for the synthesis of Example 1.099, step G. The crude was purified by chromatography on silica gel eluting with a gradient of methanol in dichloromethane. TLC: $R_f$=0.40 dichloromethane/methanol (20:1).

Step E

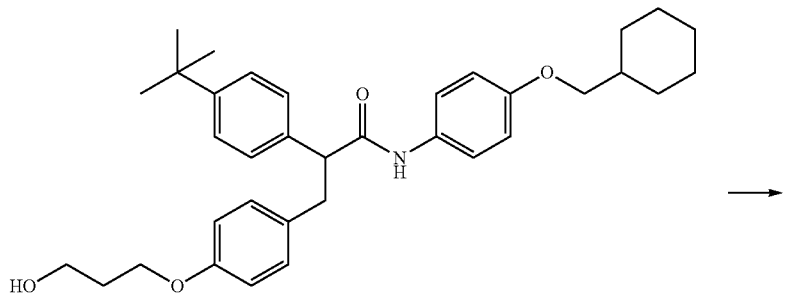

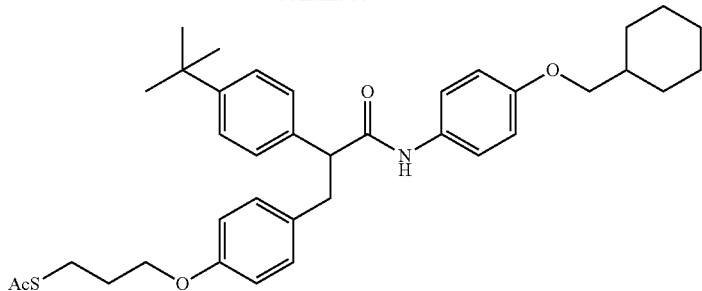

The compound Thioacetic acid S-(2-{4-[2-(4-tert-Butyl-phenyl)-2-(4-cyclohexyl methoxyphenylcarbamoyl)-propyl]-phenoxy}-ethyl) ester was prepared from 2-(4-tert-Butylphenyl)-N-(4-cyclohexylmethoxyphenyl)-3-[4-(3-hydroxypropoxy)phenyl]-propionamide according to the procedure described for the synthesis of Example 1.099, step H. (105 mg, 81%). TLC: $R_f$=0.36 hexane/ethyl acetate (4:1).

Step F

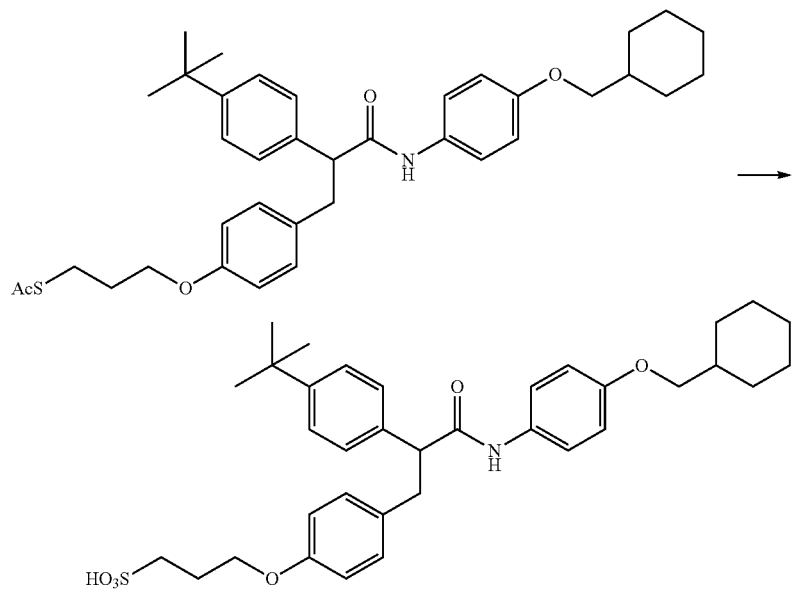

The title compound was prepared from Thioacetic acid S-(2-{4-[2-(4-tert-Butyl phenyl)-2-(4-cyclohexylmethoxy-phenylcarbamoyl)-propyl]-phenoxy}-ethyl) ester according to the procedure described for the synthesis of Example 1.099, step 1. (8 mg). $^1$H NMR (300 MHz, DMSO-d6): δ 9.84 (s, 1H), 7.40 (d, J=9.3 Hz, 2H), 7.34 (s, 4H), 7.12 (d, J=8.7 Hz, 2H), 6.81-6.77 (m, 4H), 3.97 (t, J=6.6 Hz, 2H), 3.83 (dd, J=9.6 Hz, J=9.3 Hz, 1H), 3.69 (d, J=6.3 Hz, 2H), 2.81 (dd, J=9.6 Hz, J=9.3 Hz, 1H), 1.99-1.89 (m, 2H), 1.80-1.60 (m, 6H), 1.25-1.11 (m, 12H), 1.0-0.95 (m, 2H). LC-MS m/z=606 [$C_{35}H_{45}N_2O_6S$+H]$^-$.

Example 1.101: 2-{4-[(4-tert-Butyl-phenyl)-(4-cyclohexylmethoxy-phenylcarbamoyl)-methylsulfanyl]-benzoylamino}-ethanesulfonic acid Step A

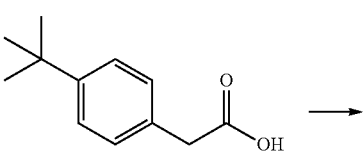

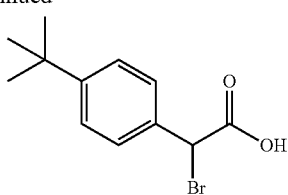

To a stirring solution of (4-tert-butyl-phenyl)-acetic acid (1.5 g, 7.8 mmol) in benzene (30 mL) at room temperature was added NBS (1.39 g, 7.8 mmol) and AIBN (15 mg, 0.08 mmol). The mixture was heated at 70° C. for 16 hrs, added EtOAc and water. The organic layer was collected and dried over Na$_2$SO$_4$, filtered and concentrated under reduced pressure to afford crude bromo-(4-tert-butyl-phenyl)-acetic acid as a light yellow solid (2.1 g, 99%): $^1$H NMR (300 MHz, DMSO-d$_6$): 7.46 (m, 4H), 5.74 (s, 1H), 1.29 (s, 9H).

Step B

To a stirring solution of bromo-(4-tert-butyl-phenyl)-acetic acid (1.2 g, 4.43 mmol) in toluene (20 mL) was added SOCl$_2$ (0.8 mL, 11.1 mmol). The mixture was stirred at 90° C. for 1 hr and concentrated under reduced pressure. This crude product was dissolved into toluene (20 ml), and 4-cyclohexylmethoxy-phenylamine (0.91 g, 4.43 mmol) and ethyl-diisopropyl-amine (0.85 mL, 4.87 mmol) were added at room temperature. The reaction mixture was stirred at room temperature for 1 hr. The reaction mixture was quenched with water and diluted with EtOAc. The organic layer was dried over Na$_2$SO$_4$, filtered and concentrated under reduced pressure. The crude product was purified by column chromatography on silica gel, eluting with ethyl acetate-hexanes (3:7) to afford 2-bromo-2-(4-tert-butyl-phenyl)-N-(4-cyclohexylmethoxy-phenyl)-acetamide as a brown oil (1.2 g, 59%): $^1$H NMR (300 MHz, DMSO-d$_6$): δ 10.35 (s, 1H) 7.49 (m, 6H), 6.87 (d, J=9.3 Hz, 2H), 5.74 (s, 1H), 3.75 (d, J=6.3 Hz, 2H), 1.69 (m, 6H), 1.27 (m, 12H), 1.09 (m, 2H).

Step C

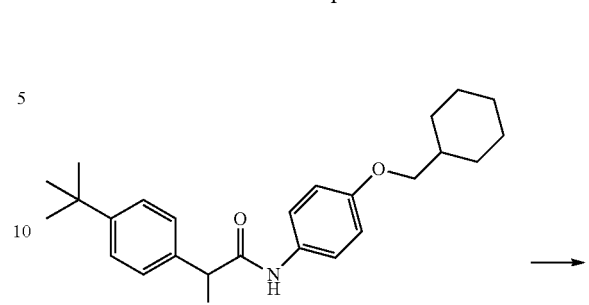

To a stirring solution of 4-mercapto-benzoic acid methyl ester (0.44 g, 2.6 mmol) in DMF (20 mL) at room temperature was added Cs$_2$CO$_3$ (1.7 g, 5.2 mmol) and a solution of 2-bromo-2-(4-tert-butyl-phenyl)-N-(4-cyclohexylmethoxy-phenyl)-acetamide (1.2 g, 2.6 mmol) in DMF (10 mL). The reaction mixture was stirred at room temperature for 16 hrs. The solvent was removed under reduced pressure and the residue was partitioned between ethyl acetate and water. The organic layer was dried over Na$_2$SO$_4$, filtered and concentrated under reduced pressure. The crude product was purified by column chromatography on silica gel, eluting with ethyl acetate-hexanes (4:6) to afford the crude product, then it was washed with MeOH to afford 4-[(4-tert-butyl-phenyl)-(4-cyclohexylmethoxy-phenylcarbamoyl)-methylsulfanyl]-benzoic acid methyl ester as a white solid (0.45 g, 32%): $^1$H NMR (300 MHz, DMSO-d$_4$): δ 10.33 (s, 1H), 7.89 (d, J=8.4 Hz, 2H), 7.59 (m, 8H), 6.86 (d, J=9.0 Hz, 2H), 5.49 (s, 1H), 3.84 (s, 3H), 3.75 (d, J=6.3 Hz, 2H), 1.69 (m, 6H), 1.27 (s, 9H), 1.24 (m, 3H), 1.08 (m, 2H).

Step D

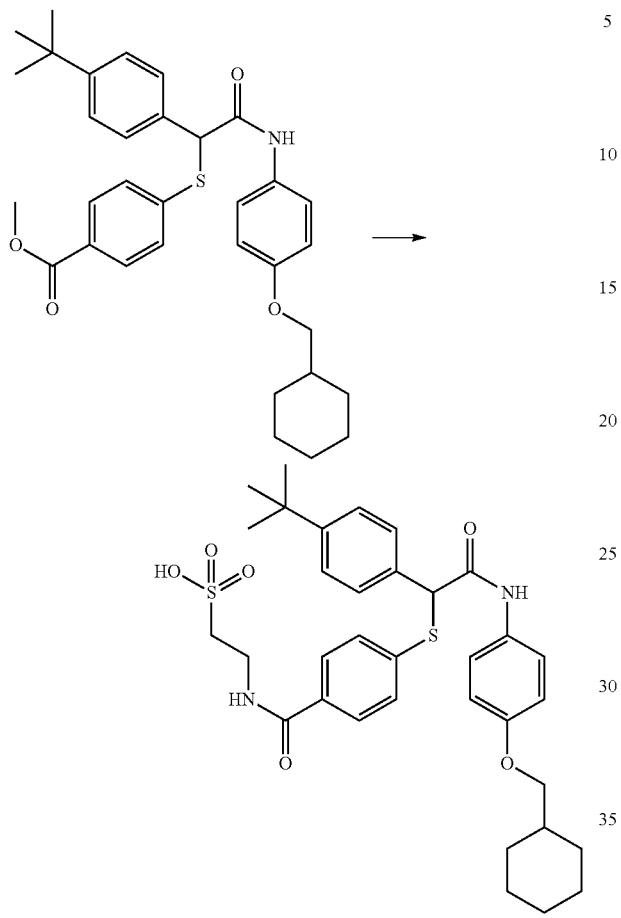

To a stirring solution of 4-[(4-tert-butyl-phenyl)-(4-cyclohexylmethoxy-phenylcarbamoyl)-methylsulfanyl]-benzoic acid methyl ester (0.33 g, 0.61 mmol) in THF (8 mL), methanol (6 mL) and water (2 mL) at room temperature was added LiOH (0.145 g, 6.1 mmol). The reaction mixture was stirred at room temperature for 16 hr. The mixture was acidified with 1M aqueous HCl and extracted with ethyl acetate. The solution was washed with water and saturated sodium chloride and dried over magnesium sulfate. The solvent was removed under reduced pressure. The crude product was purified by column chromatography on silica gel, eluting with MeOH—$CH_2Cl_2$ (5:95) to afford 4-[(4-tert-butyl-phenyl)-(4-cyclohexylmethoxy-phenylcarbamoyl)-methylsulfanyl]-benzoic acid as a white solid (0.24 g, 74%): $^1$H NMR (300 MHz, DMSO-$d_6$): δ 10.33 (s, 1H), 7.89 (d, J=8.4 Hz, 2H), 7.59 (m, 8H), 6.86 (d, J=9.0 Hz, 2H), 5.49 (s, 1H), 3.75 (d, J=6.3 Hz, 2H), 1.69 (m, 6H), 1.27 (s, 9H), 1.24 (m, 3H), 1.08 (m, 2H). Then a mixture of 4-[(4-tert-butyl-phenyl)-(4-cyclohexylmethoxy-phenylcarbamoyl)-methylsulfanyl]-benzoic acid (240 mg, 0.45 mmol), HOBt (104 mg, 0.68 mmol), EDCI (130 mg, 0.68 mmol), taurine (85 mg, 0.68 mmol) and diisopropylethylamine (0.24 mL, 1.35 mmol) in DMF (15 mL) was stirred at 23° C. for a period of 16 h. The mixture was concentrated under reduced pressure and the residue partitioned between ethyl acetate and aqueous 1M HCl. The organic phase was washed (water, sat NaCl) and dried over magnesium sulfate. The solvent was removed under reduced pressure. The crude product was purified by chromatographed on reverse phase silica gel (C18) using a gradient of acetonitrile:water (20% to 80% in acetonitrile). Evaporation of the product-containing fractions afforded 150 mg of 2-{4-[(4-tert-butyl-phenyl)-(4-cyclohexylmethoxy-phenylcarbamoyl)-methylsulfanyl]-benzoylamino}-ethanesulfonic acid as a white solid. $^1$H NMR (300 MHz, DMSO-$d_6$): δ 10.33 (s, 1H), 8.49 (m, 1H), 7.73 (d, J=8.4 Hz, 2H), 7.45 (m, 8H), 6.86 (d, J=9.0 Hz, 2H), 5.41 (s, 1H), 3.72 (d, J=6.3 Hz, 2H), 3.49 (m, 2H), 2.57 (m, 2H), 1.69 (m, 6H), 1.27 (s, 9H), 1.24 (m, 3H), 1.08 (m, 2H). LC-MS m/z=639.3 [C34H42N2O6S2+H]$^+$; Anal Calcd for (C34H42N2O6S2+2.5H$_2$O): C, 59.71; H, 6.93; N, 4.10. Found: C, 59.70; H, 6.16; N, 4.20.

Example 1.102: 2-{4-[(4-tert-Butyl-phenyl)-(4-cyclohexylmethoxy-phenylcarbamoyl)-methanesulfonyl]-benzoylamino}-ethanesulfonic acid

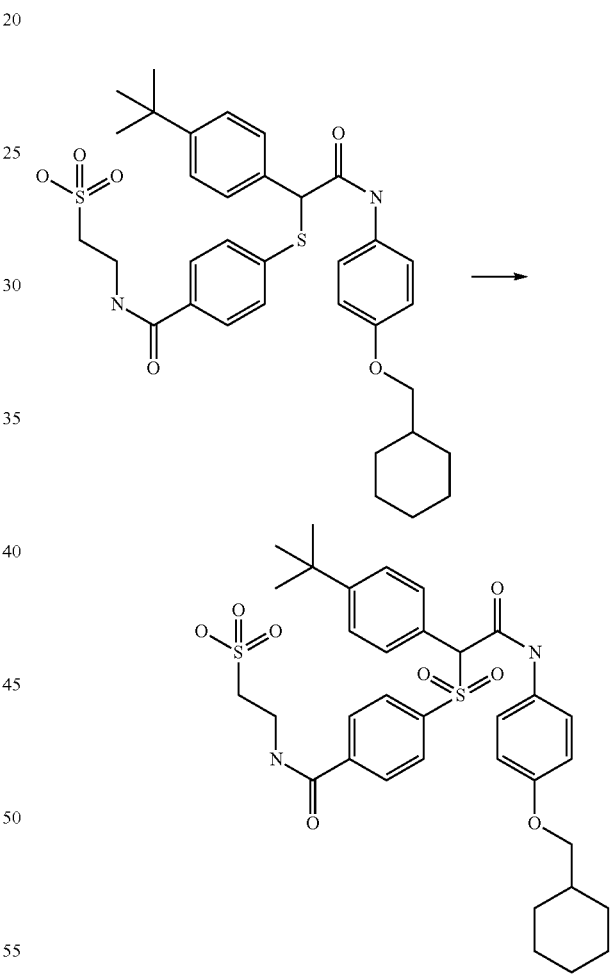

To a stirring solution of 2-{4-[(4-tert-butyl-phenyl)-(4-cyclohexylmethoxy-phenylcarbamoyl)-methylsulfanyl]-benzoylamino}-ethanesulfonic acid (Example 1.101, 80 mg, 0.125 mmol) in $CH_2Cl_2$ (15 mL) at room temperature was added m-CPBA (71 mg, 0.413 mmol). The reaction mixture was stirred at room temperature for 16 hrs. The solvent was removed under reduced pressure and the residue was purified by chromatographed on reverse phase silica gel (C18) using a gradient of acetonitrile:water (20% to 80% in acetonitrile). Evaporation of the product-containing fractions afforded 50 mg of 2-{4-[(4-tert-butyl-phenyl)-(4-cyclohexylmethoxy-phenylcarbamoyl)-methanesulfonyl]-benzoylamino}-ethanesulfonic acid as a white solid. $^1$H NMR (300 MHz, DMSO-$d_6$): δ 10.23 (s, 1H), 8.79 (m, 1H), 7.95 (d, J=8.4 Hz, 2H), 7.73 (d, J=8.4 Hz, 2H), 7.45 (m, 6H), 6.86 (d, J=9.0 Hz, 2H), 5.54 (s, 1H), 3.72 (d, J=6.3 Hz, 2H), 3.49 (m, 2H), 2.57 (m, 2H), 1.69 (m, 6H), 1.27 (s, 9H), 1.24 (m, 3H), 1.08 (m, 2H). LC-MS m/z=671.2 [C34H42N2O8S2+H]$^+$; Anal Calcd for (C34H42N2O8S2+2.3H$_2$O): C, 57.33; H, 6.59; N, 3.93. Found: C, 56.95; H, 6.36; N, 4.46.

Example 1.103: 2-{4-[(4-tert-Butyl-phenyl)-(4-cyclohexylmethoxy-phenylcarbamoyl)-methanesulfinyl]-benzoylamino}-ethanesulfonic acid

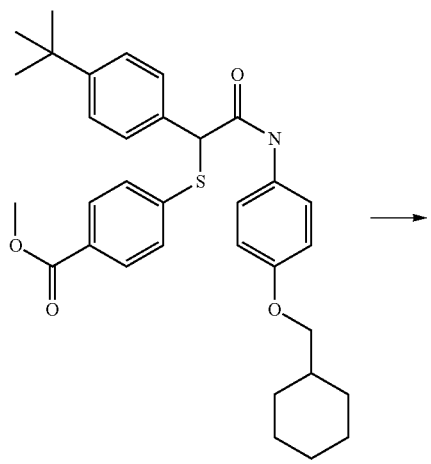

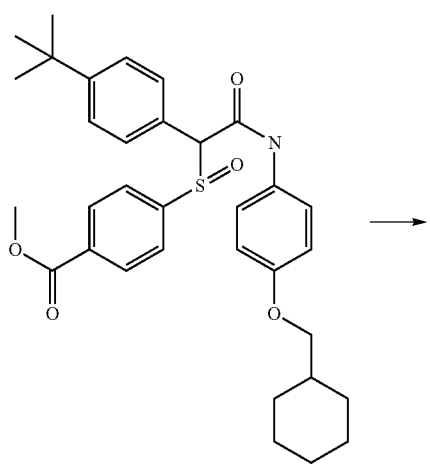

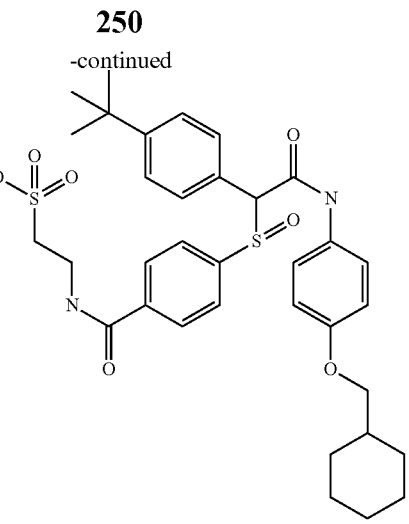

The intermediate from Example 1.101, Step C, was treated with MCPBA in dichloromethane and converted into the corresponding sulfoxide. Application of the method shown in Example 1.101 gave the targeted sulfonic acid as a white solid, LC-MS m/z=655.3 [C34H42N2O7S2+H]$^+$; Anal Calcd for (C34H42N2O7S2+3.3H$_2$O): C, 57.17; H, 6.86; N, 3.92. Found: C, 56.86; H, 6.43; N, 3.95.

Example 1.104: 2-{4-[(4-Benzofuran-2-yl-phenylcarbamoyl)-(4-tert-butyl-phenyl)-methoxy]-benzoylamino}-ethanesulfonic acid

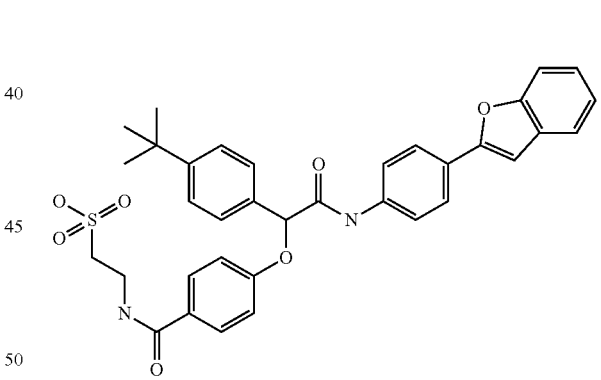

2-{4-[(4-Benzofuran-2-yl-phenylcarbamoyl)-(4-tert-butyl-phenyl)-methoxy]-benzoylamino}-ethanesulfonic acid was prepared as a white solid using methods that were described in Example 1.098.

$^1$H NMR (300 MHz, DMSO-$d_6$): δ 10.55 (s, 1H), 8.38 (m, 1H), 7.85 (d, J=8.7 Hz, 2H), 7.74 (m, 4H), 7.57 (m, 4H), 7.44 (d, J=8.7 Hz, 2H), 7.23 (m, 3H), 7.07 (d, J=9.0 Hz, 2H), 5.95 (s, 1H), 3.49 (m, 2H), 2.61 (m, 2H), 1.26 (s, 9H). LC-MS m/z=625.6 [C35H34N2O7S−H]$^−$; Anal Calcd for (C35H34N2O7S+1.2H$_2$O): C, 64.84; H, 5.66; N, 4.32. Found: C, 64.54; H, 5.60; N, 4.96.

Example 1.105: 2-{4-[(4-Benzofuran-2-yl-phenyl-carbamoyl)-(4-tert-butyl-phenyl)-methylsulfanyl]-benzoylamino}-ethanesulfonic acid

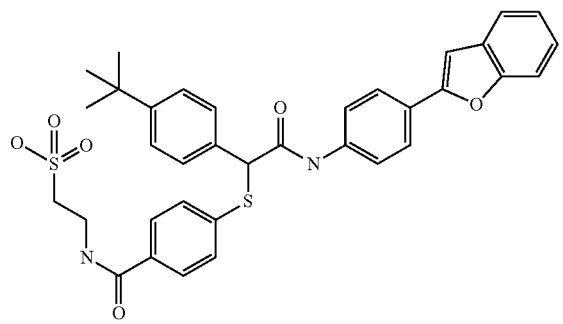 [SMILES: CC(C)(C)c1ccc(C(Sc2ccc(C(=O)NCCS(=O)(=O)O)cc2)C(=O)Nc2ccc(-c3cc4ccccc4o3)cc2)cc1]

2-{4-[(4-Benzofuran-2-yl-phenylcarbamoyl)-(4-tert-butyl-phenyl)-methylsulfanyl]-benzoylamino}-ethanesulfonic acid was prepared as a white solid using those methods that were described in Example 1.101.

$^1$H NMR (300 MHz, DMSO-$d_6$): δ 10.62 (s, 1H), 8.42 (m, 1H), 7.85 (d, J=9.0 Hz, 2H), 7.57 (m, 8H), 7.24 (m, 7H), 5.44 (s, 1H), 3.49 (m, 2H), 2.61 (m, 2H), 1.23 (s, 9H). LC-MS m/z=641.4 [C35H34N2O6S2−H]$^−$; Anal Calcd for (C35H34N2O6S2+1.7H$_2$O): C, 62.43; H, 5.60; N, 4.16. Found: C, 62.09; H, 5.22; N, 4.04.

Example 1.106

2-{4-[(4-Benzofuran-2-yl-phenylcarbamoyl)-(4-tert-butyl-phenyl)-methoxy]-3-fluoro-benzoylamino}-ethanesulfonic acid

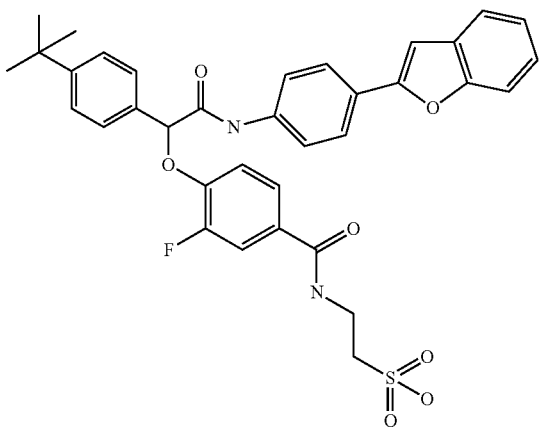 [SMILES: CC(C)(C)c1ccc(C(Oc2ccc(C(=O)NCCS(=O)(=O)O)cc2F)C(=O)Nc2ccc(-c3cc4ccccc4o3)cc2)cc1]

$^1$H NMR (CD$_3$OD): δ 7.83-7.84 (2H, d, J=8.3 Hz), 7.63-7.69 (3H, m), 7.55-7.57 (4H, m), 7.45-7.48 (3H, m), 7.10-7.26 (4H, m), 5.86 (1H, s), 3.75 (2H, m), 3.05 (3H, m), 1.30 (9H, s).

Example 1.107

Step A: 5-[(E)-2-(4-tert-Butyl-phenyl)-2-carboxy-vinyl]-thiophene-2-carboxylic acid methyl ester

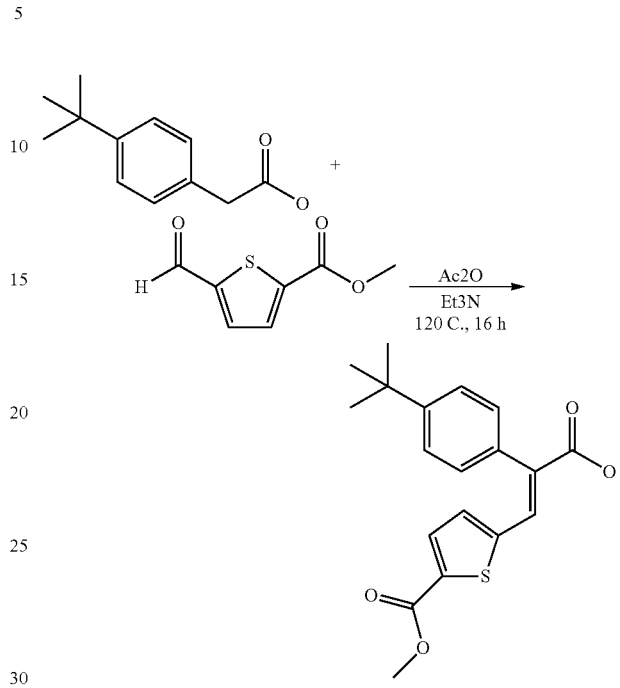

To (4-tert-butyl-phenyl)-acetic acid (1.15 g, 6.0 mmol) was added 5-formyl-thiophene-2-carboxylic acid methyl ester (1 g, 5.7 mmol), acetic anhydride (3.08 g, 30.2 mmol), and triethyl amine (574 mg, 5.7 mmol). The resulting mixture was stirred at 120° C. for 16 hours and cooled down. Water (1.9 ml) was added. The reaction mixture was heated up to 100° C. for 5 minutes in microwave and cooled down to 23° C. A mixture of acetic acid and water (2.5 ml:2.5 ml) was added. The resulting reaction mixture was stirred at 23° C. for 1 hour. The precipitate was filtered off, washed with 25% aqueous acetic acid, then water. The solid was dried under high vacuum to afford 5-[(E)-2-(4-tert-Butyl-phenyl)-2-carboxy-vinyl]-hiophene-2-carboxylic acid methyl ester as a brownish solid (1.32 g, 67%).

$^1$H NMR (CDCl$_3$): δ 8.03 (1H, s), 7.58-7.59 (1H, d, J=3.8 Hz), 7.51-7.54 (2H, d, J=8.2 Hz), 7.17-7.20 (2H, d, J=8.2 Hz), 7.09-7.10 (1H, d, J=4.1 Hz), 3.79 (3H, s), 1.39 (9H, s).

Step B: 5-[2-(4-tert-Butyl-phenyl)-2-carboxy-ethyl]-thiophene-2-carboxylic acid methyl ester

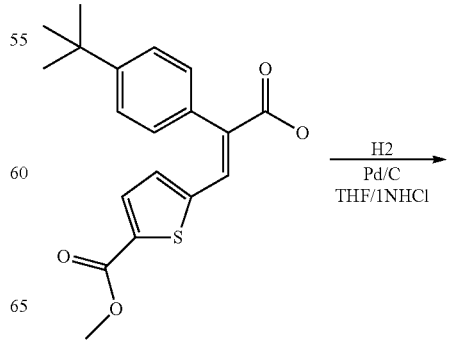

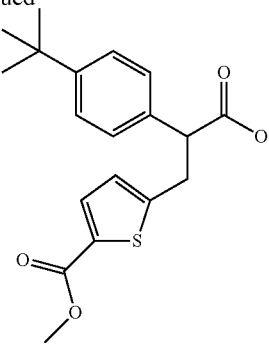

To 5-[(E)-2-(4-tert-Butyl-phenyl)-2-carboxy-vinyl]-thiophene-2-carboxylic acid methyl ester (600 mg, 1.7 mmol) in 50 ml THF and 10 ml 1N HCl was added 10% palladium on carbon (1.5 g). The resulting mixture was stirred under 50 psi hydrogen gas for 2 hours. The catalyst was filtered off and the solvent was evaporated. The residue was sonicated in hexane for 30 seconds. The solvent was filtered to afford 5-[2-(4-tert-Butyl-phenyl)-2-carboxy-ethyl]-thiophene-2-carboxylic acid methyl ester as a yellow solid (480 mg, 81%).

¹H NMR (CDCl₃): δ 7.58-7.59 (2H, d, J=3.8 Hz), 7.36-7.37 (2H, d, J=4.7 Hz), 7.24-7.26 (1H, d, J=3.7 Hz), 6.75-6.76 (1H, d, J=3.8 Hz), 3.85 (3H, s), 3.85-3.92 (1H, m), 3.60-3.68 (1H, m), 3.22-3.27 (1H, m), 1.31 (9H, s).

Step C: 5-[2-(4-tert-Butyl-phenyl)-2-(4-iodo-phenylcarbamoyl)-ethyl]-thiophene-2-carboxylic acid methyl ester

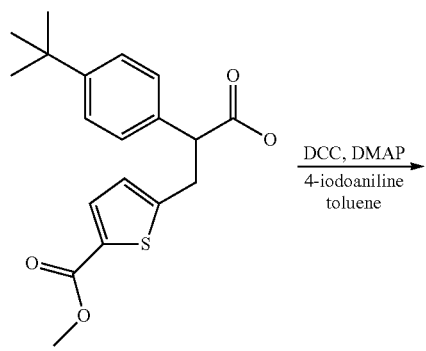

To 5-[2-(4-tert-Butyl-phenyl)-2-carboxy-ethyl]-thiophene-2-carboxylic acid methyl ester (424 mg, 1.22 mmol) in toluene (10 ml) was added N,N'-dicyclohexylcarbodiimide (504 mg, 2.44 mmmol), 4-iodoaniline (267 mg, 1.22 mmol), and 4-dimethylaminopyridine (15 mg, 0.122 mmol). The resulting mixture was stirred at 115° C. for 16 hours. The solid was filtered off and the solvent was evaporated. Chromatography of the residue (10% ethyl acetate in hexane) afforded 5-[2-(4-tert-Butyl-phenyl)-2-(4-iodo-henyl-carbamoyl)-ethyl]-thiophene-2-carboxylic acid methyl ester as a white foam (640 mg, 96%).

¹H NMR (CDCl₃): δ 7.56-7.59 (3H, m), 7.37-7.42 (2H, m), 7.20-7.35 (4H, m), 7.05 (1H, s), 6.72-6.73 (1H, d, J=3.7 Hz), 3.84 (3H, s), 3.80-3.85 (1H, m), 3.66-3.76 (1H, m), 3.22-3.26 (1H, m), 1.31 (9H, s).

Step D: 5-[2-(4-tert-Butyl-phenyl)-2-(4-iodo-phenylcarbamoyl)-ethyl]-thiophene-2-carboxylic acid

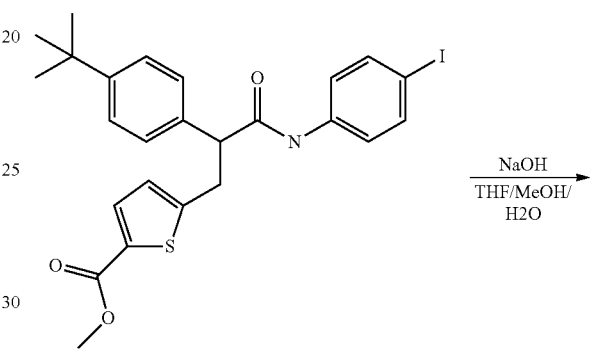

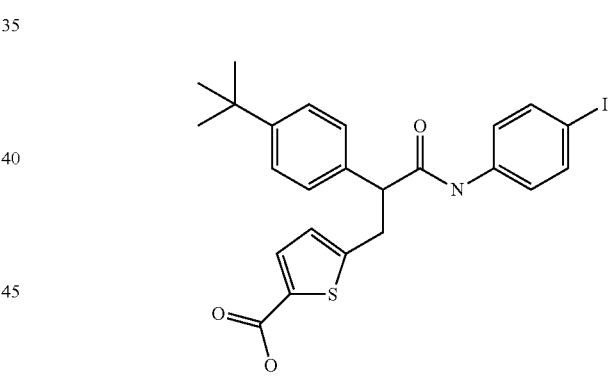

To 5-[2-(4-tert-Butyl-phenyl)-2-(4-iodo-henyl-carbamoyl)-ethyl]-thiophene-2-carboxylic acid methyl ester (640 mg, 1.2 mmol) in 15 ml tetrahydrofuran, 10 ml methanol, and 5 ml water was added sodium hydroxide (234 mg, 5.8 mmol). The reaction mixture was stirred at 40° C. for 2 hours. The solvent was evaporated. The residue was washed with 10% ethyl acetate in hexane (50 ml). The solvents were decanted. The residue was partitioned between ethyl acetate and 1N hydrochloric acid. The organic phase was washed with water, dried with magnesium sulfate, and concentrated to afford 5-[2-(4-tert-Butyl-phenyl)-2-(4-iodo-phenylcarbamoyl)-ethyl]-thiophene-2-carboxylic acid as a yellowish foam (616 mg, 96%).

¹H NMR (CDCl₃): δ 7.56-7.59 (3H, m), 7.37-7.42 (2H, m), 7.20-7.35 (4H, m), 7.05 (1H, s), 6.72-6.73 (1H, d, J=3.7 Hz), 3.80-3.85 (1H, m), 3.66-3.76 (1H, m), 3.22-3.26 (1H, m), 1.31 (9H, s).

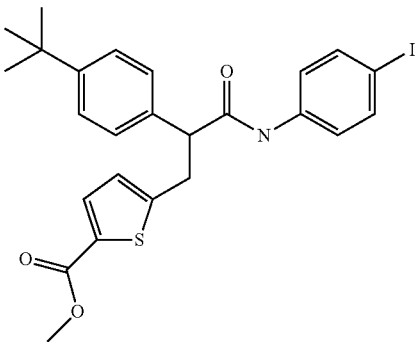

255

Step E: 2-({5-[2-(4-tert-Butyl-phenyl)-2-(4-iodo-phenylcarbamoyl)-ethyl]-thiophene-2-carbonyl}-amino)-ethanesulfonic acid

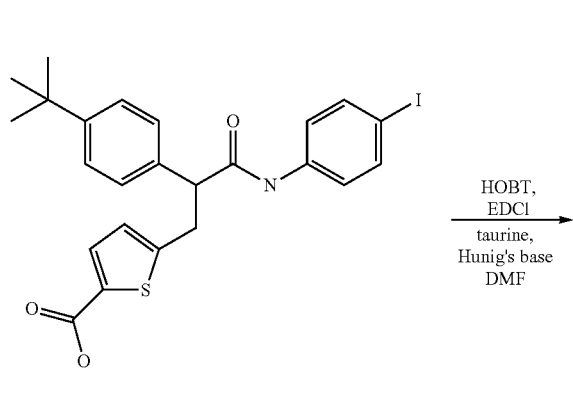

To 2-({5-[2-(4-tert-Butyl-phenyl)-2-(4-iodo-phenylcarbamoyl)-ethyl]-thiophene-2-carbonyl}-amino)-ethanesulfonic acid (616 mg, 1.15 mmol) in N,N-dimethylformamide (10 ml) was added 1-hydroxybenzotriazole hydrate (194 mg, 1.27 mmol), N-(3-dimethylaminopropyl)-N'-ethylcarbodiimide hydrochloride (243 mg, 1.27 mmol), taurine (216 mg, 1.7 mmol), and N,N-diisopropylethylamine (221 mg, 1.84 mmol). The resulting mixture was stirred at 23° C. for 16 hours. Chromatography (20% to 80% acetonitrile in water) obtained 2-({5-[2-(4-tert-Butyl-phenyl)-2-(4-iodo-phenylcarbamoyl)-ethyl]-thiophene-2-carbonyl}-amino)-ethanesulfonic acid as a white solid (440 mg, 60%).

$^1$H NMR (CD$_3$OD): δ 7.55-7.59 (2H, m), 7.29-7.40 (8H, m), 6.80-6.81 (1H, d, J=3.8 Hz), 3.91-3.96 (1H, m), 3.70-3.77 (3H, m), 3.00-3.19 (3H, m), 1.30 (9H, s).

256

Step F: 2-({5-[2-(4-Benzofuran-2-yl-phenylcarbamoyl)-2-(4-tert-butyl-phenyl)-ethyl]-thiophene-2-carbonyl}-amino)-ethanesulfonic acid

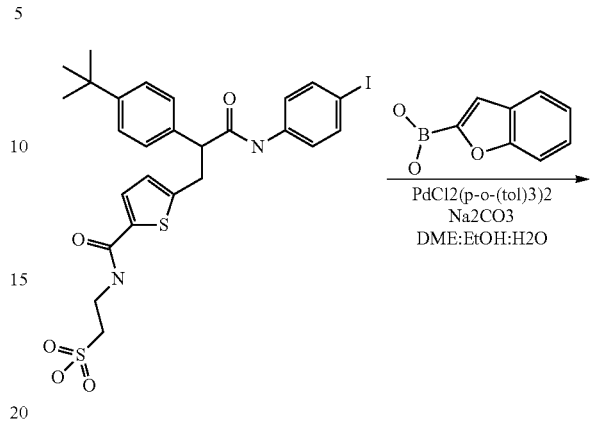

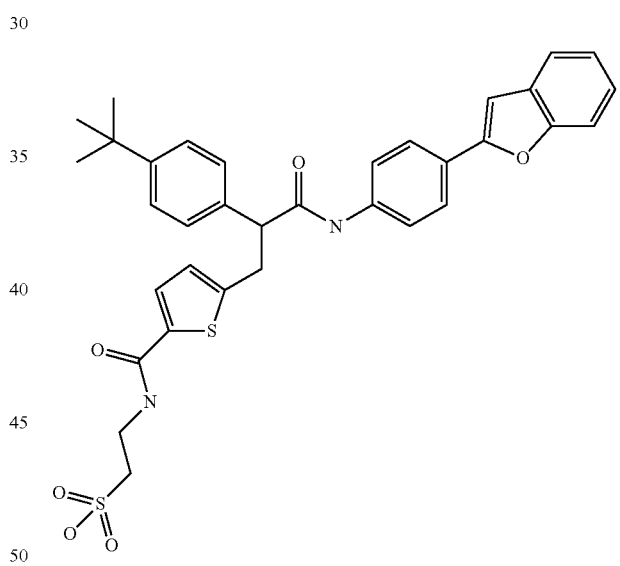

To 2-({5-[2-(4-tert-Butyl-phenyl)-2-(4-iodo-phenylcarbamoyl)-ethyl]-thiophene-2-carbonyl}-amino)-ethanesulfonic acid (100 mg, 0.16 mmol) in 2 ml 1,2-dimethoxyethane, 1 ml ethanol, and 0.5 ml water was added benzofuran-2-boronic acid (76 mg, 0.47 mmol), sodium carbonate (83 mg, 0.78 mmol), and dichlorobis(tri-o-tolylphosphine)palladium (II) (12 mg, 0.016 mmol). The resulting mixture was heated to 125° C. in microwave for 6 minutes. Chromatography of the reaction mixture (20% to 80% acetonitrile in water) obtained 2-({5-[2-(4-Benzofuran-2-yl-phenylcarbamoyl)-2-(4-tert-butyl-phenyl)-ethyl]-thiophene-2-carbonyl}-amino)-ethanesulfonic acid as a white solid (12 mg, 12%).

$^1$H NMR (CD$_3$OD): δ 7.80-7.83 (2H, d, J=8.8 Hz), 7.56-7.64 (3H, m), 7.40-7.50 (5H, m), 7.20-7.28 (3H, m), 7.10 (1H, s), 6.84-6.85 (1H, d, J=3.8 Hz), 3.97-4.02 (1H, m), 3.68-3.76 (3H, m), 3.04-3.09 (3H, m), 1.32 (9H, s).

Example 1.108

2-({5-[2-(4-tert-Butyl-phenyl)-2-(2',4'-dichloro-biphenyl-4-ylcarbamoyl)-ethyl]-thiophene-2-carbonyl}-amino)-ethanesulfonic acid

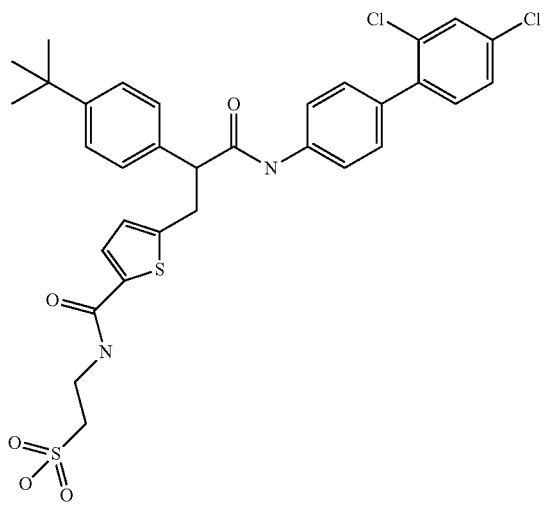 [SMILES: CC(C)(C)c1ccc(C(Cc2ccc(C(=O)NCCS(=O)(=O)O)s2)C(=O)Nc2ccc(-c3ccc(Cl)cc3Cl)cc2)cc1]

Prepared as described in Example 1.107, except that 2,4-dichlorophenylboronic acid was used instead of benzofuran-2-boronic acid in Step F.

$^1$H NMR (CD$_3$OD): δ 7.52-7.59 (3H, m), 7.31-7.42 (9H, m), 6.83-6.84 (1H, d, J=4.1 Hz), 3.97-4.02 (1H, m), 3.68-3.76 (3H, m), 3.04-3.09 (3H, m), 1.32 (9H, s).

Example 1.109: 2-{4-[(E)-2-(4-tert-Butylphenyl)-2-(4-cyclohexylmethoxy-phenylcarbamoyl)-vinyl]benzoylamino}-ethanesulfonic acid and 2-{4-[(Z)-2-(4-tert-Butylphenyl)-2-(4-cyclohexylmethoxy-phenylcarbamoyl)-vinyl]benzoylamino}-ethanesulfonic acid Step A

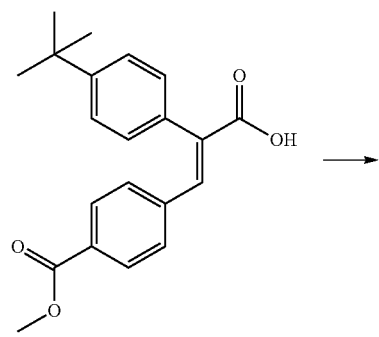

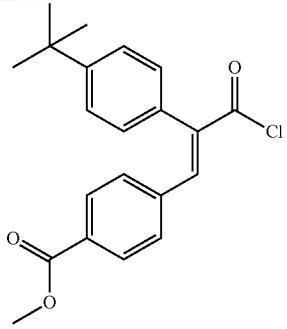

To a suspension of 864 mg of carboxylic acid (2.56 mmol) (obtained as described in WO 03/048109 A1) in 20 ml of toluene at reflux was added 5 eq (0.93 mL) of thionyl chloride. The mixture was heated to reflux further 2 hours until a solution formed. The solvent was removed under reduced pressure and the residue coevaporated with toluene. Obtained 884 mg of crude product that was used without further purification or characterization.

Step B

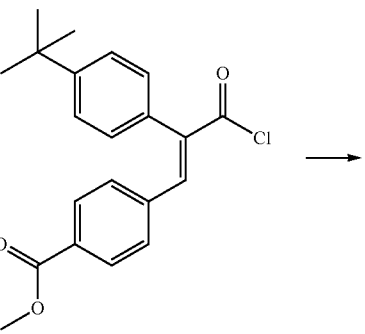

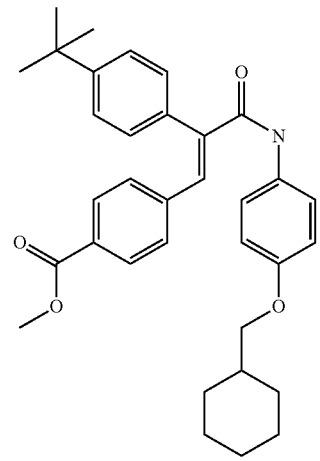

To 400 mg of the acid chloride from Step A above, added 20 ml of toluene under nitrogen. To this solution added 690 mg of 4-cyclohexylmethoxy-phenylamine and then 1.03 mL of diisopropylethylamine. This solution was heated to 90° C. for 12 hours. After cooling to room temperature, the reaction was diluted with ethyl ether and washed with 1 N HCl, saturated bicarbonate solution, water, then brine. The solvent was dried (magnesium sulfate), filtered and removed.

Isomers were separated utilizing normal phase silica using 10% EtOAc/Hexane as the eluent. After five chromatographics in this fashion, 94 mg of the upper spot and 39 mg of the lower spot were isolated and shown to be pure by HNMR.

Upper Spot (Major Isomer) HNMR Data

300 MHz-CDCl₃ (ppm) −7.975, s; 7.838, d, J=8.5 Hz; 7.534, d, J=8.5 Hz; 7.388, d, J=8.8 Hz; 7.412, d, J=8.5 Hz; 7.229, s; 7.096, d, J=8.2 Hz; 6.862, d, J=8.8 Hz; 3.757, d, J=6.48 Hz; 1.903-1.766, m; 1.424, s; 1.342-1.043, m.

Lower Spot (Minor Isomer) HNMR Data

300 MHz-CDCl₃ (ppm) −8.024, d, J=8.2 Hz; 7.632-7.575, m; 7.468, d, J=8.5; 7.355, d, J=9.1 Hz; 7.237, s; 7.092, s; 6.882, d, J=9 Hz; 3.768, d, J=6.2 Hz; 1.913-1.779, m; 1.374, s; 1.314-1.052, m.

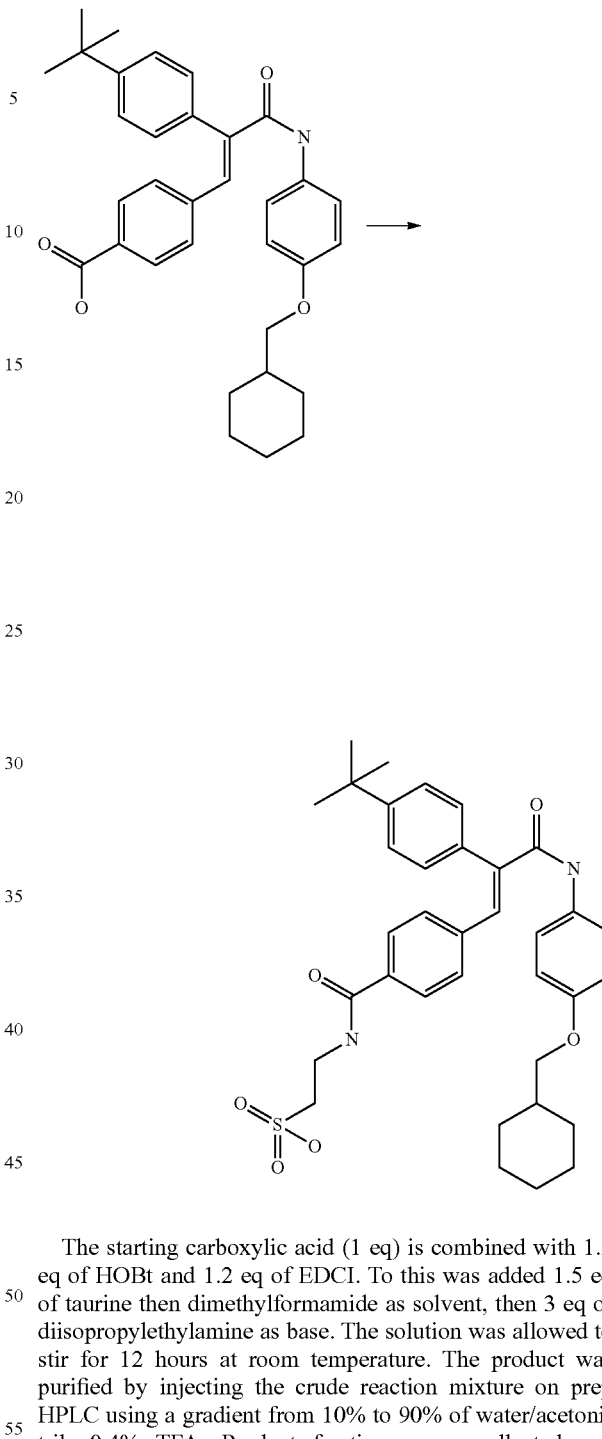

To 94 mg (0.179 mmol) of methyl ester in THF:MeOH:H2O (6 ml:3 mL:1 mL) was added six equivalents of lithium hydroxide at room temperature. Stirred at room temperature for 12 hours and removed the volatile components under reduced pressure. The residue was partitioned between H2O/Ether. The ether layer was discarded and the water layer acidified with 1N HCl. Extracted with ethyl acetate to give 85 mg of the carboxylic acid. Used without any further purification.

LCMS: (m/z)=512.3 (M+H)⁺, for both isomers.

The starting carboxylic acid (1 eq) is combined with 1.2 eq of HOBt and 1.2 eq of EDCI. To this was added 1.5 eq of taurine then dimethylformamide as solvent, then 3 eq of diisopropylethylamine as base. The solution was allowed to stir for 12 hours at room temperature. The product was purified by injecting the crude reaction mixture on prep HPLC using a gradient from 10% to 90% of water/acetonitrile+0.4% TFA. Product fractions were collected and lyophillized to give the desired product.

Major Isomer HNMR Data:

300 MHz-DMSO (ppm) −9.940, s; 8.485, bs; 7.629-7.577, m; 7.434, d, J=8.2 Hz; 7.302, s; 7.195-7.157, m; 6.898, d, J=9.1 Hz; 3.774-3.490, m; 2.682-2.636, m; 1.838-1.703, m; 1.327, s; 1.251-1.060, m.

Minor Isomer HNMR Data:

300 MHz-DMSO (ppm) −10.363, s; 8.505, bs; 7.747, d, J=8.5 Hz; 7.631-7.461, m; 7.182, s; 6.913, d, J=9; 3.782-3.503, m; 3.186, s; 2.685-2.638, bs; 1.844-1.713, m; 1.317, s; 1.257-1.227, m; 1.104-1.031, m.

Example 1.110

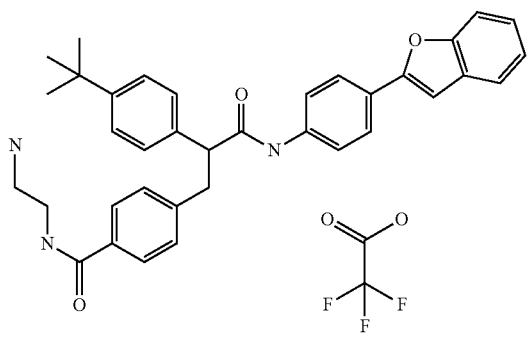 [SMILES: CC(C)(C)c1ccc(C(Cc2ccc(C(=O)NCCN)cc2)C(=O)Nc2ccc(-c3cc4ccccc4o3)cc2)cc1 ; O=C(O)C(F)(F)F]

4-[2-(4-Benzofuran-2-yl-phenylcarbamoyl)-2-(4-tert-butyl-phenyl)-ethyl]-benzoic acid was used as a starting material. This compound was prepared as in Example 1.001, Steps A-C, except that benzofuran-2-yl boronic acid was used instead of 2,4-dichlorophenyl boronic acid in Step B.

Step A t-Butyl-N-(2-aminoethyl)carbamate was coupled with 4-[2-(4-Benzofuran-2-yl-phenylcarbamoyl)-2-(4-tert-butyl-phenyl)-ethyl]-benzoic acid as described in Step D of Example 1.001.

Step B

BOC-protected amine from step A (500 mg, 0.75 mmol) was dissolved in ice-cold 70% aq trifluoroacetic acid. The reaction was warmed to room temperature and stirred for 1 h. The mixture was concentrated under reduced pressure and the residue was chromatographed on silica gel with 5% to 20% MeOH-dichloromethane to get 440 mg of pure deprotected product.

Example 1.111

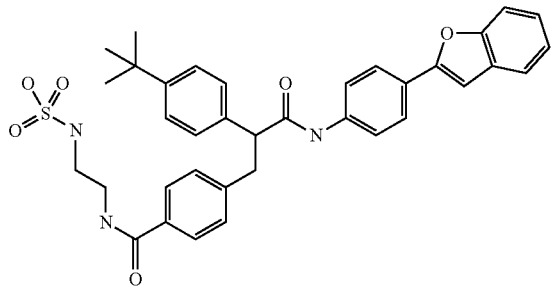 [SMILES: CC(C)(C)c1ccc(C(Cc2ccc(C(=O)NCCNS(=O)(=O)O)cc2)C(=O)Nc2ccc(-c3cc4ccccc4o3)cc2)cc1]

(Kerns et al., *Synthetic communications.*, 1996, 26, 2671-2680)

A solution of amine from Example 1.110 (110 mg, 0.2 mmol), in dichloromethane (2 mL) and triethylamine (0.27 mL, 2 mmol) was added to phenyl chlorosulfate (77 mg, 0.4 mmol) (Younker et al., *J. Org. Chem.*, 2004, 69, 9043-9048) in dichloromethane (2 mL) at 0° C. The reaction was warmed to room temperature and stirred for 1 h. Upon completion of the reaction, the mixture was concentrated under reduced pressure. The crude product was chromatographed on silica gel using 5% to 20% methanol-ethyl acetate to get 70 mg of the pure product.

LCMS: (m/z): 638 (M–H)⁻. Elemental Analysis calculated for $C_{36}H_{37}N_3O_6S+2.5 H_2O$: C: 63.14, H: 6.18, N: 6.14. Found: C: 62.70, H: 6.24, N: 6.33.

Example 1.112

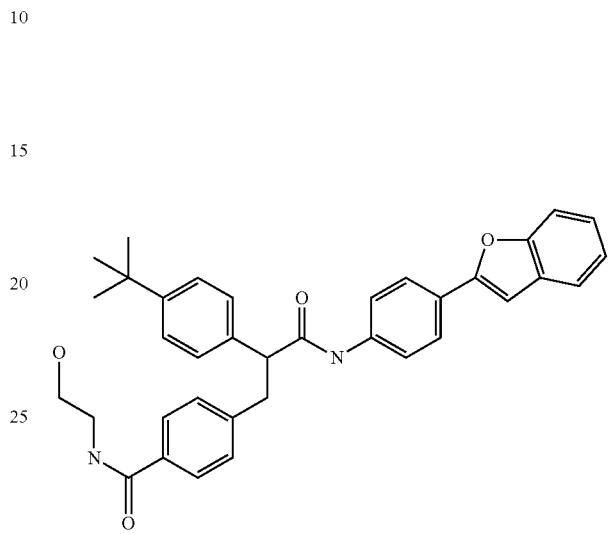

4-[2-(4-Benzofuran-2-yl-phenylcarbamoyl)-2-(4-tert-butyl-phenyl)-ethyl]-benzoic acid was used as a starting material. This compound was prepared as in Example 1.001, Steps A-C, except that benzofuran-2-yl boronic acid was used instead of 2,4-dichlorophenyl boronic acid in Step B.

2-Aminoethanol was coupled with 4-[2-(4-Benzofuran-2-yl-phenylcarbamoyl)-2-(4-tert-butyl-phenyl)-ethyl]-benzoic acid as described in Step D of Example 1.001 to generate the targeted product. LCMS: 561.3 (M+H)⁺.

Example 1.113

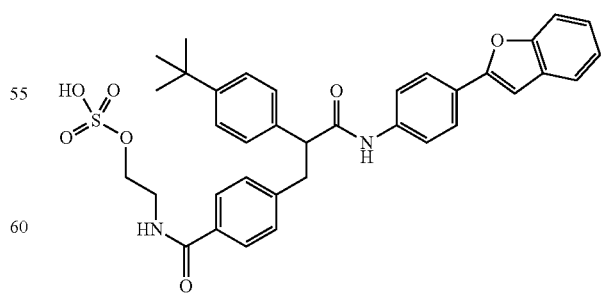

Sulfate formation of the product from Example 1.112 was carried out as described in example 1.111. LCMS: (m/z): 639 (M–H)⁻.

Example 1.114: Preparation of: 2-(4-{[(4-Benzo-furan-2-yl-phenylcarbamoyl)-(4-tert-butyl-phenyl)-methyl]-amino}-benzoylamino)-ethanesulfonic acid Step A: (4-{[(4-tert-Butyl-phenyl)-carboxy-methyl]-amino}-benzoic acid tert-butyl ester

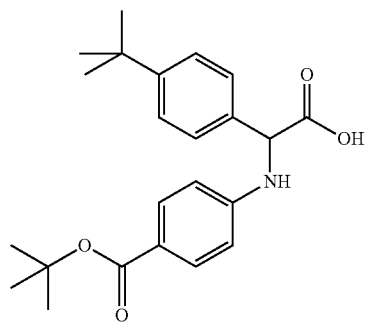 [SMILES: CC(C)(C)OC(=O)c1ccc(NC(C(=O)O)c2ccc(C(C)(C)C)cc2)cc1]

In a 100 mL round bottom flask, t-butyl phenyl boronic acid (850 mg, 4.4 mmol), glyoxylic acid (404 mg, 4.4 mmol) and 4-Amino-benzoic acid tert-butyl ester (780 mg, 4.4 mmol) were dissolved in 25 mL of dichloromethane and allowed to stir at RT. After 30 min the reaction turned cloudy, but was allowed to stir an additional 2 h. Upon completion, the reaction was quenched with 20 mL water and the organic layer was separated, dried over sodium sulfate and filtered. The solvent was removed under reduced pressure to give 1.6 g (95%). of a light yellow powder. $^1$H NMR (CDCl$_3$): δ 1.29 (9H, s), 1.55 (9H, s), 5.17 (1H, s), 6.57 (2H, d, J=8.4 Hz), 7.39 (4H, s), 7.78 (2H, d, J=8.4 Hz).

Step B: 4-{[(4-tert-Butyl-phenyl)-(4-iodo-phenyl-carbamoyl)-methyl]-amino}-benzoic acid tert-butyl ester

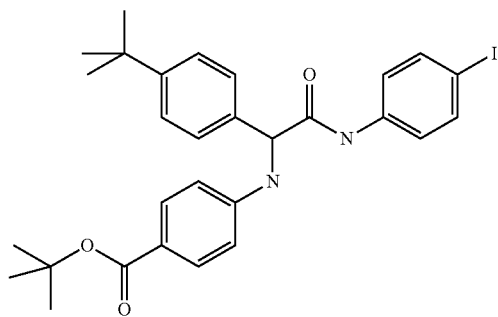 [SMILES: CC(C)(C)OC(=O)c1ccc(NC(C(=O)Nc2ccc(I)cc2)c2ccc(C(C)(C)C)cc2)cc1]

(4-{[(4-tert-Butyl-phenyl)-carboxy-methyl]-amino}-benzoic acid tert-butyl ester (760 mg, 2.0 mmol), was taken up in 5 mL of DMF followed by addition of HOBt (765 mg, 5.0 mmol) and EDCI (958 mg, 5.0 mmol). The reaction was stirred at RT for 30 min, 4-iodoaniline (657 mg, 3 mmol) was added followed by Hunig's base (640 mg, 5 mmol) and allowed to stir an additional 16 h at RT. Ethyl acetate (20 mL) and 20 mL water were added and separated. The aqueous layer was then back extracted with another 10 mL of EtOAc, the organic layer were combined and washed with water (3×20 mL). The organic layer was dried over sodium sulfate, filtered and the solvent was removed under reduced pressure to give a brown solid. The solids were triturated with methanol to give a white solid (818 mg, 70%). $^1$H NMR (CDCl$_3$): δ 1.32 (9H, s), 1.58 (9H, s), 4.89 (2H, d), 5.02 (1H, d), 6.62 (2H, d, J=8.4 Hz), 7.22-7.95 (10H, m), 8.81 (1H, s).

Step C: 4-{[(4-tert-Butyl-phenyl)-(4-iodo-phenyl-carbamoyl)-methyl]-amino}-benzoic acid

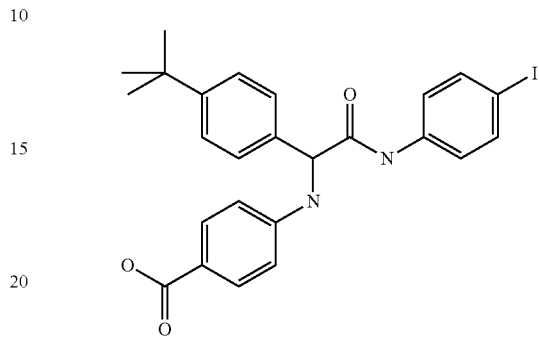

4-{[(4-tert-Butyl-phenyl)-(4-iodo-phenylcarbamoyl)-methyl]-amino}-benzoic acid tert-butyl ester (430 mg, 0.74 mmol) was taken up in 10 mL of dichloromethane followed by addition of 1 mL of TFA and stirred for 16 h at RT. Removal of the organic layer under reduced pressure followed by addition of water to the precipitate. The solids were filtered to give 340 mg (87%) of white solids. $^1$H NMR showed the compound to be very clean and sufficient for the following step. LCMS (M+1=529.6).

Step D: 4-{[(4-Benzofuran-2-yl-phenylcarbamoyl)-(4-tert-butyl-phenyl)-methyl]-amino}-benzoic acid

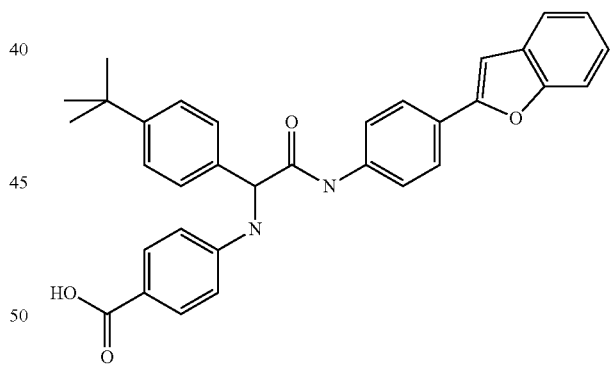

4-{[(4-tert-Butyl-phenyl)-(4-iodo-phenylcarbamoyl)-methyl]-amino}-benzoic acid acid (340 mg, 0.6 mmol) was taken up in 8 mL of DME, 4 mL of ethanol and 2 mL of water. Na$_2$CO$_3$ (254 mg, 2.4 mmol), PdCl$_2$(O-tolyl)$_2$ (61 mg, 0.0078 mmol) and benzo[B]furan-2-boronic acid (194 mg, 1.2 mmol) were then added, flushed with nitrogen and heated to reflux for 1 h. Cooled to RT, EtOAc (20 mL) was added and extracted with water (20 mL). The organic layer was washed again with water (20 mL), dried over sodium sulfate, filtered and the organic layer was removed under reduced pressure to give a white solid (120 mg, 100%). 1H NMR showed the compound to be very clean and sufficient for the following step.

LCMS (M+1=599.4)

Step E: 2-(4-{[(4-Benzofuran-2-yl-phenylcarbamoyl)-(4-tert-butyl-phenyl)-methyl]-amino}-benzoylamino)-ethanesulfonic acid

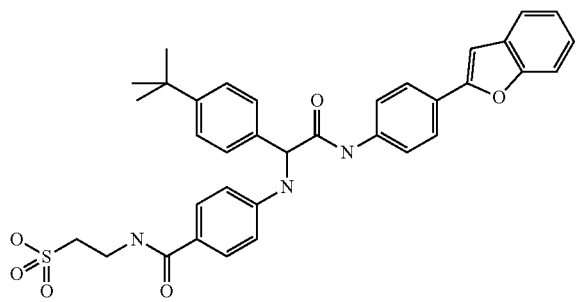 [SMILES: CC(C)(C)c1ccc(C(Nc2ccc(C(=O)NCCS(=O)(=O)O)cc2)C(=O)Nc2ccc(-c3cc4ccccc4o3)cc2)cc1]

(4-{[(4-tert-Butyl-phenyl)-carboxy-methyl]-amino}-benzoic acid tert-butyl ester (340 mg, 0.6 mmol), was taken up in 10 mL of DMF followed by addition of HOBt (251 mg, 1.6 mmol) and EDCI (314 mg, 1.6 mmol). The reaction was stirred at RT for 30 min, taurine (300 mg, 2.4 mmol) was added followed by Hunig's base (310 mg, 2.4 mmol) and allowed to stir an additional 16 h at RT. The solution was filtered through a frit and the solution was subjected to reverse phase HPLC separations. The water/acetonitrile were removed under reduced pressure, gave a white solid (320 mg, 77%). $^1$H NMR (CDCl$_3$): δ 1.21 (9H, s), 2.66 (2H, t), 3.45 (2H, m), 5.02 (1H, d), 6.62 (2H, d), 7.22-7.95 (10H, m), 8.81 (1H, s). $^{19}$F NMR (CDCl$_3$): δ−75.17 (s). Anal. Calcd. For C$_{36}$H$_{37}$N$_3$O$_6$S+1.3 H$_2$O+0.4 TFA; C=61.89; H=5.51; N=6.05. Found C=62.28; H=5.87; N=5.60.

Example 1.115: 2-(4-{[(4-Benzofuran-2-yl-phenylcarbamoyl)-(4-tert-butyl-phenyl)-methyl]-methyl-amino}-benzoylamino)-ethanesulfonic acid

Step A: 4-{[(4-tert-Butyl-phenyl)-(4-iodo-phenylcarbamoyl)-methyl]-methyl-amino}-benzoic acid tert-butyl ester

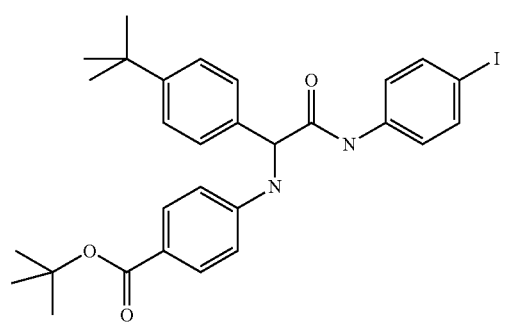

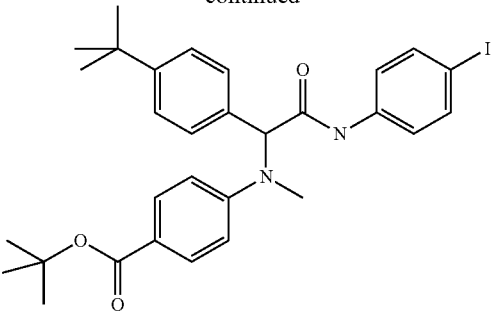

4-{[(4-tert-Butyl-phenyl)-(4-iodo-phenylcarbamoyl)-methyl]-amino}-benzoic acid tert-butyl ester (110 mg, 0.19 mmol) was dissolved in 2 mL of HOAc. paraformaldehyde (51 mg, 0.57 mmol) and sodium cyano-borohydride (36 mg, 0.57 mmol) were then added and heated to 40 C for 1. Cooled to RT, EtOAc (20 mL) was added and extracted water (20 mL). The organic layer was washed again with water (20 mL), dried over sodium sulfate, filtered and the organic layer was removed under reduced pressure to give a white solid (120 mg, 100%). 1H NMR showed the compound to be very clean and sufficient for the following step. LCMS (M+1=599.4)

Step B: 4-{[(4-Benzofuran-2-yl-phenylcarbamoyl)-(4-tert-butyl-phenyl)-methyl]-methyl-amino}-benzoic acid tert-butyl ester

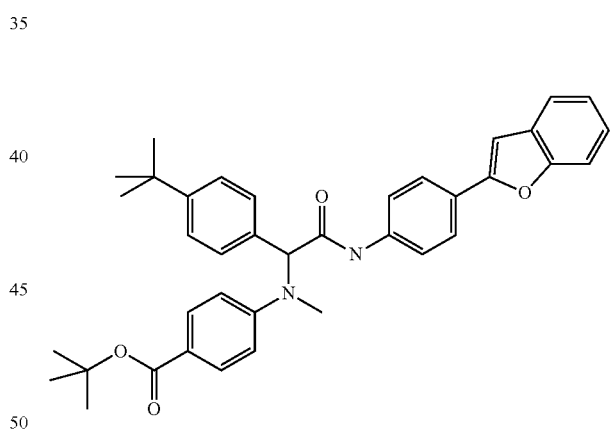

4-{[(4-tert-Butyl-phenyl)-(4-iodo-phenylcarbamoyl)-methyl]-methyl-amino}-benzoic acid tert-butyl ester (120 mg, 0.19 mmol) was taken up in 8 mL of DME, 4 mL of ethanol and 2 mL of water. Na$_2$CO$_3$ (81 mg, 2.4 mmol), PdCl$_2$(O-tolyl)$_2$, (15 mg, 0.0019 mmol) and benzo[B]furan-2-boronic acid (62 mg, 0.38 mmol) were then added, flushed with nitrogen and heated to reflux for 1 h. Cooled to RT, EtOAc (20 mL) was added, and filtered through a plug of celite. The solvents were removed under reduced pressure to give a yellow viscous solid. Water was added to the solid to give a yellow precipitate, which was filtered and triturated with methanol to give 140 mg of a white solid. LCMS (M+1=589.6)

267

Step C: 4-{[(4-Benzofuran-2-yl-phenylcarbamoyl)-(4-tert-butyl-phenyl)-methyl]-methyl-amino}-benzoic acid

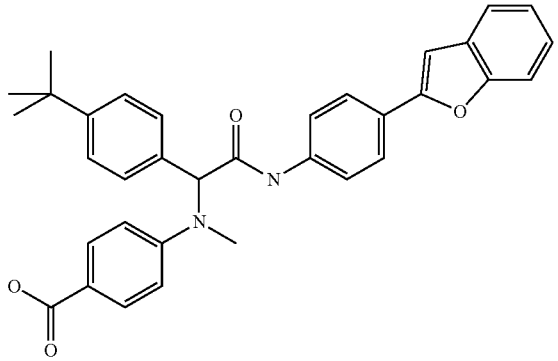 [SMILES: CN(c1ccc(C(=O)O)cc1)C(C(=O)Nc1ccc(-c2cc3ccccc3o2)cc1)c1ccc(C(C)(C)C)cc1]

4-{[(4-Benzofuran-2-yl-phenylcarbamoyl)-(4-tert-butyl-phenyl)-methyl]-methyl-amino}-benzoic acid tert-butyl ester (~140 mg, 0.19 mmol) was taken up in 5 mL of dichloromethane followed by addition of 0.5 mL of TFA and stirred for 16 h at RT. Removal of the organic layer and water was added to give a precipitate, which was filtered to give 110 mg (100%) of pinkish solids. LCMS (M−1=531.1).

Step D: 2-(4-{[(4-Benzofuran-2-yl-phenylcarbamoyl)-(4-tert-butyl-phenyl)-methyl]-methyl-amino}-benzoylamino)-ethanesulfonic acid

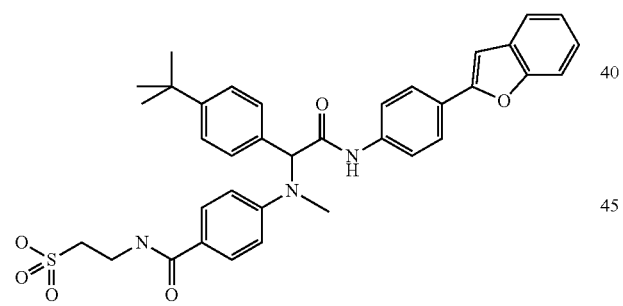

4-{[(4-Benzofuran-2-yl-phenylcarbamoyl)-(4-tert-butyl-phenyl)-methyl]-methyl-amino}-benzoic acid (110 mg, 0.2 mmol), was taken up in 3 mL of DMF followed by addition of HOBt (79 mg, 0.52 mmol) and EDCI (99 mg, 0.52 mmol). The reaction was stirred at RT for 30 min, taurine (103 mg, 0.083 mmol) was added followed by Hunig's base (107 mg, 0.083 mmol) and allowed to stir an additional 16 h at RT. The solution was filtered through a frit and the DMF was subjected to reverse phase HPLC purification. After removal acetonitrile/water under reduced pressure, followed by trituration with methanol, gave a white solid (50 mg, 39%).

$^1$H NMR (CDCl$_3$): δ 1.21 (9H, s), 2.61 (2H, brt), 3.44 (2H, br), 4.30 (3H, brt), 5.83 (1H, s), 6.87 (2H, d, J=8.4 Hz), 7.19-7.86 (10H, m), 8.19 (1 h, brs), 10.54 (1H, brs). Anal. Calcd. For C$_{36}$H$_{37}$N$_3$O$_6$S+2H$_2$O; C=63.98; H=6.12; N=6.22. Found C=63.91; H=6.16; N=6.10.

268

Example 1.116: 2-(4-{[Cyclohex-1-enyl-(4'-trifluoromethyl-biphenyl-4-ylcarbamoyl)-methyl]-amino}-benzoylamino)-ethanesulfonic acid

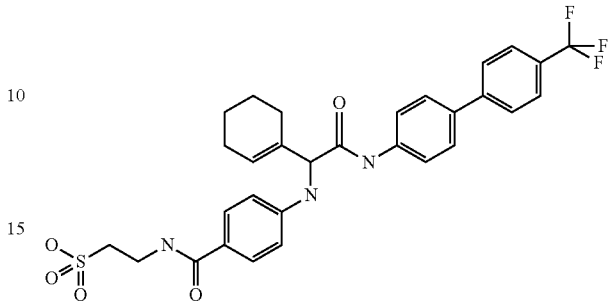

This compound was prepared using the methods described above, with modifications that will be evident to an individual skilled in the art.

Mass Spectrum: 602.7 (M+H)$^+$. Formula: C30H30F3N3O5S+1.5 H2O+0.5 CF3CO2H.

Elemental Analysis: Calculated: C: 54.30, H: 4.92, N: 6.13. Found: C: 54.38, H: 4.96, N: 6.45.

Example 1.117: N-{4-[2-(4-Benzofuran-2-yl-phenylcarbamoyl)-2-(4-tert-butyl-phenyl)-ethyl]-phenyl}-succinamic acid Step A

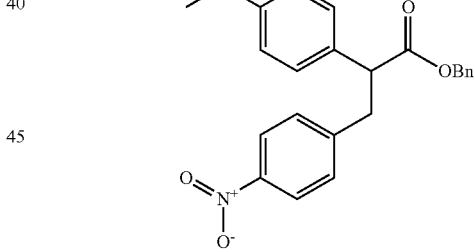

To (4-tert-Butyl-phenyl)-acetic acid benzyl ester (92 g, 7.1 mmol) in tetrahydrofuran (50 ml) was added lithium diisopropylamide (8.5 mmol) at −78° C. After 30 min, 4-nitrobenzyl bromide (1.6 g, 7.5 mmol) was added. The cold bath was removed and the reaction mixture was allowed to warm to ambient temperature in 1 h. The reaction mixture was concentrated, partitioned between ethyl acetate and 1N ammonium chloride, washed with water, and dried over magnesium sulfate. Chromatography of the residue (5% ethyl acetate in hexane) afforded 2-(4-tert-Butyl-phenyl)-3-(4-nitro-phenyl)-propionic acid benzyl ester as a yellow oil (2.46, 83%).

$^1$HNMR (CDCl$_3$) δ 8.02-8.05 (2H, d, J=8.8 Hz), 7.33-7.39 (4H, m), 7.21-7.32 (5H, m), 7.09-7.12 (2H, m), 4.95-5.12 (2H, m), 3.89-3.93 (1H, m), 3.46-3.49 (1H, m), 3.11-3.16 (1H, m), 1.31-1.32 (9H, s).

Step B

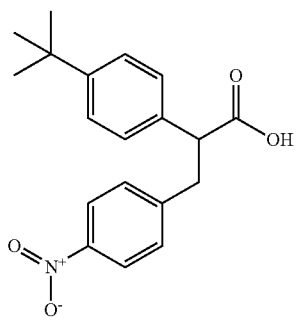 [SMILES: CC(C)(C)c1ccc(C(Cc2ccc([N+](=O)[O-])cc2)C(=O)O)cc1]

To 2-(4-tert-Butyl-phenyl)-3-(4-nitro-phenyl)-propionic acid benzyl ester (8.6 g, 20.6 mmol) in 30 ml tetrahydrofuran, 20 ml methanol and 10 ml water was added sodium hydroxide (0.6 g, 24.7 mmol). The reaction mixture was stirred at 23° C. for 16 h, acidified with 4N hydrochloride acid, and concentrated. The residue was partitioned between ethyl acetate and water. The organic phase was washed with water, dried over magnesium sulfate, and concentrated to afford 2-(4-tert-Butyl-phenyl)-3-(4-nitro-phenyl)-propionic acid as a brownish oil (8.04 g, 100%).

$^1$HNMR (CDCl$_3$) δ 8.08-8.11 (2H, d, J=8.8 Hz), 7.27-7.38 (4H, m), 7.21-7.24 (2H, d, J=8.2 Hz), 3.84-3.88 (1H, m), 3.46-3.53 (1H, m), 3.10-3.17 (1H, m), 1.31 (9H, s).

Step C

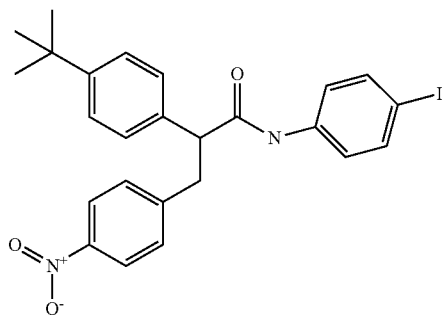 [SMILES: CC(C)(C)c1ccc(C(Cc2ccc([N+](=O)[O-])cc2)C(=O)Nc2ccc(I)cc2)cc1]

To 2-(4-tert-Butyl-phenyl)-3-(4-nitro-phenyl)-propionic acid (4.58 g, 14 mmol) in 100 ml toluene was added 4-iodoaniline (3.37 g, 15.4 mmol), N,N'-dicyclohexyl-carbodiimide (3.2 g, 15.4 mmol), and 4-dimethylaminopyridine (171 mg, 1.4 mmol). The reaction mixture was stirred at 100° C. for 16 h, and was filtered. The filtrate was concentrated and chromatography of the residue (10% ethyl acetate in hexane) afforded 2-(4-tert-Butyl-phenyl)-N-(4-iodo-phenyl)-3-(4-nitro-phenyl)-propionamide as a grey powder (3 g, 41%).

$^1$HNMR (CDCl$_3$) δ 8.06-8.09 (2H, d, J=8.8 Hz), 7.56-7.59 (2H, d, J=8.5 Hz), 7.36-7.39 (2H, d, J=8.2 Hz), 7.27-7.30 (2H, m), 7.17-7.26 (4H, m), 6.95 (1H, s), 3.67-3.75 (2H, m), 3.08-3.17 (1H, m), 1.32 (9H, s).

Step D

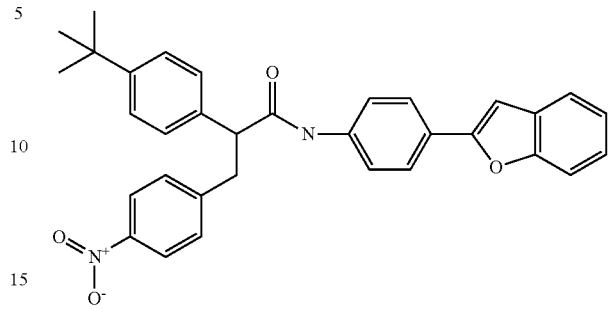

To 2-(4-tert-Butyl-phenyl)-N-(4-iodo-phenyl)-3-(4-nitrophenyl)-propionamide (1056 mg, 2 mmol) in 8 ml 1,2-dimethoxyethane, 4 ml ethanol, and 2 ml water was added benzo[b]furan-2-boronic acid (972 mg, 6 mmol), bis(tri-o-tolylphosphine)palladium(II) dichloride (158 mg, 0.2 mmol), and sodium carbonate (1060 mg, 10 mmol). The reaction mixture was stirred at 125° C. for 6 min, filtered, and concentrated. Chromatography of the residue (20% ethyl acetate in hexane) afforded N-(4-Benzofuran-2-yl-phenyl)-2-(4-tert-butyl-phenyl)-3-(4-nitro-phenyl)-propionamide as a yellow foam (830 mg, 80%).

$^1$HNMR (CDCl$_3$) δ 8.05-8.11 (4H, m), 7.77-7.79 (2H, d, J=8.8 Hz), 7.50-7.60 (6H, m), 7.38-7.41 (2H, d, J=8.5 Hz), 7.20-7.23 (3H, m), 6.95 (1H, s), 3.74-3.77 (2H, m), 3.15-3.17 (1H, m), 1.31 (9H, s).

Step E

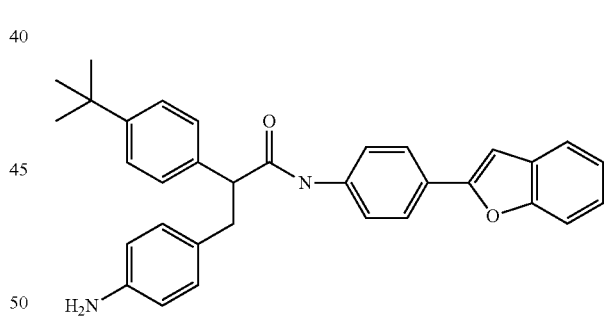

To N-(4-Benzofuran-2-yl-phenyl)-2-(4-tert-butyl-phenyl)-3-(4-nitro-phenyl)-propionamide (830 mg, 1.6 mmol) in tetrahydrofuran (20 ml) was added 20% palladium hydroxide on carbon (172 mg). The reaction mixture was stirred under hydrogen for 16 h, filtered and concentrated. Chromatography of the residue (20% ethyl acetate in hexane) afforded 3-(4-Amino-phenyl)-N-(4-benzofuran-2-yl-phenyl)-2-(4-tert-butyl-phenyl)-propionamide as a white solid (600 mg, 77%).

$^1$HNMR (DMSO-d6) δ 10.17 (1H, s), 7.79-7.82 (2H, d, J=8.8 Hz), 7.66-7.69 (2H, d, J=8.8 Hz), 7.57-7.63 (2H, m), 7.35 (4H, s), 7.21-7.29 (3H, m), 6.87-6.89 (2H, d, J=8.5 Hz), 6.41-6.42 (2H, d, J=8.2 Hz), 4.82 (2H, s), 3.87-3.92 (2H, m), 2.73-2.77 (1H, m), 1.25 (9H, s).

Step F

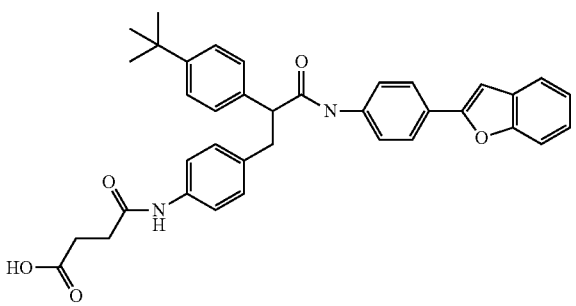 [SMILES: CC(C)(C)c1ccc(C(Cc2ccc(NC(=O)CCC(=O)O)cc2)C(=O)Nc2ccc(-c3cc4ccccc4o3)cc2)cc1]

To 3-(4-Amino-phenyl)-N-(4-benzofuran-2-yl-phenyl)-2-(4-tert-butyl-phenyl)-propionamide (100 mg, 0.2 mmol) in 2 ml diethyl ether, 2 ml toluene and 1 ml 1,4-dioxane was added succinic anhydride (22 mg, 0.22 mmol). The reaction mixture was stirred at 23° C. for 16 h. concentrated, and loaded to reverse phase silica gel. After chromatography (from 20% acetonitrile to 80% acetonitrile in water in 12 column volume), the fractions containing the desired product were collected and concentrated. The residue was diluted with methanol (1 ml) and water was added dropwise until the precipitate stop forming. The white precipitate was removed by filtration and dried under high vacuum at 50° C. to afford the title compound (6.3 mg, 5%).

$^1$HNMR (DMSO-d6) δ 10.20 (1H, s), 9.88 (1H, s), 7.79-7.82 (2H, d, J=8.8 Hz), 7.65-7.68 (2H, d, J=8.8 Hz), 7.57-7.63 (2H, m), 7.42-7.45 (2H, d, J=8.5 Hz), 7.36 (4H, s), 7.21-7.31 (3H, m), 7.13-7.16 (2H, d, J=8.5 Hz), 3.94-3.98 (2H, m), 3.30-3.40 (2H, m), 2.73-2.92 (1H, m), 2.42-2.56 (2H, m), 1.25 (9H, s).

Example 1.118: {4-[2-(4-Benzofuran-2-yl-phenyl-carbamoyl)-2-(4-tert-butyl-phenyl)-ethyl]-phenylcarbamoyl}-methanesulfonate sodium salt

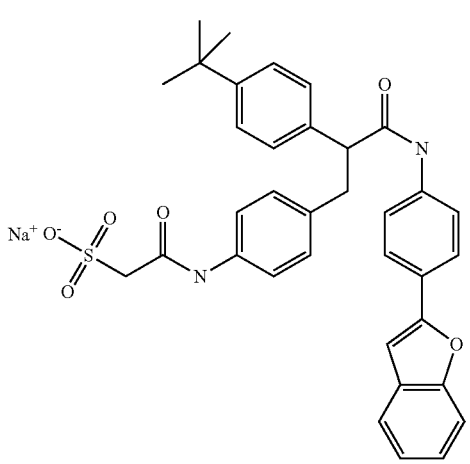 [SMILES: [Na+] ; CC(C)(C)c1ccc(C(Cc2ccc(NC(=O)CS(=O)(=O)[O-])cc2)C(=O)Nc2ccc(-c3cc4ccccc4o3)cc2)cc1]

Step A

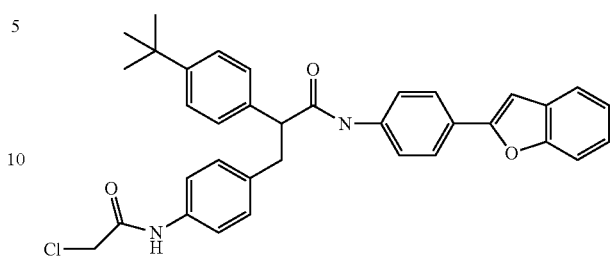

1.5 eq of chloroacetylchloride was dissolved in acetonitrile in a round bottom flask. To this mixture was drop added a solution of 3-(4-Amino-phenyl)-N-(4-benzofuran-2-yl-phenyl)-2-(4-tert-butyl-phenyl)-propionamide (Example 1.117, Step E, 1 eq), and N,N-diisoprropyl-ethyl amine (3 eq) in acetonitrile from an addition funnel at room temperature. After addition was complete, the reaction was stirred for 9 hours at room temperature. The reaction was quenched by pouring into ice water and the precipitate collected to yield the desired product.

HNMR (DMSO-d$_6$) (ppm): 10.287 (s) 1H, 10.186 (d, J=4.8 Hz) 1H, 7.960 (d, J=9.3 Hz) 2H, 7.808-7.551 (m) 5H, 7.453-7.171 (m) 10H, 4.181 (s) 2H, 3.985-3.936 (m) 1H, 2.909-2.881 (m) 1H, 1.237 (s) 9H.

Step B

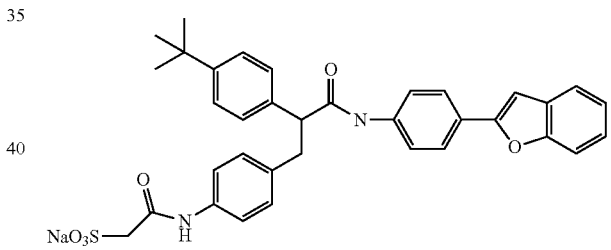

To N-(4-Benzofuran-2-yl-phenyl)-2-(4-tert-butyl-phenyl)-3-[4-(2-chloro-acetylamino)-phenyl]-propionamide dissolved in ethanol was added a solution of water containing 5 eq of Na$_2$S$_2$O$_6$ in a microwave vial. The solvent ratio was 2:1 ethanol:water. The reaction was heated to 120° C. for 6 min. The solvent was removed and the residue was purified by chromatography on reverse phase (C18) silica gel using a water/acetonitrile gradient to give the sodium salt.

HNMR (ppm): (CD$_3$OD): 7.774 (dd, J=1.8 Hz, J=6.9 Hz) 2H, 7.572-7.368 (m) 9H, 7.267-7.064 (m) 6H, 3.921 (dd, J=6 Hz, J=9.5 Hz) 1H, 3.816 (s) 2H, 3.436 (dd, J=9.3 Hz, J=13.65 Hz) 1H, 2.978 (dd, J=6 Hz, J=13.5 Hz) 1H, 1.297 (s) 9H.

Example 1.119: 2-{4-[2-(4-Benzofuran-2-yl-phenyl-carbamoyl)-2-(4-tert-butyl-phenyl)-ethyl]-phenylcarbamoyl}-ethanesulfonate sodium salt This compound was prepared by the method indicated in Example 1.118, with appropriate modifications

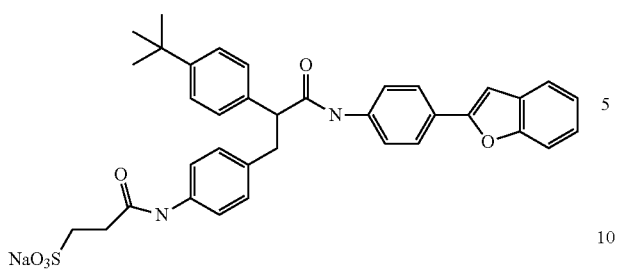

HNMR (ppm): (CD₃OD), 7.799-7.762 (m) 2H, 7.576-7.370 (m) 10H, 7.268-7.075 (m) 5H, 3.917 (dd, J=6 Hz, J=9.3 Hz) 1H, 3.432 (dd, J=13.5 Hz, J=9.3 Hz) 1H, 3.146-3.093 (m) 2H, 2.975 (dd, J=6 Hz, J=13.8 Hz) 1H, 2.823-2.770 (m) 2H, 1.302 (s) 9H Example 1.120

Step A

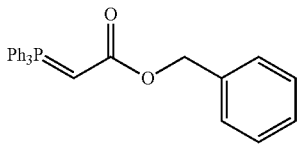

A mixture of benzyl bromoacetate (8.309 g, 36.3 mmol) and triphenylphosphine (9.546 g, 36.4 mmol) in 50 mL of ethyl acetate was heated to reflux for a period of 18 h. After cooling to ambient temperature the white precipitate formed was filtered and rinsed with ethyl acetate. The solid was partitioned between 1N NaOH (aqueous) and ethyl acetate. The organic phase was washed with water and saturated sodium chloride and dried over magnesium sulfate. Evaporation under reduced pressure left a pale yellow oil that was used without characterization in the following step. Crude yield: 8.223 g Step B

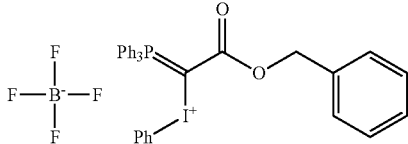

A solution of the product from Step A above (4.742 g, 11.6 mmol) in methanol (10 mL) was cooled in an acetone/ice bath. A solution of PhI(OAc)2 (3.757 g, 11.7 mmol) and HBF4 (1.6 mL of a 7.26M solution in ether, 11.6 mmol) in methanol (15 mL) was added dropwise. After the addition was complete, the mixture was stirred for an additional 1 h at the same temperature. The white precipitate was filtered, rinsed with methanol and dried under reduced pressure. The product was used without further characterization. Crude yield: 6.564 g Step C

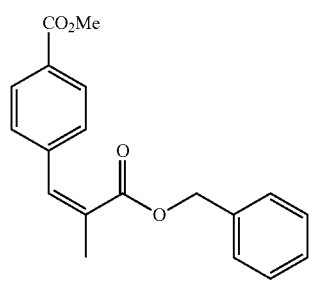 [SMILES: COC(=O)c1ccc(/C=C(/C)C(=O)OCc2ccccc2)cc1]

A mixture of 4-formyl-methyl benzoate (1.547 g, 9.4 mmol) and 6.564 g (9.4 mmol) of the product from Step B above in dichloromethane (30 mL) was treated with tetra-n-butyl ammonium iodide (3.468 g, 9.4 mmol) and the resulting mixture stirred at room temperature for a 4-day period. The mixture was then washed with aqueous sodium bisulfite, and water. The organic phase was dried over MgSO4 and concentrated under reduced pressure. The product obtained after evaporation was chromatographed on silica using an ethyl acetate-hexanes gradient. The first fraction obtained weighed 596 mg. HNMR (300 MHz, DMSO-d6): 8.35 (1H, s), 8.02 (2H, d, J=8.5 Hz), 8.00-7.85 (3H, m), 7.5-7.3 (4H, m), 5.31 (2H, s), 3.86 (3H, s). The second fraction obtained weighed 2.095 g. HNMR (300 MHz, DMSO-d6): 8.35 (1H, s), 8.02 (2H, d, J=8.5 Hz), 7.95-7.87 (3H, m), 7.5-7.3 (4H, m), 5.31 (2H, s), 3.86 (3H, s). Both fractions appeared to contain a contaminant but were used without further purification in the following steps.

Step D

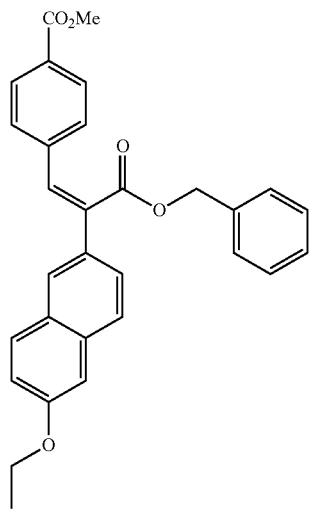 [SMILES: CCOc1ccc2cc(/C(=C/c3ccc(C(=O)OC)cc3)C(=O)OCc3ccccc3)ccc2c1]

A mixture of 343 mg (0.81 mmol) of the iodide obtained in Step C above, 705 mg (3.3 mmol) of 6-ethoxy-2-naphthalen boronic acid, dichlorobis(tri-o-tolylphosphine)palladium (67 mg, 0.085 mmol) and sodium carbonate (496 mg, 4.7 mmol) in a mixture of THF (6 mL), ethanol (4 mL) and water (2 mL) was heated in a microwave reactor at 125° C. for a 6 min period. An excess of 1M aqueous HCl was added and the mixture extracted with ethyl acetate. The organic phase was washed with water and a saturated sodium chloride solution, and dried over magnesium sulfate. Chromatography on silica gel eluting with an ethyl acetate-hexanes gradient. Obtained 178 mg of the product.

LCMS: 467.3 (M+H)+

Step E

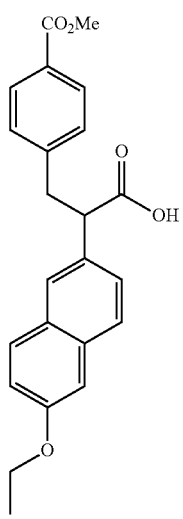

A mixture of the product from Step D above (178 mg, 0.38 mmol) and 10% Pd/C in THF (5 mL) and ethanol (9 mL) was stirred under a balloon of hydrogen for a 1.75 h period. The catalyst was removed by filtration and the product obtained after concentration (139 mg) was used without further purification. LCMS: 379.4 (M+H)+

Step F

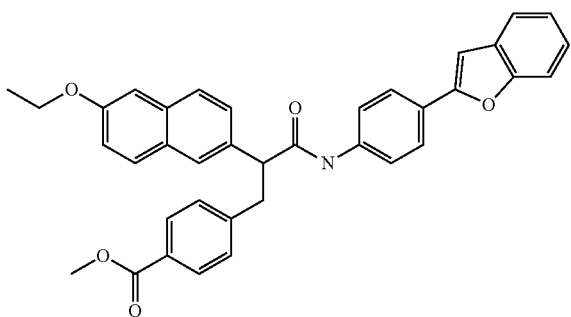 [SMILES: CCOc1ccc2cc(C(Cc3ccc(C(=O)O)cc3)C(=O)Nc3ccc(-c4cc5ccccc5o4)cc3)ccc2c1]

A mixture of the carboxylic acid from Step E above (139 mg, 0.37 mmol), 4-(benzofuran-2-yl-aniline (96 mg, 0.46 mmol), EDCI (291 mg, 1.52 mmol). HOBt-H2O (309 mg, 2.02 mmol) and N,N-diisopropyl —N ethylamine (0.303 mL, 1.85 mmol) in DMF (5.6 mL) was stirred at room temperature for a 16 h period. The crude mixture was diluted with ethyl acetate and washed successively with water, 10% aqueous NaHCO3, water, 1M aqueous HCl, water and saturated sodium chloride. The organic phase was dried over magnesium sulfate and concentrated under reduced pressure. The residue was chromatographed on silica gel using an ethyl acetate-hexanes gradient. The product was obtained as a yellowish solid. Yield: 74 mg. LC/MS: 570.6 (M+H)+

Step G

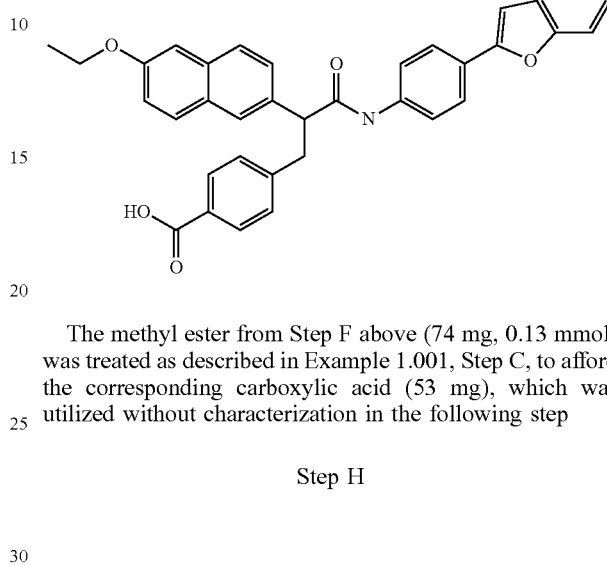

The methyl ester from Step F above (74 mg, 0.13 mmol) was treated as described in Example 1.001, Step C, to afford the corresponding carboxylic acid (53 mg), which was utilized without characterization in the following step Step H

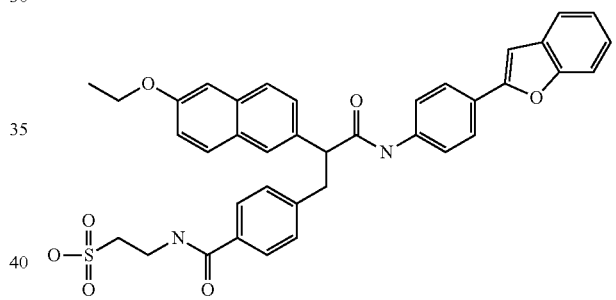

The product was synthesized from 53 mg (0.095 mmol) of the carboxylate from Step G above using the method described in Example 1.001, Step D, except that the product was purified by preparative HPLC on a reverse phase column using an acetonitrile-water gradient, with both solvents containing 0.05% of trifluoroacetic acid.

LCMS: 661.6 (M–H)− HNMR (300 MHz, DMSO-d6): 10.32 (1H, s), 8.39 (1H, m), 7.83-7.11 (19H, m), 4.2-4.0 (3H, m), 3.46 (1H, m), 3.14 (1H, m), 1.38 (3H, t, J=7.0 Hz).

Example 1.121

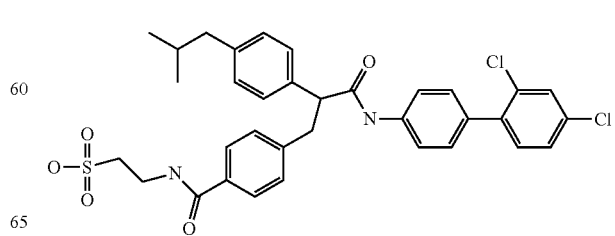

Step A

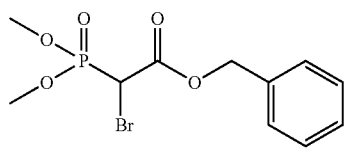 [SMILES: COP(=O)(OC)C(Br)C(=O)OCc1ccccc1]

To a solution of benzyl dimethyl phosphonoacetate (1.94 g, 7.5 mmol) in THF (15 mL) cooled to −78° C. in a dry ice/isopropanol bath was added LHMDS (9.0 mL of a 1 M solution in THF, 9.0 mmol). The reaction was allowed to warm to 10° C. over 30 min, then recooled to −78° C. NBS (1.6 g, 9.0 mmol) was added as a solution in THF (20 mL), and the reaction was allowed to warm to room temperature over 18 h. Saturated ammonium chloride was added to quench any remaining base, and the reaction was concentrated to dryness. Ethyl acetate was added, and the organic layer was washed with water and brine, and dried over sodium sulfate. The crude product was obtained as a yellow oil and was subsequently purified by flash column chromatography on silica gel eluting with 30% ethyl acetate in hexanes to afford the desired product, bromo-(dimethoxyphosphoryl)-acetic acid benzyl ester, as a pale yellow oil, 1.61 g (63%). $^1$H NMR (300 MHz, CDCl3): δ 7.36 (m, 5H), 5.24 (s, 2H), 4.44 (d, J=14.1 Hz, 1H), 3.83 (q, J=4.8 Hz, 6H). LC-MS m/z=417 $[C_{11}H_{15}O_5P+H]^+$.

Step B

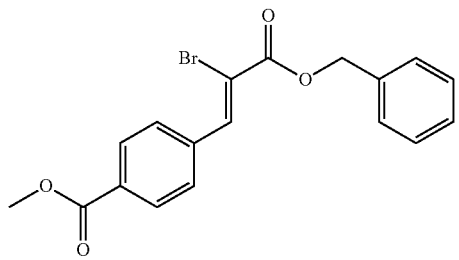 [SMILES: COC(=O)c1ccc(/C=C(\Br)C(=O)OCc2ccccc2)cc1]

To a cooled (−78° C.) solution of bromo-(dimethoxyphosphoryl)-acetic acid benzyl ester (500 mg, 1.5 mmol) in THF (10 mL) was added LHMDS (1.2 mL of a 1M solution in THF, 1.2 mmol). The reaction was warmed to 0° C. and stirred for 30 minutes, then recooled to −78° C. 4-Formylbenzoic acid methyl ester (163 mg, 1.0 mmol) in THF (2 mL) was added dropwise, and the reaction was allowed to warm to room temperature and stirred for 18 hours. The reaction was evaporated to dryness by rotary evaporator and purified by column chromatography on silica gel eluting with 50% ethyl acetate in hexanes to yield 4-(2-Benzyloxycarbonyl-2-bromo-vinyl)-benzoic acid methyl ester (358 mg, 64%) as a mixture of E and Z isomers. $^1$H NMR (300 MHz, CDCl3): δ 8.33 (s, 1H), 8.05 (d, J=7.5 Hz, 1H), 7.88 (m, 2H), 7.4-7.2 (m, 7H), 5.33 (s, 1H), 5.16 (s, 2H), 3.93-3.91 (s, 3H). LC-MS m/z=376 $[C_{18}H_{15}BrO_4+H]^+$.

Step C

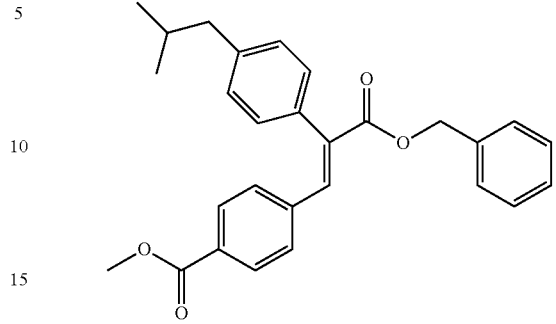

4-(2-Benzyloxycarbonyl-2-bromo-vinyl)-benzoic acid methyl ester (2.0 g, 5.33 mmol) was added to a 100 mL RB flask containing 4-isobutylphenylboronic acid (2.85 g, 15.99 mmol), sodium carbonate (2.83 g, 26.65 mmol), and dichlorobis(tri-o-tolylphosphine)palladium(II) (544 mg, 0.69 mmol). Dimethoxyethane (16 mL), ethanol (8 mL), and water (4 mL) were added, and the reaction was stirred at 120° C. for 1 hour at which point TLC analysis indicated that the reaction had gone to completion. The reaction was filtered hot through celite and concentrated to dryness. Purification by flash column chromatography was performed on an ISCO Sg-100c system, using a 40 gram pre-packed column and eluting with a linear gradient of ethyl acetate in hexanes starting at 10% EtOAc and ending at 40% EtOAc over 22 minutes. This afforded the desired product, 4-[2-Benzyloxycarbonyl-2-(4-isobutyl-phenyl)-vinyl]-benzoic acid methyl ester as a pale oil, 1.8 g, 79%. LC-MS m/z=429 $[C_{28}H_{28}O_4+H]^+$.

Step D

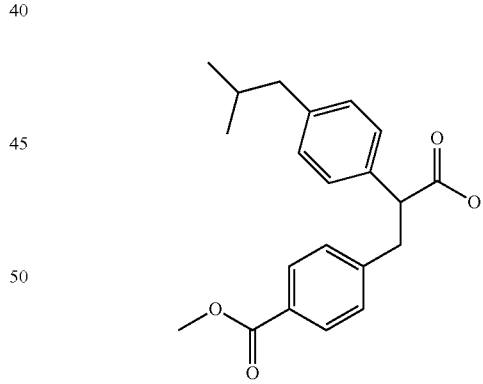

To a stirred solution of 4-[2-Benzyloxycarbonyl-2-(4-isobutyl-phenyl)-vinyl]-benzoic acid methyl ester (1.8 g, 4.2 mmol) in acetic acid (30 mL) was added palladium on activated carbon (~150 mg). The flask was purged with hydrogen and stirred under hydrogen atmosphere for 18 h. TLC and LC/MS analysis indicated that the reaction had gone to completion. The reaction was filtered through celite and concentrated by rotary evaporation. Toluene (100 mL) was added and the reaction was concentrated to dryness yielding 4-[2-Carboxy-2-(4-isobutyl-phenyl)-ethyl]-benzoic acid methyl ester as a colorless solid, 1.33 g (93%). LC-MS m/z=341 $[C_{21}H_{24}O_4+H]^+$.

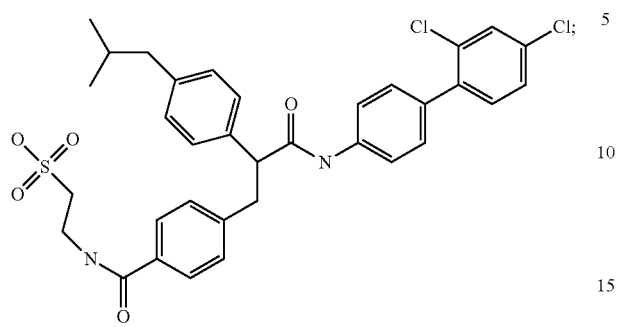

The title compound was synthesized from 4-[2-Carboxy-2-(4-isobutyl-phenyl)-ethyl]-benzoic acid methyl ester according as described in Example 1.001 with appropriate substitutions. $^1$H NMR (300 MHz, DMSO-D6): δ 10.17 (s, 1H), 8.38 (t, 1H), 7.6-7.4 (m, 5H), 7.4-7.2 (m, 8H), 7.10 (d, J=7.5 Hz, 2H), 4.0 (m, 1H), 3.40 (m, 3H), 3.00 (m, 1H), 2.60 (t, J=7.3 Hz 2H), 2.36 (d, J=6.5 Hz 2H), 1.77 (m, 1H), 0.81 (d, J=6.4 Hz, 6H). LC-MS m/z=655 [$C_{34}H_{34}Cl_2N_2O_5S$+H]$^+$. Anal. Calcd for ($C_{34}H_{34}Cl_2N_2O_5S$+1.8 H2O+0.3 TFA): C, 57.70; H, 5.30; N, 3.89. Found: C, 57.81; H, 5.30; N, 3.91. HPLC conditions: Column=Waters Atlantis; dC18-150×4.6 mm; Mobile phase=Solvent A: H2O/0.05% TFA; Solvent B: ACN/0.05% TFA. Flow rate=2.0 mL/min; UV@254 nm. Retention time in minutes. (rt=9.20/20.00, 98% purity).

LC/MS: 625.6 (M+H)$^+$.

Formula: C36H36N2O6S+2.6 H2O+0.05 CF3CO2H Elemental Analysis: Calculated: C:64.02 H:6.14 N:4.14. Found: C:64.33 H:6.52 N:4.42.

Example 1.122

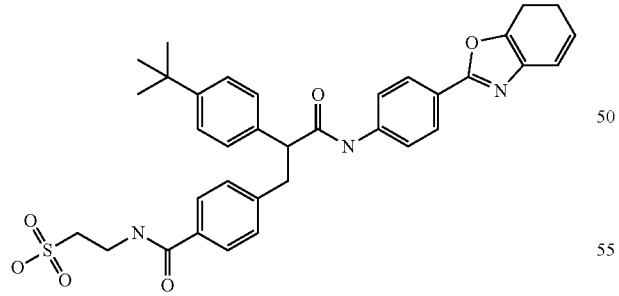

This product was synthesized as described in Example 1.001, except that 4-benzoxazol-2-yl phenyl amine was used instead of 4-iodoaniline and the Suzuki coupling step was omitted.

LC/MS: 626.6 (M+H)$^+$.

Formula: C35H35N3O6S+1.4 H2O. Elemental Analysis: Calculated: C:64.58 H:5.85 N:6.46. Found: C:64.97 H:6.29 N:6.32.

Example 1.123

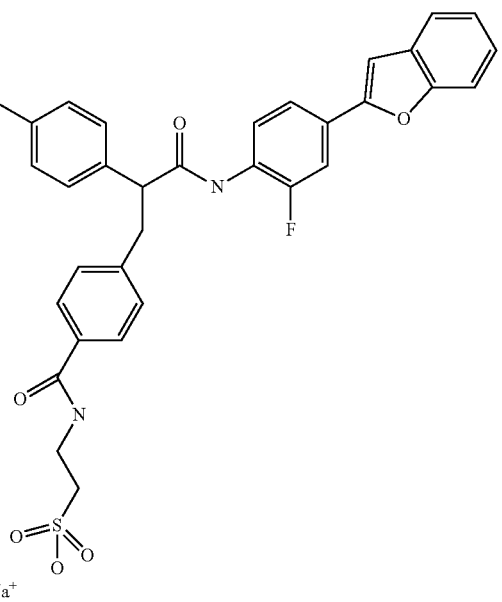

This product was synthesized as described in Example 1.001, with appropriate modifications.

LC/MS: 626.6 (M+H)+.

Formula: C35H35N3O6S+1.4 H2O. Elemental Analysis: Calculated: C:64.58 H:5.85 N:6.46. Found: C:64.97 H:6.29 N:6.32.

Example 1.124

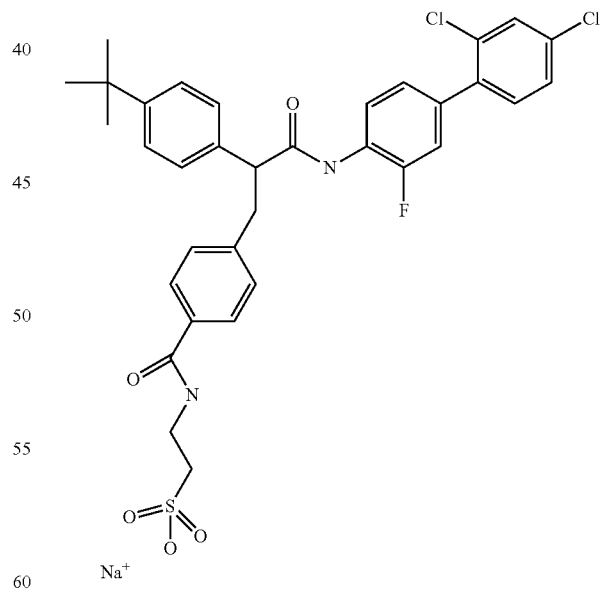

This product was synthesized as described in Example 1.001, with appropriate modifications.

LC/MS: 641.4 (M-H)$^-$.

Formula: C36H36N2O6FSNa+1.4H2O+0.1CH3CN. Elemental Analysis: Calculated: C: 62.65 H: 5.39 N: 4.24. Found: C: 62.39 H: 5.56 N: 4.48.

Example 1.125

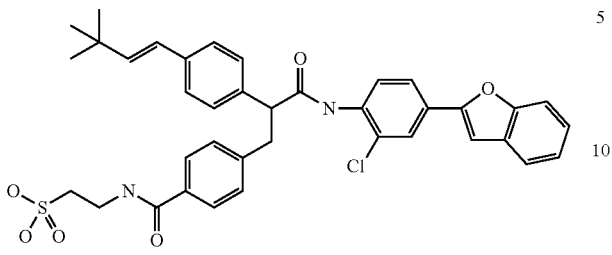

This product was synthesized as described in Example 1.003, with appropriate modifications.

LC/MS: 683.6 (M–H)⁻.

Formula: C38H37N2O6ClS+0.7H2O. Elemental Analysis: Calculated: C: 65.40 H: 5.55 N: 4.01. Found: C: 65.37 H: 5.04 N: 3.85.

Example 1.126

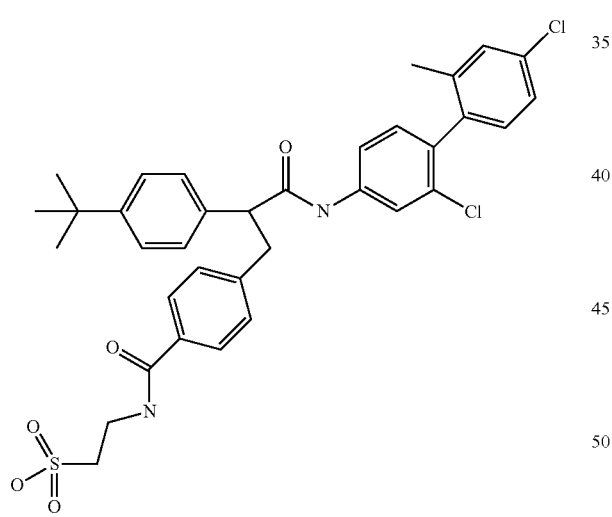

This product was synthesized as described in Example 1.001, with appropriate modifications.

LC/MS: 665.6 (M–H)⁻.

Formula: C35H36N2O5Cl2S+1.9H2O. Elemental Analysis: Calculated: C: 59.89 H: 5.72 N: 3.99. Found: C: 60.15 H: 6.09 N: 3.81.

Example 1.127

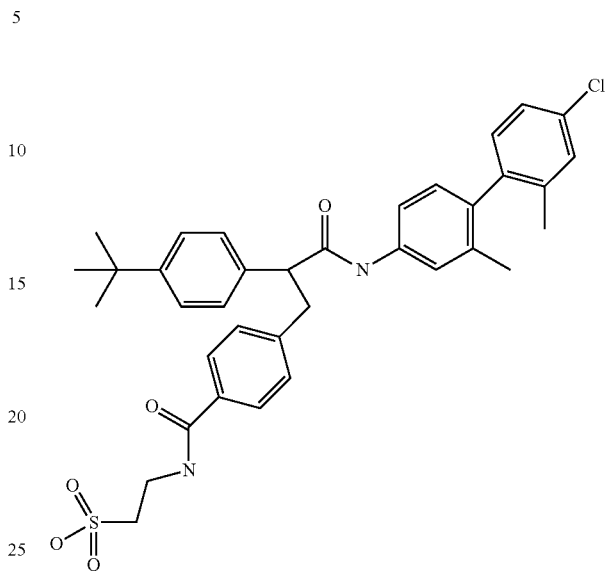

This product was synthesized as described in Example 1.001, with appropriate modifications.

LC/MS: 645.4 (M–H)⁻.

Formula: C36H39N2O5ClS+2.5H2O+0.8CF3COOH+ 0.1CH3CN. Elemental Analysis: Calculated: C: 57.65 H: 5.77 N: 3.73. Found: C: 57.40 H: 5.77 N: 4.00.

Example 1.128: 2-{4-[2-(4-Benzofuran-2-ylphenyl-carbamoyl)-3-(cyclohex-2-enylphenyl)-propyl]-benzoylamino}-ethanesulfonic acid

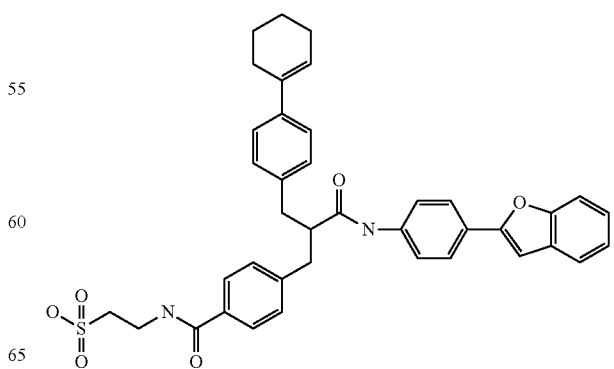

Step A

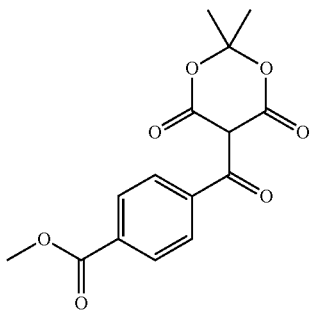 [SMILES: COC(=O)c1ccc(C(=O)C2C(=O)OC(C)(C)OC2=O)cc1]

A mixture consisting of Meldrum's acid (2 g, 13.9 mmol), terephthalic acid monomethyl ester (2.5 g, 13.9 mmol), EDC (3.5 g, 18 mmol) and DMAP (2.2 g, 18 mmol) in DCM (50 mL) was stirred at RT overnight. The reaction mixture was diluted with DCM (to ~100 mL) then washed with water (2×50 mL). The organic solution was dried over $Na_2SO_4$ and concentrated to afford 3.9 g of crude 4-(2,2-Dimethyl-4,6-dioxo-[1,3]dioxane-5-carbonyl)-benzoic acid methyl ester as a yellow solid. The crude was carried on as is for the next step.

Step B

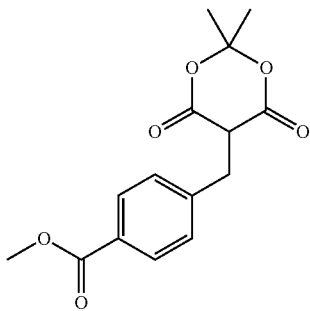 [SMILES: COC(=O)c1ccc(CC2C(=O)OC(C)(C)OC2=O)cc1]

The mixture of crude 4-(2,2-Dimethyl-4,6-dioxo-[1,3]dioxane-5-carbonyl)-benzoic acid methyl ester from step A was dissolved in DCM (50 mL) and AcOH (5 mL) and chilled to ice-bath temperature. To the solution was added portionwise, over 30 min, $NaBH_4$ (722 mg, 19.1 mmol). The reaction mixture was allowed to warm to RT overnight. The mixture was quenched with water, stirred for 10 min then extracted with DCM. The organic solution was dried over $Na_2SO_4$ and concentrated to afford an off-white solid that was suspended in $Et_2O$ to give pure 4-(2,2-Dimethyl-4,6-dioxo-[1,3]dioxan-5-ylmethyl)-benzoic acid methyl ester as a white solid (2.24 g, 60%). $^1H$ NMR (500 MHz, DMSO-d6): δ 7.87 (d, J=8 Hz, 2H), 7.43 (d, J=8 Hz, 2H), 4.86 (t, 7.87 (d, J=5 Hz, 1H), 2H), 3.84 (s, 3H), 3.35 (d, J=5 Hz, 2H), 1.83 (s, 3H), 1.64 (s, 3H)

Step C

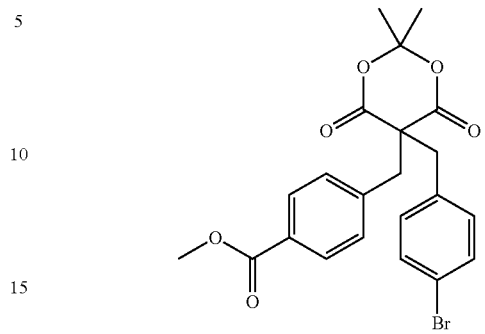

To 4-(2,2-Dimethyl-4,6-dioxo-[1,3]dioxan-5-ylmethyl)-benzoic acid methyl ester (3 g, 10.3 mmol) and $K_2CO_3$ (2.1 g, 15.4 mmol) in DMF (15 mL) was added 4-bromobenzyl bromide (3 g, 12.3 mmol). The solution was stirred at room temperature overnight. After partitioning between $Et_2O$ and water, the organic portion washed with brine, dried over $Na_2SO_4$ then concentrated to afford crude material which was crystallized from MeOH to afford 4-[5-(4-Bromobenzyl)-2,2-dimethyl-4,6-dioxo-[1,3]dioxan-5-ylmethyl]-benzoic acid methyl ester as a white solid (4.12 g, 87%). $^1H$ NMR (500 MHz, DMSO-d6): δ 7.91 (d, J=8.5 Hz, 2H), 7.55 (d, J=8.5 Hz, 2H), 7.21 (d, J=8 Hz, 2H), 7.02 (d, J=8 Hz, 2H), 3.81 (s, 3H), 3.45 (s, 2H), 3.38 (s, 2H), 0.71 (s, 3H), 0.65 (s, 3H).

Step D

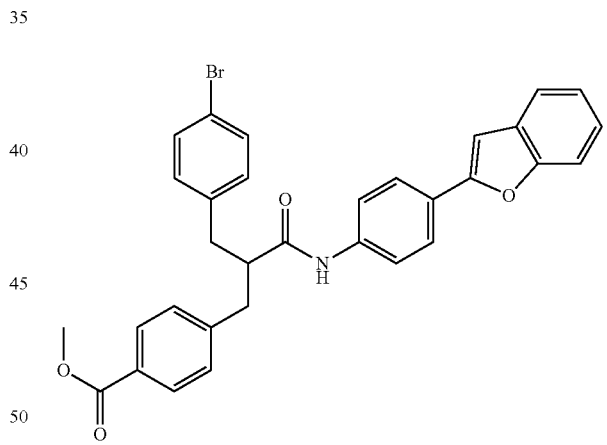

A solution of 4-[5-(4-Bromobenzyl)-2,2-dimethyl-4,6-dioxo-[1,3]dioxan-5-ylmethyl]-benzoic acid methyl ester (1.35 g, 2.93 mmol) and 4-benzofuran-2-ylphenylamine (736 mg, 3.52 mmol) in dry NMP (10 mL) was heated at 220° C. for 5 min in the microwave. The reaction mixture was diluted with water then extracted with EtOAc. After concentrating, the crude material was purified by flash chromatography on silica gel (ISCO cartridge, 40 g), eluting with a gradient of zero to 35% ethyl acetate in hexane over 30 minutes to afford 4-[2-(4-Benzofuran-2-ylphenylcarbamoyl)-3-(4-bromophenyl)-propyl]-benzoic acid methyl ester (935 mg, 56%). $^1H$ NMR (300 MHz, DMSO-d6): δ 9.92 (s, 1H), 7.86 (d, J=8.4 Hz, 2H), 7.80 (d, J=8.7 Hz, 2H), 7.64-7.17 (m, 13H), 3.81 (s, 3H), 3.10-2.93 (m, 3H), 2.85-2.71 (m, 2H).

Step E

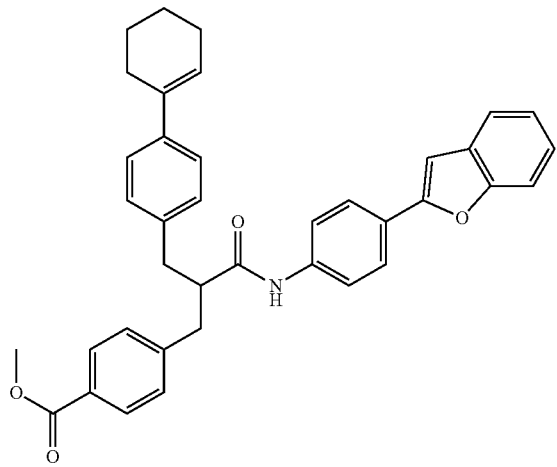 [SMILES: COC(=O)c1ccc(CC(Cc2ccc(C3=CCCCC3)cc2)C(=O)Nc2ccc(-c3cc4ccccc4o3)cc2)cc1]

A solution consisting of 4-[2-(4-Benzofuran-2-ylphenyl-carbamoyl)-3-(4-bromo phenyl)-propyl]-benzoic acid methyl ester (200 mg, 0.35 mmol), dichlorobis(tri-o-tolyl phosphine)-palladium(II), 1-cyclohexenyl boronic acid (222 mg, 1.76 mmol) and sodium carbonate (373 mg, 3.5 mmol) in DME (8 mL), EtOH (4 mL) and water (2 mL) was heated at 125° C. for 7 min in the microwave. The crude reaction mixture was partitioned between EtOAc and water. Evaporation of the organic portion afforded crude 4-[2-(4-Benzofuran-2-ylphenylcarbamoyl)-3-(4-cyclohex-1-enylphenyl)-propyl]-benzoic acid methyl ester which was carried on as is for the next step. LC-MS m/z=570 $[C_{38}H_{35}NO_4+H]^+$.

Step F

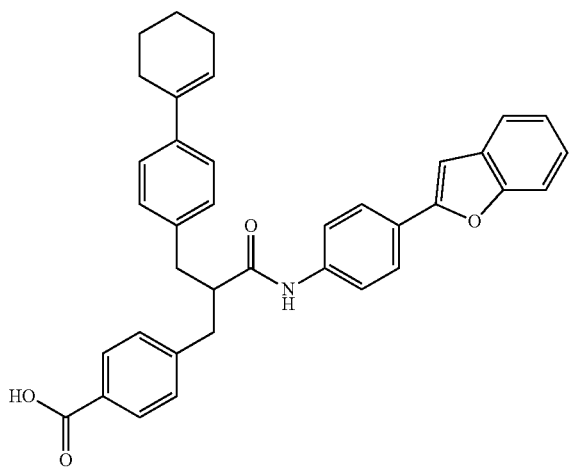 [SMILES: O=C(O)c1ccc(CC(Cc2ccc(C3=CCCCC3)cc2)C(=O)Nc2ccc(-c3cc4ccccc4o3)cc2)cc1]

To the crude 4-[2-(4-Benzofuran-2-ylphenylcarbamoyl)-3-(4-cyclohex-1-enylphenyl)-propyl]-benzoic acid methyl ester from step e dissolved in 20 mL of THF/MeOH/H$_2$O (3:1:1) was added lithium hydroxide (74 mg, 1.8 mmol) After stirring for 5 hrs at RT, the organic solvents were removed under vacuum and the reaction residue diluted further with water (25 mL). The aqueous mixture was made acidic with 1 N HCl and extracted with ethyl acetate. The ethyl acetate portion was then dried over Na$_2$SO$_4$ and concentrated under vacuum to afford 4-[2-(4-Benzofuran-2-ylphenylcarbamoyl)-3-(4-cyclohex-1-enylphenyl)-propyl]-benzoic acid which was carried on as is for the next step.

Step G

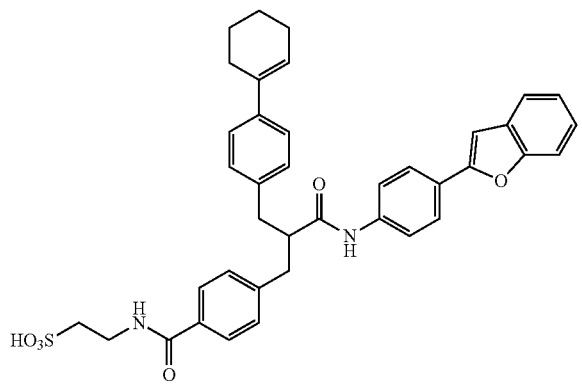 [SMILES: O=C(NCCS(=O)(=O)O)c1ccc(CC(Cc2ccc(C3=CCCCC3)cc2)C(=O)Nc2ccc(-c3cc4ccccc4o3)cc2)cc1]

A mixture consisting of 4-[2-(4-Benzofuran-2-ylphenylcarbamoyl)-3-(4-cyclohex-1-enylphenyl)-propyl]-benzoic acid from step f above, EDC (101 mg, 0.53 mmol), HOBT hydrate (80 mg, 0.53 mmol), taurine (66 mg, 0.53 mmol) and diisopropyl diethylamine (0.18 mL, 1.1 mmol) in DMF (10 mL) was stirred at RT overnight. The solvent was removed under vacuum and 1N HCl was added. The resulting precipitate was filtered, washed with water and purified by preparatory HPLC on a Shimadzu modular HPLC system using a Waters Atlantis dC18 30×75 mm preparatory column and running a gradient from 40% to 100% acetonitrile over 13 minutes. TFA was used as an ionizer and was present in 0.05% (v/v). Detection was accomplished using an in-line UV detector running at 254 nm. Rotary evaporation of the solvated compound provided the title compound (50 mg): $^1$H NMR (300 MHz, DMSO-d6): δ 9.94 (s, 1H), 8.43 (t, J=6.12 Hz, 1H), 7.80 (d, J=8.4 Hz, 2H), 7.69 (d, J=8.4 Hz, 2H) 7.64-7.21 (m, 11H), 7.15 (d, J=8.4 Hz, 2H), 3.48 (dd, J=12.6 Hz, J=6.3 Hz, 2H), 3.1-2.9 (m, 3H), 2.8-2.4 (m, 4H), 2.38 (s, 1H), 2.35-2.25 (br m, 2H), 2.19-2.09 (br m, 2H), 1.77-1.67 (br m, 2H), 1.6-1.5 (br m, 2H). LC-MS m/z=661 $[C_{349}H_{38}N_2O_6S+H]^-$.

Example 1.129: 2-{4-[2-(4-Benzofuran-2-yl-2-fluorophenylcarbamoyl)-hept-4-ynyl]-benzoylamino}-ethanesulfonic acid

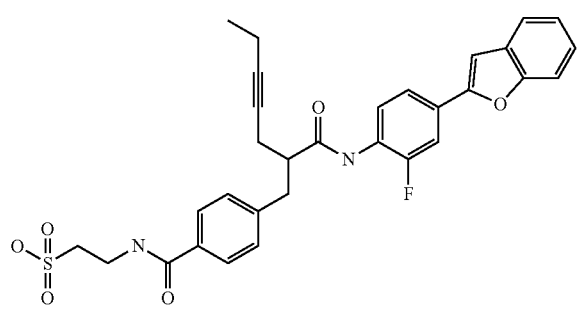 [SMILES: CCC#CCC(Cc1ccc(C(=O)NCCS(=O)(=O)O)cc1)C(=O)Nc1ccc(-c2cc3ccccc3o2)cc1F]

Step A

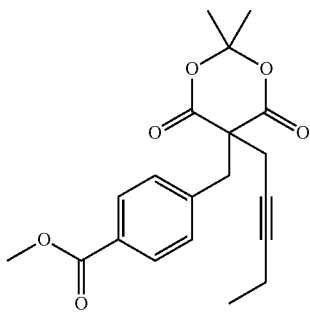 [SMILES: CCC#CCC1(Cc2ccc(C(=O)OC)cc2)C(=O)OC(C)(C)OC1=O]

The compound 4-(2,2-Dimethyl-4,6-dioxo-5-pent-2-ynyl-[1,3]dioxan-5-ylmethyl]-benzoic acid methyl ester was prepared as described in Example 1.128, step C, using 1-bromo-2-pentyne. $^1$H NMR (300 MHz, DMSO-d6): δ 7.94 (d, J=8.4 Hz, 2H), 7.20 (d, J=8.4 Hz, 2H), 3.85 (s, 3H), 3.28 (s, 2H), 2.97 (s, 2H), 2.12 (m, 2H), 1.63 (s, 3H), 0.98 (br m, 3H), 0.84 (s, 3H).

Step B

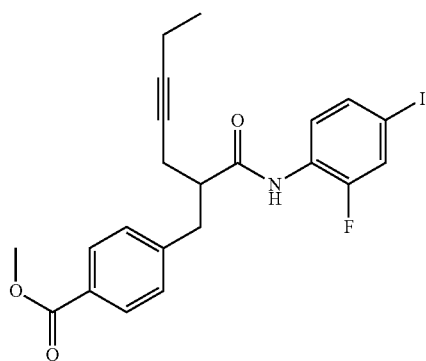 [SMILES: CCC#CCC(Cc1ccc(C(=O)OC)cc1)C(=O)Nc1ccc(I)cc1F]

The compound 4-[2-(2-Fluoro-4-iodo-phenylcarbamoyl)-hept-4-ynyl]-benzoic acid methyl ester was prepared from the corresponding methyl ester from step a above according to the procedure described for the synthesis of Example 1.128, step D using 2-fluoro-4-iodoaniline. TLC: R$_f$=0.45 hexane/ethyl acetate (4:1).

Step C

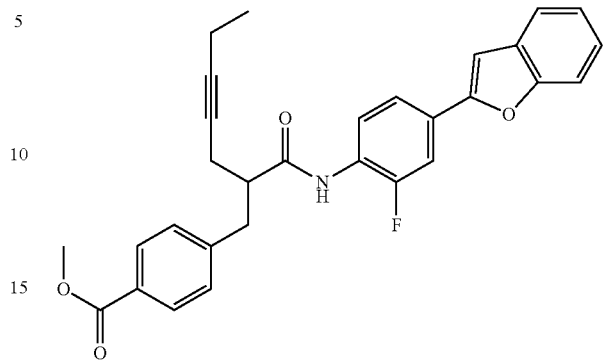

The compound 4-[2-(4-Benzofuran-2-yl-fluorophenylcarbamoyl)-hept-4-ynyl]-benzoic acid methyl ester was prepared 4-[2-(2-Fluoro-4-iodo-phenylcarbamoyl)-hept-4-ynyl]-benzoic acid methyl ester according to the procedure described for the synthesis of Example 1.128, step E. LC-MS m/z=484 $[C_{30}H_{26}FNO_4+H]^+$.

Step D

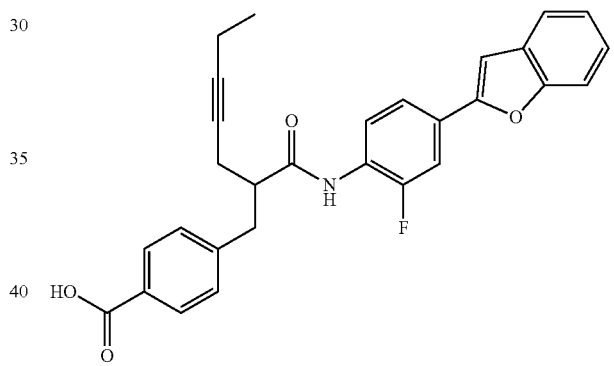

The compound 4-[2-(4-Benzofuran-2-yl-fluorophenylcarbamoyl)-hept-4-ynyl]-benzoic acid was prepared from the corresponding ester obtained from step c above according to the procedure described for the synthesis of Example 1.128, step F. The crude material was carried on without purification for the following step.

Step E

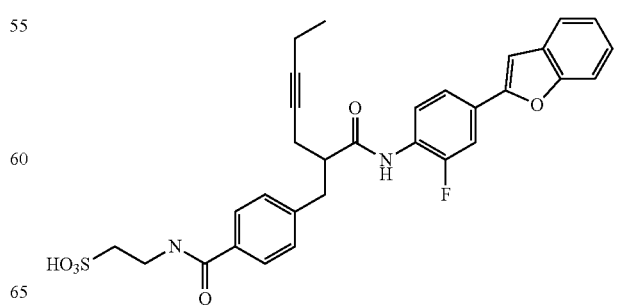

The title compound was prepared from 4-[2-(4-Benzofuran-2-yl-fluorophenylcarbamoyl)-hept-4-ynyl]-benzoic acid according to the procedure described for the synthesis of Example 1.128, step G. ¹H NMR (300 MHz, DMSO-d6): δ 9.89 (s, 1H), 8.45 (t, J=5.1 Hz, 1H), 7.95 (t, J=8.1 Hz, 1H), 7.81-7.61 (complex m, 6H), 7.45 (s, 1H), 7.36-7.24 (complex m, 4H), 6.81-6.77 (m, 4H), 3.48 (dt, J=12.6 Hz, J=7.2 Hz, 2H), 3.17-2.81 (m, 4H), 2.64 (t, J=7.2 Hz, 2H), 2.4-2.1 (complex m, 4H), 1.01 (t, (t, J=7.5 Hz, 3H);

LC-MS m/z=575 [$C_{31}H_{29}FN_2O_6S+H$]⁻.

Example 1.130

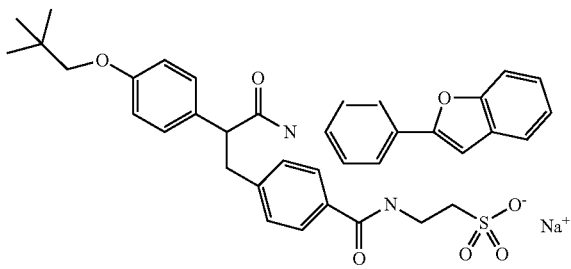 [SMILES: CC(C)(C)COc1ccc(C(Cc2ccc(C(=O)NCCS(=O)(=O)[O-])cc2)C(N)=O)cc1 ; C/C=C\C=C(/C)c1cc2ccccc2o1 ; [Na+]]

Step A: (4-Benzyloxy-phenyl) acetic acid benzyl ester

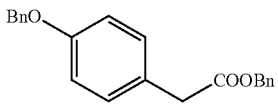

To a stirred solution of 4-hydroxy-phenyl acetic acid (10.0 g, 65.72 mmol) in DMF (70 mL) at rt were added Cs₂CO₃ (47.11 g, 144.5 mmol) and benzyl bromide (17.29 mL, 144.5 mmol). The reaction mixture was stirred overnight at room temperature, heated at 100° C. for 1 h and cooled to rt. The solvent was removed under reduced pressure and poured into H₂O. The aqueous solution was extracted with ethyl acetate and the combined organic layers were washed with brine, dried over Na₂SO₄, filtered and concentrated under reduced pressure. The crude product was recrystallization in hexanes to afford (4-benzyloxy-phenyl) acetic acid benzyl ester as a yellow solid. (20.5 g, 94%): ¹H NMR (300 MHz, CDCl₃): δ 7.25-7.34 (m, 10H), 7.14 (d, J=8.4 Hz, 2H), 7.02 (d, J=8.4 Hz, 2H), 5.50 (s, 2H), 5.12 (s, 2H), 3.61 (s, 2H); TLC conditions: Uniplate silica gel, 250 microns; mobile phase=ethyl acetate-hexanes (1:5); $R_f$=0.8.

Step B: 4-[2-Benzyloxycarbonyl-2(4-benzyloxyphenyl)-ethyl]-benzoic acid methyl ester

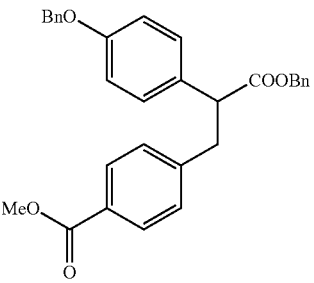

To a stirred solution of (4-benzyloxy-phenyl) acetic acid benzyl ester (Step A, 8.0 g, 24.08 mmol) in anhydrous THF (60 mL) was added LiHMDS (25.28 mL, 25.28 mmol, 1.0 M solution in toluene) at −78° C. The reaction mixture was stirred for 1.5 h at −78° C., and then methyl-4-bromo methyl benzoate (5.79 g, 25.28 mmol, in THF 10 mL) was added dropwise, stirred for 2 h at −78° C. and then allowed to warm to rt for 1 h. After completion of the reaction quenched with saturated NH₄Cl solution (20 mL) and stirred for 10 min. The reaction mixture was extracted with ethyl acetate (100 mL) and the organic layer was washed with brine, dried over Na₂SO₄ and concentrated under reduced pressure. The crude product was recrystallization from minimum amount of EtOAc and hexane at room temperature) to afford 4-[2-benzyloxycarbonyl-2(4-benzyloxy-phenyl)-ethyl]-benzoic acid methyl ester as a yellow solid (7.4 g, 64%): ¹H NMR (300 MHz, CDCl₃): δ 7.88 (d, J=8.1 Hz, 2H), 7.42-7.12 (m, 14H), 6.89 (d, J=8.7 Hz, 2H), 5.10 (d, J=6.0, Hz, 1H), 5.06-5.03 (m, 2H), 4.95 (d, J=12.6 Hz, 1H), 3.89 (s, 3H), 3.87-3.75 (m, 1H), 3.41 (dd, J=9.0, 13.8 Hz, 1H), 3.05 (dd, J=7.2, 13.8 Hz, 1H); TLC conditions: Uniplate silica gel, 250 microns; mobile phase=ethyl acetate-hexanes (1:4); $R_f$=0.6.

Step C: 4-[2-carboxy-2-(4-hydroxy-phenyl)-ethyl]-benzoic acid methyl ester

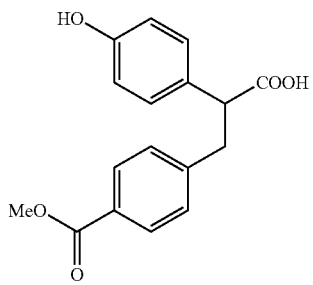 [SMILES: COC(=O)c1ccc(CC(C(=O)O)c2ccc(O)cc2)cc1]

To a stirred solution of 4-[2-benzyloxycarbonyl-2-(4-benzyloxy-phenyl)-ethyl]-benzoic acid methyl ester (Step C, 3.0 g, 6.66 mmol) in EtOH:EtOAc (50 mL, 1:1 ratio) at rt, was added 10% palladium on carbon (0.3 g), hydrogenated at 1 atm. H₂ (gas) and the reaction mixture was stirred at rt for 14 h. The reaction mixture was filtered through celite plug and washed with ethyl acetate (50 mL) and concentrated under reduced pressure. The crude product was dried under vacuum for 3 h to afford 4-[2-carboxy-2-(4-hydroxyphenyl)-ethyl]-benzoic acid methyl ester as a white solid (1.6 g, 86%): ¹H NMR (300 MHz, CDCl₃): δ 7.83 (d, J=8.4 Hz, 2H), 7.27 (d, J=8.4 Hz, 2H), 7.08 (dd, J=4.62, 12.5 Hz, 2H), 6.66 (dd, J=6.6, 12.5 Hz, 2H), 3.79 (s, 3H), 3.75 (t, J=8.1 Hz, 1H), 3.22 (dd, J=8.4, 13.5 Hz, 1H), 2.93 (dd, J=7.2, 13.8 Hz, 1H).

Step D: 4-[2-(4-hydroxy-phenyl)-2-(4-iodo-phenyl-carbamoyl)-ethyl]-benzoic acid methyl ester

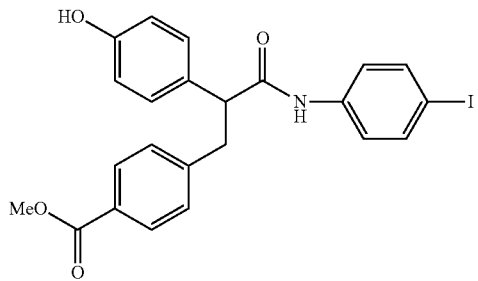 [SMILES: COC(=O)c1ccc(CC(C(=O)Nc2ccc(I)cc2)c2ccc(O)cc2)cc1]

To a stirred suspension of 4-[2-carboxy-2-(4-hydroxy-phenyl)-ethyl]-benzoic acid methyl ester (Step C, 1.5 g, 5.0 mmol) in anhydrous CH₂Cl₂ (10 mL), was added oxalyl-chloride (1.57 g, 12.5 mmol) at rt, the reaction mixture was stirred for 14 h. The reaction mixture was concentrated under reduced pressure and azeotroped with CH₂Cl₂ (2×10 mL) dried under vacuum for 3 h, The crude acid chloride (1.8 g, 5.66 mmol) was treated with 4-iodoaniline (1.48 g, 6.79 mmol) and N,N-diisopropylethylamine (3.0 mL, 16.9 mmol) in CH₂Cl₂ at 0° C. The reaction mixture was stirred for 14 h at rt and the reaction mixture was concentrated under reduced pressure. The mixture was extracted with ethyl acetate (100 mL) and the organic layer was washed with brine, dried over Na₂SO₄ and concentrated under reduced pressure. The residue was treated with CH₂Cl₂ to get solid compound, which was filtered and washed with CH₂Cl₂ to give 4-[2-(4-hydroxy-phenyl)-2-(4-iodo-phenyl-carbamoyl)-ethyl]-benzoic acid methyl ester as a yellowish solid (1.6 g, 64%): ¹H NMR (300 MHz, DMSO-d₆): δ 10.05 (s, 1H, NH), 9.28 (s, 1H, OH), 7.81 (d, J=8.1 Hz, 2H), 7.53 (d, J=8.7 Hz, 2H), 7.31 (t, J=8.4 Hz, 4H), 7.18 (d, J=8.4 Hz, 2H), 6.65 (d, J=8.4 Hz, 2H), 3.85 (t, J=6.9 Hz, 1H), 3.77 (s, 3H), 3.40-3.36 (m, 1H), 2.95 (dd, J=6.0, 12.9 Hz, 1H); TLC conditions: Uniplate silica gel, 250 microns; mobile phase=ethyl acetate/hexanes (1:2); R$_f$=0.5.

Step E: 4-[2-[4-(2,2-dimethylpropoxy)-phenyl]-2-(4-iodo-phenyl-carbamoyl)-ethyl]-benzoic acid methyl ester

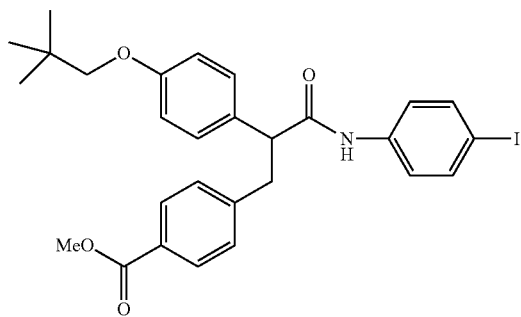 [SMILES: COC(=O)c1ccc(CC(C(=O)Nc2ccc(I)cc2)c2ccc(OCC(C)(C)C)cc2)cc1]

To a stirred solution of 4-[2-(4-hydroxy-phenyl)-2-(4-iodo-phenyl-carbamoyl)-ethyl]-benzoic acid methyl ester (Step D, 0.6 g, 1.60 mmol) in DMF (15 mL) at rt were added Cs₂CO₃ (2.07 g, 6.38 mmol) and Neopentyliodide (2.53 g, 12.7 mmol). The reaction mixture was heated at 80° C. for 14 h and cool to rt and after completion of the reaction, the solvent was removed under reduced pressure and poured into H₂O (50 mL). The aqueous solution was extracted with ethyl acetate (2×100 mL) and the combined organic layers were washed with brine, dried over Na₂SO₄, filtered and concentrated under reduced pressure. The crude product was recrystallization in hexanes to afford 4-[2-(4-(2,2-dimethyl-propoxy)-phenyl)-2-(4-iodo-phenyl-carbamoyl)-ethyl]-benzoic acid methyl ester as a yellow solid. (1.6 g, 88%): ¹H NMR (300 MHz, CDCl₃): δ 10.15 (s, 1H, NH), 7.80 (d, J=8.4 Hz, 2H), 7.53 (d, J=8.7 Hz, 2H), 7.35-7.26 (m, 6H), 6.82 (d, J=8.7 Hz, 2H), 3.93 (t, J=7.2 Hz, 1H), 3.77 (s, 3H), 3.54 (s, 2H), 3.35 (dd, J=9.0, 13.5 Hz, 1H), 2.98 (dd, J=6.6, 13.8 Hz, 1H), 0.94 (s, 9H); TLC conditions: Uniplate silica gel, 250 microns; mobile phase=ethyl acetate/hexanes (1:3); R$_f$=0.7.

Steps F, G and H

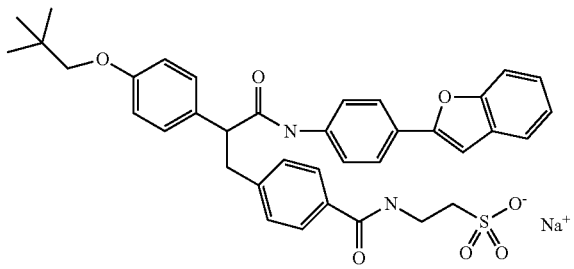 [SMILES: CC(C)(C)COc1ccc(C(Cc2ccc(C(=O)NCCS(=O)(=O)[O-])cc2)C(=O)Nc2ccc(-c3cc4ccccc4o3)cc2)cc1 ; [Na+]]

The precursor from Step E was used to synthesize the target compound by the route described in Example 1.001 with appropriate modifications Example 1.131

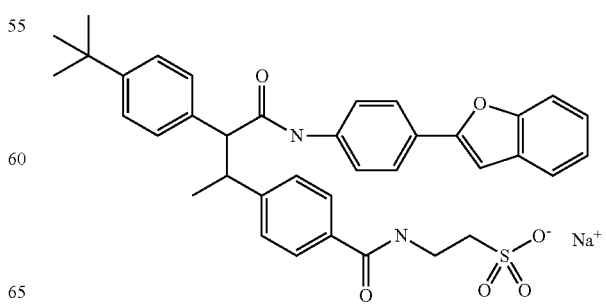

Step A: (4-tert-Butyl-phenyl) acetic acid benzyl ester

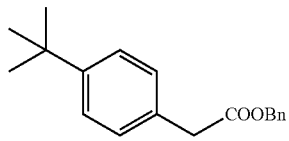

To a stirred solution of 4-tert-butyl-phenyl acetic acid (5.0 g, 26.04 mmol) in DMF (30 mL) at rt were added $Cs_2CO_3$ (12.72 g, 39.06 mmol) and benzyl bromide (4.89 g, 28.6 mmol). The reaction mixture was stirred for overnight at room temperature and then the reaction mixture was heated at 100° C. for 1 h and cool to rt. The solvent was removed under reduced pressure and poured into cold 1 N HCl (50 mL). The aqueous solution was extracted with ethyl acetate (2×100 mL) and the combined organic layers were washed with brine, dried over $Na_2SO_4$, filtered and concentrated under reduced pressure, dried under vacuum. (4-tert-butyl-phenyl) acetic acid benzyl ester was obtained as a yellowish liquid. (5.96 g, 81%): $^1$H NMR (300 MHz, $CDC_3$): δ 7.37-7.33 (m, 7H), 7.25 (dd, J=5.4, 13.2 Hz, 2H), 5.14 (s, 2H), 3.65 (s, 2H), 1.32 (s, 9H); TLC conditions: Uniplate silica gel, 250 microns; mobile phase=ethyl acetate-hexanes (1:5); $R_f$=0.8.

Step B: 4-(1-hydroxy-ethyl)-benzoic acid methyl ester

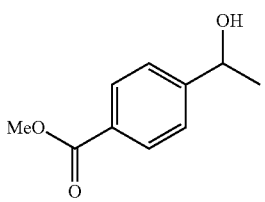

To a stirred solution of 4-Acetyl-benzoic acid methyl ester (5.0 g, 28.06 mmol) in MeOH (25 mL) at 0° C., was added sodium borohydride ($NaBH_4$) (2.12 g, 56.12 mmol), the reaction mixture was stirred at rt for 3 h. The solvent was removed under reduced pressure, was diluted with $H_2O$, the reaction mixture was extracted with ethyl acetate (150 mL), dried over $Na_2SO_4$ and concentrated under reduced pressure. The crude product was dried under vacuum for 3 h to afford 4-(1-hydroxy-ethyl)-benzoic acid methyl ester (4.9 g, 99%): $^1$H NMR (300 MHz, $CDCl_3$): δ 8.0 (d, J=7.8 Hz, 2H), 7.47 (d, J=8.1 Hz, 2H), 5.20 (q, J=6.9 Hz, 1H), 3.91 (s, 3H), 2.02 (d, J=7.2, Hz, 3H). TLC conditions: Uniplate silica gel, 250 microns; mobile phase=ethyl acetate-hexanes (1:2); $R_f$=0.5.

Step C: 4-(1-Bromo-ethyl)-benzoic acid methyl ester

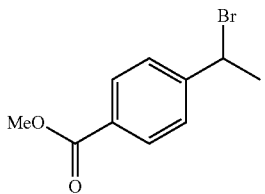

To a stirred solution of 4-(1-hydroxy-ethyl)-benzoic acid methyl ester (Step B, 2.12 g, 11.7 mmol) in $CH_2Cl_2$ (25 mL) at 0° C. were added carbon tetra bromide (5.07 g, 15.3 mmol) and triphenylphosphine (3.71 g, 14.04 mmol). The reaction mixture was stirred overnight at room temperature, after completion of the reaction, was poured into $H_2O$ (50 mL). The aqueous solution was extracted with $CH_2Cl_2$ (2×100 mL) and the combined organic layers were washed with brine, dried over $Na_2SO_4$, filtered and concentrated under reduced pressure. The crude product was purified by column chromatography in hexanes/ethyl acetate (5%) to afford 4-(1-bromo-ethyl)-benzoic acid methyl ester as a colorless liquid. (2.45 g, 85%): $^1$H NMR (300 MHz, $CDCl_3$): δ 8.0 (d, J=8.4 Hz, 2H), 7.47 (d, J=8.1 Hz, 2H), 5.11 (q, J=6.9 Hz, 1H), 3.91 (s, 3H), 1.83 (d, J=6.9 Hz, 3H); TLC conditions: Uniplate silica gel, 250 microns; mobile phase=ethyl acetate-hexanes (1:5); $R_f$=0.8.

Step D: 4-[2-Benzyloxycarbonyl-2-(4-tert-butyl-phenyl)-1-methyl-ethyl]-benzoic acid methyl ester

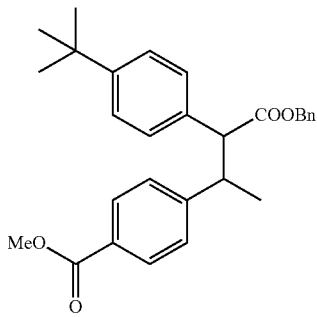

To a stirred solution of (4-tert-butyl-phenyl) acetic acid benzyl ester (Step C, 1.8 g, 6.38 mmol) in anhydrous THF (15 mL) was added LiHMDS (9.57 mL, 9.57 mmol, 1.0 M solution in toluene) at −78° C. The reaction mixture was stirred for 1.5 h at −78° C., and then 4-(1-bromo-ethyl)-benzoic acid methyl ester (1.7 g, 7.02 mmol, in THF 5.0 mL) was added dropwise, stirred for 2 h at −78° C. and then allowed to warm to rt for 1 h. After completion of the reaction quenched with saturated $NH_4Cl$ solution (20 mL) and stirred for 10 min. The reaction mixture was extracted with ethyl acetate (100 mL) and the organic layer was washed with brine, dried over $Na_2SO_4$ and concentrated under reduced pressure. The crude product was recrystallization from minimum amount of EtOAc and hexane at room temperature to afford 4-[2-benzyloxycarbonyl-2-(4-tert-butyl-phenyl)-1-methyl-ethyl]-benzoic acid methyl ester as a mixture of diastereomers (2.3 g, 80%), d/r (2:1): $^1$H NMR (300 MHz, CDCl₃): δ 8.02 (d, J=8.4 Hz, 2H), 7.47 (d, J=8.4 Hz, 2H), 7.30-7.38 (m, 7H), 7.06 (d, J=6.9 Hz, 2H), 5.11 (dd, J=6.0, 12.9 Hz, 2H), 3.92 (s, 3H), 3.75 (d, J=7.5 Hz, 1H), 3.49-3.46 (m, 1H), 1.29 (s, 9H), 1.24 (d, J=6.9, Hz, 3H); TLC conditions: Uniplate silica gel, 250 microns; mobile phase=ethyl acetate-hexanes (1:4); R$_f$=0.6.

Step E: 4-[2-(4-tert-butyl-phenyl)-2-carboxy-1-methyl-ethyl]-benzoic acid methyl ester

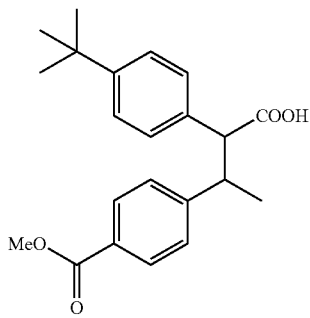 [SMILES: COC(=O)c1ccc(C(C)C(C(=O)O)c2ccc(C(C)(C)C)cc2)cc1]

To a stirred solution of 4-[2-benzyloxycarbonyl-2-(4-tert-butyl-phenyl)-1-methyl-ethyl]-benzoic acid methyl ester (Step D, 2.3 g, 5.38 mmol) in EtOH (25 mL) at rt, was added Pd/C (10% activated on carbon) (0.25 g), hydrogenated at 1 atm of H₂ (gas) and the reaction mixture was stirred at rt for 8 h. The reaction mixture was filtered through a celite plug, washed with ethyl acetate (50 mL) and concentrated under reduced pressure. The crude product was dried under vacuum for 3 h to afford 4-[2-(4-tert-butyl-phenyl)-2-carboxy-1-methyl-ethyl]-benzoic acid methyl ester (7) (1.66 g, 90%) LC-MS m/z=355 [C22H26O4+H]⁺

Steps F, G, H and I

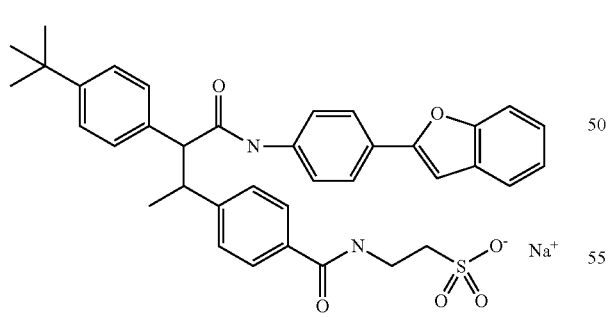

The precursor from Step E above was utilized to synthesize the target compound utilizing the route described in Example 1.001 with appropriate modifications as a mixture of diastereomers LCMS: 677 (M+Na)⁺. Elemental Analysis: Calculated for C37H37N2O7SNa+(3.0)H2O; C: 60.81, H: 5.93, H: 3.83. Found: C: 60.83, H: 5.75, H: 3.76.

Example 1.132

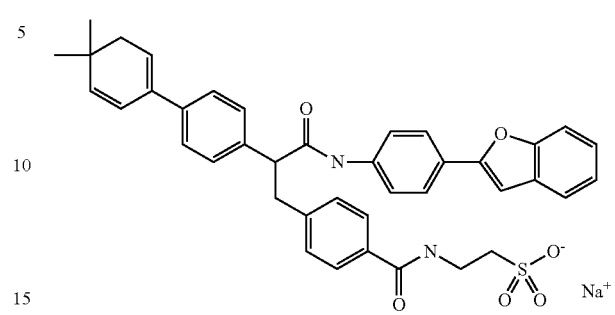

This product was synthesized as described in Example 1.003, with appropriate modifications.

LC/MS: 675 (M+H)⁺.

Formula: C40H37N2O6SNa+2.4H2O. Elemental Analysis: Calculated: C: 64.92, H:5.69, N: 3.79. Found: C: 64.86, H: 5.48, N: 3.71.

Example 1.133

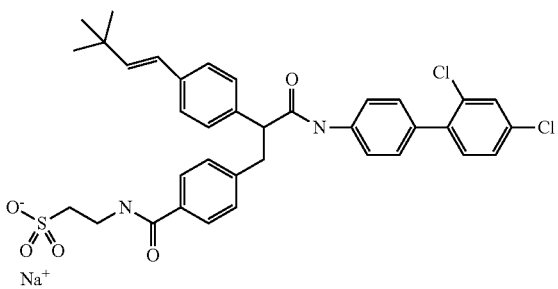 [SMILES: CC(C)(C)/C=C/c1ccc(C(Cc2ccc(C(=O)NCCS(=O)(=O)[O-])cc2)C(=O)Nc2ccc(-c3ccc(Cl)cc3Cl)cc2)cc1 ; [Na+]]

Step A

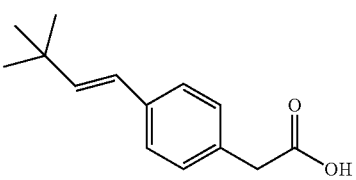 [SMILES: CC(C)(C)/C=C/c1ccc(CC(=O)O)cc1]

A mixture of 4-(bromophenyl) acetic acid (4 g, 18.6 mmol), tert-butyl-vinyl boronic acid (3.57 g, 27.90 mmol), PdCl₂ (tri-o-tolylphosphine)₂ (1.90 g, 2.42 mmol), and sodium carbonate (9.85 g, 93.0 mmol) DME/EtOH/H₂O (4:2:1)(70 mL) was heated at 130° C. for 2 h. The reaction mixture was cooled to rt, filtered and washed with EtOAc (20 mL). The filtrate was concentrated under reduced pressure. The crude residue was washed with acetonitrile and filtered. The resulting solid was treated with 1N HCl (50 mL) and extracted with $CH_2Cl_2$ (2×200 mL). The organic layer was washed with brine, dried over $Na_2SO_4$ and concentrated under reduced pressure. The product was then dried under vacuum to give [4-(3,3-dimethyl-but-1-enyl) phenyl]-acetic acid as a yellow solid (4.0 g, 100%).

$^1$H NMR (300 MHz, DMSO-$d_6$): δ 10.11 (bs, 1H), 7.78 (d, J=8.4 Hz, 2H), 7.55 (d, J=8.4 Hz, 2H), 6.24 (dd, J=16.5, 20.7 Hz, 2H), 3.78 (s, 2H), 1.05 (s, 9H); TLC conditions: Uniplate silica gel, 250 microns; mobile phase=$CH_2Cl_2$/MeOH (10%); $R_f$=0.45.

Step B

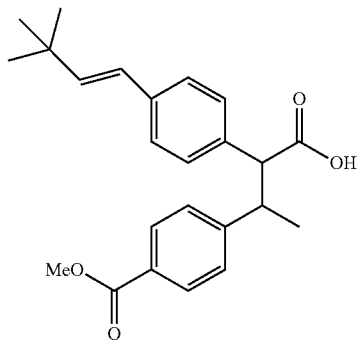 [SMILES: COC(=O)c1ccc(C(C)C(C(=O)O)c2ccc(/C=C/C(C)(C)C)cc2)cc1]

To a stirred solution of 4-(3,3-dimethyl-but-1-enyl)phenyl]-acetic acid (Step A, 1.0 g, 4.62 mmol) and to 4-(1-bromo-ethyl)-benzoic acid methyl ester (1.34 g, 5.55 mmol) in anhydrous THF (30 mL) at −20° C. was added dropwise LiHMDS (13.8 mL, 13.8 mmol, 1.0 M solution in toluene). The reaction mixture was stirred for 3 h at −20° C., and then allowed to warm to rt for 1 h. After completion of the reaction, added a saturated solution of $NH_4Cl$ (20 mL) and stirred for 10 min. The reaction mixture was extracted with ethyl acetate (100 mL) and the organic layer was washed with brine, dried over $Na_2SO_4$ and concentrated under reduced pressure. The crude product was purified by column chromatography eluted with 10% $CH_2Cl_2$/MeOH to afford (4-{2-carboxy-2-[4-(3,3-dimethyl-1-but-1-enyl)-phenyl]-1-methyl-ethyl}-benzoic acid methyl ester as a mixture of diastereomers (0.57 g, 33%), d/r (9.5:0.5): $^1$H NMR (300 MHz, DMSO-$d_6$): δ 12.06 (bs, 1H), 7.87 (d, J=8.1 Hz, 2H), 7.48 (d, J=8.4 Hz, 2H), 7.35-7.41 (m, 4H), 6.24 (dd, J=16.0, 20.1 Hz, 2H), 3.82 (s, 3H), 3.77 (d, J=14.1 Hz, 1H), 3.38-3.45 (m, 1H), 1.08 (s, 9H), 0.84 (d, J=6.9, Hz, 3H);

Using the intermediate obtained in Step B, the product was synthesized as described in Example 1.003, with appropriate modifications.

LC/MS: 679 (M+H)$^+$.

Formula: C36H35N2O5Cl2SNa+2.5H2O. Elemental Analysis: Calculated: C: 57.91, H: 5.40, N: 3.75. Found: C: 57.81, H: 5.33, N: 3.62.

Example 1.134

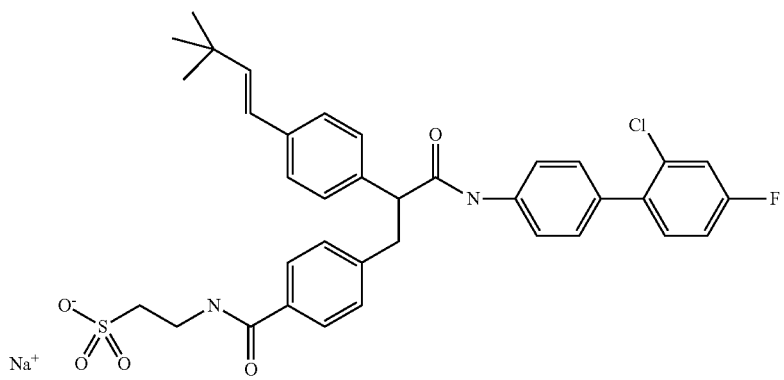 [SMILES: [Na+] ; CC(C)(C)/C=C/c1ccc(C(Cc2ccc(C(=O)NCCS(=O)(=O)[O-])cc2)C(=O)Nc2ccc(-c3ccc(F)cc3Cl)cc2)cc1]

This product was synthesized as described in Example 1.003, with appropriate modifications.

LC/MS: 663 (M+H)$^+$.

Formula: C36H35ClFN2O5S+2.5H2O. Elemental Analysis: Calculated: C: 59.21, H: 5.52, N: 3.84. Found: C: 59.16, H: 5.42, N: 4.06.

Example 1.135

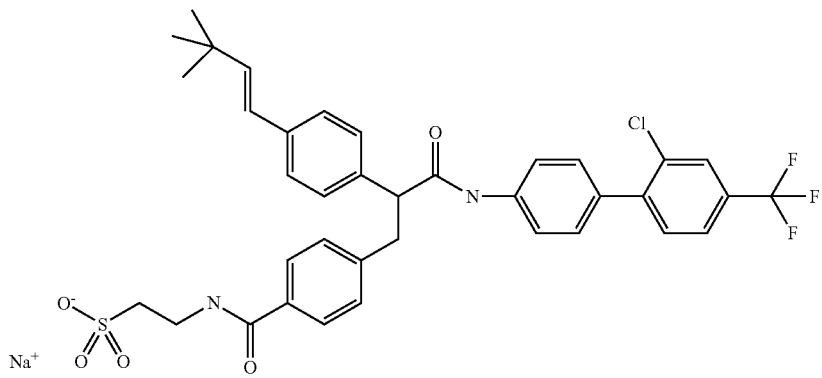 [SMILES: [Na+] ; CC(C)(C)/C=C/c1ccc(C(Cc2ccc(C(=O)NCCS(=O)(=O)[O-])cc2)C(=O)Nc2ccc(-c3ccc(C(F)(F)F)cc3Cl)cc2)cc1]

This product was synthesized as described in Example 1.003, with appropriate modifications.

LC/MS: 713 (M+H)$^+$.

Formula: C37H35N2O5F3ClSNa+2.4H2O. Elemental Analysis: Calculated: C: 57.09, H: 5.15, N: 3.60. Found: C: 57.05, H: 4.77, N: 3.59.

Example 1.136

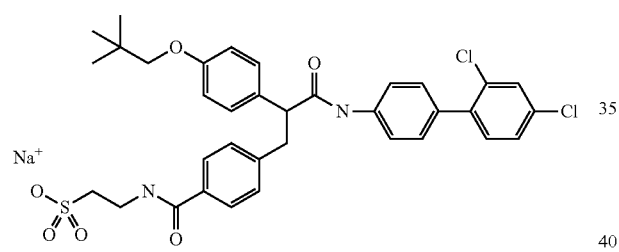

This compound was synthesized as described in Example 1.130 with appropriate modifications.

LCMS: 683 (M+H)$^+$. Calculated for C35H35N2Cl2O6SNa+(3.4)H2O: C: 54.82, H: 5.49, N: 3.65. Found: C: 54.62, H: 5.31, N: 3.52.

Example 1.137

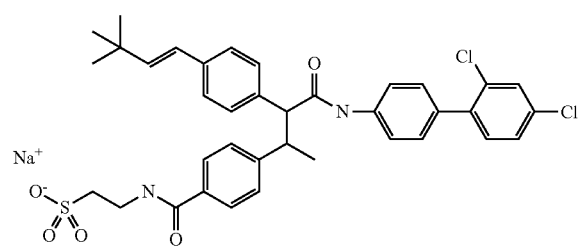 [SMILES: [Na+] ; CC(c1ccc(C(=O)NCCS(=O)(=O)[O-])cc1)C(C(=O)Nc1ccc(-c2ccc(Cl)cc2Cl)cc1)c1ccc(/C=C/C(C)(C)C)cc1]

This compound was synthesized as described in Example 1.131 with appropriate modifications.

LCMS: 715 (M+Na)$^+$. Calculated for C35H35N2Cl2O6SNa+(3.4) H2O: C: 59.69 H: 5.44 N: 3.76. Found: C: 59.81, H: 5.61, N: 3.66.

Example 1.138

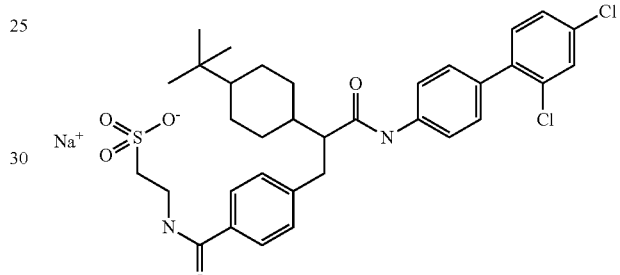

Step A

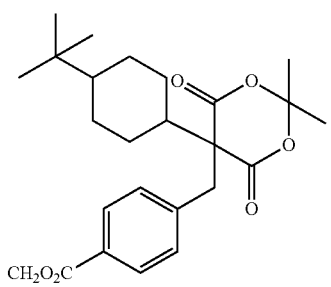

1 eq of 4-t-butylcyclohexanone (0.3 mol) and 0.1 eq of piperidine (0.03 mol) were dissolved in 100 mL of anhydrous pyridine at room temperature. To this solution was added 1 eq of Meldrum's acid (0.3 mol) dissolved in 200 mL of anhydrous pyridine at room temperature. After the addition was complete, the mixture was stirred at room temperature. After 24 hours the solvent was removed and the residue partitioned between ethyl acetate/diethyl ether (1:1) and 0.1N HCl. The combined organic phases were collected, dried over MgSO$_4$, filtered and the solvent removed. The resulting residue was then dissolved in 100 mL of methanol/dichloromethane (1:1) and placed in an ice bath. Sodium borohydride solid was added to the solution with stirring approximately every 15 minutes keeping the reaction temperature below 30 degrees centigrade. The addition was repeated until 2 eq. of sodium borohydride were added in this manner. (Caution: extremely exothermic with gas evolution) After the addition was complete, the reaction mixture was stirred to room temperature over 3 hours. The reaction mixture was then diluted with 500 mL of dichloromethane and quenched with ~500 mL of aqueous saturated ammonium chloride solution. The layers were separated and the organics collected, dried (MgSO$_4$), filtered and the solvent removed. The product was isolated from the residue by re-crystallization in methanol yielding 20 g (23%)

To 1 eq. (35 mmol) of the re-crystallized product was added 1.5 eq (52.5 mmol) of potassium carbonate, 1 eq (35 mmol) of methyl-(4-bromomethyl)-benzoate and 50 mL of anhydrous dimethyl formamide. This mixture was stirred at room temperature for 16 hours. The reaction was diluted with ethyl acetate/diethyl ether (1:1) and quenched with aqueous saturated ammonium chloride solution. The organic layer was washed with water, then brine. The organic layer was collected, dried (MgSO$_4$), filtered and the solvent was removed. The resulting residue was re-crystallized from methanol to yield 14 g (93%) of a cis-trans mixture.

HNMR (DMSO-d6) 500 MHz (ppm): 7.894-7.878 (m, 2H), 7.227-7.199 (m, 2H), 3.815 (s 3H), 3.337-3.310 (m, 2H), 2.300-2.271 (m, 0.7H), 2.098-2.004 (m, 0.3H), 1.973-1.795 (m, 1H), 1.625-1.585 (m, 3H), 1.519-1.504 (m 3H), 1.490-1.382 (m 3H), 1.215-0.839 (m 3), 0.809 (s, 9H), 0.584 (s 3H)

LCMS: 431.6 (M+1)

Step B: 4-[2-(4-Bromo-phenylcarbamoyl)-2-(4-tert-butyl-cyclohexyl)-ethyl]-benzoic acid methyl ester

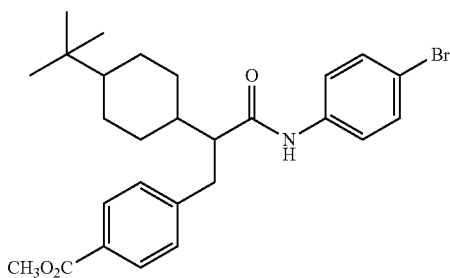

To 1 eq (2.32 mmol) of 4-[5-(4-tert-Butyl-cyclohexyl)-2,2-dimethyl-4,6-dioxo-[1,3]dioxan-5-ylmethyl]-benzoic acid methyl ester was added 1.5 eq (3.5 mmol) of 4-bromoaniline in 2 mL of n-methyl-pyrrolidinone in a microwave vial. The reaction was run for eight minutes at 220 degrees C. The reaction mixture was worked up by partitioning with ethyl acetate/diethyl ether (1:1)/1 N HCl. Product was isolated by chromatography gradient: 10% ethyl acetate/hexane to 40% ethyl acetate hexane.

HNMR CD3OD (300 MHz) (ppm): 7.885-7.848 (m, 2H), 7.370-7.192 (m, 6H), 3.851-3.844 (m, 3H), 3.091-2.757 (m, 3H), 2.090-2.007 (m, 2H), 1.915-1.053 (m, 10H), 0.908 (s, 6.4H), 0.861 (s, 2.6H)

Steps C, D and E

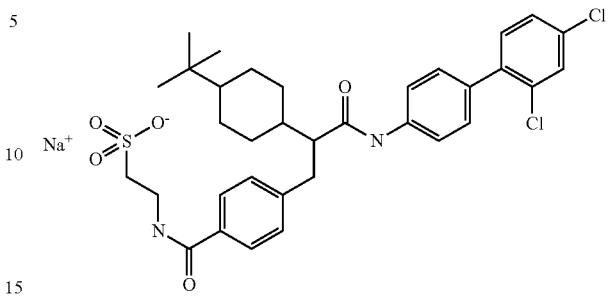

The target compound was synthesized as described in Example 1.001 with appropriate modifications.

LC/MS: 657.4 (M–H)⁻

Elemental Analysis: Calculated for C34H39N2O5Cl2SNa+(1.5) H2O: C:57.62, H: 5.97, N: 3.95. Found: C: 57.65, H: 6.07, N: 3.98.

Example 1.139

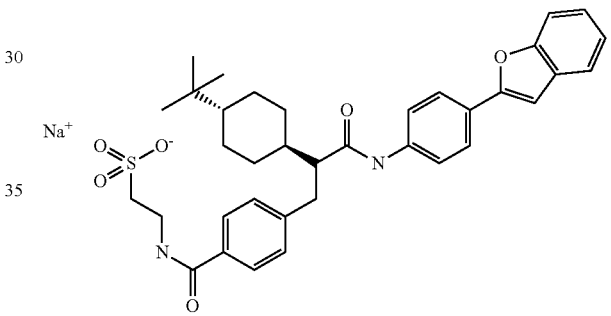

The target compound was synthesized as described in Example 1.138 with appropriate modifications.

LC/MS: 657.4 (M–H)⁻

Elemental Analysis: Calculated for C36H41N2O6SNa+ 1.8 H2O+0.2 NaHCO3: C: 61.94, H: 6.43, N: 3.99. Found: C: 61.85, H: 6.14, N: 3.88.

Example 1.140

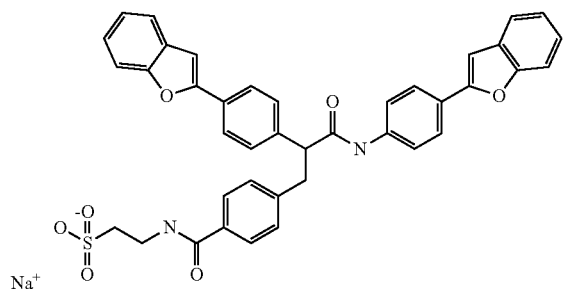

This product was synthesized as described in Example 1.003, with appropriate modifications.

LC/MS: 707.6 (M+Na)⁺.

Formula: C40H31N2O7SNa+2.5H2O. Elemental Analysis: Calculated: C: 63.91, H: 4.83, N: 3.73. Found: C: 63.87, H: 4.46, N: 3.91.

Example 1.141

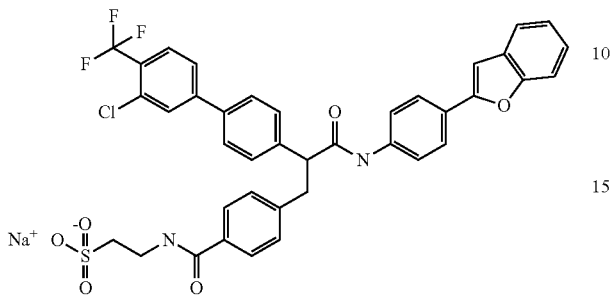

This product was synthesized as described in Example 1.003, with appropriate modifications.

LC/MS: 769.9 (M+Na)+.

Formula: C39H29N2O6F3SNa+4H2O. Elemental Analysis: Calculated: C: 58.13 H: 4.63, N: 3.48. Found: C: 58.05, H: 4.59, N: 3.87.

The following compounds were synthesized utilizing the methods described above:

| Ex# | Structure | LC/MS (mode) | Formula CHN (Calcd) CHN (Found) |
|---|---|---|---|
| 1.142 | 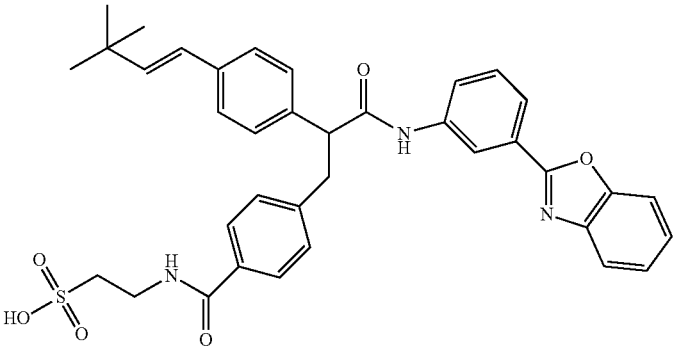 [SMILES: CC(C)(C)/C=C/c1ccc(C(Cc2ccc(C(=O)NCCS(=O)(=O)O)cc2)C(=O)Nc2cccc(-c3nc4ccccc4o3)c2)cc1] | 652.9 (+) | C37H37N3O6S + 1.5 H2O + 0.2 CF3CO2H 64.03 5.78 5.99 64.09 5.75 5.87 |
| 1.143 | 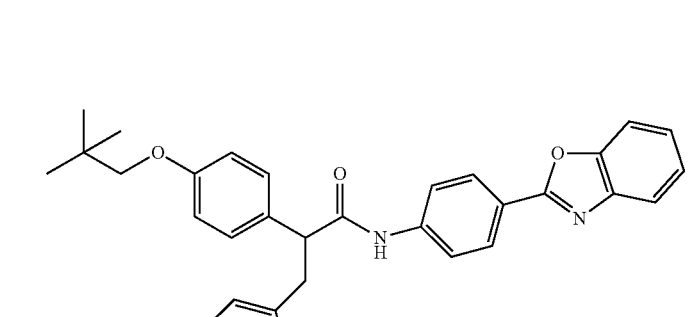 | 656.6 (+) | C36H37N3O7 S + 0.1 H2O + 0.1 CF3CO2H 64.99 5.62 6.28 64.99 5.79 6.50 |

-continued
| Ex# | Structure | LC/MS (mode) | Formula CHN (Calcd) CHN (Found) |
|---|---|---|---|
| 1.144 | 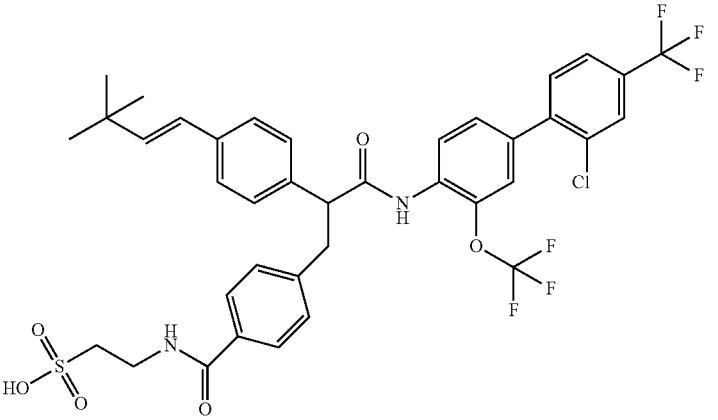 [SMILES: CC(C)(C)/C=C/c1ccc(C(Cc2ccc(C(=O)NCCS(=O)(=O)O)cc2)C(=O)Nc2ccc(-c3ccc(C(F)(F)F)cc3Cl)cc2OC(F)(F)F)cc1] | 797.9 (+) | C38H35N2O6F6ClS + 0.8 H2O + 0.3 CF3CO2H<br>54.81 4.40 3.31<br>54.79 4.17 3.20 |
| 1.145 | 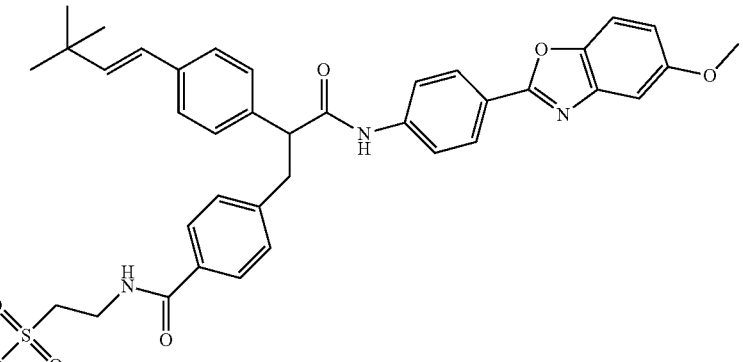 | 682.9 (+) | C38H39N3O7S + 1.7 H2O + 0.3 CF3CO2H<br>62.09 5.76 5.63<br>61.90 5.65 5.57 |
| 1.146 | 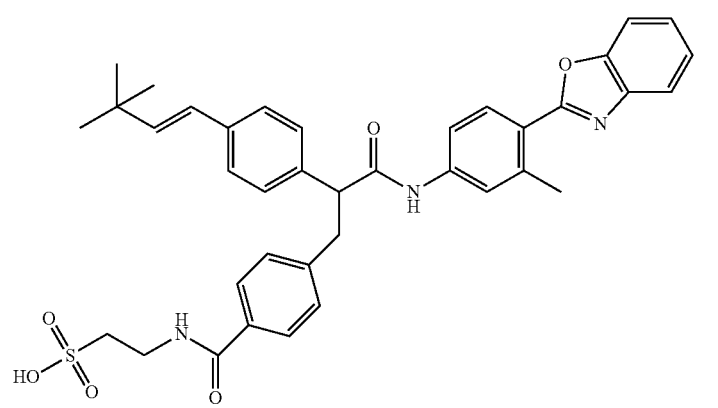 [SMILES: Cc1cc(NC(=O)C(Cc2ccc(C(=O)NCCS(=O)(=O)O)cc2)c2ccc(/C=C/C(C)(C)C)cc2)ccc1-c1nc2ccccc2o1] | 666.6 (+) | C38H39N3O6S + 0.9 H2O + 0.1 CF3CO2H<br>66.17 5.95 6.06<br>66.19 5.90 6.03 |

-continued

| Ex# | Structure | LC/MS (mode) | Formula CHN (Calcd) CHN (Found) |
|---|---|---|---|
| 1.147 | 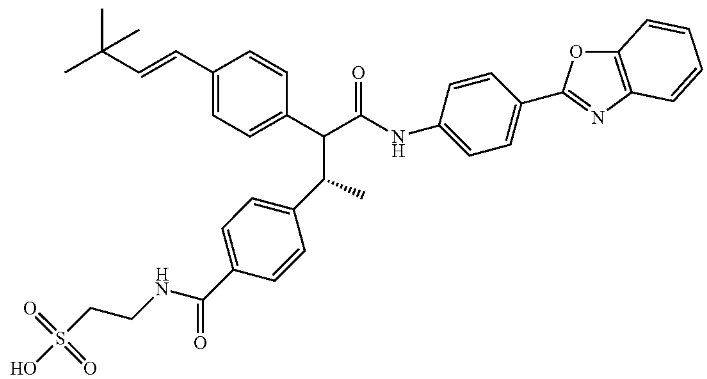 [SMILES: C[C@H](c1ccc(C(=O)NCCS(=O)(=O)O)cc1)C(C(=O)Nc1ccc(-c2nc3ccccc3o2)cc1)c1ccc(/C=C/C(C)(C)C)cc1] | 666.6 (+) | C38H39N3O6S + 0.9 H2O + 0.3 CF3CO2H 64.73 5.78 5.87 64.73 5.49 5.73 |
| 1.148 | 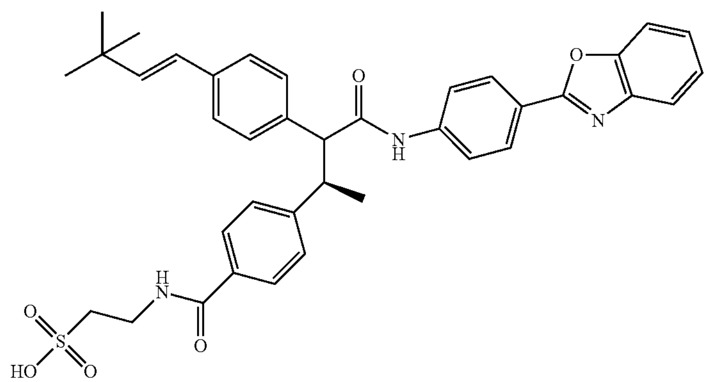 [SMILES: C[C@@H](c1ccc(C(=O)NCCS(=O)(=O)O)cc1)C(C(=O)Nc1ccc(-c2nc3ccccc3o2)cc1)c1ccc(/C=C/C(C)(C)C)cc1] | 666.6 (+) | C38H39N3O6S + 1.5 H2O + 0.3 CF3CO2H 63.77 5.86 5.78 63.74 5.85 5.67 |
| 1.149 | 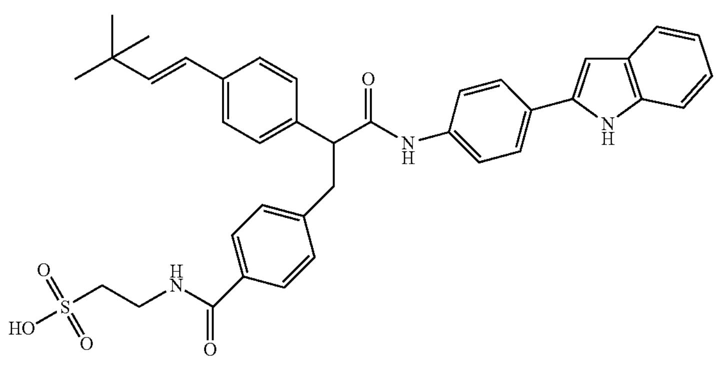 [SMILES: CC(C)(C)/C=C/c1ccc(C(Cc2ccc(C(=O)NCCS(=O)(=O)O)cc2)C(=O)Nc2ccc(-c3cc4ccccc4[nH]3)cc2)cc1] | 650.9 (+) | C38H39N3O5S + 2.1 H2O + 0.1 CF3CO2H 65.64 6.24 6.01 65.95 6.58 5.80 |
| 1.150 | 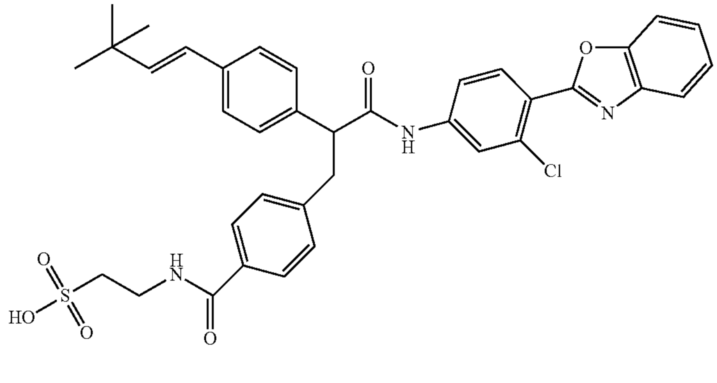 [SMILES: CC(C)(C)/C=C/c1ccc(C(Cc2ccc(C(=O)NCCS(=O)(=O)O)cc2)C(=O)Nc2ccc(-c3nc4ccccc4o3)c(Cl)c2)cc1] | 686.6 (+) | C37H36N3O6ClS + 2.0 H2O 61.53 5.58 5.82 61.55 5.40 5.84 |

-continued

| Ex# | Structure | LC/MS (mode) | Formula CHN (Calcd) CHN (Found) |
|---|---|---|---|
| 1.151 | 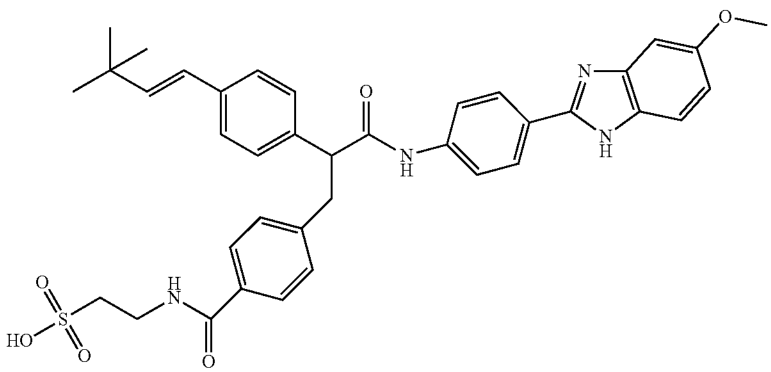 [SMILES: COc1ccc2[nH]c(-c3ccc(NC(=O)C(Cc4ccc(C(=O)NCCS(=O)(=O)O)cc4)c4ccc(/C=C/C(C)(C)C)cc4)cc3)nc2c1] | 681.6 (+) | C38H40N4O6S + 1.9 H2O + 0.1 CF3CO2H 62.51 6.01 7.59 62.47 6.07 7.44 |
| 1.152 | 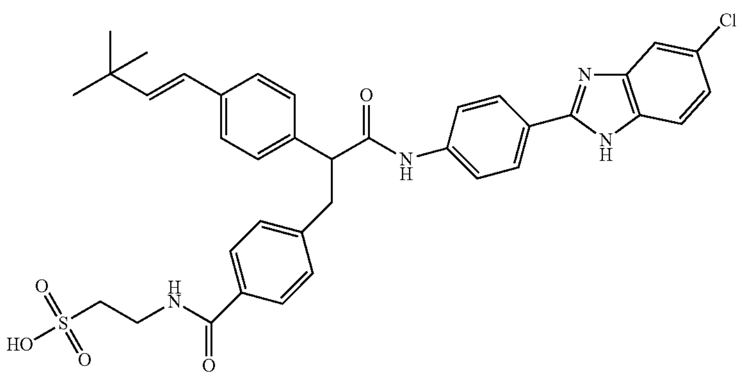 [SMILES: CC(C)(C)/C=C/c1ccc(C(Cc2ccc(C(=O)NCCS(=O)(=O)O)cc2)C(=O)Nc2ccc(-c3nc4cc(Cl)ccc4[nH]3)cc2)cc1] | 685.9 (+) | C37H37N4O5ClS + 1.5 H2O + 0.1 CF3CO2H 61.74 5.59 7.74 61.85 5.65 7.76 |
| 1.153 | 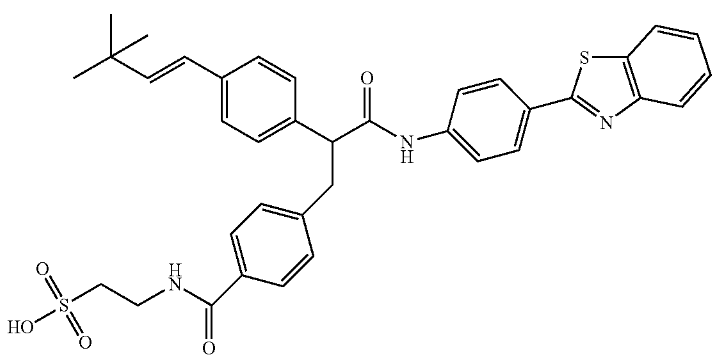 | 668.4 (+) | C37H37N3O5S2 + 0.8 H2O + 0.1(CH3)2C(O) 65.05 5.75 6.12 65.09 5.85 6.24 |
| 1.154 | 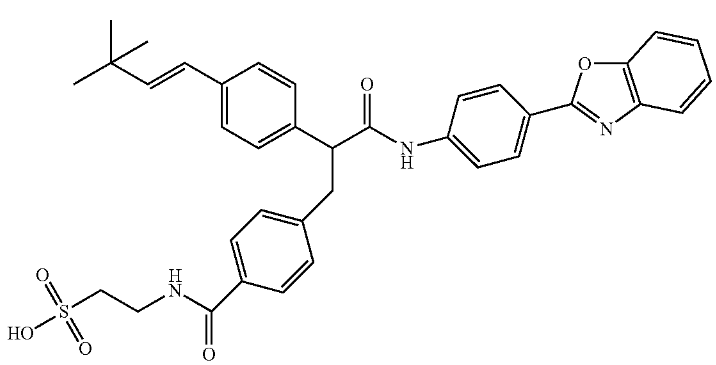 [SMILES: CC(C)(C)/C=C/c1ccc(C(Cc2ccc(C(=O)NCCS(=O)(=O)O)cc2)C(=O)Nc2ccc(-c3nc4ccccc4o3)cc2)cc1] | 652.6 (+) | C37H37N3O6S + 0.3 H2O + 0.1(CH3)2C(O) 67.51 5.82 6.35 67.68 5.93 6.38 |

| Ex# | Structure | LC/MS (mode) | Formula CHN (Calcd) CHN (Found) |
|---|---|---|---|
| 1.155 | 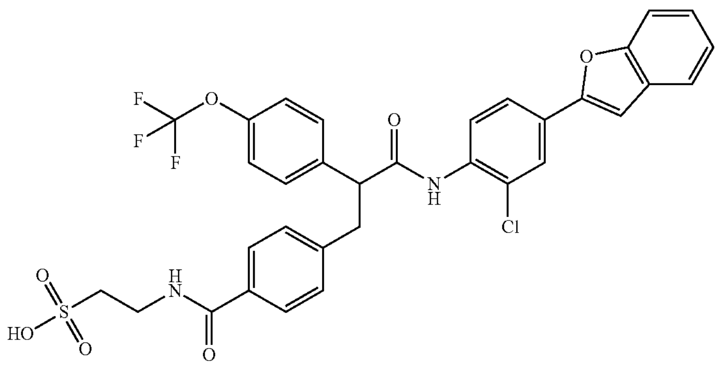 [SMILES: O=C(NCCS(=O)(=O)O)c1ccc(CC(C(=O)Nc2ccc(-c3cc4ccccc4o3)cc2Cl)c2ccc(OC(F)(F)F)cc2)cc1] | 687.6 (+) | C33H26N2O7F3ClS + 1.6 H2O + 0.1 CF3CO2H 54.83 4.06 3.85 55.11 4.44 3.84 |
| 1.156 | 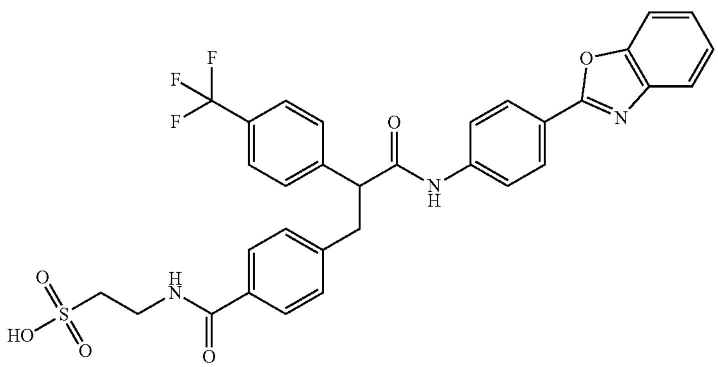 [SMILES: O=C(NCCS(=O)(=O)O)c1ccc(CC(C(=O)Nc2ccc(-c3nc4ccccc4o3)cc2)c2ccc(C(F)(F)F)cc2)cc1] | 638.6 (+) | C32H26N3O6F3S + 3.0 H2O + 0.4 CF3CO2H 53.43 4.43 5.70 53.46 4.46 5.75 |
| 1.157 | 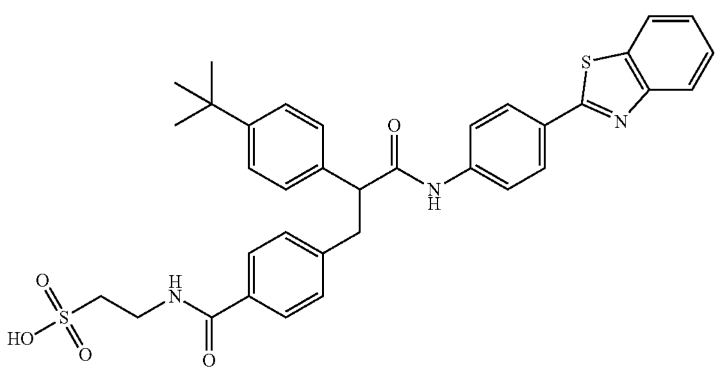 [SMILES: CC(C)(C)c1ccc(C(Cc2ccc(C(=O)NCCS(=O)(=O)O)cc2)C(=O)Nc2ccc(-c3nc4ccccc4s3)cc2)cc1] | 642.4 (+) | C35H35N3O5S2 + 0.2 H2O 65.13 5.53 6.51 65.16 5.35 6.53 |
| 1.158 | 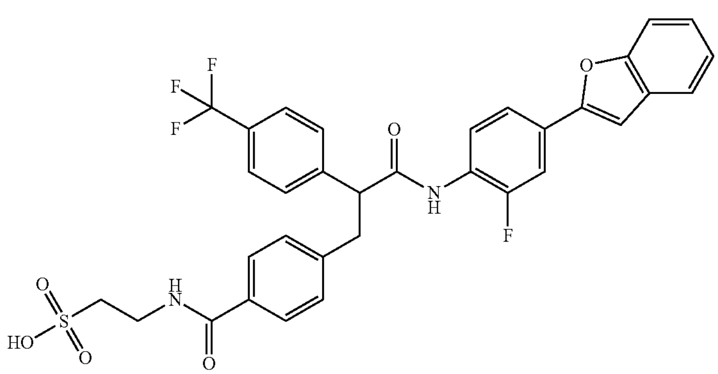 [SMILES: O=C(NCCS(=O)(=O)O)c1ccc(CC(C(=O)Nc2ccc(-c3cc4ccccc4o3)cc2F)c2ccc(C(F)(F)F)cc2)cc1] | 655.6 (+) | C33H26N2O6F4S + 1.7 H2O + 0.3 CF3CO2H 56.09 4.16 3.89 56.15 3.96 3.76 |

-continued

| Ex# | Structure | LC/MS (mode) | Formula CHN (Calcd) CHN (Found) |
|---|---|---|---|
| 1.159 | 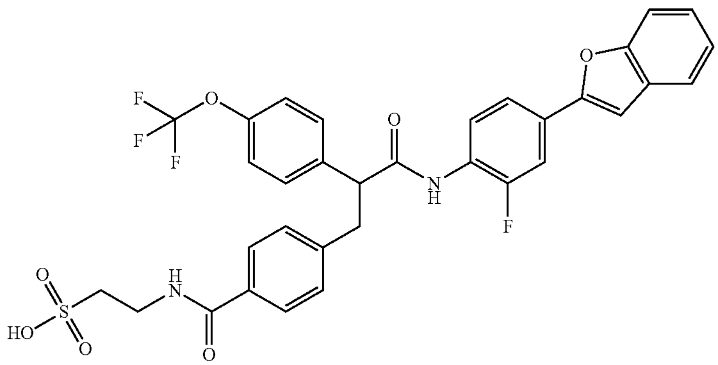 [SMILES: O=C(NCCS(=O)(=O)O)c1ccc(CC(C(=O)Nc2ccc(-c3cc4ccccc4o3)cc2F)c2ccc(OC(F)(F)F)cc2)cc1] | 671.4 (+) | C33H26N2O7F4S + 1.8 H2O + 0.2 CF3CO2H 55.27 4.14 3.86 55.38 4.05 3.75 |
| 1.160 | 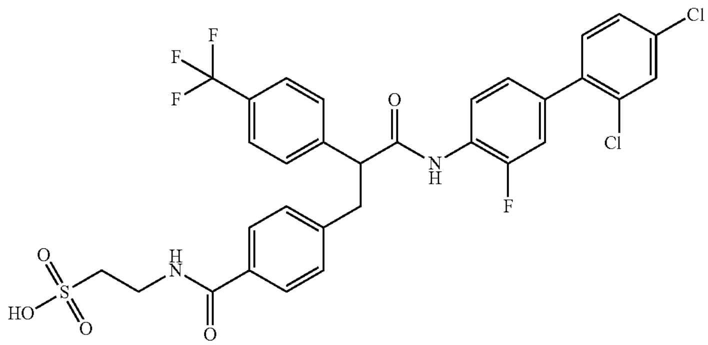 [SMILES: O=C(NCCS(=O)(=O)O)c1ccc(CC(C(=O)Nc2ccc(-c3ccc(Cl)cc3Cl)cc2F)c2ccc(C(F)(F)F)cc2)cc1] | 683.4 (+) | C31H24N2O5F4Cl2S + 1.2 H2O + 0.1 CF3CO2H 52.30 3.73 3.91 52.13 3.98 3.74 |
| 1.161 | 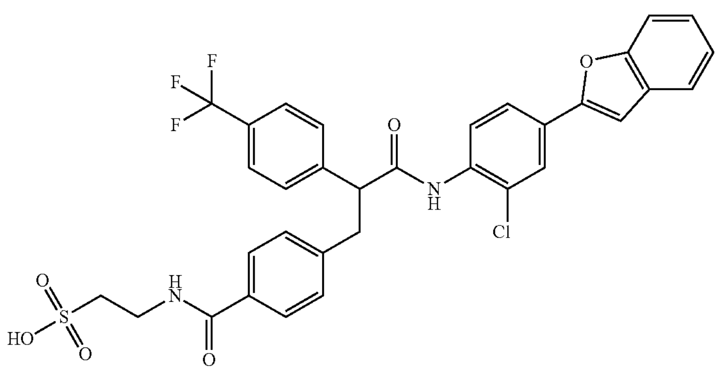 [SMILES: O=C(NCCS(=O)(=O)O)c1ccc(CC(C(=O)Nc2ccc(-c3cc4ccccc4o3)cc2Cl)c2ccc(C(F)(F)F)cc2)cc1] | 671.4 (+) | C33H26N2O6F3ClS + 1.6 H2O + 0.1 CF3CO2H 56.06 4.15 3.94 56.14 4.09 3.82 |
| 1.162 | 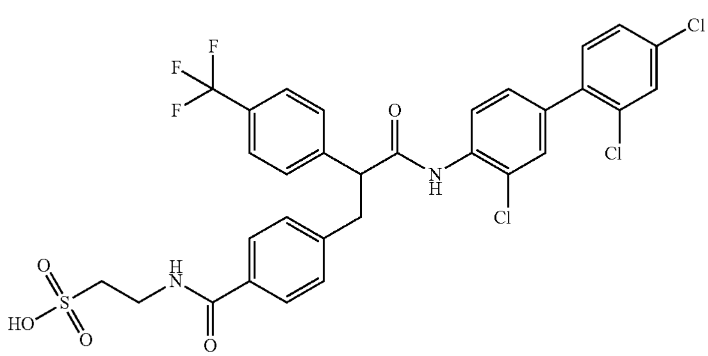 [SMILES: O=C(NCCS(=O)(=O)O)c1ccc(CC(C(=O)Nc2ccc(-c3ccc(Cl)cc3Cl)cc2Cl)c2ccc(C(F)(F)F)cc2)cc1] | 699.4 (+) | C31H24N2O5F3Cl3S + 1.7 H2O + 0.1 CF3CO2H 50.51 3.74 3.78 50.78 4.04 3.73 |

-continued

| Ex# | Structure | LC/MS (mode) | Formula CHN (Calcd) CHN (Found) |
|---|---|---|---|
| 1.163 | 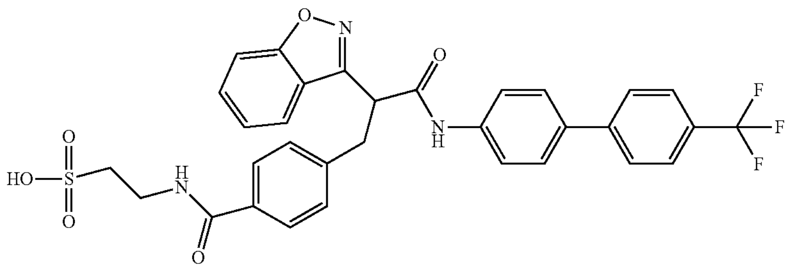 [SMILES: O=C(NCCS(=O)(=O)O)c1ccc(CC(C(=O)Nc2ccc(-c3ccc(C(F)(F)F)cc3)cc2)c2noc3ccccc23)cc1] | 638.6 (+) | C32H26N3O6F3S + 1.3 CH3OH + 0.3 CF3CO2H 57.07 4.45 5.89 57.43 4.87 5.53 |
| 1.164 | 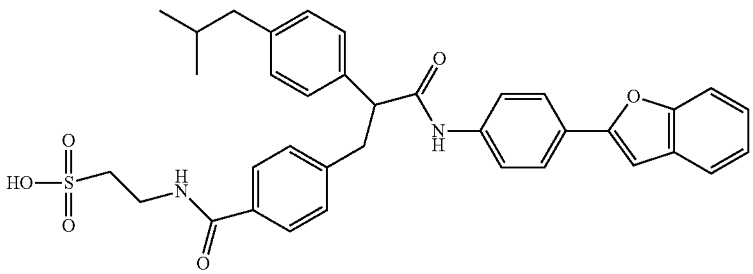 [SMILES: CC(C)Cc1ccc(C(Cc2ccc(C(=O)NCCS(=O)(=O)O)cc2)C(=O)Nc2ccc(-c3cc4ccccc4o3)cc2)cc1] | 625.6 (+) | C36H36N2O6S + 2.6 H2O + 0.05 CF3CO2H 64.02 6.14 4.14 64.33 6.52 4.42 |
| 1.165 | 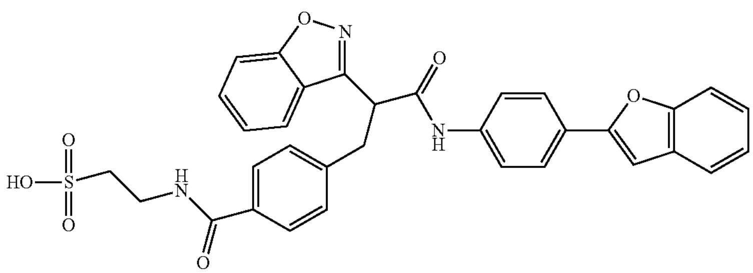 [SMILES: O=C(NCCS(=O)(=O)O)c1ccc(CC(C(=O)Nc2ccc(-c3cc4ccccc4o3)cc2)c2noc3ccccc23)cc1] | 610.6 (+) | C33H27N3O7S + 2.9 H2O 59.88 4.99 6.35 59.84 4.88 6.32 |
| 1.166 | 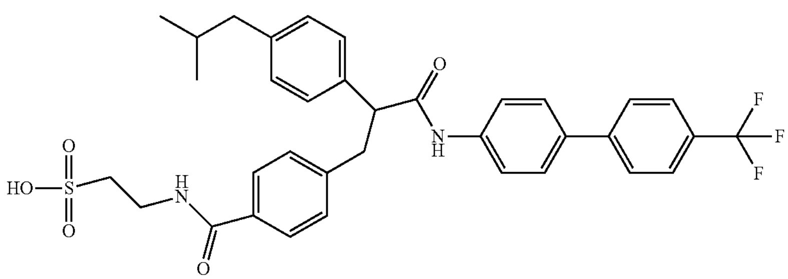 [SMILES: CC(C)Cc1ccc(C(Cc2ccc(C(=O)NCCS(=O)(=O)O)cc2)C(=O)Nc2ccc(-c3ccc(C(F)(F)F)cc3)cc2)cc1] | 653.6 (+) | C35H35N2O5F3S + 1.5 H2O + 0.3 CF3CO2H 59.89 5.41 3.92 59.78 5.73 3.95 |
| 1.167 | 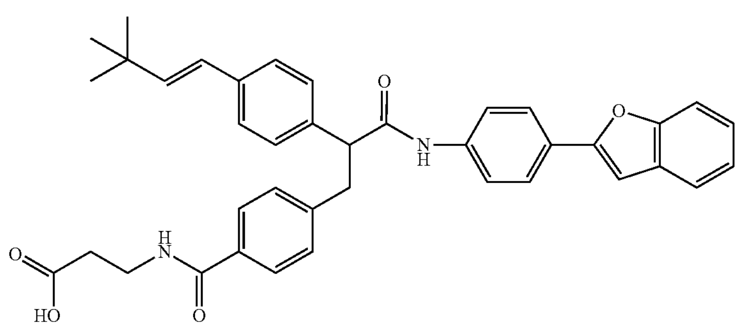 [SMILES: CC(C)(C)/C=C/c1ccc(C(Cc2ccc(C(=O)NCCC(=O)O)cc2)C(=O)Nc2ccc(-c3cc4ccccc4o3)cc2)cc1] | 615.6 (+) | C39H38N2O5 + 1.0 CH3OH 74.28 6.55 4.33 74.35 6.96 4.54 |

-continued
| Ex# | Structure | LC/MS (mode) | Formula CHN (Calcd) CHN (Found) |
|---|---|---|---|
| 1.168 | 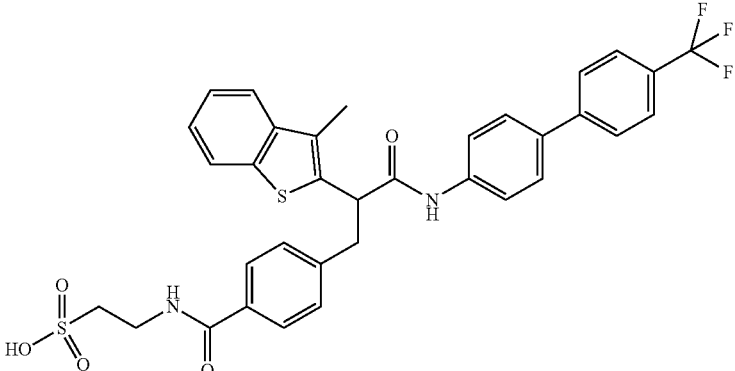 | 667.4 (+) | C34H29N2O5F3S2 + 2.5 H2O 57.37 4.81 3.94 57.40 4.63 3.96 |
| 1.169 | 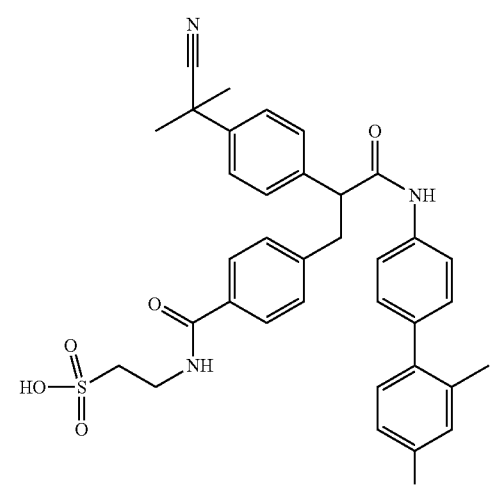 | 642.4 (−) | C35H34N3O5ClS + 2.3H2O + 0.4CF3COOH 58.80 5.38 5.75 58.76 5.07 5.58 |
| 1.170 | 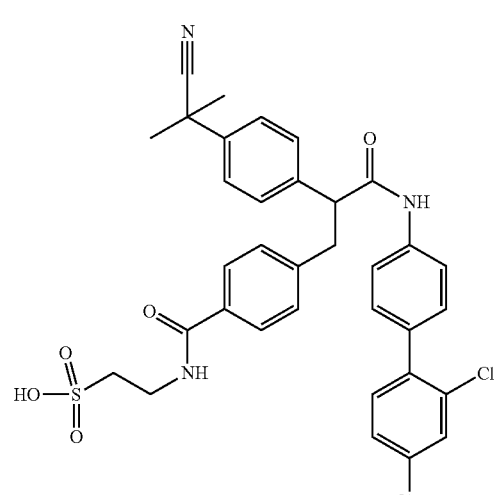 | 662.9 (−) | C34H3lN3O5 Cl2S + 0.8CF3COOH 56.57 4.24 5.56 56.53 4.16 5.64 |

-continued
| Ex# | Structure | LC/MS (mode) | Formula CHN (Calcd) CHN (Found) |
|---|---|---|---|
| 1.171 | 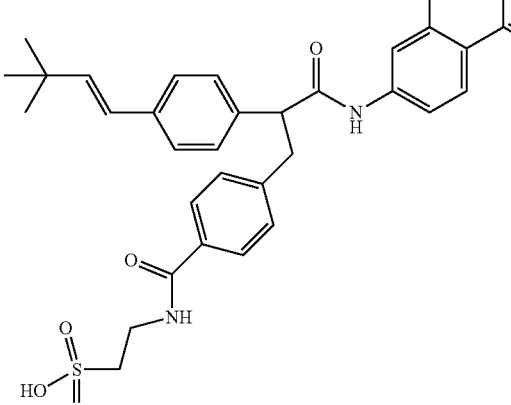 | 648.6 (−) | C38H39N3O5 S + 2H2O + 0.2CF3COOH<br>65.09 6.14 5.93<br>65.28 6.06 5.86 |
| 1.172 | 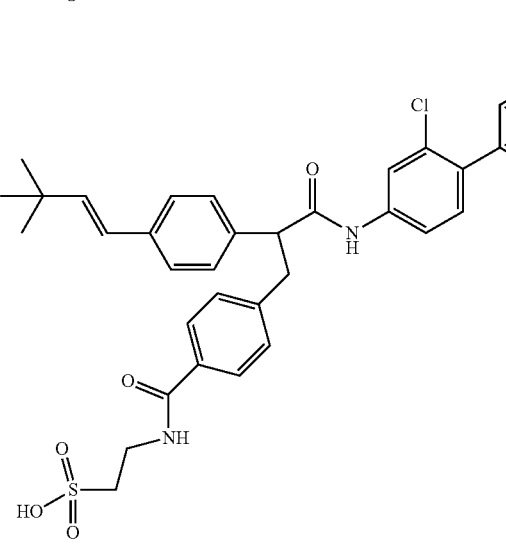 | 645.6 (−) | C37H34N2O5F3Cl2SNa + 2.3H2O<br>54.79 4.80 3.45<br>54.62 4.41 3.51 |
| 1.173 | 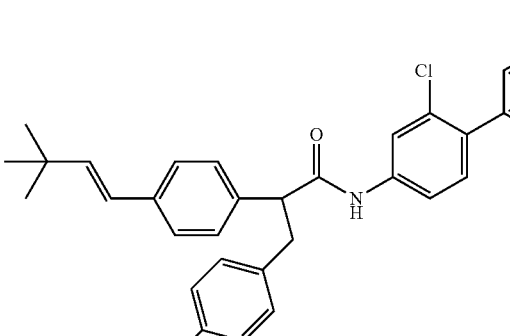 | 725.6 (−) | C38H38N2O5F3Cl S + 3H2O<br>58.42 5.68 3.59<br>58.44 5.84 3.19 |

-continued
| Ex# | Structure | LC/MS (mode) | Formula CHN (Calcd) CHN (Found) |
|---|---|---|---|
| 1.174 | 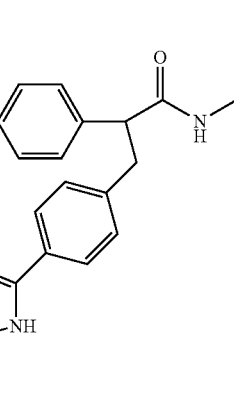 | 668.4 (−) | C37H36N3O5Cl S + 2.5H2O + 0.4CF3COOH<br>59.67 5.48 5.52<br>59.81 5.64 5.65 |
| 1.175 | 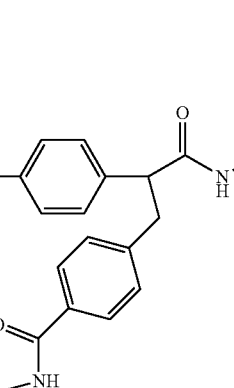 | 671.6 (−) | C38H40N2O5ClS Na + 2.5H2O<br>61.65 6.13 3.78<br>61.25 5.70 3.88 |
| 1.176 | 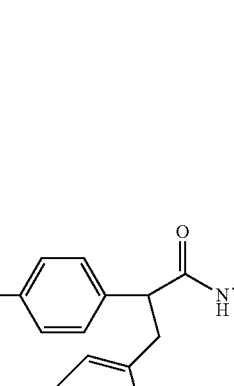 | 671.4 (−) | C38H40N2O5Cl SNa + 2.5H2O<br>61.65 6.13 3.78<br>61.59 5.83 3.81 |

-continued

| Ex# | Structure | LC/MS (mode) | Formula CHN (Calcd) CHN (Found) |
|---|---|---|---|
| 1.177 | 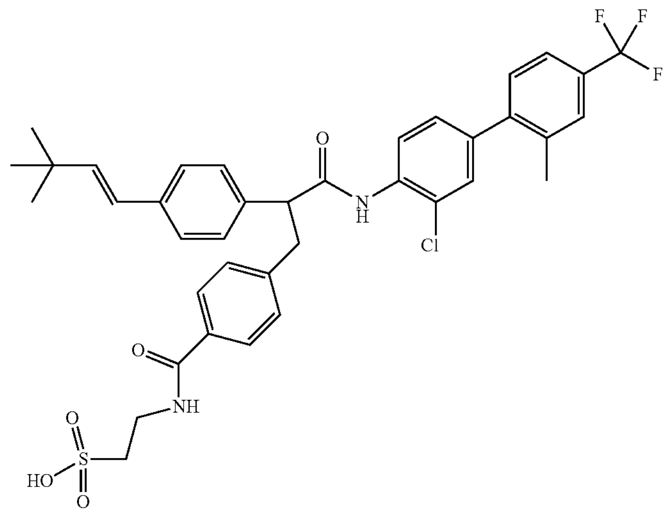 [SMILES: Cc1cc(C(F)(F)F)ccc1-c1ccc(NC(=O)C(Cc2ccc(C(=O)NCCS(=O)(=O)O)cc2)c2ccc(/C=C/C(C)(C)C)cc2)c(Cl)c1] | 725.6 (−) | C38H38N2O5Cl S + 2H2O + 0.2CF3COOH<br>58.67 5.41 3.55<br>58.67 5.32 3.55 |
| 1.178 | 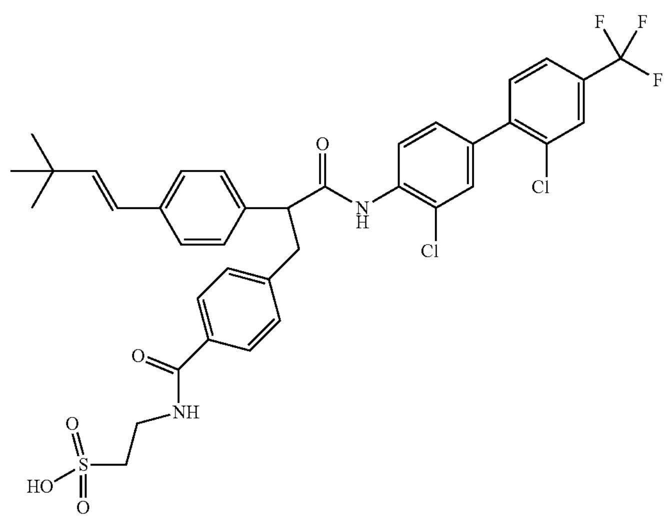 [SMILES: CC(C)(C)/C=C/c1ccc(C(Cc2ccc(C(=O)NCCS(=O)(=O)O)cc2)C(=O)Nc2ccc(-c3ccc(C(F)(F)F)cc3Cl)cc2Cl)cc1] | 745.6 (−) | C37H34N2O5F3Cl2 SNa + 2H2O<br>55.16 4.75 3.48<br>55.35 4.51 3.51 |
| 1.179 | 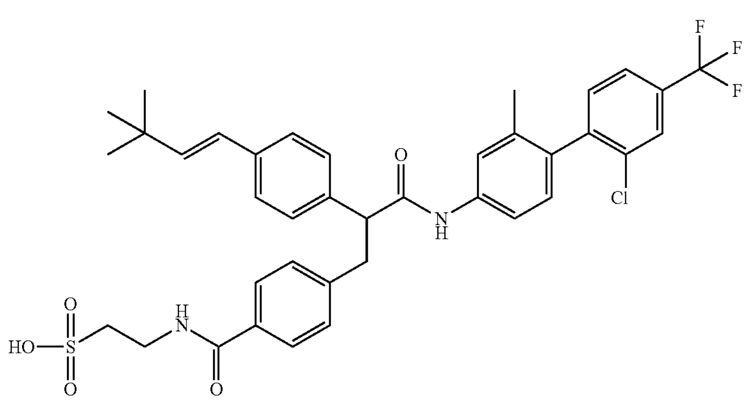 [SMILES: Cc1cc(NC(=O)C(Cc2ccc(C(=O)NCCS(=O)(=O)O)cc2)c2ccc(/C=C/C(C)(C)C)cc2)ccc1-c1ccc(C(F)(F)F)cc1Cl] | 725.6 (−) | C38H37N2O5F3Cl SNa + 2H2O + 0.3CF3COOH<br>56.58 5.08 3.42<br>56.76 5.04 3.48 |

-continued

| Ex# | Structure | LC/MS (mode) | Formula CHN (Calcd) CHN (Found) |
|---|---|---|---|
| 1.180 | 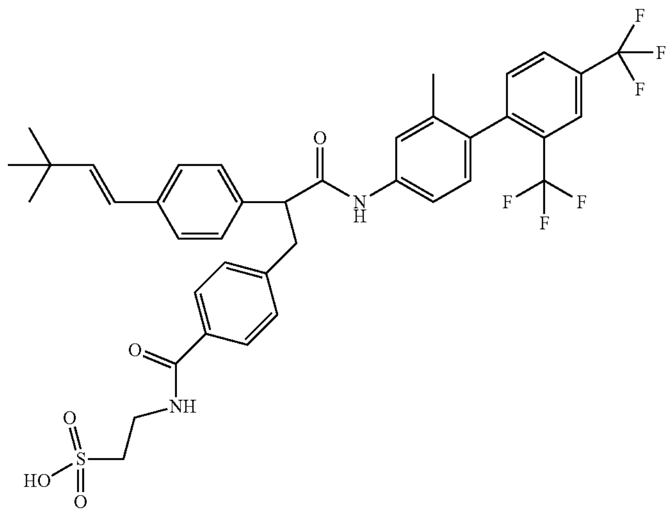 [SMILES: Cc1cc(NC(=O)C(Cc2ccc(C(=O)NCCS(=O)(=O)O)cc2)c2ccc(/C=C/C(C)(C)C)cc2)ccc1-c1ccc(C(F)(F)F)cc1C(F)(F)F] | 759.9 (−) | C39H38N2O5F6S + 1.8H2O<br>59.05 5.29 3.53<br>59.05 5.37 3.70 |
| 1.181 | 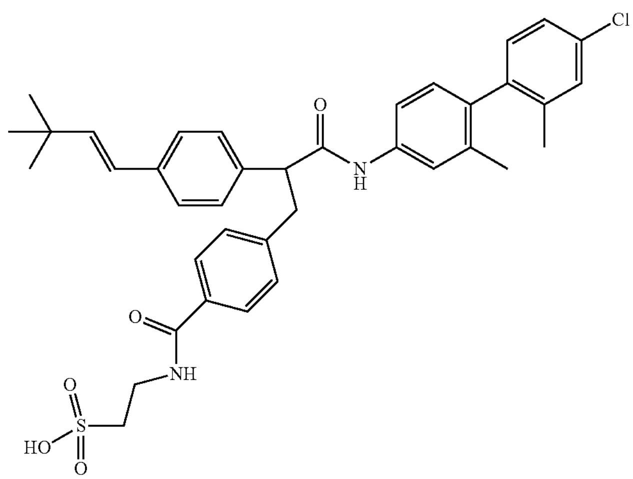 [SMILES: Cc1cc(Cl)ccc1-c1ccc(NC(=O)C(Cc2ccc(C(=O)NCCS(=O)(=O)O)cc2)c2ccc(/C=C/C(C)(C)C)cc2)cc1C] | 725.6 (−) | C38H40N2O5ClS Na + 2H2O + 0.2CF3COOH<br>61.16 5.91 3.71<br>61.2 6.27 3.83 |
| 1.182 | 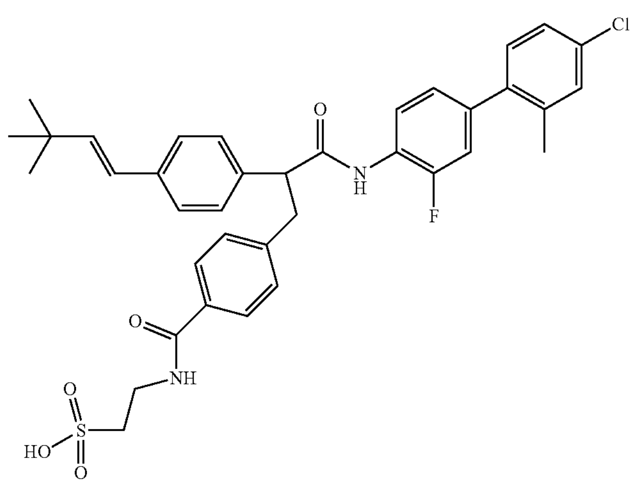 [SMILES: Cc1cc(Cl)ccc1-c1ccc(NC(=O)C(Cc2ccc(C(=O)NCCS(=O)(=O)O)cc2)c2ccc(/C=C/C(C)(C)C)cc2)c(F)c1] | 675.6 (−) | C37H38N2O5FClS + 2H2O + 0.3CF3COOH<br>60.42 5.70 3.75<br>60.66 5.51 3.57 |

-continued

| Ex# | Structure | LC/MS (mode) | Formula CHN (Calcd) CHN (Found) |
|---|---|---|---|
| 1.183 | 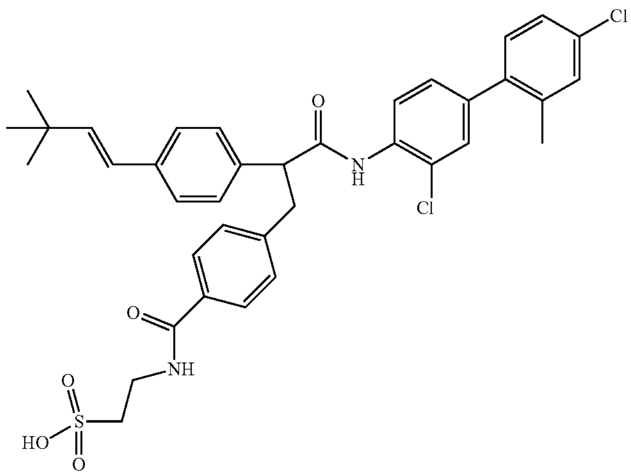 [SMILES: Cc1cc(Cl)ccc1-c1ccc(NC(=O)C(Cc2ccc(C(=O)NCCS(=O)(=O)O)cc2)c2ccc(/C=C/C(C)(C)C)cc2)c(Cl)c1] | 691.6 (−) | C37H38N2O5Cl2S 64.06 5.52 4.04 Not tested. |
| 1.184 | 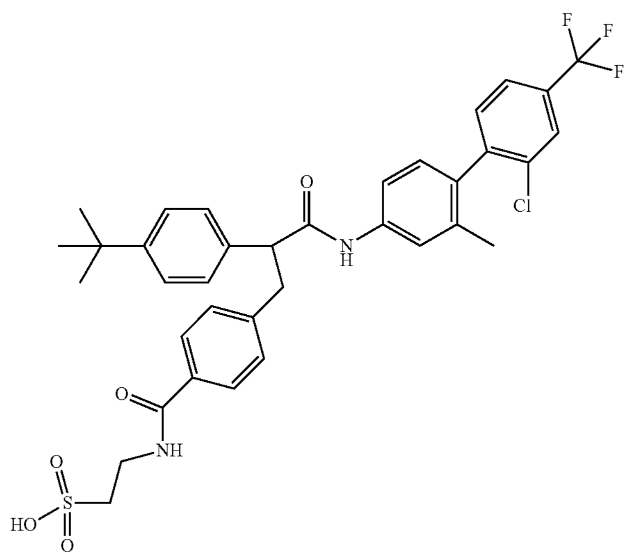 [SMILES: Cc1cc(NC(=O)C(Cc2ccc(C(=O)NCCS(=O)(=O)O)cc2)c2ccc(C(C)(C)C)cc2)ccc1-c1ccc(C(F)(F)F)cc1Cl] | 699.4 (−) | C36H36N2O5F3ClS + 2.2H2O + CF3COOH 53.39 4.88 3.28 53.13 5.01 3.11 |
| 1.185 | 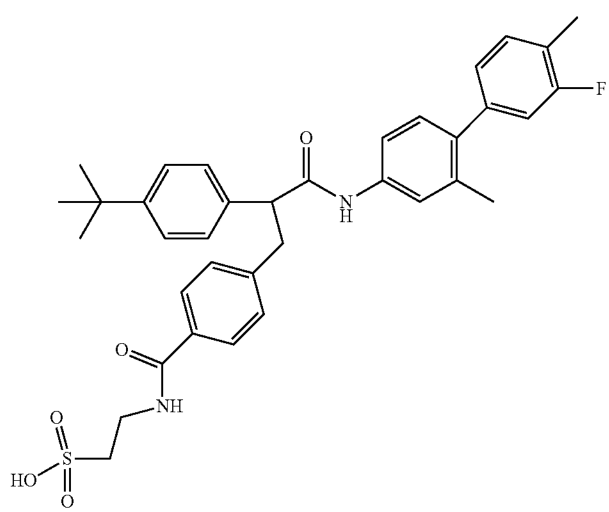 [SMILES: Cc1ccc(-c2ccc(NC(=O)C(Cc3ccc(C(=O)NCCS(=O)(=O)O)cc3)c3ccc(C(C)(C)C)cc3)cc2C)cc1F] | 649.6 (−) | C35H36N2O5FClS 64.56 5.57 4.30 Not tested. |

-continued

| Ex# | Structure | LC/MS (mode) | Formula CHN (Calcd) CHN (Found) |
|---|---|---|---|
| 1.186 | 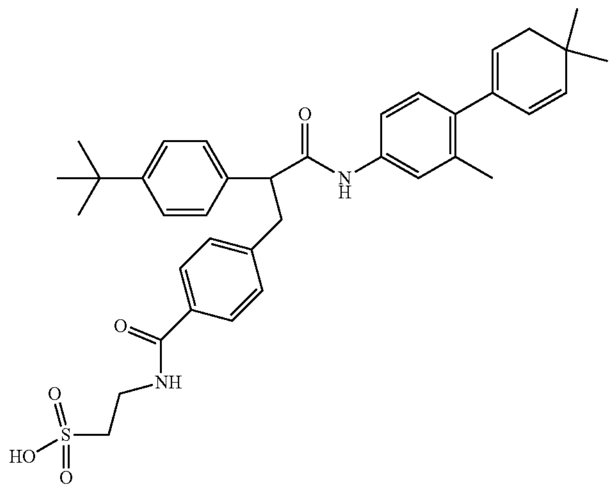 [SMILES: Cc1cc(NC(=O)C(Cc2ccc(C(=O)NCCS(=O)(=O)O)cc2)c2ccc(C(C)(C)C)cc2)ccc1C1=CCC(C)(C)C=C1] | 627.9 (−) | C37H44N2O5S + 2H2O + 0.8CF3COOH<br>61.32 6.51 3.71<br>61.03 6.25 3.34 |
| 1.187 | 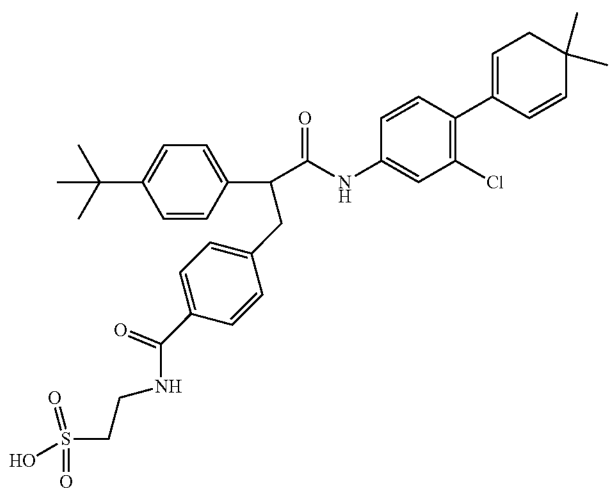 [SMILES: CC1(C)C=CC(c2ccc(NC(=O)C(Cc3ccc(C(=O)NCCS(=O)(=O)O)cc3)c3ccc(C(C)(C)C)cc3)cc2Cl)=CC1] | 647.6 (−) | C36H41N2O5ClS + 2.5H2O<br>55.49 5.72 3.37<br>55.25 5.75 3.52 |
| 1.188 | 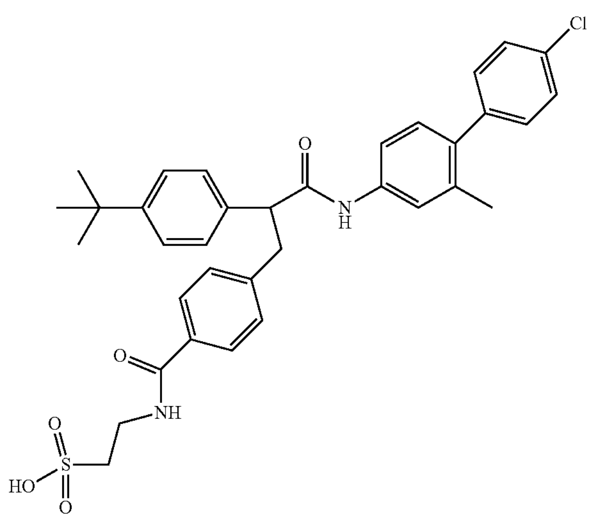 [SMILES: Cc1cc(NC(=O)C(Cc2ccc(C(=O)NCCS(=O)(=O)O)cc2)c2ccc(C(C)(C)C)cc2)ccc1-c1ccc(Cl)cc1] | 631.6 (−) | C35H37N2O5ClS + 2H2O + 0.3CF3COOH<br>60.79 5.92 3.98<br>60.91 6.25 3.72 |

-continued
| Ex# | Structure | LC/MS (mode) | Formula CHN (Calcd) CHN (Found) |
|---|---|---|---|
| 1.189 | 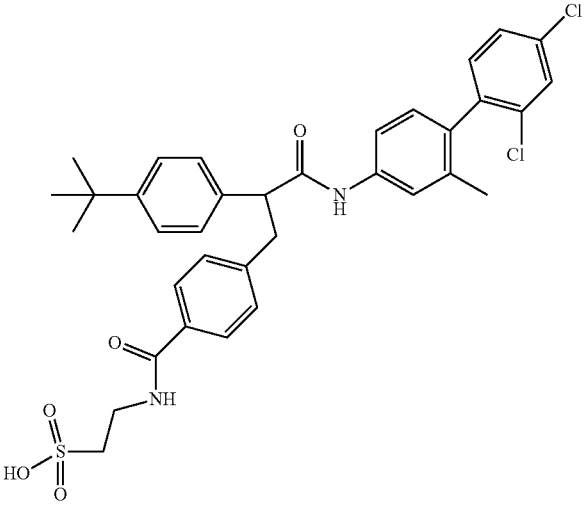 [SMILES: Cc1cc(NC(=O)C(Cc2ccc(C(=O)NCCS(=O)(=O)O)cc2)c2ccc(C(C)(C)C)cc2)ccc1-c1ccc(Cl)cc1Cl] | 665.6 (−) | C35H35N2O5Cl2SNa + 2.2H2O + 0.2CF3COOH 56.54 5.31 3.72 56.62 5.70 4.02 |
| 1.190 | 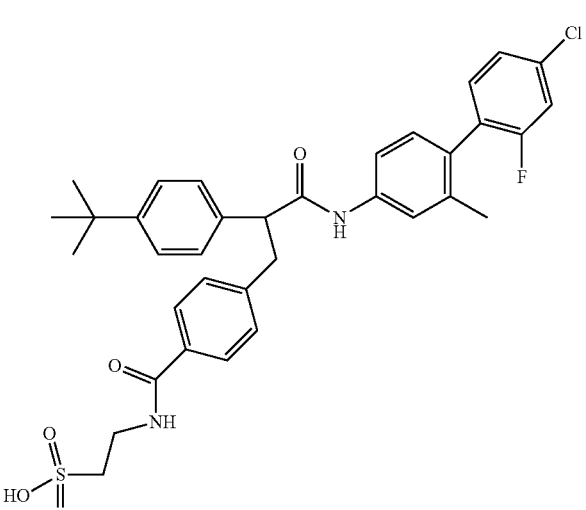 | 649.6 (−) | C35H35N2O5FClSNa + 2.2H2O + 0.3CF3COOH 57.24 5.36 3.75 57.06 5.44 3.88 |
| 1.192 | 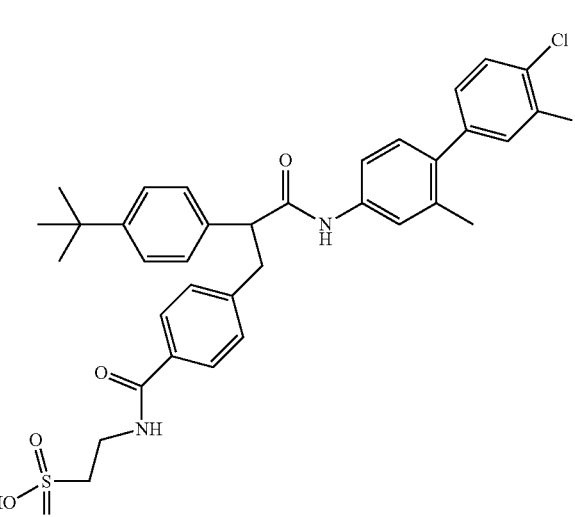 | 649.6 (−) | C35H36N2O5FClS 64.56 5.57 4.30 Not tested. |

| Ex# | Structure | LC/MS (mode) | Formula CHN (Calcd) CHN (Found) |
|---|---|---|---|
| 1.193 | 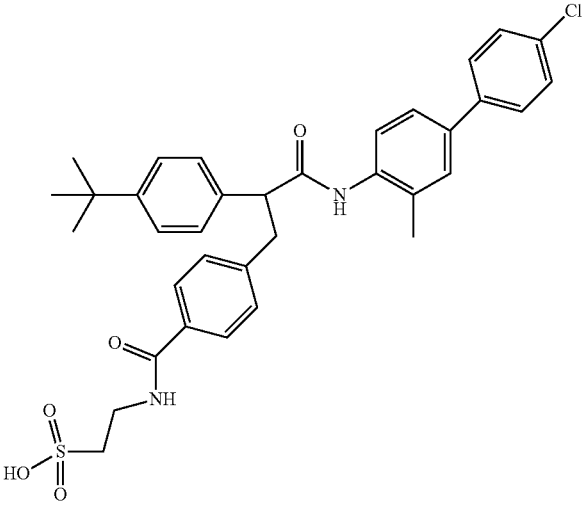 [SMILES: Cc1cc(-c2ccc(Cl)cc2)ccc1NC(=O)C(Cc1ccc(C(=O)NCCS(=O)(=O)O)cc1)c1ccc(C(C)(C)C)cc1] | 631.6 (−) | C35H37N2O5ClS + 2H2O + 0.4CF3COOH<br>60.15 5.84 3.92<br>60.34 5.98 3.99 |
| 1.194 | 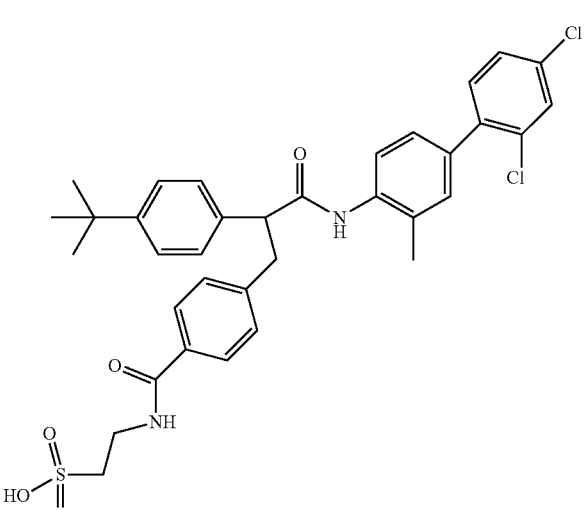 | 665.6 (−) | C35H35N2O5Cl2SNa + 1.5H2O<br>58.66 5.34 3.91<br>58.53 5.35 3.98 |
| 1.195 | 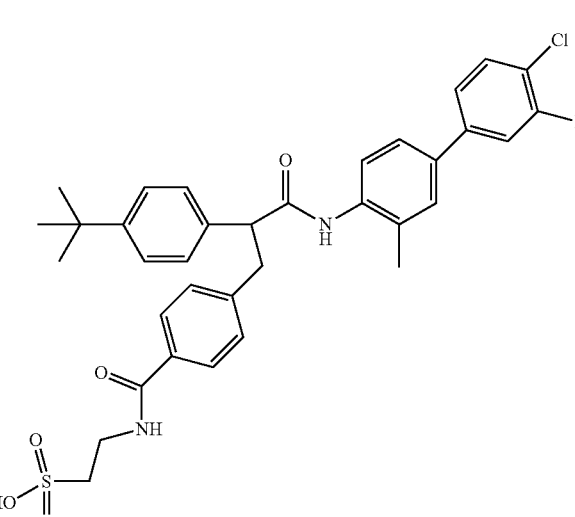 | 649.6 (−) | C35H36N2O5FClS + 2H2O + 0.3CF3COOH<br>59.27 5.63 3.88<br>59.08 5.75 3.85 |

-continued
| Ex# | Structure | LC/MS (mode) | Formula CHN (Calcd) CHN (Found) |
|---|---|---|---|
| 1.196 | 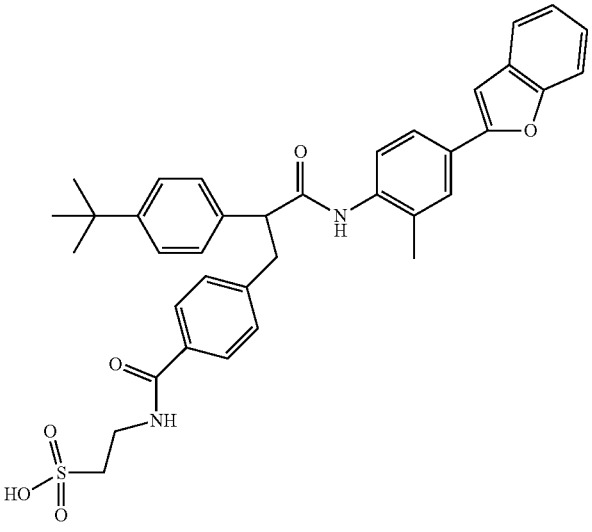 [SMILES: Cc1cc(-c2cc3ccccc3o2)ccc1NC(=O)C(Cc1ccc(C(=O)NCCS(=O)(=O)O)cc1)c1ccc(C(C)(C)C)cc1] | 637.6 (−) | C37H37N2O6SNa + 3H2O<br>62.17 6.06 3.92<br>62.02 6.35 4.13 |
| 1.197 | 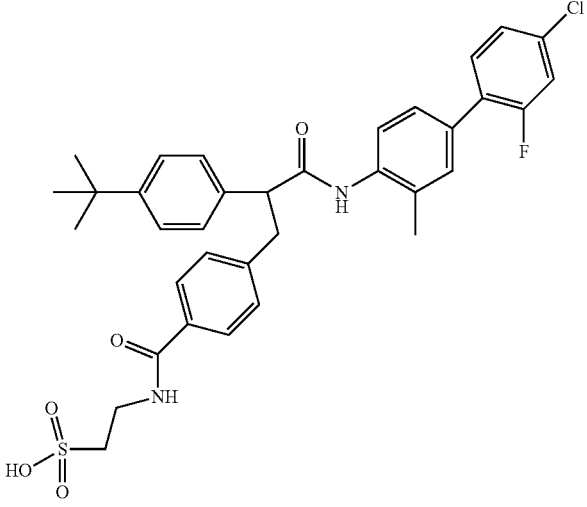 [SMILES: Cc1cc(-c2ccc(Cl)cc2F)ccc1NC(=O)C(Cc1ccc(C(=O)NCCS(=O)(=O)O)cc1)c1ccc(C(C)(C)C)cc1] | 649.6 (−) | C35H35N2O5FClSNa + 2H2O<br>59.18 5.54 3.95<br>59.19 5.94 4.07 |
| 1.198 | 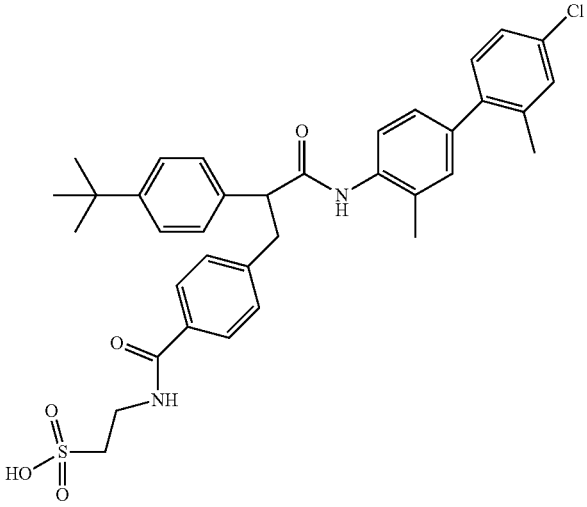 [SMILES: Cc1cc(-c2ccc(Cl)cc2C)ccc1NC(=O)C(Cc1ccc(C(=O)NCCS(=O)(=O)O)cc1)c1ccc(C(C)(C)C)cc1] | 645.4 (−) | C36H39ClN2O5S<br>66.81 6.07 4.33<br>Not tested. |

-continued
| Ex# | Structure | LC/MS (mode) | Formula CHN (Calcd) CHN (Found) |
|---|---|---|---|
| 1.199 | 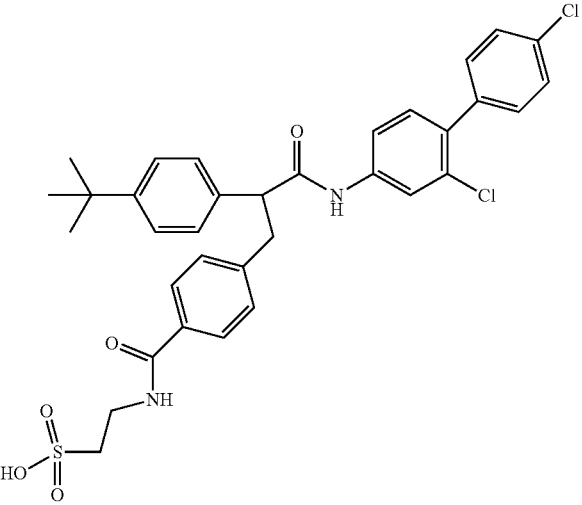 [SMILES: CC(C)(C)c1ccc(C(Cc2ccc(C(=O)NCCS(=O)(=O)O)cc2)C(=O)Nc2ccc(-c3ccc(Cl)cc3)c(Cl)c2)cc1] | 651.6 (−) | C34H34N2O5Cl2S + 1.5H2O + 0.2CF3COOH 58.74 5.33 3.98 58.89 5.03 3.88 |
| 1.200 | 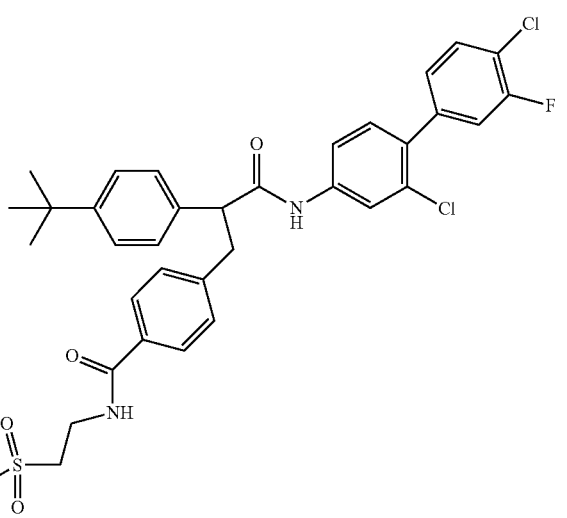 | 669.4 (−) | C34H33N2O5FCl2S + 2H2O + 0.5CF3COOH 54.98 4.94 3.66 54.85 4.65 3.52 |
| 1.201 | 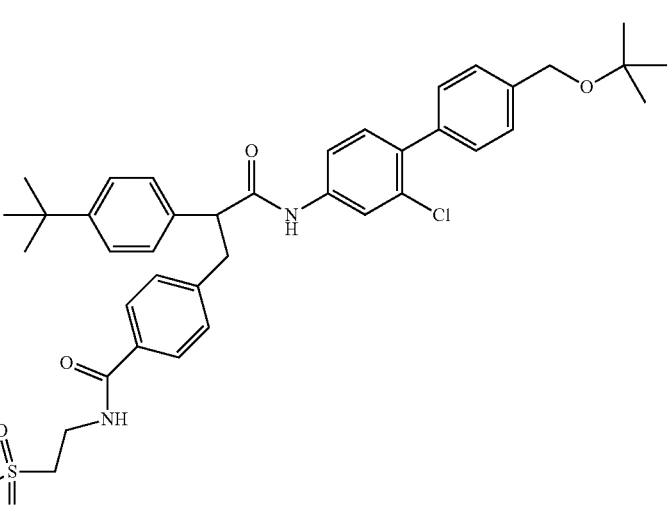 | 703.6 (−) | C39H45N2O6ClS 66.41 6.43 3.97 Not tested. |

-continued

| Ex# | Structure | LC/MS (mode) | Formula CHN (Calcd) CHN (Found) |
|---|---|---|---|
| 1.202 | 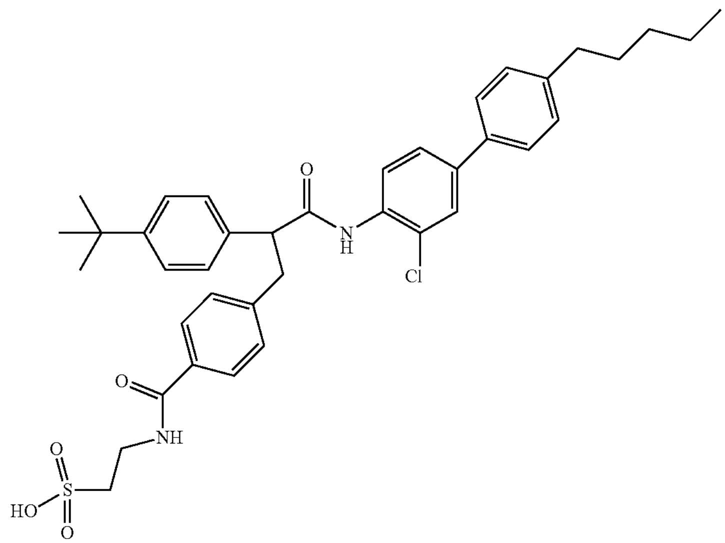 [SMILES: CCCCCc1ccc(-c2ccc(NC(=O)C(Cc3ccc(C(=O)NCCS(=O)(=O)O)cc3)c3ccc(C(C)(C)C)cc3)c(Cl)c2)cc1] | 687.9 (−) | C39H45N2O5ClS<br>67.96 6.58 4.06<br>Not tested |
| 1.203 | 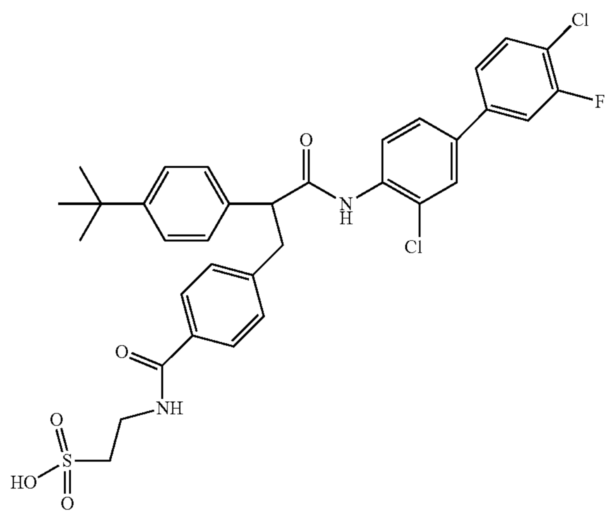 [SMILES: CC(C)(C)c1ccc(C(Cc2ccc(C(=O)NCCS(=O)(=O)O)cc2)C(=O)Nc2ccc(-c3ccc(Cl)c(F)c3)cc2Cl)cc1] | 669.4 (−) | C34H33N2O5FCl2S +<br>1.8H2O +<br>0.1CF3COOH<br>57.42 5.17 3.92<br>57.43 4.88 3.53 |
| 1.204 | 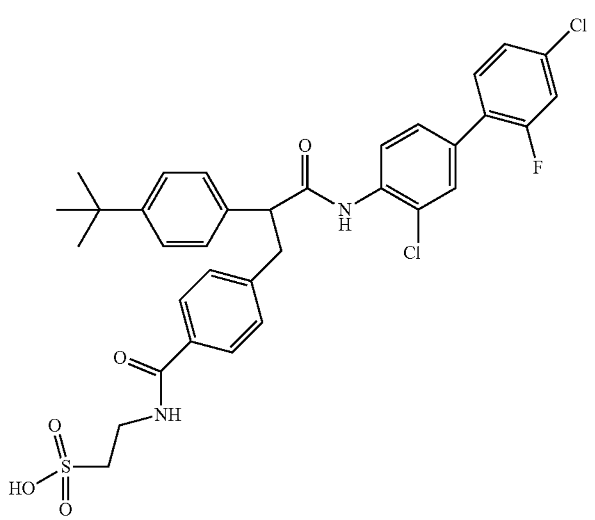 [SMILES: CC(C)(C)c1ccc(C(Cc2ccc(C(=O)NCCS(=O)(=O)O)cc2)C(=O)Nc2ccc(-c3ccc(Cl)cc3F)cc2Cl)cc1] | 669.4 (−) | C34H33N2O5FCl2S +<br>2H2O +<br>0.4CF3COOH<br>55.49 5.00 3.72<br>55.66 5.01 3.47 |

-continued

| Ex# | Structure | LC/MS (mode) | Formula CHN (Calcd) CHN (Found) |
|---|---|---|---|
| 1.205 | 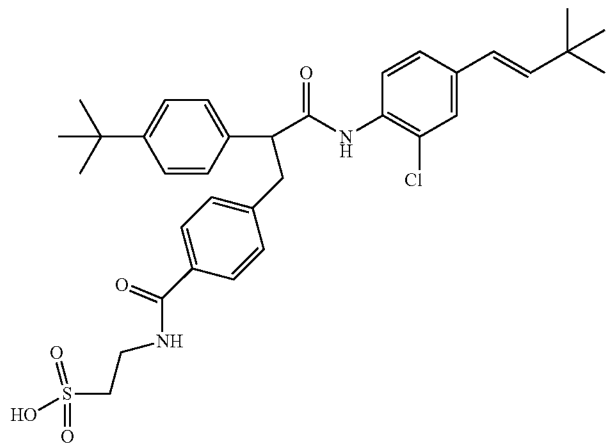 [SMILES: CC(C)(C)/C=C/c1ccc(NC(=O)C(Cc2ccc(C(=O)NCCS(=O)(=O)O)cc2)c2ccc(C(C)(C)C)cc2)c(Cl)c1] | 623.6 (−) | C34H41N2O5ClS + 0.6H2O + 0.1CF3COOH<br>63.45 6.59 4.33<br>63.14 6.24 4.24 |
| 1.206 | 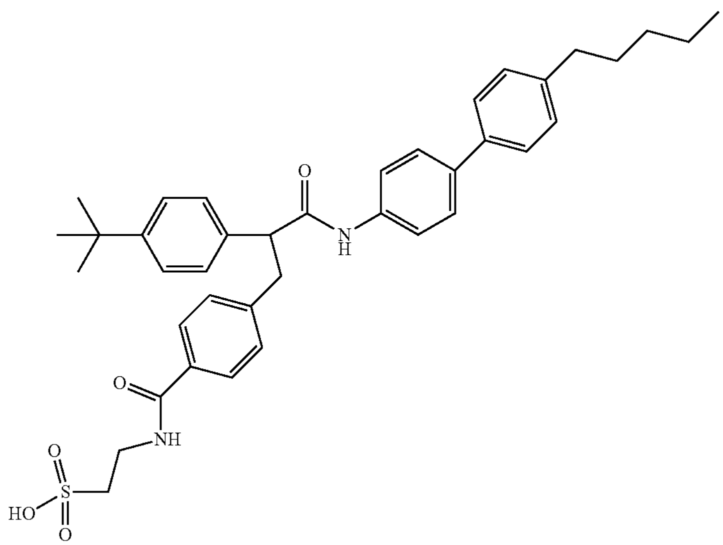 [SMILES: CCCCCc1ccc(-c2ccc(NC(=O)C(Cc3ccc(C(=O)NCCS(=O)(=O)O)cc3)c3ccc(C(C)(C)C)cc3)cc2)cc1] | 653.6 (−) | C39H46N2O5S + 3H2O<br>66.08 7.39 3.95<br>66.17 7.07 3.64 |
| 1.207 | 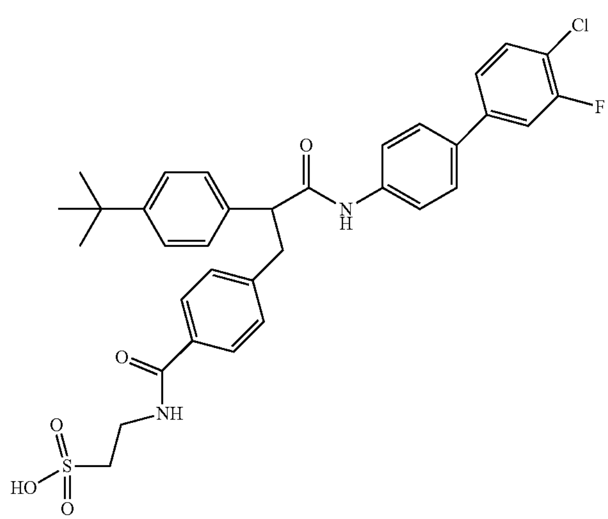 [SMILES: CC(C)(C)c1ccc(C(Cc2ccc(C(=O)NCCS(=O)(=O)O)cc2)C(=O)Nc2ccc(-c3ccc(Cl)c(F)c3)cc2)cc1] | 635.9 (−) | C34H34N2O5FClS + 2H2O + 0.2CF3COOH<br>59.36 5.53 4.02<br>59.53 5.93 3.67 |

-continued

| Ex# | Structure | LC/MS (mode) | Formula CHN (Calcd) CHN (Found) |
|---|---|---|---|
| 1.208 | 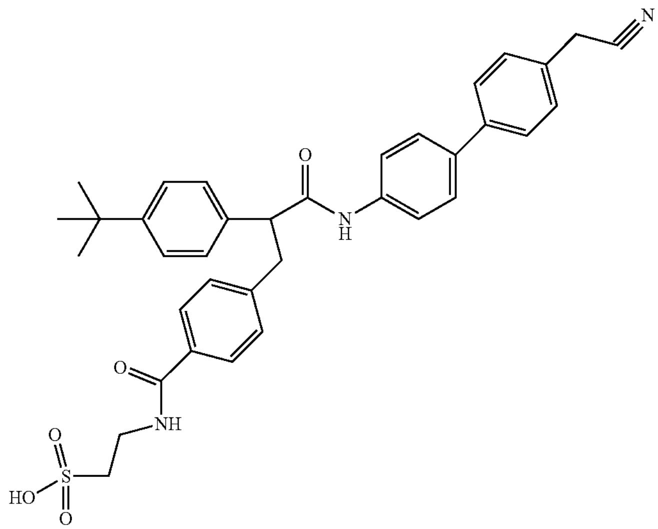 [SMILES: CC(C)(C)c1ccc(C(Cc2ccc(C(=O)NCCS(=O)(=O)O)cc2)C(=O)Nc2ccc(-c3ccc(CC#N)cc3)cc2)cc1] | 622.6 (−) | C36H37N3O5S 69.32 5.98 6.74 Not tested. |
| 1.209 | 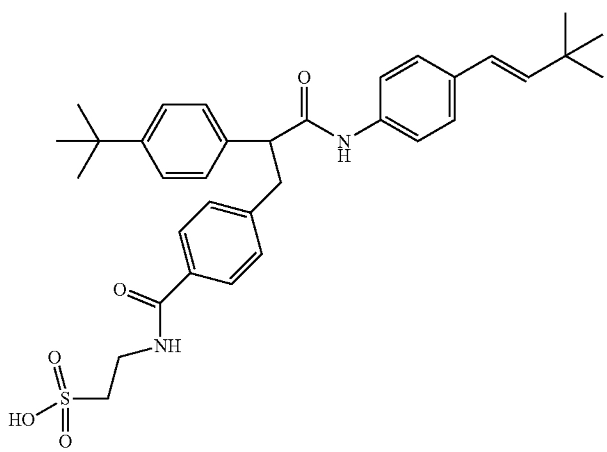 [SMILES: CC(C)(C)/C=C/c1ccc(NC(=O)C(Cc2ccc(C(=O)NCCS(=O)(=O)O)cc2)c2ccc(C(C)(C)C)cc2)cc1] | 589.6 (−) | C34H42N2O5S + 3H2O 63.33 7.50 4.34 63.19 7.27 3.99 |
| 1.210 | 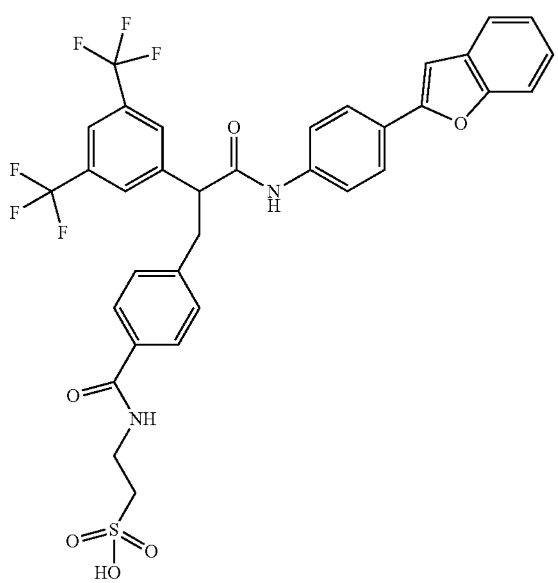 [SMILES: O=C(NCCS(=O)(=O)O)c1ccc(CC(C(=O)Nc2ccc(-c3cc4ccccc4o3)cc2)c2cc(C(F)(F)F)cc(C(F)(F)F)c2)cc1] | 703.6 (−) | C34H26N2O6F6S + 2H2O + 0.1CF3COOH 54.62 4.03 3.72 54.88 4.32 3.46 |

-continued
| Ex# | Structure | LC/MS (mode) | Formula CHN (Calcd) CHN (Found) |
|---|---|---|---|
| 1.211 | 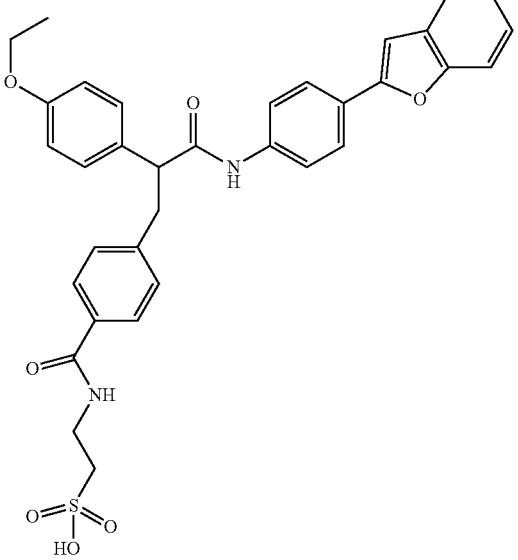 | 613.4 (−) | C34H32N2O7S + 2.5H2O + 0.3DMF 61.66 5.80 4.74 61.86 5.74 4.90 |
| 1.212 | 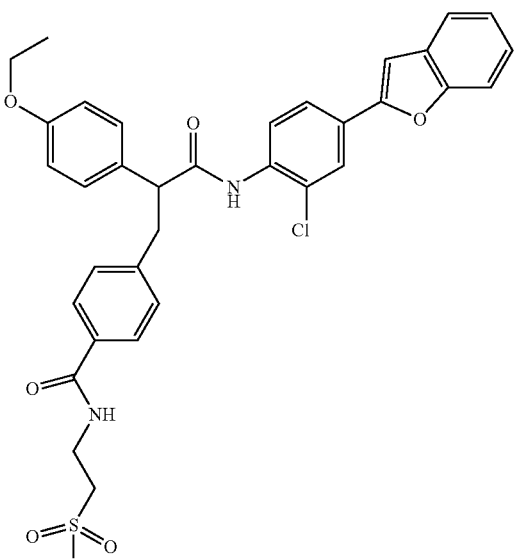 | 647.6 (+) | C34H31N2O7ClS + 0.6H2O 62.07 4.93 4.26 61.90 4.82 4.15 |

| Ex# | Structure | LC/MS (mode) | Formula CHN (Calcd) CHN (Found) |
|---|---|---|---|
| 1.213 | 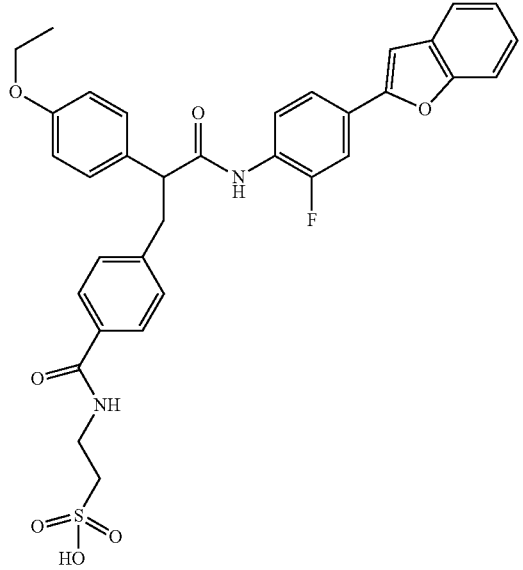 [SMILES: CCOc1ccc(C(Cc2ccc(C(=O)NCCS(=O)(=O)O)cc2)C(=O)Nc2ccc(-c3cc4ccccc4o3)cc2F)cc1] | 629.6 (−) | C34H31N2O7FS + 2.6H2O<br>60.27 5.39 4.13<br>60.11 5.24 4.07 |
| 1.214 | 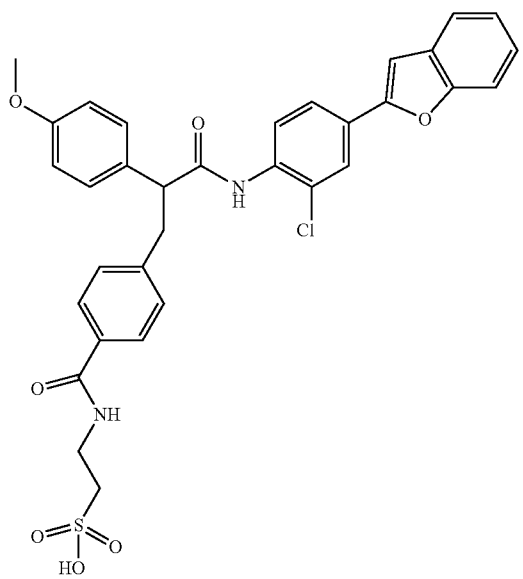 [SMILES: COc1ccc(C(Cc2ccc(C(=O)NCCS(=O)(=O)O)cc2)C(=O)Nc2ccc(-c3cc4ccccc4o3)cc2Cl)cc1] | 631.4 (−) | C33H29N2O7ClS + 2H2O + 0.4CF3COOH<br>56.80 4.71 3.92<br>56.96 4.88 3.94 |

-continued
| Ex# | Structure | LC/MS (mode) | Formula CHN (Calcd) CHN (Found) |
|---|---|---|---|
| 1.215 | 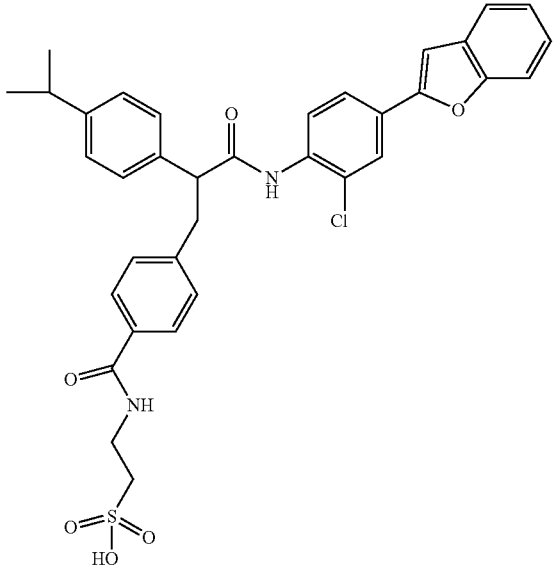 [SMILES: CC(C)c1ccc(C(Cc2ccc(C(=O)NCCS(=O)(=O)O)cc2)C(=O)Nc2ccc(-c3cc4ccccc4o3)cc2Cl)cc1] | 643.4 (−) | C35H33N2O6ClS + H2O<br>63.39 5.32 4.22<br>63.36 5.16 4.17 |
| 1.216 | 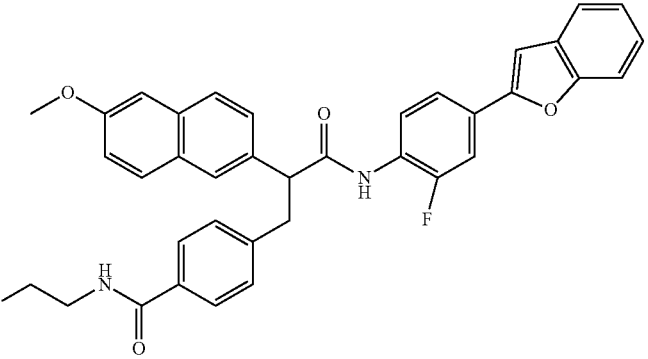 | 665.6 (−) | C37H31N2O7FS + 3H2O<br>61.67 5.17 3.89<br>61.73 5.45 3.66 |
| 1.217 | 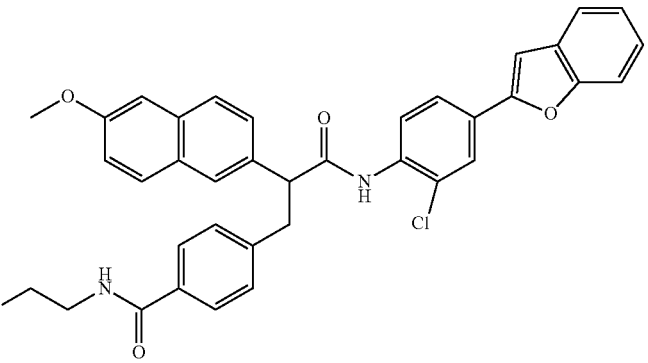 | 681.6 (−) | C37H31N2O7ClS + 3H2O<br>60.28 5.06 3.80<br>60.21 4.87 3.67 |

| Ex# | Structure | LC/MS (mode) | Formula CHN (Calcd) CHN (Found) |
|---|---|---|---|
| 1.218 | 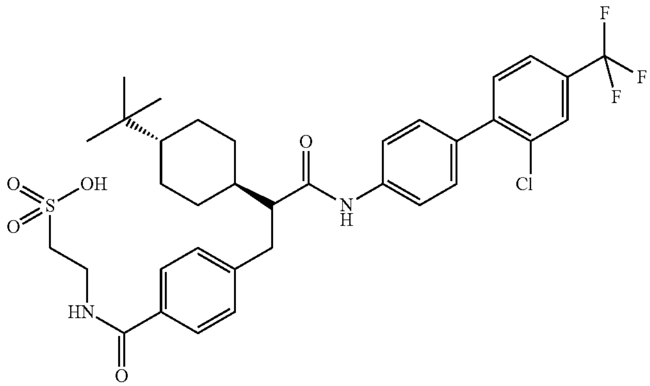 [SMILES: CC(C)(C)[C@H]1CC[C@H](C(Cc2ccc(C(=O)NCCS(=O)(=O)O)cc2)C(=O)Nc2ccc(-c3ccc(C(F)(F)F)cc3Cl)cc2)CC1] | 691.9 (−) | C35H39N2O5F3ClSNa + 1H2O<br>57.33 5.64 3.82<br>57.07 5.83 3.90 |
| 1.219 | 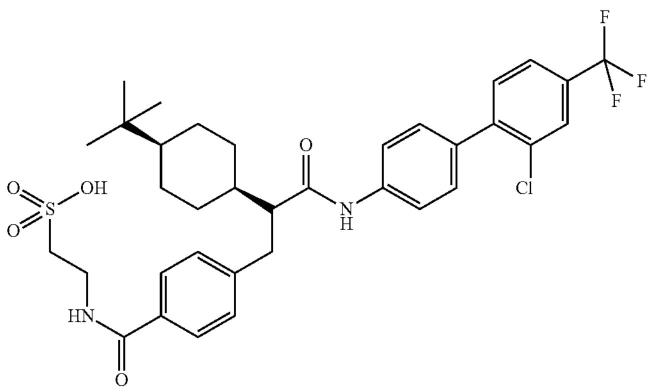 [SMILES: CC(C)(C)[C@H]1CC[C@@H](C(Cc2ccc(C(=O)NCCS(=O)(=O)O)cc2)C(=O)Nc2ccc(-c3ccc(C(F)(F)F)cc3Cl)cc2)CC1] | 691.9 (−) | C35 H39N2O5F3ClSNa + 1H2O<br>57.33 5.64 3.82<br>57.11 5.74 4.06 |
| 1.220 | 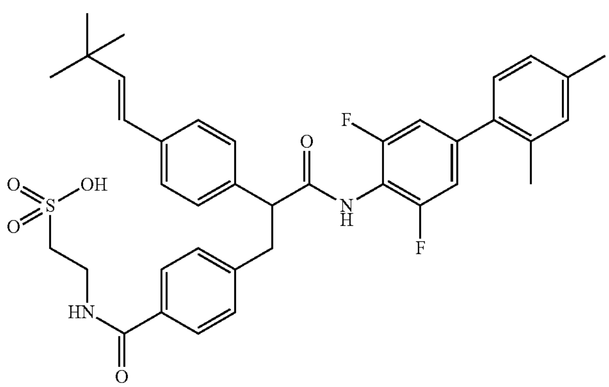 [SMILES: Cc1ccc(-c2cc(F)c(NC(=O)C(Cc3ccc(C(=O)NCCS(=O)(=O)O)cc3)c3ccc(/C=C/C(C)(C)C)cc3)c(F)c2)c(C)c1] | 673.6 (−) | C38H39N2O5F2SNa + 1.4H2O<br>63.21 5.84 3.88<br>63.11 5.70 4.14 |
| 1.221 | 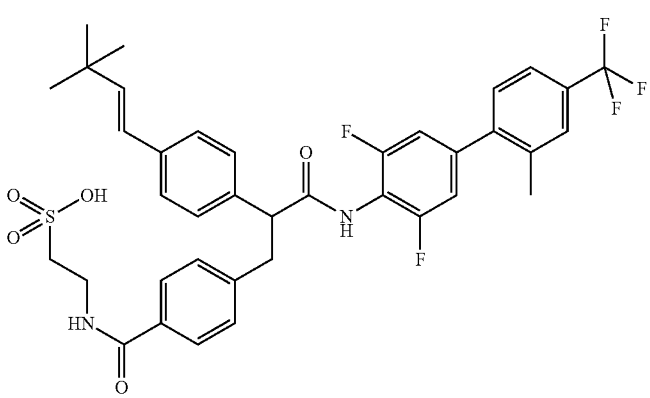 [SMILES: Cc1cc(C(F)(F)F)ccc1-c1cc(F)c(NC(=O)C(Cc2ccc(C(=O)NCCS(=O)(=O)O)cc2)c2ccc(/C=C/C(C)(C)C)cc2)c(F)c1] | 727.6 (−) | C38H36N2O5F5SNa + 1.5H2O<br>58.68 5.05 3.60<br>58.60 4.90 3.87 |

-continued

| Ex# | Structure | LC/MS (mode) | Formula CHN (Calcd) CHN (Found) |
|---|---|---|---|
| 1.222 | 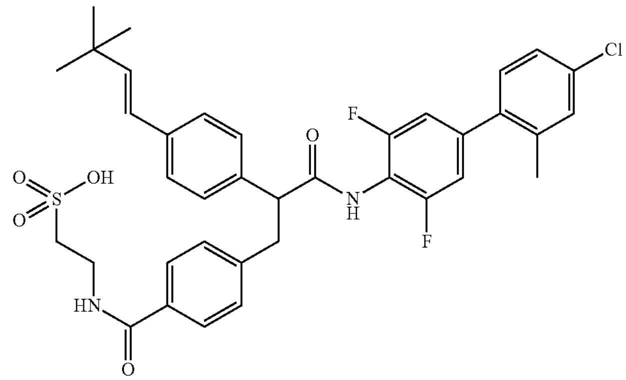 [SMILES: Cc1cc(Cl)ccc1-c1cc(F)c(NC(=O)C(Cc2ccc(C(=O)NCCS(=O)(=O)O)cc2)c2ccc(/C=C/C(C)(C)C)cc2)c(F)c1] | 693.6 (−) | C37H36N2O5F2ClSNa + 2.5 H2O<br>58.30 5.42 3.68<br>57.94 5.22 4.04 |
| 1.223 | 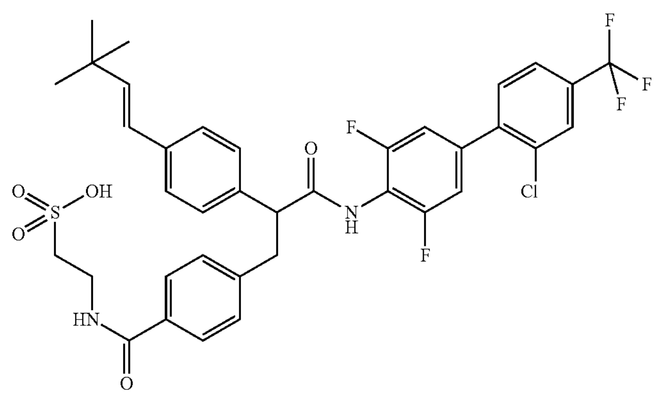 [SMILES: CC(C)(C)/C=C/c1ccc(C(Cc2ccc(C(=O)NCCS(=O)(=O)O)cc2)C(=O)Nc2c(F)cc(-c3ccc(C(F)(F)F)cc3Cl)cc2F)cc1] | 747.6 (−) | C37H34N2O5F5ClSNa + 1 H2O<br>56.31 4.47 3.55<br>56.39 4.65 3.69 |
| 1.224 | 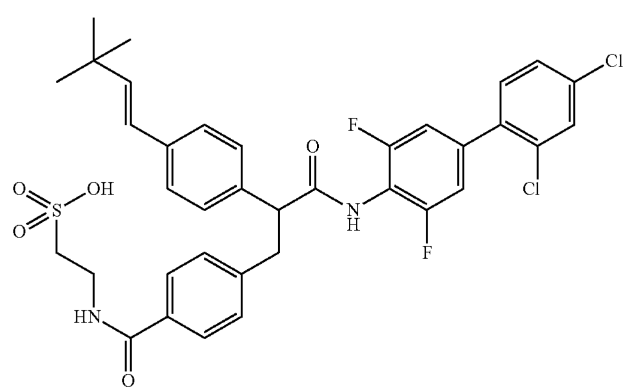 [SMILES: CC(C)(C)/C=C/c1ccc(C(Cc2ccc(C(=O)NCCS(=O)(=O)O)cc2)C(=O)Nc2c(F)cc(-c3ccc(Cl)cc3Cl)cc2F)cc1] | 713.6 (−) | C36H33N2O5F2Cl2SNa + 1.5H2O<br>56.55 4.75 3.66<br>56.62 4.56 3.69 |

-continued

| Ex# | Structure | LC/MS (mode) | Formula CHN (Calcd) CHN (Found) |
|---|---|---|---|
| 1.225 | 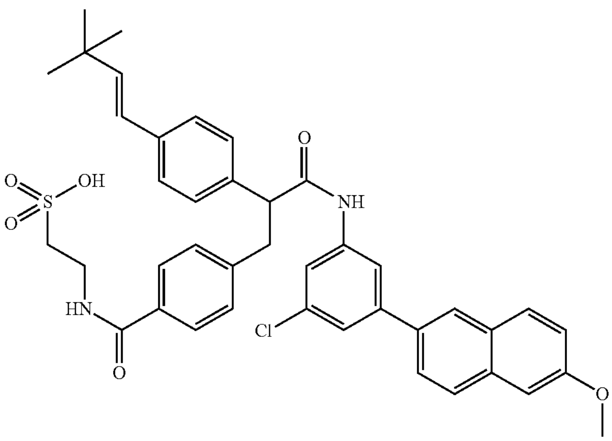 [SMILES: COc1ccc2cc(-c3cc(Cl)cc(NC(=O)C(Cc4ccc(C(=O)NCCS(=O)(=O)O)cc4)c4ccc(/C=C/C(C)(C)C)cc4)c3)ccc2c1] | 723.6 (−) | C41H40N2O6ClSNa + 2.5 H2O + 0.5 NaHCO3<br>59.74 5.50 3.36<br>59.74 5.16 3.27 |
| 1.226 | 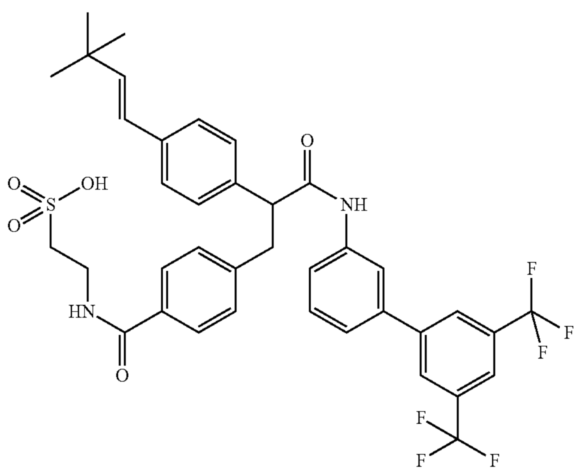 [SMILES: CC(C)(C)/C=C/c1ccc(C(Cc2ccc(C(=O)NCCS(=O)(=O)O)cc2)C(=O)Nc2cccc(-c3cc(C(F)(F)F)cc(C(F)(F)F)c3)c2)cc1] | 745.9 (−) | C38H35N2O5F6SNa + 3 H2O + 0.5 NaHCO3<br>53.47 4.84 3.24<br>53.18 4.63 3.06 |
| 1.227 | 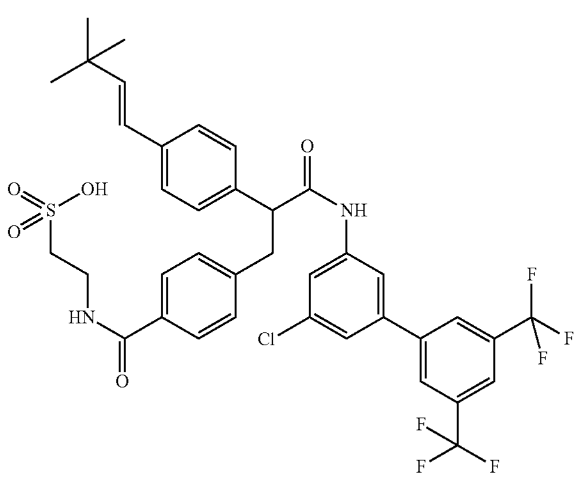 [SMILES: CC(C)(C)/C=C/c1ccc(C(Cc2ccc(C(=O)NCCS(=O)(=O)O)cc2)C(=O)Nc2cc(Cl)cc(-c3cc(C(F)(F)F)cc(C(F)(F)F)c3)c2)cc1] | 779.6 (−) | C38H34N2O5F6ClSNa + 3 H2O + 0.5 NaHCO3<br>51.42 4.54 3.12<br>51.54 4.21 2.99 |

-continued

| Ex# | Structure | LC/MS (mode) | Formula CHN (Calcd) CHN (Found) |
|---|---|---|---|
| 1.228 | 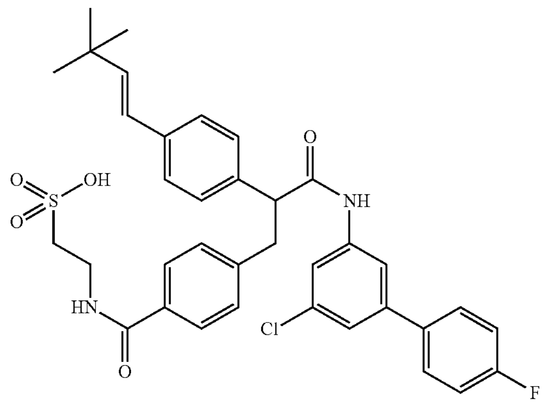 [SMILES: CC(C)(C)/C=C/c1ccc(C(Cc2ccc(C(=O)NCCS(=O)(=O)O)cc2)C(=O)Nc2cc(Cl)cc(-c3ccc(F)cc3)c2)cc1] | 661.9 (−) | C36H36N2O5FClSNa + 2 H2O<br>59.87 5.58 3.88<br>59.69 5.39 3.71 |
| 1.229 | 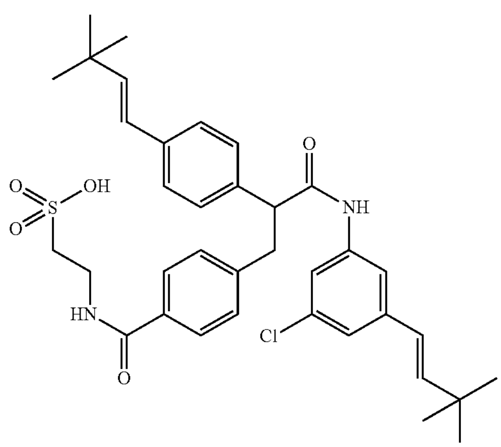 [SMILES: CC(C)(C)/C=C/c1ccc(C(Cc2ccc(C(=O)NCCS(=O)(=O)O)cc2)C(=O)Nc2cc(Cl)cc(/C=C/C(C)(C)C)c2)cc1] | 649.6 (−) | C36H42N2O5ClSNa + 0.1 NaHCO3 + 3 H2O<br>58.94 6.59 3.81<br>58.79 6.26 3.65 |
| 1.230 | 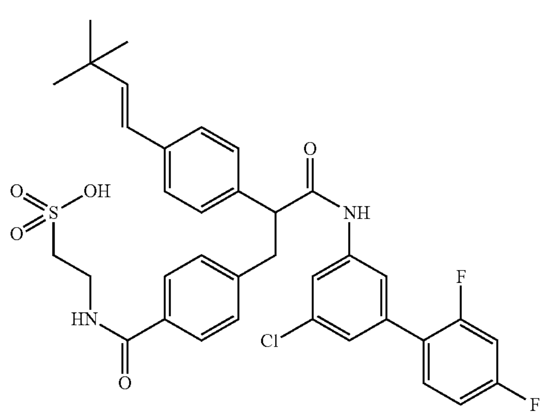 [SMILES: CC(C)(C)/C=C/c1ccc(C(Cc2ccc(C(=O)NCCS(=O)(=O)O)cc2)C(=O)Nc2cc(Cl)cc(-c3ccc(F)cc3F)c2)cc1] | 679.6 (−) | C36H34N2O5F2ClSNa + 1.5 H2O<br>59.22 5.31 3.84<br>59.06 5.06 3.73 |

-continued

| Ex# | Structure | LC/MS (mode) | Formula CHN (Calcd) CHN (Found) |
|---|---|---|---|
| 1.231 | 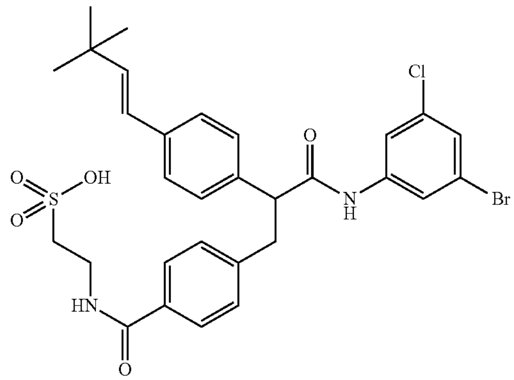 [SMILES: CC(C)(C)/C=C/c1ccc(C(Cc2ccc(C(=O)NCCS(=O)(=O)O)cc2)C(=O)Nc2cc(Cl)cc(Br)c2)cc1] | 647.4 (−) | C30H31N2O5ClBrSNa + 1.4 H2O 51.83 4.90 4.03 51.84 4.87 3.97 |
| 1.232 | 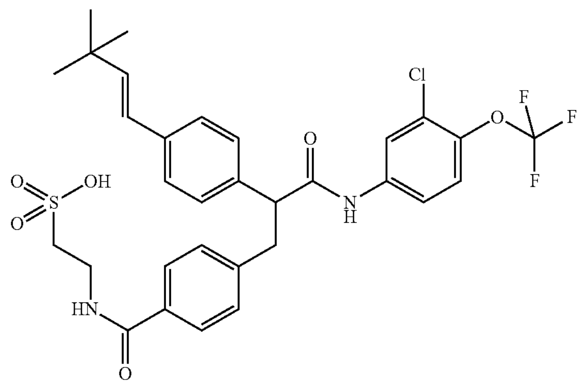 [SMILES: CC(C)(C)/C=C/c1ccc(C(Cc2ccc(C(=O)NCCS(=O)(=O)O)cc2)C(=O)Nc2ccc(OC(F)(F)F)c(Cl)c2)cc1] | 651.6 (−) | C31H31N2O6F3ClSNa + 1.5 H2O 53.03 4.88 3.99 53.06 4.58 3.93 |
| 1.233 | 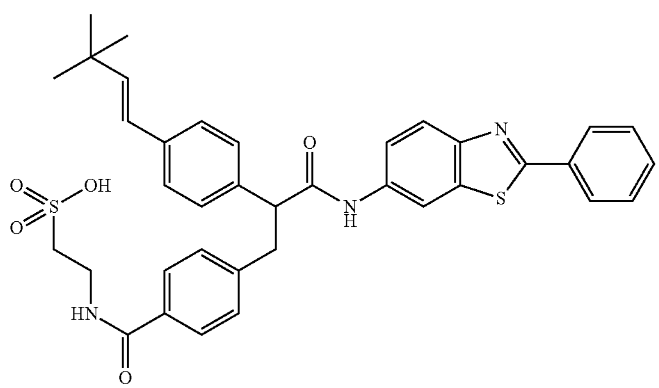 [SMILES: CC(C)(C)/C=C/c1ccc(C(Cc2ccc(C(=O)NCCS(=O)(=O)O)cc2)C(=O)Nc2ccc3nc(-c4ccccc4)sc3c2)cc1] | 666.6 (−) | C37H36N3O5S2Na + 2 H2O 61.22 5.55 5.79 61.03 5.43 5.69 |
| 1.234 | 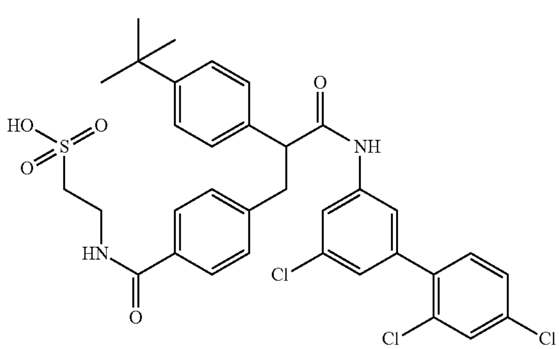 [SMILES: CC(C)(C)c1ccc(C(Cc2ccc(C(=O)NCCS(=O)(=O)O)cc2)C(=O)Nc2cc(Cl)cc(-c3ccc(Cl)cc3Cl)c2)cc1] | 687.6 (−) | C34H32N2O5Cl3SNa + 2.5 H2O 54.08 4.94 3.71 54.01 4.68 3.49 |

-continued

| Ex# | Structure | LC/MS (mode) | Formula CHN (Calcd) CHN (Found) |
|---|---|---|---|
| 1.236 | 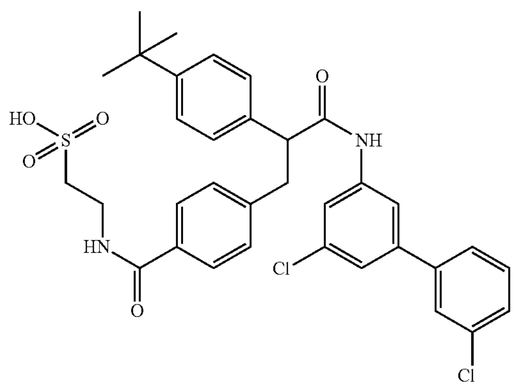 [SMILES: CC(C)(C)c1ccc(C(Cc2ccc(C(=O)NCCS(=O)(=O)O)cc2)C(=O)Nc2cc(Cl)cc(-c3cccc(Cl)c3)c2)cc1] | 655.6 (−) | C34H33N2O5Cl2SNa + 2.5 H2O<br>56.67 5.31 3.89<br>56.55 4.94 3.71 |
| 1.237 | 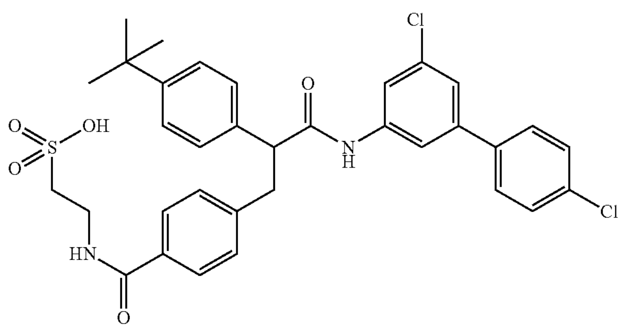 [SMILES: CC(C)(C)c1ccc(C(Cc2ccc(C(=O)NCCS(=O)(=O)O)cc2)C(=O)Nc2cc(Cl)cc(-c3ccc(Cl)cc3)c2)cc1] | 653.6 (+) | C34H33N2O5ClSNa + 3H2O<br>55.97 5.39 3.84<br>55.88 5.24 3.74 |
| 1.238 | 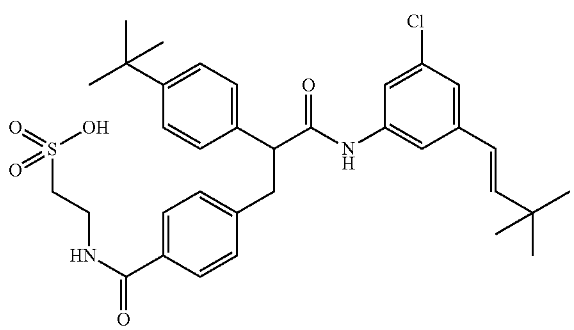 [SMILES: CC(C)(C)/C=C/c1cc(Cl)cc(NC(=O)C(Cc2ccc(C(=O)NCCS(=O)(=O)O)cc2)c2ccc(C(C)(C)C)cc2)c1] | 625.6 (+) | C34H40N2O5ClSNa + 1.8 H2O<br>60.09 6.47 4.12<br>60.04 6.31 3.95 |
| 1.239 | 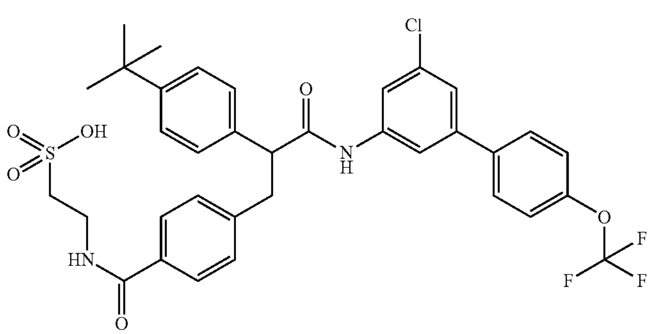 [SMILES: CC(C)(C)c1ccc(C(Cc2ccc(C(=O)NCCS(=O)(=O)O)cc2)C(=O)Nc2cc(Cl)cc(-c3ccc(OC(F)(F)F)cc3)c2)cc1] | 703.6 (+) | C35H33N2O6F3ClSNa + 2.5 H2O<br>54.58 4.97 3.64<br>54.40 4.79 3.42 |

-continued

| Ex# | Structure | LC/MS (mode) | Formula CHN (Calcd) CHN (Found) |
|---|---|---|---|
| 1.240 | 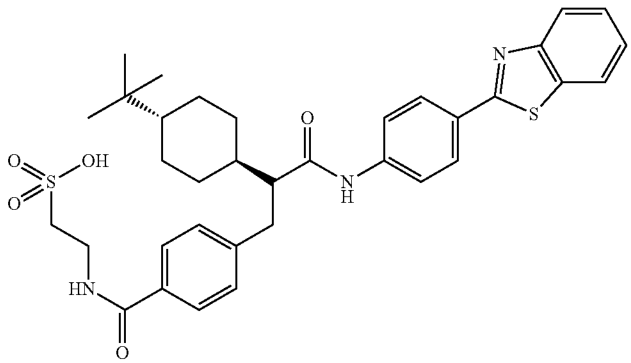 [SMILES: CC(C)(C)[C@H]1CC[C@H](C(Cc2ccc(C(=O)NCCS(=O)(=O)O)cc2)C(=O)Nc2ccc(-c3nc4ccccc4s3)cc2)CC1] | 648.6 (+) | C35H40N3O5S2Na + 4 H2O + 0.2 NaHCO3<br>55.72 6.40 5.54<br>55.60 6.71 5.36 |
| 1.241 | 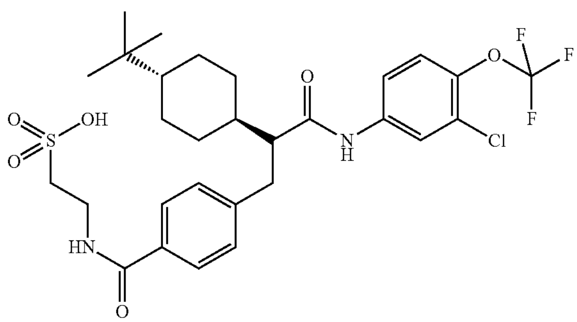 [SMILES: CC(C)(C)[C@H]1CC[C@H](C(Cc2ccc(C(=O)NCCS(=O)(=O)O)cc2)C(=O)Nc2ccc(OC(F)(F)F)c(Cl)c2)CC1] | 633.6 (+) | C29H35N2O6F3ClSNa + 1.8 H2O + 0.3 NaHCO3<br>49.38 5.50 3.93<br>48.53 5.92 3.75 |
| 1.242 | 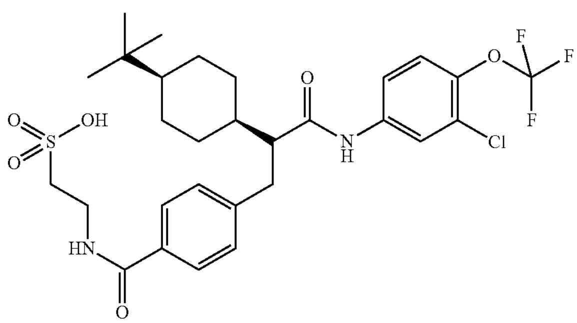 [SMILES: CC(C)(C)[C@H]1CC[C@@H](C(Cc2ccc(C(=O)NCCS(=O)(=O)O)cc2)C(=O)Nc2ccc(OC(F)(F)F)c(Cl)c2)CC1] | 633.6 (+) | C29H35N2O6F3ClSNa + 1.8 H2O + 0.1 NaHCO3<br>50.22 5.60 4.03<br>49.98 5.23 3.79 |
| 1.243 | 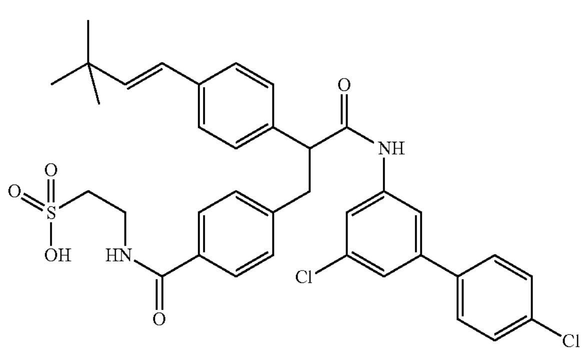 [SMILES: CC(C)(C)/C=C/c1ccc(C(Cc2ccc(C(=O)NCCS(=O)(=O)O)cc2)C(=O)Nc2cc(Cl)cc(-c3ccc(Cl)cc3)c2)cc1] | 679.6 (+) | C36H35N2O5Cl2SNa + 3 H2O + 0.4 NaHCO3<br>55.39 5.29 3.55<br>55.07 4.89 3.43 |

| Ex# | Structure | LC/MS (mode) | Formula CHN (Calcd) CHN (Found) |
|---|---|---|---|
| 1.244 | 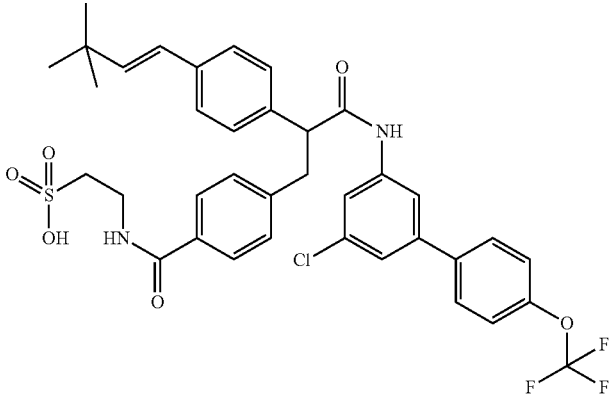 [SMILES: CC(C)(C)/C=C/c1ccc(C(Cc2ccc(C(=O)NCCS(=O)(=O)O)cc2)C(=O)Nc2cc(Cl)cc(-c3ccc(OC(F)(F)F)cc3)c2)cc1] | 726.6 (+) | C37H35N2O6F3ClSNa + 3 H2O + 0.2 NaHCO3 54.35 5.05 3.41 54.17 4.77 3.49 |
| 1.245 | 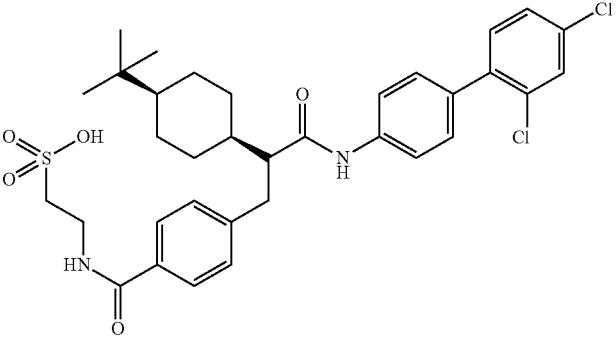 [SMILES: CC(C)(C)[C@H]1CC[C@@H](C(Cc2ccc(C(=O)NCCS(=O)(=O)O)cc2)C(=O)Nc2ccc(-c3ccc(Cl)cc3Cl)cc2)CC1] | 659.6 (+) | C34H39N2O5Cl2SNa + 1.9 H2O 57.04 6.03 3.91 56.71 5.82 3.64 |
| 1.246 | 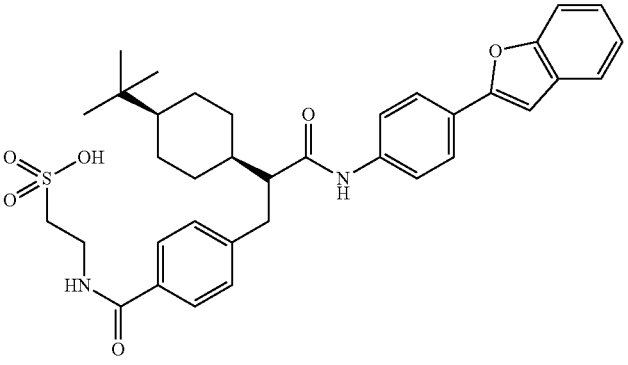 [SMILES: CC(C)(C)[C@H]1CC[C@@H](C(Cc2ccc(C(=O)NCCS(=O)(=O)O)cc2)C(=O)Nc2ccc(-c3cc4ccccc4o3)cc2)CC1] | 629.6 (+) | C36H41N2O6SNa + 2.5 H2O + 0.2 NaHCO3 60.84 6.52 3.92 60.82 6.25 3.90 |
| 1.247 | 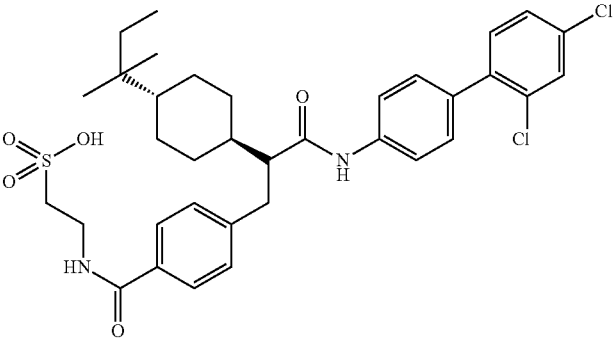 [SMILES: CCC(C)(C)[C@H]1CC[C@H](C(Cc2ccc(C(=O)NCCS(=O)(=O)O)cc2)C(=O)Nc2ccc(-c3ccc(Cl)cc3Cl)cc2)CC1] | 673.4 (+) | C35H41N2Cl2SNa + 3 H2O 56.07 6.32 3.74 56.41 5.10 3.74 |

| Ex# | Structure | LC/MS (mode) | Formula CHN (Calcd) CHN (Found) |
|---|---|---|---|
| 1.248 | 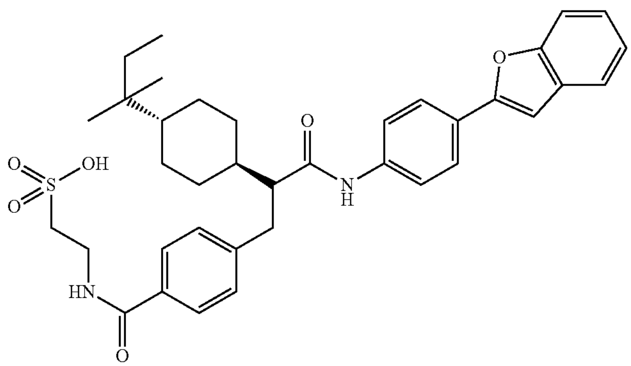 [SMILES: CCC(C)(C)[C@H]1CC[C@H](C(Cc2ccc(C(=O)NCCS(=O)(=O)O)cc2)C(=O)Nc2ccc(-c3cc4ccccc4o3)cc2)CC1] | 645.4 (+) | C37H43N2O6SNa + 4 H2O 60.15 6.96 3.79 59.85 6.32 3.68 |
| 1.249 | 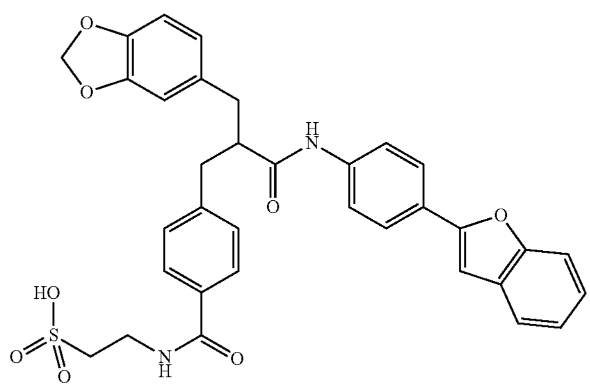 [SMILES: O=C(NCCS(=O)(=O)O)c1ccc(CC(Cc2ccc3c(c2)OCO3)C(=O)Nc2ccc(-c3cc4ccccc4o3)cc2)cc1] | 627.6 (+) | C34H29N2O8SNa + 2.7 H2O 58.56 4.97 4.02 58.32 4.62 4.04 |
| 1.250 | 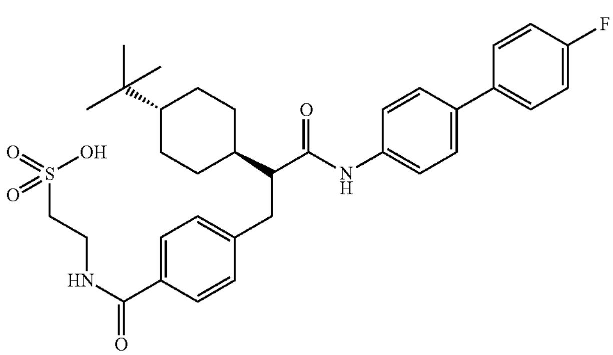 [SMILES: CC(C)(C)[C@H]1CC[C@H](C(Cc2ccc(C(=O)NCCS(=O)(=O)O)cc2)C(=O)Nc2ccc(-c3ccc(F)cc3)cc2)CC1] | 609.9 (+) | C34H40N2O5FSNa + 1.5 H2O + 0.1 NaHCO3 61.48 6.52 4.21 61.24 6.22 4.18 |

-continued

| Ex# | Structure | LC/MS (mode) | Formula CHN (Calcd) CHN (Found) |
|---|---|---|---|
| 1.251 | 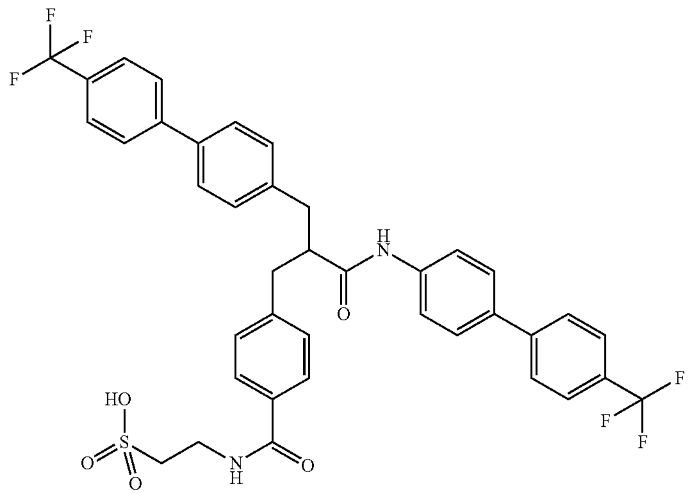 [SMILES: O=C(NCCS(=O)(=O)O)c1ccc(CC(Cc2ccc(-c3ccc(C(F)(F)F)cc3)cc2)C(=O)Nc2ccc(-c3ccc(C(F)(F)F)cc3)cc2)cc1] | 753.4 (−) | C39H31N2O5F6SNa + 2.2 H2O<br>57.38 4.37 3.43<br>57.45 4.17 3.33 |
| 1.252 | 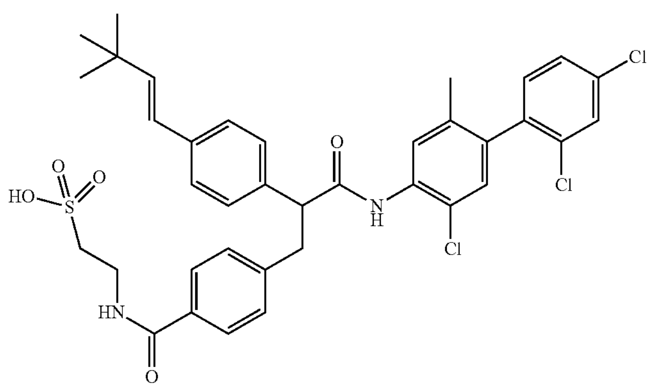 [SMILES: Cc1cc(NC(=O)C(Cc2ccc(C(=O)NCCS(=O)(=O)O)cc2)c2ccc(/C=C/C(C)(C)C)cc2)c(Cl)cc1-c1ccc(Cl)cc1Cl] | 725.6 (−) | C37H36Cl3N2O5SNa + 1.8H2O<br>56.79 5.10 3.58<br>56.54 4.81 3.35 |
| 1.253 | 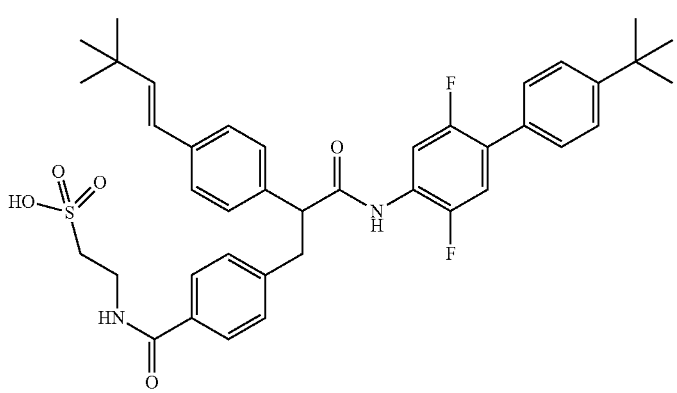 [SMILES: CC(C)(C)/C=C/c1ccc(C(Cc2ccc(C(=O)NCCS(=O)(=O)O)cc2)C(=O)Nc2cc(F)c(-c3ccc(C(C)(C)C)cc3)cc2F)cc1] | 701.6 (−) | C40H43 F2N2O5SNa + 2H2O<br>63.14 6.23 3.68<br>63.25 6.08 3.68 |

| Ex# | Structure | LC/MS (mode) | Formula CHN (Calcd) CHN (Found) |
|---|---|---|---|
| 1.254 | 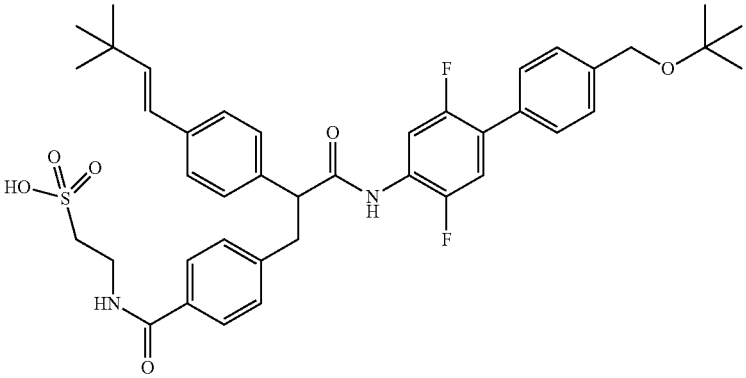 [SMILES: CC(C)(C)/C=C/c1ccc(C(Cc2ccc(C(=O)NCCS(=O)(=O)O)cc2)C(=O)Nc2cc(F)c(-c3ccc(COC(C)(C)C)cc3)cc2F)cc1] | 732.1 (−) | C41H45F2N2O6SNa + 1.6H2O<br>62.84 6.20 3.57<br>62.97 5.97 3.45 |
| 1.255 | 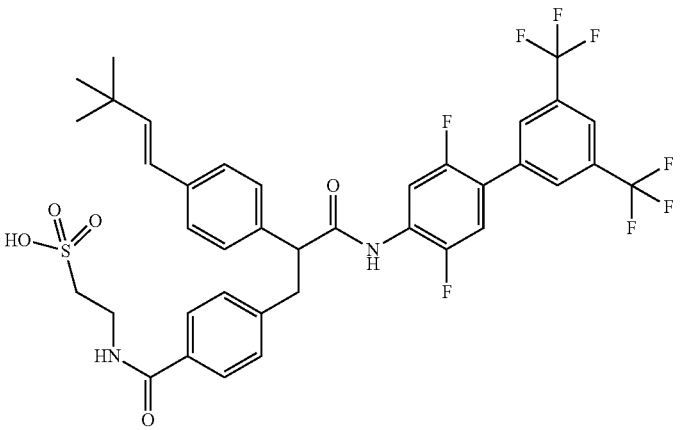 [SMILES: CC(C)(C)/C=C/c1ccc(C(Cc2ccc(C(=O)NCCS(=O)(=O)O)cc2)C(=O)Nc2cc(F)c(-c3cc(C(F)(F)F)cc(C(F)(F)F)c3)cc2F)cc1] | 781.6 (−) | C38H33F8N2O5SNa + 0.6H2O + 0.4Na2CO3<br>53.76 4.02 3.27<br>53.59 3.62 2.95 |
| 1.256 | 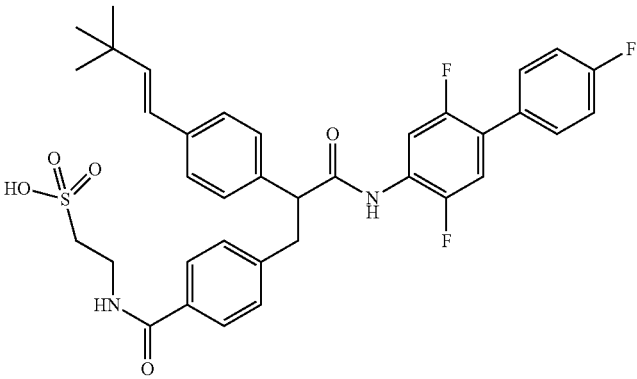 [SMILES: CC(C)(C)/C=C/c1ccc(C(Cc2ccc(C(=O)NCCS(=O)(=O)O)cc2)C(=O)Nc2cc(F)c(-c3ccc(F)cc3)cc2F)cc1] | 664.1 (−) | C36H34F3N2O5SNa + 1.7H2O<br>60.28 5.26 3.91<br>60.15 5.10 3.75 |

| Ex# | Structure | LC/MS (mode) | Formula CHN (Calcd) CHN (Found) |
|---|---|---|---|
| 1.257 | 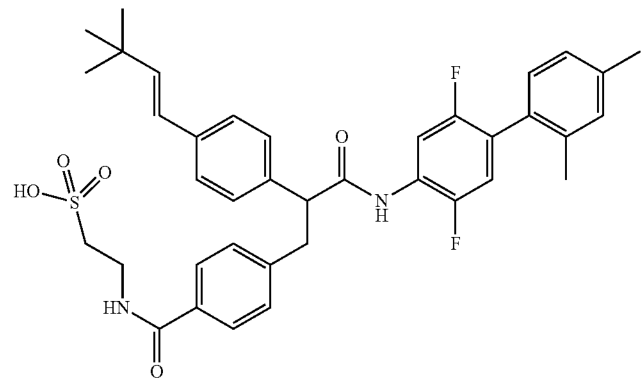 [SMILES: Cc1ccc(-c2cc(F)c(NC(=O)C(Cc3ccc(C(=O)NCCS(=O)(=O)O)cc3)c3ccc(/C=C/C(C)(C)C)cc3)cc2F)c(C)c1] | 673.6 (−) | C38H39F2N2O5SNa + 2H2O<br>62.28 5.91 3.82<br>62.23 5.52 3.60 |
| 1.258 | 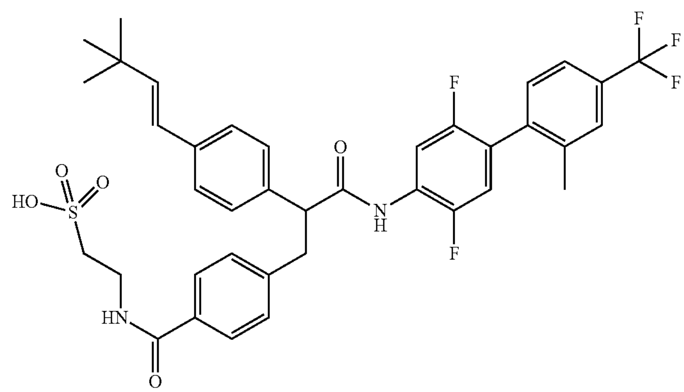 | 727.6 (−) | C38H36F5N2O5SNa + 1.2H2O + 0.15Na2CO3<br>58.13 4.91 3.55<br>58.52 4.50 3.14 |
| 1.259 | 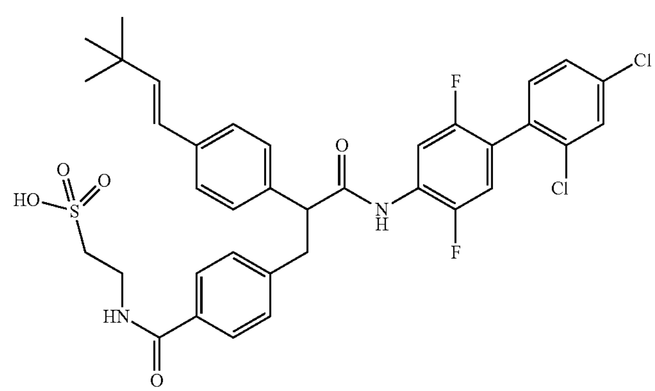 [SMILES: CC(C)(C)/C=C/c1ccc(C(Cc2ccc(C(=O)NCCS(=O)(=O)O)cc2)C(=O)Nc2cc(F)c(-c3ccc(Cl)cc3Cl)cc2F)cc1] | 713.6 (−) | C36H33Cl2F2N2O5SNa + 2.5H2O<br>55.25 4.89 3.58<br>55.19 4.81 3.40 |
| 1.260 | 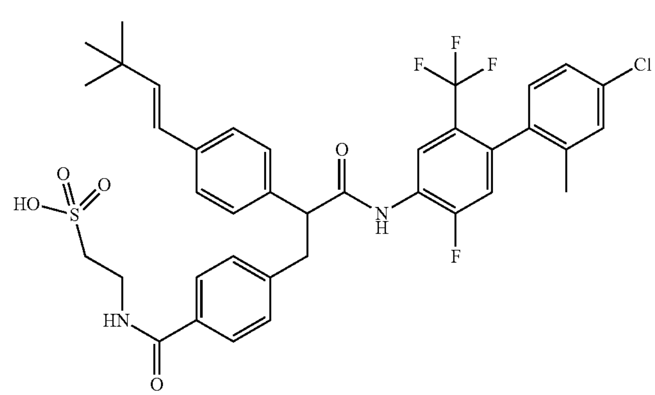 [SMILES: Cc1cc(Cl)ccc1-c1cc(F)c(NC(=O)C(Cc2ccc(C(=O)NCCS(=O)(=O)O)cc2)c2ccc(/C=C/C(C)(C)C)cc2)cc1C(F)(F)F] | 743.9 (−) | C38H36ClF4N2O5SNa + 2.4H2O<br>56.32 5.07 3.46<br>56.32 4.85 3.30 |

-continued

| Ex# | Structure | LC/MS (mode) | Formula CHN (Calcd) CHN (Found) |
|---|---|---|---|
| 1.261 | 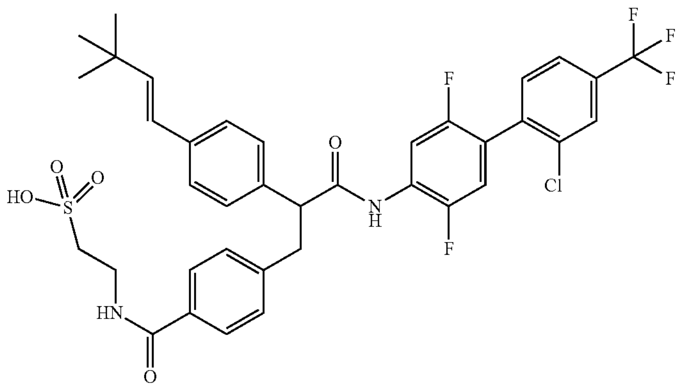 [SMILES: CC(C)(C)/C=C/c1ccc(C(Cc2ccc(C(=O)NCCS(=O)(=O)O)cc2)C(=O)Nc2cc(F)c(-c3ccc(C(F)(F)F)cc3Cl)cc2F)cc1] | 747.6 (−) | C37H33ClF5N2O5SNa + 2.6H2O<br>54.33 4.71 3.42<br>54.30 4.38 3.09 |
| 1.262 | 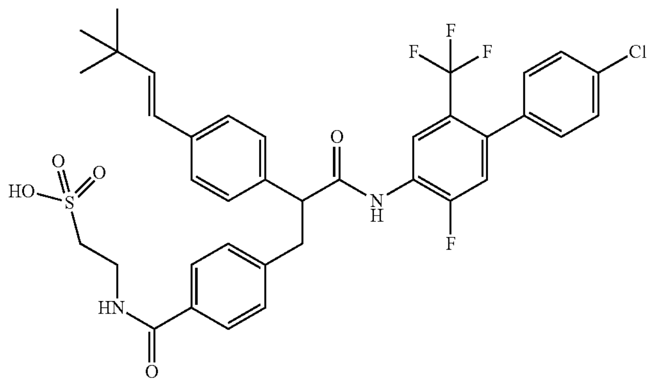 [SMILES: CC(C)(C)/C=C/c1ccc(C(Cc2ccc(C(=O)NCCS(=O)(=O)O)cc2)C(=O)Nc2cc(C(F)(F)F)c(-c3ccc(Cl)cc3)cc2F)cc1] | 729.6 (−) | C37H34ClF4N2O5SNa + 2H2O<br>56.31 4.85 3.55<br>56.36 4.68 3.42 |
| 1.263 | 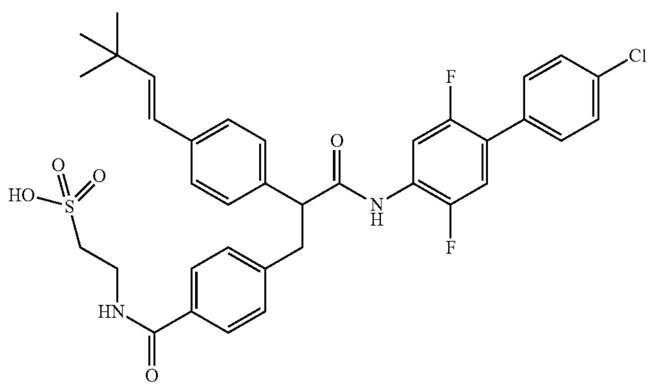 [SMILES: CC(C)(C)/C=C/c1ccc(C(Cc2ccc(C(=O)NCCS(=O)(=O)O)cc2)C(=O)Nc2cc(F)c(-c3ccc(Cl)cc3)cc2F)cc1] | 679.6 (−) | C36H34ClF2N2O5SNa + 3.2H2O<br>56.83 5.35 3.68<br>57.15 4.96 3.15 |
| 1.264 | 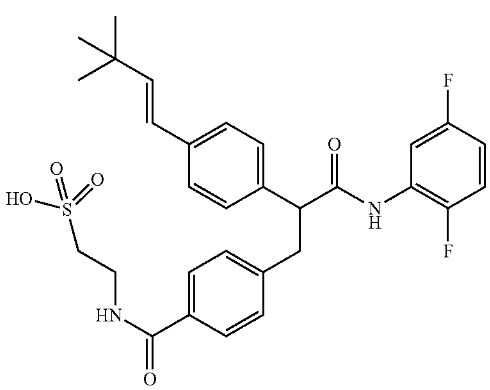 [SMILES: CC(C)(C)/C=C/c1ccc(C(Cc2ccc(C(=O)NCCS(=O)(=O)O)cc2)C(=O)Nc2cc(F)ccc2F)cc1] | 569.6 (−) | C30H31F2N2O5SNa + 2.9H2O<br>55.88 5.75 4.34<br>55.63 5.36 4.25 |

| Ex# | Structure | LC/MS (mode) | Formula CHN (Calcd) CHN (Found) |
|---|---|---|---|
| 1.265 | 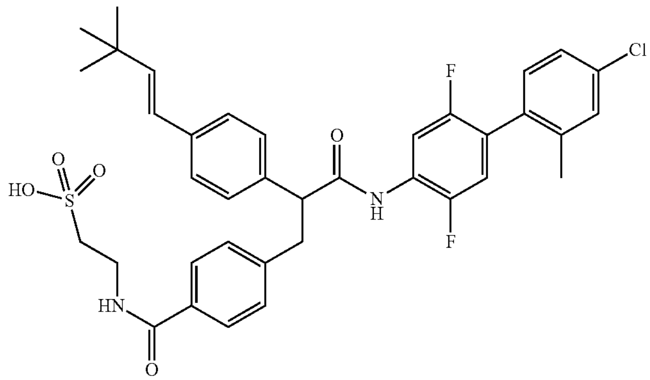 [SMILES: Cc1cc(Cl)ccc1-c1cc(F)c(NC(=O)C(Cc2ccc(C(=O)NCCS(=O)(=O)O)cc2)c2ccc(/C=C/C(C)(C)C)cc2)cc1F] | 693.6 (−) | C37H36ClF2N2O5SNa + 2.2H2O<br>58.72 5.38 3.70<br>58.57 5.26 3.56 |
| 1.266 | 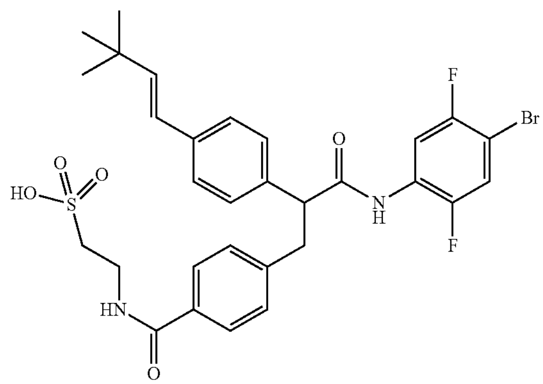 [SMILES: CC(C)(C)/C=C/c1ccc(C(Cc2ccc(C(=O)NCCS(=O)(=O)O)cc2)C(=O)Nc2cc(F)c(Br)cc2F)cc1] | 649.6 (−) | C30H30BrF2N2O5SNa + 1.9H2O<br>51.06 4.83 3.97<br>51.08 4.54 4.02 |
| 1.267 | 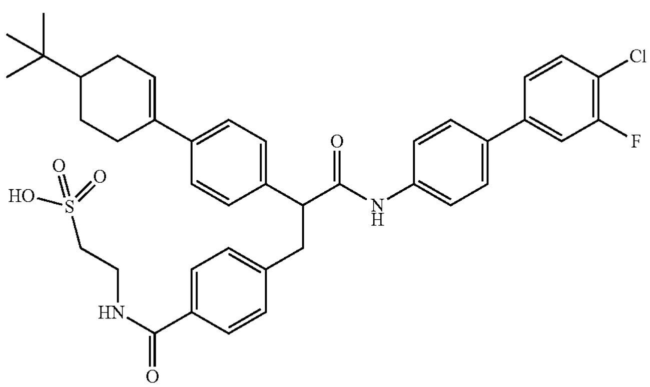 [SMILES: CC(C)(C)C1CC=C(c2ccc(C(Cc3ccc(C(=O)NCCS(=O)(=O)O)cc3)C(=O)Nc3ccc(-c4ccc(Cl)c(F)c4)cc3)cc2)CC1] | 715.9 (−) | C40H41ClFN2O5SNa + 2H2O + 0.1Na2CO3<br>61.28 5.77 3.56<br>60.96 5.44 3.44 |
| 1.268 | 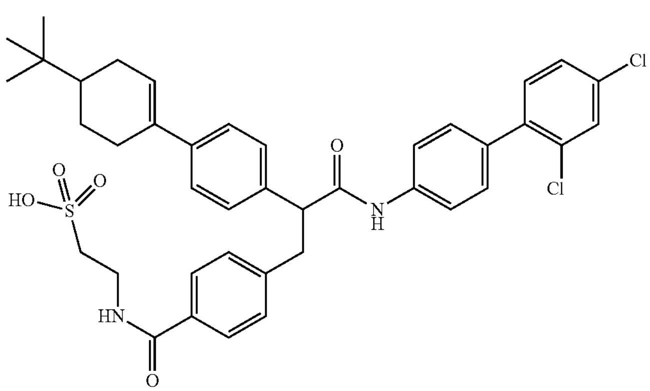 [SMILES: CC(C)(C)C1CC=C(c2ccc(C(Cc3ccc(C(=O)NCCS(=O)(=O)O)cc3)C(=O)Nc3ccc(-c4ccc(Cl)cc4Cl)cc3)cc2)CC1] | 731.9 (−) | C40H41Cl2N2O5SNa + 1.6H2O<br>61.24 5.68 3.57<br>61.21 5.71 3.32 |

-continued

| Ex# | Structure | LC/MS (mode) | Formula CHN (Calcd) CHN (Found) |
|---|---|---|---|
| 1.269 | 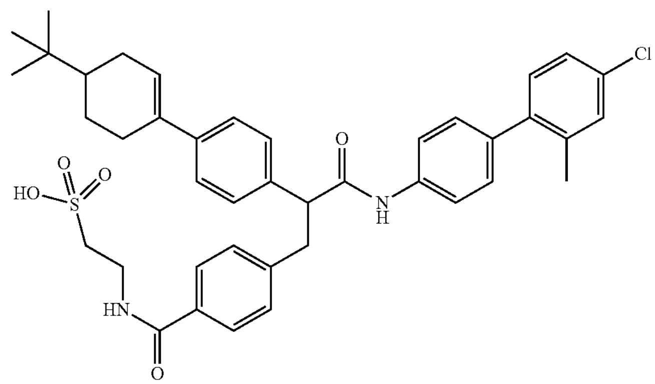 [SMILES: Cc1cc(Cl)ccc1-c1ccc(NC(=O)C(Cc2ccc(C(=O)NCCS(=O)(=O)O)cc2)c2ccc(C3=CCC(C(C)(C)C)CC3)cc2)cc1] | 711.6 (−) | C41H44ClN2O5SNa + 2H2O 63.84 6.27 3.63 63.82 6.23 3.34 |
| 1.270 | 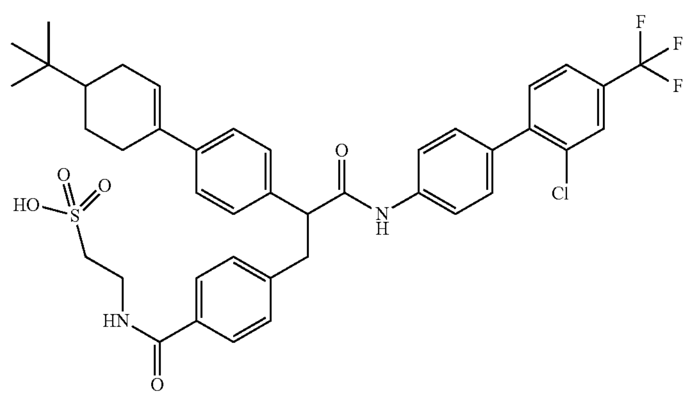 [SMILES: CC(C)(C)C1CC=C(c2ccc(C(Cc3ccc(C(=O)NCCS(=O)(=O)O)cc3)C(=O)Nc3ccc(-c4ccc(C(F)(F)F)cc4Cl)cc3)cc2)CC1] | 765.6 (−) | C41H41ClF3N2O5SNa + 2.9H2O + 0.1Na2CO3 57.93 5.54 3.29 57.56 5.17 3.12 |
| 1.271 | 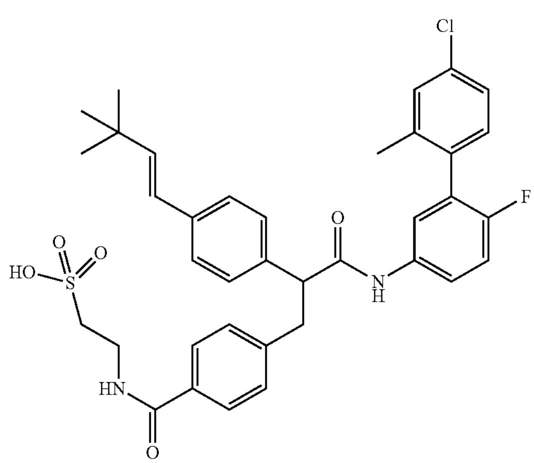 [SMILES: Cc1cc(Cl)ccc1-c1cc(NC(=O)C(Cc2ccc(C(=O)NCCS(=O)(=O)O)cc2)c2ccc(/C=C/C(C)(C)C)cc2)ccc1F] | 675.6 (−) | C37H37ClFN2O5SNa + 3H2O 59.00 5.75 3.72 58.88 5.62 3.53 |

-continued

| Ex# | Structure | LC/MS (mode) | Formula CHN (Calcd) CHN (Found) |
|---|---|---|---|
| 1.272 | 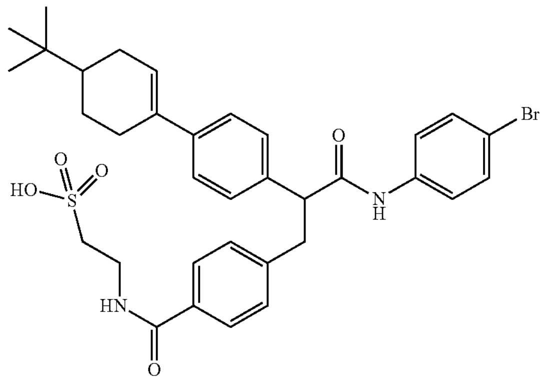 [SMILES: CC(C)(C)C1CC=C(c2ccc(C(Cc3ccc(C(=O)NCCS(=O)(=O)O)cc3)C(=O)Nc3ccc(Br)cc3)cc2)CC1] | 665.6 (−) | C34H38BrN2O5SNa + 2.8H2O<br>55.18 5.94 3.79<br>55.45 6.68 3.76 |
| 1.273 | 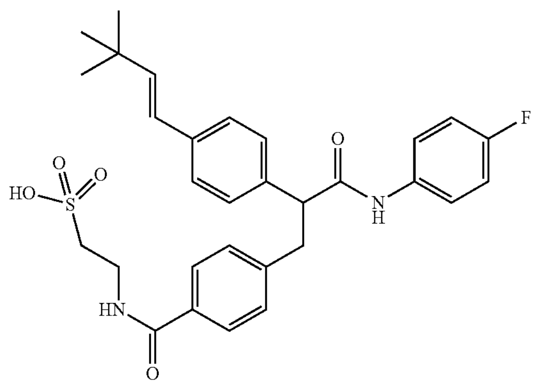 [SMILES: CC(C)(C)/C=C/c1ccc(C(Cc2ccc(C(=O)NCCS(=O)(=O)O)cc2)C(=O)Nc2ccc(F)cc2)cc1] | 551.6 (−) | C30H32FN2O5SNa + 2.5H2O + 0.1Na2CO3<br>57.36 5.92 4.44<br>57.35 5.61 4.31 |
| 1.274 | 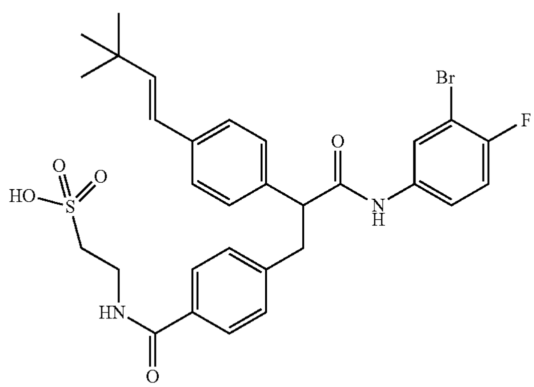 [SMILES: CC(C)(C)/C=C/c1ccc(C(Cc2ccc(C(=O)NCCS(=O)(=O)O)cc2)C(=O)Nc2ccc(F)c(Br)c2)cc1] | 631.4 (−) | C30H31BrFN2O5SNa + 2H2O<br>52.25 5.12 4.05<br>51.96 4.95 3.96 |
| 1.275 | 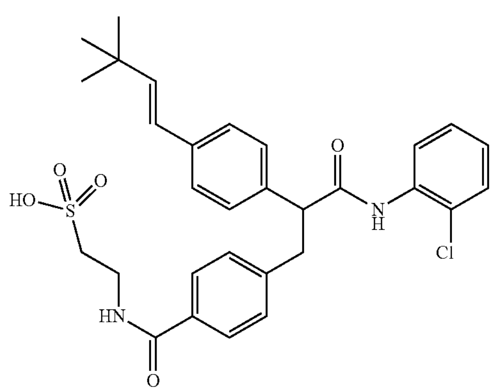 [SMILES: CC(C)(C)/C=C/c1ccc(C(Cc2ccc(C(=O)NCCS(=O)(=O)O)cc2)C(=O)Nc2ccccc2Cl)cc1] | 567.6 (−) | C30H32ClN2O5SNa + 1.7H2O + 0.25Na2CO3<br>56.05 5.50 4.32<br>55.74 5.13 4.07 |

-continued
| Ex# | Structure | LC/MS (mode) | Formula CHN (Calcd) CHN (Found) |
|---|---|---|---|
| 1.276 | 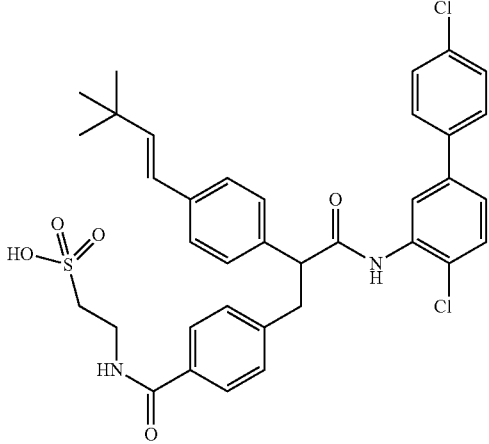 [SMILES: CC(C)(C)/C=C/c1ccc(C(Cc2ccc(C(=O)NCCS(=O)(=O)O)cc2)C(=O)Nc2cc(-c3ccc(Cl)cc3)ccc2Cl)cc1] | 677.6 (−) | C36H35Cl2N2O5SNa + 3.2H2O + 0.2Na2CO3<br>55.71 5.35 3.59<br>55.33 4.95 3.38 |
| 1.277 | 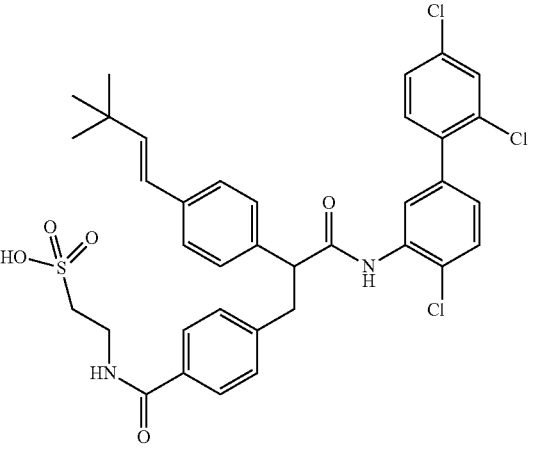 [SMILES: CC(C)(C)/C=C/c1ccc(C(Cc2ccc(C(=O)NCCS(=O)(=O)O)cc2)C(=O)Nc2cc(-c3ccc(Cl)cc3Cl)ccc2Cl)cc1] | 711.4 (−) | C36H34Cl3N2O5SNa + 2.2H2O<br>55.74 4.99 3.61<br>54.49 4.68 3.43 |
| 1.278 | 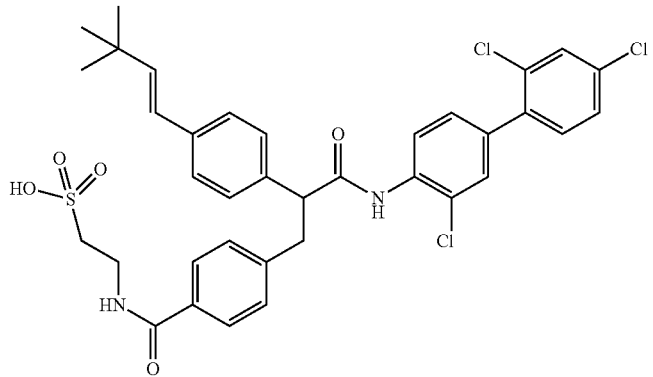 [SMILES: CC(C)(C)/C=C/c1ccc(C(Cc2ccc(C(=O)NCCS(=O)(=O)O)cc2)C(=O)Nc2ccc(-c3ccc(Cl)cc3Cl)cc2Cl)cc1] | 711.4 (−) | C36H34Cl3N2O5SNa + 2H2O<br>56.00 4.96 3.63<br>55.83 4.94 3.61 |

-continued

| Ex# | Structure | LC/MS (mode) | Formula CHN (Calcd) CHN (Found) |
|---|---|---|---|
| 1.279 | 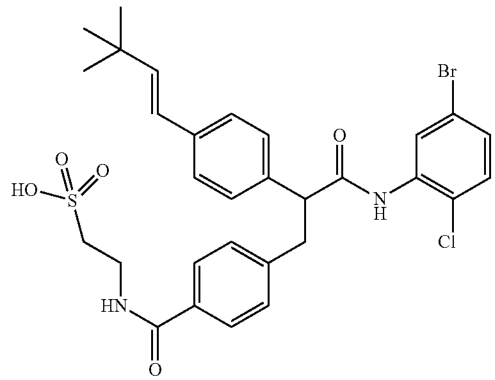 [SMILES: CC(C)(C)/C=C/c1ccc(C(Cc2ccc(C(=O)NCCS(=O)(=O)O)cc2)C(=O)Nc2cc(Br)ccc2Cl)cc1] | 647.4 (−) | C30H31BrClN2O5SNa + 2H2O + 0.1Na2CO3<br>50.45 4.92 3.91<br>50.21 4.57 4.10 |
| 1.280 | 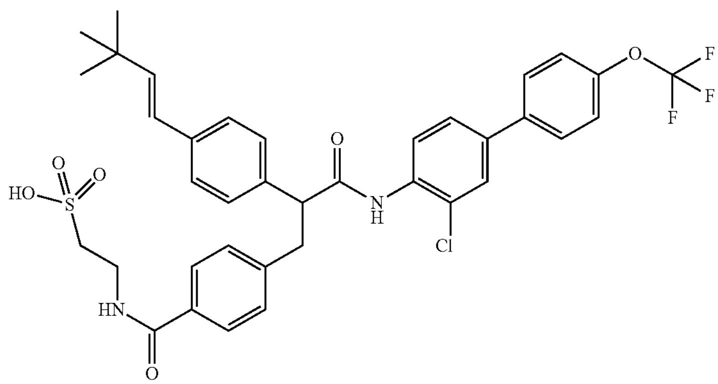 [SMILES: CC(C)(C)/C=C/c1ccc(C(Cc2ccc(C(=O)NCCS(=O)(=O)O)cc2)C(=O)Nc2ccc(-c3ccc(OC(F)(F)F)cc3)cc2Cl)cc1] | 727.4 (−) | C37H35ClF3N2O6SNa + 1.8H2O + 0.2Na2CO3<br>55.52 4.83 3.48<br>55.21 4.45 3.56 |
| 1.281 | 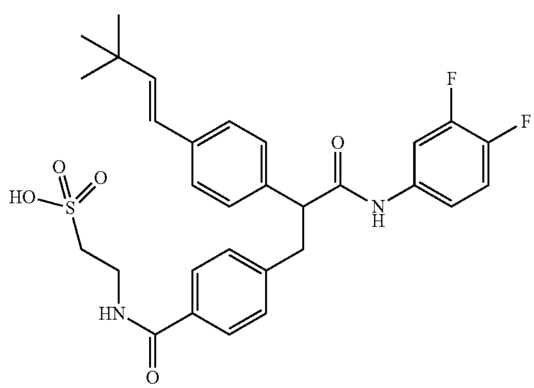 [SMILES: CC(C)(C)/C=C/c1ccc(C(Cc2ccc(C(=O)NCCS(=O)(=O)O)cc2)C(=O)Nc2ccc(F)c(F)c2)cc1] | 569.6 (−) | C30H31F2N2O5SNa + 2.3H2O + 0.1Na2CO3<br>56.08 5.57 4.35<br>55.83 5.27 4.26 |
| 1.282 | 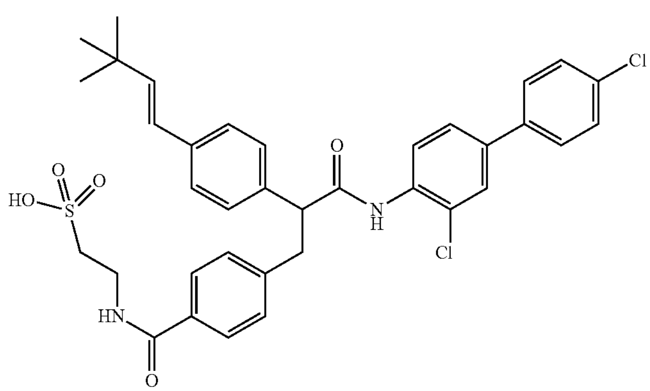 [SMILES: CC(C)(C)/C=C/c1ccc(C(Cc2ccc(C(=O)NCCS(=O)(=O)O)cc2)C(=O)Nc2ccc(-c3ccc(Cl)cc3)cc2Cl)cc1] | 677.6 (−) | C36H35Cl2N2O5SNa + 2.3H2O<br>58.19 5.37 3.77<br>57.87 4.98 3.54 |

-continued
| Ex# | Structure | LC/MS (mode) | Formula CHN (Calcd) CHN (Found) |
|---|---|---|---|
| 1.283 | 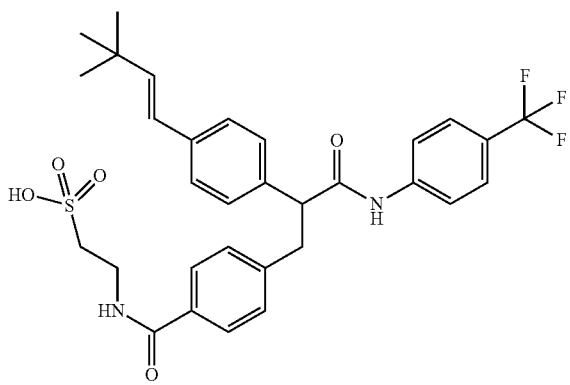 [SMILES: CC(C)(C)/C=C/c1ccc(C(Cc2ccc(C(=O)NCCS(=O)(=O)O)cc2)C(=O)Nc2ccc(C(F)(F)F)cc2)cc1] | 601.69 (−) | C31H32F3N2O5SNa + 2.9H2O + 0.15Na2CO3<br>54.00 5.50 4.04<br>53.66 5.13 3.87 |
| 1.284 | 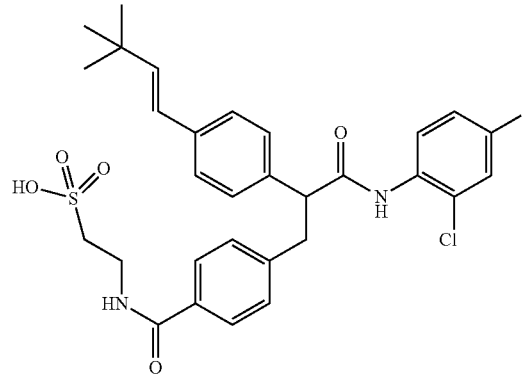 | 693.4 (−) | C30H31ClIN2O5SNa + 3H2O<br>46.73 4.84 3.63<br>46.68 4.65 3.67 |
| 1.285 | 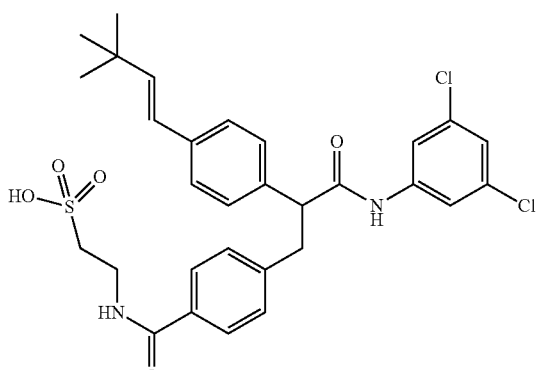 | 601.6 (−) | C30H31Cl2N2O5SNa + 2.5H2O<br>53.73 5.41 4.18<br>54.10 5.74 4.27 |
| 1.286 | 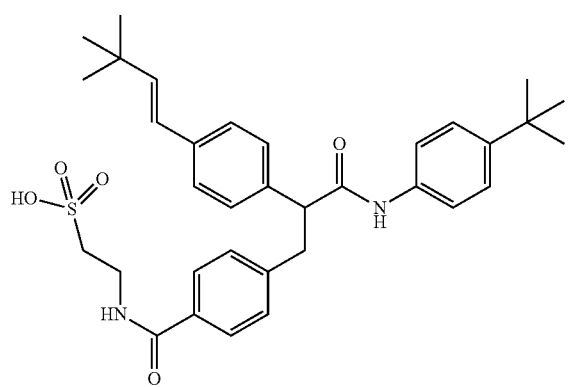 [SMILES: CC(C)(C)/C=C/c1ccc(C(Cc2ccc(C(=O)NCCS(=O)(=O)O)cc2)C(=O)Nc2ccc(C(C)(C)C)cc2)cc1] | 589.6 (−) | C34H41N2O5SNa + 2.9H2O<br>61.41 7.09 4.21<br>61.13 6.57 3.94 |

-continued

| Ex# | Structure | LC/MS (mode) | Formula CHN (Calcd) CHN (Found) |
|---|---|---|---|
| 1.287 | 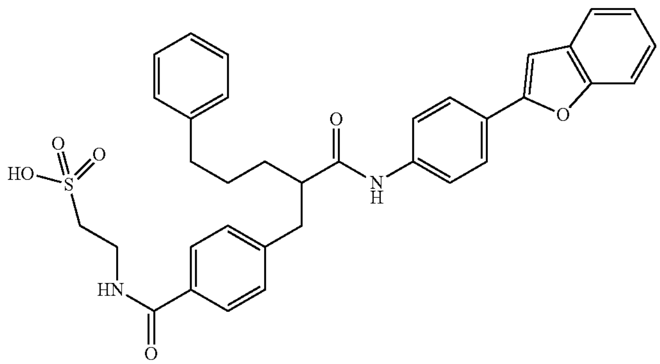 [SMILES: O=C(NCCS(=O)(=O)O)c1ccc(CC(CCCc2ccccc2)C(=O)Nc2ccc(-c3cc4ccccc4o3)cc2)cc1] | 609.9 (−) | C35H33N2NaO6S + 3H2O<br>61.21 5.72 4.08<br>61.12 5.57 3.82 |
| 1.288 | 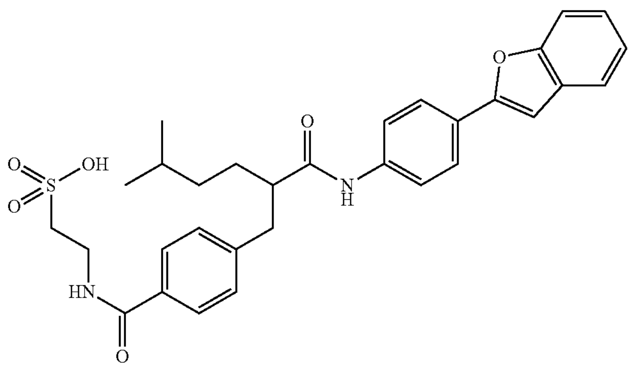 [SMILES: CC(C)CCC(Cc1ccc(C(=O)NCCS(=O)(=O)O)cc1)C(=O)Nc1ccc(-c2cc3ccccc3o2)cc1] | 561.4 (−) | C31H33N2O6SNa + 4.7H2O<br>55.63 6.38 4.19<br>55.25 5.44 4.00 |
| 1.289 | 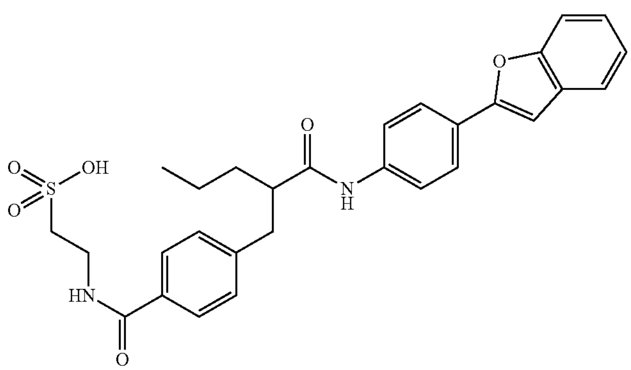 [SMILES: CCCC(Cc1ccc(C(=O)NCCS(=O)(=O)O)cc1)C(=O)Nc1ccc(-c2cc3ccccc3o2)cc1] | 533.1 (−) | C29H29N2O6SNa + 4.1H2O<br>55.25 5.95 4.44<br>54.96 5.57 4.28 |
| 1.290 | 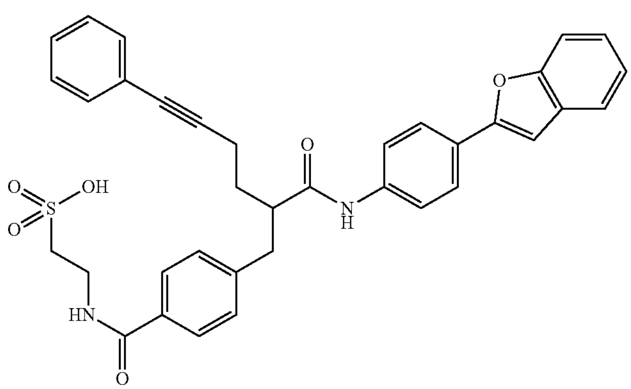 [SMILES: O=C(NCCS(=O)(=O)O)c1ccc(CC(CCC#Cc2ccccc2)C(=O)Nc2ccc(-c3cc4ccccc4o3)cc2)cc1] | 605.6 (−) | C35H29N2O6SNa + 3H2O<br>61.57 5.17 4.10<br>61.38 4.92 4.05 |

-continued
| Ex# | Structure | LC/MS (mode) | Formula CHN (Calcd) CHN (Found) |
|---|---|---|---|
| 1.291 | 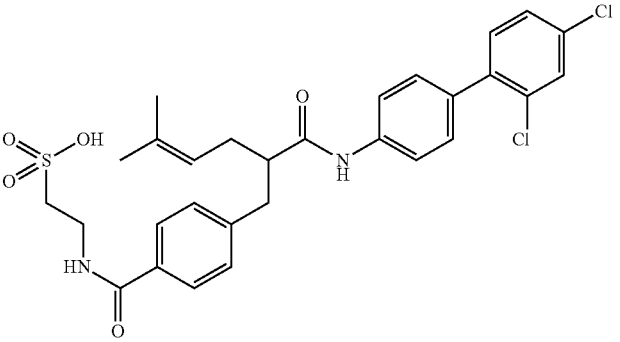 [SMILES: CC(C)=CCC(Cc1ccc(C(=O)NCCS(=O)(=O)O)cc1)C(=O)Nc1ccc(-c2ccc(Cl)cc2Cl)cc1] | 589.4 (−) | C29H29Cl2N2O5SNa + 2H2O<br>53.79 5.14 4.33<br>53.51 4.42 4.26 |
| 1.292 | 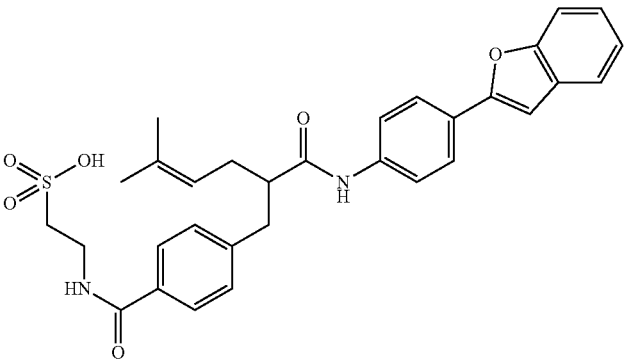 [SMILES: CC(C)=CCC(Cc1ccc(C(=O)NCCS(=O)(=O)O)cc1)C(=O)Nc1ccc(-c2cc3ccccc3o2)cc1] | 559.4 (−) | C31H31N2O6SNa + 3.2H2O<br>58.15 5.89 4.38<br>57.83 5.57 4.26 |
| 1.293 | 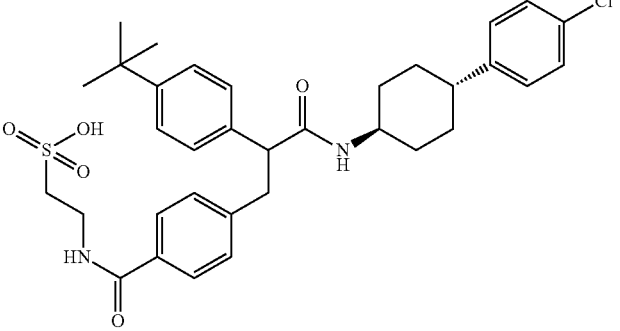 | 623.9 (−) | C34H41ClN2O5S + 2.5H2O<br>60.93 6.92 4.18<br>60.69 6.55 4.44 |
| 1.294 | 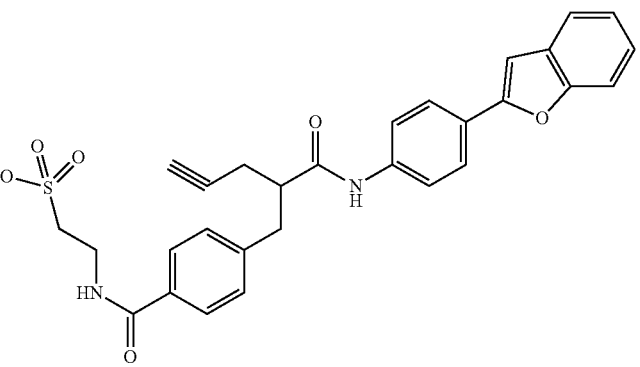 | 529.6 (−) | C29H26N2O6S + 2.3H2O<br>60.89 5.39 4.90<br>60.78 5.23 5.05 |

US 10,239,829 B2

393 394

-continued

| Ex# | Structure | LC/MS (mode) | Formula CHN (Calcd) CHN (Found) |
|---|---|---|---|
| 1.295 | 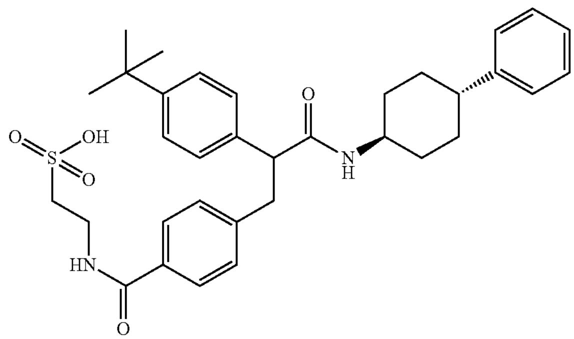 [SMILES: CC(C)(C)c1ccc(C(Cc2ccc(C(=O)NCCS(=O)(=O)O)cc2)C(=O)N[C@H]2CC[C@H](c3ccccc3)CC2)cc1] | 589.6 (−) | C34H42N2O5S + 1.8H2O<br>65.53 7.38 4.50<br>65.30 6.90 4.49 |
| 1.296 | 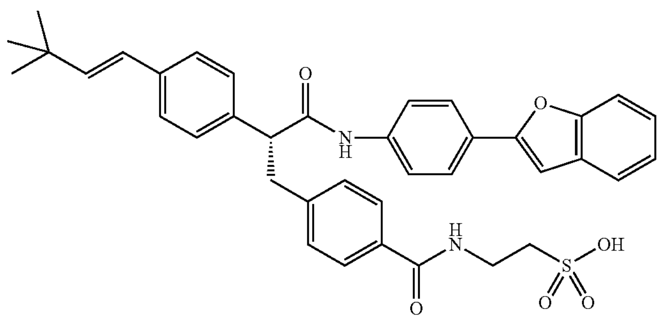 [SMILES: CC(C)(C)/C=C/c1ccc([C@@H](Cc2ccc(C(=O)NCCS(=O)(=O)O)cc2)C(=O)Nc2ccc(-c3cc4ccccc4o3)cc2)cc1] | 651 (+) | C38H37N2O6SNa + 2.5 H2O<br>63.58, 5.90, 3.90<br>63.49, 5.90, 3.71 |
| 1.297 | 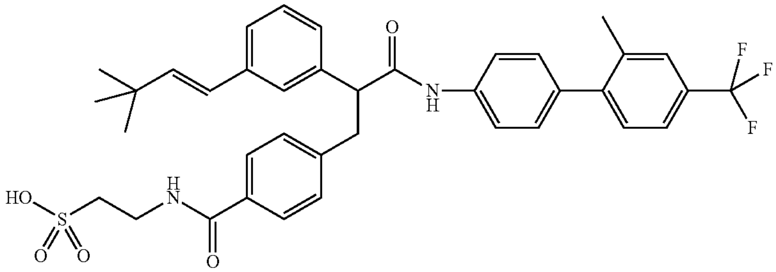 [SMILES: Cc1cc(C(F)(F)F)ccc1-c1ccc(NC(=O)C(Cc2ccc(C(=O)NCCS(=O)(=O)O)cc2)c2cccc(/C=C/C(C)(C)C)c2)cc1] | 693 (+) | C38H38N2O5F3SNa + 0.65H2O<br>62.82, 5.45, 3.86<br>62.82, 5.37, =3.80 |
| 1.298 | 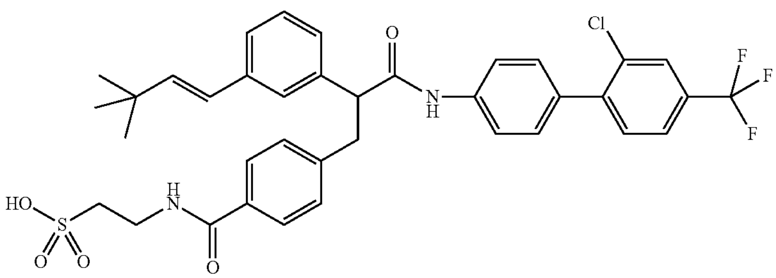 [SMILES: CC(C)(C)/C=C/c1cccc(C(Cc2ccc(C(=O)NCCS(=O)(=O)O)cc2)C(=O)Nc2ccc(-c3ccc(C(F)(F)F)cc3Cl)cc2)c1] | 711 (−) | C37H35N2O5F3ClSNa + 1.2H2O<br>58.72, 4.98, 3.70<br>58.77, 4.75, 3.60 |
| 1.299 | 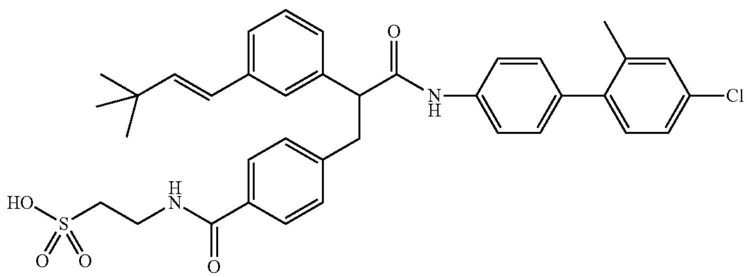 [SMILES: Cc1cc(Cl)ccc1-c1ccc(NC(=O)C(Cc2ccc(C(=O)NCCS(=O)(=O)O)cc2)c2cccc(/C=C/C(C)(C)C)c2)cc1] | 661 (+) | C37H38N2O5ClSNa + 0.7H2O<br>64.05, 5.72, 4.04<br>64.09, 5.47. 4.04 |

-continued

| Ex# | Structure | LC/MS (mode) | Formula CHN (Calcd) CHN (Found) |
|---|---|---|---|
| 1.300 | 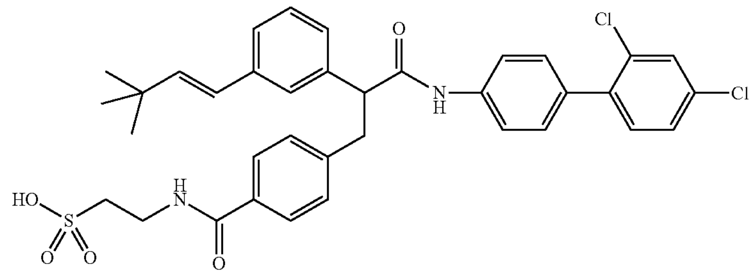 [SMILES: CC(C)(C)/C=C/c1cccc(C(Cc2ccc(C(=O)NCCS(=O)(=O)O)cc2)C(=O)Nc2ccc(-c3ccc(Cl)cc3Cl)cc2)c1] | 681 (+) | C36H35N2O5Cl2SNa + 0.7H2O<br>60.54, 5.14, 3.92<br>60.54, 4.99, 3.88 |
| 1.301 | 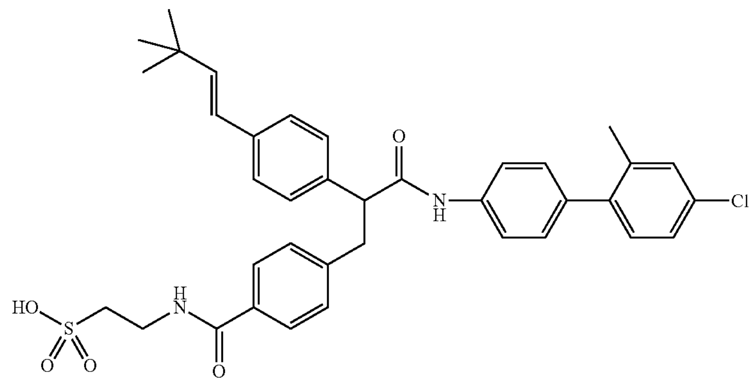 [SMILES: Cc1cc(Cl)ccc1-c1ccc(NC(=O)C(Cc2ccc(C(=O)NCCS(=O)(=O)O)cc2)c2ccc(/C=C/C(C)(C)C)cc2)cc1] | 661 (+) | C37H38N2O5ClSNa + 0.8H2O<br>63.88, 5.74, 4.03<br>63.85, 5.85, 3.76 |
| 1.302 | 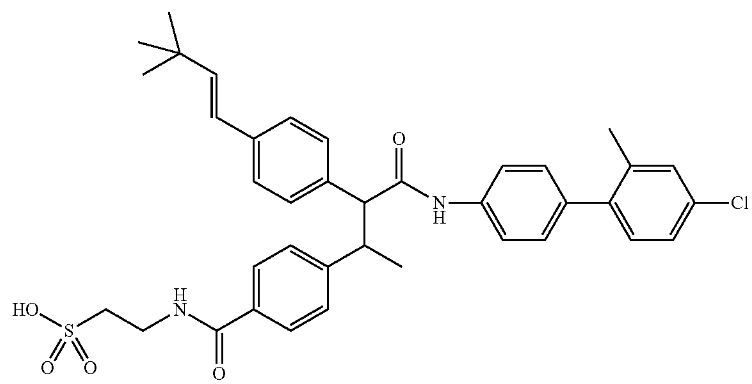 [SMILES: Cc1cc(Cl)ccc1-c1ccc(NC(=O)C(c2ccc(/C=C/C(C)(C)C)cc2)C(C)c2ccc(C(=O)NCCS(=O)(=O)O)cc2)cc1] | 675 (+) | C38H40N2O5ClSNa + 1.2H2O<br>63.67, 5.96, 3.91<br>63.71, 5.87, 3.86 |
| 1.303 | 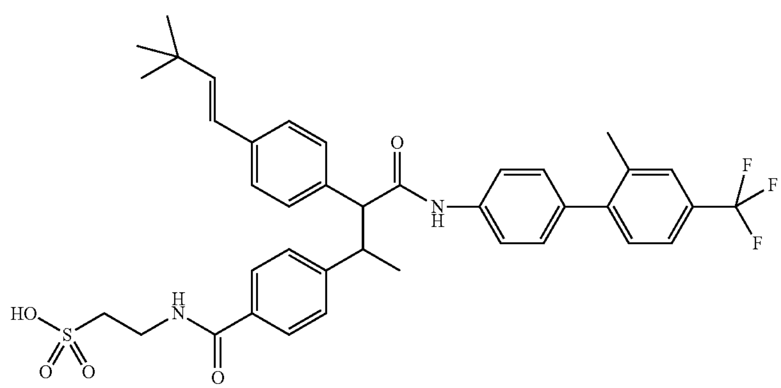 [SMILES: Cc1cc(C(F)(F)F)ccc1-c1ccc(NC(=O)C(c2ccc(/C=C/C(C)(C)C)cc2)C(C)c2ccc(C(=O)NCCS(=O)(=O)O)cc2)cc1] | 705 (M+) | C39H40N2O5F3SNa + 1.1H2O<br>62.57, 5.68, 3.74<br>62.58, 5.87, 3.69 |

-continued
| Ex# | Structure | LC/MS (mode) | Formula CHN (Calcd) CHN (Found) |
|---|---|---|---|
| 1.304 | 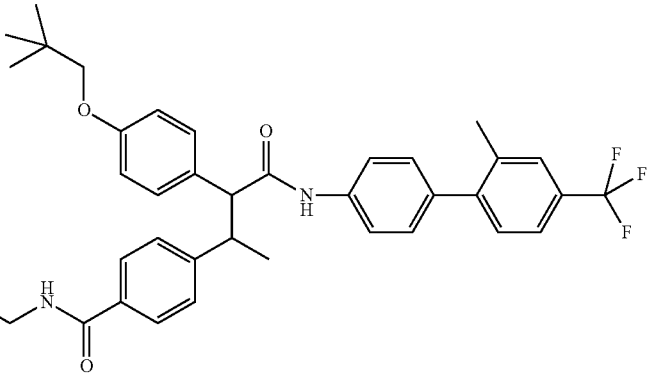 | 711 (+) | C38H40N2O6F3SNa + 1.2H2O<br>60.50, 5.66, 3.71<br>60.43, 5.65, 3.97 |
| 1.305 | 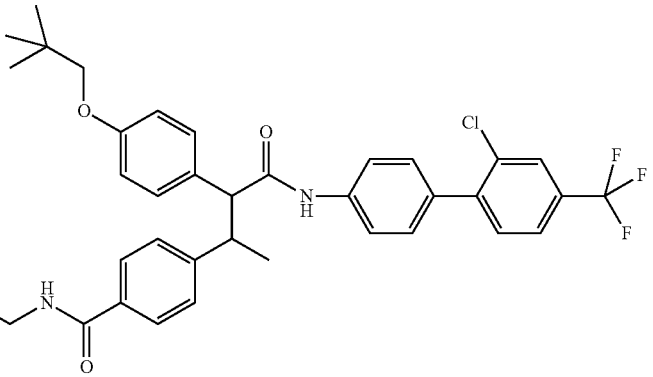 | 733 (+) | C37H37N2O6F3ClSNa + 2.3H2O<br>55.92, 5.28, 3.53<br>55.89, 4.94, 3.74 |
| 1.306 | 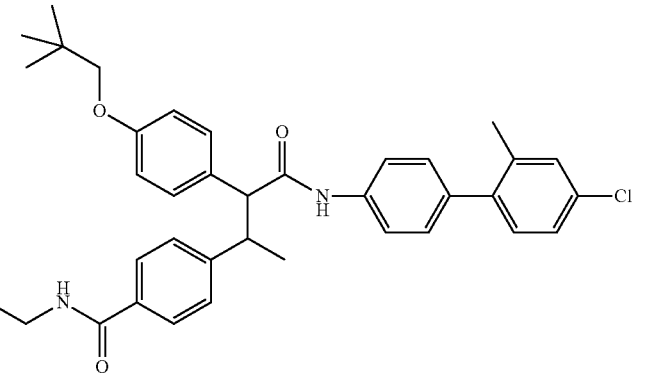 | 677 (M+) | C37H40N2O6ClSNa+ 1.3H20<br>61.50, 5.94, 3.88<br>61.47, 5.94, 3.73 |
| 1.307 | 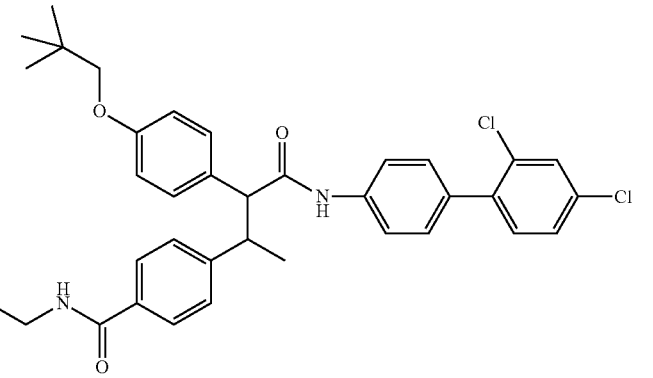 | 699 (+) | C36H37N2O6Cl2SNa + 1.5H2O<br>57.91, 5.40, 3.75<br>57.91, 5.51, 3.70 |

-continued
| Ex# | Structure | LC/MS (mode) | Formula CHN (Calcd) CHN (Found) |
|---|---|---|---|
| 1.308 | 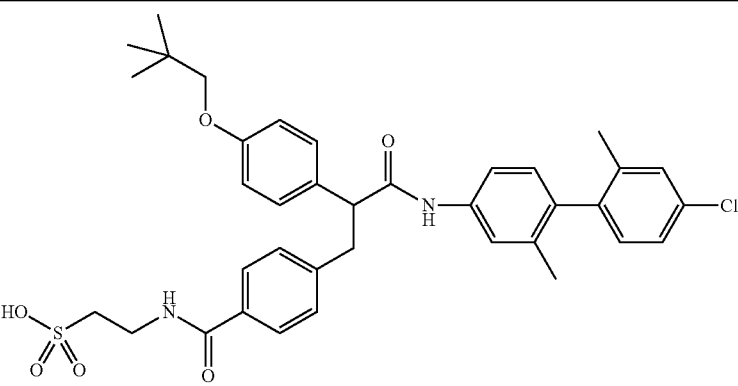 | 679 (+) | C37H40N2O6SClNa + 2.2 H2O 60.15, 6.06, 3.79 59.96, 5.65, 3.65 |
| 1.309 | 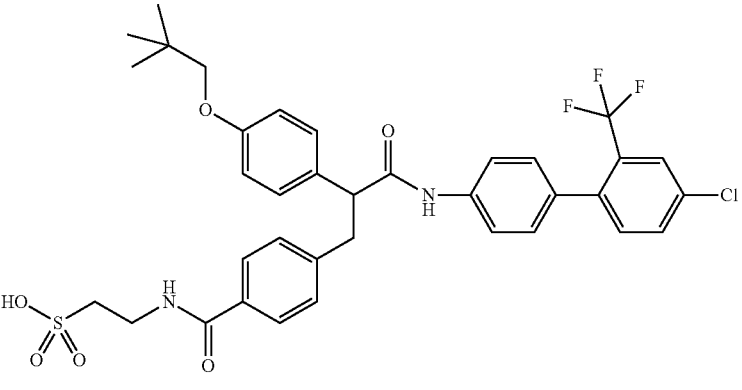 [SMILES: CC(C)(C)COc1ccc(C(Cc2ccc(C(=O)NCCS(=O)(=O)O)cc2)C(=O)Nc2ccc(-c3ccc(Cl)cc3C(F)(F)F)cc2)cc1] | 719 (+) | C36H35N2O6SF3ClNa + 2.0 H2O 55.78, 5.07, 3.61 55.71, 4.82, 3.52 |
| 1.310 | 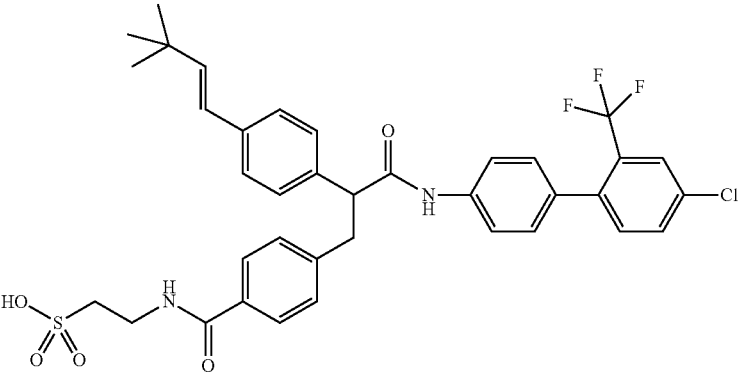 [SMILES: CC(C)(C)/C=C/c1ccc(C(Cc2ccc(C(=O)NCCS(=O)(=O)O)cc2)C(=O)Nc2ccc(-c3ccc(Cl)cc3C(F)(F)F)cc2)cc1] | 716 (+) | C37H35N2O5F3ClSNa + 0.8 H2O 59.28, 4.92, 3.74 59.33, 5.15, 3.63 |
| 1.311 | 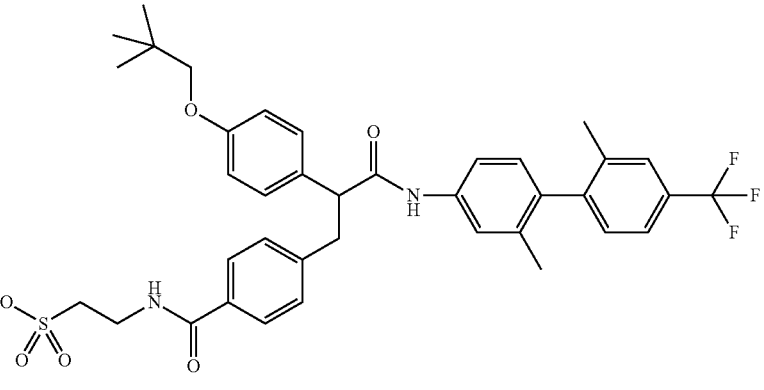 | 709 (−) | C38H40N2O6F3SNa + 0.8 H2O 61.08, 5.61, 3.75 61.09, 5.24, 3.59 |

-continued
| Ex# | Structure | LC/MS (mode) | Formula CHN (Calcd) CHN (Found) |
|---|---|---|---|
| 1.312 | 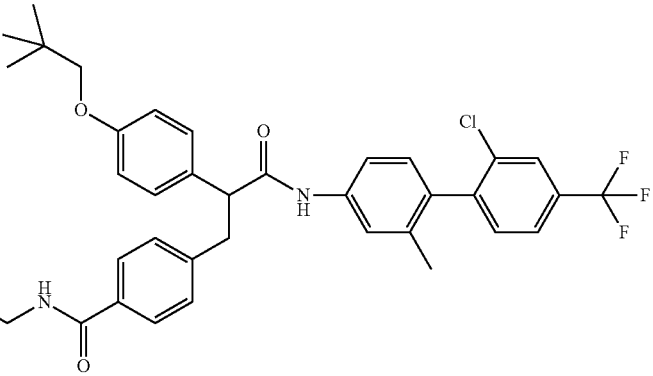 | 732 (+) | 57.62, 5.10, 3.63 57.61, 4.66, 3.42 (C37H37N2O6F3SClNa + 1.0 H2O) |
| 1.313 | 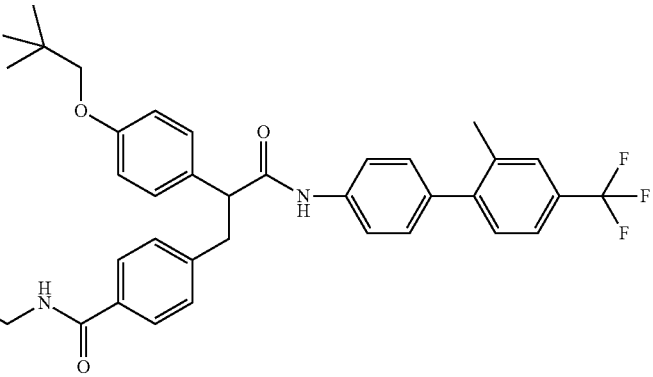 | 697 (−) | C37H38N2O6F3SClNa + 1.1 H2O 60.17, 5.49, 3.79 60.17, 5.61, 3.70 |
| 1.314 | 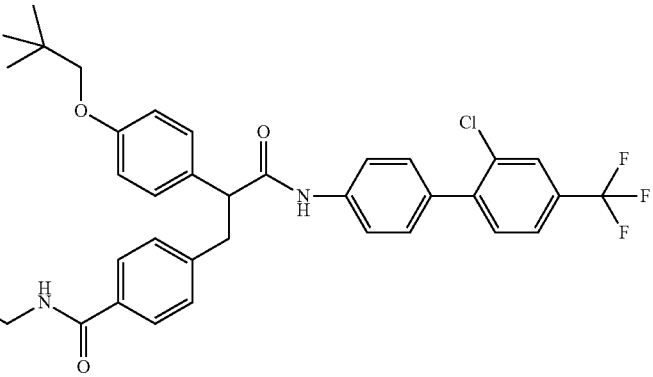 | 717 (M+) | C36H35N2O6SF3ClNa + 1.0 H2O 57.10, 4.93, 3.70 57.04, 4.56, 3.44 |
| 1.315 | 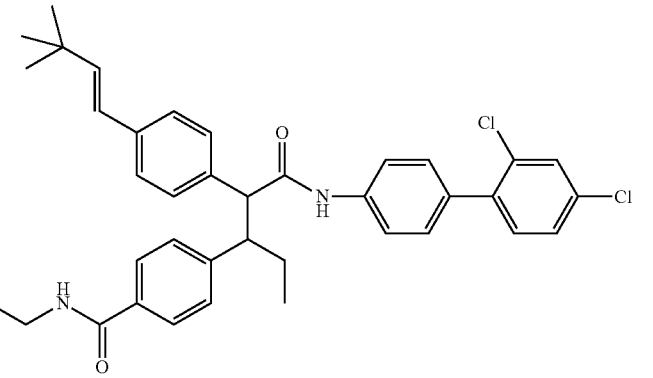 | 709 (+) | C38H39N2O5Cl2SNa + 1.3 H2O 60.60, 5.57, 3.72 60.50, 5.41, 3.67 |

-continued

| Ex# | Structure | LC/MS (mode) | Formula CHN (Calcd) CHN (Found) |
|---|---|---|---|
| 1.316 | 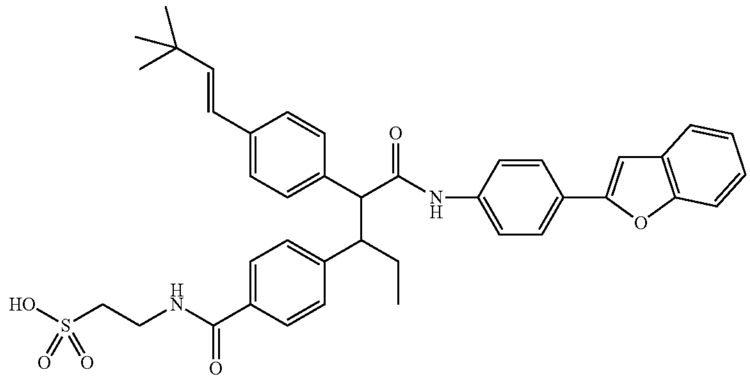 [SMILES: CCC(c1ccc(C(=O)NCCS(=O)(=O)O)cc1)C(C(=O)Nc1ccc(-c2cc3ccccc3o2)cc1)c1ccc(/C=C/C(C)(C)C)cc1] | 677 (M+) | C40H41N2O6SNa + 2.2 H2O 64.88, 6.18, 3.78 64.81, 6.06, 3.7 |
| 1.317 | 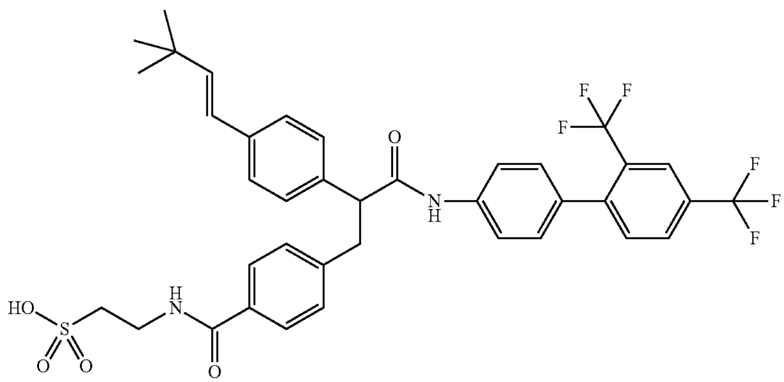 [SMILES: CC(C)(C)/C=C/c1ccc(C(Cc2ccc(C(=O)NCCS(=O)(=O)O)cc2)C(=O)Nc2ccc(-c3ccc(C(F)(F)F)cc3C(F)(F)F)cc2)cc1] | 745 (M+) | 58.28, 4.71, 3.58 58.26, 4.89, 3.69 (C38H35N2O5F6SNa + 0.8 H2O) |
| 1.318 | 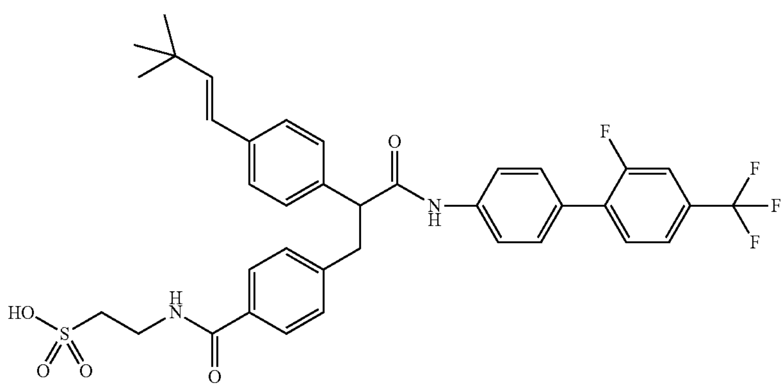 [SMILES: CC(C)(C)/C=C/c1ccc(C(Cc2ccc(C(=O)NCCS(=O)(=O)O)cc2)C(=O)Nc2ccc(-c3ccc(C(F)(F)F)cc3F)cc2)cc1] | 697 (+) | C37H35N2O5F4SNa + 0.6 H2O 60.91, 5.00, 3.87 60.92, 4.95, 3.88 |
| 1.319 | 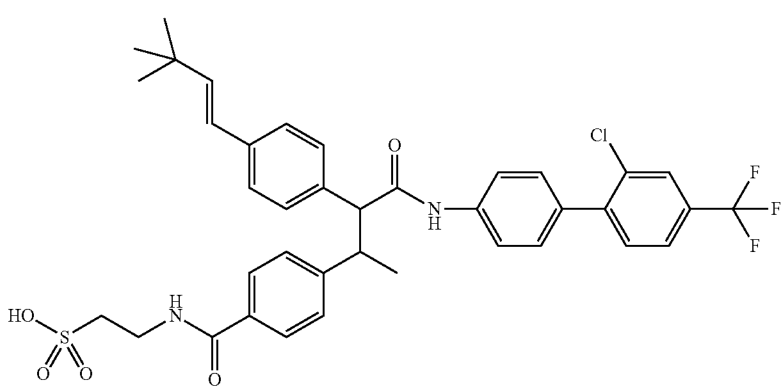 [SMILES: CC(c1ccc(C(=O)NCCS(=O)(=O)O)cc1)C(C(=O)Nc1ccc(-c2ccc(C(F)(F)F)cc2Cl)cc1)c1ccc(/C=C/C(C)(C)C)cc1] | 728 (+) | C38H37N2O5F3ClSNa + 1.1 H2O 59.35, 5.14, 3.64 59.23, 5.14, 3.75 |

-continued

| Ex# | Structure | LC/MS (mode) | Formula CHN (Calcd) CHN (Found) |
|---|---|---|---|
| 1.320 | 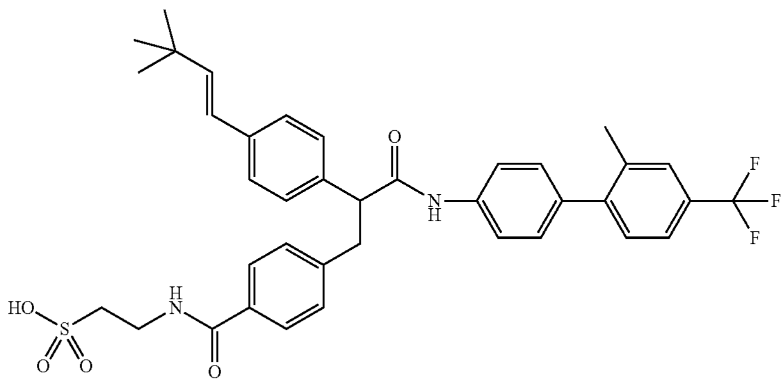 [SMILES: Cc1cc(C(F)(F)F)ccc1-c1ccc(NC(=O)C(Cc2ccc(C(=O)NCCS(=O)(=O)O)cc2)c2ccc(/C=C/C(C)(C)C)cc2)cc1] | 693 (+) | C38H38N2O5F3SNa + 0.8 H2O<br>62.59, 5.47, 3.84<br>62.64, 5.36, 3.83 |
| 1.321 | 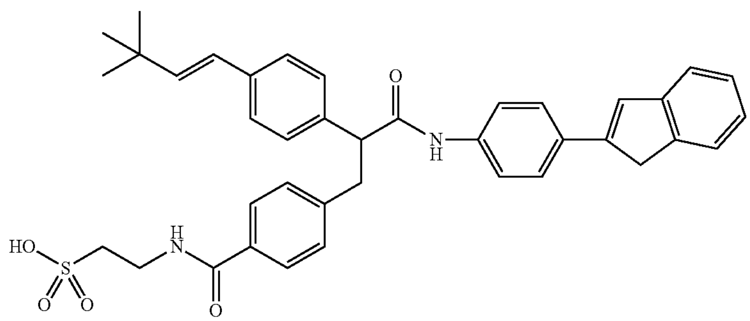 [SMILES: CC(C)(C)/C=C/c1ccc(C(Cc2ccc(C(=O)NCCS(=O)(=O)O)cc2)C(=O)Nc2ccc(C3=Cc4ccccc4C3)cc2)cc1] | 647 (−) | C39H39N2O5SNa + 1.6 H2O<br>66.95, 6.08, 4.00<br>66.95, 5.93, 3.98 |
| 1.322 | 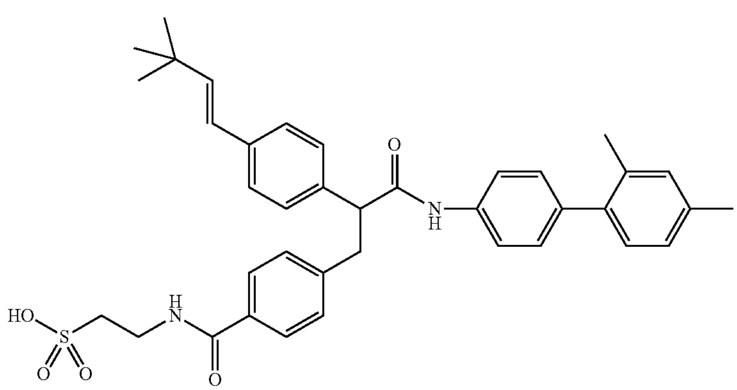 [SMILES: Cc1ccc(-c2ccc(NC(=O)C(Cc3ccc(C(=O)NCCS(=O)(=O)O)cc3)c3ccc(/C=C/C(C)(C)C)cc3)cc2)c(C)c1] | 637 (−) | C38H42N2O5S + 1.8 H2O<br>67.99, 6.85, 4.17<br>67.80, 7.12, 4.35 |
| 1.323 | 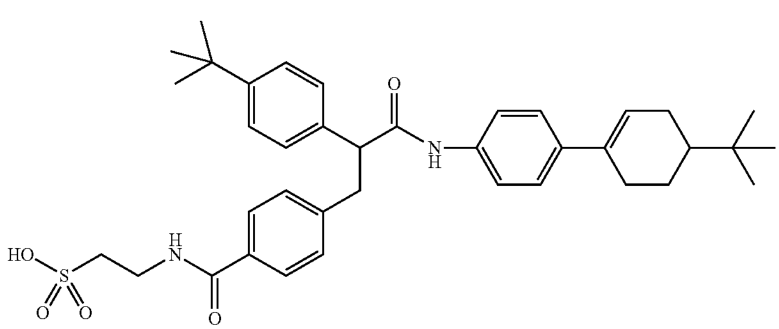 [SMILES: CC(C)(C)c1ccc(C(Cc2ccc(C(=O)NCCS(=O)(=O)O)cc2)C(=O)Nc2ccc(C3=CCC(C(C)(C)C)CC3)cc2)cc1] | 643 (M+) | C38H47N2O5SNa + 1.8 H2O<br>65.27, 7.29, 4.01<br>65.22, 7.68, 3.90 |

-continued
| Ex# | Structure | LC/MS (mode) | Formula CHN (Calcd) CHN (Found) |
|---|---|---|---|
| 1.324 | 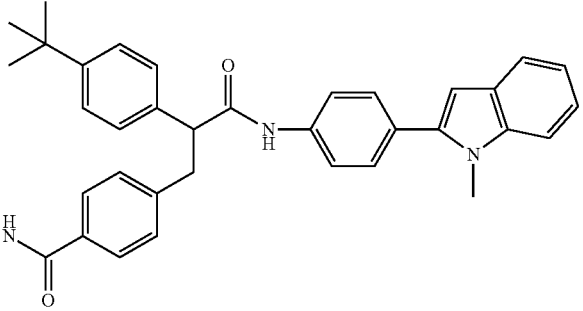 | 638 (+) | C37H38N3O5SNa + 2.6 H2O 62.89, 6.16, 5.95 62.97, 6.30, 6.30 |
| 1.325 | 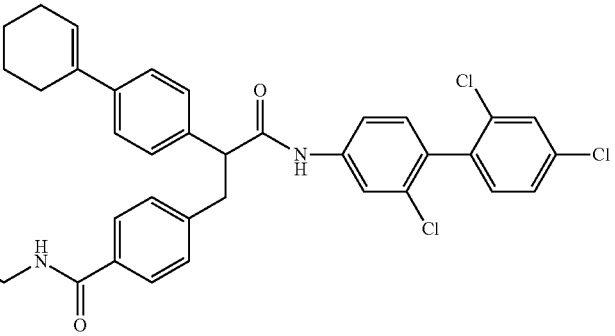 | 713 (+) | C36H32N2O5Cl3SNa + 1.0 H2O + 0.1 CH3CN 57.50, 4.57, 3.89 57.34, 4.50, 4.20 |
| 1.326 | 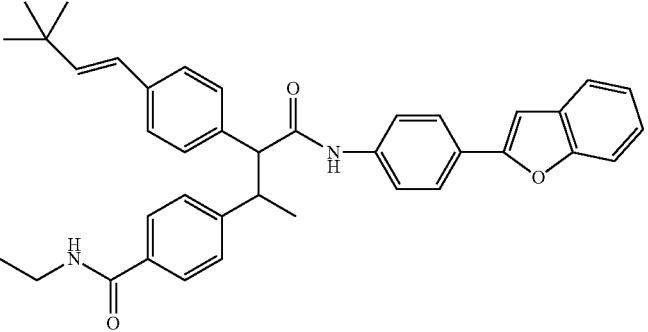 | 665 (+) | C39H39N2O6SNa + 2.0 H2O 64.80, 6.00, 3.88 64.75, 6.11, 3.71 |
| 1.327 | 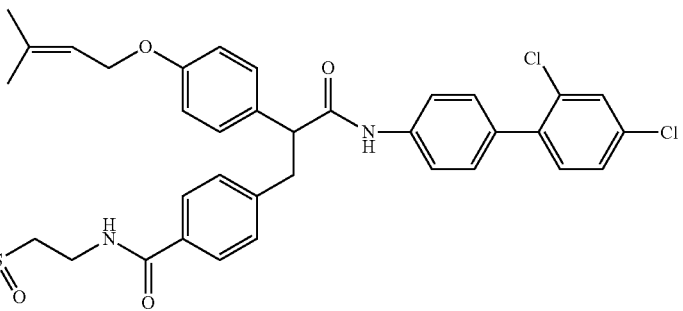 | 683 (+) | C35H33N2O6Cl2S + 1.6 H2O 57.39, 4.98, 3.82 57.35, 4.66, 3.82 |

| Ex# | Structure | LC/MS (mode) | Formula CHN (Calcd) CHN (Found) |
|---|---|---|---|
| 1.328 | 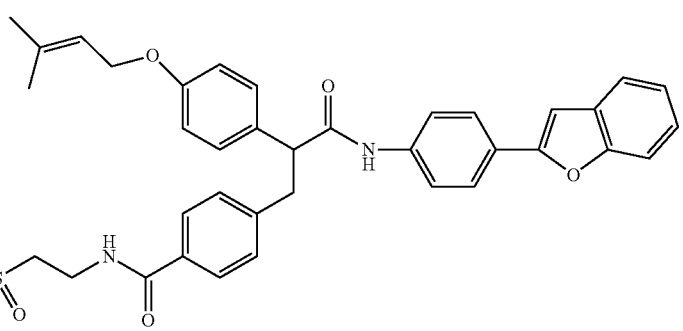 | 653 (+) | C36H35N2O7SNa + 1.1 H2O 63.98, 5.40, 4.03 63.86, 4.93, 3.71 |
| 1.329 | 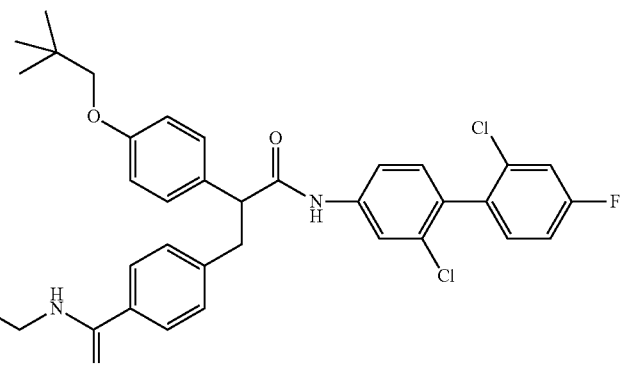 | 670 (+) | C35H35N2O6FSClNa + 3.7 H2O 55.62, 5.65, 3.71 55.44, 5.21, 3.71 |
| 1.330 | 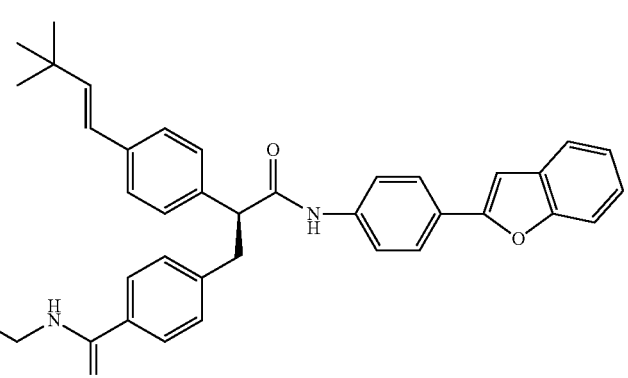 | 651 (+) | C38H37N2O6SNa + 3.7 H2O 61.73, 6.05, 3.79 61.52, 5.74, 3.74 |
| 1.331 | 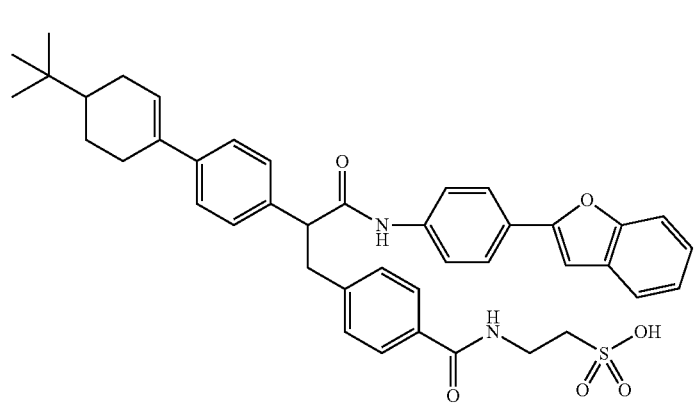 [SMILES: CC(C)(C)C1CC=C(c2ccc(C(Cc3ccc(C(=O)NCCS(=O)(=O)O)cc3)C(=O)Nc3ccc(-c4cc5ccccc5o4)cc3)cc2)CC1] | 705 (+) | C42H43N2O6SNa + 2.1 H2O 65.97, 6.22, 3.66 65.91, 6.29, 3.57 |

| Ex# | Structure | LC/MS (mode) | Formula CHN (Calcd) CHN (Found) |
|---|---|---|---|
| 1.332 | 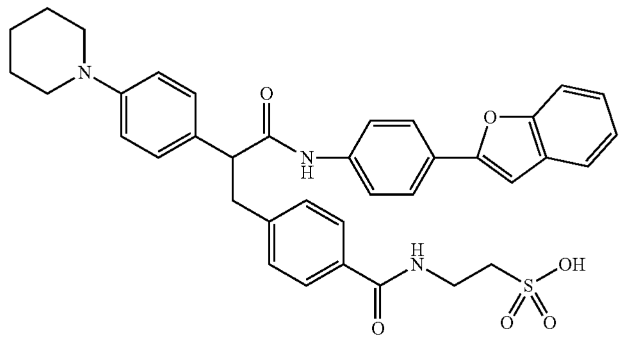 [SMILES: O=C(NCCS(=O)(=O)O)c1ccc(CC(C(=O)Nc2ccc(-c3cc4ccccc4o3)cc2)c2ccc(N3CCCCC3)cc2)cc1] | 652 (+) | C37H36N3O6SNa + 4.0 H2O 59.59, 5.95, 5.63 59.50, 5.67, 5.36 |
| 1.333 | 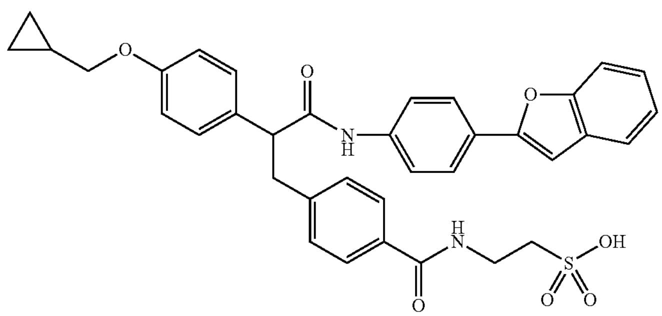 [SMILES: O=C(NCCS(=O)(=O)O)c1ccc(CC(C(=O)Nc2ccc(-c3cc4ccccc4o3)cc2)c2ccc(OCC3CC3)cc2)cc1] | 639 (+) | C36H33N2O7SNa + 1.6 H2O 62.71, 5.29, 4.06 62.72, 5.26, 3.81 |
| 1.334 | 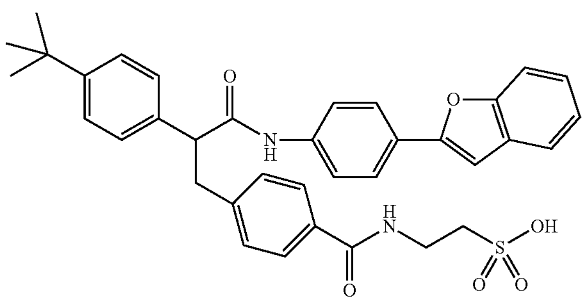 [SMILES: CC(C)(C)c1ccc(C(Cc2ccc(C(=O)NCCS(=O)(=O)O)cc2)C(=O)Nc2ccc(-c3cc4ccccc4o3)cc2)cc1] | 623 (+) | C36H33N2O6SNa + 2.9 H2O 62.04, 5.61, 4.02 61.77, 5.15, 4.15 |
| 1.335 | 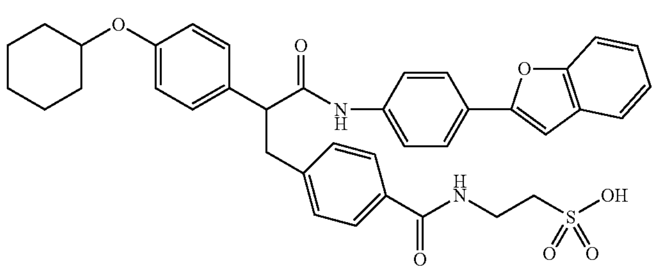 [SMILES: O=C(NCCS(=O)(=O)O)c1ccc(CC(C(=O)Nc2ccc(-c3cc4ccccc4o3)cc2)c2ccc(OC3CCCCC3)cc2)cc1] | 665 (−) | C38H38N2O7SNa + 1.2 H2O + 0.2 CH3CN 64.09, 5.74, 4.28 64.10, 5.90, 4.54 |
| 1.336 | 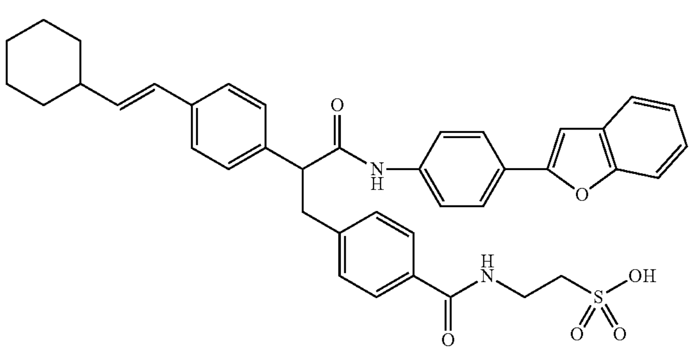 [SMILES: O=C(NCCS(=O)(=O)O)c1ccc(CC(C(=O)Nc2ccc(-c3cc4ccccc4o3)cc2)c2ccc(/C=C/C3CCCCC3)cc2)cc1] | 677 (+) | C40H39N2O6SNa + 2.0 H2O 65.38, 5.90, 3.81 65.34, 5.72, 4.01 |

-continued

| Ex# | Structure | LC/MS (mode) | Formula CHN (Calcd) CHN (Found) |
|---|---|---|---|
| 1.337 | 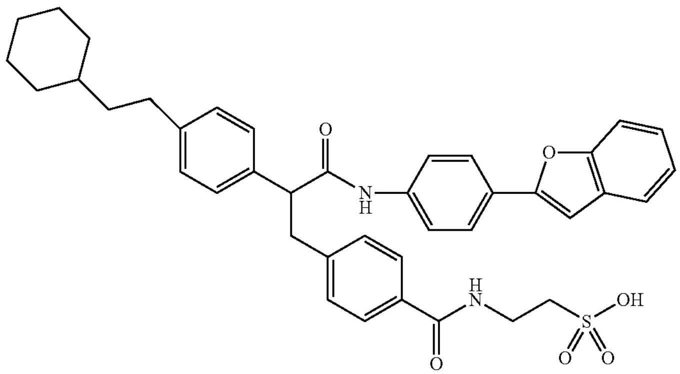 [SMILES: O=C(NCCS(=O)(=O)O)c1ccc(CC(C(=O)Nc2ccc(-c3cc4ccccc4o3)cc2)c2ccc(CCC3CCCCC3)cc2)cc1] | 679 (+) | C40H41N2O6SNa + 1.8 H2O<br>65.52, 6.13, 3.82<br>65.55, 6.20, 3.74 |
| 1.338 | 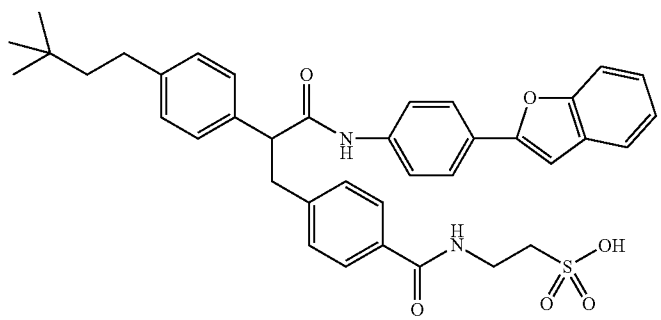 [SMILES: CC(C)(C)CCc1ccc(C(Cc2ccc(C(=O)NCCS(=O)(=O)O)cc2)C(=O)Nc2ccc(-c3cc4ccccc4o3)cc2)cc1] | 653 (+) | C38H39N2O6SNa + 1.5 H2O + 0.4 CH3CN<br>64.88, 6.06, 4.68<br>64.61, 5.63, 5.12 |
| 1.339 | 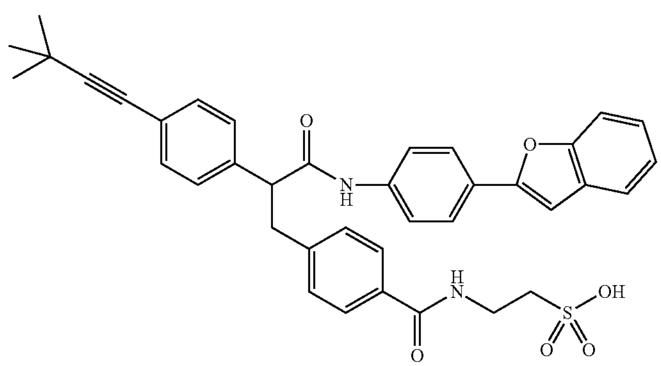 [SMILES: CC(C)(C)C#Cc1ccc(C(Cc2ccc(C(=O)NCCS(=O)(=O)O)cc2)C(=O)Nc2ccc(-c3cc4ccccc4o3)cc2)cc1] | 649 (+) | C38H35N2O6SNa + 3.2 H2O<br>62.66, 5.73, 3.85<br>62.55, 5.66, 3.86 |
| 1.340 | 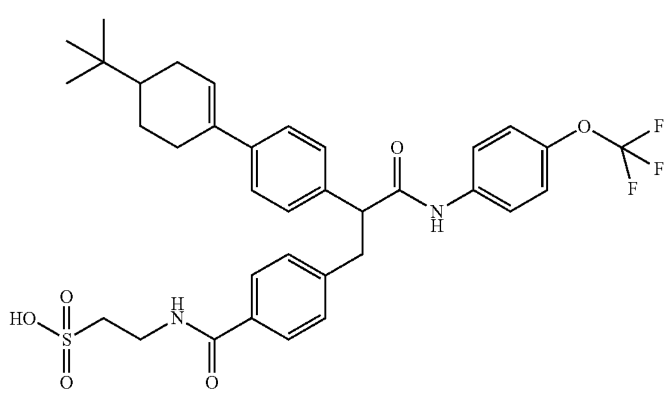 [SMILES: CC(C)(C)C1CC=C(c2ccc(C(Cc3ccc(C(=O)NCCS(=O)(=O)O)cc3)C(=O)Nc3ccc(OC(F)(F)F)cc3)cc2)CC1] | 671.4 (−) | C35H39F3N2O6S + 2.25H2O<br>58.94 6.15 3.93<br>59.02 6.25 3.74 |

-continued
| Ex# | Structure | LC/MS (mode) | Formula CHN (Calcd) CHN (Found) |
|---|---|---|---|
| 1.341 | 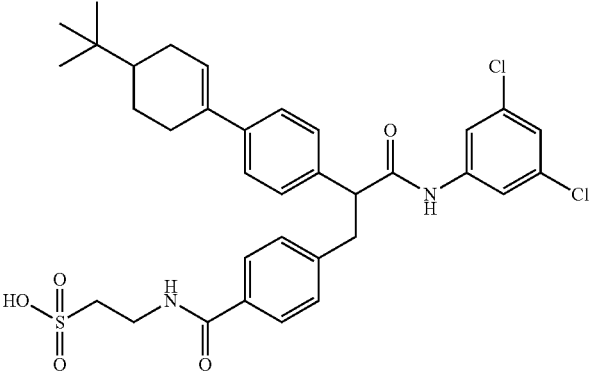 [SMILES: CC(C)(C)C1CC=C(c2ccc(C(Cc3ccc(C(=O)NCCS(=O)(=O)O)cc3)C(=O)Nc3cc(Cl)cc(Cl)c3)cc2)CC1] | 655.6 657.6 (−) | C34H38Cl2N2O5S + 3H2O + 0.1CF3CO2H 56.81 6.15 3.87 56.57 5.99 3.71 |
| 1.342 | 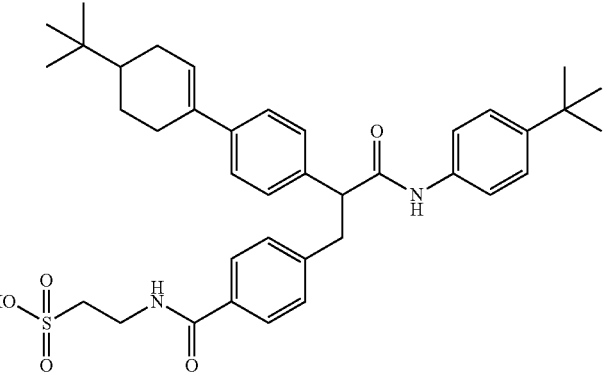 | 643.6 (−) | C38H48N2O5S + 3H2O + 0.2CF3CO2H 63.91 7.57 3.88 63.83 7.23 3.82 |
| 1.343 | 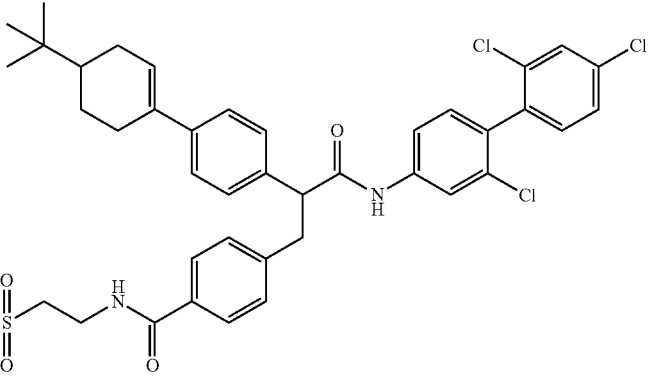 | 765.4 767.4 (−) | C40H40Cl3N2O5SN + 3H2O 56.91 5.49 3.32 56.75 5.08 3.32 |
| 1.344 | 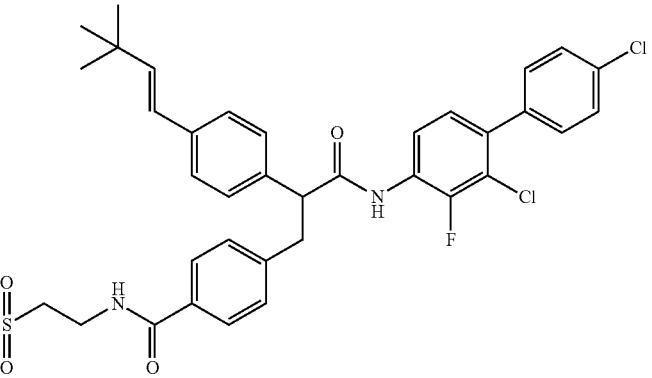 | 695.4 697.4 (−) | C36H34Cl2FN2O5SNa + 1.75H2O 57.56 5.03 3.73 57.50 4.90 3.57 |

-continued

| Ex# | Structure | LC/MS (mode) | Formula CHN (Calcd) CHN (Found) |
|---|---|---|---|
| 1.345 | 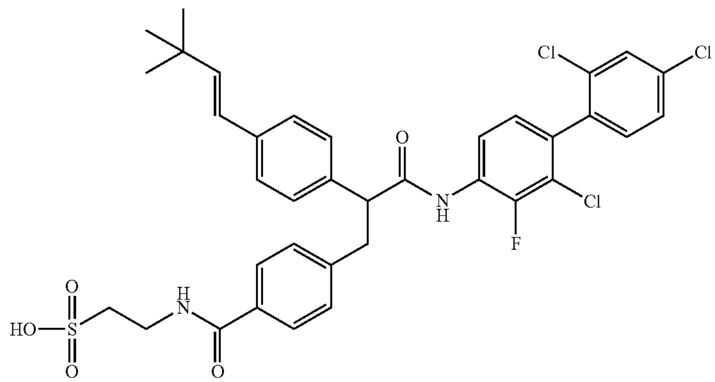 [SMILES: CC(C)(C)/C=C/c1ccc(C(Cc2ccc(C(=O)NCCS(=O)(=O)O)cc2)C(=O)Nc2ccc(-c3ccc(Cl)cc3Cl)c(Cl)c2F)cc1] | 731.6 733.6 (−) | C36H33Cl3FN2O5SNa + 2.25H2O 54.42 4.76 3.53 54.30 4.43 3.47 |
| 1.346 | 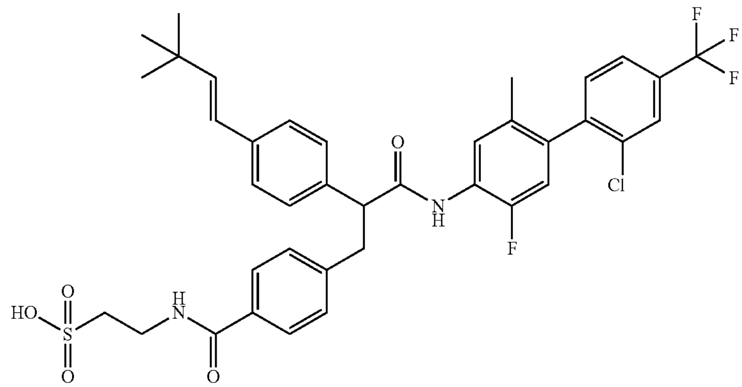 [SMILES: Cc1cc(NC(=O)C(Cc2ccc(C(=O)NCCS(=O)(=O)O)cc2)c2ccc(/C=C/C(C)(C)C)cc2)c(F)cc1-c1ccc(C(F)(F)F)cc1Cl] | 743.9 (−) | C38H37ClF4N2O5S + 3H2O + 0.2CF3CO2H 56.10 5.30 3.41 55.93 5.41 3.30 |
| 1.347 | 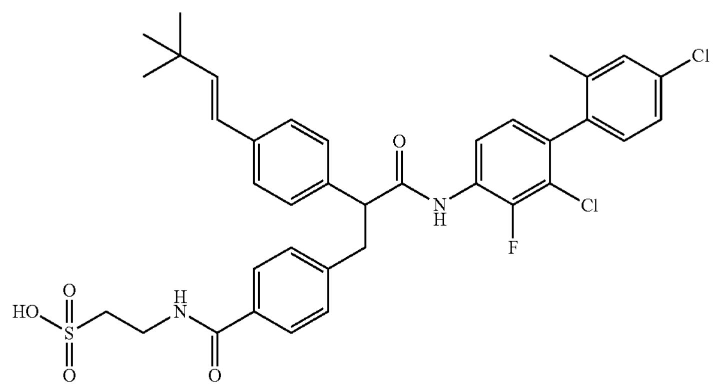 [SMILES: Cc1cc(Cl)ccc1-c1ccc(NC(=O)C(Cc2ccc(C(=O)NCCS(=O)(=O)O)cc2)c2ccc(/C=C/C(C)(C)C)cc2)c(F)c1Cl] | 709.6 711.6 (−) | C37H37Cl2FN2O5S + 2.25H2O + 0.2CF3CO2H 57.96 5.42 3.61 57.81 5.44 3.60 |
| 1.348 | 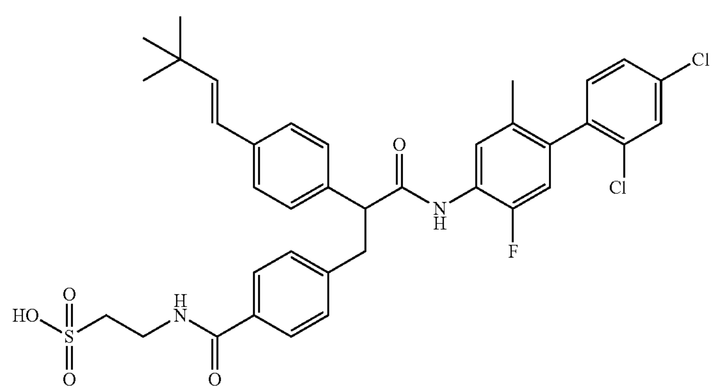 [SMILES: Cc1cc(NC(=O)C(Cc2ccc(C(=O)NCCS(=O)(=O)O)cc2)c2ccc(/C=C/C(C)(C)C)cc2)c(F)cc1-c1ccc(Cl)cc1Cl] | 709.6 711.6 (−) | C37H37Cl2FN2O5S + 2.25H2O + 0.1CF3CO2H 58.51 5.49 3.67 58.52 5.59 3.55 |

| Ex# | Structure | LC/MS (mode) | Formula CHN (Calcd) CHN (Found) |
|---|---|---|---|
| 1.349 | 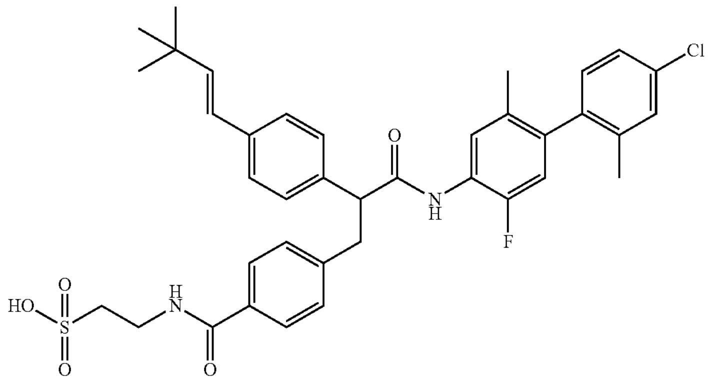 [SMILES: Cc1cc(Cl)ccc1-c1cc(F)c(NC(=O)C(Cc2ccc(C(=O)NCCS(=O)(=O)O)cc2)c2ccc(/C=C/C(C)(C)C)cc2)cc1C] | 689.9 (−) | C38H40ClFN2O5S + 3H2O<br>61.24 6.22 3.76<br>61.22 6.36 3.75 |
| 1.350 | 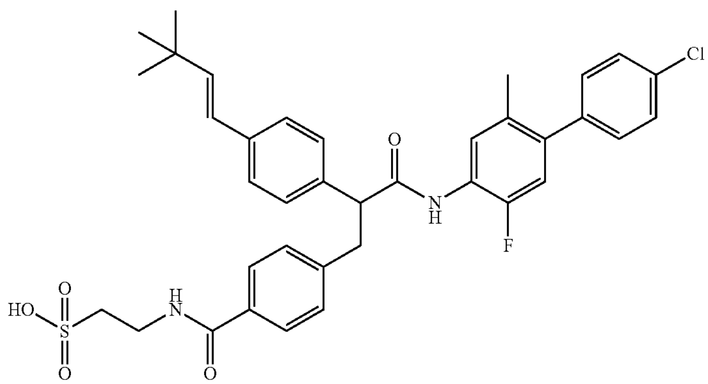 [SMILES: Cc1cc(NC(=O)C(Cc2ccc(C(=O)NCCS(=O)(=O)O)cc2)c2ccc(/C=C/C(C)(C)C)cc2)c(F)cc1-c1ccc(Cl)cc1] | 675.6 (−) | C37H38ClFN2O5S + 2.25H2O + 0.1CF3CO2H<br>61.28 5.89 3.84<br>61.09 6.13 4.15 |
| 1.351 | 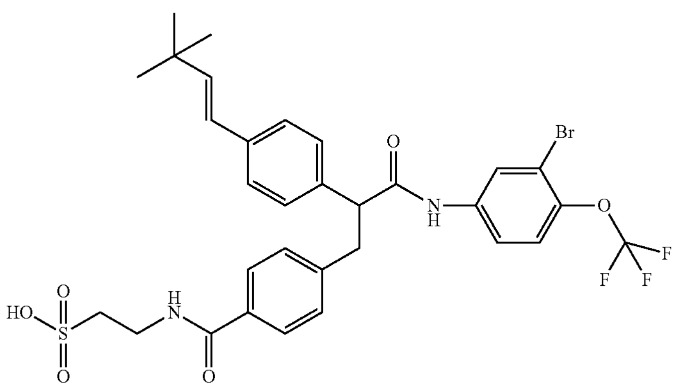 [SMILES: CC(C)(C)/C=C/c1ccc(C(Cc2ccc(C(=O)NCCS(=O)(=O)O)cc2)C(=O)Nc2ccc(OC(F)(F)F)c(Br)c2)cc1] | 695.1 697.4 (−) | C31H32BrF3N2O6S + 3H2O<br>49.54 5.10 3.73<br>49.49 4.72 3.71 |
| 1.352 | 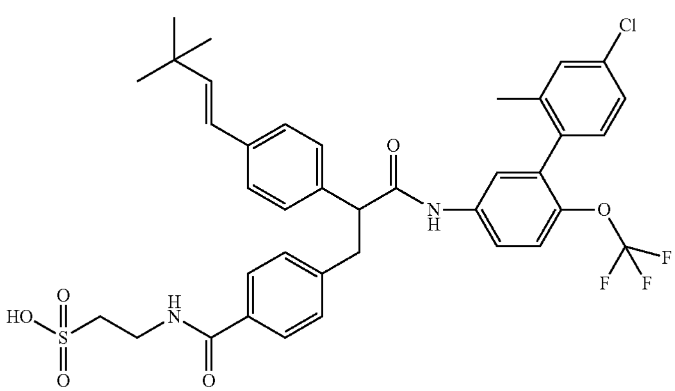 [SMILES: Cc1cc(Cl)ccc1-c1cc(NC(=O)C(Cc2ccc(C(=O)NCCS(=O)(=O)O)cc2)c2ccc(/C=C/C(C)(C)C)cc2)ccc1OC(F)(F)F] | 741.6 (−) | C38H38ClF3N2O6S + 2.5H2O + 0.2CF3CO2H<br>56.86 5.37 3.45<br>56.91 5.50 3.82 |

-continued

| Ex# | Structure | LC/MS (mode) | Formula CHN (Calcd) CHN (Found) |
|---|---|---|---|
| 1.353 | 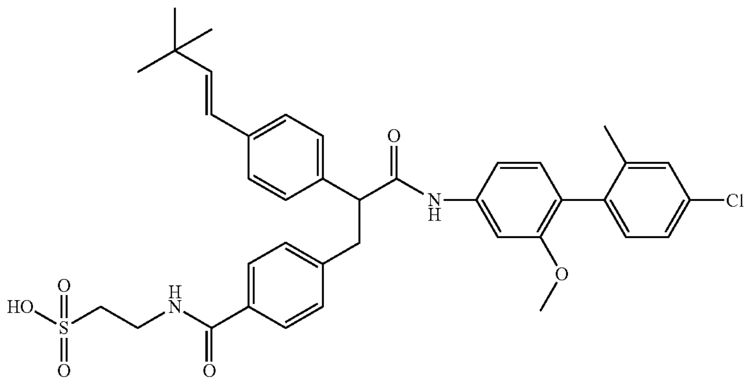 [SMILES: COc1cc(NC(=O)C(Cc2ccc(C(=O)NCCS(=O)(=O)O)cc2)c2ccc(/C=C/C(C)(C)C)cc2)ccc1-c1ccc(Cl)cc1C] | 687.6 (−) | C38H41ClN2O6S + 3H2O + 0.3CF3CO2H<br>59.63 6.13 3.60<br>59.85 6.00 3.59 |
| 1.354 | 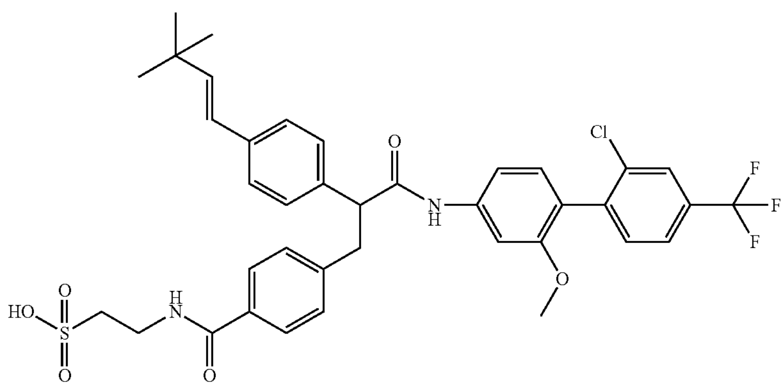 [SMILES: COc1cc(NC(=O)C(Cc2ccc(C(=O)NCCS(=O)(=O)O)cc2)c2ccc(/C=C/C(C)(C)C)cc2)ccc1-c1ccc(C(F)(F)F)cc1Cl] | 741.6 (−) | C38H38ClF3N2O6S + 3H2O + 0.1CF3CO2H<br>56.74 5.50 3.46<br>56.67 5.74 3.18 |
| 1.355 | 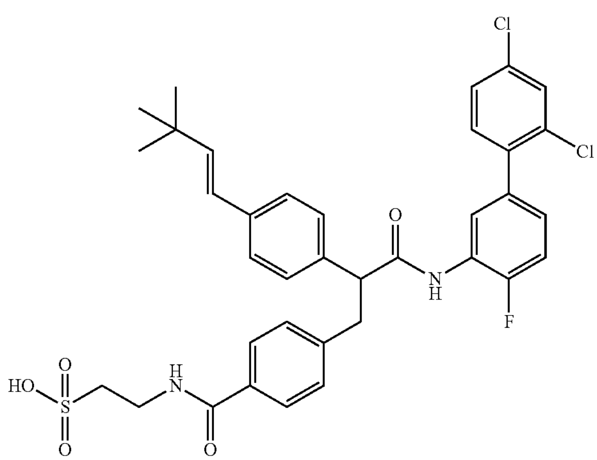 [SMILES: CC(C)(C)/C=C/c1ccc(C(Cc2ccc(C(=O)NCCS(=O)(=O)O)cc2)C(=O)Nc2cc(-c3ccc(Cl)cc3Cl)ccc2F)cc1] | 695.4 697.6 (−) | C36H35Cl2FN2O5S + 2.75H2O + 0.5CF3CO2H<br>55.26 5.14 3.48<br>55.24 4.23 3.38 |

-continued
| Ex# | Structure | LC/MS (mode) | Formula CHN (Calcd) CHN (Found) |
|---|---|---|---|
| 1.356 | 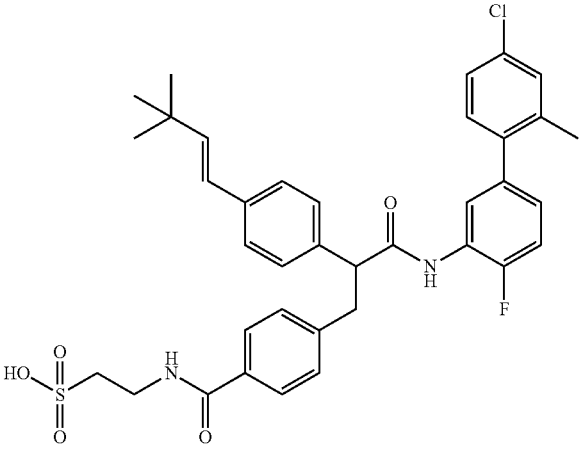 [SMILES: Cc1cc(Cl)ccc1-c1ccc(F)c(NC(=O)C(Cc2ccc(C(=O)NCCS(=O)(=O)O)cc2)c2ccc(/C=C/C(C)(C)C)cc2)c1] | 675.6 (−) | C37H38ClFN2O5S + 2.75H2O + 0.2CF3CO2H<br>59.93 5.88 3.74<br>60.11 5.96 3.49 |
| 1.357 | 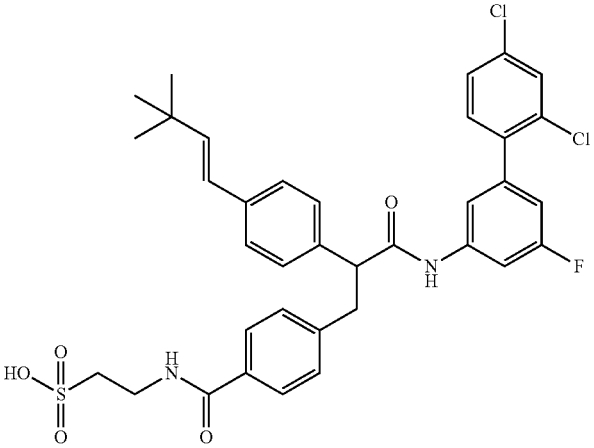 [SMILES: CC(C)(C)/C=C/c1ccc(C(Cc2ccc(C(=O)NCCS(=O)(=O)O)cc2)C(=O)Nc2cc(F)cc(-c3ccc(Cl)cc3Cl)c2)cc1] | 695.6<br>697.4<br>(−) | C36H35Cl2FN2O5S + 2.75 H2O + 0.1 CF3CO2H<br>57.32 5.39 3.69<br>57.33 5.53 3.57 |
| 1.358 | 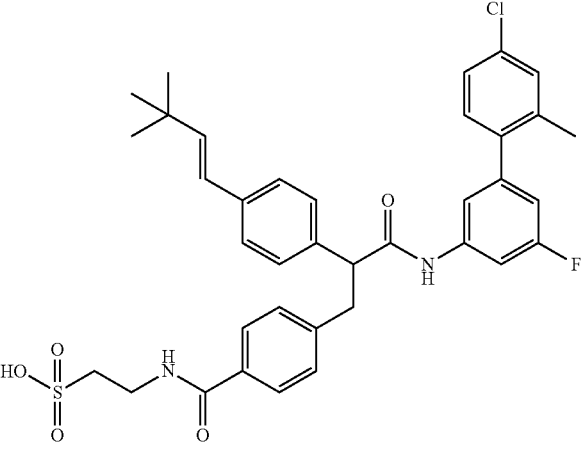 [SMILES: Cc1cc(Cl)ccc1-c1cc(F)cc(NC(=O)C(Cc2ccc(C(=O)NCCS(=O)(=O)O)cc2)c2ccc(/C=C/C(C)(C)C)cc2)c1] | 675.6 (−) | C37H38ClFN2O5S + 2.75H2O + 0.2CF3CO2H<br>59.93 5.88 3.74<br>60.01 5.82 3.75 |

-continued

| Ex# | Structure | LC/MS (mode) | Formula CHN (Calcd) CHN (Found) |
|---|---|---|---|
| 1.359 | 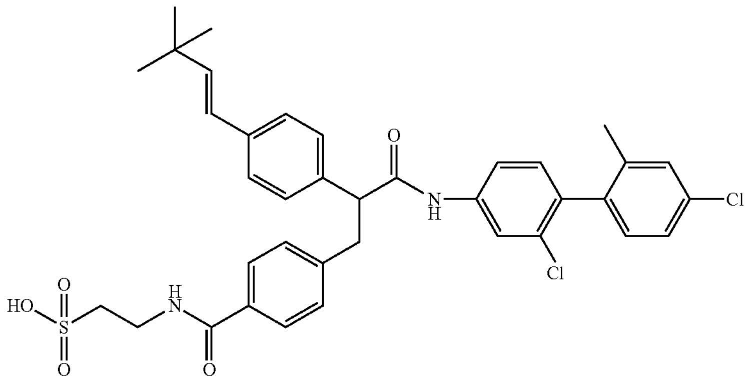 [SMILES: Cc1cc(Cl)ccc1-c1ccc(NC(=O)C(Cc2ccc(C(=O)NCCS(=O)(=O)O)cc2)c2ccc(/C=C/C(C)(C)C)cc2)cc1Cl] | 691.6 693.4 (−) | C37H38Cl2N2O5S + 3H2O + 0.2CF3CO2H 58.30 5.78 3.64 58.37 5.71 3.66 |
| 1.360 | 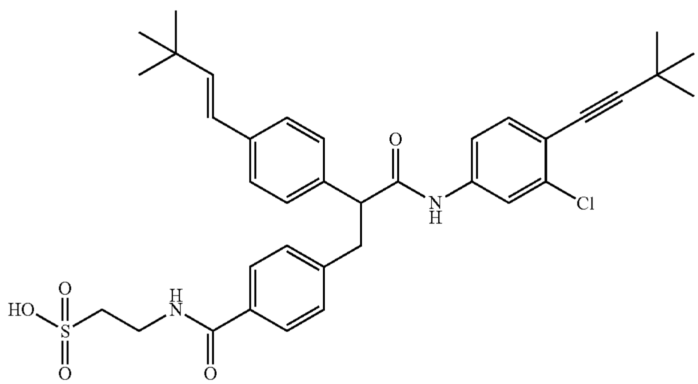 [SMILES: CC(C)(C)C#Cc1ccc(NC(=O)C(Cc2ccc(C(=O)NCCS(=O)(=O)O)cc2)c2ccc(/C=C/C(C)(C)C)cc2)cc1Cl] | 647.6 (−) | C36H39ClN2O5S + 3H2O 61.48 6.74 3.98 61.66 6.89 4.08 |
| 1.361 | 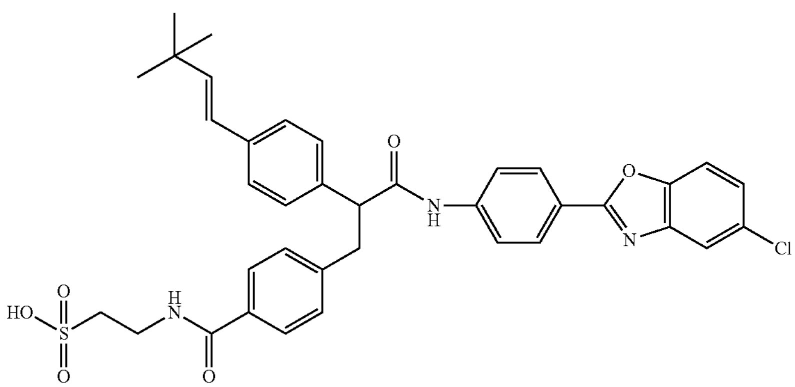 [SMILES: CC(C)(C)/C=C/c1ccc(C(Cc2ccc(C(=O)NCCS(=O)(=O)O)cc2)C(=O)Nc2ccc(-c3nc4cc(Cl)ccc4o3)cc2)cc1] | 684.6 (−) | C37H36ClN3O6S + 2.75H2O + 0.2CF3CO2H 59.22 5.54 5.54 59.13 5.10 5.54 |
| 1.362 | 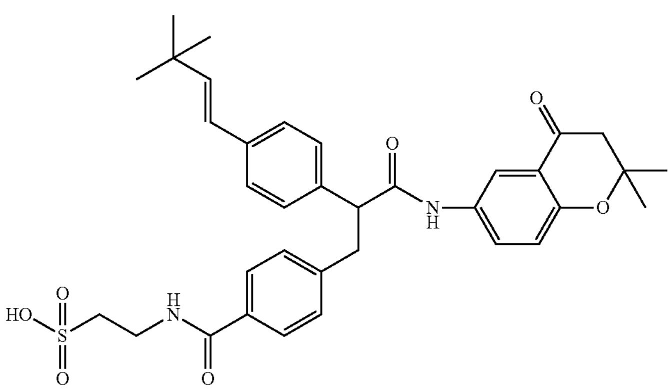 [SMILES: CC(C)(C)/C=C/c1ccc(C(Cc2ccc(C(=O)NCCS(=O)(=O)O)cc2)C(=O)Nc2ccc3c(c2)C(=O)CC(C)(C)O3)cc1] | 631.6 (−) | C35H40N2O7S + 3.25 H2O 60.81 6.78 4.05 60.65 6.77 4.16 |

| Ex# | Structure | LC/MS (mode) | Formula CHN (Calcd) CHN (Found) |
|---|---|---|---|
| 1.363 | 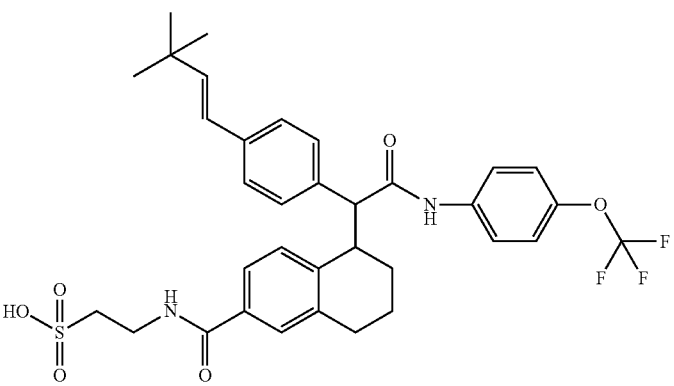 [SMILES: CC(C)(C)/C=C/c1ccc(C(C(=O)Nc2ccc(OC(F)(F)F)cc2)C2CCCc3cc(C(=O)NCCS(=O)(=O)O)ccc32)cc1] | 657.6 (−) | C34H37F3N2O6S + 3.5H2O<br>56.58 6.14 3.88<br>56.40 6.16 3.59 |
| 1.364 | 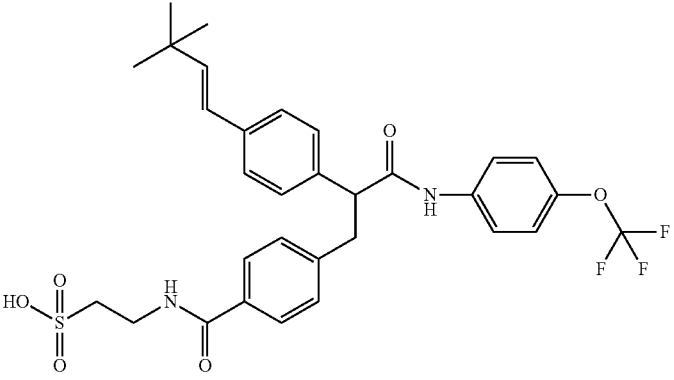 [SMILES: CC(C)(C)/C=C/c1ccc(C(Cc2ccc(C(=O)NCCS(=O)(=O)O)cc2)C(=O)Nc2ccc(OC(F)(F)F)cc2)cc1] | 617.4 (−) | C31H33F3N2O6S + 3H2O + 0.1CF3CO2H<br>54.78 5.76 4.09<br>54.52 5.41 4.32 |
| 1.365 | 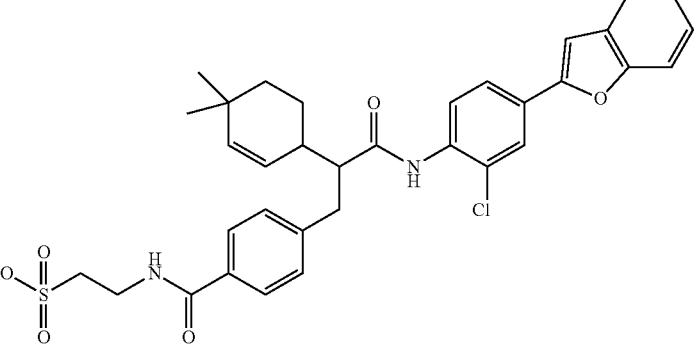 | 633.6 (−) | C34H35ClN2O6S + 3H2O + 0.3CF3CO2H<br>57.45 5.75 3.87<br>57.44 5.49 3.80 |
| 1.366 | 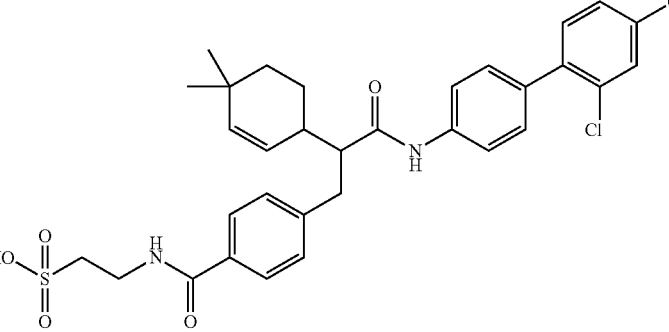 | 627.4 629.4 (−) | C32H34Cl2N2O5S + 2.25H2O<br>57.35 5.79 4.18<br>57.58 5.88 4.10 |

-continued
| Ex# | Structure | LC/MS (mode) | Formula CHN (Calcd) CHN (Found) |
|---|---|---|---|
| 1.367 | 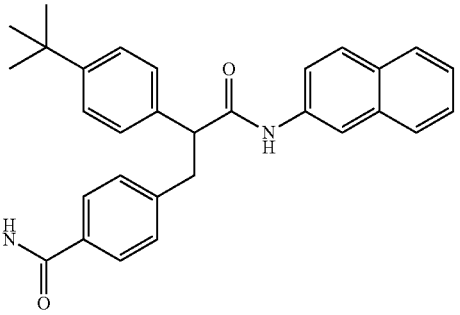 | 557.6 (−) | C32H34N2O5S + 3.5H2O<br>62.27 6.61 4.54<br>62.23 6.71 4.84 |
| 1.368 | 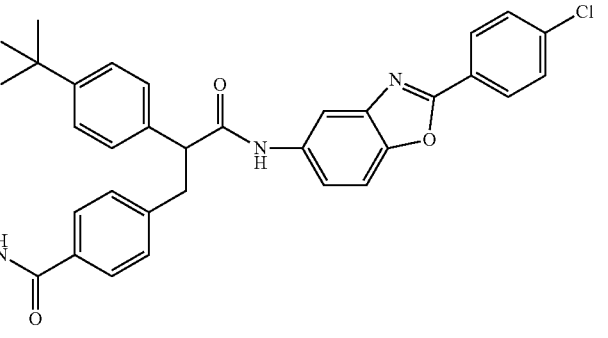 | 658.6, 660.6 (−) | C35H34ClN3O6S + 3.5H2O<br>58.12 5.71 5.81<br>58.37 6.37 5.73 |
| 1.369 | 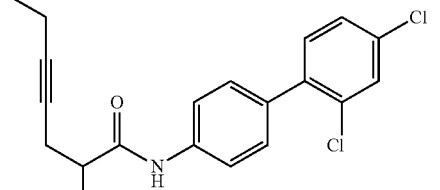1p;1p | 585.4, 587.1 (−) | C29H28Cl2N2O5S + 1.75H2O<br>56.27 5.13 4.53<br>56.52 5.54 4.61 |
| 1.370 | 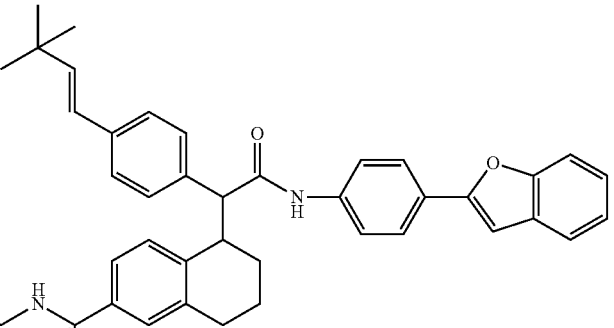 | 689.9 (−) | C42H42N2O6S + 3H2O + 0.4CF3CO2H<br>63.51 6.17 3.54<br>63.17 6.25 3.67 |

-continued

| Ex# | Structure | LC/MS (mode) | Formula CHN (Calcd) CHN (Found) |
|---|---|---|---|
| 1.371 | 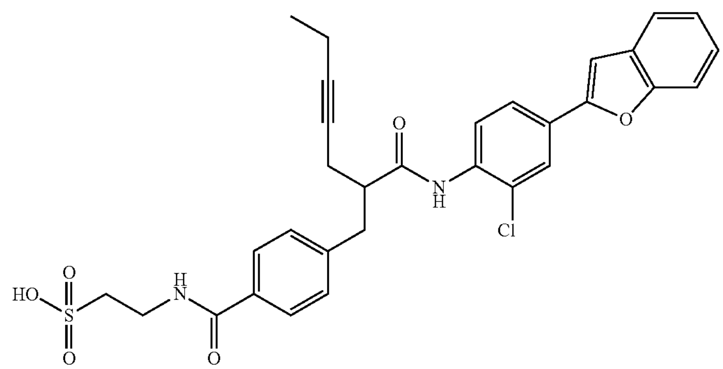 [SMILES: CCC#CCC(Cc1ccc(C(=O)NCCS(=O)(=O)O)cc1)C(=O)Nc1ccc(-c2cc3ccccc3o2)cc1Cl] | 687.9 689.9 (−) | C31H29ClN2O6S + 1.5H2O 60.04 5.20 4.52 59.71 5.47 5.10 |
| 1.372 | 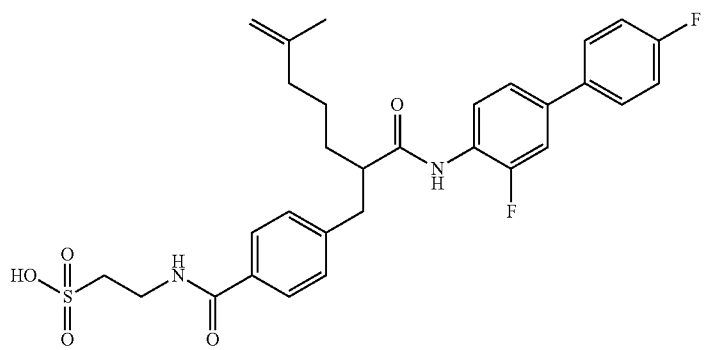 [SMILES: C=C(C)CCCC(Cc1ccc(C(=O)NCCS(=O)(=O)O)cc1)C(=O)Nc1ccc(-c2ccc(F)cc2)cc1F] | 569.6 (−) | C30H31F2N2O5SNa + 1.75H2O 57.73 5.57 4.49 57.93 5.50 4.87 |
| 1.373 | 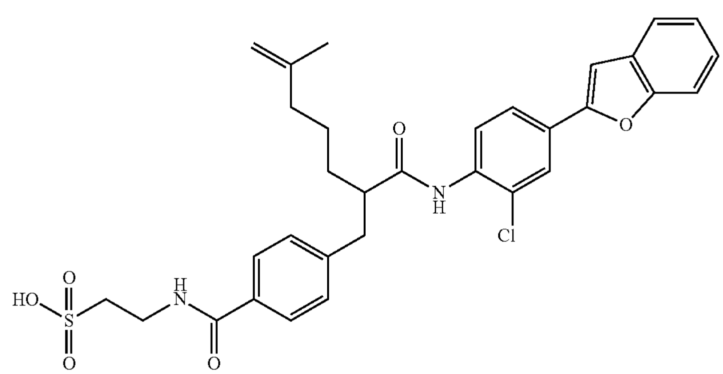 [SMILES: C=C(C)CCCC(Cc1ccc(C(=O)NCCS(=O)(=O)O)cc1)C(=O)Nc1ccc(-c2cc3ccccc3o2)cc1Cl] | 607.6 (−) | C32H32ClN2O6Na + 2.25 H2O 57.22 5.48 4.17 57.29 5.59 4.44 |
| 1.374 | 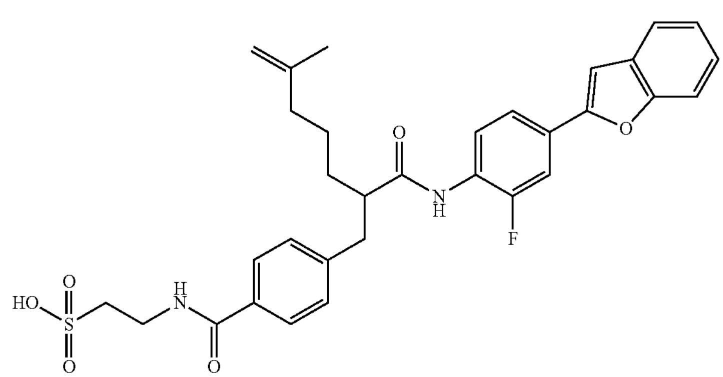 [SMILES: C=C(C)CCCC(Cc1ccc(C(=O)NCCS(=O)(=O)O)cc1)C(=O)Nc1ccc(-c2cc3ccccc3o2)cc1F] | 591.4 (−) | C32H32FN2O6SNa + 1.7H2O 59.96 5.53 4.34 59.75 6.10 5.70 |

-continued

| Ex# | Structure | LC/MS (mode) | Formula CHN (Calcd) CHN (Found) |
|---|---|---|---|
| 1.375 | 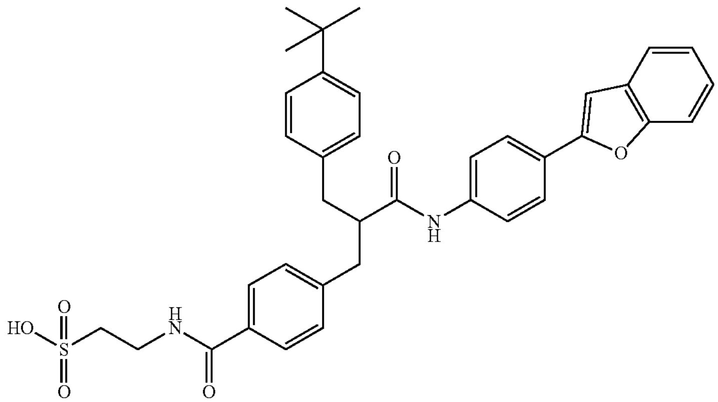 [SMILES: CC(C)(C)c1ccc(CC(Cc2ccc(C(=O)NCCS(=O)(=O)O)cc2)C(=O)Nc2ccc(-c3cc4ccccc4o3)cc2)cc1] | 637.6 (−) | C37H37N2O6SNa + 4.5H2O<br>59.91 6.25 3.78<br>59.92 6.02 3.60 |
| 1.376 | 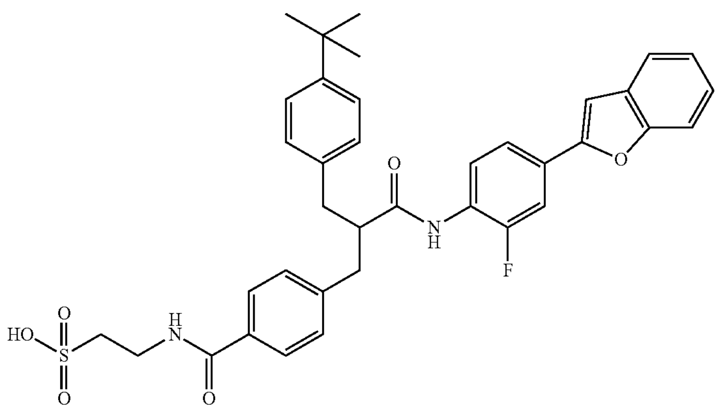 [SMILES: CC(C)(C)c1ccc(CC(Cc2ccc(C(=O)NCCS(=O)(=O)O)cc2)C(=O)Nc2ccc(-c3cc4ccccc4o3)cc2F)cc1] | 655.6 (−) | C37H37FN2O6S + 1H2O<br>65.86 5.83 4.15<br>65.98 5.98 3.09 |
| 1.377 | 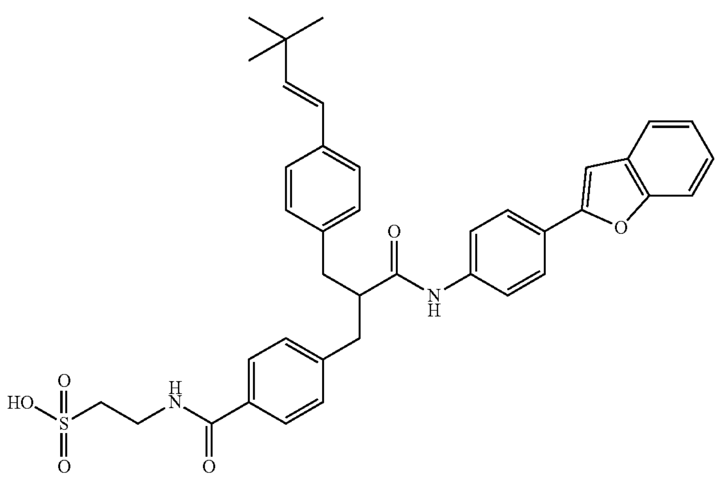 [SMILES: CC(C)(C)/C=C/c1ccc(CC(Cc2ccc(C(=O)NCCS(=O)(=O)O)cc2)C(=O)Nc2ccc(-c3cc4ccccc4o3)cc2)cc1] | 663.9 (−) | C39H40N2O6S + 2.5H2O<br>65.99 6.39 3.95<br>65.69 6.40 3.76 |

-continued
| Ex# | Structure | LC/MS (mode) | Formula CHN (Calcd) CHN (Found) |
|---|---|---|---|
| 1.378 | 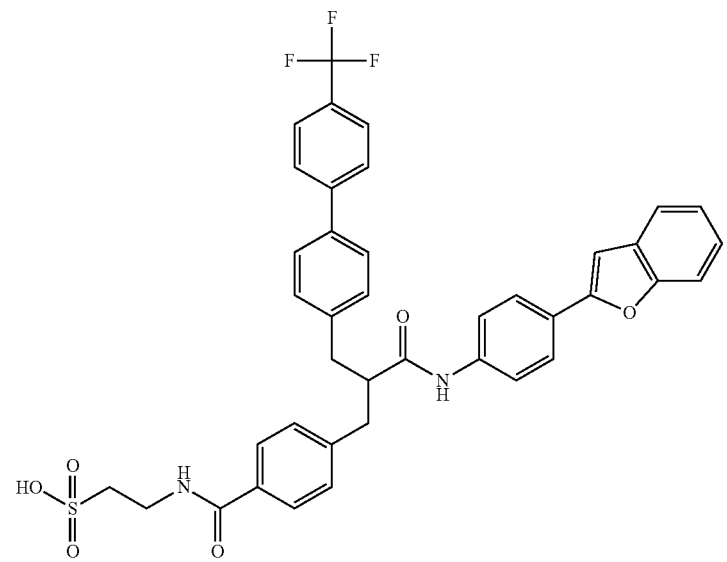 [SMILES: O=C(NCCS(=O)(=O)O)c1ccc(CC(Cc2ccc(-c3ccc(C(F)(F)F)cc3)cc2)C(=O)Nc2ccc(-c3cc4ccccc4o3)cc2)cc1] | 725.4 (−) | C40H33F3N2O6S + 2.5H2O<br>62.25 4.9 3.63<br>62.37 4.89 3.40 |
| 1.379 | 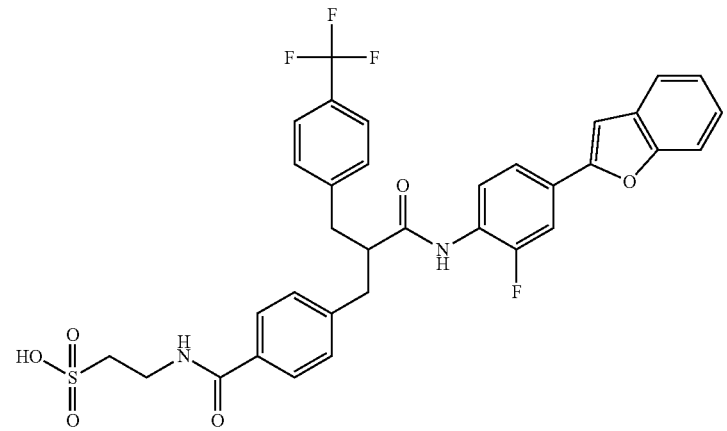 [SMILES: O=C(NCCS(=O)(=O)O)c1ccc(CC(Cc2ccc(C(F)(F)F)cc2)C(=O)Nc2ccc(-c3cc4ccccc4o3)cc2F)cc1] | 667.4 (−) | C34H28F4N2O6S + 3H2O + 0.3CF3CO2H<br>54.90 4.57 3.70<br>54.81 4.49 3.65 |
| 1.380 | 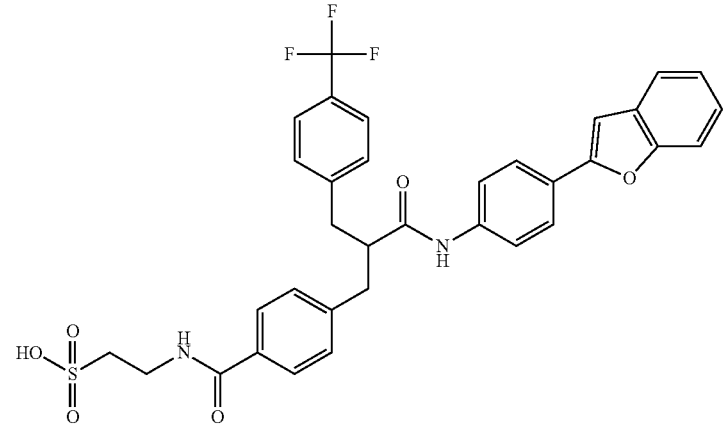 [SMILES: O=C(NCCS(=O)(=O)O)c1ccc(CC(Cc2ccc(C(F)(F)F)cc2)C(=O)Nc2ccc(-c3cc4ccccc4o3)cc2)cc1] | 649.6 (−) | C34H29F3N2O6S + 0.5 H2O + 0.4 CF3CO2H<br>59.26 4.34 3.97<br>58.84 4.04 4.46 |

-continued

| Ex# | Structure | LC/MS (mode) | Formula CHN (Calcd) CHN (Found) |
|---|---|---|---|
| 1.381 | 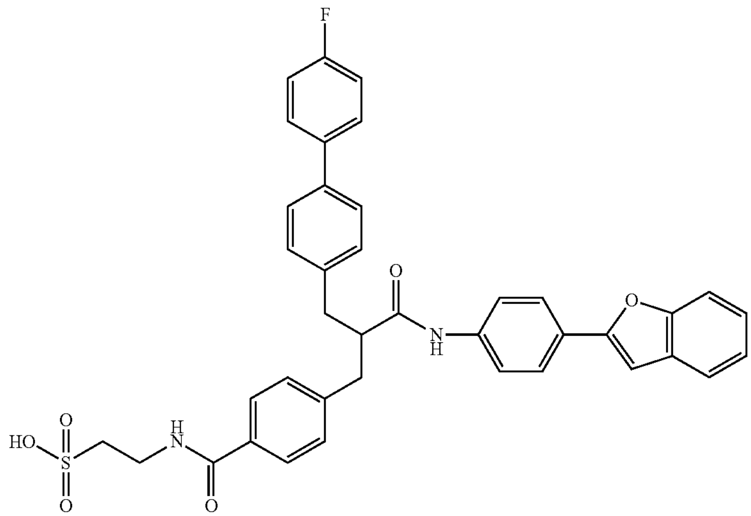 [SMILES: O=C(NCCS(=O)(=O)O)c1ccc(CC(Cc2ccc(-c3ccc(F)cc3)cc2)C(=O)Nc2ccc(-c3cc4ccccc4o3)cc2)cc1] | 675.6 (−) | C39H33FN2O6S + 3H2O<br>64.10 5.38 3.83<br>63.91 5.13 3.80 |
| 1.382 | 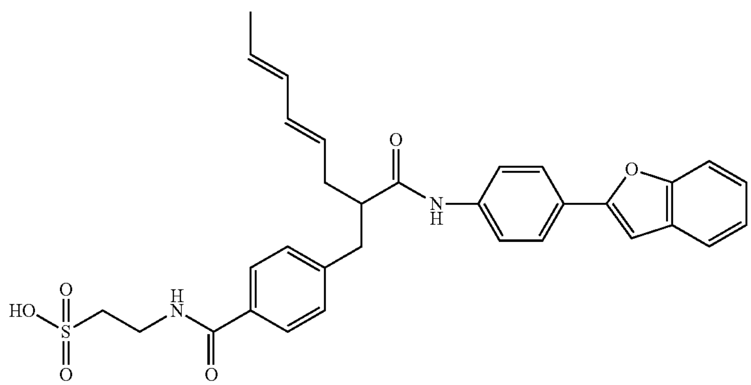 [SMILES: C/C=C/C=C/CC(Cc1ccc(C(=O)NCCS(=O)(=O)O)cc1)C(=O)Nc1ccc(-c2cc3ccccc3o2)cc1] | 571.5 (−) | C32H32N2O6S + 2H2O + 0.3CF3CO2H<br>60.90 5.69 4.36<br>60.57 5.57 4.59 |
| 1.383 | 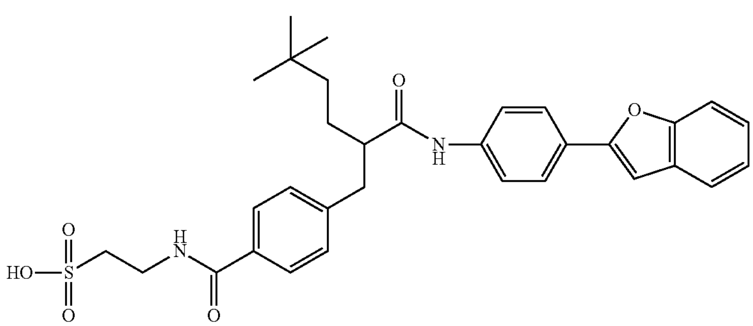 [SMILES: CC(C)(C)CCC(Cc1ccc(C(=O)NCCS(=O)(=O)O)cc1)C(=O)Nc1ccc(-c2cc3ccccc3o2)cc1] | 575.6 (−) | C32H36N2O6S + 0.5 H2O + 0.3 CF3CO2H<br>63.16 6.06 4.52<br>63.27 5.74 3.70 |
| 1.384 | 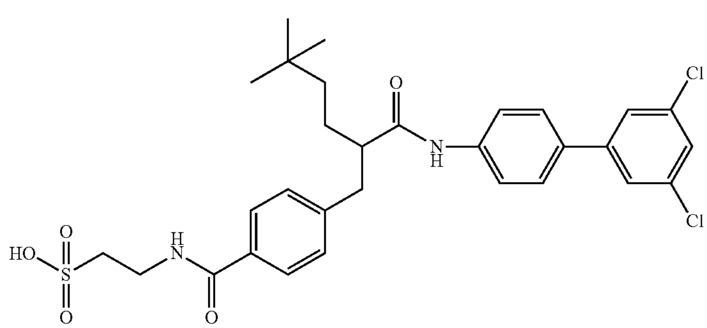 [SMILES: CC(C)(C)CCC(Cc1ccc(C(=O)NCCS(=O)(=O)O)cc1)C(=O)Nc1ccc(-c2cc(Cl)cc(Cl)c2)cc1] | 603.6 (−) | C30H34Cl2N2O5S + 1H2O + 0.2 CF3CO2H<br>56.49 5.64 4.33<br>56.13 5.47 4.57 |

-continued

| Ex# | Structure | LC/MS (mode) | Formula CHN (Calcd) CHN (Found) |
|---|---|---|---|
| 1.385 | 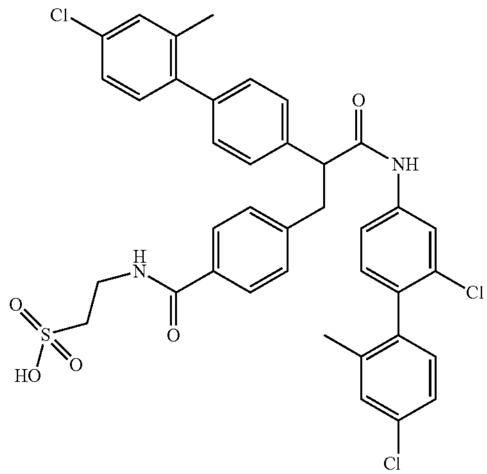 [SMILES: Cc1cc(Cl)ccc1-c1ccc(C(Cc2ccc(C(=O)NCCS(=O)(=O)O)cc2)C(=O)Nc2ccc(-c3ccc(Cl)cc3C)c(Cl)c2)cc1] | 759.6 (+) | C38H32Cl3N2O5SNa + 1 H2O + 0.2 Na2CO3<br>57.55 4.30 3.51<br>57.25 3.91 3.26 |
| 1.386 | 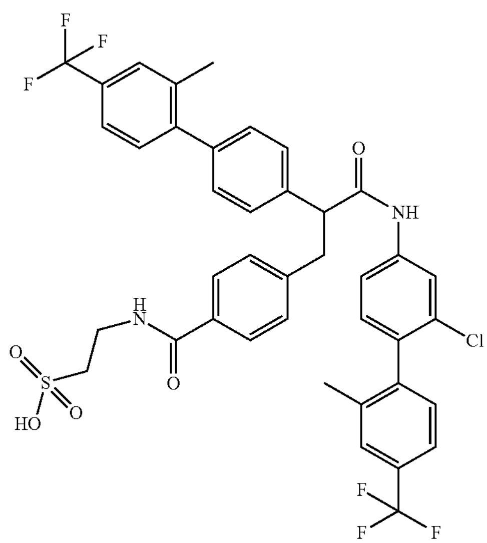 [SMILES: Cc1cc(C(F)(F)F)ccc1-c1ccc(C(Cc2ccc(C(=O)NCCS(=O)(=O)O)cc2)C(=O)Nc2ccc(-c3ccc(C(F)(F)F)cc3C)c(Cl)c2)cc1] | 803.4 (+) | C40H32ClF6N2O5SNa + 0.5 Na2CO3<br>55.39 3.67 3.19<br>55.49 3.39 3.26 |
| 1.387 | 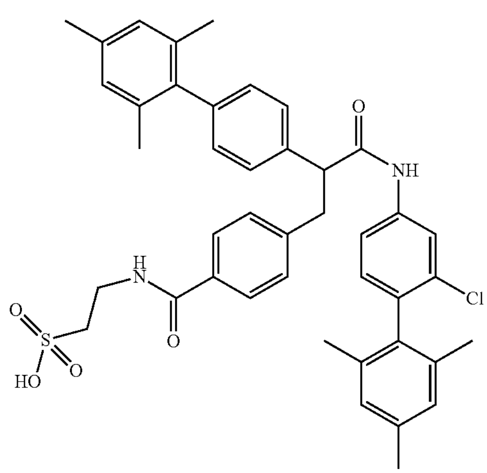 [SMILES: Cc1cc(C)c(-c2ccc(C(Cc3ccc(C(=O)NCCS(=O)(=O)O)cc3)C(=O)Nc3ccc(-c4c(C)cc(C)cc4C)c(Cl)c3)cc2)c(C)c1] | 745.9 (+) | C42H42ClN2O5SNa + 0.8 H2O<br>61.77 5.38 3.43<br>61.73 5.50 3.59 |

-continued

| Ex# | Structure | LC/MS (mode) | Formula CHN (Calcd) CHN (Found) |
|---|---|---|---|
| 1.388 | 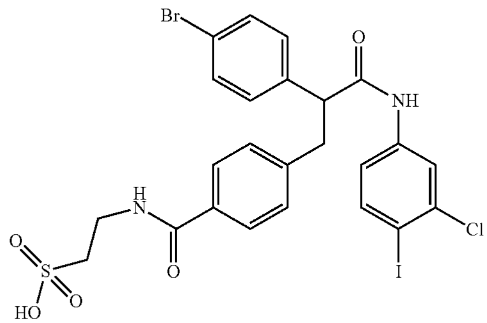 [SMILES: O=C(NCCS(=O)(=O)O)c1ccc(CC(C(=O)Nc2ccc(I)c(Cl)c2)c2ccc(Br)cc2)cc1] | 693.4 (+) | C24H20BrClN2O5SNa<br>37.40 2.62 3.63<br>37.30 2.51 3.54 |
| 1.389 | 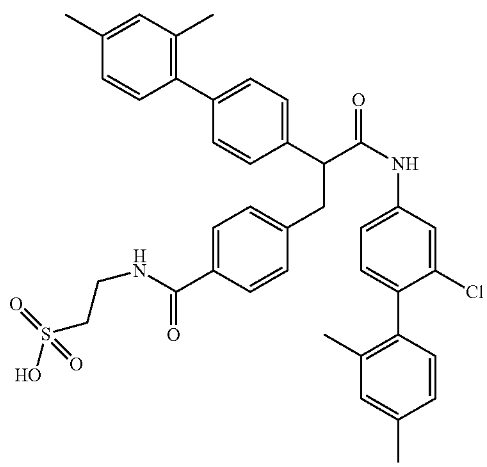 [SMILES: Cc1ccc(-c2ccc(C(Cc3ccc(C(=O)NCCS(=O)(=O)O)cc3)C(=O)Nc3ccc(-c4ccc(C)cc4C)c(Cl)c3)cc2)c(C)c1] | 717.6 (+) | C40H38ClN2O5SNa +<br>2.2 H2O<br>63.48 5.65 3.70<br>63.08 5.25 3.77 |
| 1.390 | 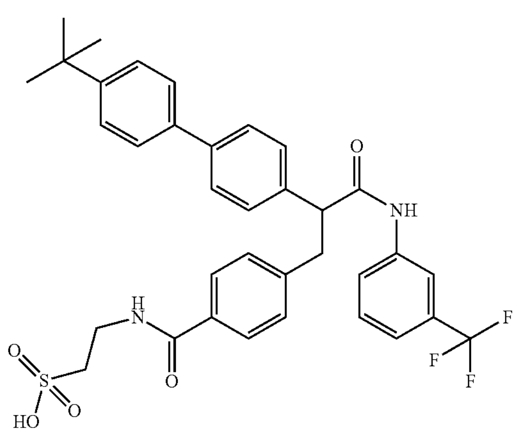 [SMILES: CC(C)(C)c1ccc(-c2ccc(C(Cc3ccc(C(=O)NCCS(=O)(=O)O)cc3)C(=O)Nc3cccc(C(F)(F)F)c3)cc2)cc1] | 653.6 (+) | C35H34N2O5F3SNa +<br>1 H2O<br>60.69 5.24 4.04<br>60.37 5.39 4.05 |

-continued

| Ex# | Structure | LC/MS (mode) | Formula CHN (Calcd) CHN (Found) |
|---|---|---|---|
| 1.391 | 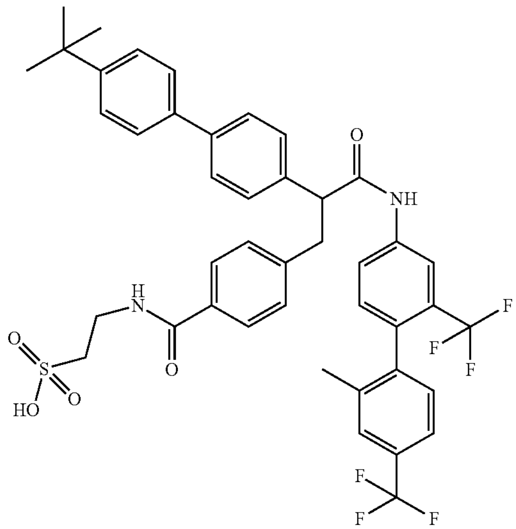 [SMILES: Cc1cc(C(F)(F)F)ccc1-c1ccc(NC(=O)C(Cc2ccc(C(=O)NCCS(=O)(=O)O)cc2)c2ccc(-c3ccc(C(C)(C)C)cc3)cc2)cc1C(F)(F)F] | 833.6 (+) | C43H39N2O5F6SNa + 1 H2O<br>60.70 4.86 3.29<br>60.87 5.19 3.57 |
| 1.392 | 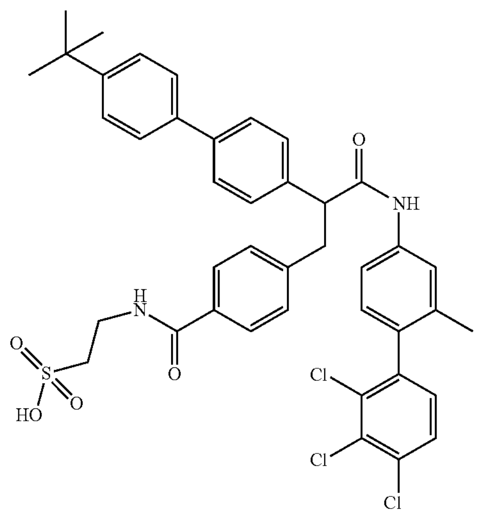 [SMILES: Cc1cc(NC(=O)C(Cc2ccc(C(=O)NCCS(=O)(=O)O)cc2)c2ccc(-c3ccc(C(C)(C)C)cc3)cc2)ccc1-c1ccc(Cl)c(Cl)c1Cl] | 779.6 (+) | C41H38N2O5Cl3SNa + 1.3 H2O<br>59.79 4.97 3.40<br>59.76 5.14 3.67 |
| 1.393 | 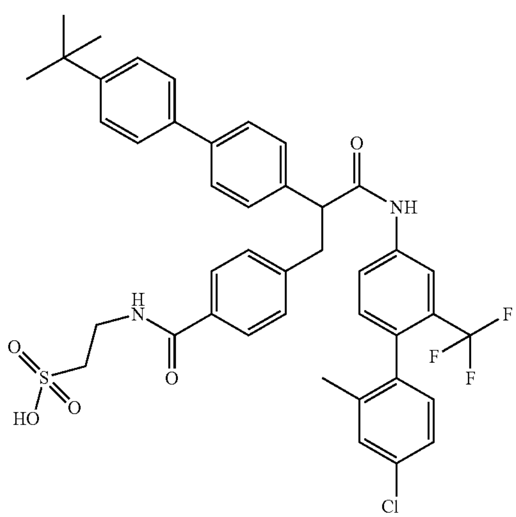 [SMILES: Cc1cc(Cl)ccc1-c1ccc(NC(=O)C(Cc2ccc(C(=O)NCCS(=O)(=O)O)cc2)c2ccc(-c3ccc(C(C)(C)C)cc3)cc2)cc1C(F)(F)F] | 777.6 (+) | C42H39N2O5F3ClSNa + 3.1 H2O<br>58.99 5.33 3.28<br>58.73 5.00 3.10 |

-continued

| Ex# | Structure | LC/MS (mode) | Formula CHN (Calcd) CHN (Found) |
|---|---|---|---|
| 1.394 | 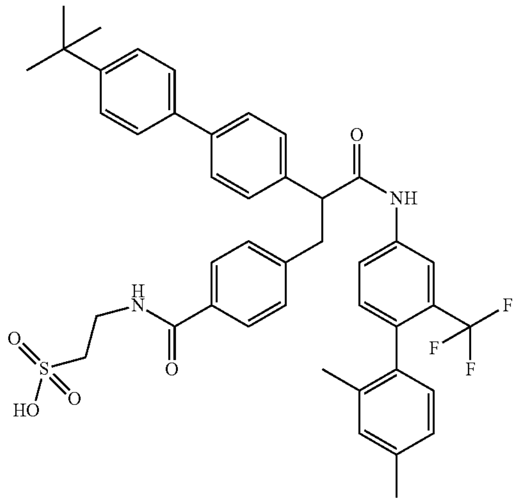 [SMILES: Cc1ccc(-c2ccc(NC(=O)C(Cc3ccc(C(=O)NCCS(=O)(=O)O)cc3)c3ccc(-c4ccc(C(C)(C)C)cc4)cc3)cc2C(F)(F)F)c(C)c1] | 779.6 (+) | C43H42N2O5F3SNa + 2.7 H2O<br>62.41 5.77 3.39<br>62.67 5.60 3.14 |
| 1.395 | 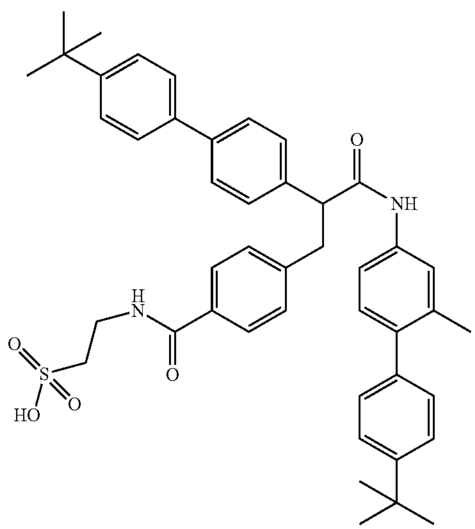 [SMILES: Cc1cc(NC(=O)C(Cc2ccc(C(=O)NCCS(=O)(=O)O)cc2)c2ccc(-c3ccc(C(C)(C)C)cc3)cc2)ccc1-c1ccc(C(C)(C)C)cc1] | 732.1 (+) | C45H49N2O5SNa + 1.2 H2O<br>69.78 6.69 3.62<br>69.40 7.02 3.83 |
| 1.396 | 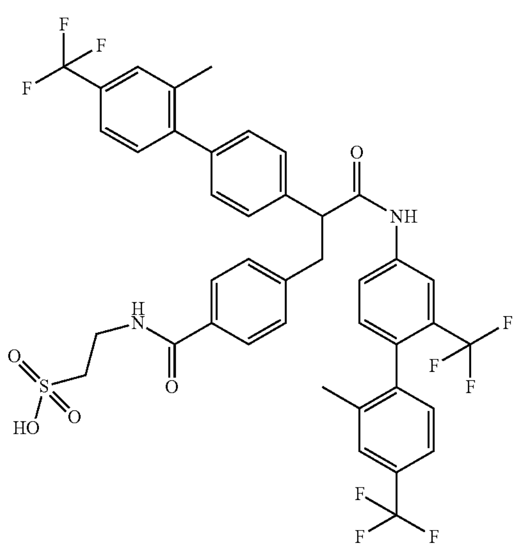 [SMILES: Cc1cc(C(F)(F)F)ccc1-c1ccc(C(Cc2ccc(C(=O)NCCS(=O)(=O)O)cc2)C(=O)Nc2ccc(-c3ccc(C(F)(F)F)cc3C)c(C(F)(F)F)c2)cc1] | 837.6 (+) | C41H32N2O5F9SNa + 1 H2O + 0.2 Na2CO3<br>55.39 3.84 3.14<br>55.21 3.44 3.07 |

| Ex# | Structure | LC/MS (mode) | Formula CHN (Calcd) CHN (Found) |
|---|---|---|---|
| 1.397 | 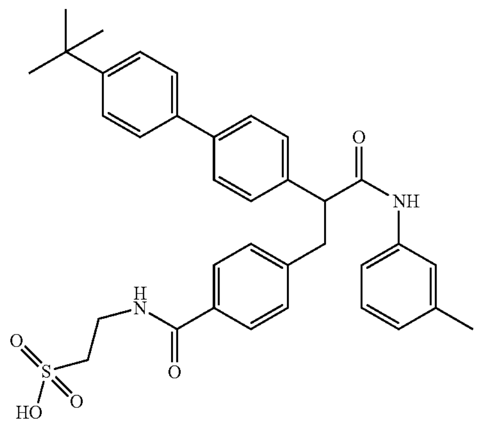 [SMILES: Cc1cccc(NC(=O)C(Cc2ccc(C(=O)NCCS(=O)(=O)O)cc2)c2ccc(-c3ccc(C(C)(C)C)cc3)cc2)c1] | 599.9 (+) | C35H37N2O5SNa + (0.4)NaO3SCH2CH2NH2 63.27 5.84 4.95 63.07 6.07 5.25 |
| 1.398 | 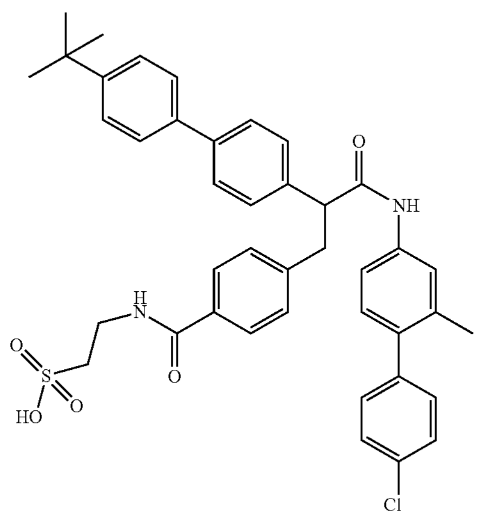 [SMILES: Cc1cc(NC(=O)C(Cc2ccc(C(=O)NCCS(=O)(=O)O)cc2)c2ccc(-c3ccc(C(C)(C)C)cc3)cc2)ccc1-c1ccc(Cl)cc1] | 710.4 (+) | C41H40N2O5ClSNa + 1.7 H2O 64.63 5.74 3.68 64.56 5.70 3.56 |
| 1.399 | 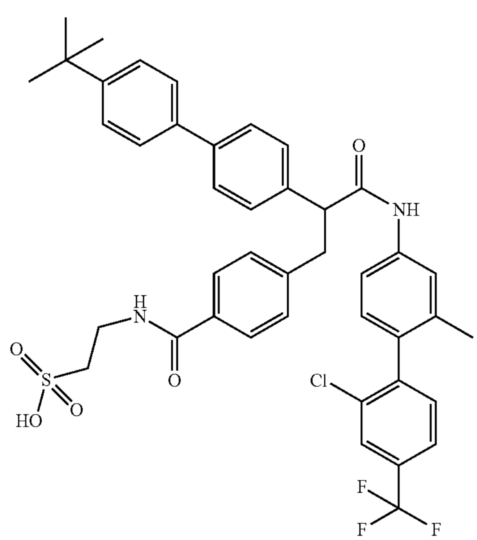 [SMILES: Cc1cc(NC(=O)C(Cc2ccc(C(=O)NCCS(=O)(=O)O)cc2)c2ccc(-c3ccc(C(C)(C)C)cc3)cc2)ccc1-c1ccc(C(F)(F)F)cc1Cl] | 779.6 (+) | C42H39N2O5F3ClSNa + 1 H2O 61.72 5.06 3.43 61.50 5.33 3.32 |

-continued

| Ex# | Structure | LC/MS (mode) | Formula CHN (Calcd) CHN (Found) |
|---|---|---|---|
| 1.400 | 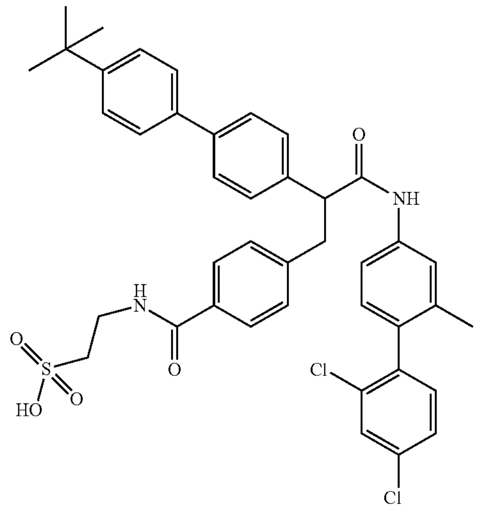 [SMILES: Cc1cc(NC(=O)C(Cc2ccc(C(=O)NCCS(=O)(=O)O)cc2)c2ccc(-c3ccc(C(C)(C)C)cc3)cc2)ccc1-c1ccc(Cl)cc1Cl] | 745.6 (+) | C41H39Cl2N2O5SNa + 3.7 H2O  59.16 5.62 3.37  59.17 5.46 3.54 |
| 1.401 | 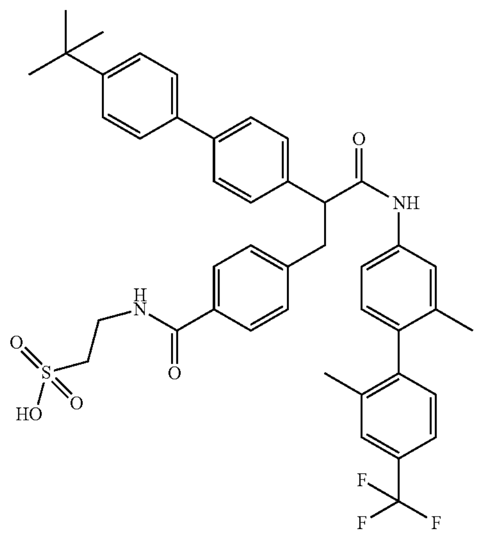 [SMILES: Cc1cc(NC(=O)C(Cc2ccc(C(=O)NCCS(=O)(=O)O)cc2)c2ccc(-c3ccc(C(C)(C)C)cc3)cc2)ccc1-c1ccc(C(F)(F)F)cc1C] | 757.6 (+) | C43H42F3N2O5SNa + 3 H2O  62.01 5.81 3.36  61.86 5.65 3.52 |
| 1.402 | 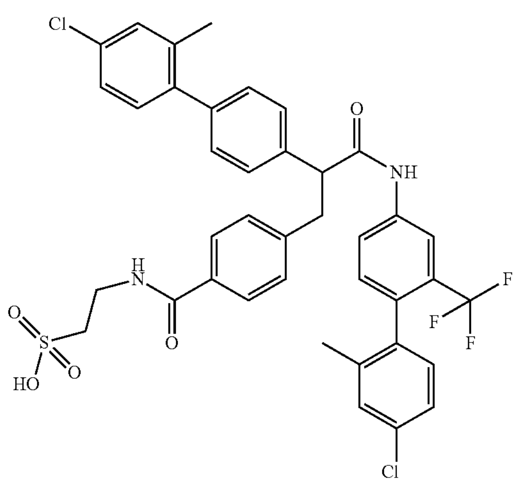 [SMILES: Cc1cc(Cl)ccc1-c1ccc(C(Cc2ccc(C(=O)NCCS(=O)(=O)O)cc2)C(=O)Nc2ccc(-c3ccc(Cl)cc3C)c(C(F)(F)F)c2)cc1] | 769.6 (+) | C39H32Cl2F3N2O5SNa + 3 H2O  55.39 4.53 3.31  55.39 4.17 3.57 |

-continued

| Ex# | Structure | LC/MS (mode) | Formula CHN (Calcd) CHN (Found) |
|---|---|---|---|
| 1.403 | 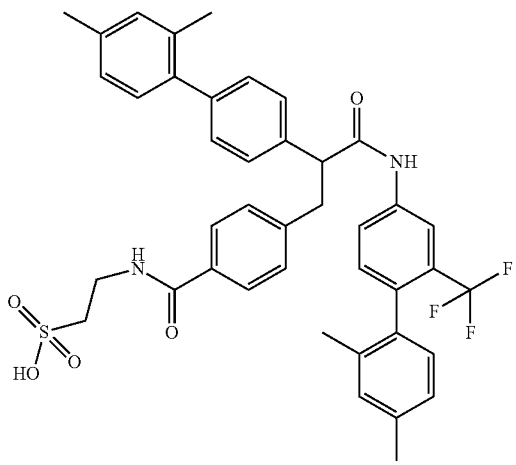 [SMILES: Cc1ccc(-c2ccc(C(Cc3ccc(C(=O)NCCS(=O)(=O)O)cc3)C(=O)Nc3ccc(-c4ccc(C)cc4C)c(C(F)(F)F)c3)cc2)c(C)c1] | 729.6 (+) | C41H38N2O5F3SNa + 0.6 H2O + 0.3 Na2CO3<br>63.07 5.02 3.56<br>62.74 4.71 3.42 |
| 1.404 | 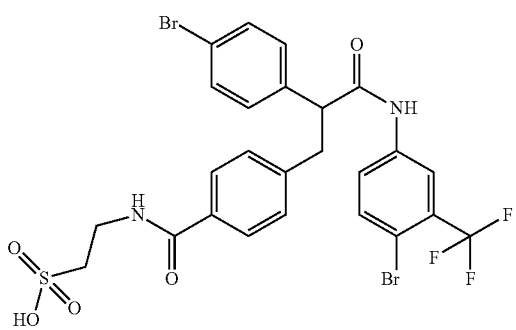 [SMILES: O=C(NCCS(=O)(=O)O)c1ccc(CC(C(=O)Nc2ccc(Br)c(C(F)(F)F)c2)c2ccc(Br)cc2)cc1] | 679.4 (+) | C25H20N2O5F3Br2SNa + 1.5 H2O<br>41.28 3.19 3.85<br>41.16 2.97 3.96 |
| 1.405 | 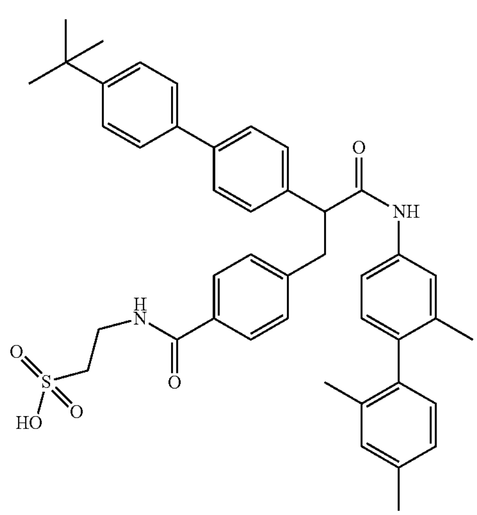 [SMILES: Cc1ccc(-c2ccc(NC(=O)C(Cc3ccc(C(=O)NCCS(=O)(=O)O)cc3)c3ccc(-c4ccc(C(C)(C)C)cc4)cc3)cc2C)c(C)c1] | 703.6 (+) | C43H45N2O5SNa + 2.5 H2O + 0.1 Na2CO3<br>66.52 6.48 3.60<br>66.47 6.11 3.73 |

-continued
| Ex# | Structure | LC/MS (mode) | Formula CHN (Calcd) CHN (Found) |
|---|---|---|---|
| 1.406 | 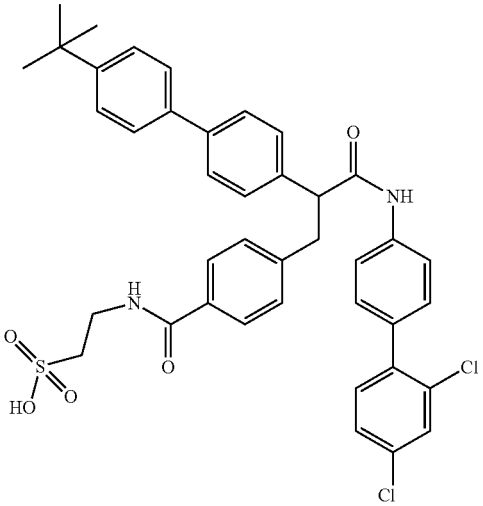 [SMILES: CC(C)(C)c1ccc(-c2ccc(C(Cc3ccc(C(=O)NCCS(=O)(=O)O)cc3)C(=O)Nc3ccc(-c4ccc(Cl)cc4Cl)cc3)cc2)cc1] | 752.6 (+) | C40H37N2O5Cl2SNa + 1.7 H2O<br>61.41 5.21 3.58<br>61.07 4.82 3.42 |
| 1.407 | 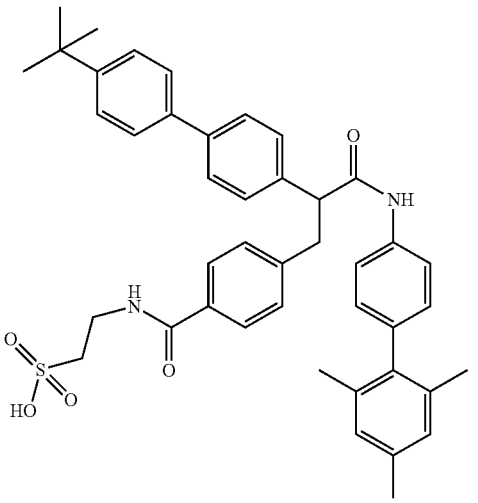 [SMILES: Cc1cc(C)c(-c2ccc(NC(=O)C(Cc3ccc(C(=O)NCCS(=O)(=O)O)cc3)c3ccc(-c4ccc(C(C)(C)C)cc4)cc3)cc2)c(C)c1] | 703.6 (+) | C43H45N2O5SNa + 2.6 H2O<br>66.92 6.56 3.63<br>66.83 6.32 3.43 |
| 1.408 | 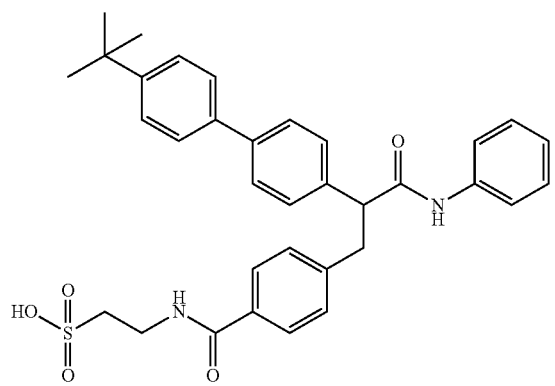 [SMILES: CC(C)(C)c1ccc(-c2ccc(C(Cc3ccc(C(=O)NCCS(=O)(=O)O)cc3)C(=O)Nc3ccccc3)cc2)cc1] | 585.6 (+) | C34H35N2O5SNa + 2.4 H2O<br>62.83 6.17 4.31<br>62.66 6.23 4.51 |

-continued

| Ex# | Structure | LC/MS (mode) | Formula CHN (Calcd) CHN (Found) |
|---|---|---|---|
| 1.409 | 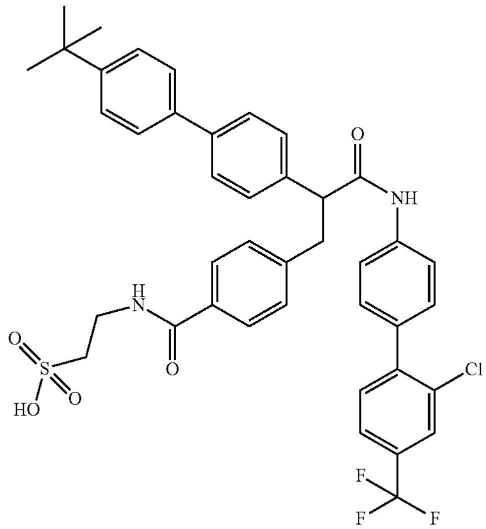 [SMILES: CC(C)(C)c1ccc(-c2ccc(C(Cc3ccc(C(=O)NCCS(=O)(=O)O)cc3)C(=O)Nc3ccc(-c4ccc(C(F)(F)F)cc4Cl)cc3)cc2)cc1] | 787.4 (+) | C41H37ClF3N2O5SNa + 1.5 H2O<br>60.63 4.96 3.45<br>60.89 5.25 3.31 |
| 1.410 | 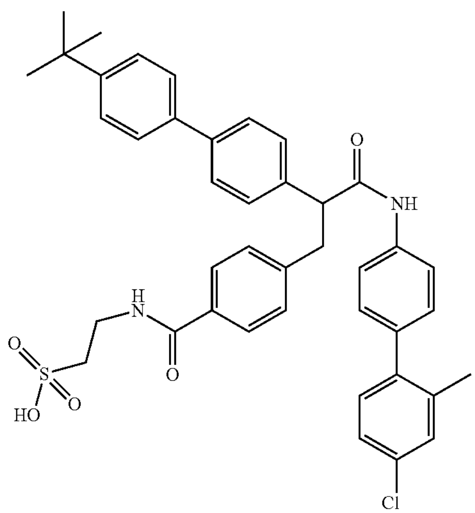 [SMILES: Cc1cc(Cl)ccc1-c1ccc(NC(=O)C(Cc2ccc(C(=O)NCCS(=O)(=O)O)cc2)c2ccc(-c3ccc(C(C)(C)C)cc3)cc2)cc1] | 709.6 (+) | C41H40N2O5ClSNa + 1.8 H2O<br>64.48 5.75 3.67<br>64.27 5.43 3.61 |
| 1.411 | 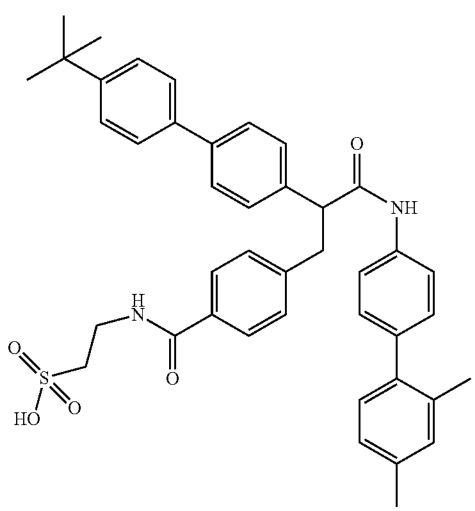 [SMILES: Cc1ccc(-c2ccc(NC(=O)C(Cc3ccc(C(=O)NCCS(=O)(=O)O)cc3)c3ccc(-c4ccc(C(C)(C)C)cc4)cc3)cc2)c(C)c1] | 689.6 (+) | C42H43N2O5SNa + 2.9 H2O<br>66.11 6.45 3.67<br>66.13 6.13 3.54 |

-continued

| Ex# | Structure | LC/MS (mode) | Formula CHN (Calcd) CHN (Found) |
|---|---|---|---|
| 1.412 | 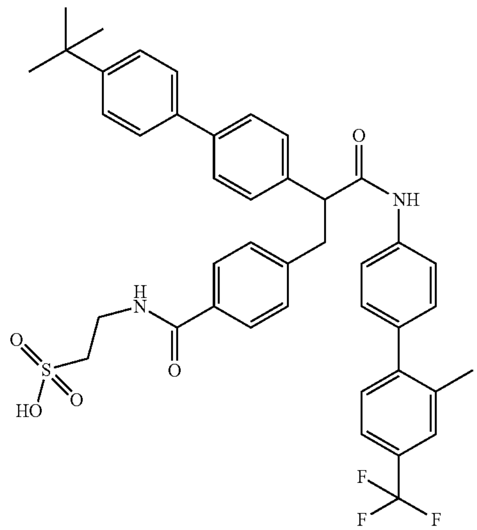 [SMILES: Cc1cc(C(F)(F)F)ccc1-c1ccc(NC(=O)C(Cc2ccc(C(=O)NCCS(=O)(=O)O)cc2)c2ccc(-c3ccc(C(C)(C)C)cc3)cc2)cc1] | 743.6 (+) | C42H41F3N2O5SNa + 1.8 H2O 63.27 5.51 3.51 63.26 5.55 3.64 |
| 1.413 | 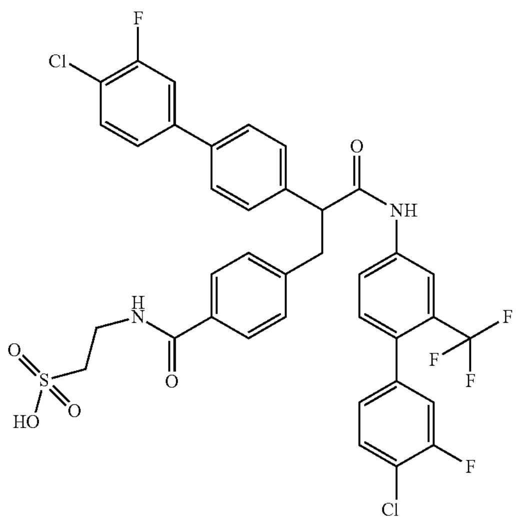 [SMILES: O=C(NCCS(=O)(=O)O)c1ccc(CC(C(=O)Nc2ccc(-c3ccc(Cl)c(F)c3)c(C(F)(F)F)c2)c2ccc(-c3ccc(Cl)c(F)c3)cc2)cc1] | 799.4 (+) | C37H26N2O5Cl2SNa + 2.5 H2O 52.62 3.70 3.32 52.69 3.53 3.29 |
| 1.414 | 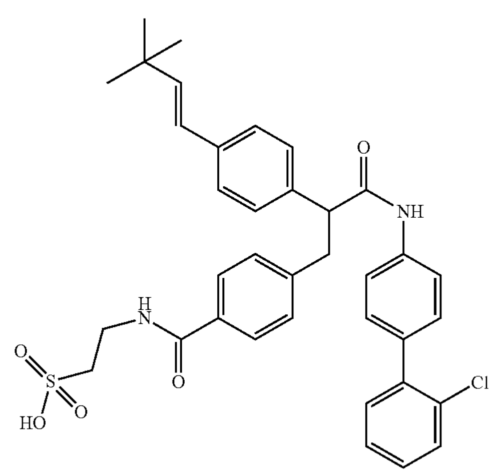 [SMILES: CC(C)(C)/C=C/c1ccc(C(Cc2ccc(C(=O)NCCS(=O)(=O)O)cc2)C(=O)Nc2ccc(-c3ccccc3Cl)cc2)cc1] | 645.1 (+) | C36H36N2ClSNa + 2.1 H2O 61.33 5.75 3.97 61.38 5.83 4.13 |

-continued

| Ex# | Structure | LC/MS (mode) | Formula CHN (Calcd) CHN (Found) |
|---|---|---|---|
| 1.415 | 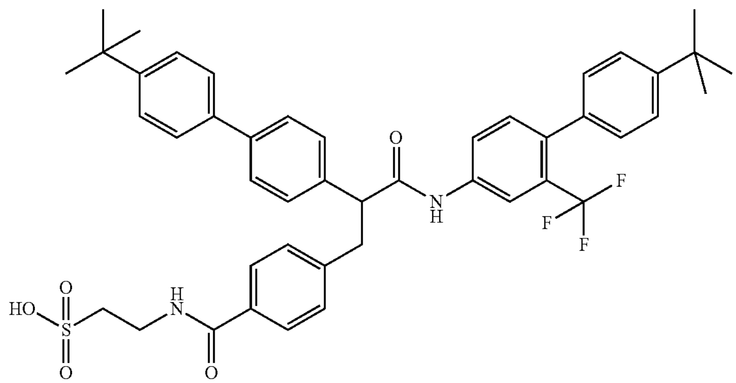 [SMILES: CC(C)(C)c1ccc(-c2ccc(C(Cc3ccc(C(=O)NCCS(=O)(=O)O)cc3)C(=O)Nc3ccc(-c4ccc(C(C)(C)C)cc4)c(C(F)(F)F)c3)cc2)cc1] | 807.6 (+) | C45H46N2O5F3SNa + 2.5 H2O + 0.4 MeOH<br>63.06 6.13 3.24<br>63.43 5.90 2.84 |
| 1.416 | 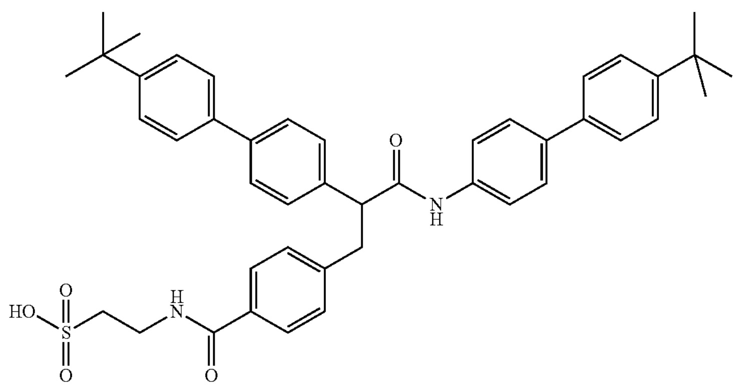 [SMILES: CC(C)(C)c1ccc(-c2ccc(NC(=O)C(Cc3ccc(C(=O)NCCS(=O)(=O)O)cc3)c3ccc(-c4ccc(C(C)(C)C)cc4)cc3)cc2)cc1] | 717.9 (+) | C44H47N2O5SNa + 3.2 H2O<br>66.34 6.76 3.52<br>66.05 6.47 3.49 |
| 1.417 | 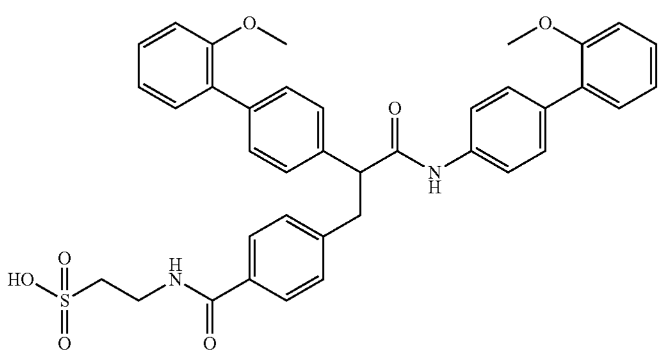 [SMILES: COc1ccccc1-c1ccc(NC(=O)C(Cc2ccc(C(=O)NCCS(=O)(=O)O)cc2)c2ccc(-c3ccccc3OC)cc2)cc1] | 685.6 (+) | C38H35N2O7SNa + 4 H2O<br>60.15 5.71 3.69<br>60.12 5.38 3.44 |
| 1.418 | 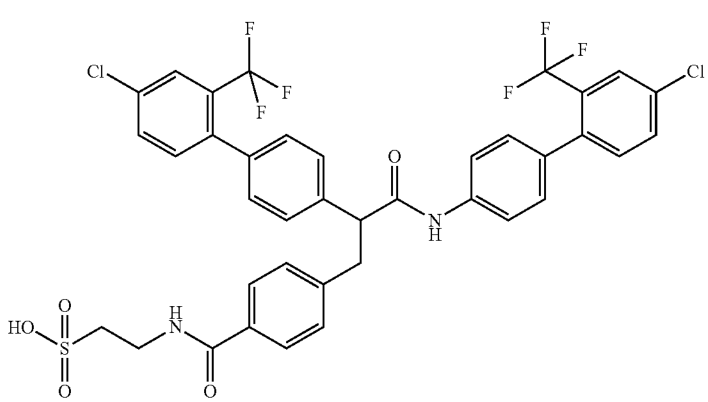 [SMILES: O=C(NCCS(=O)(=O)O)c1ccc(CC(C(=O)Nc2ccc(-c3ccc(Cl)cc3C(F)(F)F)cc2)c2ccc(-c3ccc(Cl)cc3C(F)(F)F)cc2)cc1] | 811.6 (+) | C38H27N2O5F6Cl2SNa + 2.3 H2O<br>52.28 3.65 3.21<br>52.13 3.50 3.25 |

| Ex# | Structure | LC/MS (mode) | Formula CHN (Calcd) CHN (Found) |
|---|---|---|---|
| 1.419 | 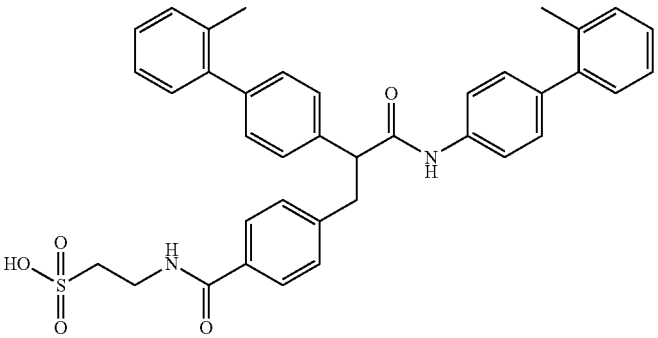 [SMILES: Cc1ccccc1-c1ccc(NC(=O)C(Cc2ccc(C(=O)NCCS(=O)(=O)O)cc2)c2ccc(-c3ccccc3C)cc2)cc1] | 633.4 (+) | C38H35N2O5SNa + 3 H2O<br>64.39 5.83 3.95<br>64.66 5.72 4.04 |
| 1.420 | 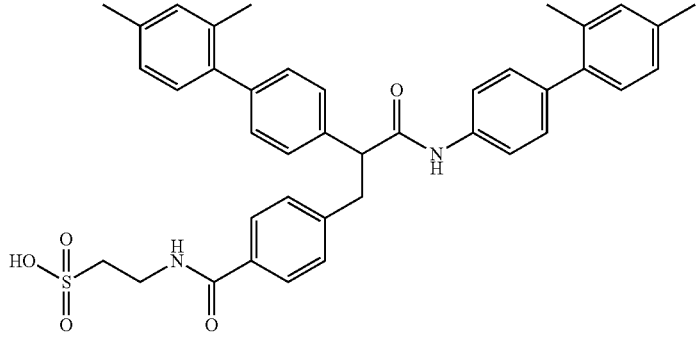 [SMILES: Cc1ccc(-c2ccc(NC(=O)C(Cc3ccc(C(=O)NCCS(=O)(=O)O)cc3)c3ccc(-c4ccc(C)cc4C)cc3)cc2)c(C)c1] | 661.6 (+) | C40H39N2O5SNa + 2.3 H2O<br>66.34 6.07 3.87<br>66.33 6.05 3.88 |
| 1.421 | 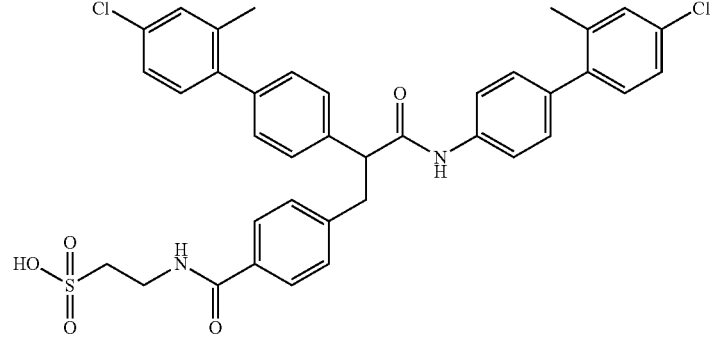 [SMILES: Cc1cc(Cl)ccc1-c1ccc(NC(=O)C(Cc2ccc(C(=O)NCCS(=O)(=O)O)cc2)c2ccc(-c3ccc(Cl)cc3C)cc2)cc1] | 703.6 (+) | C38H33N2O5Cl2SNa + 1.8 H2O<br>60.37 4.88 3.71<br>60.27 4.67 3.71 |
| 1.422 | 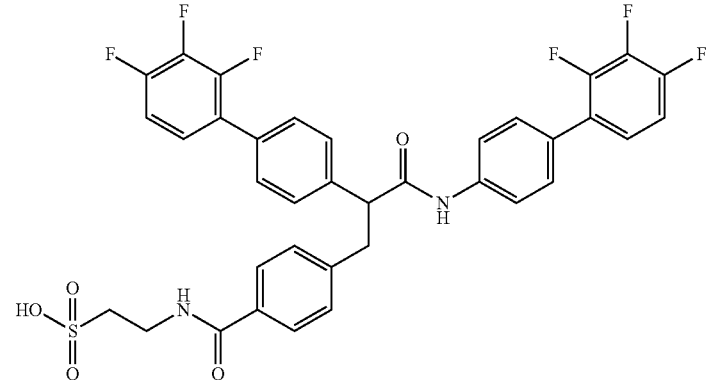 [SMILES: O=C(NCCS(=O)(=O)O)c1ccc(CC(C(=O)Nc2ccc(-c3ccc(F)c(F)c3F)cc2)c2ccc(-c3ccc(F)c(F)c3F)cc2)cc1] | 735.9 (+) | C36H25N2O5F6SNa + 1.5 H2O + 0.1 Na2CO3<br>56.15 3.65 3.63<br>56.11 3.32 3.80 |

-continued

| Ex# | Structure | LC/MS (mode) | Formula CHN (Calcd) CHN (Found) |
|---|---|---|---|
| 1.423 | 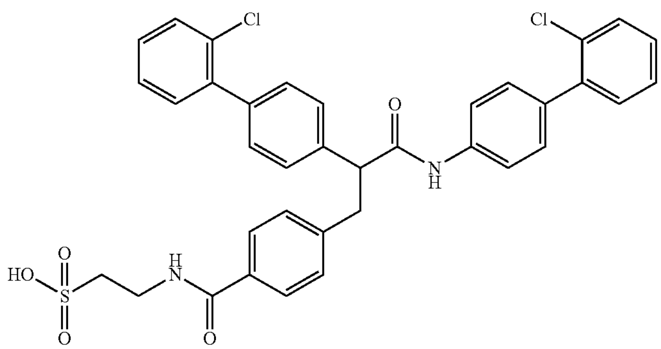 [SMILES: O=C(NCCS(=O)(=O)O)c1ccc(CC(C(=O)Nc2ccc(-c3ccccc3Cl)cc2)c2ccc(-c3ccccc3Cl)cc2)cc1] | 675.4 (+) | C36H29N2O5Cl2SNa + 3 H2O 57.68 4.71 3.74 57.86 4.67 3.81 |
| 1.424 | 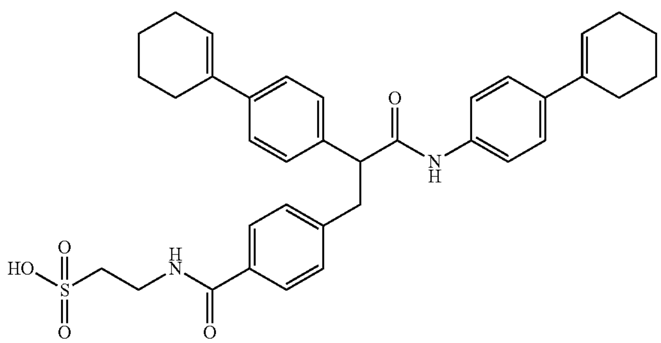 [SMILES: O=C(NCCS(=O)(=O)O)c1ccc(CC(C(=O)Nc2ccc(C3=CCCCC3)cc2)c2ccc(C3=CCCCC3)cc2)cc1] | 613.6 (+) | C36H39N2O5SNa + 2.5 H2O 63.61 6.52 4.12 63.47 6.46 4.04 |
| 1.425 | 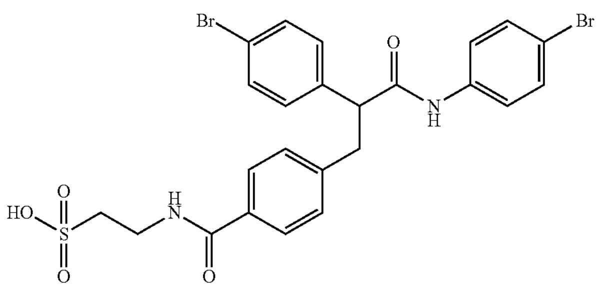 [SMILES: O=C(NCCS(=O)(=O)O)c1ccc(CC(C(=O)Nc2ccc(Br)cc2)c2ccc(Br)cc2)cc1] | 611.1 (+) | C24H21N2O5Br2SNa + 4.1 H2O 40.82 4.17 3.97 40.48 3.78 3.82 |
| 1.426 | 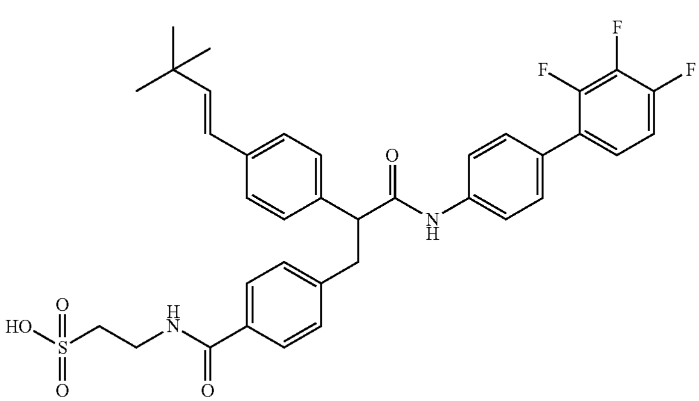 [SMILES: CC(C)(C)/C=C/c1ccc(C(Cc2ccc(C(=O)NCCS(=O)(=O)O)cc2)C(=O)Nc2ccc(-c3ccc(F)c(F)c3F)cc2)cc1] | 688.9 (+) | C36H34N2O5F3SNa + 2.5 H2O + 0.3 Na2CO3 57.10 5.15 3.67 56.85 4.85 3.84 |

| Ex# | Structure | LC/MS (mode) | Formula CHN (Calcd) CHN (Found) |
|---|---|---|---|
| 1.427 | 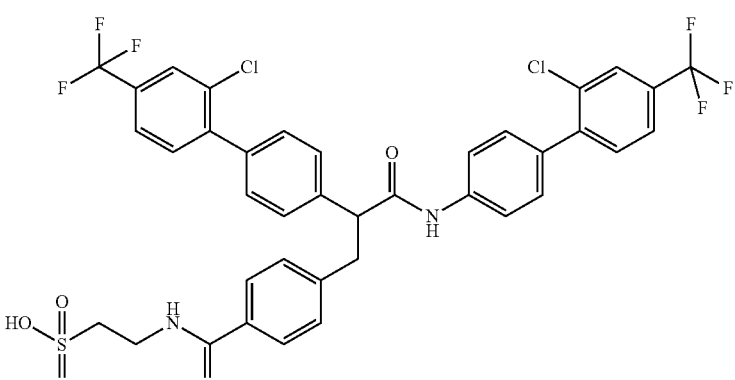 | 809.4 (+) | C38H27N2O5F6Cl2SNa + 2.9 H2O<br>51.64 3.74 3.17<br>51.33 3.66 3.17 |
| 1.428 | 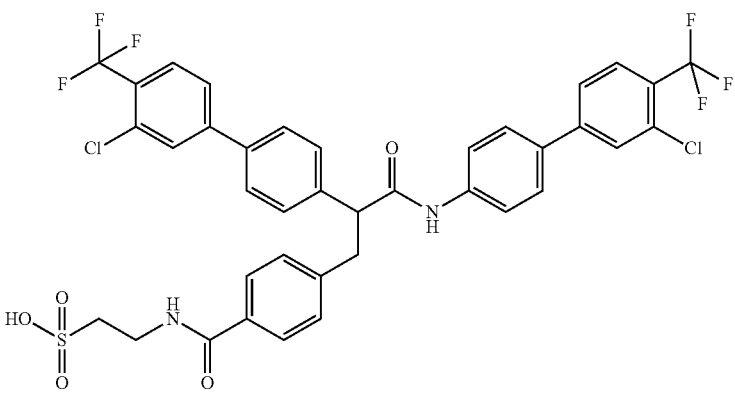 [SMILES: O=C(NCCS(=O)(=O)O)c1ccc(CC(C(=O)Nc2ccc(-c3ccc(C(F)(F)F)c(Cl)c3)cc2)c2ccc(-c3ccc(C(F)(F)F)c(Cl)c3)cc2)cc1] | 810.4 (+) | C38H27N2O5F6Cl2SNa + 2.5 H2O<br>52.06 3.68 3.20<br>51.71 3.54 3.20 |
| 1.429 | 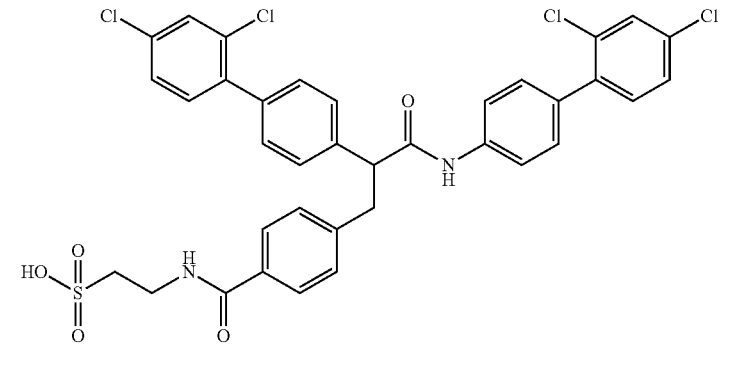 [SMILES: O=C(NCCS(=O)(=O)O)c1ccc(CC(C(=O)Nc2ccc(-c3ccc(Cl)cc3Cl)cc2)c2ccc(-c3ccc(Cl)cc3Cl)cc2)cc1] | 743.6 (+) | C36H28N2O5Cl4S + 0.5 H2O<br>57.54 3.89 3.73<br>57.63 3.99 3.71 |
| 1.430 | 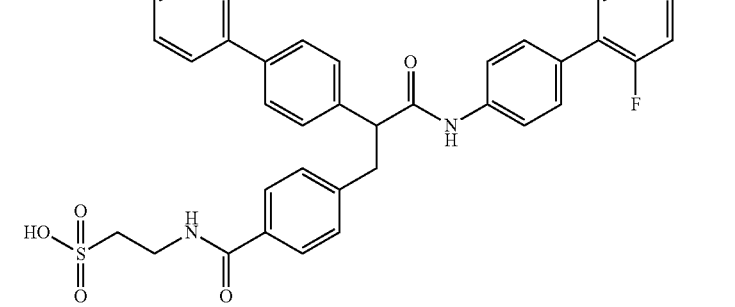 | 699.4 (+) | C36H27N2O5F4SNa + 3.5 H2O<br>56.77 4.50 3.68<br>56.60 4.18 3.63 |

-continued

| Ex# | Structure | LC/MS (mode) | Formula CHN (Calcd) CHN (Found) |
|---|---|---|---|
| 1.431 | 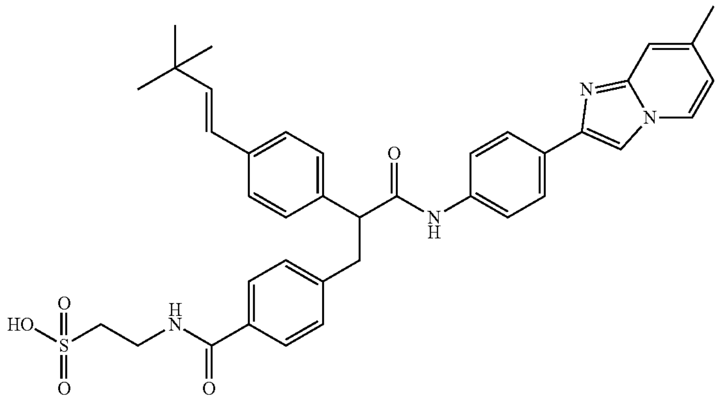 [SMILES: Cc1ccn2cc(-c3ccc(NC(=O)C(Cc4ccc(C(=O)NCCS(=O)(=O)O)cc4)c4ccc(/C=C/C(C)(C)C)cc4)cc3)nc2c1] | 687.6 (+) | C38H39N4O5SNa + 3H2O + 1 MeOH 60.32 6.47 7.16 60.64 6.16 6.77 |
| 1.432 | 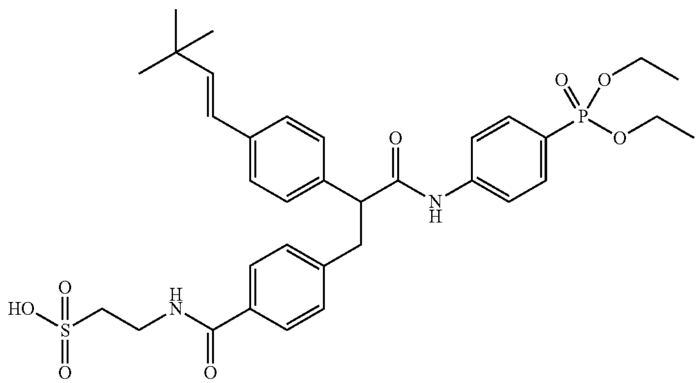 [SMILES: CCOP(=O)(OCC)c1ccc(NC(=O)C(Cc2ccc(C(=O)NCCS(=O)(=O)O)cc2)c2ccc(/C=C/C(C)(C)C)cc2)cc1] | 693.4 (+) | C34H42N2O8SPNa + 2H2O 56.04 6.36 3.84 55.86 6.40 3.96 |
| 1.433 | 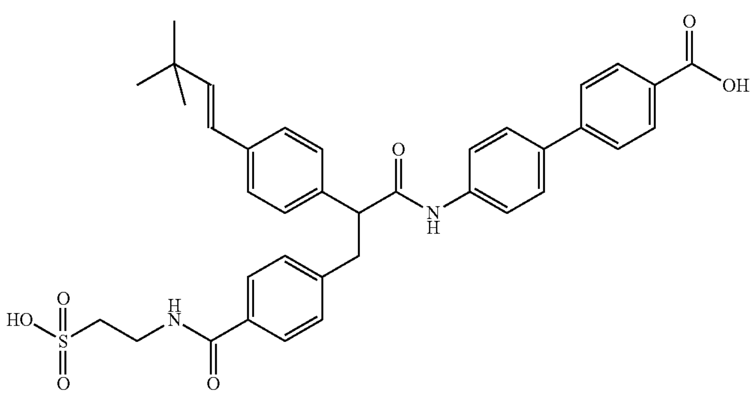 [SMILES: CC(C)(C)/C=C/c1ccc(C(Cc2ccc(C(=O)NCCS(=O)(=O)O)cc2)C(=O)Nc2ccc(-c3ccc(C(=O)O)cc3)cc2)cc1] | 655.10 (+) | C37H37N2O7SNa + 5.5 H2O 57.28 6.24 3.61 57.26 5.97 3.78 |
| 1.434 | 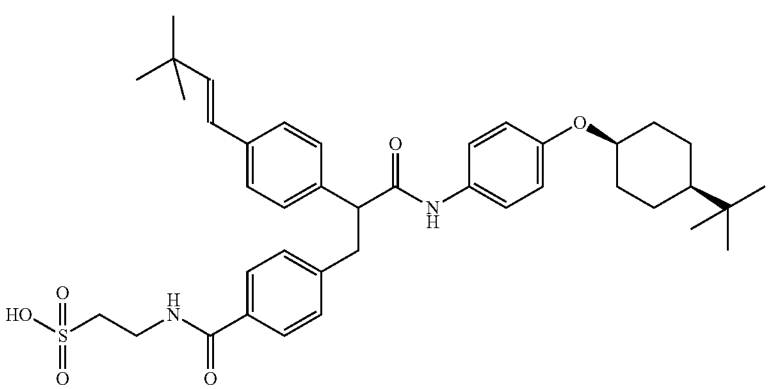 [SMILES: CC(C)(C)/C=C/c1ccc(C(Cc2ccc(C(=O)NCCS(=O)(=O)O)cc2)C(=O)Nc2ccc(O[C@H]3CC[C@@H](C(C)(C)C)CC3)cc2)cc1] | 690.1 (+) | C40H51N2O6SNa + (1.5) H2O + (0.3) C9H20N3O 64.61 7.62 5.12 64.94 7.96 5.28 |

-continued

| Ex# | Structure | LC/MS (mode) | Formula CHN (Calcd) CHN (Found) |
|---|---|---|---|
| 1.435 | 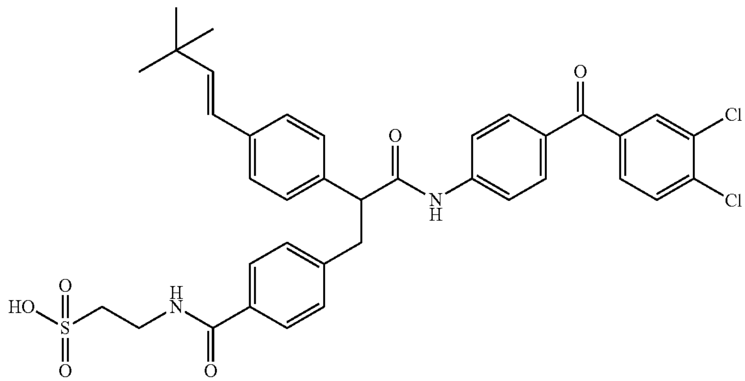 [SMILES: CC(C)(C)/C=C/c1ccc(C(Cc2ccc(C(=O)NCCS(=O)(=O)O)cc2)C(=O)Nc2ccc(C(=O)c3ccc(Cl)c(Cl)c3)cc2)cc1] | 707.6 (+) | C37H35N2O6Cl2SNa + (4.0) H2O + (0.5) C9H20N3O 55.70 5.97 5.48 55.48 6.11 5.79 |
| 1.436 | 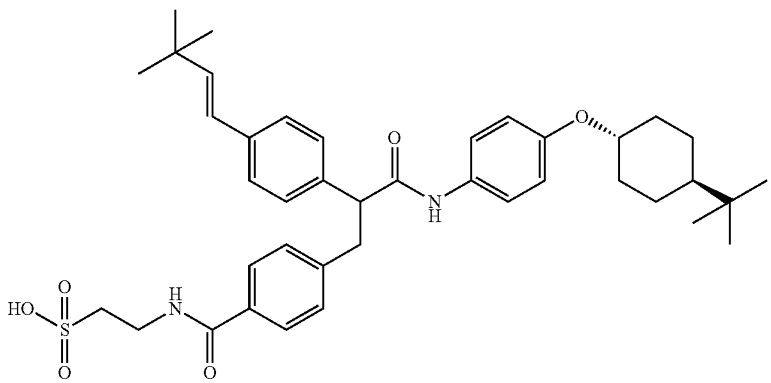 [SMILES: CC(C)(C)/C=C/c1ccc(C(Cc2ccc(C(=O)NCCS(=O)(=O)O)cc2)C(=O)Nc2ccc(O[C@H]3CC[C@H](C(C)(C)C)CC3)cc2)cc1] | 689.9 (+) | C40H51N2O6SNa + (1.5) H2O + (0.35) C9H20N3O 64.53 7.66 5.32 64.24 7.65 5.38 |
| 1.437 | 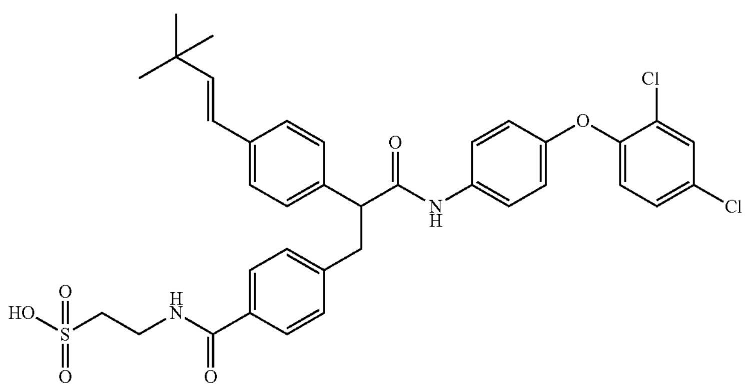 [SMILES: CC(C)(C)/C=C/c1ccc(C(Cc2ccc(C(=O)NCCS(=O)(=O)O)cc2)C(=O)Nc2ccc(Oc3ccc(Cl)cc3Cl)cc2)cc1] | 697.4 (+) | C36H35Cl2N2O6SNa + 3.5 H2O 55.46 5.30 3.59 55.41 4.95 3.54 |
| 1.438 | 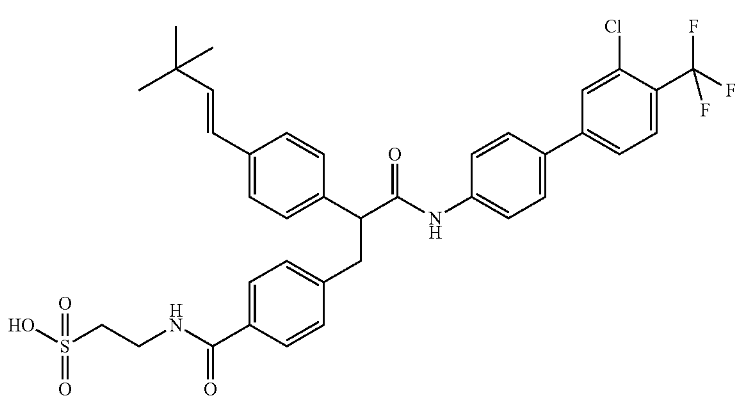 [SMILES: CC(C)(C)/C=C/c1ccc(C(Cc2ccc(C(=O)NCCS(=O)(=O)O)cc2)C(=O)Nc2ccc(-c3ccc(C(F)(F)F)c(Cl)c3)cc2)cc1] | 713.6 (+) | C37H35N2O5F3ClSNa + 3.6 H2O 55.55 5.32 3.50 55.17 5.29 3.72 |

-continued

| Ex# | Structure | LC/MS (mode) | Formula CHN (Calcd) CHN (Found) |
|---|---|---|---|
| 1.439 | 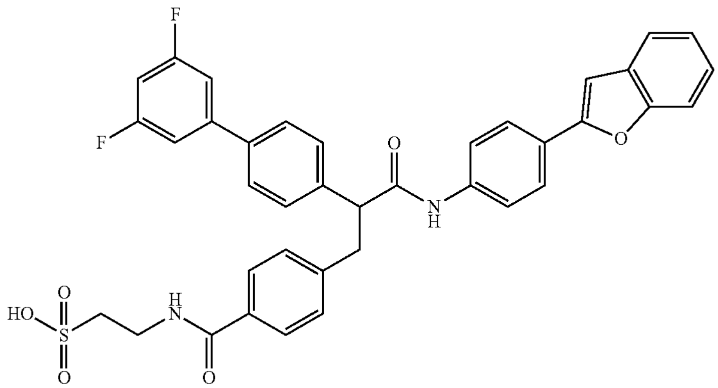 [SMILES: O=C(NCCS(=O)(=O)O)c1ccc(CC(C(=O)Nc2ccc(-c3cc4ccccc4o3)cc2)c2ccc(-c3cc(F)cc(F)c3)cc2)cc1] | 681.6 (+) | C38H29N2O6F2SNa + 2.7 H2O 60.75 4.61 3.73 60.44 4.21 3.56 |
| 1.440 | 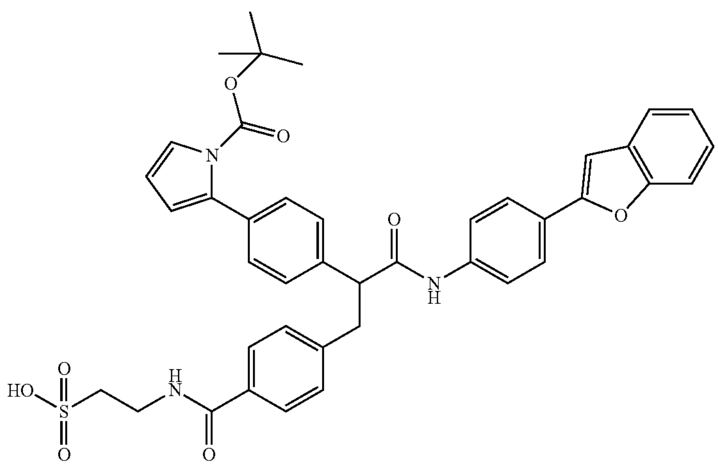 [SMILES: CC(C)(C)OC(=O)n1cccc1-c1ccc(C(Cc2ccc(C(=O)NCCS(=O)(=O)O)cc2)C(=O)Nc2ccc(-c3cc4ccccc4o3)cc2)cc1] | 733.1 (+) | C41H38N3O8SNa + 2.5 H2O 61.49 5.41 5.25 61.26 5.55 5.37 |
| 1.441 | 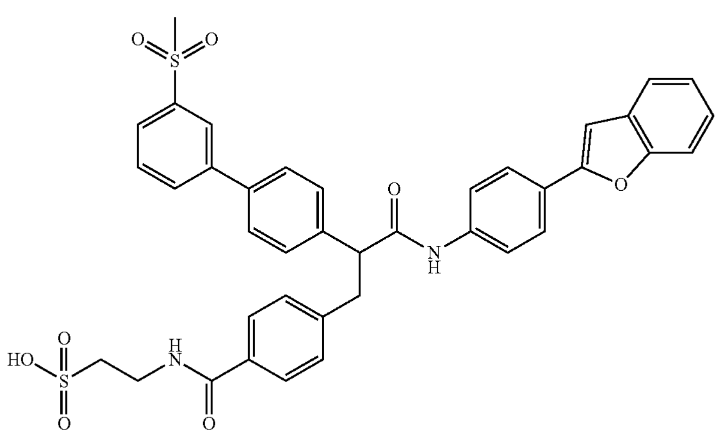 [SMILES: CS(=O)(=O)c1cccc(-c2ccc(C(Cc3ccc(C(=O)NCCS(=O)(=O)O)cc3)C(=O)Nc3ccc(-c4cc5ccccc5o4)cc3)cc2)c1] | 745.6 (+) | C39H33N2O8S2Na + 2.5 H2O 59.31 4.88 3.93 59.12 4.68 3.55 |

-continued
| Ex# | Structure | LC/MS (mode) | Formula CHN (Calcd) CHN (Found) |
|---|---|---|---|
| 1.442 | 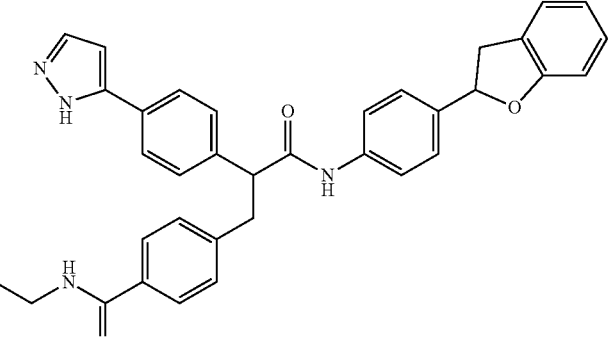 | 657.6 (+) | C35H29N4O6SNa + 3.5 H2O 58.41 5.04 7.78 58.18 4.86 7.73 |
| 1.443 | 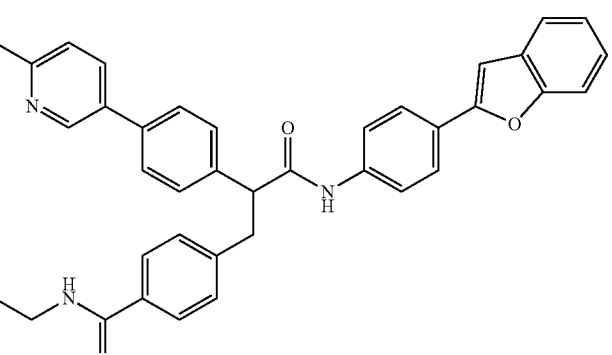 | 702.6 (+) | C37H29N3O6ClSNa + 5.8 H2O 55.09 5.07 5.21 54.72 4.67 5.34 |
| 1.444 | 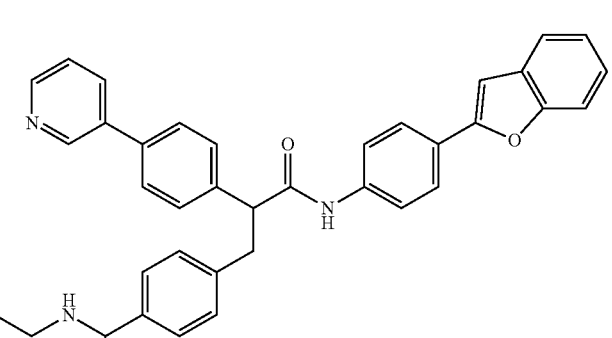 | 668.4 (+) | C37H30N3O6SNa + 4.2 H2O 59.78 5.21 5.65 59.50 4.87 5.86 |
| 1.445 | 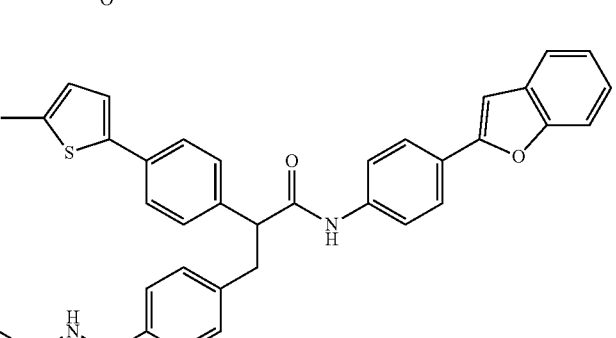 | 665.4 (+) | C37H32N2O6S2 + 0.5 H2O 65.95 4.94 4.16 65.73 4.83 4.20 |

-continued

| Ex# | Structure | LC/MS (mode) | Formula CHN (Calcd) CHN (Found) |
|---|---|---|---|
| 1.446 | 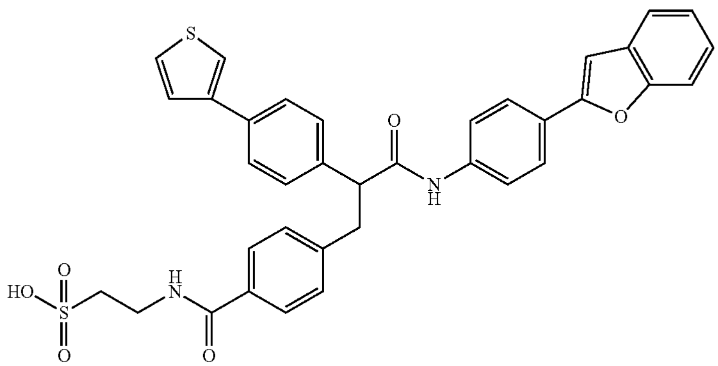 [SMILES: O=C(NCCS(=O)(=O)O)c1ccc(CC(C(=O)Nc2ccc(-c3cc4ccccc4o3)cc2)c2ccc(-c3ccsc3)cc2)cc1] | 673.4 (+) | C36H29N2O6S2Na + 3.5 H2O 58.76 4.93 3.81 58.92 4.56 4.00 |
| 1.447 | 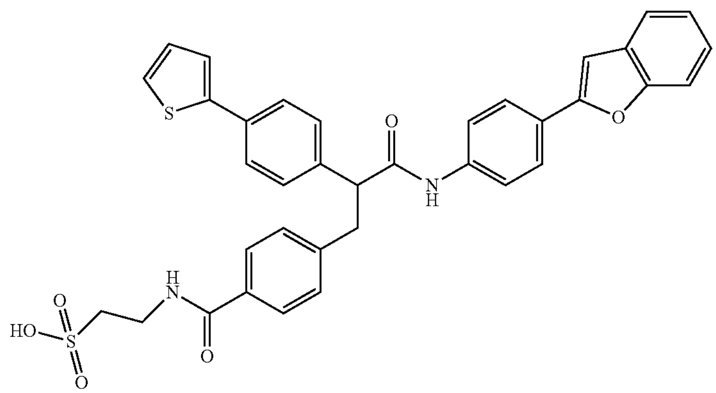 [SMILES: O=C(NCCS(=O)(=O)O)c1ccc(CC(C(=O)Nc2ccc(-c3cc4ccccc4o3)cc2)c2ccc(-c3cccs3)cc2)cc1] | 673.1 (+) | C36H29N2O6S2Na + 3.5 H2O 58.76 4.93 3.81 58.39 4.68 3.96 |
| 1.448 | 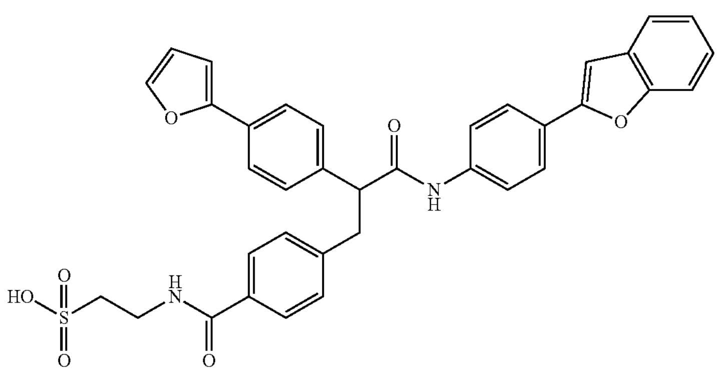 [SMILES: O=C(NCCS(=O)(=O)O)c1ccc(CC(C(=O)Nc2ccc(-c3cc4ccccc4o3)cc2)c2ccc(-c3ccco3)cc2)cc1] | 657.4 (+) | C36H29N2O7SNa + 3 H2O 60.84 4.96 3.94 60.51 4.58 4.12 |
| 1.449 | 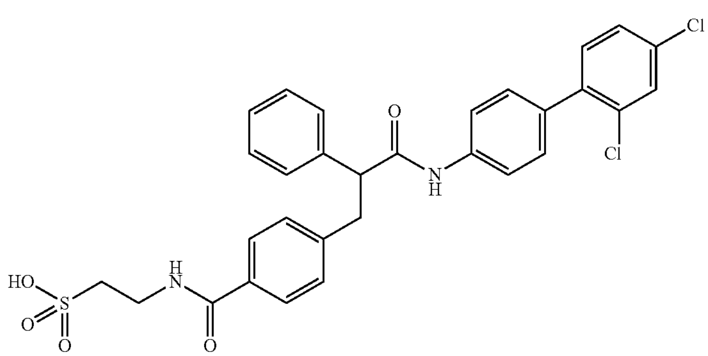 [SMILES: O=C(NCCS(=O)(=O)O)c1ccc(CC(C(=O)Nc2ccc(-c3ccc(Cl)cc3Cl)cc2)c2ccccc2)cc1] | 597.4 (+) | C30H26Cl2N2O5S + 3.8 H2O + 0.4 TFA 51.99 4.80 3.94 51.67 4.50 4.44 |

| Ex# | Structure | LC/MS (mode) | Formula CHN (Calcd) CHN (Found) |
|---|---|---|---|
| 1.450 | 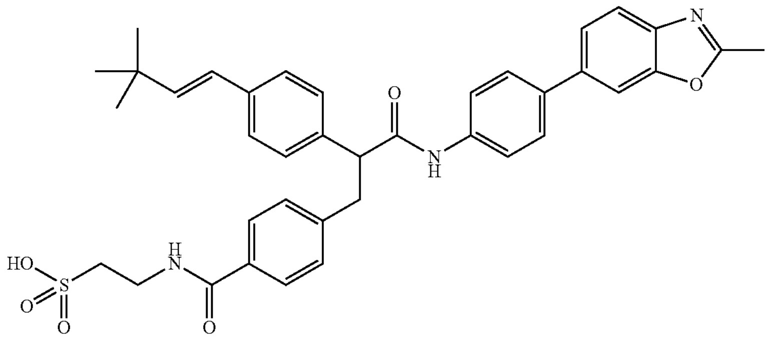 [SMILES: Cc1nc2ccc(-c3ccc(NC(=O)C(Cc4ccc(C(=O)NCCS(=O)(=O)O)cc4)c4ccc(/C=C/C(C)(C)C)cc4)cc3)cc2o1] | 665.6 (+) | C38H39N3O6S + H2O + 0.7 TFA 61.97 5.50 5.50 62.00 5.20 5.34 |
| 1.451 | 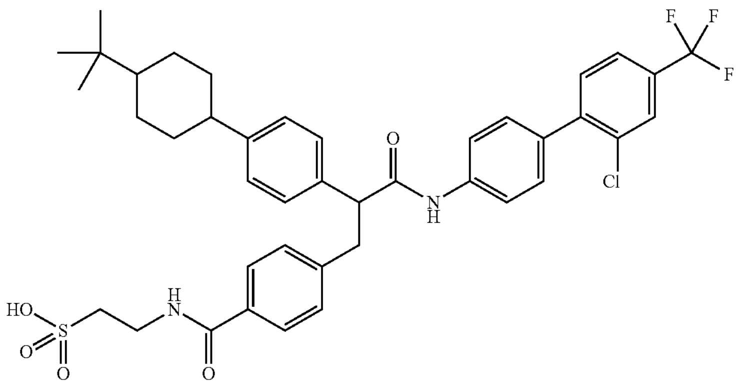 [SMILES: CC(C)(C)C1CCC(c2ccc(C(Cc3ccc(C(=O)NCCS(=O)(=O)O)cc3)C(=O)Nc3ccc(-c4ccc(C(F)(F)F)cc4Cl)cc3)cc2)CC1] | 769.9 (+) | C41H44ClF3N2O5S + 2 H2O + TFA 56.18 5.37 3.05 55.86 5.48 3.21 |
| 1.452 | 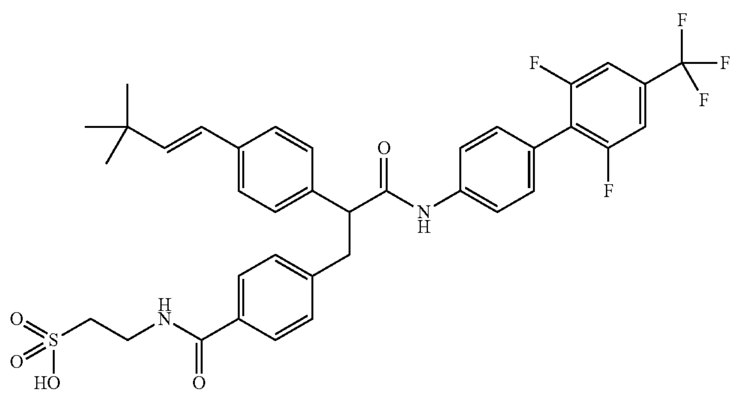 [SMILES: CC(C)(C)/C=C/c1ccc(C(Cc2ccc(C(=O)NCCS(=O)(=O)O)cc2)C(=O)Nc2ccc(-c3c(F)cc(C(F)(F)F)cc3F)cc2)cc1] | 715.6 (+) | C37H35F5N2O5S + 1.2 H2O + 0.2 TFA 59.17 4.99 3.69 59.04 5.26 3.30 |
| 1.453 | 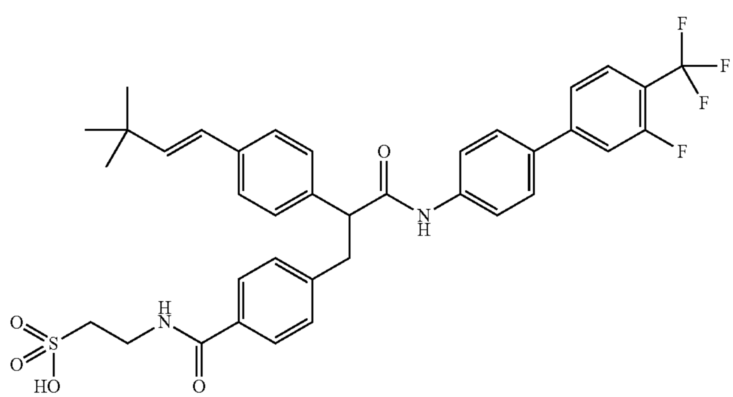 [SMILES: CC(C)(C)/C=C/c1ccc(C(Cc2ccc(C(=O)NCCS(=O)(=O)O)cc2)C(=O)Nc2ccc(-c3ccc(C(F)(F)F)c(F)c3)cc2)cc1] | 696.6 (+) | C37H36F4N2O5S + 0.5 H2O + 0.1 TFA 62.30 5.21 3.91 62.24 5.25 2.65 |

-continued

| Ex# | Structure | LC/MS (mode) | Formula CHN (Calcd) CHN (Found) |
|---|---|---|---|
| 1.454 | 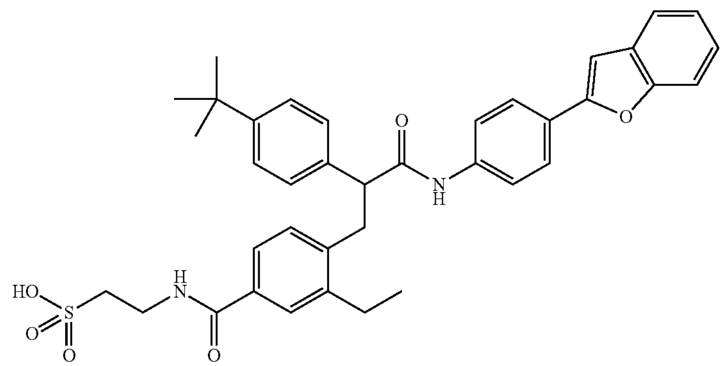 [SMILES: CCc1cc(C(=O)NCCS(=O)(=O)O)ccc1CC(C(=O)Nc1ccc(-c2cc3ccccc3o2)cc1)c1ccc(C(C)(C)C)cc1] | 653.6 (+) | C38H40N2O6S + 2 H2O + 0.2 TFA<br>64.81 6.21 3.94<br>64.51 5.99 3.82 |
| 1.455 | 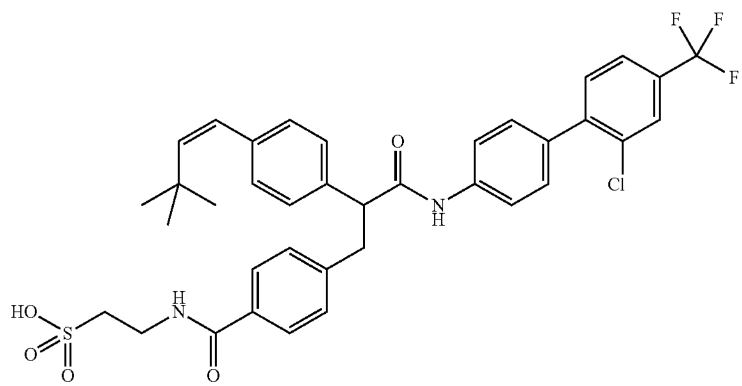 [SMILES: CC(C)(C)/C=C\c1ccc(C(Cc2ccc(C(=O)NCCS(=O)(=O)O)cc2)C(=O)Nc2ccc(-c3ccc(C(F)(F)F)cc3Cl)cc2)cc1] | 713.6 (+) | C37H36ClF3N2O5S + 0.8 H2O + 0.1 TFA<br>60.46 5.14 3.79<br>60.75 6.39 4.68 |
| 1.456 | 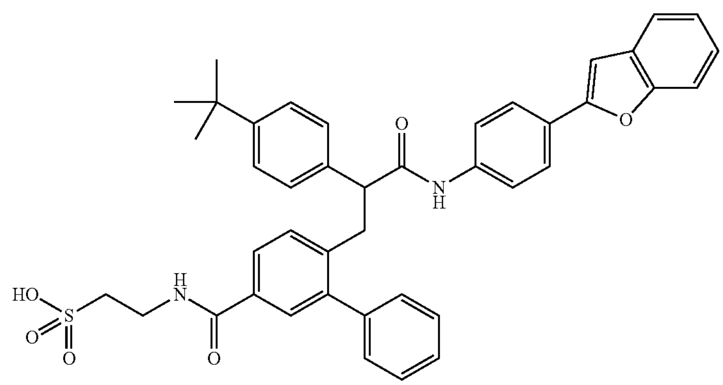 [SMILES: CC(C)(C)c1ccc(C(Cc2ccc(C(=O)NCCS(=O)(=O)O)cc2-c2ccccc2)C(=O)Nc2ccc(-c3cc4ccccc4o3)cc2)cc1] | 701.6 (+) | C42H40N2O6 + H2O + 0.4 TFA<br>67.24 5.59 3.66<br>67.13 5.89 3.39 |
| 1.457 | 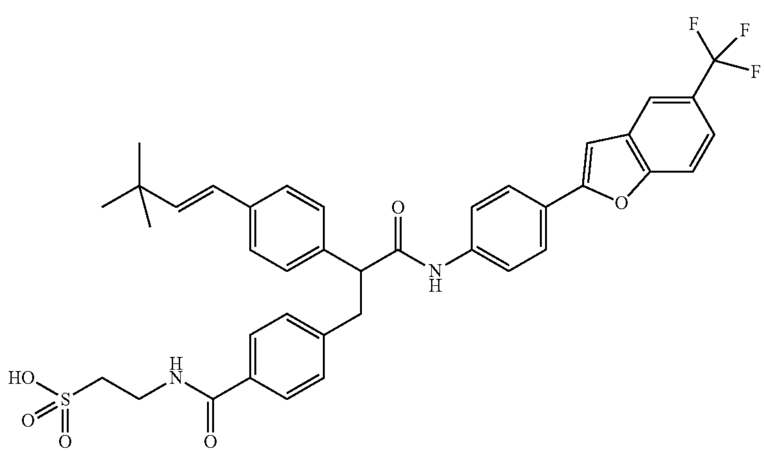 [SMILES: CC(C)(C)/C=C/c1ccc(C(Cc2ccc(C(=O)NCCS(=O)(=O)O)cc2)C(=O)Nc2ccc(-c3cc4cc(C(F)(F)F)ccc4o3)cc2)cc1] | 719.6 (+) | C39H37F3N2O6S + H2O + 0.2 TFA<br>62.30 5.19 3.90<br>62.54 5.16 3.71 |

-continued
| Ex# | Structure | LC/MS (mode) | Formula CHN (Calcd) CHN (Found) |
|---|---|---|---|
| 1.458 | 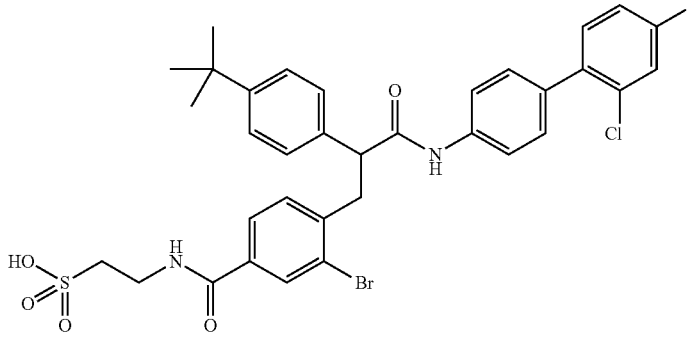 | 733.6 (+) | C34H33BrCl2N2O5S + H2O + 0.5 TFA<br>52.06 4.43 3.47<br>51.86 4.21 3.25 |
| 1.459 | 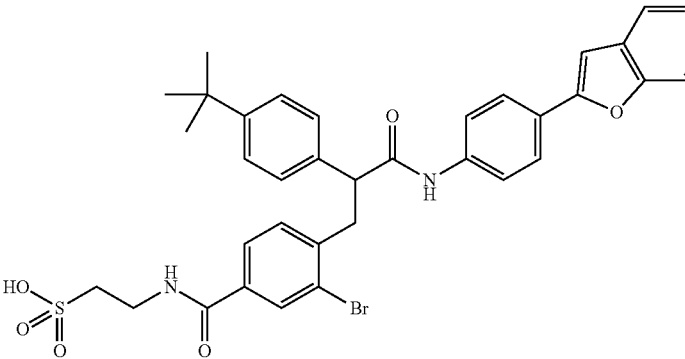 | 705.6 (+) | C36H35BrN2O6S + 3 H2O + 0.3 TFA<br>55.51 5.26 3.54<br>55.12 5.03 3.77 |
| 1.460 | 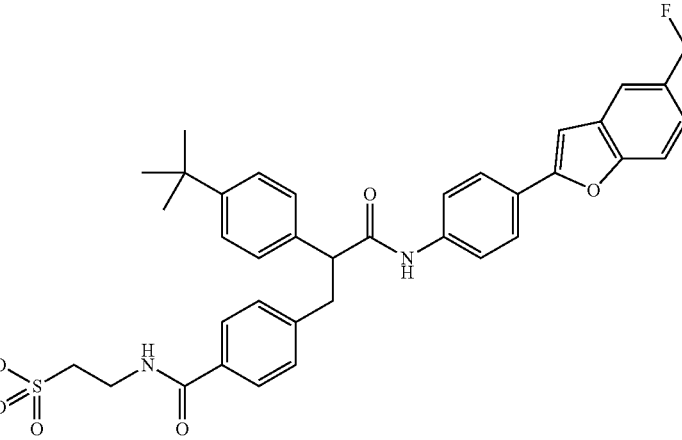 | 693.6 (−) | C37H35F3N2O6S + 3 H2O + 0.1 TFA + 0.1 DMF<br>58.84 5.50 3.84<br>58.93 5.55 4.24 |

-continued

| Ex# | Structure | LC/MS (mode) | Formula CHN (Calcd) CHN (Found) |
|---|---|---|---|
| 1.461 | 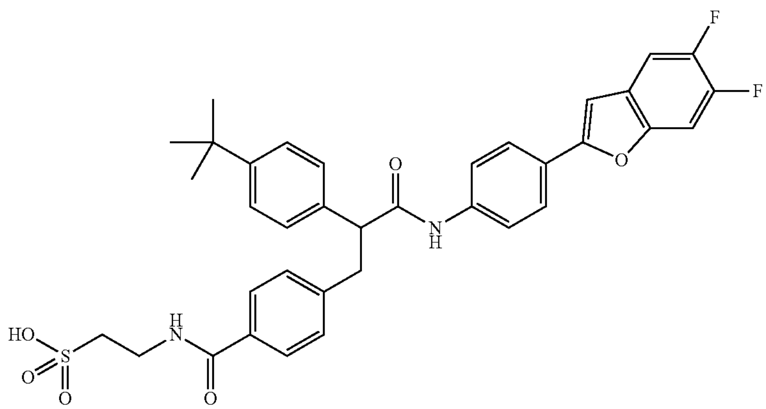 [SMILES: CC(C)(C)c1ccc(C(Cc2ccc(C(=O)NCCS(=O)(=O)O)cc2)C(=O)Nc2ccc(-c3cc4cc(F)c(F)cc4o3)cc2)cc1] | 661.6 (+) | C36H34F2N2O6S + 1.4 H2O + 0.1 TFA<br>62.35 5.33 4.02<br>62.55 5.64 3.67 |
| 1.462 | 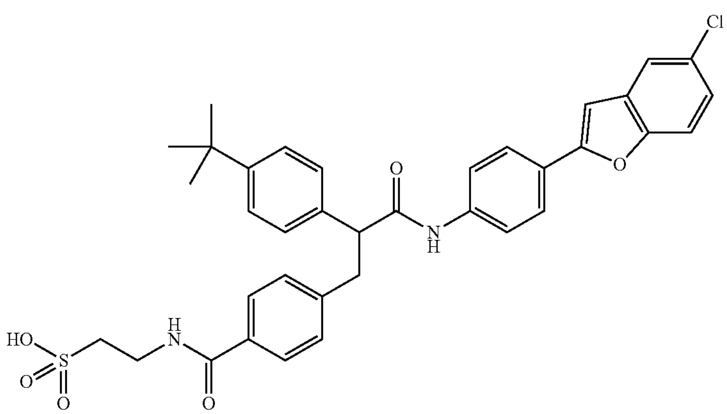 [SMILES: CC(C)(C)c1ccc(C(Cc2ccc(C(=O)NCCS(=O)(=O)O)cc2)C(=O)Nc2ccc(-c3cc4cc(Cl)ccc4o3)cc2)cc1] | 659.6 (+) | C36H35ClN2O6S + 2 H2O + 0.2 TFA<br>60.89 5.50 3.90<br>60.59 5.25 4.27 |
| 1.463 | 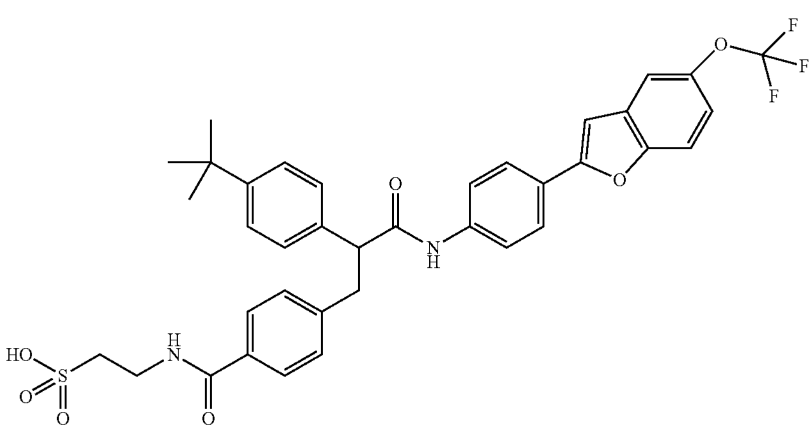 [SMILES: CC(C)(C)c1ccc(C(Cc2ccc(C(=O)NCCS(=O)(=O)O)cc2)C(=O)Nc2ccc(-c3cc4cc(OC(F)(F)F)ccc4o3)cc2)cc1] | 709.6 (+) | C37H35F3N2O7S + 0.5 TFA<br>59.60 4.67 3.66<br>59.29 4.58 3.51 |

| Ex# | Structure | LC/MS (mode) | Formula CHN (Calcd) CHN (Found) |
|---|---|---|---|
| 1.464 | 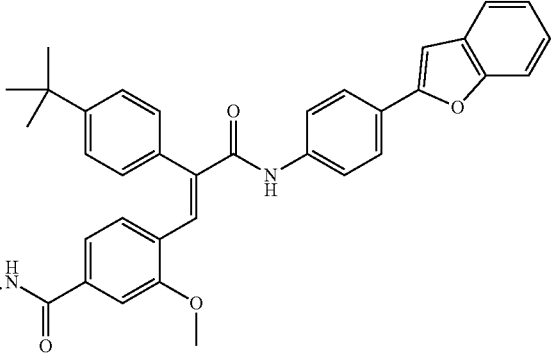 | 653.6 (+) | C37H36N2O7S + 2 H2O + 0.1 TFA 63.81 5.57 4.00 63.69 5.48 3.91 |
| 1.465 | 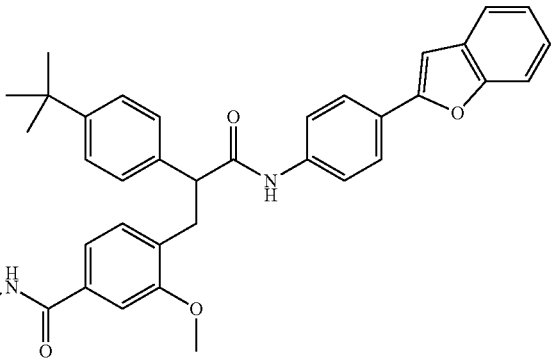 | 655.6 (+) | C37H38N2O7S + 3 H2O + 0.4 TFA 60.18 5.93 3.71 59.98 5.78 3.55 |
| 1.466 | 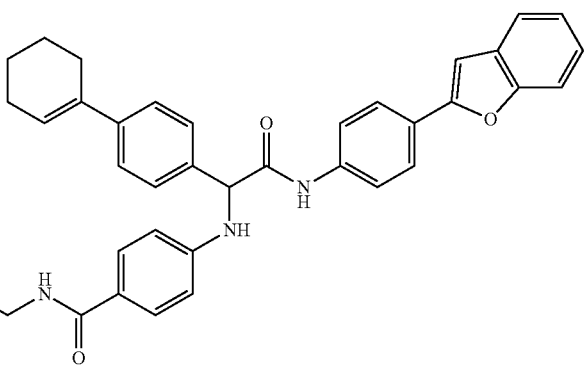 | 650.9 (+) | C37H35N3O6S + 3.4 H2O 63.14 5.87 5.97 62.13 5.99 6.91 |
| 1.467 | 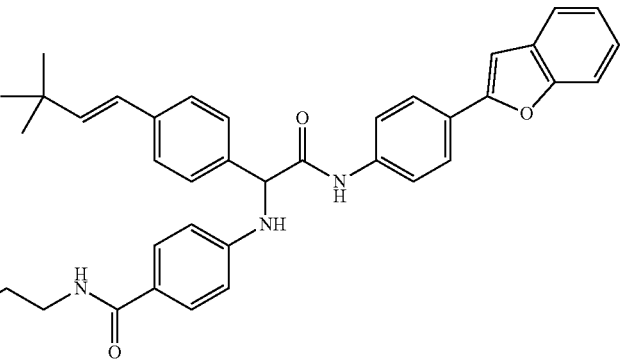 | 653.1 (+) | C37H37N3O6S + 2.5 H2O 63.78 6.08 6.03 64.09 6.48 7.31 |

-continued

| Ex# | Structure | LC/MS (mode) | Formula CHN (Calcd) CHN (Found) |
|---|---|---|---|
| 1.468 | 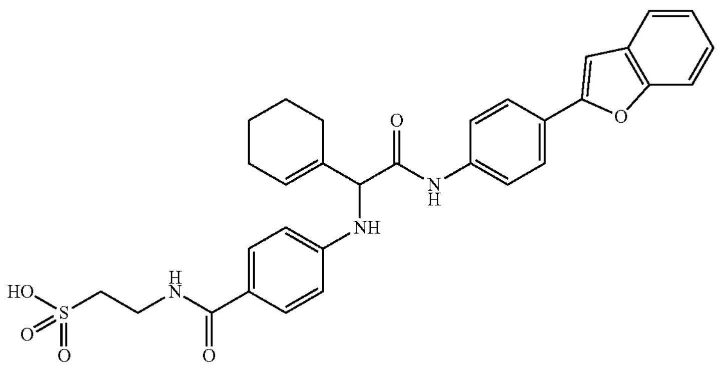 [SMILES: O=C(NCCS(=O)(=O)O)c1ccc(NC(C(=O)Nc2ccc(-c3cc4ccccc4o3)cc2)C2=CCCCC2)cc1] | 574.5 (+) | C31H31N3O6S + 0.5 TFA 60.94 5.03 6.66 60.60 4.74 6.79 |
| 1.469 | 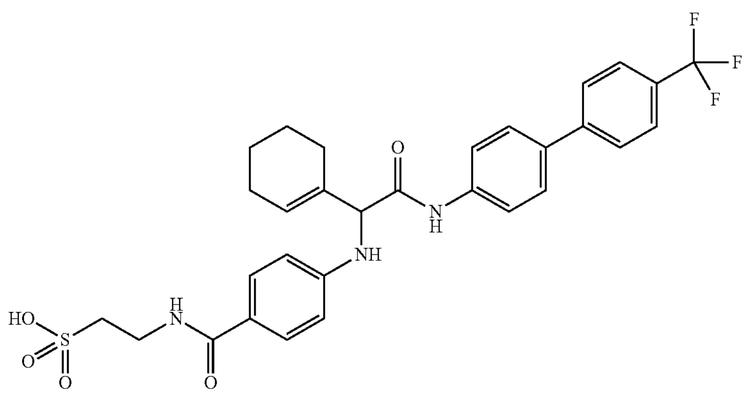 [SMILES: O=C(NCCS(=O)(=O)O)c1ccc(NC(C(=O)Nc2ccc(-c3ccc(C(F)(F)F)cc3)cc2)C2=CCCCC2)cc1] | 602.7 (+) | C31H31N3O6S + 0.5 TFA 60.94 5.03 6.66 60.60 4.74 6.79 |
| 1.470 | 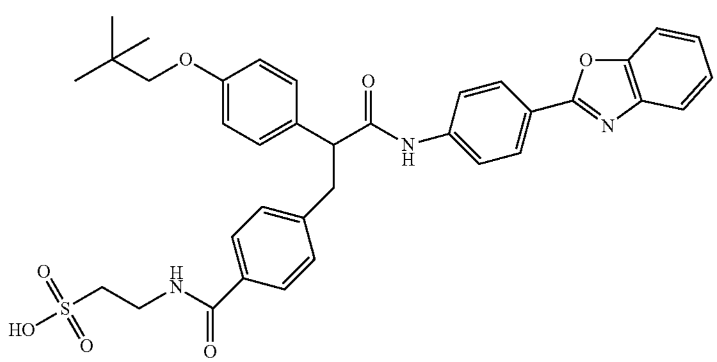 [SMILES: CC(C)(C)COc1ccc(C(Cc2ccc(C(=O)NCCS(=O)(=O)O)cc2)C(=O)Nc2ccc(-c3nc4ccccc4o3)cc2)cc1] | 656.6 (+) | C36H37N3O7S + (0.1) H2O + (0.1) TFA C: 64.99 H: 5.62 N: 6.28 C: 64.99 H: 5.79 N: 6.50 |
| 1.471 | 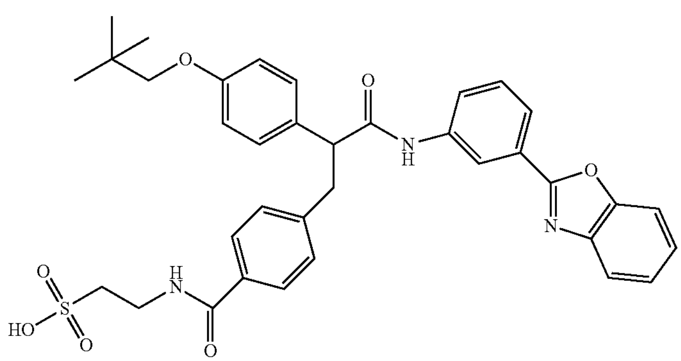 [SMILES: CC(C)(C)COc1ccc(C(Cc2ccc(C(=O)NCCS(=O)(=O)O)cc2)C(=O)Nc2cccc(-c3nc4ccccc4o3)c2)cc1] | 652.9 (+) | C37H37N3O6S + (1.5) H2O + (0.2) TFA C: 64.03 H: 5.78 N: 5.99 C: 64.09 H: 5.75 N: 5.87 |

-continued

| Ex# | Structure | LC/MS (mode) | Formula CHN (Calcd) CHN (Found) |
|---|---|---|---|
| 1.472 | 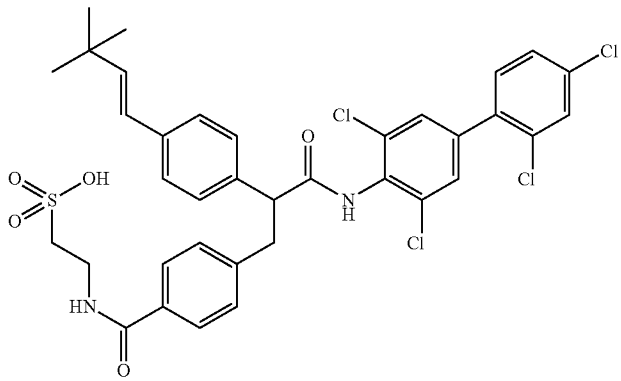 [SMILES: CC(C)(C)/C=C/c1ccc(C(Cc2ccc(C(=O)NCCS(=O)(=O)O)cc2)C(=O)Nc2c(Cl)cc(-c3ccc(Cl)cc3Cl)cc2Cl)cc1] | 747.6 (−) | 36H33N2O5Cl4SNa + (1) H2O<br>C: 54.83 H: 4.47 N: 3.55<br>C: 54.68 H: 4.47 N: 3.52 |
| 1.473 | 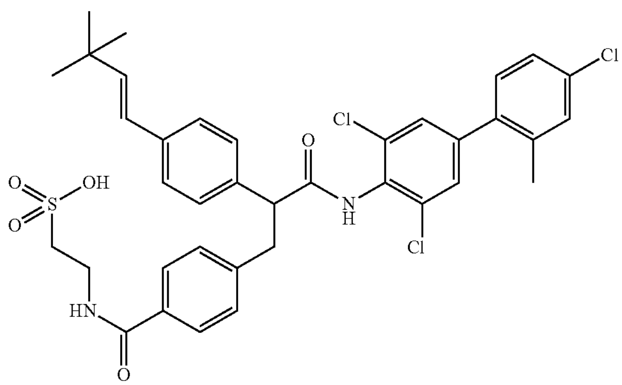 [SMILES: Cc1cc(Cl)ccc1-c1cc(Cl)c(NC(=O)C(Cc2ccc(C(=O)NCCS(=O)(=O)O)cc2)c2ccc(/C=C/C(C)(C)C)cc2)c(Cl)c1] | 727.4 (−) | C37H36N2O5Cl3SNa + (1.5) H2O<br>C: 57.18 H: 5.06 N: 3.60<br>C: 57.20 H: 4.90 N: 3.59 |
| 1.474 | 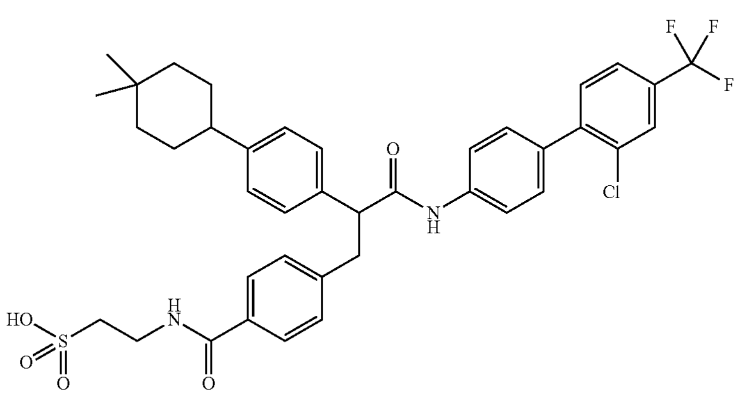 [SMILES: CC1(C)CCC(c2ccc(C(Cc3ccc(C(=O)NCCS(=O)(=O)O)cc3)C(=O)Nc3ccc(-c4ccc(C(F)(F)F)cc4Cl)cc3)cc2)CC1] | 741.9 (+) | C39H40ClF3N2O5S + (0.9) EtOH<br>C: 62.61 H: 5.85 N: 3.53<br>C: 62.84 H: 5.46 N: 4.02 |

-continued

| Ex# | Structure | LC/MS (mode) | Formula CHN (Calcd) CHN (Found) |
|---|---|---|---|
| 1.475 | 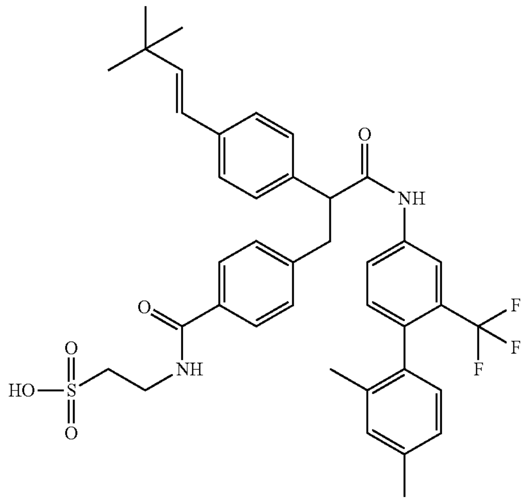 [SMILES: Cc1ccc(-c2ccc(NC(=O)C(Cc3ccc(C(=O)NCCS(=O)(=O)O)cc3)c3ccc(/C=C/C(C)(C)C)cc3)cc2C(F)(F)F)c(C)c1] | 705.9 (−) | C39H41F3N2O5S<br>C: 66.27 H: 5.85 N: 3.96<br>Not Tested |
| 1.476 | 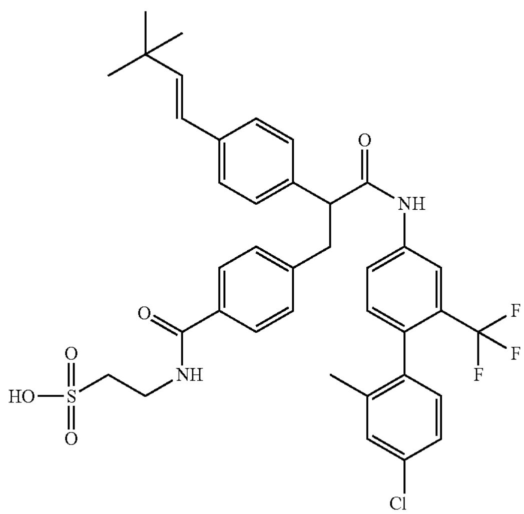 [SMILES: Cc1cc(Cl)ccc1-c1ccc(NC(=O)C(Cc2ccc(C(=O)NCCS(=O)(=O)O)cc2)c2ccc(/C=C/C(C)(C)C)cc2)cc1C(F)(F)F] | 725.6 (−) | C38H38ClF3N2O5S<br>C: 62.76 H: 5.27 N: 3.85<br>Not Tested |
| 1.477 | 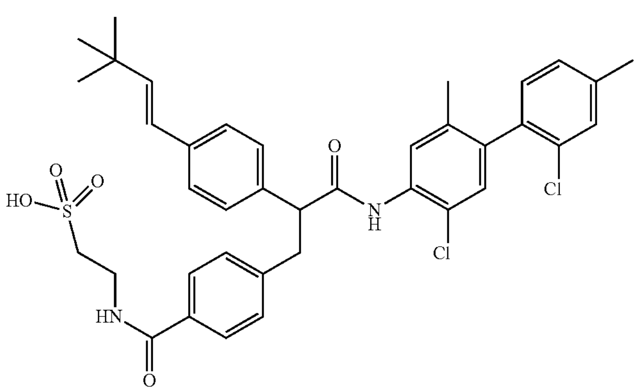 [SMILES: Cc1ccc(-c2cc(Cl)c(NC(=O)C(Cc3ccc(C(=O)NCCS(=O)(=O)O)cc3)c3ccc(/C=C/C(C)(C)C)cc3)cc2C)c(Cl)c1] | 705.9 (−) | C38H39Cl2N2O5SNa +<br>(1.7) H2O<br>C: 60.03 H: 5.62 N: 3.68<br>C: 59.82 H: 5.40 N: 3.61 |

-continued

| Ex# | Structure | LC/MS (mode) | Formula CHN (Calcd) CHN (Found) |
|---|---|---|---|
| 1.478 | 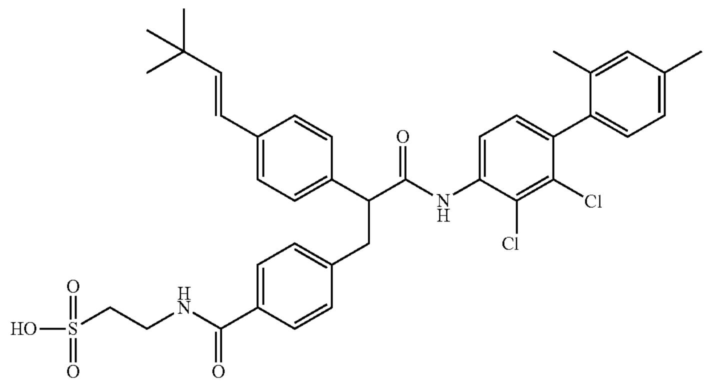 [SMILES: Cc1ccc(-c2ccc(NC(=O)C(Cc3ccc(C(=O)NCCS(=O)(=O)O)cc3)c3ccc(/C=C/C(C)(C)C)cc3)c(Cl)c2Cl)c(C)c1] | 705.9 (−) | C38H39Cl2N2O5SNa + (0.5) H2O + (0.2) NaHCO3<br>C: 60.73 H: 5.36 N: 3.71<br>C: 60.65 H: 4.88 N: 3.57 |
| 1.479 | 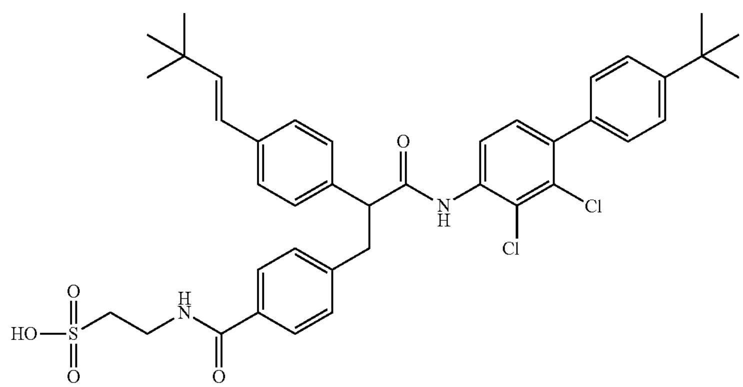 [SMILES: CC(C)(C)/C=C/c1ccc(C(Cc2ccc(C(=O)NCCS(=O)(=O)O)cc2)C(=O)Nc2ccc(-c3ccc(C(C)(C)C)cc3)c(Cl)c2Cl)cc1] | 733.9 (−) | C40H43Cl2N2O5SNa + (1.5) H2O + (0.2) NaHCO3<br>C: 60.24 H: 5.81 N: 3.49<br>C: 60.59 H: 5.47 N: 3.22 |
| 1.480 | 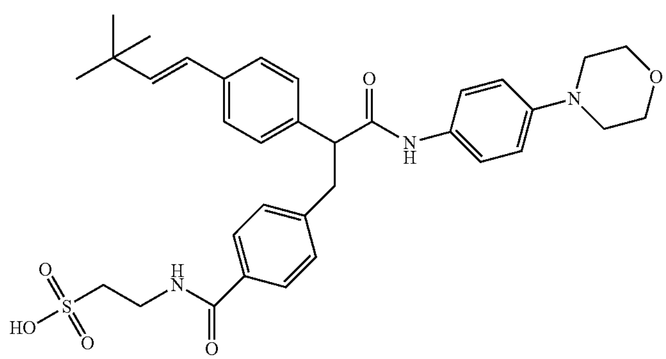 [SMILES: CC(C)(C)/C=C/c1ccc(C(Cc2ccc(C(=O)NCCS(=O)(=O)O)cc2)C(=O)Nc2ccc(N3CCOCC3)cc2)cc1] | 620.6 (+) | C34H41N3O6S + (2.0) H2O + (0.3) TFA<br>C: 60.23 H: 6.62 N: 6.09<br>C: 60.04 H: 6.43 N: 5.96 |
| 1.481 | 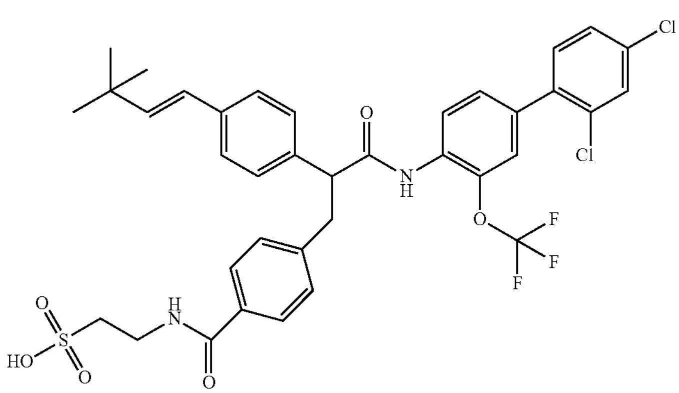 [SMILES: CC(C)(C)/C=C/c1ccc(C(Cc2ccc(C(=O)NCCS(=O)(=O)O)cc2)C(=O)Nc2ccc(-c3ccc(Cl)cc3Cl)cc2OC(F)(F)F)cc1] | 765.6 (+) | C37H35N2O6F3Cl2S + (1.5) H2O + (0.1) TFA<br>C: 55.71 H: 4.79 N: 3.49<br>C: 55.45 H: 4.87 N: 3.44 |

-continued

| Ex# | Structure | LC/MS (mode) | Formula CHN (Calcd) CHN (Found) |
|---|---|---|---|
| 1.482 | 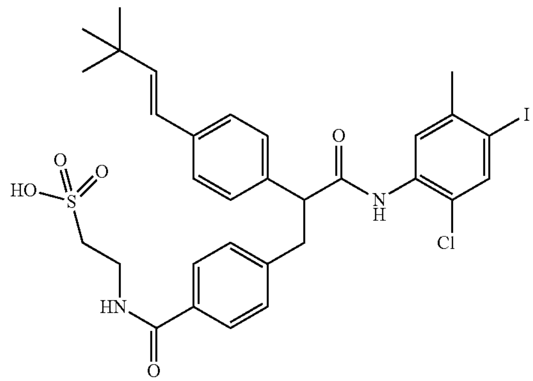 [SMILES: Cc1cc(NC(=O)C(Cc2ccc(C(=O)NCCS(=O)(=O)O)cc2)c2ccc(/C=C/C(C)(C)C)cc2)c(Cl)cc1I] | 707.6 (−) | C31H33ClIN2O5SNa + (1.7) H2O<br>C: 48.89 H: 4.82 N: 3.68<br>C: 48.70 H: 4.63 N: 3.50 |
| 1.483 | 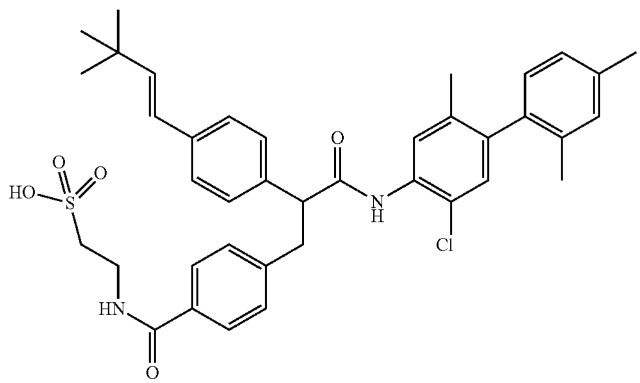 [SMILES: Cc1ccc(-c2cc(Cl)c(NC(=O)C(Cc3ccc(C(=O)NCCS(=O)(=O)O)cc3)c3ccc(/C=C/C(C)(C)C)cc3)cc2C)c(C)c1] | 685.9 (−) | C39H42ClN2O5SNa + (1.5) H2O<br>C: 63.62 H: 6.16 N: 3.80<br>C: 63.63 H: 6.01 N: 3.70 |
| 1.484 | 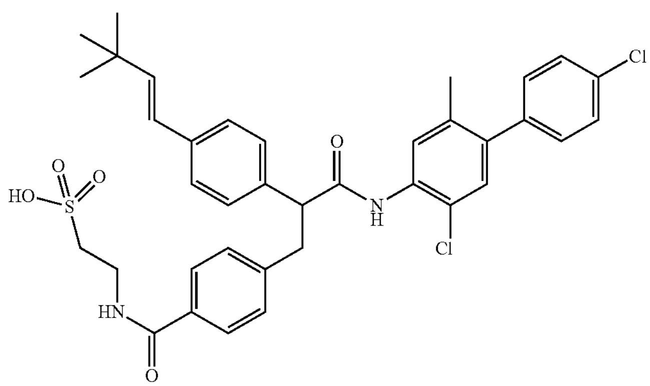 [SMILES: Cc1cc(NC(=O)C(Cc2ccc(C(=O)NCCS(=O)(=O)O)cc2)c2ccc(/C=C/C(C)(C)C)cc2)c(Cl)cc1-c1ccc(Cl)cc1] | 691.9 (−) | C37H37Cl2N2O5SNa + (1.6) H2O<br>C: 59.69 H: 5.44 N: 3.76<br>C: 59.57 H: 5.10 N: 3.66 |
| 1.485 | 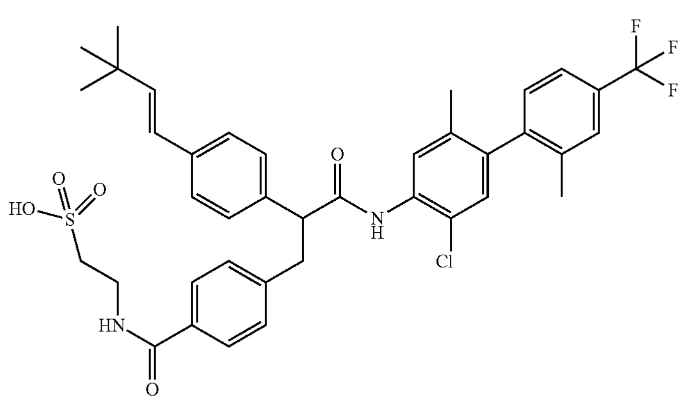 [SMILES: Cc1cc(C(F)(F)F)ccc1-c1cc(Cl)c(NC(=O)C(Cc2ccc(C(=O)NCCS(=O)(=O)O)cc2)c2ccc(/C=C/C(C)(C)C)cc2)cc1C] | 759.9 (−) | C38H36Cl2F3N2O5SNa + (2.3) H2O<br>C: 55.32 H: 4.96 N: 3.40<br>C: 55.67 H: 4.70 N: 3.30 |

| Ex# | Structure | LC/MS (mode) | Formula CHN (Calcd) CHN (Found) |
|---|---|---|---|
| 1.486 | 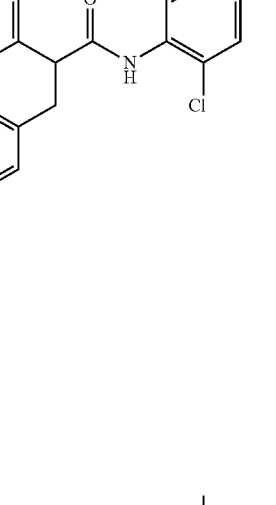 | 739.9 (−) | C39H39ClF3N2O5SNa + (2.0) H2O<br>C: 58.61 H: 5.42 N: 3.50<br>C: 58.67 H: 5.27 N: 3.34 |
| 1.487 | 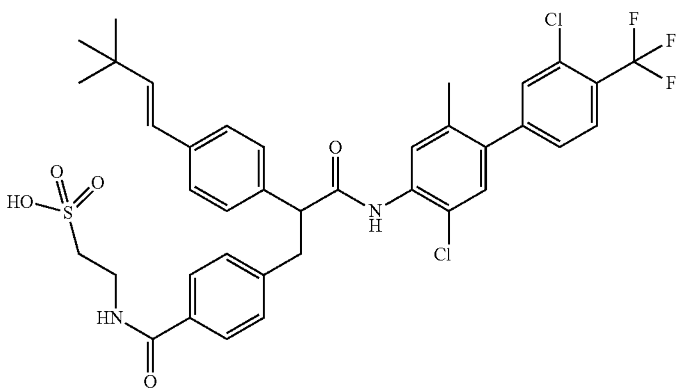 [SMILES: Cc1cc(NC(=O)C(Cc2ccc(C(=O)NCCS(=O)(=O)O)cc2)c2ccc(/C=C/C(C)(C)C)cc2)c(Cl)cc1-c1ccc(C(F)(F)F)c(Cl)c1] | 761.9 (+) | C38H36Cl2F3N2O5SNa + (2.3) H2O<br>C: 55.32 H: 4.96 N: 3.40<br>C: 55.09 H: 4.70 N: 3.29 |
| 1.488 | 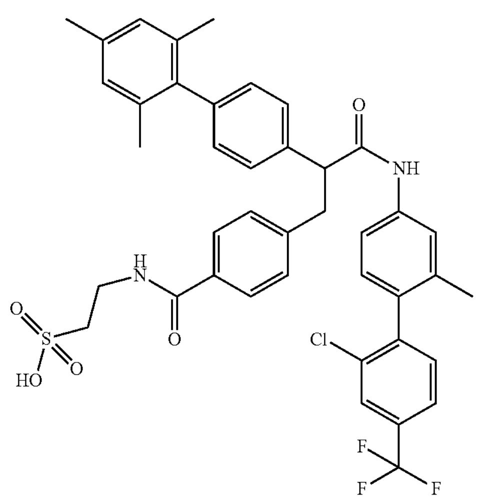 [SMILES: Cc1cc(C)c(-c2ccc(C(Cc3ccc(C(=O)NCCS(=O)(=O)O)cc3)C(=O)Nc3ccc(-c4ccc(C(F)(F)F)cc4Cl)c(C)c3)cc2)c(C)c1] | 763.9 (+) | C41H37ClF3N2O5SNa + (2.2) H2O<br>C: 59.70 H: 5.06 N: 3.40<br>C: 59.67 H: 4.96 N: 3.24 |

-continued
| Ex# | Structure | LC/MS (mode) | Formula CHN (Calcd) CHN (Found) |
|---|---|---|---|
| 1.489 | 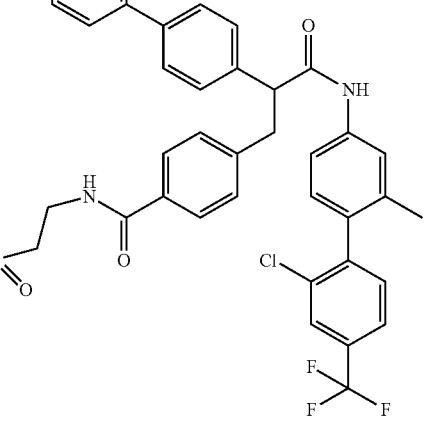 | 750.6 (+) | C40H35ClF3N2O5SNa + (2.1) H2O<br>C: 59.38 H: 4.88 N: 3.46<br>C: 59.04 H: 4.52 N: 3.39 |
| 1.490 | 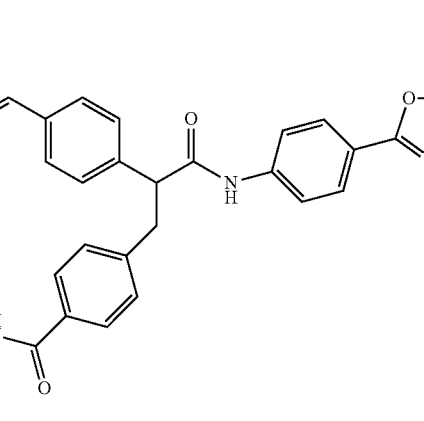 | 653.6 (+) | C36H36N4O6S + (1.5) H2O + (0.2) TFA<br>C: 62.23 H: 5.63 N: 7.97<br>C: 62.26 H: 5.63 N: 7.67 |
| 1.491 | 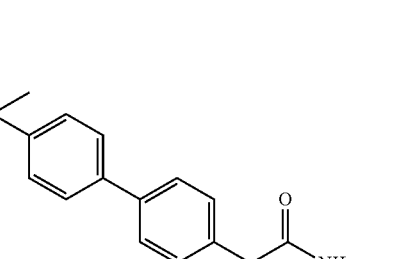 | 733.6 (+) | C35H33N2O5F3BrSNa + (1.0) H2O<br>C: 54.48 H: 4.57 N: 3.63<br>C: 54.48 H: 4.28 N: 3.42 |

US 10,239,829 B2
| Ex# | Structure | LC/MS (mode) | Formula CHN (Calcd) CHN (Found) |
|---|---|---|---|
| 1.492 | 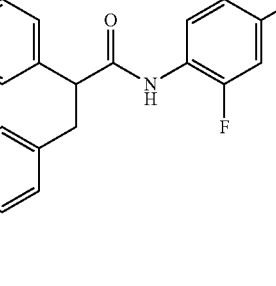 | 677.9 (−) | C37H36F3N2O5SNa + (1.5) H2O<br>C: 61.06 H: 5.40 N: 3.85<br>C: 61.06 H: 5.31 N: 3.74 |
| 1.493 | 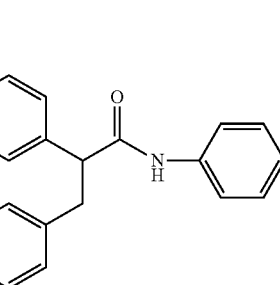 | 701.9 (−) | C43H45N2O5SNa + (2.8) H2O<br>C: 66.61 H: 6.58 N: 3.61<br>C: 66.54 H: 6.15 N: 3.60 |
| 1.494 | 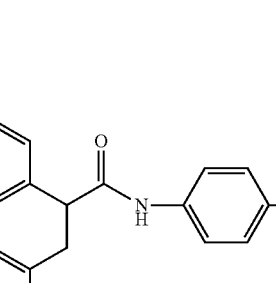 | 735.9 (−) | C39H37N2O5F3ClSNa + (0.8) H2O<br>C: 60.39 H: 5.02 N: 3.61<br>C: 60.38 H: 4.76 N: 3.59 |
| 1.495 | 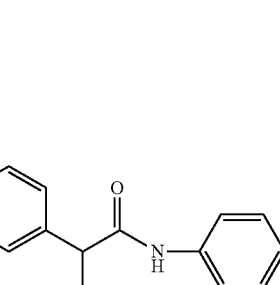 | 671.6 (−) | C41H41N2O5Na + (1.0) H2O + (0.2) NaHCO3<br>C: 65.35 H: 5.67 N: 3.66<br>C: 65.36 H: 5.49 N: 3.58 |

| Ex# | Structure | LC/MS (mode) | Formula CHN (Calcd) CHN (Found) |
|---|---|---|---|
| 1.496 | 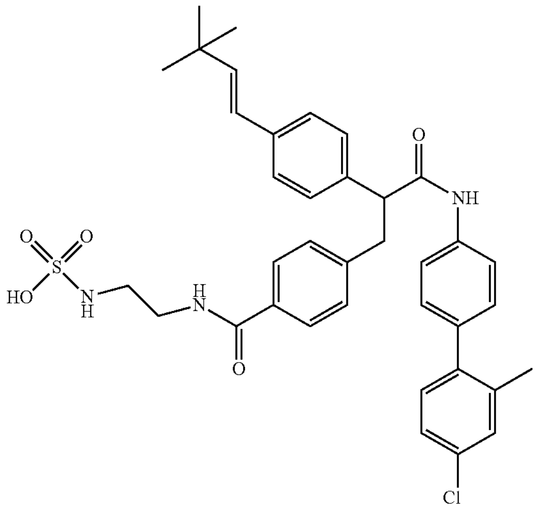 [SMILES: Cc1cc(Cl)ccc1-c1ccc(NC(=O)C(Cc2ccc(C(=O)NCCNS(=O)(=O)O)cc2)c2ccc(/C=C/C(C)(C)C)cc2)cc1] | 672.6 (−) | C37H39N3O5ClSNa + (2.8) H2O + (0.3) NaCO3<br>C: 57.55 H: 5.77 N: 5.40<br>C: 57.49 H: 5.54 N: 5.28 |

Benzoxazole containing anilines required for the synthesis of compounds such as the one in Example 1.146 were generated using known methods as shown below:

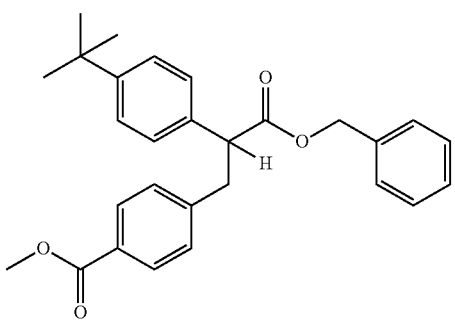

To a suspension of 4-acetylamino-2-methyl-benzoic acid (2.0 g, 10.3 mmol) in PPA (~85 g) was added aminophenol (1.2 g, 10.8 mmol). The reaction was heated to 200° C. for 2 h, then carefully quenched in aqueous sodium carbonate (~50% saturated) at room temperature. Ethyl acetate was added, and the organic layer was washed with water and brine, and dried over sodium sulfate. The crude product was obtained as an orange oil and was subsequently purified by flash column chromatography on silica gel eluting with ethyl acetate in hexanes to afford the desired product, 4-benzoxazol-2-yl-3-methyl-phenylamine as a colorless solid, 290 mg (13%). $^1$H NMR (300 MHz, DMSO-d6): δ 7.84-7.81 (m, 1H), 7.64-7.62 (m, 2H), 7.32-7.27 (m, 2H), 6.51 (d, J=9.0 Hz, 2H), 5.83 (s, 2H), 2.61 (s, 3H).

LC-MS m/z=225 $[C_{14}H_{12}N_2O+H]^+$.

Example 1.497

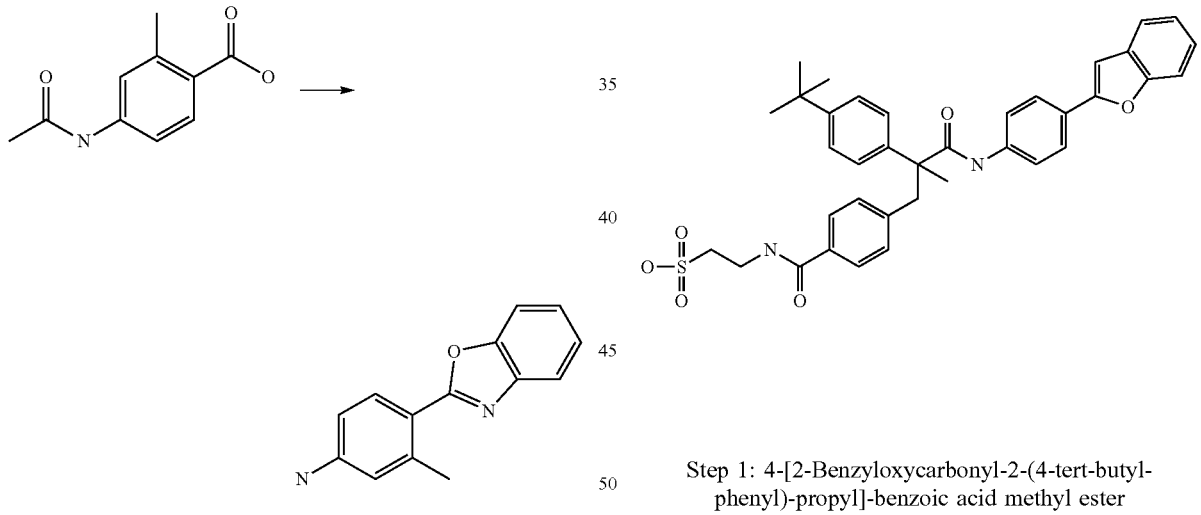

Step 1: 4-[2-Benzyloxycarbonyl-2-(4-tert-butyl-phenyl)-propyl]-benzoic acid methyl ester -continued

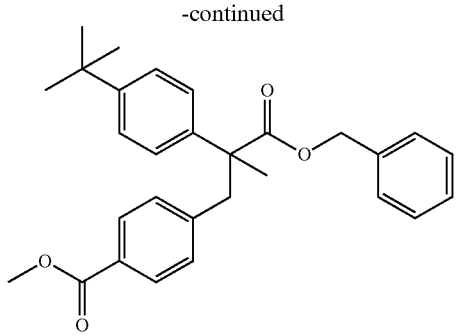

A solution of LiHMDS in toluene (1.0M, 1.6 mL, 1.6 mmol) was cooled in a dry-ice acetone bath (−78° C.) and diluted with 3 mL of THF. A solution of 4-[2-Benzyloxy-carbonyl-2-(4-tert-butyl-phenyl)-ethyl]-benzoic acid methyl ester (675 mg, prepared as described in Bioorg. Med. Chem Lett. 2004, 14, 2047-2050) in 5 mL of THF was added via cannula. The mixture was stirred at the same temperature 30 min. It was then transferred to an acetone/ice bath, where it was warmed to ~10° C. over a 1.5 h period. The mixture was cooled back to −78° C. and iodomethane (0.11 mL) was added via syringe. The mixture was then stirred for a 2 h period while allowing it to warm up to room temperature (approximately 2 h). The mixture was poured over a mixture of ethyl acetate and ice cold aqueous ammonium chloride. The organic phase was washed with water and saturated aqueous sodium chloride and dried over magnesium sulfate. The residue obtained after removal of the solvent was treated with hexanes/ethyl acetate to cause the formation to precipitate the title compound (307 mg, 44%) HNMR (500 MHz, DMSO-d6, selected signals): 5.12 (2H, ABquartet), 3.82 (3H, s), 3.47 (1H, d, J=13.0 Hz), 3.22 (1H, d, J=13.2 Hz), 1.37 (3H, s), 1.28 (9H, s)

Step 2: 4-[2-(4-tert-Butyl-phenyl_2-carboxy-propyl]-benzoic acid methyl ester

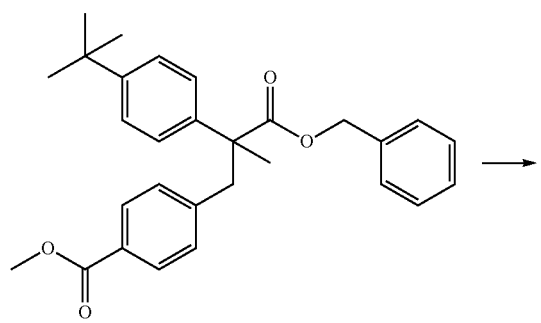

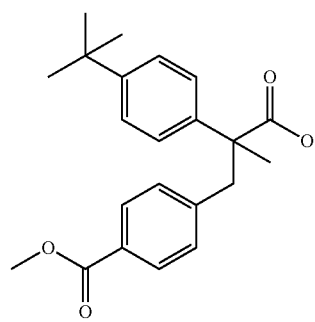

To a mixture of 4-[2-Benzyloxycarbonyl-2-(4-tert-butyl-phenyl)-propyl]-benzoic acid methyl ester (307 mg), ethanol (10 mL) and ethyl acetate (5 mL) added diisopropyl ethyl amine (0.15 mL) and 10% Pd/C (351 mg). The heterogeneous mixture was stirred under an atmosphere of hydrogen for a period of 3 h. The solids were removed at this time by filtration and the solvents removed under educed pressure. The residue was partitioned between ethyl acetate and 0.5M aqueous hydrochloric acid. The organic phase was washed (water, saturated sodium chloride and dried over magnesium sulfate. Concentration afforded the carboxylic acid as a white powder. LCMS: 355.6 (M+H)+

Step 3: 2-{4-[2-(4-Benzofuran-2-yl-phenylcarbamoyl)-2-(4-tert-butyl-phenyl)-propyl]-benzoylamino}-ethanesulfonic acid Using the methods described in Example 1.001 with appropriate modifications, the title compound was obtained.

LCMS: 637.9 (M−H)− Elemental Analysis: Calculated for C37H38N2O6S+(2.0)H2O: C: 65.86, H: 6.27, N: 4.15. Found: C: 65.92, H: 6.23, N: 3.98.

Enantiomerically enriched compounds of this class were synthesized using the methods illustrated below:

J4-{3-(4-Benzyl-2-oxo-oxazolidin-3-yl)-2-[4-(3,3-dimethyl-but-1-enyl)-phenyl)-3-oxo-propyl}-benzoic acid methyl ester

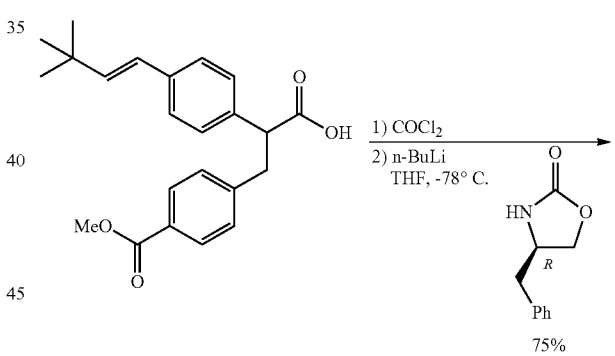

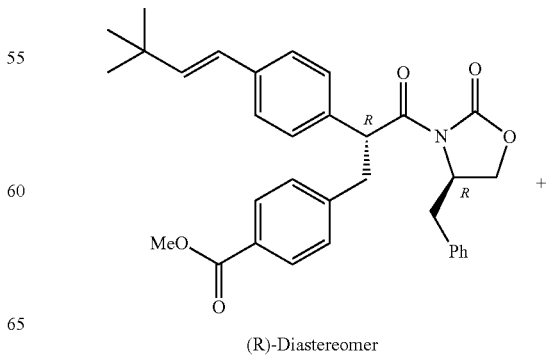

(R)-Diastereomer

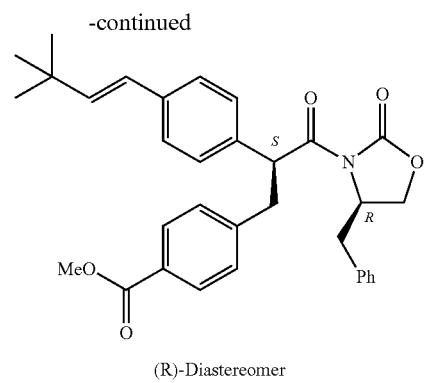

(R)-Diastereomer

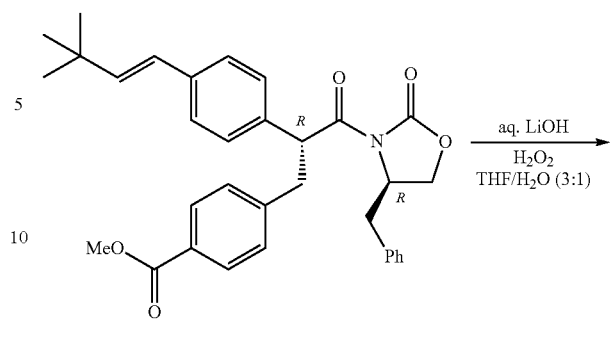

Step 1

To a solution of 4-[2-carboxy-2-[4-(3,3-dimethyl-but-1-enyl)-phenyl]-ethyl]-benzoic acid methyl ester (1) (1.5 g, 4.0 mmol) in $CH_2Cl_2$ (25 mL) at room temperature was added oxalyl chloride (1.03 g, 8.19 mmol). The reaction mixture was stirred overnight at room temperature and the solvent was removed under reduced pressure. The residue was dried under vacuum for 3-4 h. The crude product was used in the next step.

Step-2

To a stirred solution of R-(+)-4-benzyl-oxazolidinone (2) (0.89 g, 4.9 mmol) in THF (30 mL) at −78° C. was added n-BuLi (4.9 mL, 4.9 mmol, 1.0 M solution in hexane). The reaction mixture was stirred for 45 min, at −78° C., then acid chloride (1.6 g, 4.16 mmole) was added dropwise, stirred for 2 h at −78° C. then allowed to warm to room temperature and stirred for another hour (monitored by TLC). The reaction mixture was quenched with saturated $NH_4Cl$ solution (50 mL) and stirred for 10 min. The reaction mixture was extracted with ethyl acetate (2×150 mL) and the combined organic layers were washed with brine, dried over $MgSO_4$ and concentrated under reduced pressure. The crude product was purified by column chromatography on silica gel, eluting with $CH_2Cl_2$-hexanes (40%) to separate the (R)- and (S)-diastereomers of 4-{3-(4-(R)-Benzyl-2-oxo-oxazolidin-3-yl)-2-[4-(3,3-dimethyl-but-1-enyl)-phenyl]-3-oxo-propyl}-benzoic acid methyl ester (3) and (4) as a mixture (0.82 g, and 0.8 g, 75%):

(R)-Diastereomer $^1$H NMR (300 MHz, DMSO-$d_6$): 7.92 (d, J=8.7 Hz, 2H), 7.35-7.00 (m, 9H), 7.0-6.96 (m, 2H), 6.24 (s, 2H), 5.42 (dd, J=6.3, 9.0 Hz, 1H), 4.56-4.51 (m, 1H), 4.04-3.99 (m, 2H), 3.87 (s, 3H), 3.54 (dd, J=9.3, 13.5 Hz, 1H), 3.13-3.10 (m, 2H), 2.59 (dd, J=6.3, 9.0 Hz, 1H), 1.11 (s, 9H); TLC conditions: Uniplate silica gel, 250 microns; mobile phase=ethyl acetate/hexanes (4:1); $R_f$=0.55.

(S)-Diastereomer $^1$H NMR (300 MHz, DMSO-$d_6$): 7.88 (d, J=8.1 Hz, 2H), 7.36-7.16 (m, 9H), 6.95-6.92 (m, 2H), 6.27 (s, 2H), 5.35 (dd, J=7.2, 9.0 Hz, 1H), 4.66-4.60 (m, 1H), 4.09-3.98 (m, 2H), 3.88 (s, 3H), 3.49 (dd, J=9.3, 13.5 Hz, 1H), 3.13-3.02 (m, 2H), 2.52 (dd, J=6.3, 9.0 Hz, 1H), 1.12 (s, 9H); TLC conditions: Uniplate silica gel, 250 microns; mobile phase=ethyl acetate/hexanes (4:1); $R_f$=0.4.

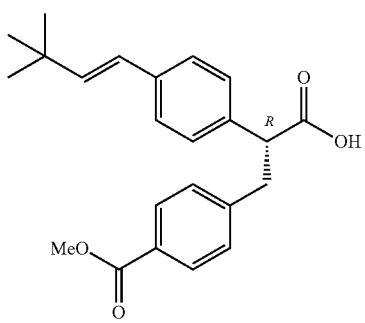

(R)-4-[2-carboxy-2-[4-(3,3-dimethyl-but-1-enyl)-phenyl]-ethyl]-benzoic acid methyl ester To a stirred solution of the (R)-diastereomer of 4-{3-(4-(R)-Benzyl-2-oxo-oxazolidin-3-yl)-2-[4-(3,3-dimethyl-but-1-enyl)-phenyl]-3-oxo-propyl}-benzoic acid methyl ester (0.43 g, 0.81 mmol) in THF/$H_2O$ (20 mL) (3:1) at room temperature were added $H_2O_2$ (2.2 mL, 8.1 mmol 35% in $H_2O$) followed by LiOH (40 mg, 1.63 mmol). The reaction mixture was stirred for 3 h, at room temperature, quenched with (0.1 N HCl). The reaction mixture was extracted with ethyl acetate (100 mL) and dried over $MgSO_4$, filtered and concentrated under reduced pressure to afford corresponding acid. The crude product was purified by column chromatography on silica gel, eluting with $CH_2Cl_2$/MeOH 2%-15% to afford the title compound (0.4 g, 100%).

$^1$H NMR (300 MHz, CDCl$_3$): δ 7.77 (d, J=8.1 Hz, 2H), 7.28 (d, J=8.7 Hz, 4H), 7.18 (d, J=8.4 Hz, 2H), 6.24 (dd, J=4.5, 13.4 Hz, 2H), 3.90 (t, J=6.9 Hz, 1H), 3.78 (s, 3H), 3.43 (dd, J=7.2, 12.9 Hz, 1H), 2.95 (dd, J=7.2, 12.9 Hz, 1H), 1.05 (s, 9H); TLC conditions: Uniplate silica gel, 250 microns; mobile phase=$CH_2Cl_2$/MeOH (10%); $R_f$=0.35.

Chiral HPLC conditions: Kromasil 100-5-TBB chiral column 250×4.6 cm, (5% hexane/2-propanol to 30%), 35 min, flow rate 1 mL/min, RT=12.41 min (enantiomeric excess=>96% single enantiomer)

(S)_4-[2-carboxy-2-[4-(3,3-dimethyl-but-1-enyl)-phenyl]-ethyl]-benzoic acid methyl ester The procedure described for the synthesis of the (R)-isomer was followed with appropriate modifications.

509

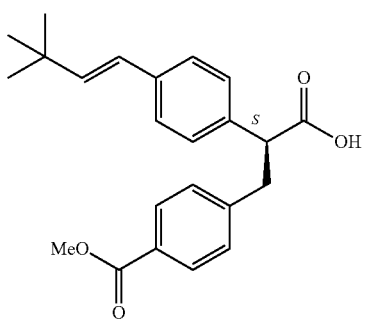

¹H NMR (300 MHz, CDCl₃): δ 7.77 (d, J=8.1 Hz, 2H), 7.28 (d, J=8.7 Hz, 4H), 7.18 (d, J=8.4 Hz, 2H), 6.24 (dd, J=4.5, 13.4 Hz, 2H), 3.90 (t, J=6.9 Hz, 1H), 3.78 (s, 3H), 3.43 (dd, J=7.2, 12.9 Hz, 1H), 2.95 (dd, J=7.2, 12.9 Hz, 1H), 1.05 (s, 9H); TLC conditions: Uniplate silica gel, 250 microns; mobile phase=CH₂Cl₂/MeOH (10%); R_f=0.35. Chiral HPLC conditions: Kromasil 100-5-TBB chiral column 250×4.6 cm, (5% hexane/2-propanol to 30%), 35 min, flow rate 1 m/min, RT=14.03 min (enantiomeric excess=>96% single enantiomer)

(R)-4-[2-(4-Benzofuran-2-yl-phenylcarbamoyl)-2-[4-(3,3-dimethyl-but-1-enyl)-phenyl-ethyl]-benzoic acid methyl ester

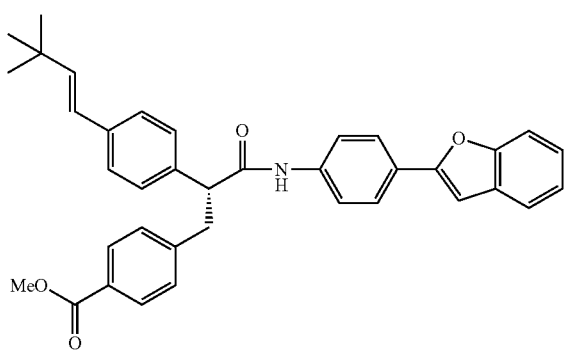 [SMILES: COC(=O)c1ccc(C[C@@H](C(=O)Nc2ccc(-c3cc4ccccc4o3)cc2)c2ccc(/C=C/C(C)(C)C)cc2)cc1]

To a stirred suspension of 4-[2-carboxy-2-[4-(3,3-dimethyl-but-1-enyl)-phenyl)-ethyl]-benzoic acid methyl ester (0.56 g, 1.10 mmol) in anhydrous CH₂Cl₂ (20 mL), was added oxalylchloride (0.38 g, 3.06 mmol) at rt. The reaction mixture was stirred for 14 h, concentrated under reduced pressure and azeotroped with CH₂Cl₂ (2×10 mL). The crude acid chloride (0.062 g, 1.61 mmol) was treated with 4-benzofuran phenyl amine (0.37 g, 1.93 mmol) and N,N-diisopropylethylamine (0.83 g, 6.44 mmol) in CH₂Cl₂ (25 mL) at 0° C. The reaction mixture was stirred for 14 h at rt and concentrated under reduced pressure. The crude product was purified by column chromatography on silica gel, eluting with CH₂Cl₂-hexanes (30%-100%) to afford (R)-4-[2-(4-Benzofuran-2-yl-phenylcarbamoyl)-2-[4-(3,3-dimethyl-but-1-enyl)-phenyl-ethyl]-benzoic acid methyl ester as a brownish solid (0.35 g, 48%) ¹H NMR (300 MHz, CDCl₃): δ 7.80 (d, J=8.1 Hz, 2H), 7.71-7.66 (m, 2H), 7.50-7.43 (m, 4H), 7.28-6.94 (m, 8H), 6.87 (s, 1H), 6.20 (s, 2H), 3.81 (s, 3H), 3.71-3.59 (m, 2H), 3.03 (dd, J=7.2, 12.9 Hz, 1H), 1.04 (s, 9H); TLC conditions: Uniplate silica gel, 250 microns; mobile phase=ethyl acetate/hexanes (2:1); R_f=0.55.

510

(S)-4-[2-(4-Benzofuran-2-yl-phenylcarbamoyl)-2-[4-(3,3-dimethyl-but-1-enyl)-phenyl-ethyl]-benzoic acid methyl ester

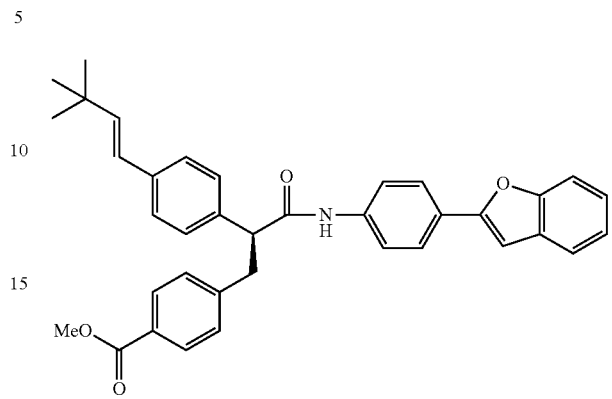

The procedure described in for the synthesis of the (R)-isomer was followed with appropriate modifications.

¹H NMR (300 MHz, CDCl₃): δ 7.80 (d, J=8.4 Hz, 2H), 7.74 (d, J=8.7 Hz, 2H), 7.56-7.47 (m, 4H), 7.34-7.11 (m, 8H), 6.93 (s, 1H), 6.27 (s, 2H), 3.87 (s, 3H), 3.77-3.65 (m, 2H), 3.10 (dd, J=7.5, 12.6 Hz, 1H), 1.11 (s, 9H); LC-MS m/z=554 [C₃₁H₄₂NBrO₄+H]⁺; TLC conditions: Uniplate silica gel, 250 microns; mobile phase=ethyl acetate/hexanes (2:1); R_f=0.55.

(R)-4-[2-(4-Benzofuran-2-yl-phenylcarbamoyl)-2-[4-(3,3-dimethyl-but-1-enyl)-phenyl-ethyl]-benzoic acid

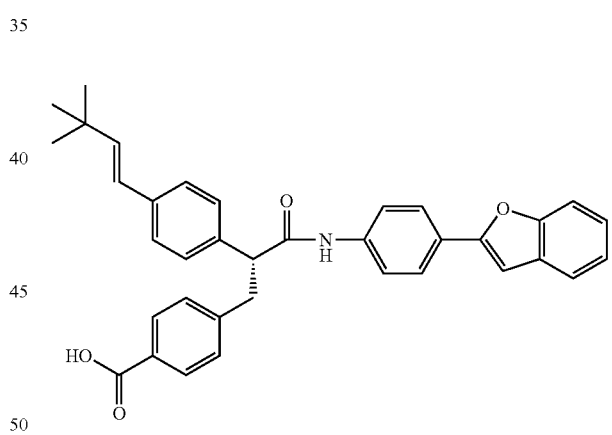

To a stirred solution of (R)-4-[2-(4-Benzofuran-2-yl-phenylcarbamoyl)-2-[4-(3,3-dimethyl-but-1-enyl)-phenyl-ethyl]-benzoic acid methyl ester (0.29 g, 0.52 mmol) in EtOH/THF/H₂O(4:2:1) (12 mL) at rt, was added aq. 40% NaOH (2.5 ml), The reaction mixture was stirred for overnight, After completion of the reaction, the solvent was removed under reduced pressure. The crude was taken to pH=2 with 4N HCl and the resulting mixture was extracted with ethyl acetate. The organic layer was dried over MgSO₄ and concentrated, the resulting compound was dried under vacuum to afford 4-[2-(4-Benzofuran-2-yl-phenylcarbamoyl)-2-[4-(3,3-dimethyl-but-1-enyl)-phenyl-ethyl]-benzoic acid as a solid (0.27 g, 98%):

¹H NMR (300 MHz, CD₃OD): 10.23 (s, 1H), 7.78 (d, J=8.7 Hz, 4H), 7.55-7.66 (m, 4H), 7.20-7.40 (m, 9H), 6.10 (bt, 1H), 4.03 (t, J=7.2 Hz, 1H), 3.45 (dd, J=5.0, 9.0 Hz, 1H), 3.03 (dd, J=5.7, 12.9 Hz, 1H), 2.20-2.40 (m, 2H), 2.10-2.15 (m, 2H), 1.65-1.75 (m, 2H), 1.50-1.60 (m, 2H); LC-MS m/z=541 $[C_{37}H_{34}NO_3+H]^+$.

Example 1.498: (R)-2-(4-{2-(4-Benzofuran-2-yl-phenylcarbamoyl)-2-[4-(3,3-dimethyl-but-1-enyl)-phenyl]-ethyl}-benzoyl amino-ethane sulfonic acid sodium salt

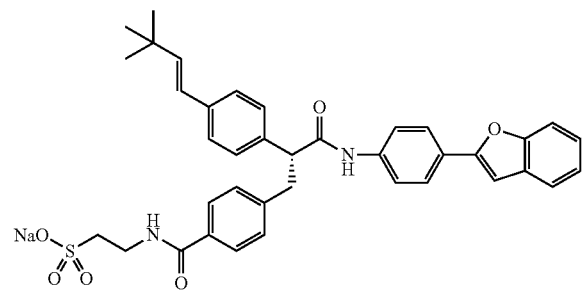

To a mixed of (R)-4-[2-(4-Benzofuran-2-yl-phenylcarbamoyl)-2-[4-(3,3-dimethyl-but-1-enyl)-phenyl-ethyl]-benzoic acid (0.14 g, 0.25 mmol), EDCI (95 mg, 0.5 mmol), HOBt (79 mg, 0.5 mmol), N,N-diisopropylethylamine (134 mg, 1.0 mmol) in DMF (7 mL), and followed by taurine (65 mg, 0.5 mmol) was added. The resulting mixture was stirred for 14 h and monitored by LCMS. After completion of the reaction the solvent was removed under reduced pressure. The resulting mixture was treated with an excess of sodium bicarbonate and loaded on top of a C-18 chromatography column. The column was eluted with H₂O/Acetonitrile 0%-100%, the product-containing fractions were lypholized to give 2-(4-{2-(4-Benzofuran-2-yl-phenylcarbamoyl)-2-[4-(3,3-dimethyl-but-1-enyl)-phenyl]-ethyl}-benzoyl amino-ethane sulfonic acid sodium salt as a white solid. (95 mg)

¹H NMR (500 MHz, DMSO-d₆): 10.25 (s, 1H), 8.40 (t, J=5.5 Hz, 1H), 7.80 (d, J=8.5 Hz, 2H), 7.67-7.57 (m, 6H), 7.34 (s, 1H), 7.28-7.21 (m, 8H), 6.28 (d, J=9.9 Hz, 2H), 4.0 (t, J=4.8 Hz, 1H), 3.48-3.42 (m, 3H), 3.04 (dd, J=4.2, 8.4 Hz, 1H), 2.62 (t, J=11.0 Hz, 2H), 1.09 (s, 9H); LC-MS m/z=651 $[C_{38}H_{35}N_2O_6SNa+H]^+$; HPLC conditions: Waters Atlantis C-18 OBD 4.6×150 mm; mobile phase=ACN/(H₂O: 0.1TFA) flow rate=1.0 mL/min; detection=UV@254 and 220 nm retention time in min: 24.03; Anal Calcd: (MF: $C_{38}H_{37}N_2O_6SNa+2.5H_2O$) Calcd: C:63.58, H:5.90, N:3.90. Found: C: 63.49, H:5.90, N:3.71.

Chiral HPLC conditions: Regis-Whelh-01-786615 T=30° C.; mobile phase=100% ACN/(5% Phosphate pH=7.0, ACN) flow rate=1.0 mL/min; detection=320 nm. Retention time in min: 26.34 min (enantiomeric excess=75.8%)

Example 1.499: (S)-2-(4-{2-(4-Benzofuran-2-yl-phenylcarbamoyl)-2-[4-(3,3-dimethyl-but-1-enyl)-phenyl]-ethyl}-benzoyl amino-ethane sulfonic acid sodium salt (13)

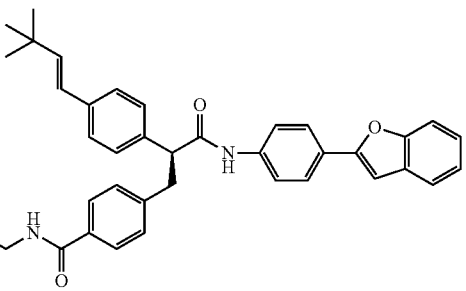

The procedure described for the synthesis of the (R)-isomer was followed with appropriate modifications.

¹H NMR (500 MHz, DMSO-d₆): 10.25 (s, 1H), 8.39 (t, J=5.5 Hz, 1H), 7.80 (d, J=8.5 Hz, 2H), 7.67-7.57 (m, 6H), 7.34 (s, 1H), 7.28-7.21 (m, 8H), 6.28 (dd, J=16.5, 25.5 Hz, 2H), 4.0 (t, J=7.5 Hz, 1H), 3.47-3.41 (m, 3H), 3.04 (dd, J=4.2, 6.5 Hz, 1H), 2.62 (t, J=7.0 Hz, 2H), 1.07 (s, 9H); LC-MS m/z=651 $[C_{38}H_{35}N_2O_6SNa+H]^+$; HPLC conditions: Waters Atlantis C-18 OBD 4.6×150 mm; mobile phase=ACN/(H₂O:0.1TFA) flow rate=1.0 mL/min; detection=UV @254 and 220 nm retention time in min: 23.55; Anal Calcd: (MF:$C_{38}H_{37}N_2O_6SNa+3.7H_2O$) Calcd: C:61.73, H:6.05, N:3.79. Found: C: 61.52, H:5.74, N:3.74.

Chiral HPLC conditions: Regis-Whelh-01-786615 T=30° C.; mobile phase=100% ACN/(5% Phosphate pH=7.0, ACN) flow rate=1.0 mL/min; detection=320 nm. Retention time in min: 20.29 min (enantiomeric excess=66.4%)

Example 2.001: 2-{4-[2-[5-(4-Bromo-phenyl)-isoxazol-3-yl]-2-(4-tert-butyl-phenyl)-ethyl]-benzoylamino}-ethanesulfonic acid Step A

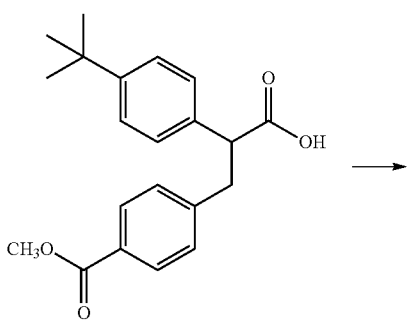

-continued

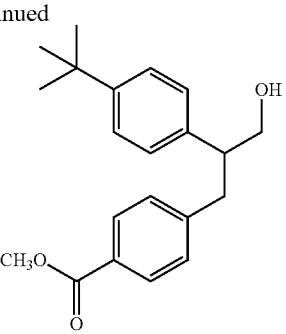

A solution of 10 g (30 mmol) of the carboxylic acid in THF was cooled to 0° C. and treated with 60 mL of a 1M solution of borane in THF (60 mmol). The cooling bath was removed and the mixture stirred at room temperature for 2.5 h. Added 8 mL of a 1:1 mixture of acetic acid and water and concentrated under reduced pressure. The residue was partitioned between ethyl acetate and saturated aqueous sodium bicarbonate. The organic phase was washed (water, saturated sodium chloride) and dried over magnesium sulfate. Concentration under reduced pressure left 9.73 g of the alcohol as a yellow oil.

HNMR (300 MHz, CDCl3): 7.90 (2H, m), 7.33 (2H, m), 7.18-7.11 (4H, m), 3.89 (3H, s), 3.77 (2H, m), 3.09 (2H, m), 2.95 (1H, m), 1.31 (9H, s)

Step B

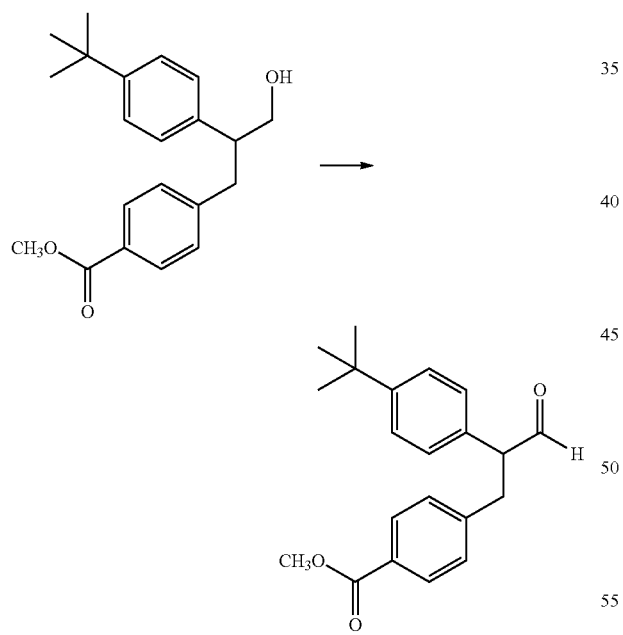

To a solution of the alcohol (9.73 g, 30 mmol) in dichloromethane added pyridinium chlorochromate (4.8 g, 150 mmol) and stirred at room temperature for a period of 16 h. Added further PCC (2.0 equivalents) and stirred for an additional 1 h, followed by the addition of 3.0 more equivalents of PCC and stirring for 3 more hours. The mixture was filtered through a silica plug and the solution concentrated and chromatographed on silica, using an ethyl acetate-hexanes gradient. Obtained 7.9 g of the aldehyde as a yellow oil.

HNMR (300 MHz, CDCl3): 9.72 (1H, d, J=1.5 Hz), 7.89 (2H, d, J=8.5 Hz), 7.37 (2H, d, J=8.5 Hz), 7.14 (2H, d, J=8.5 Hz), 7.06 (2H, d, J=8.2 Hz), 3.91 (3H, s), 3.90 (1H, m), 3.54 (1H, m), 3.03 (1H, m), 1.34 (9H, s)

Alternative oxidation conditions: To a solution of the alcohol (9.730 g) in dichloromethane (100 mL) at 0° C. was slowly added a 15% w/w solution of Dess-Martin periodinane (20.43 g) in dichloromethane. The reaction was warmed to 23° C. and stirred at the same temperature for a 3 h period, when it was quenched by addition of saturated sodium bicarbonate. The organic phase was separated, washed with brine and dried over sodium sulfate. Removal of the solvent and chromatography on silica gel using an ethyl acetate-hexanes gradient yielded 9.7 g of the aldehyde Step C

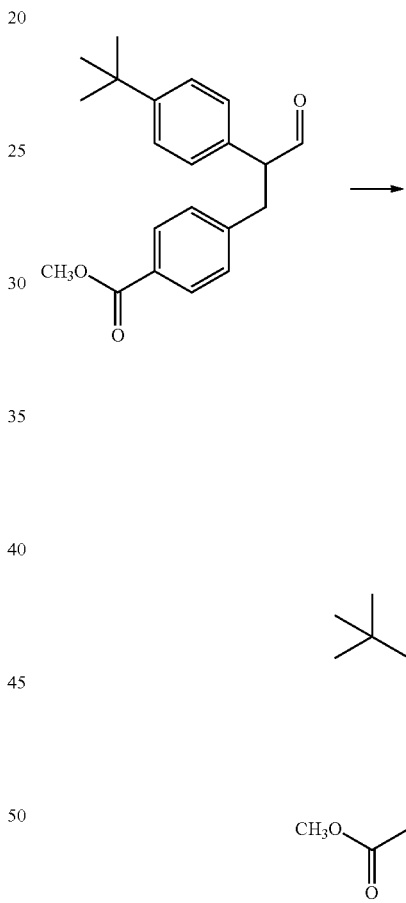

A mixture of 7.9 g (24.4 mmol) of the aldehyde, 4 g (48.8 mmol) of sodium acetate and 1.7 g (24.4 mmol) of hydroxylamine hydrochloride in THF was stirred at room temperature for 16 h. Further 0.17 g of hydroxylamine hydrochloride were added and after three additional hours the mixture was concentrated and the residue was partitioned between ethyl acetate and water. The organic phase was washed (water, saturated sodium chloride) and dried (magnesium sulfate). Concentrated and chromatographed on silica gel using a gradient of ethyl acetate and hexanes to afford a mixture of geometric isomers of the oxime (5.19 g).

LCMS (C21H25NO3+H): 340

Step D

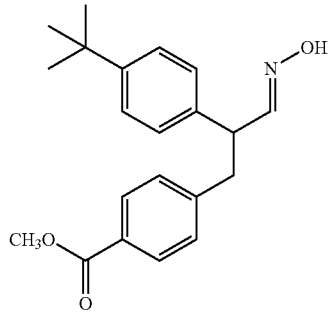 

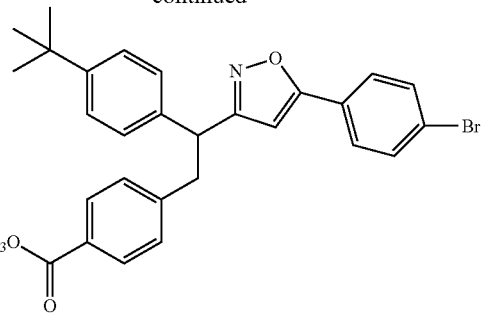

To a mixture of 1.0 g (5.5 mmol) of 4-bromophenyl acetylene and 0.767 mL (5.5 mmol) of triethylamine in dichloromethane (10 mL) was added dropwise a solution of 516 mg (1.4 mmol) of the starting chloroooxime. The mixture was stirred at room temperature overnight and worked up by washing with aqueous hydrochloric acid and half saturated sodium chloride solution. The solution was dried (magnesium sulfate), concentrated under reduced pressure and the residue was chromatographed on silica using an ethyl acetate hexane gradient. Obtained a light yellow foam (280 mg). LCMS (C29H28BrNO3+H): 520.2

Step F

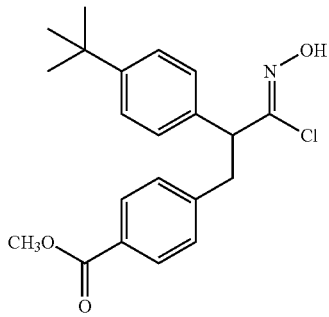

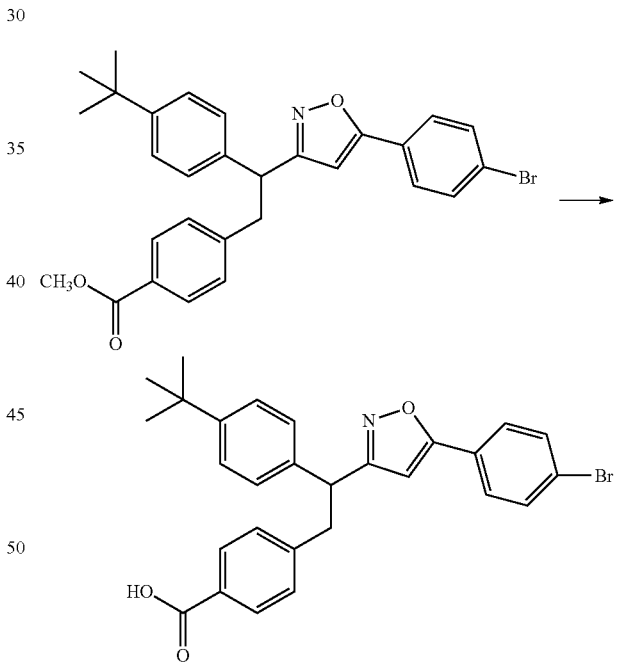

A solution of 3.53 g (10.4 mmol) of the starting oxime in DMF was treated with 1.39 g of N-chlorosuccinimide (10.4 mmol) and the resulting mixture was stirred at room temperature for 3 h. The DMF was evaporated under reduced pressure and the residue was partitioned between ether and water. The organic phase was washed (water, saturated sodium chloride) and dried (magnesium sulfate). Obtained 3.5 g of the product as a yellow oil. LCMS (C21H24ClNO3+H): 374.1

Step E

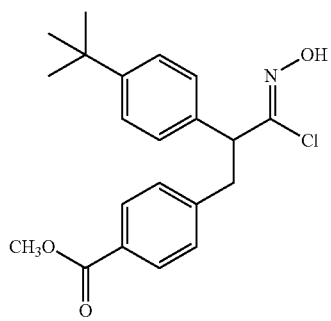 

To the starting methyl ester 280 mg (0.54 mmol) in THF (6 mL), methanol (4 mL) and water (2 mL) added sodium hydroxide (24 mg, 0.6 mmol). The reaction mixture was stirred at room temperature for 16 h. Added further 24 mg (0.6 mmol) of sodium hydroxide and stirred for an additional 3 h at the same temperature. The mixture was acidified with 1M aqueous HCl and extracted with ethyl acetate. The solution was washed with water and saturated sodium chloride and dried over magnesium sulfate. Concentration left a white solid that was used without further purification. LCMS (C28H26BrNO3+H): 505

Step G

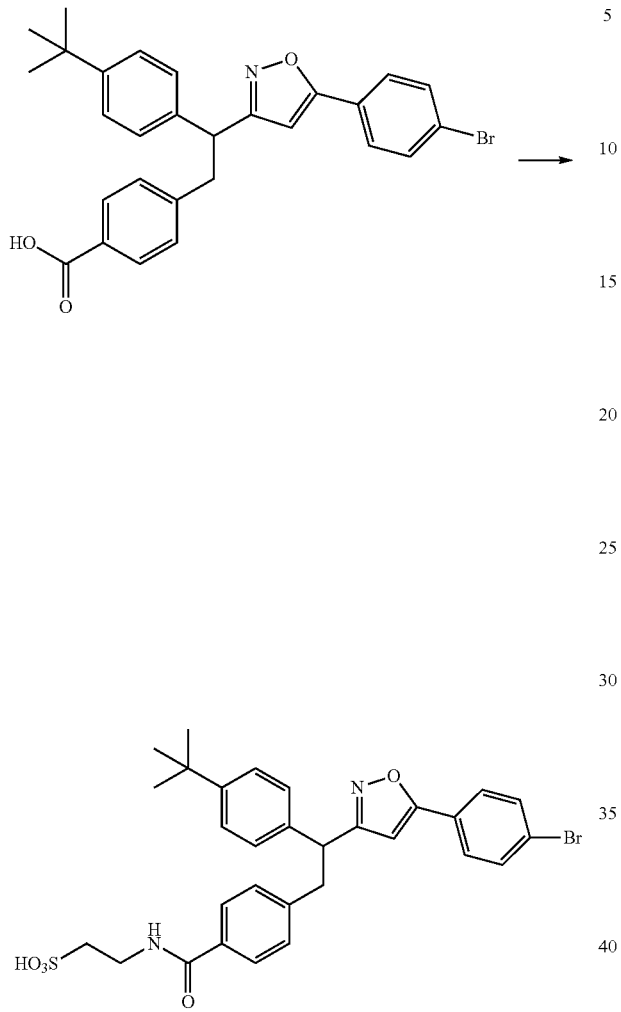

Example 2.002: 2-(4-{2-(4-tert-Butyl-phenyl)-2-[5-(2',4'-dichlorobiphenyl-4-yl)-isoxazol-3-yl]-ethyl}-benzoylamino)-ethanesulfonic acid

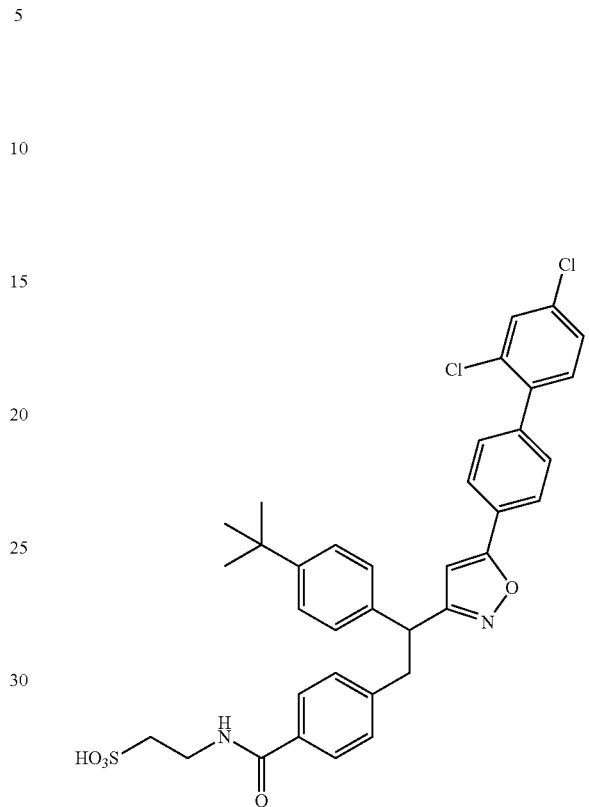

A mixture of the starting carboxylic acid (100 mg, 0.2 mmol), HOBt-H$_2$O (33 mg, 0.22 mmol), EDCI (42 mg, 0.22 mmol), taurine (38 mg, 0.3 mmol) and N,N-diisopropylethylamine (49 mg, 0.32 mmol) in DMF (5 mL) was stirred at 23° C. for a period of 16 h. The mixture was concentrated under reduced pressure and the residue partitioned between ethyl acetate and aqueous 4M HCl. The organic phase was washed (water, sat NaCl) and dried over magnesium sulfate. The reaction was repeated in the same scale and the two batches were combined and chromatographed on reverse phase silica gel (C18) using a gradient of acetonitrile:water (20% to 80% in acetonitrile). Evaporation of the product-containing fractions afforded 20 mg of a white solid.

HNMR (300 MHz, CD3OD): 7.71-7.61 (6H, m), 7.35-7.22 (6H, m), 6.76 (1H, s), 4.33 (1H, t, J=8.2 Hz), 3.8 (2H, m), 3.54 (1H, m), 3.22 (1H, m), 3.06 (1H, m), 1.28 (9H, s)

The starting bromide (Step G, 50 mg, 0.08 mmol) in DME (2 mL), ethanol (1 mL) and water (0.5 mL) was treated with 2,4-dichlorophenyl boronic acid (46 mg, 0.24 mmol), bistri(o-tolylphosphine) palladium dichloride (6 mg, 0.008 mmol) and sodium carbonate (42 mg, 0.4 mmol) and the container was sealed and irradiated in a microwave reactor at 125° C. for a 6 min period. The precipitated palladium was removed by filtration. The residue was loaded on top of a reverse phase silica column (C18) and eluted with an acetonitrile-water gradient (20% to 80% in acetonitrile. The sodium salt of the product was obtained as a white solid.

LCMS for C36H33Cl2N2O5S$^{(-)}$: 675.6; 677.6. HNMR (300 Mz, CD3OD): 7.88 (2H, d, J=8.5 Hz), 7.67 (2H, d, J=8.5 Hz), 7.61 (1H, s), 7.58 (2H, d, J=11.1 Hz), 7.53-7.26 (8H, m), 6.81 (1H, s), 4.46 (1H, t, J=7.9 Hz), 3.78 (2H, t, J=6.7 Hz), 3.6 (1H, m), 3.4 (1H, m), 3.07 (2H, t, J=6.5 Hz), 1.30 (9H, s)

The following compounds were made by the methods illustrated above, with modifications that will be evident to individuals skilled in the art

| Example | STRUCTURE | MASS SPECTRUM (mode) | Formula CHN (Calcd) CHN (Found) |
|---|---|---|---|
| 2.003 | 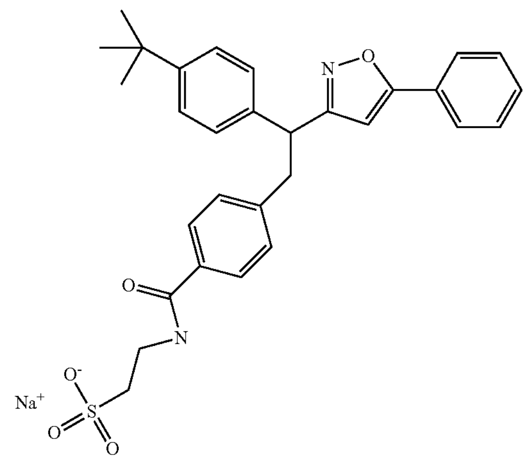 [SMILES: [Na+] ; CC(C)(C)c1ccc(C(Cc2ccc(C(=O)NCCS(=O)(=O)[O-])cc2)c2cc(-c3ccccc3)on2)cc1] | 531.4 (−) | C30H31N2O5SNa + 2H2O<br>61.00  5.97  4.74<br>60.66  5.86  4.58 |
| 2.005 | 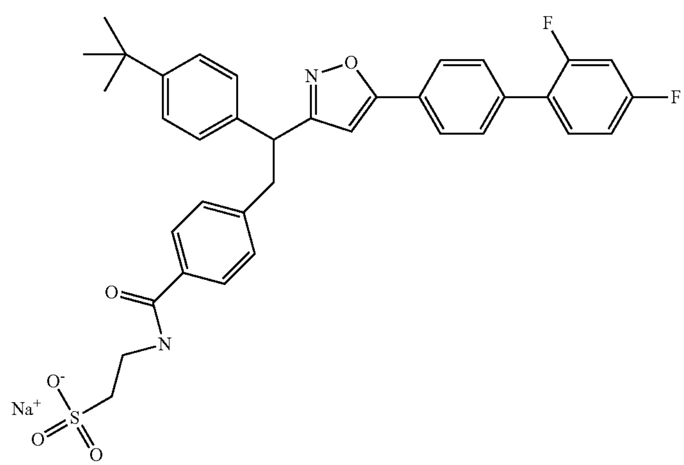 [SMILES: [Na+] ; CC(C)(C)c1ccc(C(Cc2ccc(C(=O)NCCS(=O)(=O)[O-])cc2)c2cc(-c3ccc(-c4ccc(F)cc4F)cc3)on2)cc1] | 643.6 (−) | C36H33N2O5F2SNa + 2.2H2O<br>61.22  5.34  3.97<br>60.91  4.93  4.21 |
| 2.007 | 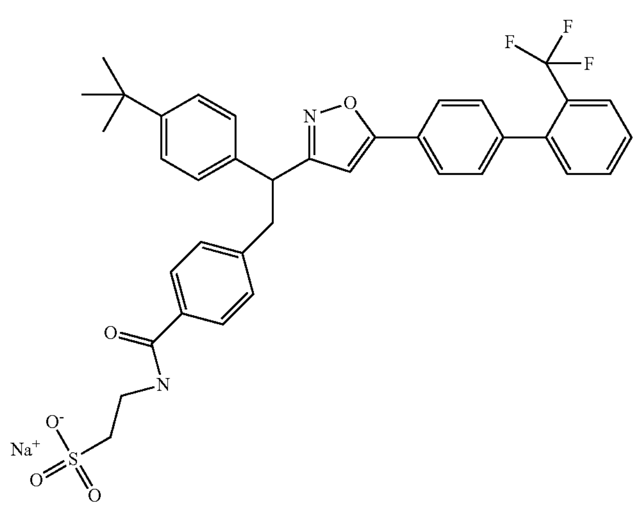 [SMILES: [Na+] ; CC(C)(C)c1ccc(C(Cc2ccc(C(=O)NCCS(=O)(=O)[O-])cc2)c2cc(-c3ccc(-c4ccccc4C(F)(F)F)cc3)on2)cc1] | 675.6 (−) | C37H34N2O5F3SNa + 1.1H2O<br>'61.85  5.08  3.90<br>61.50  5.16  3.87 |

| Example | STRUCTURE | MASS SPECTRUM (mode) | Formula CHN (Calcd) CHN (Found) |
|---|---|---|---|
| 2.008 | 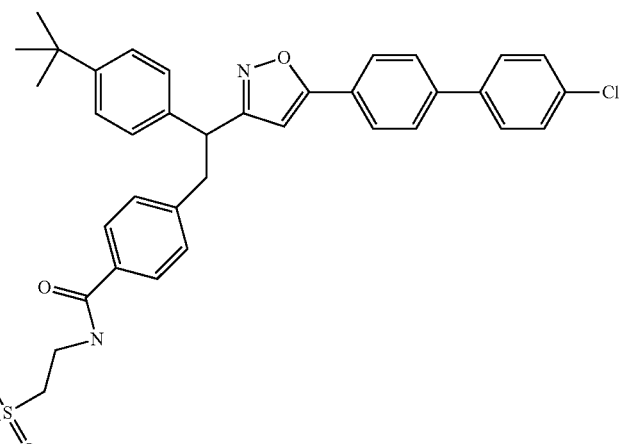 | 641.4, 643.6 (−) | C36H34N2O5ClSNa + 0.2NaOH + 1.4 H2O<br>61.91  5.34  4.01<br>61.56  4.97  4.09 |
| 2.009 | 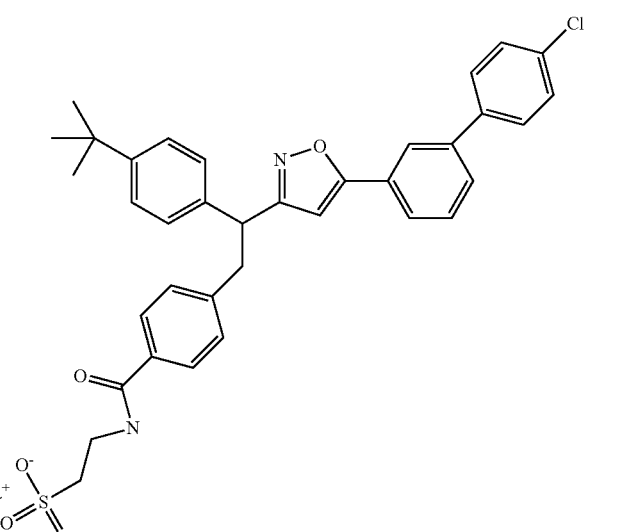 | 641.4, 643.6 (−) | C36H34N2O5ClSNa + 1.5H2O<br>'62.47  5.39  4.05<br>62.29  5.25  4.09 |
| 2.010 | 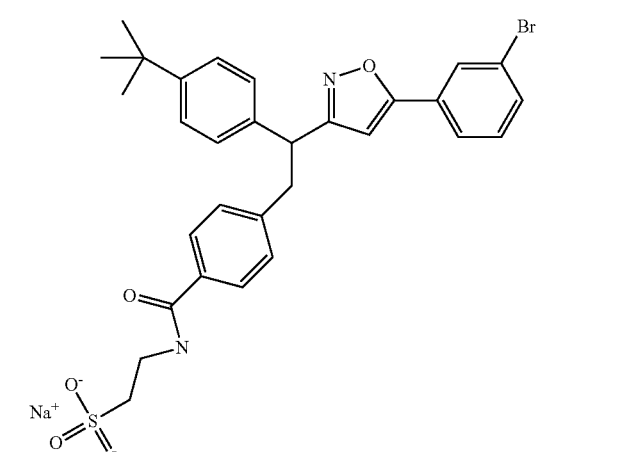 | 609.6 (−) | C30H30N2O5BrSNa + 1.2 H2O<br>55.00  4.98  4.28<br>54.67  4.97  4.43 |

-continued
| Example | STRUCTURE | MASS SPECTRUM (mode) | Formula CHN (Calcd) CHN (Found) |
|---|---|---|---|
| 2.011 | 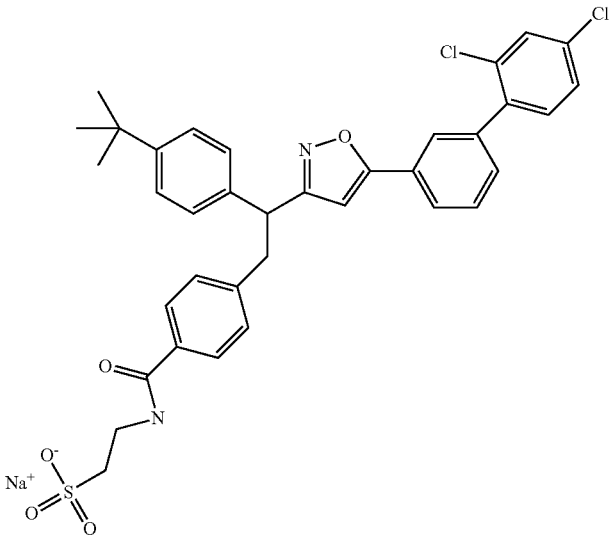 [SMILES: [Na+] ; CC(C)(C)c1ccc(C(Cc2ccc(C(=O)NCCS(=O)(=O)[O-])cc2)c2cc(-c3cccc(-c4ccc(Cl)cc4Cl)c3)on2)cc1] | 675.6 (−) | C36H33N2O5Cl2SNa + 2.5H2O<br>58.07  5.14  3.76<br>58.47  5.58  4.02 |
| 2.012 | 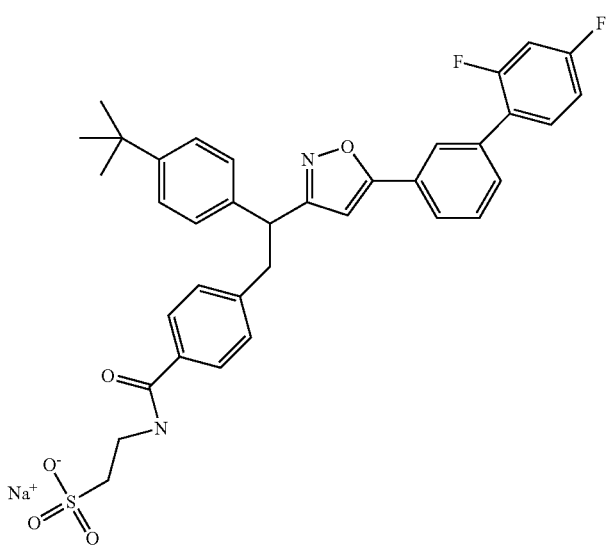 [SMILES: [Na+] ; CC(C)(C)c1ccc(C(Cc2ccc(C(=O)NCCS(=O)(=O)[O-])cc2)c2cc(-c3cccc(-c4ccc(F)cc4F)c3)on2)cc1] | 643.3 (−) | C36H33N2O5F2SNa + 1H2O<br>'63.15  5.15  4.09<br>62.95  5.29  4.14 |

-continued
| Example | STRUCTURE | MASS SPECTRUM (mode) | Formula CHN (Calcd) CHN (Found) |
|---|---|---|---|
| 2.013 | 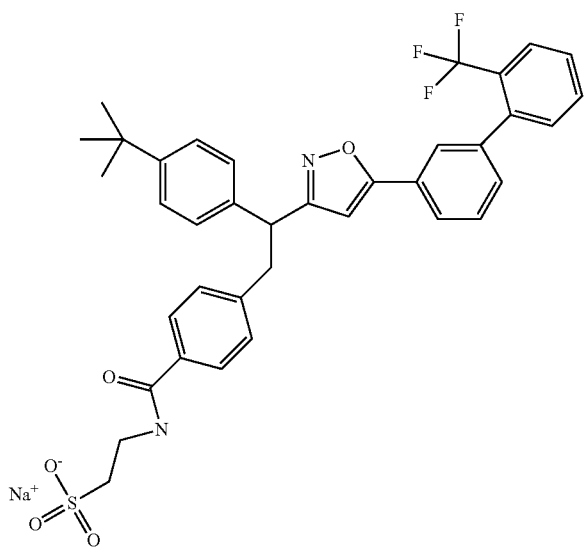 [SMILES: [Na+] ; CC(C)(C)c1ccc(C(Cc2ccc(C(=O)NCCS(=O)(=O)[O-])cc2)c2cc(-c3cccc(-c4ccccc4C(F)(F)F)c3)on2)cc1] | 675.6 (−) | C37H34N2O5F3SNa + 2H2O<br>60.48  5.21  3.81<br>60.23  4.87  3.77 |
| 2.014 | 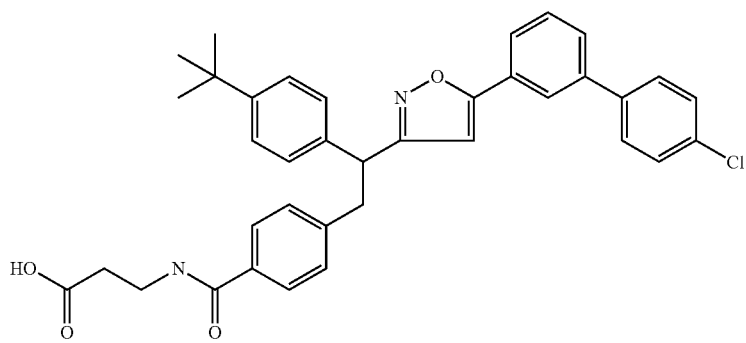 [SMILES: CC(C)(C)c1ccc(C(Cc2ccc(C(=O)NCCC(=O)O)cc2)c2cc(-c3cccc(-c4ccc(Cl)cc4)c3)on2)cc1] | 607.3 (+) | C37H35ClN2O4 + (1.0)H2O<br>C: 71.09; H: 5.97 N: 4.48<br>C: 71.33; H: 6.11; N: 4.60 |
| 2.015 | 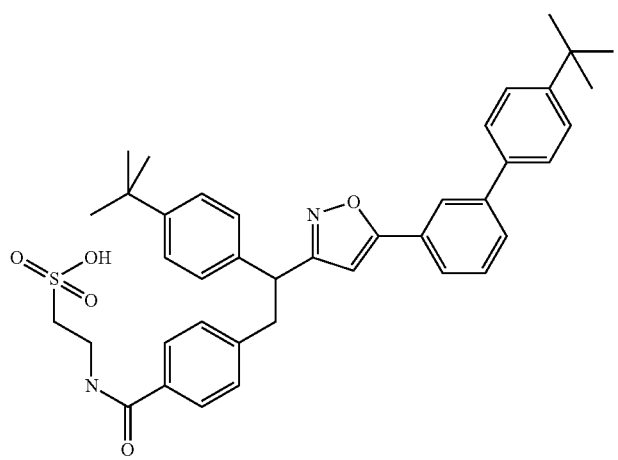 [SMILES: CC(C)(C)c1ccc(-c2cccc(-c3cc(C(Cc4ccc(C(=O)NCCS(=O)(=O)O)cc4)c4ccc(C(C)(C)C)cc4)no3)c2)cc1] | 675.0 (−) | C37H35F3N2O5S + 2H2O<br>C: 62.35; H: 5.51; N: 3.93<br>C: 62.18; H: 5.60; N: 3.89 |

-continued

| Example | STRUCTURE | MASS SPECTRUM (mode) | Formula CHN (Calcd) CHN (Found) |
|---|---|---|---|
| 2.016 | 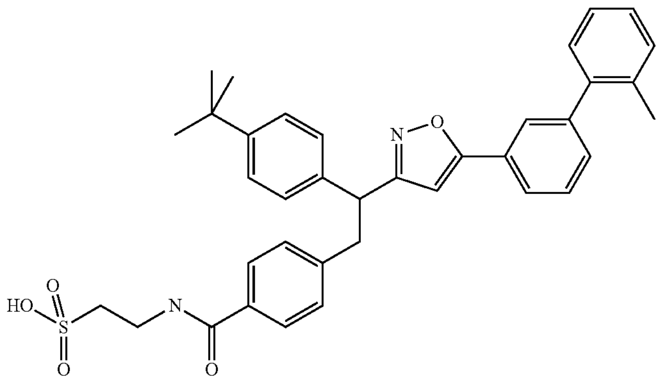 [SMILES: Cc1ccccc1-c1cccc(-c2cc(C(Cc3ccc(C(=O)NCCS(=O)(=O)O)cc3)c3ccc(C(C)(C)C)cc3)no2)c1] | 621.3 (−) | C37H38N2O5S + 1 H2O + 0.2 TFA<br>C: 67.69 H: 6.11 N: 4.22<br>C: 67.97 H: 6.37 N: 4.17 |
| 2.017 | 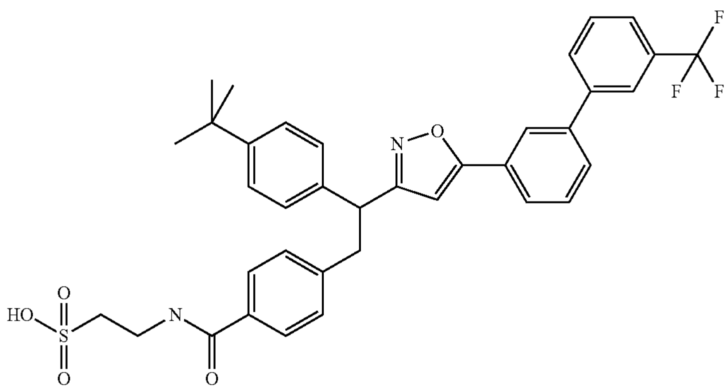 [SMILES: CC(C)(C)c1ccc(C(Cc2ccc(C(=O)NCCS(=O)(=O)O)cc2)c2cc(-c3cccc(-c4cccc(C(F)(F)F)c4)c3)on2)cc1] | 675.0 (−) | C37H35F3N2O5S + 1.5 H2O + 0.25 CF3CO2H<br>C: 61.51 H: 5.26 N: 3.83<br>C: 61.66 H: 5.55 N: 3.78 |
| 2.018 | 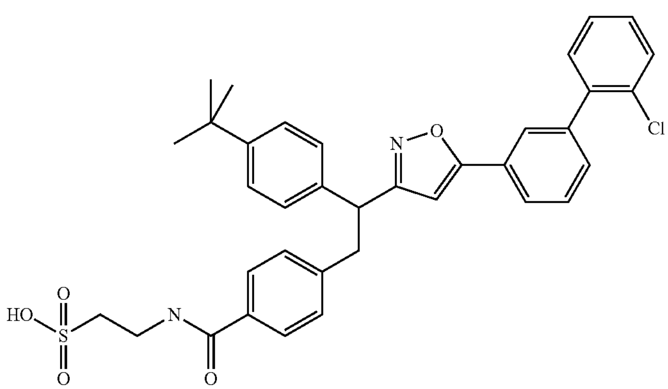 [SMILES: CC(C)(C)c1ccc(C(Cc2ccc(C(=O)NCCS(=O)(=O)O)cc2)c2cc(-c3cccc(-c4ccccc4Cl)c3)on2)cc1] | | C36H35ClN2O5S + 2 H2O + 0.1 TFA<br>C: 62.96 H: 5.71 N: 4.06<br>C: 63.03 H: 5.91 N: 3.87 |
| 2.019 | 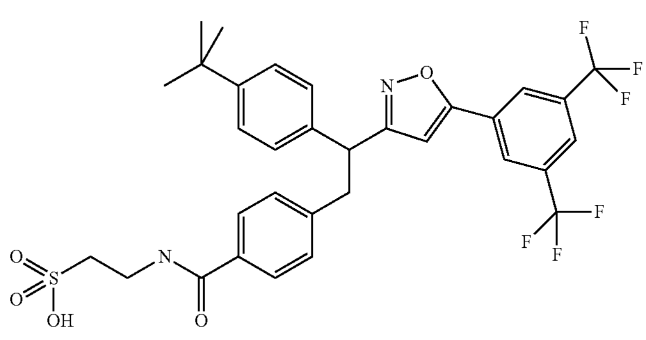 [SMILES: CC(C)(C)c1ccc(C(Cc2ccc(C(=O)NCCS(=O)(=O)O)cc2)c2cc(-c3cc(C(F)(F)F)cc(C(F)(F)F)c3)on2)cc1] | 668.66 | C32H30F6N2O5S<br>55.83  4.80  4.39<br>56.21  5.17  4.22 |

| Example | STRUCTURE | MASS SPECTRUM (mode) | Formula CHN (Calcd) CHN (Found) |
|---|---|---|---|
| 2.020 | 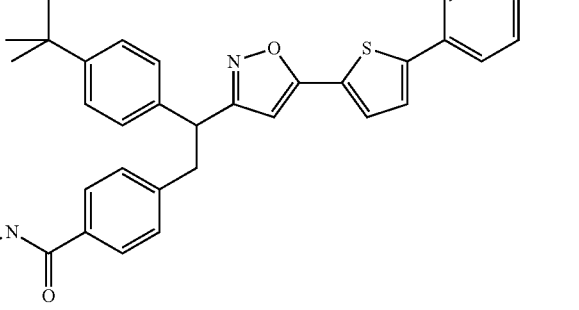 | 644.81 | C35H32ClF3N2O6S2 + 2 H2O + 0.5 CF3CO2H<br>54.44  4.63  3.53<br>54.03  4.96  3.56 |
| 2.021 | 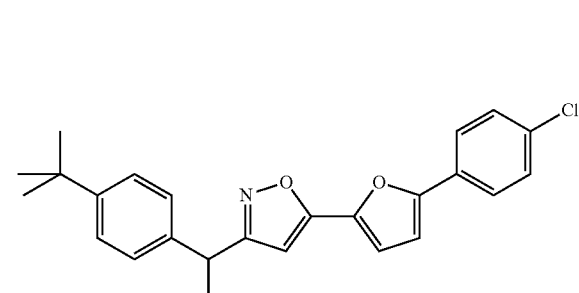 | 590.30 (+) | C34H33ClN2O6S + 2 H2O<br>C: 61.02; H: 5.57; N: 4.19<br>C: 60.74; H: 5.67; N: 4.14 |
| 2.022 | 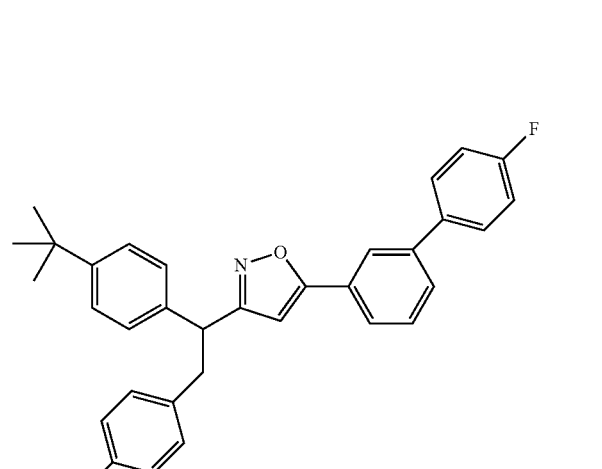 | 625.6 (−) | C36H34N2O5FSNa + 1.2 H2O<br>C: 64.50; H: 5.47; N: 4.18<br>C: 64.12; H: 5.10; N: 4.12 |

-continued

| Example | STRUCTURE | MASS SPECTRUM (mode) | Formula CHN (Calcd) CHN (Found) |
|---|---|---|---|
| 2.023 | 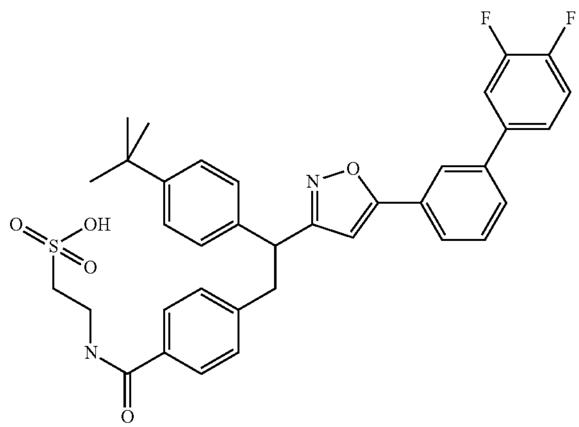 [SMILES: CC(C)(C)c1ccc(C(Cc2ccc(C(=O)NCCS(=O)(=O)O)cc2)c2cc(-c3cccc(-c4ccc(F)c(F)c4)c3)on2)cc1] | 643.2 (−) | C36H34F2N2O5S + 2.2H2O<br>C: 63.18; H: 5.66; N: 4.09<br>C: 62.95; H: 5.73; N: 4.21 |
| 2.024 | 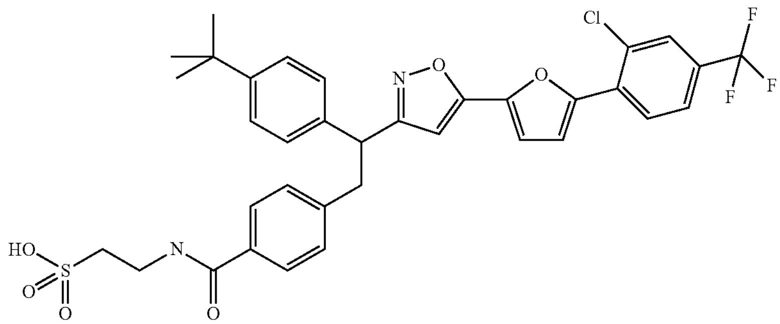 [SMILES: CC(C)(C)c1ccc(C(Cc2ccc(C(=O)NCCS(=O)(=O)O)cc2)c2cc(-c3ccc(-c4ccc(C(F)(F)F)cc4Cl)o3)on2)cc1] | 701.16 | C35H32ClF3N2O6S2 + 2 H2O + 0.5 CF3CO2H<br>54.44  4.63  3.53<br>54.30  4.96  3.56 |
| 2.025 | 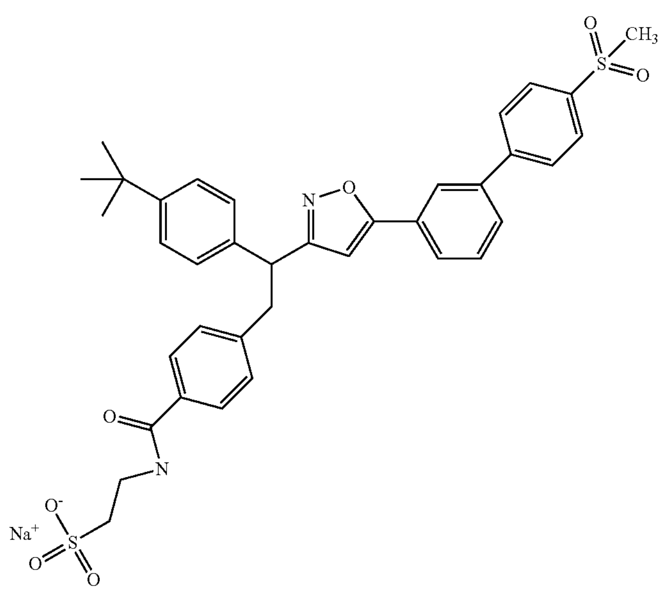 [SMILES: [Na+] ; CC(C)(C)c1ccc(C(Cc2ccc(C(=O)NCCS(=O)(=O)[O-])cc2)c2cc(-c3cccc(-c4ccc(S(C)(=O)=O)cc4)c3)on2)cc1] | 685.6 (−) | C37H37N2O7S2Na + 1.8H2O<br>C: 59.95; H: 5.52; N: 3.78<br>C: 60.06; H: 5.55; N: 3.97 |

-continued

| Example | STRUCTURE | MASS SPECTRUM (mode) | Formula CHN (Calcd) CHN (Found) |
|---|---|---|---|
| 2.026 | 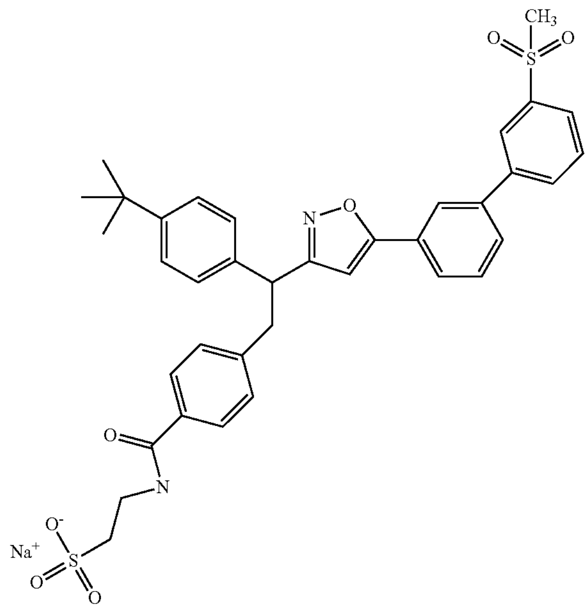 [SMILES: [Na+] ; CC(C)(C)c1ccc(C(Cc2ccc(C(=O)NCCS(=O)(=O)[O-])cc2)c2cc(-c3cccc(-c4cccc(S(C)(=O)=O)c4)c3)on2)cc1] | 685.6 (−) | C37H37N2O7S2Na + 1.9H2O<br>C: 59.81; H: 5.53; N: 3.77<br>C: 59.57; H: 5.13; N: 3.43 |
| 2.027 | 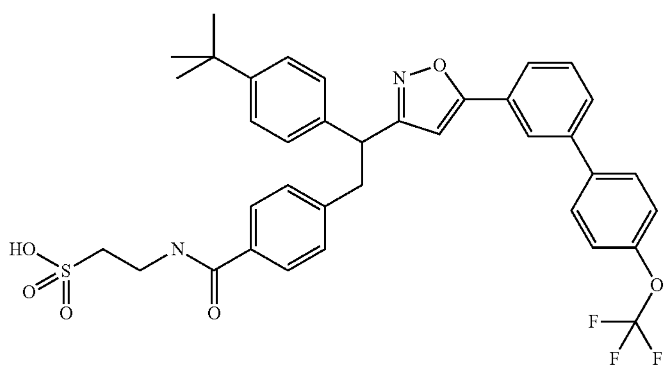 [SMILES: CC(C)(C)c1ccc(C(Cc2ccc(C(=O)NCCS(=O)(=O)O)cc2)c2cc(-c3cccc(-c4ccc(OC(F)(F)F)cc4)c3)on2)cc1] | 692.76 | C37H35F3N2O6S + CF3CO2H + 0.5 H2O<br>C: 57.42; H: 4.57; N: 3.43<br>C: 57.13; H: 4.73; N: 3.55 |
| 2.028 | 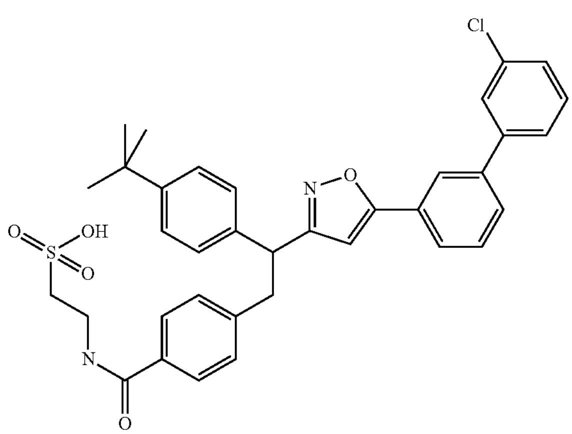 [SMILES: CC(C)(C)c1ccc(C(Cc2ccc(C(=O)NCCS(=O)(=O)O)cc2)c2cc(-c3cccc(-c4cccc(Cl)c4)c3)on2)cc1] | 643.2 (−) | C36H34F2N2O5S + 2.2H2O<br>C: 63.18; H: 5.66; N: 4.09<br>C: 62.95; H: 5.73; N: 4.21 |

-continued
| Example | STRUCTURE | MASS SPECTRUM (mode) | Formula CHN (Calcd) CHN (Found) |
|---|---|---|---|
| 2.029 | 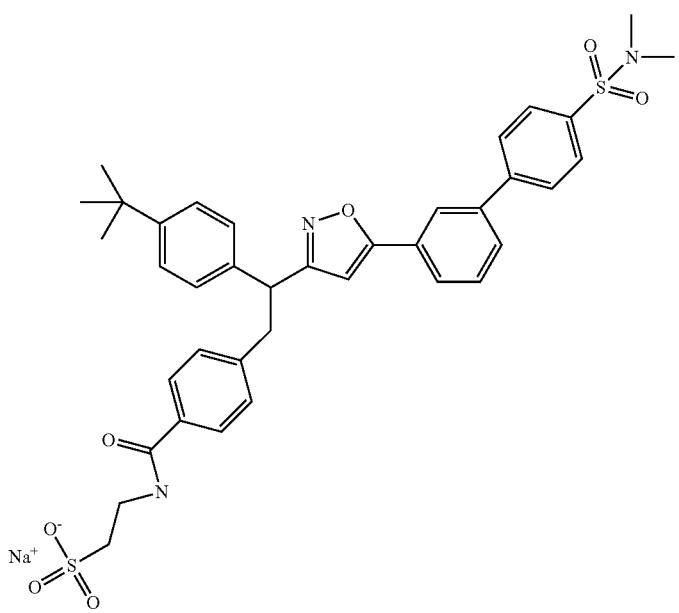 [SMILES: [Na+] ; CN(C)S(=O)(=O)c1ccc(-c2cccc(-c3cc(C(Cc4ccc(C(=O)NCCS(=O)(=O)[O-])cc4)c4ccc(C(C)(C)C)cc4)no3)c2)cc1] | 714.6 (−) | C38H40N3O7S2Na + 1.2H2O<br>60.10  5.63  5.53<br>59.96  5.53  5.50 |
| 2.030 | 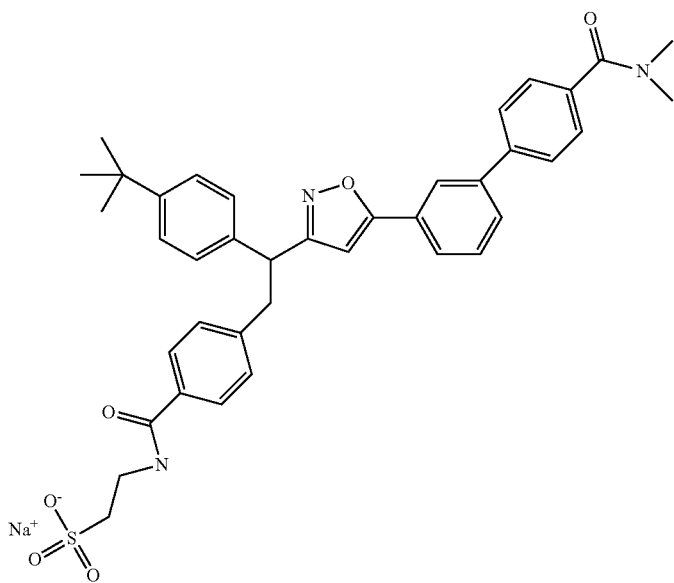 [SMILES: [Na+] ; CN(C)C(=O)c1ccc(-c2cccc(-c3cc(C(Cc4ccc(C(=O)NCCS(=O)(=O)[O-])cc4)c4ccc(C(C)(C)C)cc4)no3)c2)cc1] | 768.6 (−) | C39H40N3O6SNa + 1H2O<br>65.07  5.88  5.84<br>64.71  5.99  5.72 |

| Example | STRUCTURE | MASS SPECTRUM (mode) | Formula CHN (Calcd) CHN (Found) |
|---|---|---|---|
| 2.031 | 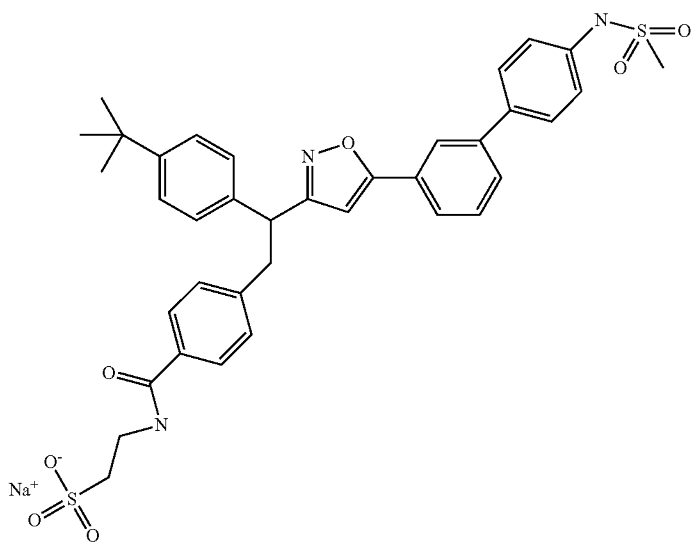 [SMILES: [Na+] ; CC(C)(C)c1ccc(C(Cc2ccc(C(=O)NCCS(=O)(=O)[O-])cc2)c2cc(-c3cccc(-c4ccc(NS(C)(=O)=O)cc4)c3)on2)cc1] | 700.4 (−) | C37H38N3O7SNa + 2H2O<br>58.48  5.57  5.53<br>58.24  5.67  5.69 |
| 2.032 | 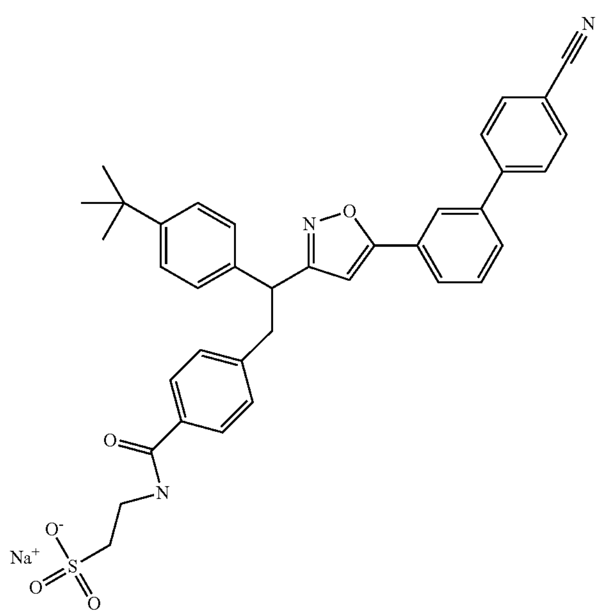 [SMILES: [Na+] ; CC(C)(C)c1ccc(C(Cc2ccc(C(=O)NCCS(=O)(=O)[O-])cc2)c2cc(-c3cccc(-c4ccc(C#N)cc4)c3)on2)cc1] | 632.6 (−) | C37H34N3O5SNa + 0.8H2O<br>66.31  5.35  6.27<br>66.26  5.36  5.96 |

-continued
| Example | STRUCTURE | MASS SPECTRUM (mode) | Formula CHN (Calcd) CHN (Found) |
|---|---|---|---|
| 2.033 | 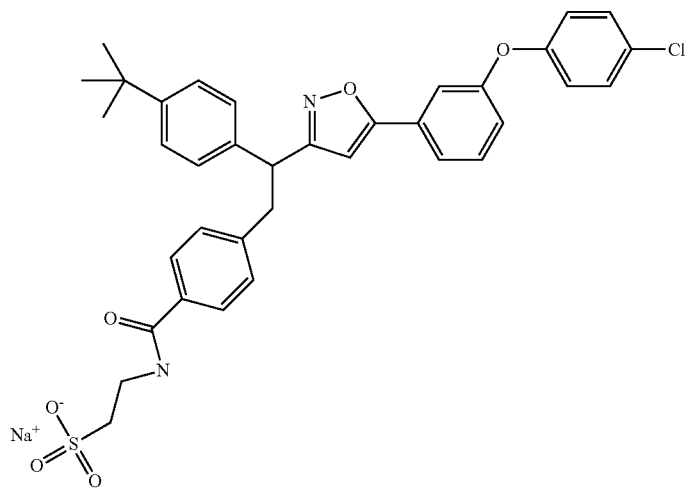 [SMILES: [Na+] ; CC(C)(C)c1ccc(C(Cc2ccc(C(=O)NCCS(=O)(=O)[O-])cc2)c2cc(-c3cccc(Oc4ccc(Cl)cc4)c3)on2)cc1] | 650.6 (−) | C36H34N2O6SClNa + 2.5H2O + 0.2 CH3CN<br>59.53  5.43  4.20<br>59.32  5.51  4.59 |
| 2.034 | 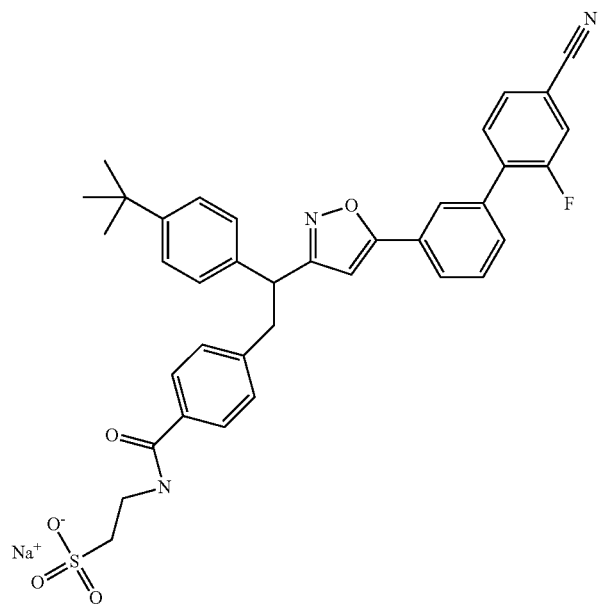 [SMILES: [Na+] ; CC(C)(C)c1ccc(C(Cc2ccc(C(=O)NCCS(=O)(=O)[O-])cc2)c2cc(-c3cccc(-c4ccc(C#N)cc4F)c3)on2)cc1] | 650.6 (−) | C37H33N3O5FSNa + 1H2O<br>64.24  5.10  6.07<br>64.08  5.15  5.96 |

| Example | STRUCTURE | MASS SPECTRUM (mode) | Formula CHN (Calcd) CHN (Found) |
|---|---|---|---|
| 2.035 | 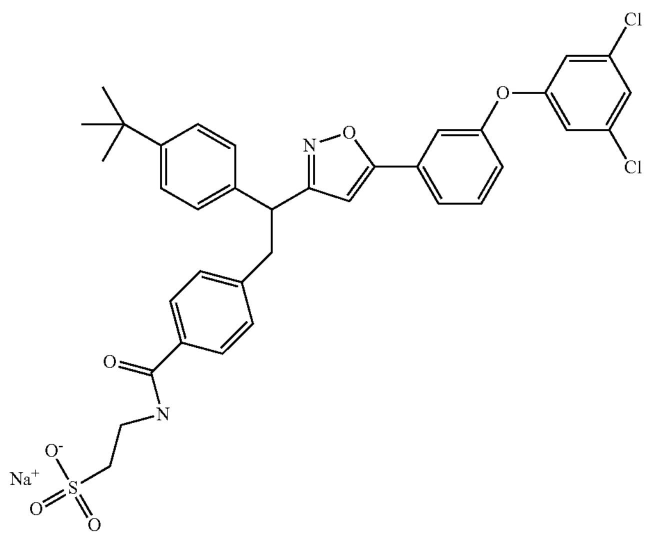 [SMILES: [Na+] ; CC(C)(C)c1ccc(C(Cc2ccc(C(=O)NCCS(=O)(=O)[O-])cc2)c2cc(-c3cccc(Oc4cc(Cl)cc(Cl)c4)c3)on2)cc1] | 691.6 (−) | C36H33N2O6Cl2SNa + 1.5H2O<br>58.22  4.89  3.77<br>58.55  4.67  3.42 |
| 2.036 | 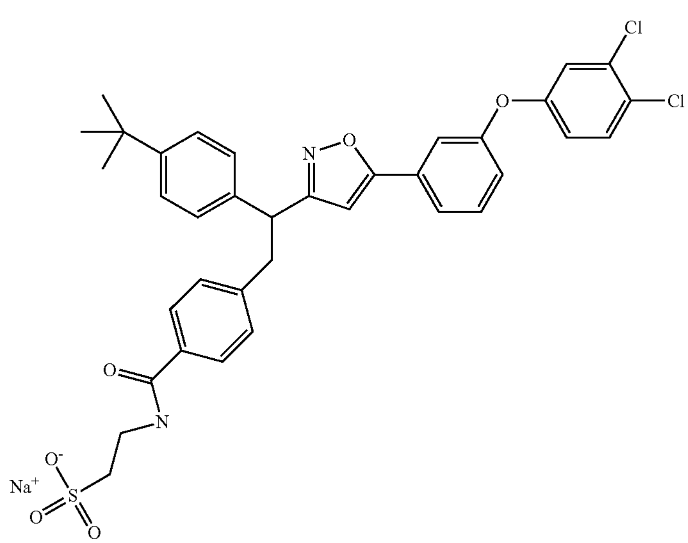 [SMILES: [Na+] ; CC(C)(C)c1ccc(C(Cc2ccc(C(=O)NCCS(=O)(=O)[O-])cc2)c2cc(-c3cccc(Oc4ccc(Cl)c(Cl)c4)c3)on2)cc1] | 691.6 (−) | C36H33N2O6Cl2SNa + 1H2O<br>58.94  4.81  3.82<br>59.13  4.61  3.45 |

| Example | STRUCTURE | MASS SPEC-TRUM (mode) | Formula CHN (Calcd) CHN (Found) |
|---|---|---|---|
| 2.037 | 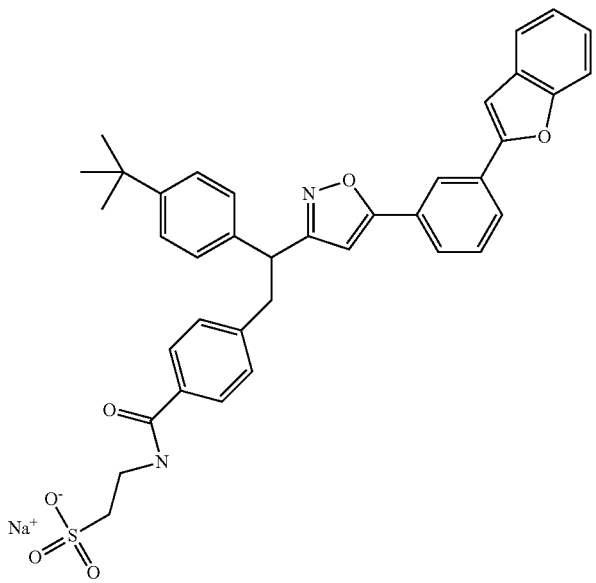 [SMILES: [Na+] ; CC(C)(C)c1ccc(C(Cc2ccc(C(=O)NCCS(=O)(=O)[O-])cc2)c2cc(-c3cccc(-c4cc5ccccc5o4)c3)on2)cc1] | 647.4 (−) | C38H35N2O6SNa + 1H2O<br>66.27 5.41 4.07<br>65.95 5.41 4.02 |
| 2.038 | 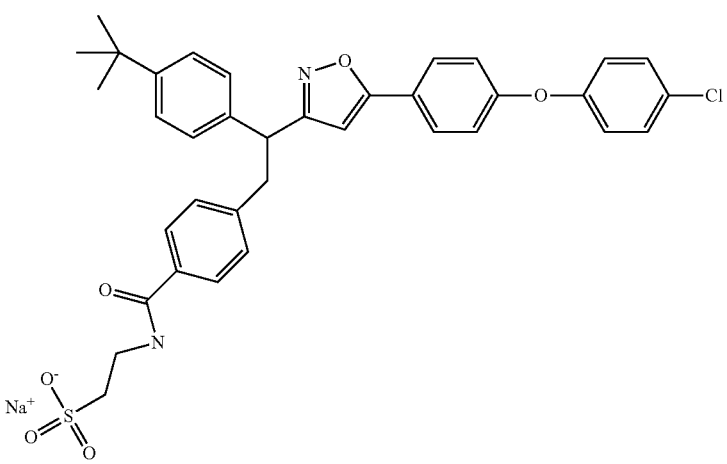 [SMILES: [Na+] ; CC(C)(C)c1ccc(C(Cc2ccc(C(=O)NCCS(=O)(=O)[O-])cc2)c2cc(-c3ccc(Oc4ccc(Cl)cc4)cc3)on2)cc1] | 657.2 (−) | C36H34N2O6ClSNa + 3H2O + 0.1 CH3CN<br>58.81 5.49 3.98<br>59.04 5.22 4.33 |
| 2.039 | 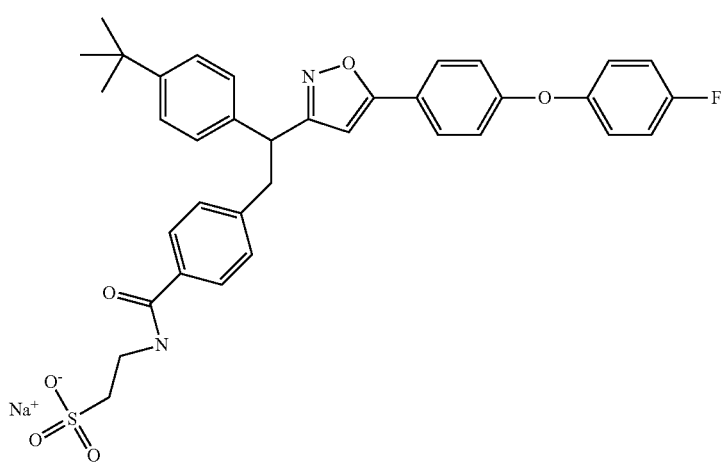 [SMILES: [Na+] ; CC(C)(C)c1ccc(C(Cc2ccc(C(=O)NCCS(=O)(=O)[O-])cc2)c2cc(-c3ccc(Oc4ccc(F)cc4)cc3)on2)cc1] | 643.2 (−) | C36H35N2O6FS + 2.5 H2O<br>62.87 5.86 4.07<br>62.70 5.73 4.02 |

-continued

| Example | STRUCTURE | MASS SPECTRUM (mode) | Formula CHN (Calcd) CHN (Found) |
|---|---|---|---|
| 2.040 | 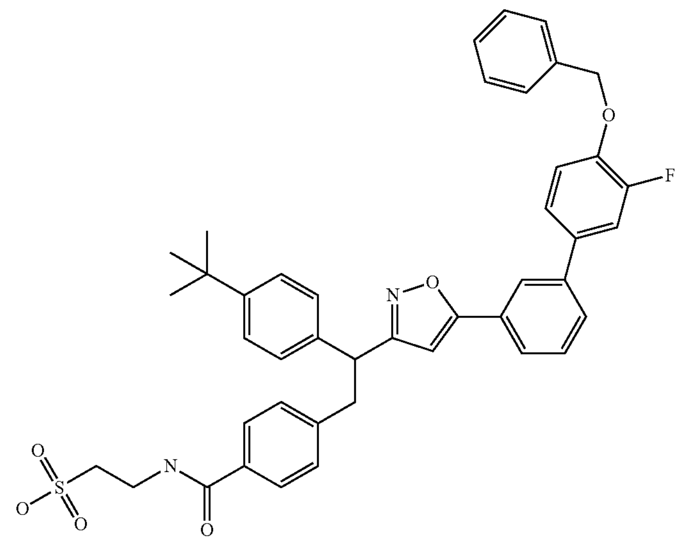 [SMILES: CC(C)(C)c1ccc(C(Cc2ccc(C(=O)NCCS(=O)(=O)O)cc2)c2cc(-c3cccc(-c4ccc(OCc5ccccc5)c(F)c4)c3)on2)cc1] | 733 (+) | C43H41N2O6FS + (0.9) H2O + (0.2) CF3CO2H<br>C: 67.53 H: 5.61 N: 3.63<br>C: 67.57 H: 5.83 N: 3.67 |
| 2.041 | 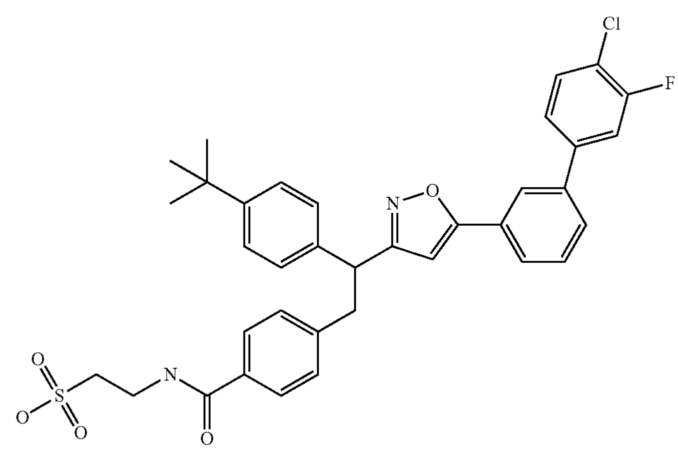 [SMILES: CC(C)(C)c1ccc(C(Cc2ccc(C(=O)NCCS(=O)(=O)O)cc2)c2cc(-c3cccc(-c4ccc(Cl)c(F)c4)c3)on2)cc1] | 661.6 (+) | C36H34N2O5FClS + (0.5) H2O + (0.2) TFA<br>C: 63.09 H: 5.12 N: 4.04<br>C: 63.09 H: 5.23 N: 3.79 |
| 2.042 | 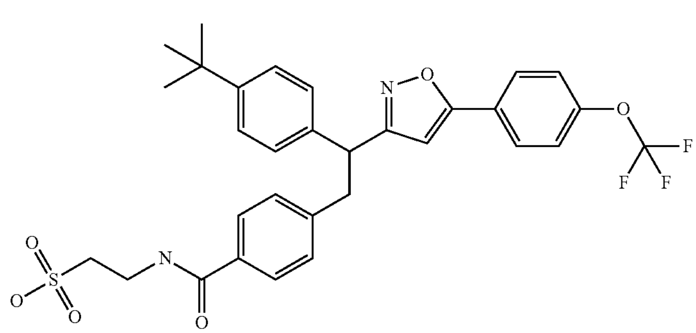 [SMILES: CC(C)(C)c1ccc(C(Cc2ccc(C(=O)NCCS(=O)(=O)O)cc2)c2cc(-c3ccc(OC(F)(F)F)cc3)on2)cc1] | 617.4 (+) | C31H31N2O6F3S + (1.5) H2O + (0.6) TFA<br>C: 54.31 H: 4.90 N: 3.93<br>C: 54.29 H: 5.00 N: 3.93 |

-continued

| Example | STRUCTURE | MASS SPECTRUM (mode) | Formula CHN (Calcd) CHN (Found) |
|---|---|---|---|
| 2.043 | 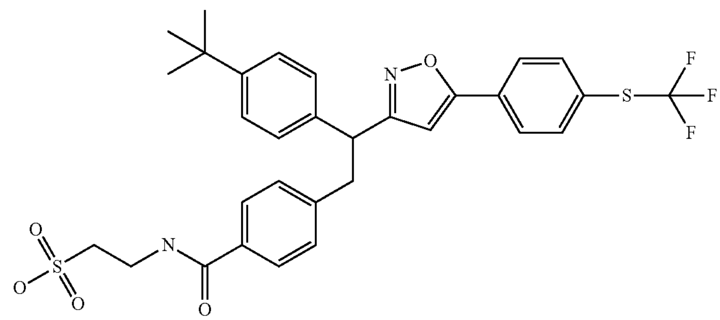 [SMILES: CC(C)(C)c1ccc(C(Cc2ccc(C(=O)NCCS(=O)(=O)O)cc2)c2cc(-c3ccc(SC(F)(F)F)cc3)on2)cc1] | 633.6 (+) | C31H31N2O5S2 + (1.0) H2O<br>C: 57.22 H: 5.11 N: 4.30<br>C: 57.22 H: 5.45 N: 4.04 |
| 2.044 | 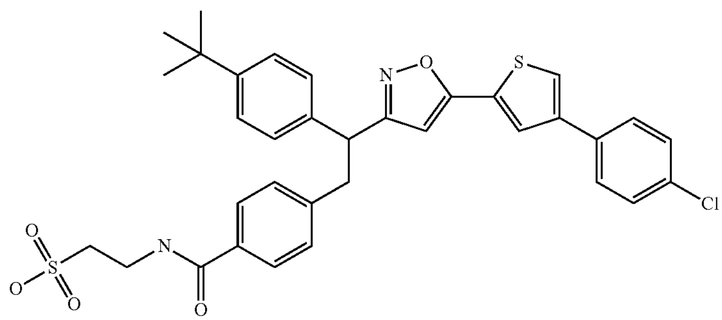 [SMILES: CC(C)(C)c1ccc(C(Cc2ccc(C(=O)NCCS(=O)(=O)O)cc2)c2cc(-c3cc(-c4ccc(Cl)cc4)cs3)on2)cc1] | 649.6 (+) | C34H33N2O5ClS2 + (1.5) H2O<br>C: 60.39 H: 5.37 N: 4.14<br>C: 60.49 H: 5.75 N: 4.10 |
| 2.045 | 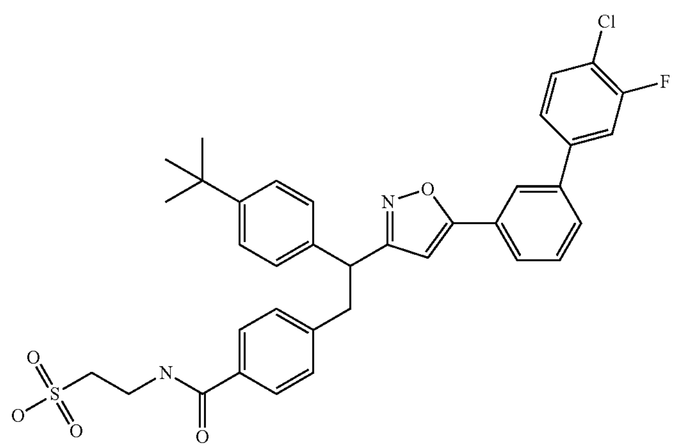 [SMILES: CC(C)(C)c1ccc(C(Cc2ccc(C(=O)NCCS(=O)(=O)O)cc2)c2cc(-c3cccc(-c4ccc(Cl)c(F)c4)c3)on2)cc1] | 643.6 (+) | C36H35N2O6FS + (1.2) H2O + (0.8) TFA<br>C: 59.77 H: 5.10 N: 3.71<br>C: 59.69 H: 5.38 N: 3.58 |
| 2.046 | 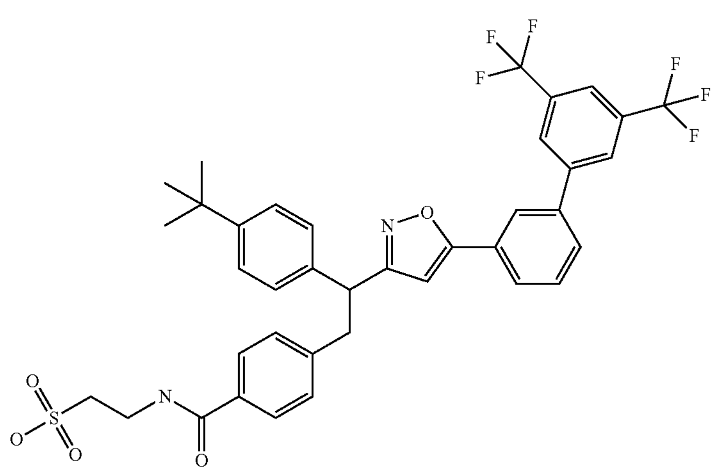 [SMILES: CC(C)(C)c1ccc(C(Cc2ccc(C(=O)NCCS(=O)(=O)O)cc2)c2cc(-c3cccc(-c4cc(C(F)(F)F)cc(C(F)(F)F)c4)c3)on2)cc1] | 745.6 (+) | C38H34N2O5F6S + (1.2) TFA<br>C: 55.04 H: 4.02 N: 3.18<br>C: 55.18 H: 3.93 N: 2.84 |

| Example | STRUCTURE | MASS SPECTRUM (mode) | Formula CHN (Calcd) CHN (Found) |
|---|---|---|---|
| 2.047 | 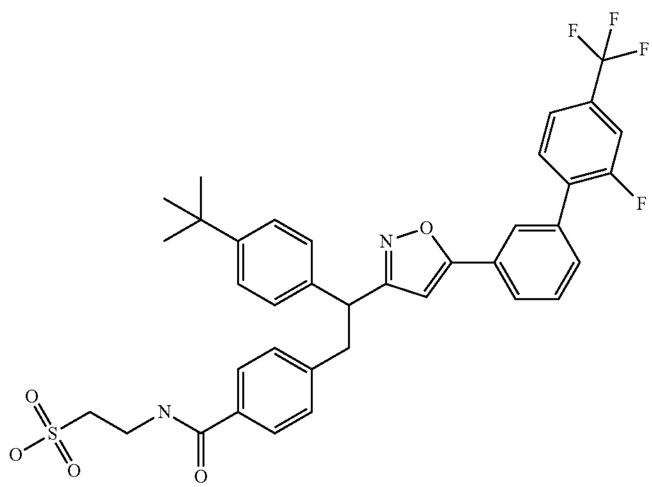 [SMILES: CC(C)(C)c1ccc(C(Cc2ccc(C(=O)NCCS(=O)(=O)O)cc2)c2cc(-c3cccc(-c4ccc(C(F)(F)F)cc4F)c3)on2)cc1] | 695.4 (+) | C37H34N2O5F4S + (1.5) TFA<br>C: 55.49 H: 4.13 N: 3.24<br>C: 55.28 H: 3.97 N: 2.89 |
| 2.048 | 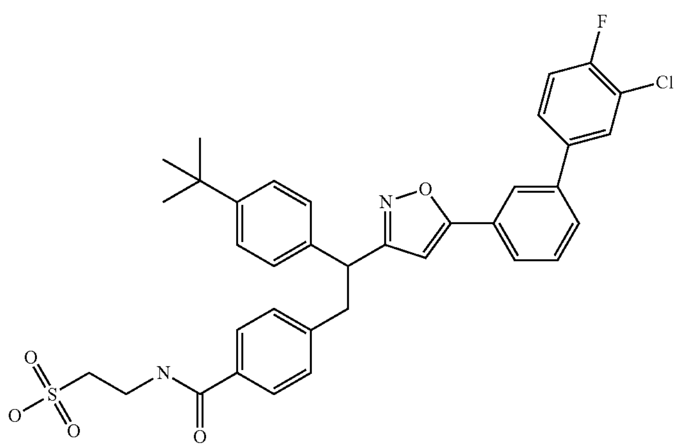 [SMILES: CC(C)(C)c1ccc(C(Cc2ccc(C(=O)NCCS(=O)(=O)O)cc2)c2cc(-c3cccc(-c4ccc(F)c(Cl)c4)c3)on2)cc1] | 661.6 (+) | C36H34N2O5FClS + (1.1) H2O + (0.1) TFA<br>C: 62.79 H: 5.28 N: 4.05<br>C: 62.78 H: 5.59 N: 4.20 |
| 2.049 | 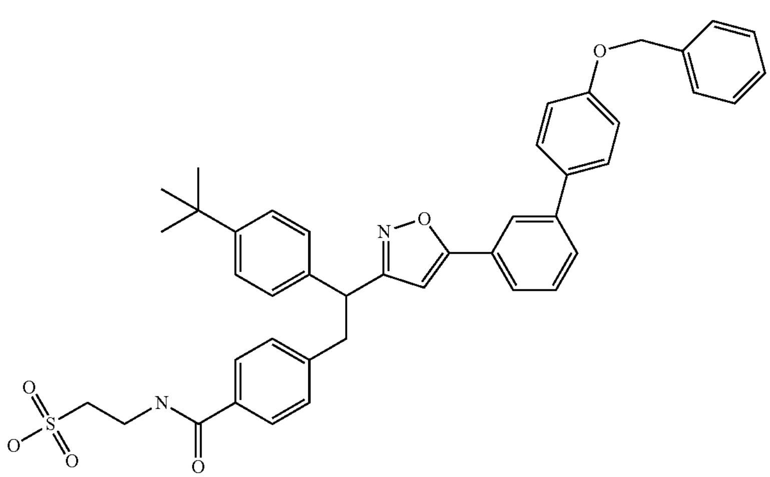 [SMILES: CC(C)(C)c1ccc(C(Cc2ccc(C(=O)NCCS(=O)(=O)O)cc2)c2cc(-c3cccc(-c4ccc(OCc5ccccc5)cc4)c3)on2)cc1] | 715.9 (+) | C43H42N2O6S + (2.2) H2O + (0.1) TFA<br>C: 67.75 H: 6.12 N: 3.66<br>C: 67.60 H: 6.30 N: 3.71 |

-continued

| Example | STRUCTURE | MASS SPECTRUM (mode) | Formula CHN (Calcd) CHN (Found) |
|---|---|---|---|
| 2.050 | 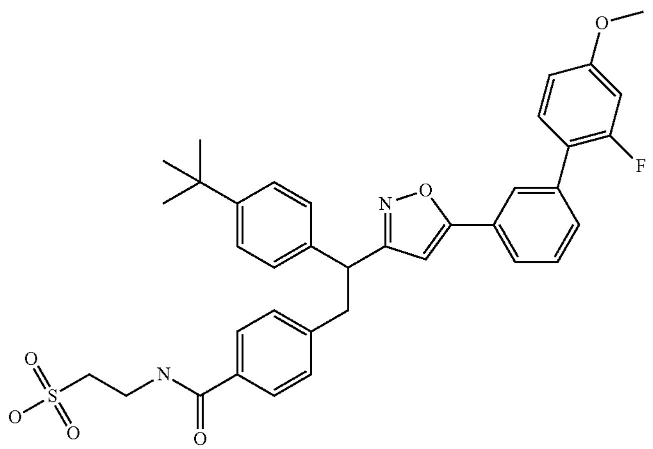 [SMILES: COc1ccc(-c2cccc(-c3cc(C(Cc4ccc(C(=O)NCCS(=O)(=O)O)cc4)c4ccc(C(C)(C)C)cc4)no3)c2)c(F)c1] | 657.2 (+) | C37H37N2O6FS + (1.8) H2O + (0.1) TFA C: 63.77 H: 5.86 N: 4.00 C: 63.79 H: 6.22 N: 4.39 |
| 2.051 | 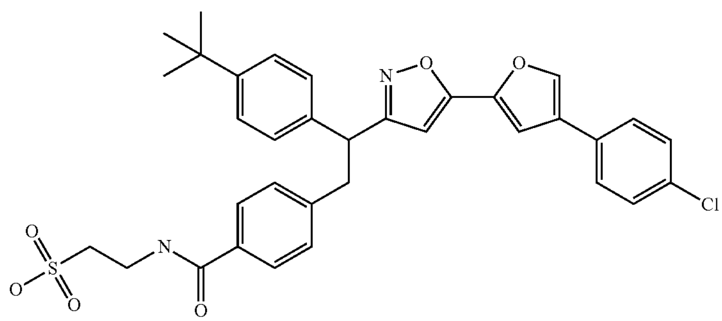 [SMILES: CC(C)(C)c1ccc(C(Cc2ccc(C(=O)NCCS(=O)(=O)O)cc2)c2cc(-c3cc(-c4ccc(Cl)cc4)co3)on2)cc1] | 633.3 (+) | C34H33N2O6ClS + (2.2) H2O + (0.1) TFA C: 60.04 H: 5.52 N: 4.09 C: 60.01 H: 5.86 N: 4.23 |
| 2.052 | 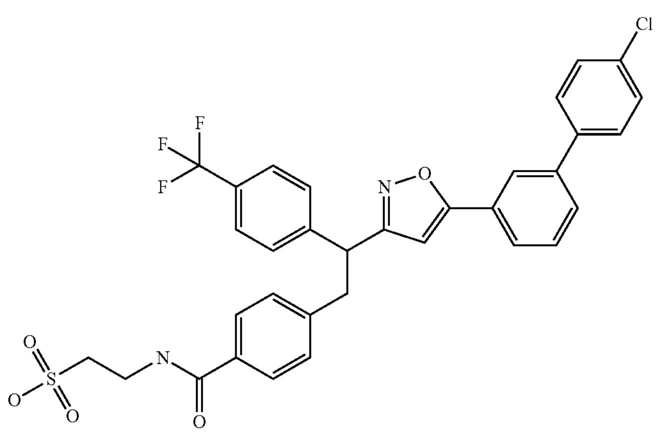 [SMILES: O=C(NCCS(=O)(=O)O)c1ccc(CC(c2ccc(C(F)(F)F)cc2)c2cc(-c3cccc(-c4ccc(Cl)cc4)c3)on2)cc1] | 655.6 (+) | C33H26ClF3N2O5S + (0.3) H2O + (0.1) TFA C: 59.35 H: 4.01 N: 4.17 C: 59.40 H: 3.68 N: 3.98 |
| 2.053 | 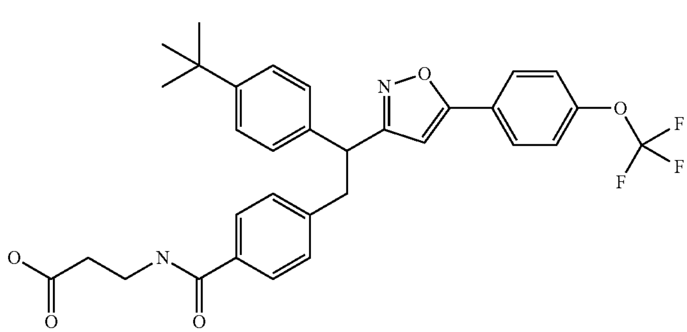 [SMILES: CC(C)(C)c1ccc(C(Cc2ccc(C(=O)NCCC(=O)O)cc2)c2cc(-c3ccc(OC(F)(F)F)cc3)on2)cc1] | 581.6 (+) | C32H31N2O5F3 + (0.1) DMF + (0.5) H2O C: 64.99 H: 5.52 N: 4.93 C: 65.36 H: 5.99 N: 4.88 |

-continued

| Example | STRUCTURE | MASS SPECTRUM (mode) | Formula CHN (Calcd) CHN (Found) |
|---|---|---|---|
| 2.054 | 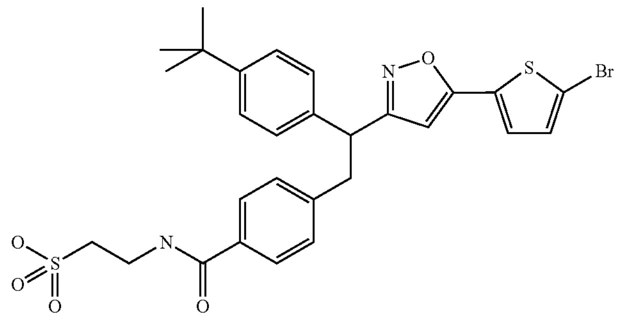 [SMILES: CC(C)(C)c1ccc(C(Cc2ccc(C(=O)NCCS(=O)(=O)O)cc2)c2cc(-c3ccc(Br)s3)on2)cc1] | 618.4 (+) | C$_{28}$H$_{29}$BrN$_2$O$_5$S$_2$ + H$_2$O + (0.6) TFA C: 49.82 H: 4.52 N: 3.98 Found: C = 49.86 H: 4.59 N = 4.03 |
| 2.055 | 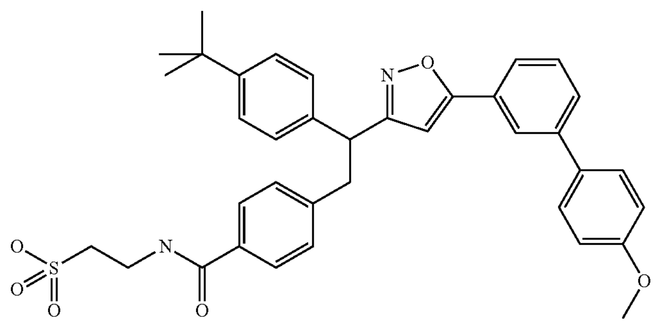 [SMILES: COc1ccc(-c2cccc(-c3cc(C(Cc4ccc(C(=O)NCCS(=O)(=O)O)cc4)c4ccc(C(C)(C)C)cc4)no3)c2)cc1] | 639.6 (+) | C$_{37}$H$_{38}$N$_2$O$_6$S + (3.0) H$_2$O C: 64.14 H: 6.40 N: 4.04 C: 64.12 H: 6.03 N: 4.06 |
| 2.056 | 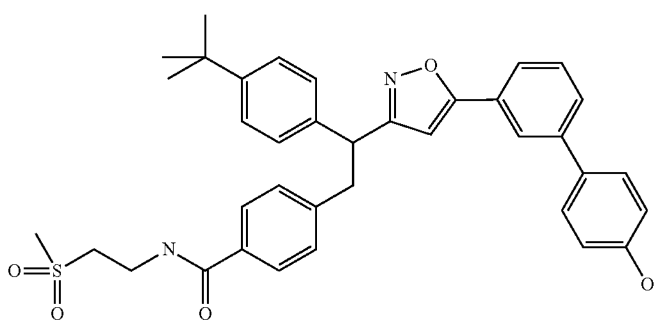 [SMILES: CC(C)(C)c1ccc(C(Cc2ccc(C(=O)NCCS(C)(=O)=O)cc2)c2cc(-c3cccc(-c4ccc(O)cc4)c3)on2)cc1] | 625.6 (+) | C$_{36}$H$_{36}$N$_2$O$_6$S + 5H$_2$O C: 60.19 H: 6.51 N: 3.90 C: 60.02 H: 6.15 N: 3.95 |
| 2.057 | 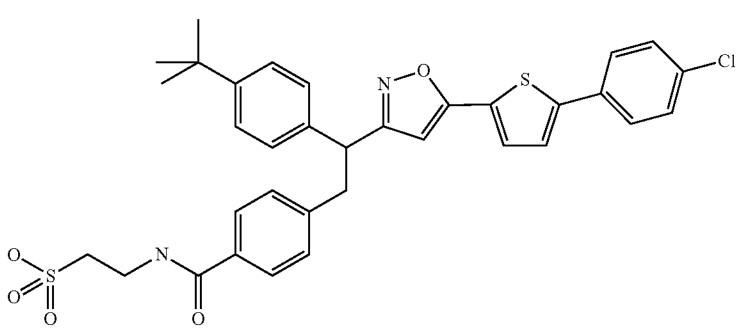 [SMILES: CC(C)(C)c1ccc(C(Cc2ccc(C(=O)NCCS(=O)(=O)O)cc2)c2cc(-c3ccc(-c4ccc(Cl)cc4)s3)on2)cc1] | 650.6 (+) | C$_{34}$H$_{33}$ClN$_2$O$_5$S$_2$ + (0.6) TFA C: 57.19 H: 4.54 N: 3.73 C: 57.19 H: 4.59 N: 3.69 |

-continued

| Example | STRUCTURE | MASS SPECTRUM (mode) | Formula CHN (Calcd) CHN (Found) |
|---|---|---|---|
| 2.058 | 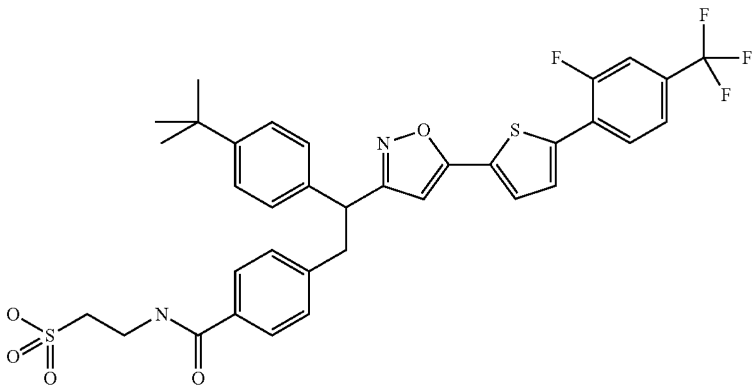 [SMILES: CC(C)(C)c1ccc(C(Cc2ccc(C(=O)NCCS(=O)(=O)O)cc2)c2cc(-c3ccc(-c4ccc(C(F)(F)F)cc4F)s3)on2)cc1] | 650.6 (+) | C₃₅H₃₂F₄N₂O₅S₂ + (1.1) DMF + (0.2) H₂O<br>C: 58.62 H: 5.15 N: 5.53<br>C: 59.02 H: 5.55 N: 5.28 |
| 2.059 | 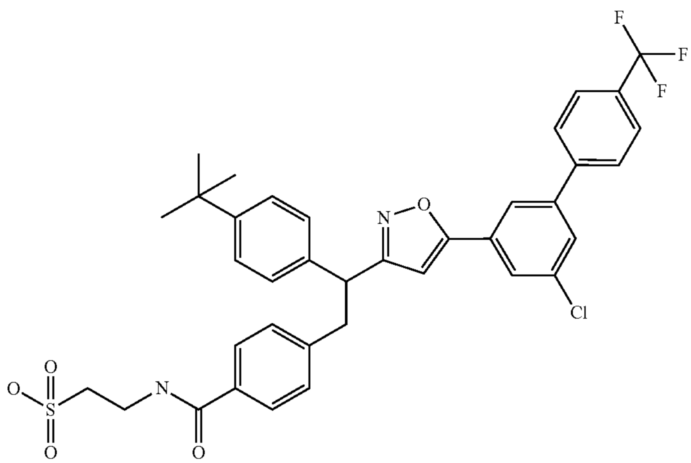 [SMILES: CC(C)(C)c1ccc(C(Cc2ccc(C(=O)NCCS(=O)(=O)O)cc2)c2cc(-c3cc(Cl)cc(-c4ccc(C(F)(F)F)cc4)c3)on2)cc1] | 709 (−) | C37H34ClF3N2O5S + (0.3) TFA + (1.2) H2O<br>C: 58.88, H: 4.82, N: 3.65<br>C: 58.86, H: 4.95, N: 3.57 |
| 2.060 | 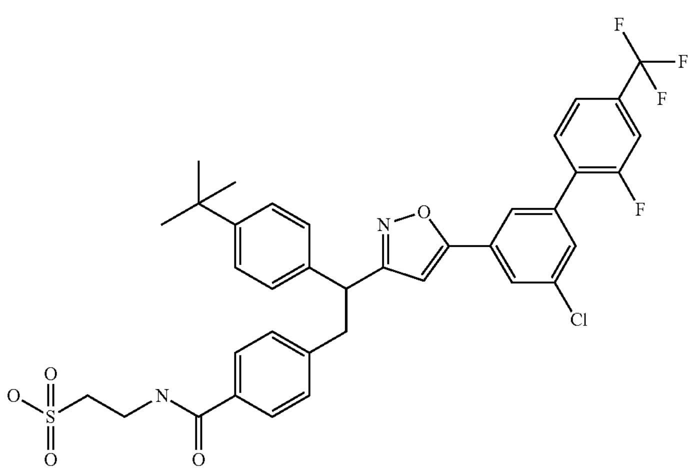 [SMILES: CC(C)(C)c1ccc(C(Cc2ccc(C(=O)NCCS(=O)(=O)O)cc2)c2cc(-c3cc(Cl)cc(-c4ccc(C(F)(F)F)cc4F)c3)on2)cc1] | 727, 729 (−) | C37H33ClF4N2O5S + (0.7) TFA + (0.3) H2O<br>C: 56.63, H: 4.25, N: 3.44<br>C: 56.20, H: 4.47, N: 3.64 |

-continued

| Example | STRUCTURE | MASS SPECTRUM (mode) | Formula CHN (Calcd) CHN (Found) |
| --- | --- | --- | --- |
| 2.061 | 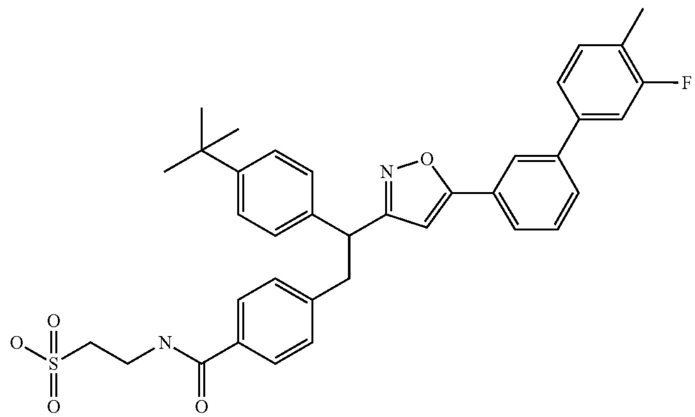 [SMILES: Cc1ccc(-c2cccc(-c3cc(C(Cc4ccc(C(=O)NCCS(=O)(=O)O)cc4)c4ccc(C(C)(C)C)cc4)no3)c2)cc1F] | 639 (−) | C37H37FN2O5S + (0.1) TFA + (1.1) H2O C: 66.49, H: 5.89, N: 4.17 C: 66.33, H: 5.89, N: 4.0 |
| 2.062 | 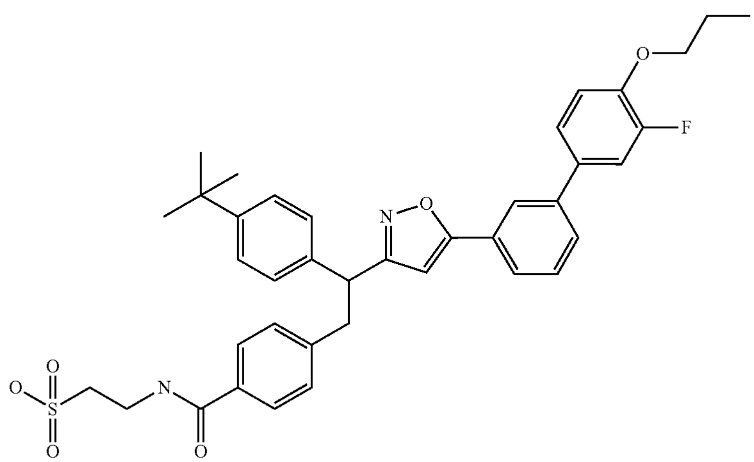 [SMILES: CCCOc1ccc(-c2cccc(-c3cc(C(Cc4ccc(C(=O)NCCS(=O)(=O)O)cc4)c4ccc(C(C)(C)C)cc4)no3)c2)cc1F] | 683 (−) | C39H41FN2O6S + (0.2) TFA + (1.7) H2O C: 64.10, H: 6.09, N: 3.79 C: 64.02, H: 5.92, N: 3.7 |
| 2.063 | 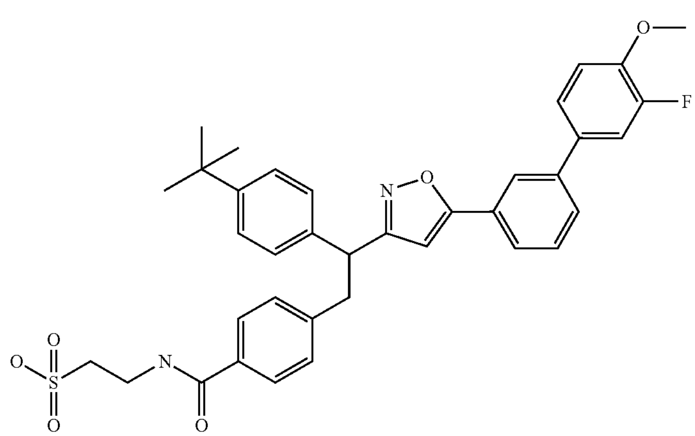 [SMILES: COc1ccc(-c2cccc(-c3cc(C(Cc4ccc(C(=O)NCCS(=O)(=O)O)cc4)c4ccc(C(C)(C)C)cc4)no3)c2)cc1F] | 655 (−) | C37H37FN2O6S + (0.7) TFA + (1.7) H2O C: 60.12, H: 5.40, N: 3.65 C: 60.19, H: 5.26, N: 3.50 |

-continued
| Example | STRUCTURE | MASS SPEC-TRUM (mode) | Formula CHN (Calcd) CHN (Found) |
|---|---|---|---|
| 2.064 | 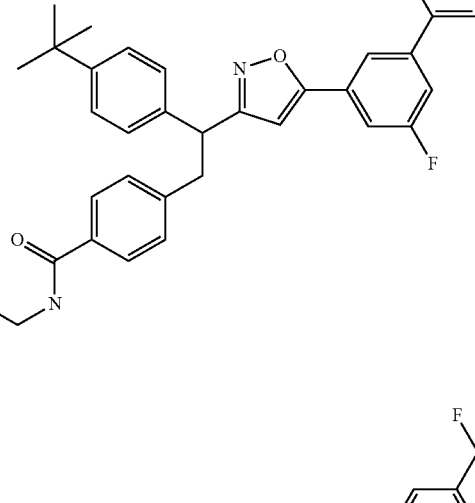 | 659.6 (−) | C36H34ClFN2O5S + 0.6 H2O<br>C: 64.34 H: 5.28 N: 4.17<br>C: 64.27 H: 5.48 N: 4.1 |
| 2.065 | 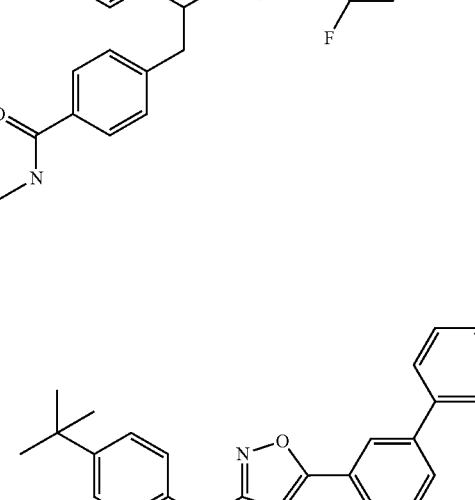 | 695.4 (+) | C37H34N2O5F4S + 1.6 H2O<br>C: 61.42; H: 5.18; N: 3.87<br>C: 61.63; H: 5.53; N: 3.79 |
| 2.066 | 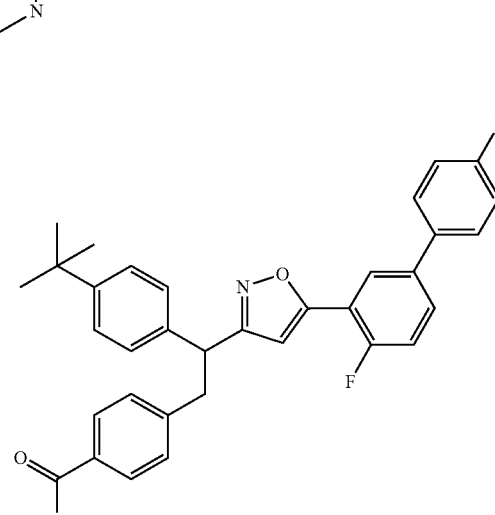 | 645.4 (−)? | C36H34N2O5S + 0.7 H2O + 1.2 CF3CO2H<br>C: 60.99 H: 4.88 N: 3.70<br>C: 61.08 H: 4.55 N: 3.84 |

-continued

| Example | STRUCTURE | MASS SPECTRUM (mode) | Formula CHN (Calcd) CHN (Found) |
|---|---|---|---|
| 2.067 | 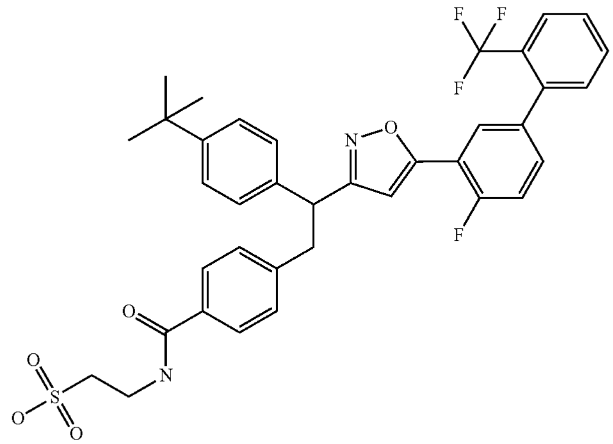 [SMILES: CC(C)(C)c1ccc(C(Cc2ccc(C(=O)NCCS(=O)(=O)O)cc2)c2cc(-c3cc(-c4ccccc4C(F)(F)F)ccc3F)on2)cc1] | 695.4 (+) | C37H34N2O5F4S + 1.5H2O<br>C: 61.57 H: 5.17 N: 3.88<br>C: 61.94 H: 5.54 N: 3.72 |
| 2.068 | 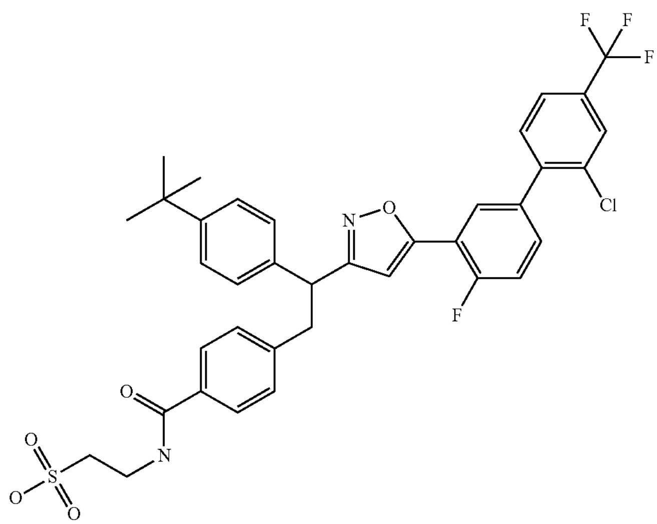 [SMILES: CC(C)(C)c1ccc(C(Cc2ccc(C(=O)NCCS(=O)(=O)O)cc2)c2cc(-c3cc(-c4ccc(C(F)(F)F)cc4Cl)ccc3F)on2)cc1] | 729.6 (+) | C37H33N2O5F4ClS + 0.6 H2O + 0.2 CF3CO2H<br>C: 58.89 H: 4.55 N: 3.67<br>C: 58.88 H: 4.28 N: 3.65 |
| 2.069 | 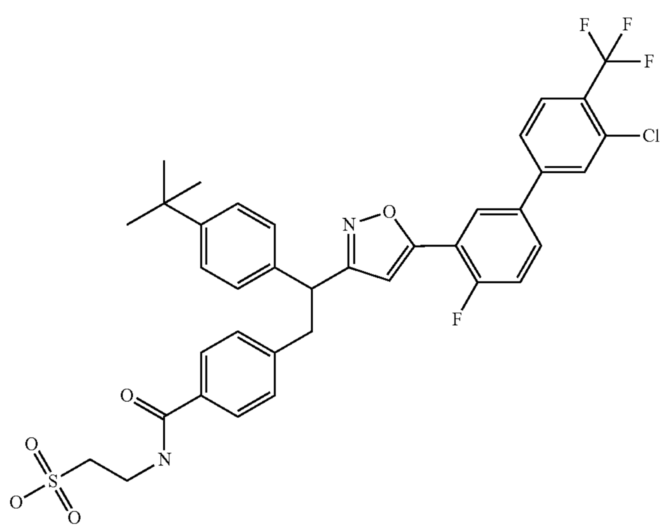 [SMILES: CC(C)(C)c1ccc(C(Cc2ccc(C(=O)NCCS(=O)(=O)O)cc2)c2cc(-c3cc(-c4ccc(C(F)(F)F)c(Cl)c4)ccc3F)on2)cc1] | 729.6 (+) | C37H33N2O5FClS + 1 H2O + 0.4 CF3CO2H<br>C: 57.21 H: 4.50 N: 3.53<br>C: 57.25 H: 4.34 N: 3.43 |

-continued
| Example | STRUCTURE | MASS SPECTRUM (mode) | Formula CHN (Calcd) CHN (Found) |
|---|---|---|---|
| 2.070 | 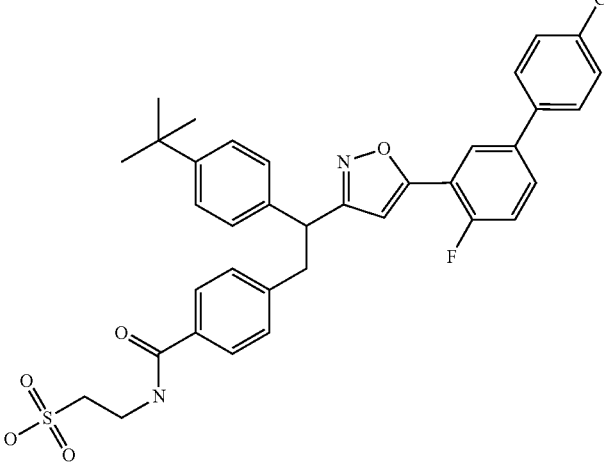 | 661.9 (+) | C36H34N2O5FClS + 0.9 CF3CO2H<br>C: 59.76 H: 4.93 N: 3.76<br>C: 59.50 H: 4.44 N: 3.66 |
| 2.071 | 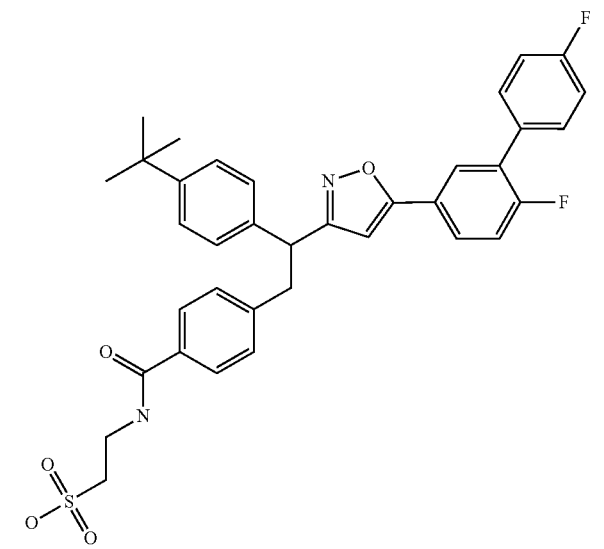 [SMILES: CC(C)(C)c1ccc(C(Cc2ccc(C(=O)NCCS(=O)(=O)O)cc2)c2cc(-c3ccc(F)c(-c4ccc(F)cc4)c3)on2)cc1] | 645.4 (+) | C36H34N2O5F2S + 0.5 H2O<br>C: 66.14 H: 5.40 N: 4.29<br>C: 66.17 H: 5.46 N: 4.09 |
| 2.072 | 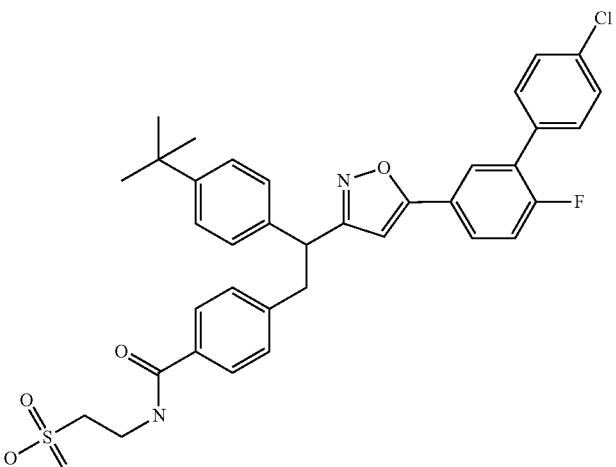 | 661.2 (+) | C36H34N2O5FClS + 1 H2O<br>C: 63.66 H: 5.34 N: 4.12<br>C: 63.36 H: 5.48 N: 4.07 |

-continued

| Example | STRUCTURE | MASS SPECTRUM (mode) | Formula CHN (Calcd) CHN (Found) |
|---|---|---|---|
| 2.073 | 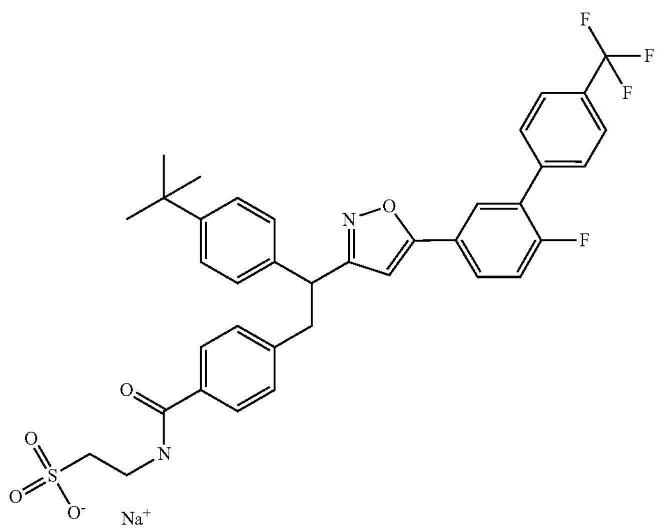 [SMILES: CC(C)(C)c1ccc(C(Cc2ccc(C(=O)NCCS(=O)(=O)[O-])cc2)c2cc(-c3ccc(F)c(-c4ccc(C(F)(F)F)cc4)c3)on2)cc1 ; [Na+]] | 693.0 (−) | C37H34N2O5F4SNa + 2H2O<br>C: 58.96 H: 5.08 N: 3.72<br>C: 58.79 H: 5.05 N: 3.76 |
| 2.074 | 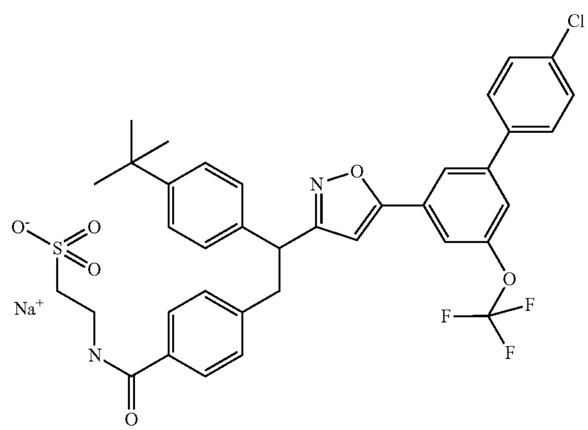 [SMILES: CC(C)(C)c1ccc(C(Cc2ccc(C(=O)NCCS(=O)(=O)[O-])cc2)c2cc(-c3cc(OC(F)(F)F)cc(-c4ccc(Cl)cc4)c3)on2)cc1 ; [Na+]] | 725 (−) | C37H33ClF3N2O6SNa + 3H2O<br>C: 55.33 H: 4.89 N: 3.49<br>C: 55.42 H: 5.03 N: 3.24 |
| 2.075 | 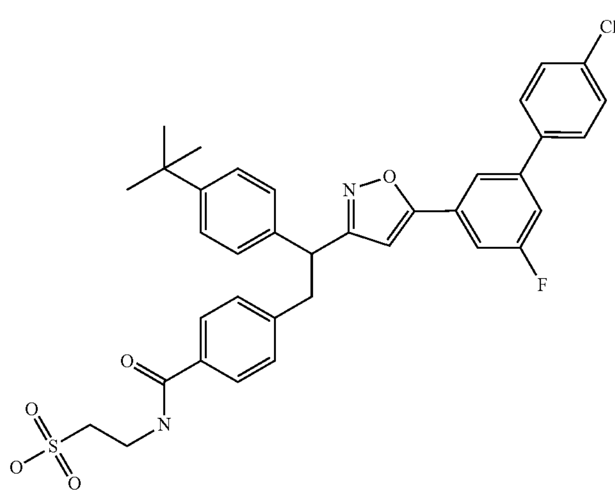 | 659.6 (−) | C36H34N2O5FClS + 1.2 H2O<br>C: 63.33 H: 5.37 N: 4.10<br>C: 63.25 H: 5.14 N: 4.13 |

| Example | STRUCTURE | MASS SPECTRUM (mode) | Formula CHN (Calcd) CHN (Found) |
|---|---|---|---|
| 2.076 | (Chiral structure) | 645.4 (+) | C36H34N2O5F2S + 1.3 H2O<br>C: 64.71 H: 5.52 N: 4.19<br>C: 64.71 H: 5.29 N: 4.20 |
| 2.077 | (Chiral structure) | 692.8 (−) | C37H35N2O6F3S + 0.6 H2O<br>C: 63.17 H: 5.19 N: 3.98<br>C: 63.22 H: 5.47 N: 4.14 |
| 2.078 | (structure) | 633.9 (+) | C39H36N2O4ClNa + (1.3)H2O<br>C: 69.03 H: 5.73 N: 4.13<br>C: 69.05 H: 5.48 N: 4.07 |

-continued
| Example | STRUCTURE | MASS SPEC-TRUM (mode) | Formula CHN (Calcd) CHN (Found) |
|---|---|---|---|
| 2.079 | 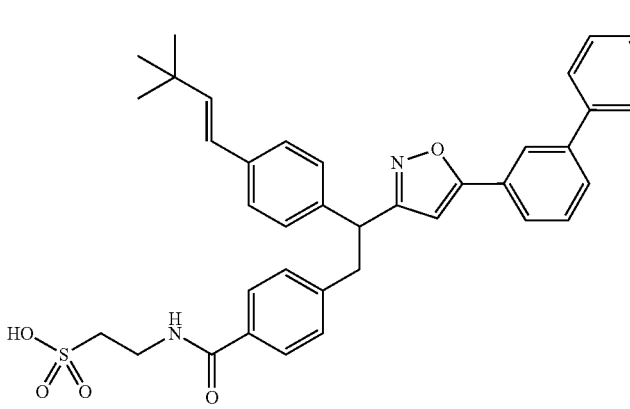 | 669.6 (+) | C38H36N2O5ClSNa + (0.6)H2O<br>C: 65.01 H: 5.34 N: 3.99<br>C: 64.94 H: 5.51 N: 3.87 |
| 2.080 | 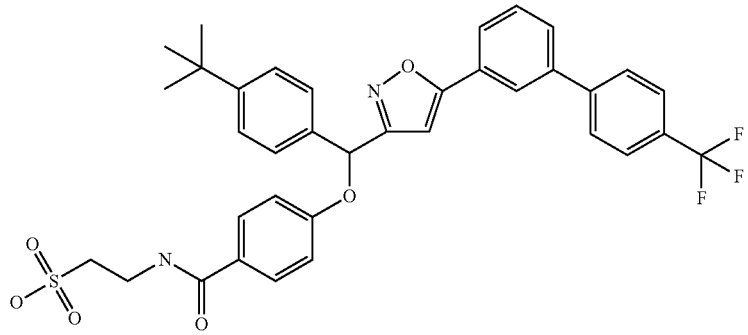 [SMILES: CC(C)(C)c1ccc(C(Oc2ccc(C(=O)NCCS(=O)(=O)O)cc2)c2cc(-c3cccc(-c4ccc(C(F)(F)F)cc4)c3)on2)cc1] | 677 (−) | C36H33F3N2O6S + 1.5 H2O<br>C: 61.27, H: 5.14, N: 3.97<br>C: 61.04, H: 5.02, N: 3.88 |
| 2.081 | 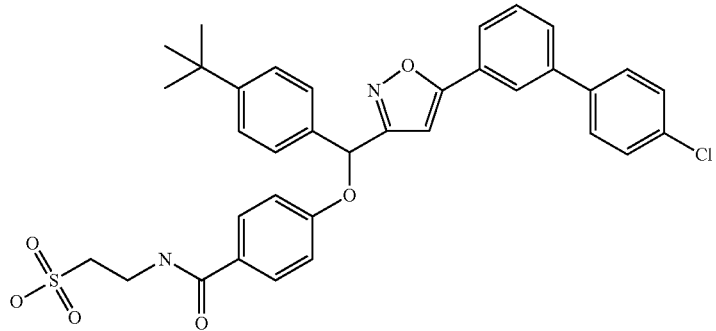 [SMILES: CC(C)(C)c1ccc(C(Oc2ccc(C(=O)NCCS(=O)(=O)O)cc2)c2cc(-c3cccc(-c4ccc(Cl)cc4)c3)on2)cc1] | 647 (−) | C35H33ClN2O6S + 1.5 H2O<br>C: 62.54, H: 5.40, N: 4.17<br>C: 62.27, H: 5.20, N: 4.09 |

-continued

| Example | STRUCTURE | MASS SPECTRUM (mode) | Formula CHN (Calcd) CHN (Found) |
|---|---|---|---|
| 2.082 | 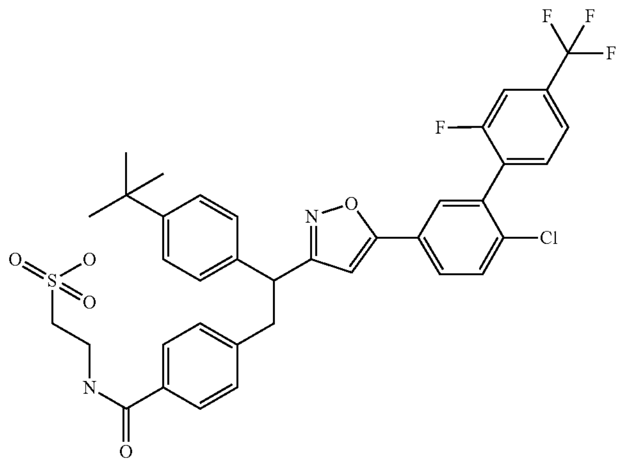 [SMILES: CC(C)(C)c1ccc(C(Cc2ccc(C(=O)NCCS(=O)(=O)O)cc2)c2cc(-c3ccc(Cl)c(-c4ccc(C(F)(F)F)cc4F)c3)on2)cc1] | 727.4 (−) | C37H33N2O5SClF4 + (0.7) CF3CO2H C: 57.01; H: 4.20; N: 3.46 C: 56.93; H: 4.47; N: 3.40 |
| 2.083 | 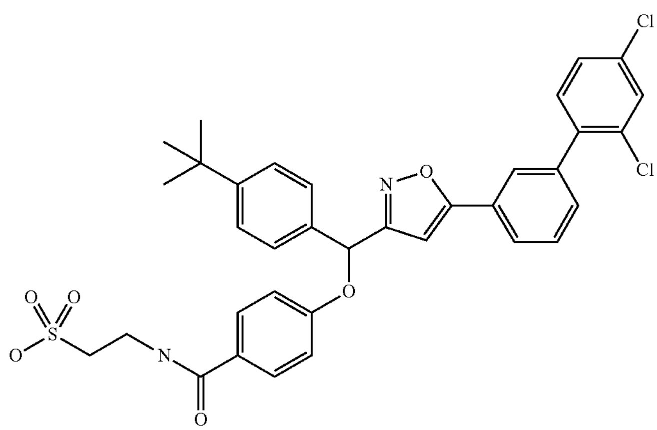 [SMILES: CC(C)(C)c1ccc(C(Oc2ccc(C(=O)NCCS(=O)(=O)O)cc2)c2cc(-c3cccc(-c4ccc(Cl)cc4Cl)c3)on2)cc1] | 681 (−) | C35H32Cl2N2O6S + 2.0 H2O + 0.6CH2Cl2 C: 55.78; H: 4.89, N: 3.65 C: 55.68, H: 4.73, N: 3.32 |
| 2.084 | 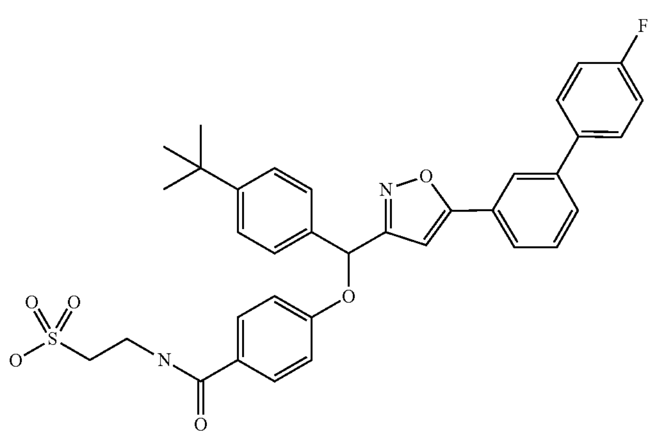 [SMILES: CC(C)(C)c1ccc(C(Oc2ccc(C(=O)NCCS(=O)(=O)O)cc2)c2cc(-c3cccc(-c4ccc(F)cc4)c3)on2)cc1] | 630 (−) | C35H33FN2O6S + 2.0 H2O + 0.1CH3CN C: 63.21, H: 5.62, N: 4.40 C: 63.19, H: 5.02, N: 4.71 |

| Example | STRUCTURE | MASS SPEC- TRUM (mode) | Formula CHN (Calcd) CHN (Found) |
|---|---|---|---|
| 2.085 | 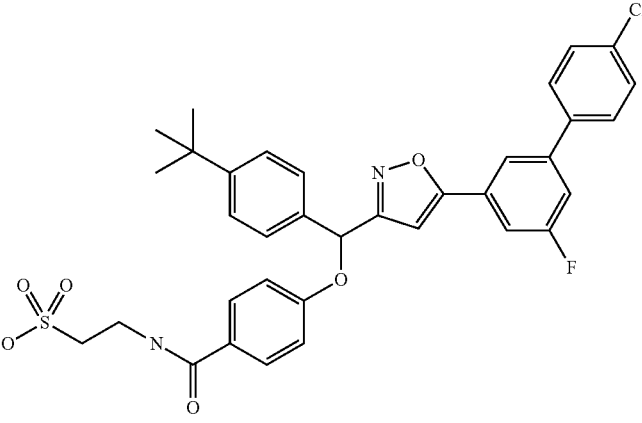 | 664 (−) | C35H32ClFN2O6S + 1.5 H2O + 0.1CH3CN C: 60.89, H: 5.12, N: 4.24 C: 60.75, H: 5.00, N: 4.35 |
| 2.086 | 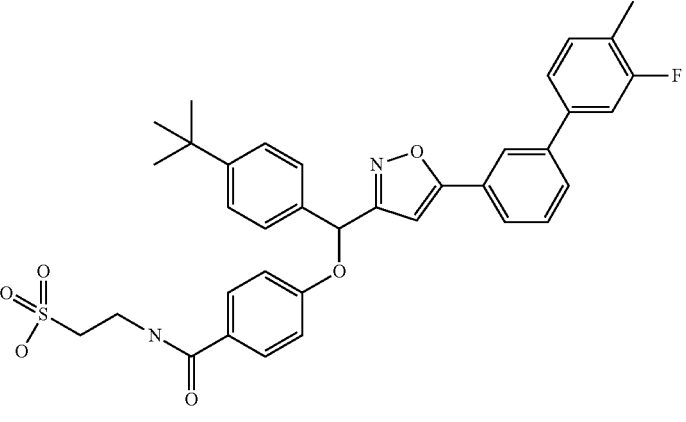 [SMILES: Cc1ccc(-c2cccc(-c3cc(C(Oc4ccc(C(=O)NCCS(=O)(=O)O)cc4)c4ccc(C(C)(C)C)cc4)no3)c2)cc1F] | 641 (−) | C36H35FN2O6S + 2.5 H2O C: 62.87, H: 5.86, N: 4.07 C: 62.89, H: 5.82, N: 4.02 |
| 2.087 | 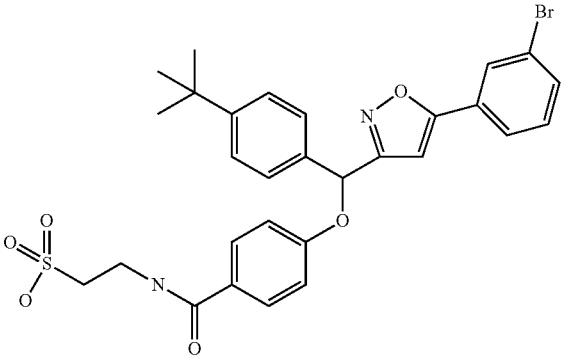 [SMILES: CC(C)(C)c1ccc(C(Oc2ccc(C(=O)NCCS(=O)(=O)O)cc2)c2cc(-c3cccc(Br)c3)on2)cc1] | 613 (+) | C29H29BrN2O6S + 1.5 H2O C: 54.38, H: 5.04, N: 4.37 C: 54.21, H: 4.74, N: 4.49 |

| Example | STRUCTURE | MASS SPECTRUM (mode) | Formula CHN (Calcd) CHN (Found) |
|---|---|---|---|
| 2.088 | 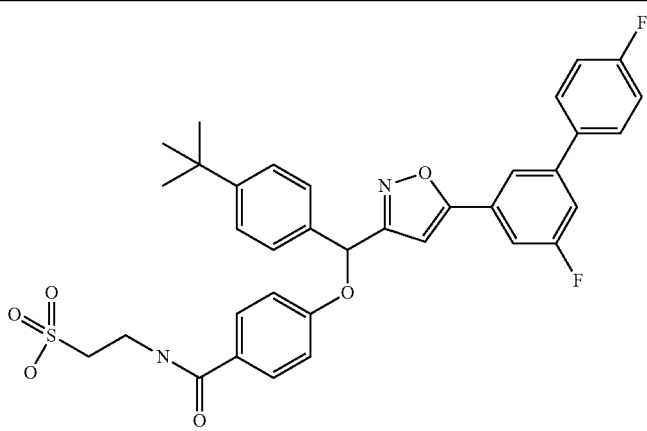 | 645 (−) | C35H32F2N2O6S + 2.7 H2O + 0.2CH3CN<br>C: 60.43, H: 5.44, N: 4.38<br>C: 60.16, H: 5.00, N: 4.62 |
| 2.089 | 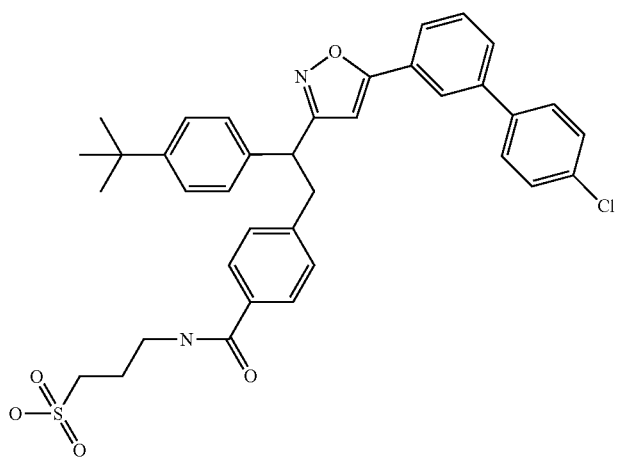 [SMILES: CC(C)(C)c1ccc(C(Cc2ccc(C(=O)NCCCS(=O)(=O)O)cc2)c2cc(-c3cccc(-c4ccc(Cl)cc4)c3)on2)cc1] | 657.0 (+) | C36H35N2O5ClS + (1.4) H2O + (1.0) LiCl<br>C: 61.31, H: 5.53, N: 3.86<br>C: 61.27, H: 5.63, N: 3.94 |
| 2.090 | 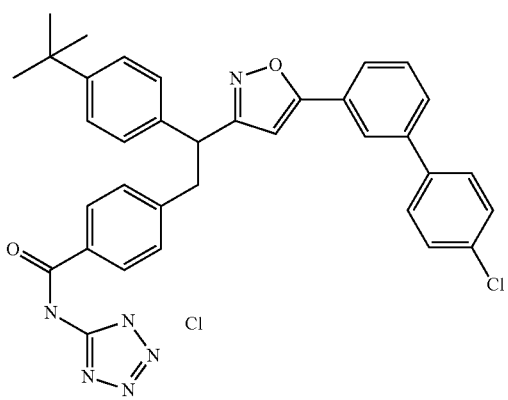 [SMILES: CC(C)(C)c1ccc(C(Cc2ccc(C(=O)Nc3nnn[nH]3)cc2)c2cc(-c3cccc(-c4ccc(Cl)cc4)c3)on2)cc1 ; Cl] | 601.9 (+) | C35H31N6O2Cl + (1.2) HCl + (0.1) CH3CO2H<br>C: 64.87, H: 503, N: 12.93<br>C: 65.15, H: 4.65, N: 12.53 |

-continued

| Example | STRUCTURE | MASS SPECTRUM (mode) | Formula CHN (Calcd) CHN (Found) |
|---|---|---|---|
| 2.091 | 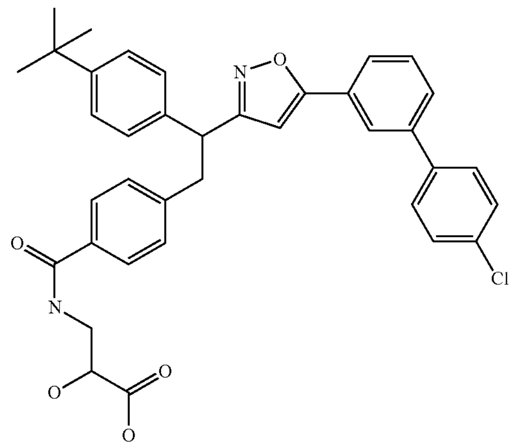 [SMILES: CC(C)(C)c1ccc(C(Cc2ccc(C(=O)NCC(O)C(=O)O)cc2)c2cc(-c3cccc(-c4ccc(Cl)cc4)c3)on2)cc1] | 623.6 (+) | C37H35N2O5Cl + (1.4) H2O + (0.4) CF3CO2H C: 65.42, H: 5.55, N: 4.04 C: 65.16, H: 5.24, N: 4.37 |
| 2.092 | 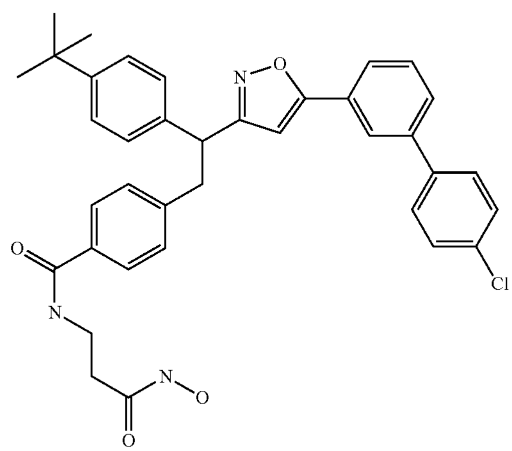 [SMILES: CC(C)(C)c1ccc(C(Cc2ccc(C(=O)NCCC(=O)NO)cc2)c2cc(-c3cccc(-c4ccc(Cl)cc4)c3)on2)cc1] | 622.3 (+) | C37H36N3O4Cl + (1.2) C6H6 + (0.4) CF3CO2H C: 70.98, H: 5.77, N: 5.52 C: 71.36, H: 5.69, N: 5.16 |
| 2.093. | 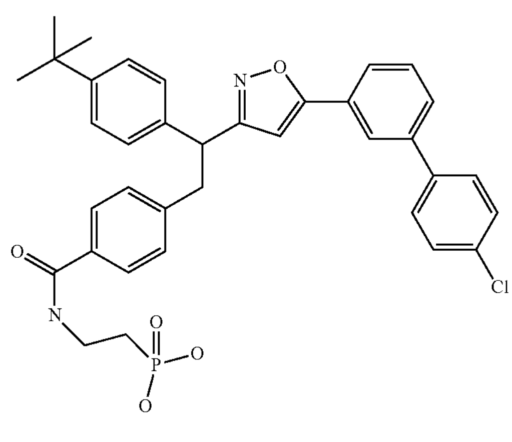 [SMILES: CC(C)(C)c1ccc(C(Cc2ccc(C(=O)NCCP(=O)(O)O)cc2)c2cc(-c3cccc(-c4ccc(Cl)cc4)c3)on2)cc1] | 643.2 (+) | C36H36N2O5ClP + (0.8) H2O C: 65.76, H: 5.76, N: 4.26 C: 65.81, H: 5.70, N: 4.27 |

-continued

| Example | STRUCTURE | MASS SPECTRUM (mode) | Formula CHN (Calcd) CHN (Found) |
|---|---|---|---|
| 2.094 | 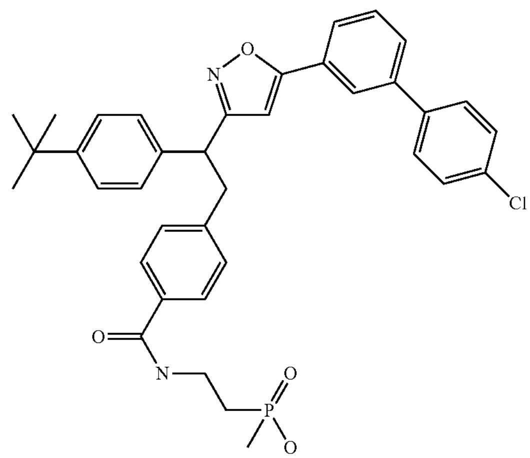 [SMILES: CC(C)(C)c1ccc(C(Cc2ccc(C(=O)NCCP(C)(=O)O)cc2)c2cc(-c3cccc(-c4ccc(Cl)cc4)c3)on2)cc1] | 641.3 (+) | C37H38N2O4ClP + (2.1) H2O + (1.2) CH3OH C: 63.95, H: 6.60, N: 3.90 C: 64.21, H: 7.00, N: 3.84 |
| 2.095 | 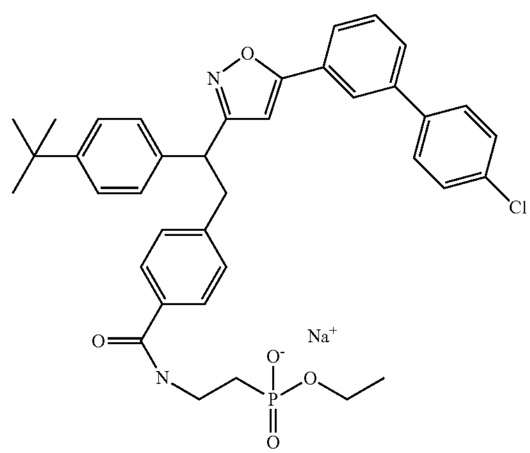 [SMILES: CCOP(=O)([O-])CCNC(=O)c1ccc(CC(c2ccc(C(C)(C)C)cc2)c2cc(-c3cccc(-c4ccc(Cl)cc4)c3)on2)cc1 ; [Na+]] | 671.3 (+) | C38H39N2O5ClPNa + (1.7) H2O + (0.2) CH3OH C: 62.84, H: 5.96, N: 3.84 C: 62.90, H: 5.73, N: 3.77 |
| 2.096 | 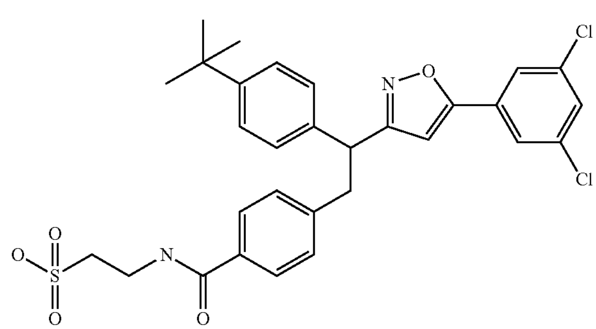 [SMILES: CC(C)(C)c1ccc(C(Cc2ccc(C(=O)NCCS(=O)(=O)O)cc2)c2cc(-c3cc(Cl)cc(Cl)c3)on2)cc1] | 601.2 (+) | C30H30N2O5Cl2SNa + (1.5) H2O C: 55.30, H: 5.10, N: 4.30 C: 55.25, H: 4.93, N: 4.25 |

-continued
| Example | STRUCTURE | MASS SPECTRUM (mode) | Formula CHN (Calcd) CHN (Found) |
|---|---|---|---|
| 2.097 | 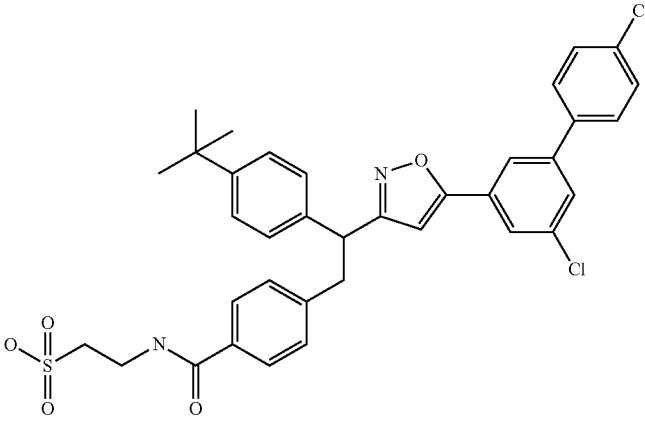 [SMILES: CC(C)(C)c1ccc(C(Cc2ccc(C(=O)NCCS(=O)(=O)O)cc2)c2cc(-c3cc(Cl)cc(-c4ccc(F)cc4)c3)on2)cc1] | 675, 677 (−) | C36H34Cl2N2O5S + 0.25 CF3CO2H<br>C: 61.61, H: 4.94, N: 3.94<br>C: 61.38, H: 5.31, N: 3.88 |
| 2.098 | 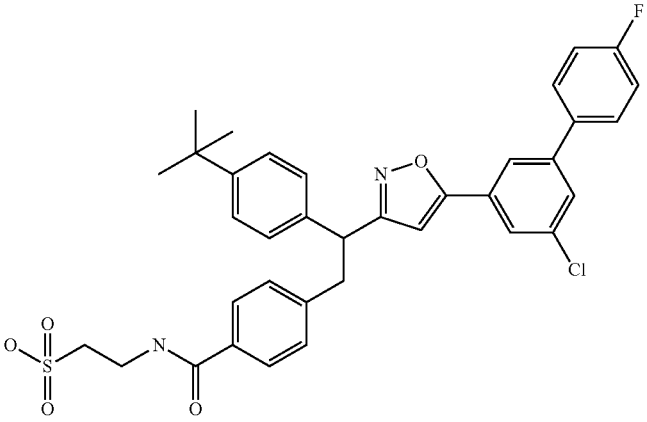 | 659.6 (−) | C36H34ClFN2O5S + 0.5 CF3CO2H + 0.5 H2O<br>C: 61.11, H: 4.92, N: 3.85<br>C: 61.18, H: 4.57, N: 3.96 |
| 2.099 | 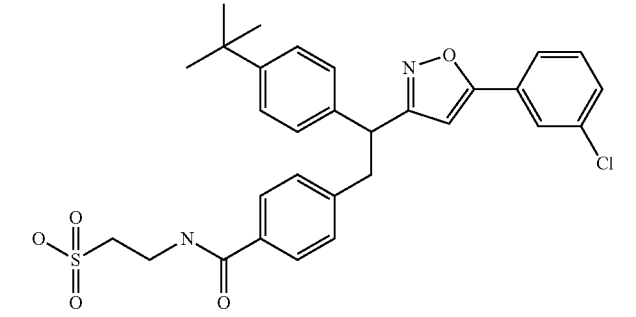 [SMILES: CC(C)(C)c1ccc(C(Cc2ccc(C(=O)NCCS(=O)(=O)O)cc2)c2cc(-c3cccc(Cl)c3)on2)cc1] | 565 (−) | C30H31ClN2O5S + 0.1 CF3CO2H + 1.5 H2O<br>Expected C: 59.90, H: 5.68, N: 4.63 Found C: 60.22, H: 5.66, N: 4.56 |

-continued

| Example | STRUCTURE | MASS SPECTRUM (mode) | Formula CHN (Calcd) CHN (Found) |
|---|---|---|---|
| 2.100 | 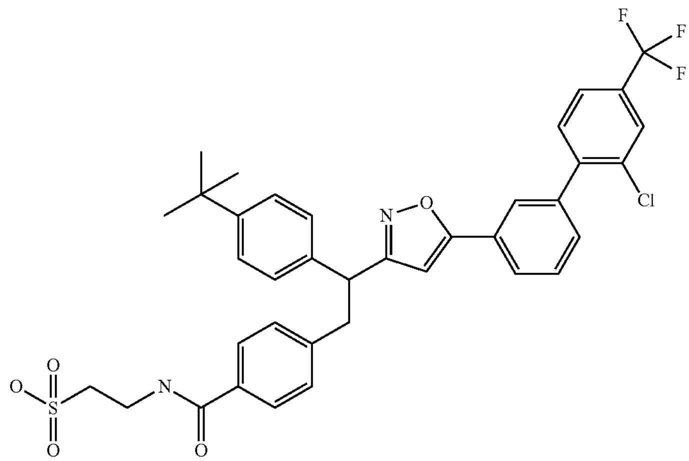 [SMILES: CC(C)(C)c1ccc(C(Cc2ccc(C(=O)NCCS(=O)(=O)O)cc2)c2cc(-c3cccc(-c4ccc(C(F)(F)F)cc4Cl)c3)on2)cc1] | 710 (−) | C37H36F2N2O6S + 0.1 CF3CO2H + 1.7 H2O C: 63.76, H: 5.68, N: 4.00 C: 63.53, H: 5.64, N: 3.88 |
| 2.101 | 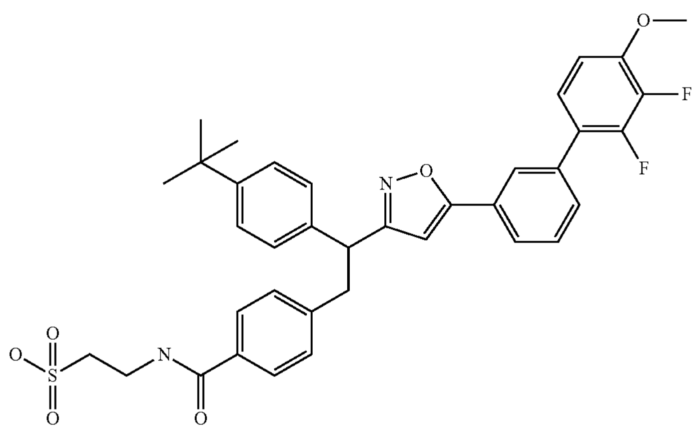 [SMILES: COc1ccc(-c2cccc(-c3cc(C(Cc4ccc(C(=O)NCCS(=O)(=O)O)cc4)c4ccc(C(C)(C)C)cc4)no3)c2)c(F)c1F] | 673 (−) | C37H36F2N2O6S + 0.1 CF3CO2H + 1.7 H2O Expected C: 63.76, H: 5.68, N: 4.00 Found C: 63.53, H: 5.64, N: 3.88 |
| 2.102 | 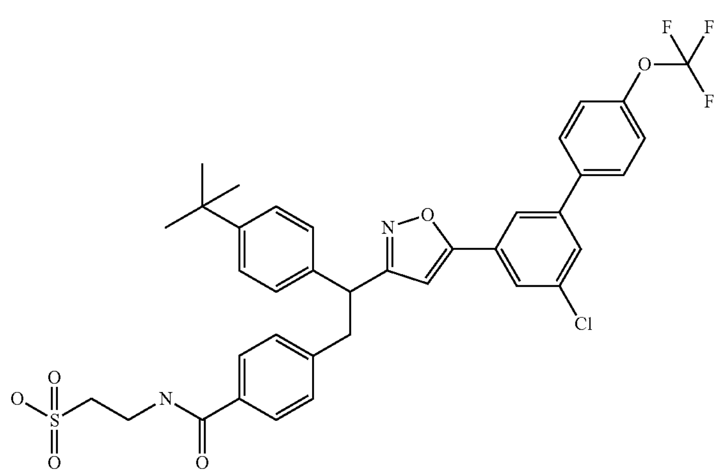 [SMILES: CC(C)(C)c1ccc(C(Cc2ccc(C(=O)NCCS(=O)(=O)O)cc2)c2cc(-c3cc(Cl)cc(-c4ccc(OC(F)(F)F)cc4)c3)on2)cc1] | | C33H35ClN2O5S + 0.2 CF3CO2H + 1.5 H2O C: 61.06, H: 5.86, N: 4.26 C: 60.92, H: 6.13, N: 4.58 |

| Example | STRUCTURE | MASS SPECTRUM (mode) | Formula CHN (Calcd) CHN (Found) |
|---|---|---|---|
| 2.103 | 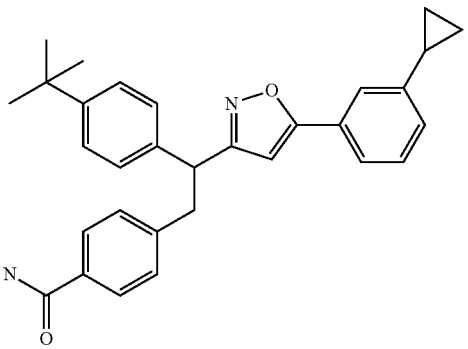 | 571 (−) | C33H35ClN2O5S + 0.2 CF3CO2H + 1.5 H2O<br>C: 61.06, H: 5.86, N: 4.26<br>C: 60.92, H: 6.13, N: 4.58 |
| 2.104 | 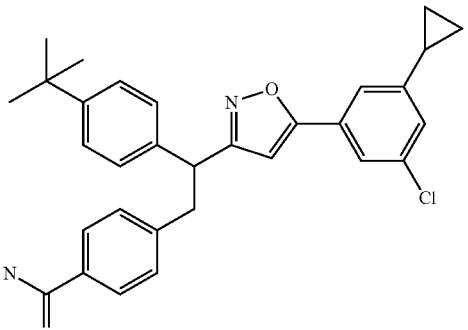 | 605, 607 (−) | C33H35ClN2O5S + 0.2 CF3CO2H + 1.5 H2O<br>C: 61.06, H: 5.86, N: 4.26<br>C: 60.92, H: 6.13, N: 4.58 |
| 2.105 | 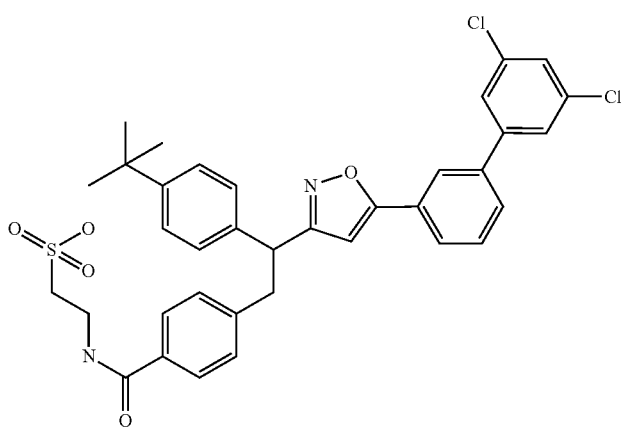 [SMILES: CC(C)(C)c1ccc(C(Cc2ccc(C(=O)NCCS(=O)(=O)O)cc2)c2cc(-c3cccc(-c4cc(Cl)cc(Cl)c4)c3)on2)cc1] | 675.4 (−) | C36H34Cl2N2O5S + 1.2H2O<br>C: 61.84, H: 5.25, N: 4.01<br>C: 61.71, H: 4.99, N: 4.18 |

-continued

| Example | STRUCTURE | MASS SPECTRUM (mode) | Formula CHN (Calcd) CHN (Found) |
|---|---|---|---|
| 2.106 | 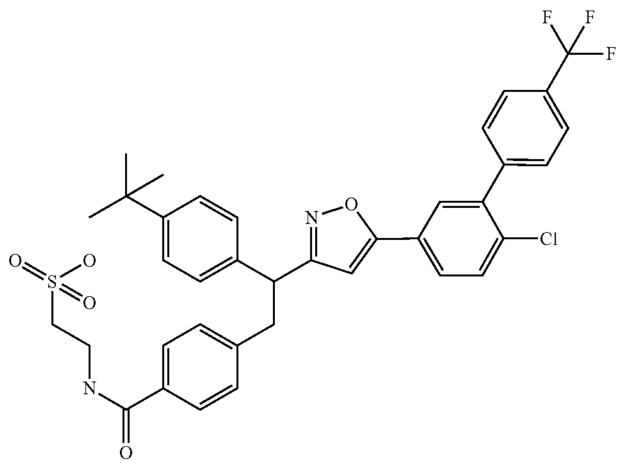 [SMILES: CC(C)(C)c1ccc(C(Cc2ccc(C(=O)NCCS(=O)(=O)O)cc2)c2cc(-c3ccc(Cl)c(-c4ccc(C(F)(F)F)cc4)c3)on2)cc1] | 709.6 (−) | C37H34ClF3N2O5S + 1H2O 60.94  4.98  3.84 60.91  4.63  3.67 |
| 2.107 | 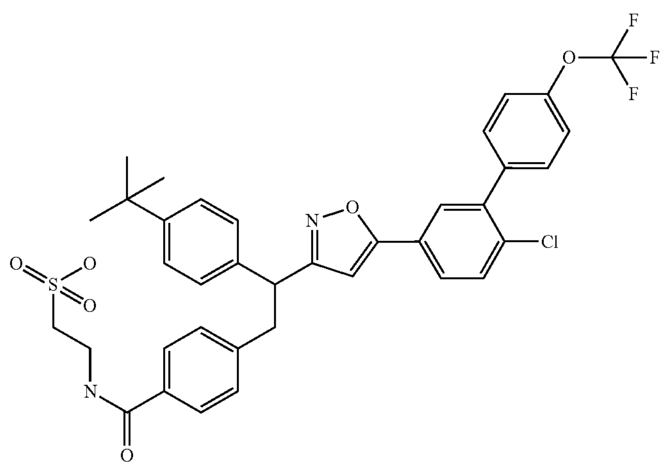 [SMILES: CC(C)(C)c1ccc(C(Cc2ccc(C(=O)NCCS(=O)(=O)O)cc2)c2cc(-c3ccc(Cl)c(-c4ccc(OC(F)(F)F)cc4)c3)on2)cc1] | 725.4 (−) | C37H34ClF3N2O6S + 1.8H2O C: 58.50, H: 4.99, N: 3.69 C: 58.18, H: 4.33, N: 3.64 |
| 2.108 | 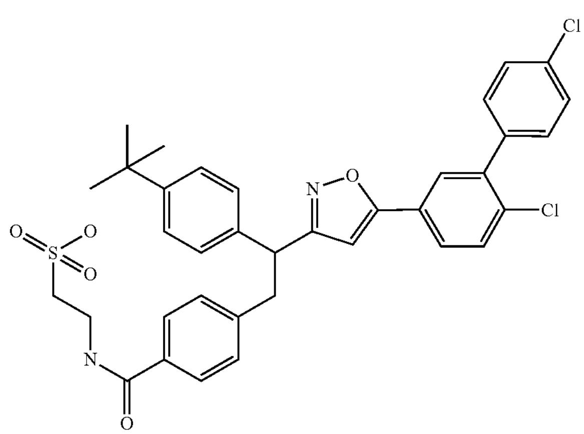 [SMILES: CC(C)(C)c1ccc(C(Cc2ccc(C(=O)NCCS(=O)(=O)O)cc2)c2cc(-c3ccc(Cl)c(-c4ccc(Cl)cc4)c3)on2)cc1] | 677.6 (−) | C36H34ClN2O5S + 1.2H2O + 0.1CH2Cl2 C: 61.62, H: 5.21, N: 3.96 C: 60.93, H: 4.61, N: 3.90 |

-continued

| Example | STRUCTURE | MASS SPECTRUM (mode) | Formula CHN (Calcd) CHN (Found) |
|---|---|---|---|
| 2.109 | 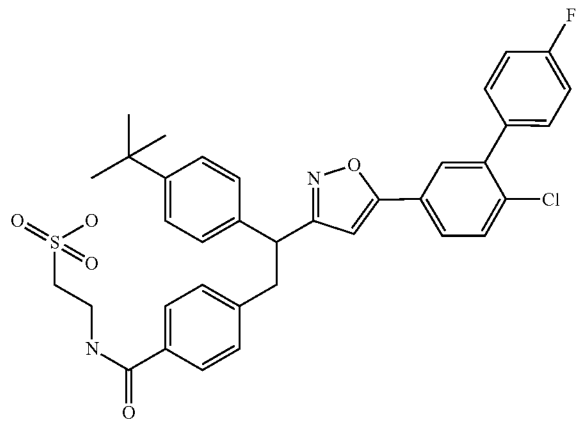 [SMILES: CC(C)(C)c1ccc(C(Cc2ccc(C(=O)NCCS(=O)(=O)O)cc2)c2cc(-c3ccc(Cl)c(-c4ccc(F)cc4)c3)on2)cc1] | 659.6 (−) | C36H34ClFN2O5S + 1.0H2O + 1.0TFA<br>C: 57.54, H: 4.70, N: 3.53<br>C: 57.35, H: 4.53, N: 3.44 |
| 2.110 | 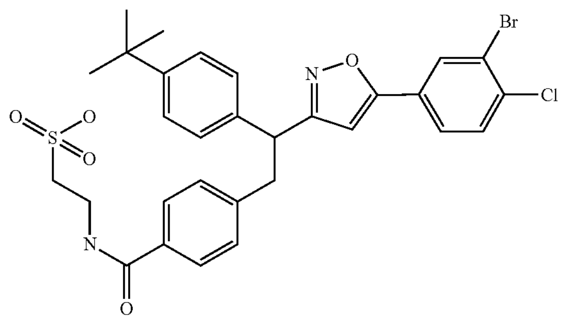 [SMILES: CC(C)(C)c1ccc(C(Cc2ccc(C(=O)NCCS(=O)(=O)O)cc2)c2cc(-c3ccc(Cl)c(Br)c3)on2)cc1] | 645.0 (−) | C30H30BrClN2O5S + 0.5TFA<br>C: 52.96, H: 4.37, N: 3.98<br>C: 52.64, H: 4.69, N: 3.81 |
| 2.111 | 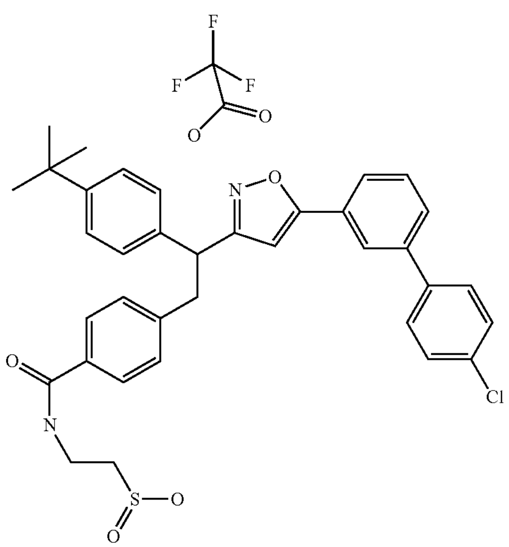 [SMILES: CC(C)(C)c1ccc(C(Cc2ccc(C(=O)NCCS(=O)O)cc2)c2cc(-c3cccc(-c4ccc(Cl)cc4)c3)on2)cc1 ; O=C(O)C(F)(F)F] | 739.6 (+) | C36H35ClN2O4S + 0.5 CF3CO2H<br>C: 64.95, H: 5.23, N: 4.09<br>C: 64.91, H: 4.97, N: 4.19 |

-continued

| Example | STRUCTURE | MASS SPECTRUM (mode) | Formula CHN (Calcd) CHN (Found) |
|---|---|---|---|
| 2.112 | 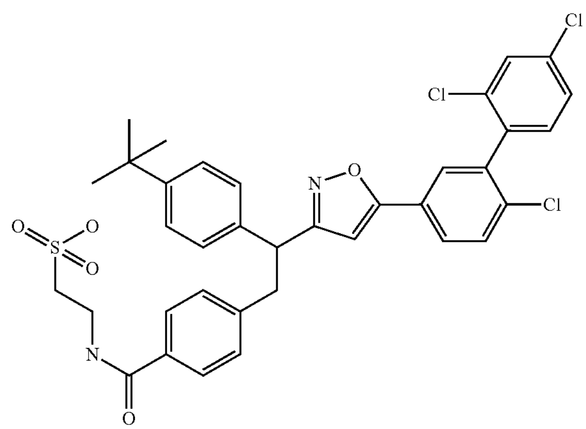 [SMILES: CC(C)(C)c1ccc(C(Cc2ccc(C(=O)NCCS(=O)(=O)O)cc2)c2cc(-c3ccc(Cl)c(-c4ccc(Cl)cc4Cl)c3)on2)cc1] | 711.4 (−) | C36H33Cl3N2O5S + 1.2H2O<br>C: 58.93, H: 4.86, N: 3.82<br>C: 58.66, H: 5.16, N: 4.16 |
| 2.113 | 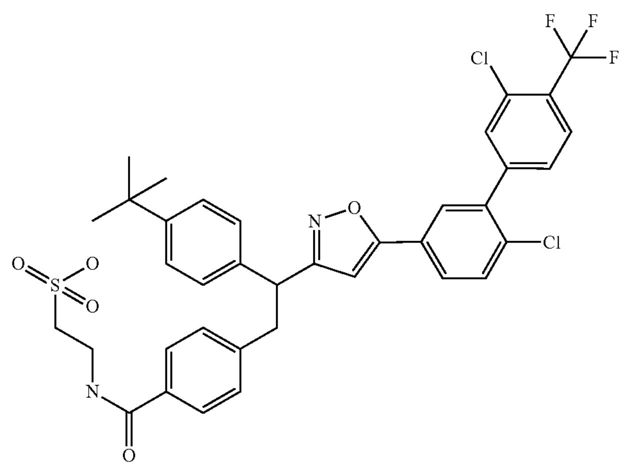 [SMILES: CC(C)(C)c1ccc(C(Cc2ccc(C(=O)NCCS(=O)(=O)O)cc2)c2cc(-c3ccc(Cl)c(-c4ccc(C(F)(F)F)c(Cl)c4)c3)on2)cc1] | 743.6 (−) | C37H33Cl2F3N2O5S + 1.3H2O<br>C: 57.79, H: 4.67, N: 3.64<br>C: 57.83, H: 4.43, N: 3.77 |
| 2.114 | 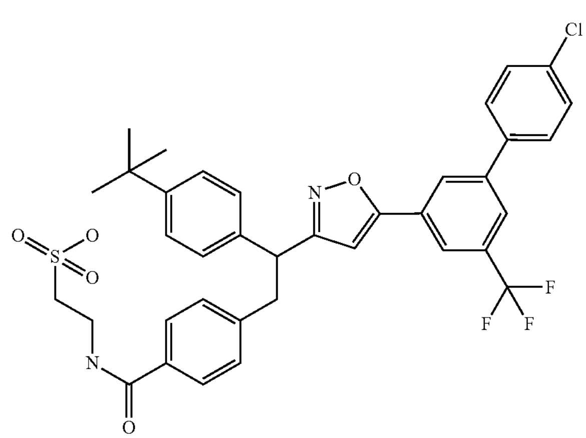 [SMILES: CC(C)(C)c1ccc(C(Cc2ccc(C(=O)NCCS(=O)(=O)O)cc2)c2cc(-c3cc(-c4ccc(Cl)cc4)cc(C(F)(F)F)c3)on2)cc1] | 709.2 (−) | C37H34ClF3N2O5S + 1.3H2O<br>C: 60.49, H: 5.02, N: 3.81<br>C: 60.18, H: 4.95, N: 4.14 |

-continued

| Example | STRUCTURE | MASS SPECTRUM (mode) | Formula<br>CHN (Calcd)<br>CHN (Found) |
|---|---|---|---|
| 2.115 | 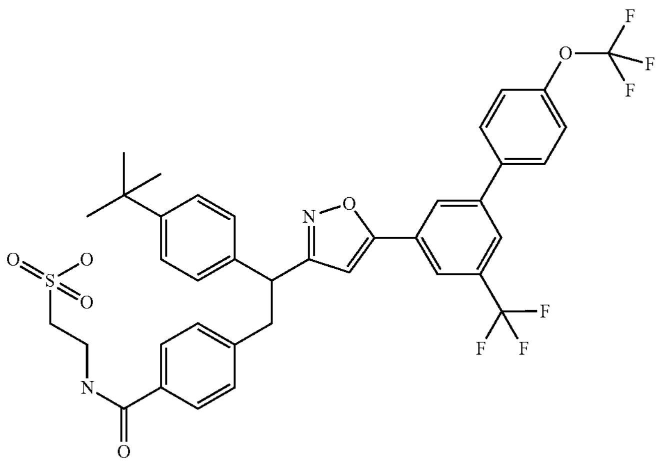 [SMILES: CC(C)(C)c1ccc(C(Cc2ccc(C(=O)NCCS(=O)(=O)O)cc2)c2cc(-c3cc(-c4ccc(OC(F)(F)F)cc4)cc(C(F)(F)F)c3)on2)cc1] | 759.2 (−) | C38H34F6N2O6S +<br>1.3H2O<br>C: 58.20, H: 4.70, N: 3.57<br>C: 57.94, H: 4.67, N: 3.73 |
| 2.116 | 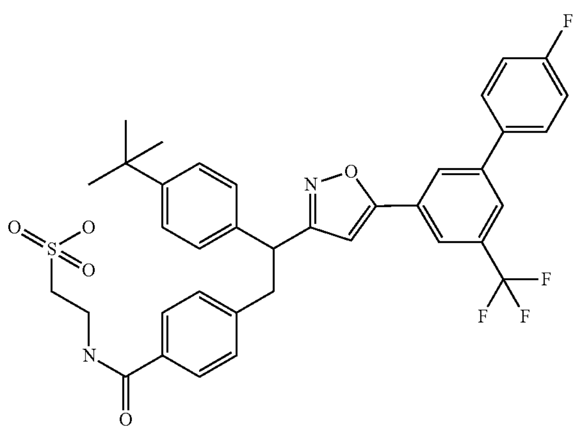 [SMILES: CC(C)(C)c1ccc(C(Cc2ccc(C(=O)NCCS(=O)(=O)O)cc2)c2cc(-c3cc(-c4ccc(F)cc4)cc(C(F)(F)F)c3)on2)cc1] | 693.0 (−) | C37H34F4N2O5S +<br>1.5H2O<br>C: 61.57, H: 5.17, N: 3.88<br>C: 61.26, H: 4.86, N: 4.10 |
| 2.117 | 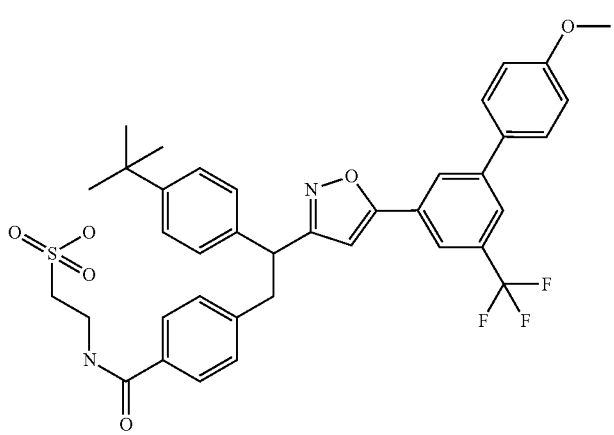 [SMILES: COc1ccc(-c2cc(-c3cc(C(Cc4ccc(C(=O)NCCS(=O)(=O)O)cc4)c4ccc(C(C)(C)C)cc4)no3)cc(C(F)(F)F)c2)cc1] | 705.6 (−) | C38H37F3N2O6S +<br>1.5H2O<br>C: 62.20, H: 5.49, N: 3.82<br>C: 61.99, H: 5.54, N: 4.22 |

| Example | STRUCTURE | MASS SPECTRUM (mode) | Formula CHN (Calcd) CHN (Found) |
|---|---|---|---|
| 2.118 | 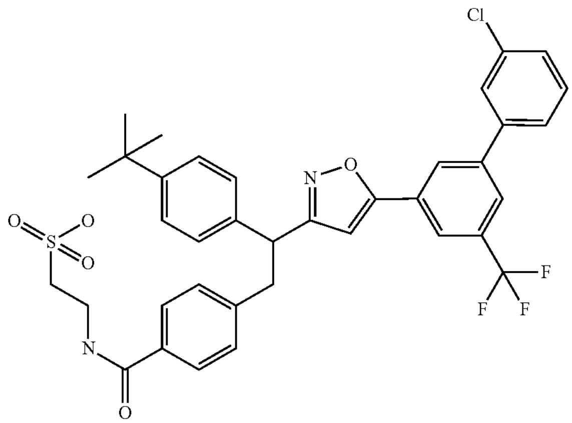 [SMILES: CC(C)(C)c1ccc(C(Cc2ccc(C(=O)NCCS(=O)(=O)O)cc2)c2cc(-c3cc(-c4cccc(Cl)c4)cc(C(F)(F)F)c3)on2)cc1] | 709.6 (−) | C37H34ClF3N2O5S + 1.3H2O C: 60.49, H: 5.02, N: 3.81 C: 60.20, H: 4.83, N: 4.43 |
| 2.119 | 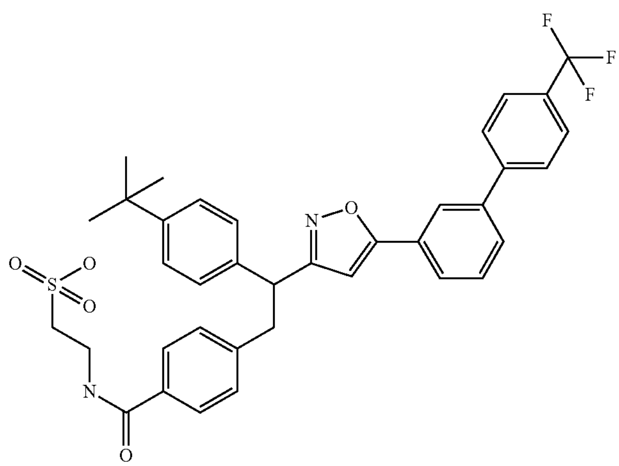 [SMILES: CC(C)(C)c1ccc(C(Cc2ccc(C(=O)NCCS(=O)(=O)O)cc2)c2cc(-c3cccc(-c4ccc(C(F)(F)F)cc4)c3)on2)cc1] | 675.0 (−) | C37H35F3N2O5S + 2 H2O C: 62.35, H: 5.51, N: 3.93 C: 62.18, H: 5.60, N: 3.89 |
Enantiomerically enriched compounds of this class were synthesized as described below:
4-[3-(4-Benzyl-2-oxo-oxazolidin-3-yl)-[2-(4-tert-butyl-phenyl)-3-oxo-propyl]-benzoic acid methyl ester
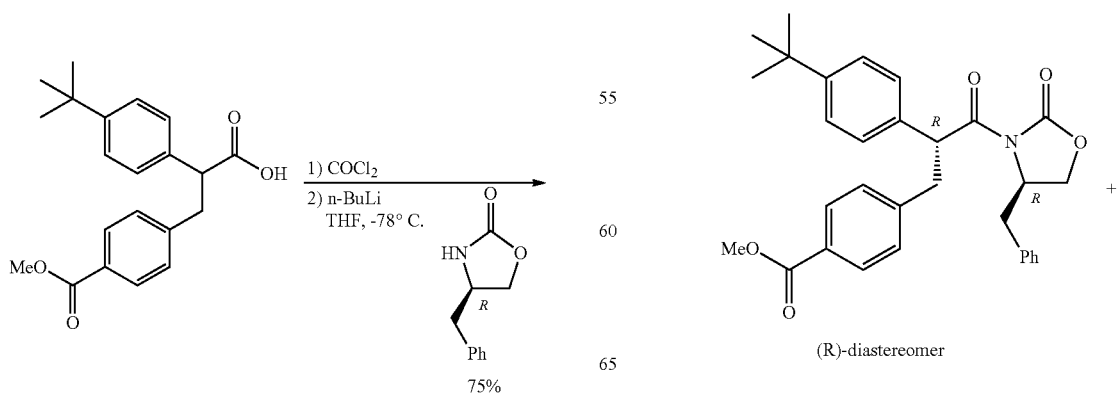

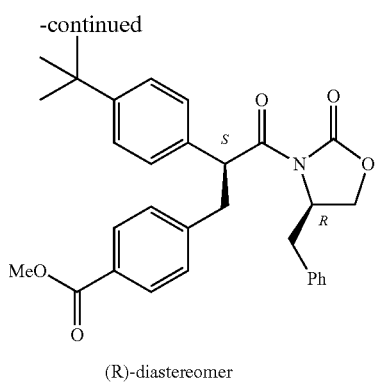

(R)-diastereomer

Step 1

To a solution of 4-tert-butyl-phenyl)-2-carboxy-ethyl]-benzoic acid methyl ester (2.5 g, 5.20 mmol, prepared as reported in Bioorg. Med. Chem Lett. 2004, 14, 2047-2050) in $CH_2Cl_2$ (50 mL) at room temperature was added oxalyl chloride (0.98 g, 7.81 mmol). The reaction mixture was stirred at room temperature for overnight and the solvent was removed under reduced pressure. The residue was dried under vacuum for 3-4 h. The crude acid chloride was used in the next step.

Step 2

To a stirred solution of R-(+)-4-benzyl-oxazolidinone (1.48 g, 8.37 mmol) in THF (20 mL) at −78° C. was added n-BuLi (5.2 mL, 8.37 mmol, 1.6 M solution in hexane). The reaction mixture was stirred for 30 min, at −78° C., then acid chloride (2.5 g, 6.98 mmol) was added dropwise, stirred for 1 h at −78° C. then allowed to warm to rt and stirred for another hour (monitored by TLC). The reaction mixture was quenched with saturated $NH_4Cl$ solution (20 mL) and stirred for 10 min. The reaction mixture was extracted with ethyl acetate (2×50 mL) and the combined organic layers were washed with brine, dried over $Na_2SO_4$ and concentrated under reduced pressure. The crude product was purified by column chromatography on silica gel, eluting with ethyl acetate-hexanes 5-15% to afford 4-[3-(4-benzyl-2-oxo-oxazolidin-3-yl)-[2-(4-tert-butyl-phenyl)-3-oxo-propyl]-benzoic acid methyl ester as a mixture of (R) and (S) diastereomers (1.56 g, and 1.25 g respectively, 79% overall yield).

(R)-Diastereomer $^1$H NMR (300 MHz, $CDCl_3$): 7.97 (d, J=8.4 Hz, 2H), 7.41-7.26 (m, 9H), 7.0-6.97 (m, 2H), 5.52 (dd, J=5.7, 9.6 Hz, 1H), 4.61-4.57 (m, 1H), 4.04 (d, J=4.8 Hz, 2H), 3.91 (s, 3H), 3.61 (dd, J=9.6, 13.2 Hz, 1H), 3.16-3.07 (m, 2H), 2.58 (dd, J=9.3, 13.5 Hz, 1H), 1.34 (s, 9H); TLC conditions: Uniplate silica gel, 250 microns; mobile phase=ethyl acetate/hexanes (2:1); $R_f$=0.55.

(S)-Diastereomer $^1$H NMR (300 MHz, $CDCl_3$): 7.95 (d, J=8.4 Hz, 2H), 7.41-7.26 (m, 9H), 6.90 (dd, J=7.5, 12.5 Hz, 2H), 5.43 (dd, J=5.7, 9.9 Hz, 1H), 4.68-4.63 (m, 1H), 4.11-4.03 (m, 2H), 3.92 (s, 3H), 3.56 (dd, J=9.9, 13.8 Hz, 1H), 3.16-3.02 (m, 2H), 2.64 (dd, J=8.4, 13.8 Hz, 1H), 1.35 (s, 9H); TLC conditions: Uniplate silica gel, 250 microns; mobile phase=ethyl acetate/hexanes (2:1); $R_f$=0.4.

The Stereochemistry was Assigned by X-Ray Crystal Structure (R)-4-[2-(4-tert-butyl-phenyl)-2-carboxy-ethyl]-benzoic acid methyl ester

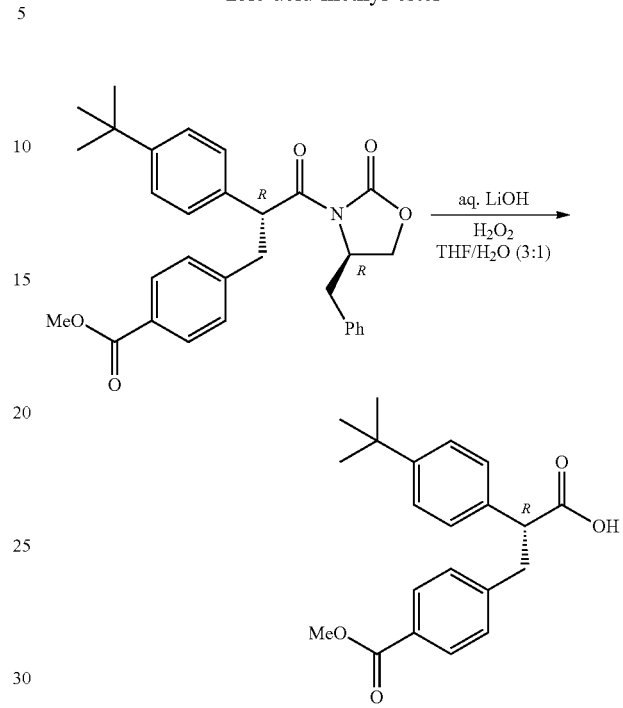

To a stirred solution of the (R)-diastereomer obtained in the step above (0.62 g, 1.24 mmol) in THF/$H_2O$ (20 mL) (3:1) at room temperature was added $H_2O_2$ (0.42 g, 12.4 mmol 30% in H2O) followed by LiOH (60 mg, 2.48 mmol). The reaction mixture was stirred for 2 h, at room temperature, and quenched with 0.1 N HCl. The reaction mixture was extracted with ethyl acetate (100 mL) and dried over $Na_2SO_4$, filtered and concentrated under reduced pressure to afford corresponding acid. The crude title product was used in the next step without further purification (0.34 g, 80%):

$^1$H NMR (300 MHz, $CD_3OD$): δ 7.85 (d, J=4.8 Hz, 2H), 7.34-7.22 (m, 6H), 3.86 (s, 3H), 3.85-3.83 (m, 1H), 3.40 (dd, J=5.4, 8.4 Hz, 1H), 3.03 (dd, J=4.2, 8.4 Hz, 1H), 1.30 (s, 9H); TLC conditions: Uniplate silica gel, 250 microns; mobile phase=$CH_2Cl_2$/MeOH (10%); $R_f$=0.35.

Chiral HPLC conditions: Kromasil 100-5-TBB chiral column 250×4.6 cm, 5% Hexane/2-propanol, 1 mL/min, RT=4.2 min. Enantiomeric excess: >90%

(S)-4-[2-(4-tert-butyl-phenyl)-2-carboxy-ethyl]-benzoic acid methyl ester

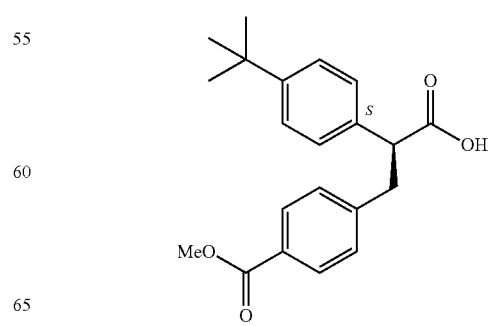

The title compound was synthesized as described above from the (S)-diastereomer of the isoxazolone precursor.

¹H NMR (300 MHz, CDCl₃): δ 7.85 (d, J=4.8 Hz, 2H), 7.34-7.22 (m, 6H), 3.86 (s, 3H), 3.85-3.83 (m, 1H), 3.40 (dd, J=5.4, 8.4 Hz, 1H), 3.03 (dd, J=4.2, 8.4 Hz, 1H), 1.30 (s, 9H); TLC conditions: Uniplate silica gel, 250 microns; mobile phase=CH₂Cl₂/MeOH (10%); R$_f$=0.35.

Chiral HPLC conditions: Kromasil 100-5-TBB chiral column 250×4.6 cm, 5% Hexane/2-propanol, 1 mL/min, RT=3.5 min. Enantiomeric excess: >94%

(R)- and (S)-4-{2-(4-tert-Butyl-phenyl)-2-[5-(4'-chloro-biphenyl-3-yl)-isoxazol-3-yl]-ethyl}-benzoic acid)

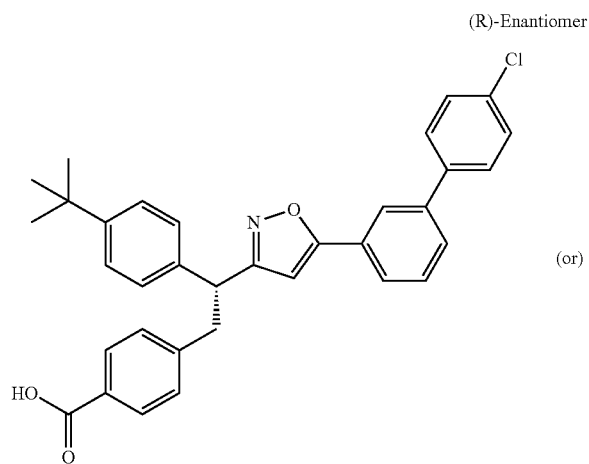

(R)-Enantiomer (or)

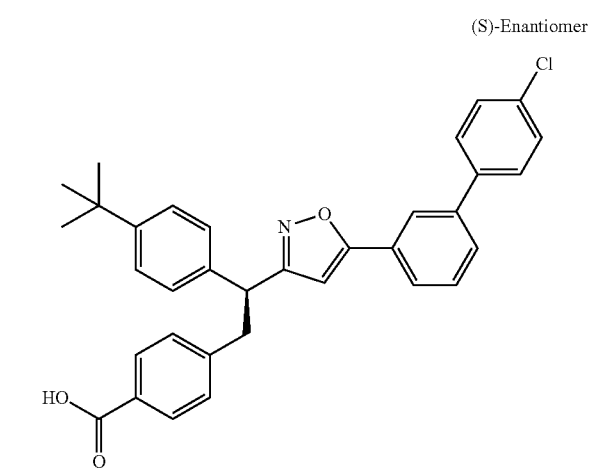

(S)-Enantiomer

The methods described in Example 2.002 were utilized to synthesize the title compounds from the (R)-4-[2-(4-tert-butyl-phenyl)-2-carboxy-ethyl]-benzoic acid methyl ester and (S)-4-[2-(4-tert-butyl-phenyl)-2-carboxy-ethyl]-benzoic acid methyl ester respectively Example 2.120: (S)-2-(4-{2-(4-tert-Butyl-phenyl)-2-[5-(4'-chloro-biphenyl-3-yl)-isoxazol-3-yl]-ethyl}-benzoylamino)-ethane sulfonic acid (29)

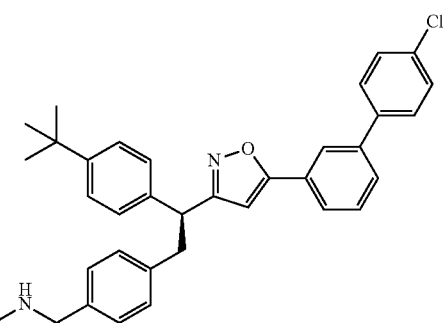

To a mixture of (S)-4-{2-(4-tert-Butyl-phenyl)-2-[5-(4'-chloro-biphenyl-3-yl)-isoxazol-3-yl]-ethyl}-benzoic acid (0.25 g, 0.46 mmol), EDCI (133 mg, 0.69 mmol), HOBt (107 mg, 0.69 mmol), N,N-diisopropylethylamine (0.25 mL, 1.95 mmol) in DMF (10 mL), and followed by taurine (116 mg, 0.093 mmol) was added. The resulting mixture was stirred for 14 h and monitored by LCMS after completion of the reaction the solvent was removed under reduced pressure. The resulting mixture was purified by column chromatography on C-18, eluting with H₂O/Acetonitrile 40% to afford (4-{2-(4-tert-Butyl-phenyl)-2-[5-(4'-chloro-biphenyl-3-yl)-isoxazol-3-yl]-ethyl}-benzoylamino)ethane sulfonic acid (29) as a white solid. (125 mg, 42%): ¹H NMR (300 MHz, MeOD): 8.01 (s, 1H), 7.78 (d, J=6.9 Hz, 2H), 7.70-7.47 (m, 6H), 7.35 (d, J=9.0 Hz, 2H), 7.30 (d, J=8.1 Hz, 2H), 6.86 (s, 1H), 4.47 (t, J=6.9 Hz, 1H), 3.85-3.70 (m, 2H), 3.75 (dd, J=4.9, 13.2 Hz, 1H), 3.25-3.05 (m, 2H), 1.31 (s, 9H); LC-MS m/z=643 [C36H35ClN2O5S]⁺; HPLC conditions: Waters Atlantis C-18 OBD 4.6×150 mm; mobile phase=ACN/(H₂O:0.1TFA) flow rate=1.0 mL/min; detection=UV @254 and 220 nm retention time in min: 21.20; Anal Calcd: (MF:C36H35ClN2O5S+1.5H₂O+0.2 CH2Cl2) Calcd: C:63.27, H:5.63, N:4.08. Found: C: 63.24, H:5.75, N:3.96. α$_{D[25]}$ MeOH (4.66 mg in 1.0 mL)=+13.487.

Example 2.121: (R)-2-(4-{2-(4-tert-Butyl-phenyl)-2-[5-(4'-chloro-biphenyl-3-yl)-isoxazol-3-yl]-ethyl}-benzoylamino)-ethane sulfonic acid (30)

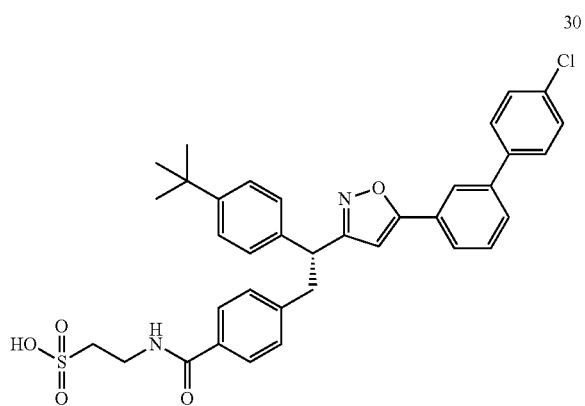 [SMILES: CC(C)(C)c1ccc([C@@H](Cc2ccc(C(=O)NCCS(=O)(=O)O)cc2)c2cc(-c3cccc(-c4ccc(Cl)cc4)c3)on2)cc1]

The method described in Example 2.120 was followed to synthesize the title compound, except that (R)-4-({2-(4-tert-Butyl-phenyl)-2-[5-(4'-chloro-biphenyl-3-yl)-isoxazol-3-yl]-ethyl}-benzoic acid was used as a starting material $^1$H NMR (300 MHz, MeOD): 8.03 (s, 1H), 7.79 (d, J=6.9 Hz, 2H), 7.73-7.49 (m, 6H), 7.36 (d, J=9.3 Hz, 2H), 7.30 (d, J=8.1 Hz, 2H), 6.87 (s, 1H), 4.48 (t, J=6.9 Hz, 1H), 3.79 (t, J=6.6 Hz, 2H), 3.43 (dd, J=4.9, 13.2 Hz, 1H), 3.41 (dd, J=5.7, 14.1 Hz, 1H), 3.08 (t, J=6.9 Hz, 2H), 1.31 (s, 9H); LC-MS m/z=644 [C36H35ClN2O5S+H]$^+$; HPLC conditions: Waters Atlantis C-18 OBD 4.6×150 mm; mobile phase=ACN/(H$_2$O:0.1TFA) flow rate=1.0 mL/min; detection=UV @254 and 220 nm, retention time in min: 21.20; Anal Calcd: (MF:C36H35ClN2O5S+2.0H$_2$O) Calcd: C:63.66, H:5.79, N:4.12. Found: C: 63.53, H:5.68, N:4.34. $\alpha_{D[25]}$ MeOH (4.12 mg in 1.0 mL)=−15.460.

EXAMPLES: BIOLOGICAL EXAMPLES

Example A—Human Glucagon Receptor Affinity

Compounds of the invention are dissolved in a suitable solvent (e.g. dimethlysulfoxide) at a concentration of 10 mM and then diluted in buffer (50 mM Hepes, pH 7.4, 5 mM MgCl$_2$, 1 mM CaCl$_2$, 0.2% BSA) to concentrations ranging from 1 nM to 100 µM. Compounds (20 µl/well) and [$^{125}$I] Glucagon (Perkin Elmer; final concentration: 0.125 nM; 20 µl/well) are added to and mixed in wells of a 96-well plate (Costar, Corning) containing 120 µl of buffer. Next, an appropriate aliquot of a membrane preparation containing the human glucagon receptor (isolated from human liver samples or obtained from a recombinant cell line) is added to the wells. The binding mixtures are incubated for 2 hour at room temperature. In the meantime, a MultiScreen 96-well filter plate (Millipore) is incubated with 200 µl of buffer, which is vacuumed through the filter just before the binding mixtures are transferred to the plate. At the end of incubation, binding mixtures are transferred to the wells of the MultiScreen 96-well filter plate and filtered through by applying vacuum. The plate is washed once with 200 µl per well of buffer and the filters are dried and counted by means of a gamma counter.

Exemplified compounds displace radiolabeled glucagon from the human glucagon receptor by ≥15% at 1000 nM or have an IC$_{50}$ of <10,000 nM.

Example B—Functional Antagonism in Hepatocytes from Various Species

Primary human, monkey, dog, rat, or mouse hepatocytes are seeded onto collagen-coated 24-well plates in Williams E medium (supplemented with 10% fetal bovine serum) and incubated at 37° C. overnight in M199 medium (supplemented with 15 mM glucose and 10 nM human insulin). The following day cells are washed twice with a glucose-free Kreb-bicarbonate buffer, pH 7.4, containing 0.1% BSA. Cells are then incubated at 37° C. with the aforementioned buffer containing 1 nM glucagon and varying concentrations of a glucagon antagonist (0-100 microM). Control wells without glucagon or antagonist are also included. After 1 hour, an aliquot of the medium is removed and analyzed for glucose content by means of the glucose oxidase method. The background glucose levels observed in the control wells are subtracted from the glucagon and antagonist containing wells. A graph of % glucose concentration vs drug concentration is plotted and an EC50 value for inhibition of glucose production generated using Sigmaplot software (SAS, Cary, N.C.). Alternatively, intracellular cAMP levels are measured using standard kits and EC50 values determined by plotting these levels against drug concentration. Antagonists of the glucagon receptor inhibit glucagon-induced cAMP production.

Example C—Glucose Lowering in Diabetic Animals

The effects of compounds of the invention on blood glucose levels are assessed in animal models of type 1 or 2 diabetes such as, but not limited to, the db/db mouse, the Zucker fatty (ZF) rat, the Zucker diabetic (ZDF) rat, the glucagon-challenged dog, the alloxan- or streptozotocin-treated mouse or rat, the NOD mouse or the BB rat.

Compounds are dissolved in an appropriate vehicle such as polyethylene glycol-400 or cyclodextrin and administered to animals at doses of 0.1 to 100 mg/kg either by intraperitoneal injection, intravenous injection, or oral gavage. Animal models used in this evaluation [e.g. the db/db mouse, the ZF rat, the ZDF rat, the glucagon-challenged (0.3-5 µg/kg) dog, the alloxan- or streptozotocin-treated mouse or rat, the NOD mouse, or BB rat] are either freely-feeding or fasted from 3 to 24 hours prior to compound administration. In some instances, animals may be subjected to a glucose tolerance test following compound administration by intravenous or oral administration of up to 2 g/kg of glucose. Blood glucose levels are assessed in blood samples obtained by tail bleed or by sampling an appropriate blood vessel by means of a syringe or catheter. Glucose is measured using a portable glucometer such as the OneTouch or HemoCue meters at regular time intervals for up to 24 hours. The extent of blood glucose lowering elicited by the compounds of the invention is determined by comparison to those in control animals administered only the vehicle. The percentage of blood glucose lowering attained is calculated relative to blood glucose levels in vehicle-treated nondiabetic or non-glucagon-challenged control animals.

Example D—Glucose Lowering in db/db Mice

Purpose: To assess the effects of compounds of the invention on blood glucose levels in the db/db mouse, an animal model of type 2 diabetes.

Methods: Compounds were dissolved in polyethylene glycol-400 and administered by oral gavage to db/db mice in the freely-feeding state at doses of 30 and/or 100 mg/kg. Blood glucose levels were assessed in blood samples obtained by tail bleed at baseline (prior to drug administration) and at regular time intervals over 24 hours using a portable glucometer such as the OneTouch or HemoCue meters. The magnitude of blood glucose lowering elicited by the compounds of the invention was determined by comparison to those in db/db mice administered only the vehicle. The percentage glucose lowering was calculated by factoring in the blood glucose levels of vehicle-treated lean db/+(heterozygote) mice, with 100% representing the normalization of blood glucose levels from the hyperglycemic state (vehicle-treated db/db mice) to the normoglycemic state (vehicle-treated db/+ mice).

Results: As shown in the table below, compounds of the invention lowered blood glucose of db/db mice in the freely-feeding state by 19 to 172 mg/dL. The percentage blood glucose lowering achieved ranged from 6 to 68% relative to lean control animals.

| Example# | DOSE (mg/Kg) | Glucose lowering (mg/dL) | % Glucose lowering |
|---|---|---|---|
| 1.052 | 30 | 147 | 61 |
| 1.155 | 30 | 108 | 49 |
| 1.321 | 30 | 161 | 68 |
| 1.135 | 100 | 131 | 41 |
| 1.137 | 30 | 159 | 53 |
| 1.136 | 30 | 47 | 16 |
| 1.320 | 30 | 121 | 39 |
| 1.270 | 30 | 63 | 24 |
| 1.138 | 30 | 19 | 6 |
| 1.315 | 30 | 172 | 57 |
| 1.311 | 30 | 109 | 36 |
| 1.359 | 100 | 150 | 48 |
| 1.179 | 30 | 102 | 34 |
| 1.314 | 30 | 95 | 40 |
| 1.173 | 30 | 172 | 50 |
| 1.269 | 30 | 124 | 42 |
| 1.133 | 30 | 157 | 57 |

Conclusion: Compounds of the invention have pronounced antihyperglycemic activity in animal models of type 2 diabetes and may therefore have utility for the treatment of type 2 diabetes.

Example E—Glucose Lowering in Glucagon-Challenged Beagle Dogs

Purpose: To assess the effects of compounds of the invention on blood glucose levels in glucagon-challenged Beagle dogs.

Methods: Beagle dogs (n=3) were treated with vehicle (polyethylenelglycol-400) by oral gavage. After 1.5 hours, glucagon (20 μg) was administered subcutaneously. Blood glucose levels were measured prior to glucagon administration and at 10-minute intervals thereafter for up to an hour. Blood samples for these determinations were obtained from a superficial ear vein and were measured using a OneTouch glucometer. After a 1-week washout, the animals were treated by oral gavage with the compound of Example 2.009 at a dose of 38 mg/kg (polyethylenelglycol-400 formulation). The glucagon challenge and blood sampling were then performed as before.

Results: As shown in FIGS. 1A and 1B, treatment with the compound of Example 2.009 attenuated the glucagon-induced glucose excursion by approximately 40%.

Conclusion: The compound of Example 2.009 is a potent glucagon antagonist in the dog. The in vivo profile obtained suggests the compound of Example 2.009 may have utility for the treatment of hyperglycemia in patients with type 2 diabetes, a disorder believed to be caused in part by inappropriately elevated glucagon levels.

What is claimed is:
1. A compound of formula (I):

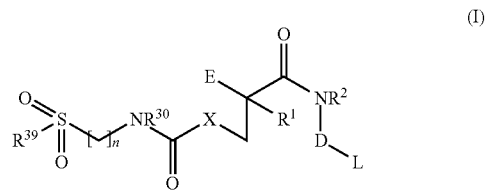

wherein: D is a substituted group selected from carbocyclic aryl, $C_{1-8}$-alkyl carbocyclic aryl, or heteroaryl, wherein said group is substituted with L and, optionally, one or more additional substituents independently selected from optionally substituted $C_{1-6}$-alkyl, optionally substituted $C_{2-6}$-alkenyl, optionally substituted $C_{2-6}$-alkynyl, optionally substituted $C_{3-8}$-cycloalkyl, optionally substituted $C_{4-8}$-cycloalkenyl, optionally substituted $C_{3-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —$CF_3$, —$NO_2$, or —CN, L is a group selected from carbocyclic aryl, carbocyclic aryloxy-, carbocyclic arylalkoxy-, carbocyclic arylalketyl-, carbocyclic arylketyl-, carbocyclic aryl-NH—, carbocyclic aryl-N—$C_{1-3}$-alkyl-, heteroaryloxy, heteroarylalkoxy, heteroarylketyl, heteroarylalketyl, or heteroaryl;

wherein L is optionally substituted with one, two, or three groups selected from halogen, $CF_3$, hydroxyl, amido, optionally substituted $C_{1-6}$-alkyl, optionally substituted $C_{2-6}$-alkenyl, optionally substituted $C_{2-6}$-alkynyl, optionally substituted $C_{3-6}$-cycloalkyl, optionally substituted $C_{4-8}$-cycloalkenyl, optionally substituted $C_{1-8}$-alkyoxy, optionally substituted $C_{3-8}$-alkylthio-, optionally substituted $C_{3-8}$-cycloalkylalkoxy, optionally substituted $C_{3-8}$-cycloalkylalkylthio, —$NO_2$, or —CN, $R^1$ is a group selected from hydrogen, fluoro or $C_{1-8}$-alkyl optionally substituted with fluoro up to perfluoro, $R^2$ is a group selected from hydrogen or $C_{1-8}$-alkyl;

E is a group selected from $C_{1-12}$-alkyl, $C_{2-12}$-alkenyl, $C_{2-12}$-alkynyl, $C_{3-8}$-cycloalkyl, $C_{4-8}$-cycloalkenyl, carbocyclic aryl, or heteroaryl; wherein each group is optionally substituted with one to six groups independently selected from halogen, —CN, —$C_{1-6}$-alkyl, —$CHF_2$, —$CF_3$, —$OCF_3$, —$OCHF_2$, —$OCH_2CF_3$, —$OCF_2CHF_2$, —$SCF_3$, optionally substituted $C_{3-8}$-cycloalkyl, optionally substituted $C_{4-8}$-cycloalkenyl, optionally substituted phenyl or optionally substituted five- or six-membered heteroaryl;

X is a group selected from phenylene, heterocyclic monoarylene, $C_{5-8}$-cycloalkylene or $C_{5-8}$-cycloalkenylene; wherein X is optionally substituted with one or two groups independently selected from halogen, —CN, —$CF_3$, —$OCF_3$, —$OCHF_2$, —$NO_2$, —$OR^{30}$, $C_{1-6}$-alkyl, $C_{2-6}$-alkenyl, or $C_{1-6}$-alkynyl;

$R^{30}$ is a group selected from hydrogen or $C_{1-6}$-alkyl optionally substituted with fluoro up to perfluoro;

n is 0, 1, 2, or 3;

$R^{39}$ is a group selected from —OH, —NHOH, or —NH$_2$; or pharmaceutically acceptable salts, cocrystals and prodrugs thereof.

2. The compound of claim 1, wherein D is carbocyclic aryl or heteroaryl substituted with L;
L is carbocyclic aryl or heteroaryl,
wherein L is optionally substituted with one, two, or three groups selected from halogen, CF$_3$, hydroxyl, amido, optionally substituted $C_{1-6}$-alkyl, optionally substituted $C_{2-6}$-alkenyl, optionally substituted $C_{2-6}$-alkynyl, optionally substituted $C_{3-6}$-cycloalkyl, optionally substituted $C_{4-8}$-cycloalkenyl, or optionally substituted $C_{1-8}$-alkyoxy;
E is carbocyclic aryl, or heteroaryl substituted with optionally substituted phenyl or optionally substituted five- or six-membered heteroaryl;
X is phenylene,
wherein X is optionally substituted with one or two groups independently selected from halogen, —CN, —CF$_3$, —OCF$_3$, or —OCHF$_2$; and
$R^{39}$ is a group selected from —OH, —NHOH, or —NH$_2$.

3. The compound of claim 1, wherein D is carbocyclic aryl substituted with L; and L is carbocyclic aryl substituted with substituted $C_{1-6}$-alkyl; and E is carbocyclic aryl substituted with phenyl substituted with $C_{1-6}$-alkyl.

4. The compound of claim 1, wherein X is phenylene or heterocyclic monoarylene; $R^{30}$ is hydrogen and n is 1 or 2.

5. The compound of claim 1, wherein $R^1$ is hydrogen; X is a phenylene; $R^{30}$ is hydrogen and n is 2.

6. The compound of claim 1, wherein E is phenyl-substituted phenyl substituted with one to three groups independently selected from halogen, —CN, or —$C_{1-6}$-alkyl.

7. The compound of claim 1, wherein E is phenyl-substituted phenyl substituted with a t-butyl group.

8. The compound of claim 1, wherein the compound is a pharmaceutically acceptable salt or cocrystal of the following structure:

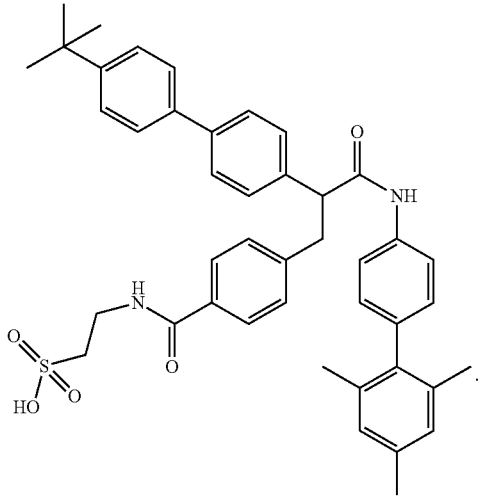 [SMILES: Cc1cc(C)c(-c2ccc(NC(=O)C(Cc3ccc(C(=O)NCCS(=O)(=O)O)cc3)c3ccc(-c4ccc(C(C)(C)C)cc4)cc3)cc2)c(C)c1]

9. A pharmaceutical composition comprising a compound of formula (I):

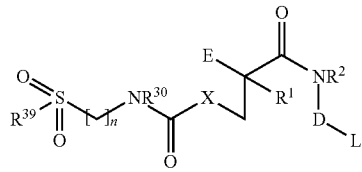

wherein: D is a substituted group selected from carbocyclic aryl, $C_{1-8}$-alkyl carbocyclic aryl, or heteroaryl, wherein said group is substituted with L and, optionally, one or more additional substituents independently selected from optionally substituted $C_{1-6}$-alkyl, optionally substituted $C_{2-6}$-alkenyl, optionally substituted $C_{2-6}$-alkynyl, optionally substituted $C_{3-8}$-cycloalkyl, optionally substituted $C_{4-8}$-cycloalkenyl, optionally substituted $C_{3-8}$-alkoxy, optionally substituted $C_{3-8}$-alkylthio-, optionally substituted $C_{3-8}$-cycloalkylalkoxy, optionally substituted $C_{3-8}$-cycloalkylalkylthio-, optionally substituted $C_{3-8}$-cycloalkyloxy, optionally substituted $C_{3-8}$-cycloalkylthio, halogen, —CF$_3$, —NO$_2$, or —CN, L is a group selected from carbocyclic aryl, carbocyclic aryloxy-, carbocyclic arylalkoxy-, carbocyclic arylalketyl-, carbocyclic arylketyl-, carbocyclic aryl-NH—, carbocyclic aryl-N—$C_{1-3}$-alkyl-, heteroaryloxy, heteroarylalkoxy, heteroarylketyl, heteroarylalketyl, or heteroaryl;

wherein L is optionally substituted with one, two, or three groups selected from halogen, CF$_3$, hydroxyl, amido, optionally substituted $C_{1-6}$-alkyl, optionally substituted $C_{2-6}$-alkenyl, optionally substituted $C_{2-6}$-alkynyl, optionally substituted $C_{3-6}$-cycloalkyl, optionally substituted $C_{4-8}$-cycloalkenyl, optionally substituted $C_{1-8}$-alkyoxy, optionally substituted $C_{3-8}$-alkylthio-, optionally substituted $C_{3-8}$-cycloalkylalkoxy, optionally substituted $C_{3-8}$-cycloalkylalkylthio, —NO$_2$, or —CN, $R^1$ is a group selected from hydrogen, fluoro or $C_{1-8}$-alkyl optionally substituted with fluoro up to perfluoro, $R^2$ is a group selected from hydrogen or $C_{1-8}$-alkyl;

E is a group selected from $C_{1-12}$-alkyl, $C_{2-12}$-alkenyl, $C_{2-12}$-alkynyl, $C_{3-8}$-cycloalkyl, $C_{4-8}$-cycloalkenyl, carbocyclic aryl, or heteroaryl; wherein each group is optionally substituted with one to six groups independently selected from halogen, —CN, —$C_{1-6}$-alkyl, —CHF$_2$, —CF$_3$, —OCF$_3$, —OCHF$_2$, —OCH$_2$CF$_3$, —OCF$_2$CHF$_2$, —SCF$_3$, optionally substituted $C_{3-8}$-cycloalkyl, optionally substituted $C_{4-8}$-cycloalkenyl, optionally substituted phenyl or optionally substituted five- or six-membered heteroaryl;

X is a group selected from phenylene, heterocyclic monoarylene, $C_{5-8}$-cycloalkylene or $C_{5-8}$-cycloalkenylene; wherein X is optionally substituted with one or two groups independently selected from halogen, —CN, —CF$_3$, —OCF$_3$, —OCHF$_2$, —NO$_2$, —OR$^{30}$, $C_{1-6}$-alkyl, $C_{2-6}$-alkenyl, or $C_{1-6}$-alkynyl;

$R^{30}$ is a group selected from hydrogen or $C_{1-6}$-alkyl optionally substituted with fluoro up to perfluoro;

n is 0, 1, 2, or 3;

$R^{39}$ is a group selected from —OH, —NHOH, or —NH$_2$; or pharmaceutically acceptable salts, cocrystals and prodrugs thereof; and a pharmaceutically acceptable carrier.

10. The pharmaceutical composition of claim 9, wherein D is carbocyclic aryl or heteroaryl substituted with L;
L is carbocyclic aryl or heteroaryl,
wherein L is optionally substituted with one, two, or three groups selected from halogen, $CF_3$, hydroxyl, amido, optionally substituted $C_{1-6}$-alkyl, optionally substituted $C_{2-6}$-alkenyl, optionally substituted $C_{2-6}$-alkynyl, optionally substituted $C_{3-6}$-cycloalkyl, optionally substituted $C_{4-8}$-cycloalkenyl, or optionally substituted $C_{1-8}$-alkyoxy;
E is carbocyclic aryl, or heteroaryl substituted with optionally substituted phenyl or optionally substituted five- or six-membered heteroaryl;
X is phenylene,
wherein X is optionally substituted with one or two groups independently selected from halogen, —CN, —$CF_3$, —$OCF_3$, or —$OCHF_2$; and
$R^{39}$ is a group selected from —OH, —NHOH, or —$NH_2$.

11. The pharmaceutical composition of claim 9, wherein D is carbocyclic aryl substituted with L; and L is carbocyclic aryl substituted with substituted $C_{1-6}$-alkyl; and E is carbocyclic aryl substituted with phenyl substituted with $C_{1-6}$-alkyl.

12. The pharmaceutical composition of claim 9, wherein X is phenylene or heterocyclic monoarylene; $R^{30}$ is hydrogen and n is 1 or 2.

13. The pharmaceutical composition of claim 9, wherein $R_1$ is hydrogen; X is a phenylene; $R^{30}$ is hydrogen and n is 2.

14. The pharmaceutical composition of claim 9, wherein E is phenyl-substituted phenyl substituted with one to three groups independently selected from halogen, —CN, or —$C_{1-6}$-alkyl.

15. The pharmaceutical composition of claim 9, wherein E is phenyl-substituted phenyl substituted with a t-butyl group.

16. The pharmaceutical composition of claim 9, wherein the compound is a pharmaceutically acceptable salt or cocrystal of the following structure:

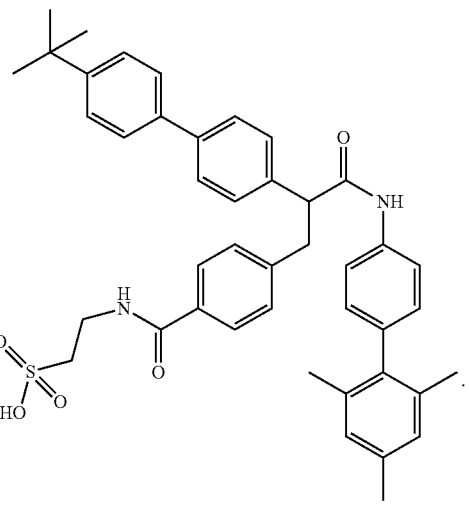

17. The pharmaceutical composition of claim 9, wherein the compound is in an amount of about 10 mg to about 120 mg.

18. The pharmaceutical composition of claim 9, wherein the compound is in an amount of about 20 mg to about 60 mg.

19. The pharmaceutical composition of claim 9, wherein the compound is in an amount of about 40 mg.

20. The pharmaceutical composition of claim 9, further comprising cyclodextrin.

* * * * *